(12) United States Patent
Santamaria

(10) Patent No.: US 10,485,882 B2
(45) Date of Patent: Nov. 26, 2019

(54) NANOPARTICLE COMPOSITIONS FOR SUSTAINED THERAPY

(71) Applicant: UTI LIMITED PARTNERSHIP, Calgary (CA)

(72) Inventor: Pedro Santamaria, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 0 days.

(21) Appl. No.: 15/348,959

(22) Filed: Nov. 10, 2016

(65) Prior Publication Data

US 2017/0095544 A1 Apr. 6, 2017

Related U.S. Application Data

(63) Continuation of application No. PCT/IB2016/000691, filed on May 6, 2016.

(60) Provisional application No. 62/157,933, filed on May 6, 2015, provisional application No. 62/273,953, filed on Dec. 31, 2015, provisional application No. 62/296,032, filed on Feb. 16, 2016.

(51) Int. Cl.
*A61K 47/69* (2017.01)
*A61K 39/00* (2006.01)
*A61K 47/60* (2017.01)
*A61K 39/285* (2006.01)
*A61K 39/385* (2006.01)
*A61K 47/54* (2017.01)
*C07K 14/74* (2006.01)

(52) U.S. Cl.
CPC ...... *A61K 47/6929* (2017.08); *A61K 39/0008* (2013.01); *A61K 39/385* (2013.01); *A61K 47/545* (2017.08); *A61K 47/60* (2017.08); *A61K 47/6909* (2017.08); *A61K 47/6935* (2017.08); *A61K 2039/57* (2013.01); *A61K 2039/60* (2013.01); *A61K 2039/627* (2013.01)

(58) Field of Classification Search
None
See application file for complete search history.

(56) References Cited

U.S. PATENT DOCUMENTS

| | | |
|---|---|---|
| 4,367,110 A | 1/1983 | Yoshikawa |
| 4,414,148 A | 11/1983 | Jansen et al. |
| 4,452,901 A | 6/1984 | Gordon et al. |
| 4,478,946 A | 10/1984 | Van Der Merwe et al. |
| 4,554,101 A | 11/1985 | Hopp |
| 4,569,789 A | 2/1986 | Blattler et al. |
| 4,589,071 A | 5/1986 | Yamamuro et al. |
| 4,589,330 A | 5/1986 | Teron |
| 4,659,839 A | 4/1987 | Nicolotti et al. |
| 4,671,958 A | 6/1987 | Rodwell et al. |
| 4,680,338 A | 7/1987 | Sundoro |
| 4,699,784 A | 10/1987 | Shih et al. |
| 4,818,542 A | 4/1989 | Deluca et al. |
| 4,859,839 A | 8/1989 | Tetelman et al. |
| 5,258,499 A | 11/1993 | Konigsberg et al. |
| 5,543,391 A | 8/1996 | Yatvin et al. |
| 5,676,926 A | 10/1997 | Platzek et al. |
| 5,676,928 A | 10/1997 | Klaveness et al. |
| 5,840,839 A | 11/1998 | Wang et al. |
| 6,103,379 A | 8/2000 | Margel et al. |
| 6,387,498 B1 | 5/2002 | Coulter et al. |
| 6,651,655 B1 | 11/2003 | Licalsi et al. |
| 6,688,494 B2 | 2/2004 | Pozarnsky et al. |
| 6,712,997 B2 | 3/2004 | Won et al. |
| 6,797,514 B2 | 9/2004 | Berenson et al. |
| 6,846,474 B2 | 1/2005 | Nayfeh et al. |
| 6,929,675 B1 | 8/2005 | Bunge et al. |
| 7,060,121 B2 | 6/2006 | Lin et al. |
| 7,285,289 B2 | 10/2007 | Nagy et al. |
| 7,326,399 B2 | 2/2008 | Zhou et al. |
| 7,332,586 B2 | 2/2008 | Franzen et al. |
| 7,361,733 B2 | 4/2008 | Hershberg et al. |
| 7,572,631 B2 | 8/2009 | Berenson et al. |
| 8,354,110 B2 | 1/2013 | Santamaria et al. |
| 8,835,144 B2 | 9/2014 | Jiang et al. |
| 9,149,440 B2 | 10/2015 | Turos et al. |
| 9,511,151 B2 | 12/2016 | Santamaria et al. |
| 2003/0068363 A1 | 4/2003 | Clark et al. |
| 2003/0124149 A1 | 7/2003 | Shalaby et al. |
| 2004/0115216 A1 | 6/2004 | Schneck et al. |
| 2004/0137642 A1 | 7/2004 | Erfle et al. |
| 2004/0265392 A1 | 12/2004 | Tovar et al. |
| 2005/0003431 A1 | 1/2005 | Wucherpfennig et al. |

(Continued)

FOREIGN PATENT DOCUMENTS

| | | |
|---|---|---|
| CA | 2517097 A1 | 9/2004 |
| CA | 2717719 A | 8/2009 |

(Continued)

OTHER PUBLICATIONS

Ma et al (PLOS one, Nov. 2014, 9(11): e112292, pp. 1-10).*
Clemente-Caseres et al (J. Mol. Med., 2011, 89: 733-742).*
Saengruengrit et al (J. Colloid and Interface Science, 2018, 520: 101-111) (Year: 2018).*
Advisory Action in U.S. Appl. No. 12/044,435, dated Aug. 23, 2011.
Aichele, P. et al. (1994) "Peptide-induced T-cell tolerance to prevent autoimmune diabetes in a transgenic mouse model," Proc. Natl. Acad. Sci. USA 91:444-448.
Amrani, A. et al. (2000) "Progression of autoimmune diabetes driven by avidity maturation of a T-cell population," Nature 406:739-742.

(Continued)

*Primary Examiner* — G. R. Ewoldt
*Assistant Examiner* — Marianne DiBrino
(74) *Attorney, Agent, or Firm* — Wilson Sonsini Goodrich & Rosati

(57) ABSTRACT

This disclosure provides compositions and methods for promoting the formation, expansion and recruitment of $T_R1$ cells and/or B cells in an antigen-specific manner and treating diseases and disorders in a subject in need thereof.

11 Claims, 58 Drawing Sheets

Specification includes a Sequence Listing.

(56) References Cited

U.S. PATENT DOCUMENTS

| | | |
|---|---|---|
| 2005/0118102 A1 | 6/2005 | Xiang et al. |
| 2005/0129617 A1 | 6/2005 | Tan et al. |
| 2005/0202032 A1 | 9/2005 | Kaufman et al. |
| 2005/0208120 A1 | 9/2005 | Albani |
| 2006/0219239 A1 | 10/2006 | Plaschkes |
| 2007/0054337 A1 | 3/2007 | Ferning et al. |
| 2007/0059775 A1 | 3/2007 | Hultman et al. |
| 2007/0129307 A1 | 6/2007 | Tan et al. |
| 2007/0154953 A1 | 7/2007 | Brunner et al. |
| 2009/0155292 A1 | 6/2009 | Santamaria et al. |
| 2009/0258355 A1 | 10/2009 | Maye et al. |
| 2010/0061984 A1 | 3/2010 | Greene et al. |
| 2010/0095544 A1 | 4/2010 | Haseloh |
| 2010/0104503 A1 | 4/2010 | Mellman et al. |
| 2010/0303866 A1 | 12/2010 | Saint-Remy |
| 2011/0029121 A1 | 2/2011 | Amit |
| 2011/0059121 A1 | 3/2011 | Santamaria et al. |
| 2011/0250146 A1 | 10/2011 | Zhang et al. |
| 2011/0318380 A1 | 12/2011 | Brix et al. |
| 2012/0093934 A1 | 4/2012 | Santamaria |
| 2012/0121649 A1 | 5/2012 | Santamaria |
| 2013/0128138 A1 | 5/2013 | Kuo et al. |
| 2013/0171179 A1 | 7/2013 | Burrows |
| 2013/0302421 A1 | 11/2013 | Santamaria et al. |
| 2013/0330414 A1 | 12/2013 | Santamaria |
| 2014/0105980 A1 | 4/2014 | Santamaria |
| 2014/0294982 A1 | 10/2014 | Freund et al. |
| 2014/0341938 A1 | 11/2014 | Rademacher et al. |
| 2014/0370099 A1 | 12/2014 | Green et al. |
| 2015/0125536 A1 | 5/2015 | Santamaria |
| 2015/0150996 A1 | 6/2015 | Miller et al. |
| 2015/0209446 A1 | 7/2015 | Santamaria |
| 2015/0250871 A1 | 9/2015 | Santamaria |
| 2015/0374815 A1 | 12/2015 | Kishimoto et al. |
| 2016/0271237 A1 | 9/2016 | Santamaria |
| 2017/0095544 A1 | 4/2017 | Santamaria |
| 2017/0274096 A1 | 9/2017 | Santamaria |
| 2017/0312348 A1 | 11/2017 | Santamaria |
| 2017/0333540 A1 | 11/2017 | Santamaria et al. |
| 2019/0134171 A1 | 5/2019 | Santamaria |

FOREIGN PATENT DOCUMENTS

| | | |
|---|---|---|
| CA | 2868551 A1 | 10/2013 |
| CN | 101678090 A | 3/2010 |
| EP | 0 188 256 | 7/1986 |
| EP | 2614834 A1 | 7/2013 |
| EP | 2 621 523 | 8/2013 |
| EP | 3269384 A1 | 1/2018 |
| EP | 3291832 A2 | 3/2018 |
| JP | H07508503 A | 9/1995 |
| JP | 2002504342 A | 2/2002 |
| JP | 2002544170 A | 12/2002 |
| JP | 2005538083 A | 12/2005 |
| JP | 2006522319 A | 9/2006 |
| JP | 2007508503 A | 4/2007 |
| JP | 2008514686 A | 5/2008 |
| WO | WO-9007339 A1 | 7/1990 |
| WO | WO-1992/18150 A1 | 10/1992 |
| WO | WO-9301716 A1 | 2/1993 |
| WO | WO-1993/16725 A1 | 9/1993 |
| WO | WO-94/09823 A1 | 5/1994 |
| WO | WO-99/14236 A1 | 3/1999 |
| WO | WO-0043662 A1 | 7/2000 |
| WO | WO-0067788 A2 | 11/2000 |
| WO | WO-0124764 A2 | 4/2001 |
| WO | WO-2004006951 A1 | 1/2004 |
| WO | WO-2004/078909 A2 | 9/2004 |
| WO | WO-2005/033267 A2 | 4/2005 |
| WO | WO-2005036035 A2 | 4/2005 |
| WO | WO-2006037979 A2 | 4/2006 |
| WO | WO-2006/080951 A2 | 8/2006 |
| WO | WO-2007/024026 | 3/2007 |
| WO | WO-2008051245 A2 | 5/2008 |
| WO | WO-2008/109852 A2 | 9/2008 |
| WO | WO2008109852 A2 * | 9/2008 |
| WO | WO-2008/118861 A2 | 10/2008 |
| WO | WO-2009003492 A1 | 1/2009 |
| WO | WO-2009/031258 | 3/2009 |
| WO | WO-2009/040811 A2 | 4/2009 |
| WO | WO-2009/078799 | 6/2009 |
| WO | WO-2009094273 A2 | 7/2009 |
| WO | WO-2009/111588 A1 | 9/2009 |
| WO | WO-2009/126835 A2 | 10/2009 |
| WO | WO-2010025324 A2 | 3/2010 |
| WO | WO-2010027827 A2 | 3/2010 |
| WO | WO-2010/037395 A2 | 4/2010 |
| WO | WO-2010/042876 A1 | 4/2010 |
| WO | WO-2010037397 A1 | 4/2010 |
| WO | WO-2010/080032 A2 | 7/2010 |
| WO | WO-2010/085509 A1 | 7/2010 |
| WO | WO-2011/073685 A1 | 6/2011 |
| WO | WO-2011/104497 A1 | 9/2011 |
| WO | WO-2012012874 A1 | 2/2012 |
| WO | WO-2012/031258 A1 | 3/2012 |
| WO | WO-2012/041968 A1 | 4/2012 |
| WO | WO 2012041968 A1 * | 4/2012 |
| WO | WO-2012/062904 A2 | 5/2012 |
| WO | WO-2013/043662 | 3/2013 |
| WO | WO-2013/072051 A1 | 5/2013 |
| WO | WO-2013/144811 A2 | 10/2013 |
| WO | WO-2014/080286 A2 | 5/2014 |
| WO | WO-2015/063616 A2 | 5/2015 |
| WO | WO-2016198932 A2 | 12/2016 |
| WO | WO-2018087597 A1 | 5/2018 |

OTHER PUBLICATIONS

Amrani, A. et al. (2001) "Expansion of the Antigenic Repertoire of a Single T Cell Receptor upon T Cell Activation," J. Immunol. 167:655-666.

Anderson, B. et al. (1999) "Prevalent CD8(+) T cell response against one peptide/MHC complex in autoimmune diabetes," Proc. Natl. Acad. Sci. USA 96:9311-9316.

Anderton, S.M. et al. (1998) "Hierarchy in the ability of T cell epitopes to induce peripheral tolerance to antigens from myelin," Eur. J. Immunol. 28:1251-1261.

Appay, V. et al. (2000) "HIV-specific CD8(+) T Cells Produce Antiviral Cytokines but Are Impaired in Cytoltic Function," J. Exp. Med. 192(1):63-72.

Author Unknown (2002) Diabetes Prevention Trial-Type 1 Diabetes Study Group, "Effects of Insulin in Relatives of Patients with Type 1 Diabetes Mellitus," N. Engl. J. Med. 346:1685-1691.

Author Unknown (2010) KidsHealth from Nemours, "Can Diabetes Be Prevented?," Website article from kidshealth.org/PageManager. jsp?dn=KidsHealth&lic=1&ps=107&caUd=139&article; downloaded Nov. 9, 2010, 2 pages.

Bachmann, M.F. et al. (1999) "Developmental Regulation of Lck Targeting to the CD8 Coreceptor Controls Signaling in Naive and Memory T Cells," J. Exp. Med. 189:1521-1530.

Barber, D.L. et al. (2006) "Restoring function in exhausted CD8 T cells during chronic viral infection," Nature 439:682-687.

Becker, T.C. et al. (2002) "Interleukin 15 Is Required for Proliferative Renewal of Virus-specific Memory CD8 T Cells," J. Exp. Med. 195(12):1541-1548.

Behan, P.O. et al. (2010) "The sad plight of multiple sclerosis research (low on fact, high on fiction): critical data to support it being a neurocristopathy," Inflammopharmacol 18:265-290.

Betts, R.J. et al. (2009) "CD8( ) T cells in asthma: Friend or foe?" Pharmacology & Therapeutics 121:123-131.

Bibliographic data page from EPO website at espacenet.com/ publicationDetails/biblio?CC=WO&NR=2004078909A2& KC= . . . , downloaded Nov. 15, 2010, showing that W02004078909 was also published as US2007154953: 1 page total.

Bielekova, B. et al. (2000) "Encephalitogenic potential of the myelin basic protein peptide (amino acids 83-99) in multiple sclerosis: Results of a phase II clinical trial with an altered peptide ligand," Nat. Med. 6(10):1167-1175.

(56) References Cited

OTHER PUBLICATIONS

Blancou, P. et al. (2007) "Immunization of HLA Class I Transgenic Mice Identifies Autoantigenic Epitopes Eliciting Dominant Responses in Type 1 Diabetes Patients," J. Immunol. 178:7458-7466.
Bottazzo, G.F. et al. (1985) "In situ characterization of autoimmune phenomena and expression of HLA molecules in the pancreas in diabetic insulitis," N. Engl. J. Med. 313(6):353-360.
Bour-Jordan, H. et al. (2007) "B cell depletion: a novel therapy for autoimmune diabetes?" J. Clin. Invest. 117:3642-3645.
Braud, V.M. et al. (1999) "Functions of nonclassical MHC and non-MHC-encoded class I molecules," Current Opinion in Immunology 11:100-108.
Cao, K. et al. (2001) "Analysis of the Frequencies of HLA-A, B, and C Alleles and Haplotypes in the Five Major Ethnic Groups of the United States Reveals High Levels of Diversity in These Loci and Contrasting Distribution Patterns in These Populations," Hum. Immunol. 62:1009-1030.
Chang, J.W. et al. (2001) "Design, engineering, and production of human recombinant T-cell receptor ligands derived from human leukocyte antigen DR2," Journal of Biological Chemistry 276(26):24170-6.
Chatenoud, L. (2002) "Do NKT cells control autoimmunity?" J. Clin. Invest. 110(6):747-748.
Cirillo, C. et al. (2011) "S100B protein in the gut: The evidence for enteroglial-sustained intestinal inflammation," World J Gastroenterol. 17(10):1261-1266.
Cnop, M. et al. (2005) "Mechanisms of Pancreatic beta-Cell Death in Type 1 and Type 2 Diabetes," Diabetes 54(2):S97-S107.
Constantinescu, C.S. et al. (2011) "Experimental autoimmune encephalomyelitis (EAE) as a model for multiple sclerosis (MS)," British Journal of Pharmacology 164:1079-1106.
Croxford, A.L. et al. (2011) "Mouse models for multiple sclerosis: Historical facts and future implications," Biochimica et Biophysica Acta 1812:177-183.
Cuiv, P.O. et al. (2011) "Draft Genome Sequence of Bacteroides vulgatus PC510, a Strain Isolated from Human Feces," Journal of Bacteriology 193(15):4025-4026.
Database Accession No. ADK001000110 (2011) "Bacteroides vulgatus PC510 contig00041, whole genome shotgun sequence."
Denic, A. et al. (2011) "The relevance of animal models in multiple sclerosis research," Pathophysiology 18:21-29.
Dilorenzo, T.P. et al. (1998) "Major histocompatibility complex class I-restricted T cells are required for all but the end stages of diabetes development in nonobese diabetic mice and use a prevalent T cell receptor alpha chain gene rearrangement," Proc. Natl. Acad. Sci. USA 95:12538-12543.
Dressel, A. et al. (1997) "Autoantigen recognition by human CD8 T cell clones: enhanced agonist response induced by altered peptide ligands," J. Immunol. 159: 4943-4951.
Eggena, M. et al. (2000) "Identification of Histone H1 as a Cognate Antigen of the Ulcerative Colitis-associated Marker Antibody pANCA," Journal of Autoimmunity 14:83-97.
Fennessy, M. et al. (1994) "A gene in the HLA class I region contributes to susceptibility to IDDM in the Finnish population," Diabetologia 37:937-944.
Final Office Action in U.S. Appl. No. 12/044,435, dated Jun. 8, 2011.
Final Office Action in U.S. Appl. No. 12/848,055, dated Aug. 23, 2012.
Final Office Action in U.S. Appl. No. 12/848,055, dated Dec. 24, 2014.
Final Office Action in U.S. Appl. No. 12/848,055, dated Jul. 12, 2013.
Final Office Action in U.S. Appl. No. 13/249,105, dated Nov. 30, 2015.
Final Office Action in U.S. Appl. No. 13/830,521, dated Mar. 5, 2015.
Final Office Action in U.S. Appl. No. 13/842,302, dated Feb. 18, 2015.
Final Office Action in U.S. Appl. No. 14/723,268, dated Mar. 30, 2016.
Flad, T. et al. (2003) "Development of an MHC-class I peptide selection assay combining nanoparticle technology and matrix-assisted laser desorption/ionisation mass spectrometry," J. Immunol. Meth. 283:205-213.
Gill, R.G. et al. (1989) "Characterization of Primary T Cell Subsets Mediating Rejection of Pancreatic Islet Grafts," Journal of Immunology 143(7):2176-2178.
Gimmi, C.D. et al. (1993) "Human T-cell clonal anergy is induced by antigen presentation in the absence of B7 costimulation," Proc. Natl. Acad. Sci. USA 90:6586-6590.
Gold, R. et al. (2006) "Understanding pathogenesis and therapy of multiple sclerosis via animal models: 70 years of merits and culprits in experimental autoimmune encephalomyelitis research," Brain 129:1953-1971.
Gregori, S. et al. (2008) "Re-establishing immune tolerance in type 1 diabetes via regulatory T cells," Novartis Found Symp. 292:abstract.
Guarda, G. et al. (2007) "L-selectin-negative CCR7(−) effector and memory CD8(+) T cells enter reactive lymph nodes and kill dendritic cells," Nat. Immunol. 8(7):743-752.
Gunn, J. et al. (2008) "A multimodal targeting nanoparticle for selectively labeling T cells," Small. 4(6):712-715.
Gupta, A.K. et al. (2005) "Synthesis and surface engineering of iron oxide nanoparticles for biomedical applications," Biomaterials 26:3995-4021.
Hamilton-Williams, E.E. et al. (2001) "Transgenic rescue implicates beta2-microglobulin as a diabetes susceptibility gene in nonobese diabetic (NOD) mice," Proc. Natl. Acad. Sci. USA 98(20): 11533-11538.
Han, B. et al. (2005) "Developmental control of CD8(+) T cell-avidity maturation in autoimmune diabetes," J. Clin. Invest. 115(7):1879-1887.
Han, B. et al. (2005) "Prevention of diabetes by manipulation of anti-IGRP autoimmunity: high efficiency of a low-affinity peptide," Nat. Med. 11:645-652.
Han, G. et al. (2009) "Interleukin-17-producing γs T Cells protect NOD mice from type 1 diabetes through a mechanism involving transforming growth factor-b," Immunology 129:197-206.
Hassainya, Y. et al. (2005) "Identification of Naturally Processed HLA-A2-Restricted Proinsulin Epitopes by Reverse Immunology," Diabetes 54:2053-2059.
Herold, K.C. et al. (2002) "Anti-CD3 monoclonal antibody in new onset type I diabetes mellitus," N. Eng. J. Med. 346:1692-1698.
Holgate, S.T. et al. (2008) "Treatment strategies for allergy and asthma," Nature 8:218-230.
Honeyman, M.C. et al. (1995) "Analysis of Families at Risk for Insulin-Dependent Diabetes Mellitus Reveals that HLA Antigens Influence Progression to Clinical Disease," Molecular Medicine 1(5):576-582.
Itoh, N. et al. (1993) "Mononuclear Cell Infiltration and Its Relation to the Expression of Major Histocompatibility Complex Antigens and Adhesion Molecules in Pancreas Biopsy Specimens from Newly Diagnosed Insulin-dependent Diabetes Mellitus Patients," J. Clin. Invest. 92:2313-2322.
Jarchum, I. et al. (2007) "In Vivo Cytotoxicity of Insulin-Specific CD8(+) T-Cells in HLA-A *0201 Transgenic NOD Mice," Diabetes 56:2551-2560.
Jarchum, I. et al. (2008) "Identification of novel IGRP epitopes targeted in type 1 diabetes patients," Clin. Immunol. 127:359-365.
Judge, A.D. et al. (2002) "Interleukin 15 Controls both Proliferation and Survival of a Subset of Memory-Phenotype CD8(+) T Cells," J. Exp. Med. 196(7):935-946.
Jun, H-S. et al. (2003) "A new look at viruses in type 1 diabetes," Diabetes Metab. Res. Rev. 19:8-31.
Jurewicz, A. et al. (1998) "MHC Class I-Restricted Lysis of Human Oligodendrocytes by Myelin Basic Protein Peptide-Specific CD8 T Lymphocytes," J. Immunol. 160:3056-3059.
Kappos, L. et al. (2000) "Induction of a non-encephalitogenic type 2 T helper-cell autoimmune response in multiple sclerosis after administration of an altered peptide ligand in a placebo-controlled, randomized phase II trial," Nat. Med. 6(10):1176-1182.

(56) References Cited

OTHER PUBLICATIONS

Karin, N. et al. (1994) "Reversal of Experimental Autoimmune Encephalomyelitis by a Soluble Peptide Variant of a Myelin Basic Protein Epitope: T Cell Receptor Antagonism and Reduction of Interferon gamma and Tumor Necrosis Factor alpha Production," J. Exp. Med. 180:2227-2237.
Karounos, D.G. et al. (1997) "Metabolically Inactive Insulin Analog Prevents Type I Diabetes in Prediabetic NOD Mice," J. Clin. Invest. 100:1344-1348.
Kent, S.C. et al. (2005) "Expanded T cells from pancreatic lymph nodes of type 1 diabetic subjects recognize an insulin epitope," Nature 435:224-228.
Keymeulen, B. et al. (2005) "Insulin Needs after CD3-Antibody Therapy in New-Onset Type 1 Diabetes," N. Engl. J. Med. 352:2598-2608.
Kim, S-K. et al. (1999) "Induction and Visualization of Mucosal Memory CD8 T Cells Following Systemic Virus Infection," J. Immunol. 163:4125-4132.
Krishnamoorthy, G. et al. (2009) "Myelin-specific T cells also recognize neuronal autoantigen in a transgenic mouse model of multiple sclerosis," Nature Medicine 15(6):626-633.
Kukreja, A. et al. (2002) "NKT Cells and Type-1 Diabetes and the "hygiene Hypothesis" to Explain the Rising Incidence Rate," Diabetes Technology & Therapeutics 4(3):323-333.
Kulmala, P. (2003) "Prediabetes in Children," Pediatr Drugs, 5(4):211-221.
Lechner, F. et al. (2000) "Analysis of Successful Immune Responses in Persons Infected with Hepatitis C Virus," J. Exp. Med. 191(9):1499-1512.
Liblau, R.S. et al. (2002) "Autoreactive CD8 T cells in Organ-Specific Autoimmunity: Emerging Targets for Therapeutic Intervention," Immunity 17:1-6.
Lieberman, S.M. et al. (2003) "A comprehensive guide to antibody and T-cell responses in type 1 diabetes," Tissue Antigens 62:359-377.
Lieberman, S.M. et al. (2003) "Identification of the beta cell antigen targeted by a prevalent population of pathogenic CD8(+) T cells in autoimmune diabetes," PNAS 100(14):8384-8388.
Lieberman, S.M. et al. (2004) "Individual Nonobese Diabetic Mice Exhibit Unique Patterns of CD8(+) T Cell Reactivity to Three Islet Antigens, Including the Newly Identified Widely Expressed Dystrophia Myotonica Kinase," J. Immunol. 173:6727-6734.
Mallone, R. et al. (2007) "CD8(+) T-Cell Responses Identify beta-Cell Autoimmunity in Human Type 1 Diabetes," Diabetes 56:613-621.
Mallone, R. et al. (2011) "T Cell Recognition of Autoantigens in Human Type 1 Diabetes: Clinical Perspectives," Clinical and Developmental Immunology 2011(513210):1-16.
Maree, A.F.M. et al. (2006) "Modeling competition among autoreactive CD8(+) T cells in autoimmune diabetes: implications for antigen-specific therapy," International Immunology 18(7):1067-1077.
Mars, L.T. et al. (2007) "CD8 T Cell Responses to Myelin Oligodendrocyte Glycoprotein-Derived Peptides in Humanized HLA-A*0201-Transgenic Mice," J. Immunol. 179:5090-5098.
McKown, K.M. et al. (1999) "Lack of efficacy of oral bovine type II collagen added to existing therapy in rheumatoid arthritis," Arthritis & Rheumatism 42(6):1204-1208.
Mei, X. et al., Chemical Industry Press (2004) Biotechnology pharmaceutical preparation: foundation and application:199.
Mescher, M.F. et al. (2006) "Signals required for programming effector and memory development by CD8(+) T cells," Immunol. Rev. 211:81-92.
Metzler, B. et al. (1993) "Inhibition of experimental autoimmune encephalomyelitis by inhalation but not oral administration of the encephalitogenic peptide: influence of MHC binding affinity," Int. Immunol. 5(9):1159-1165.
Miller, S.D. et al. (1979) "The induction of cell-mediated immunity and tolerance with protein antigens coupled to syngeneic lymphoid cells," J. Exp. Med. 149:758-773.
Moore, A. et al. (2004) "Tracking the Recruitment of Diabetogenic CD8(+) T-Cells to the Pancreas in Real Time," Diabetes 53(6):1459-1466.
Nakayama, M. et al. (2005) "Prime role for an insulin epitope in the development of type 1 diabetes in NOD mice," Nature 435(7039):220-223.
Nelson, J. et al. (2015) "6 types of asthma and how they're treated," Mother Nature Network, mnn.com.
Non-Final Office Action in U.S. Appl. No. 12/044,435, dated May 2, 2012.
Non-Final Office Action in U.S. Appl. No. 12/044,435, dated Nov. 24, 2010.
Non-Final Office Action in U.S. Appl. No. 12/848,055, dated Apr. 4, 2012.
Non-Final Office Action in U.S. Appl. No. 12/848,055, dated Dec. 19, 2012.
Non-Final Office Action in U.S. Appl. No. 12/848,055, dated Jun. 6, 2014.
Non-Final Office Action in U.S. Appl. No. 13/249,105, dated Apr. 3, 2015.
Non-Final Office Action in U.S. Appl. No. 13/712,832, dated Feb. 27, 2015.
Non-Final Office Action in U.S. Appl. No. 13/830,521, dated Jul. 25, 2014.
Non-Final Office Action in U.S. Appl. No. 13/830,521, dated Jun. 28, 2016.
Non-Final Office Action in U.S. Appl. No. 13/842,302, dated Apr. 30, 2014.
Non-Final Office Action in U.S. Appl. No. 13/842,302, dated Jul. 6, 2016.
Non-Final Office Action in U.S. Appl. No. 14/684,153, dated Jun. 30, 2016.
Non-Final Office Action in U.S. Appl. No. 14/723,268, dated Oct. 16, 2015.
Non-Final Office Action in U.S. Appl. No. 12/848,055, dated May 13, 2016.
Notice of Allowance in U.S. Appl. No. 12/044,435, dated Sep. 12, 2012.
Notice to the Applicant Regarding a Non-Compliant or Non-Responsive Amendment in U.S. Appl. No. 12/044,435, dated Aug. 16, 2010.
Oh, S. et al. (2004) "IL-15 / IL-15R alpha-mediated avidity maturation of memory CD8(+) T cells," PNAS 101(42):15154-15159.
Oleszak, E.L. et al. (2004) "Theiler's Virus Infection: a Model for Multiple Sclerosis," Clinical Microbiology Reviews 17(1):174-207.
Ouyang, Q. et al. (2006) "Recognition of HLA Class I-Restricted beta-Cell Epitopes in Type 1 Diabetes," Diabetes 55:3068-3074.
Pachner, A.R. (2011) "Experimental models of multiple sclerosis," Current Opinion in Neurology 24:291-299.
Palmer, J.P. et al. (1983) "Insulin Antibodies in Insulin-Dependent Diabetics Before Insulin Treatment," Science 222:1337-1339.
Pascolo, S. et al. (1997) "HLA-A2.1-restricted Education and Cytolytic activity of CD8(+) T Lymphocytes from beta2 Microglobulin (beta2m) HLA-A2.1 Monochain Transgenic H-2D(b) beta2m Double Knockout Mice," J. Exp. Med. 185(12):2043-2051.
Pinkse, G.G.M. et al. (2005) "Autoreactive CD8 T cells associated with beta cell destruction in type 1 diabetes," PNAS 102(51):18425-18430.
Ransohoff, R.M. et al. (2012) "Animal models of multiple sclerosis: the good, the bad and the bottom line," Nature Neuroscience 15(8):1074-1077.
Restriction Requirement in U.S. Appl. No. 12/044,435, dated May 12, 2010.
Restriction Requirement in U.S. Appl. No. 12/848,055, dated Jan. 10, 2012.
Restriction Requirement in U.S. Appl. No. 12/848,055, dated Sep. 13, 2011.
Restriction Requirement in U.S. Appl. No. 13/249,105, dated Nov. 24, 2014.
Restriction Requirement in U.S. Appl. No. 13/712,832, dated Aug. 11, 2014.
Restriction Requirement in U.S. Appl. No. 13/830,521, dated Mar. 31, 2014.

(56) References Cited

OTHER PUBLICATIONS

Restriction Requirement in U.S. Appl. No. 13/842,302, dated Dec. 12, 2013.
Santamaria, P. (2001) "Effector lymphocytes in autoimmunity," Curr. Opin. Immunol. 13:663-669.
Santamaria, P. et al. (1992) "Characterization of T lymphocytes infiltrating human pancreas allograft affected by isletitis and recurrent diabetes," Diabetes 41:53-61.
Santamaria, P. et al. (1994) "Skewed T-cell receptor usage and junctional heterogeneity among isletitis alpha beta and gamma omega T cells in human IDDM (insulin-dependent diabetes mellitus)," Diabetes 43:599-606.
Santamaria, P. et al. (1995) "Beta-Cell-Cytotoxic CD8(+) T Cells from Nonobese Diabetic Mice Use Highly Homologous T Cell Receptor alpha-Chain CDR3 Sequences," J. Immunol. 154:2494-2503.
Saragovi, H.U. et al. (1999) "Small molecule and protein-based neurotrophic ligands: agonists and antagonists as therapeutic agents," Exp. Opin. Ther. Patents 9(6):737-751.
Schirle, M. et al. (2001) "Combining computer algorithms with experimental approaches permits the rapid and accurate identification of T cell epitopes from defined antigens," J. Immunol. Methods 257:1-16.
Schnutgen, F. et al. (2003) "A directional strategy for monitoring Cre-mediated recombination and the cellular level in the mouse," Nat. Biotech. 21:562-566.
Serreze, D.V. et al. (2001) "Autoreactive Diabetogenic T-Cells in NOD Mice Can Efficiently Expand From a Greatly Reduced Precursor Pool," Diabetes 50:1992-2000.
Sibley, R.K et al. (1985) "Recurrent Diabetes Mellitus in the Pancreas Iso- and Allograf: A Light and Electron Microscopic and Immunohistochemical Analysis of Four Cases," Lab. Invest. 53(2):132-144.
Somoza, N. et al. (1994) "Pancreas in Recent Onset Insulin-Dependent Diabetes Mellitus. Changes in HLA, Adhesion Molecules and Autoantigens, Restricted T Cell Receptor V beta Usage, and Cytokine Profile," J. Immunol. 153:1360-1377.
Spada, F.M., et al. (2000) "Self-Recognition of CD1 by γ/s T Cells: Implications for Innate Immunity," J. Exp. Med. 191(6):937-948.
Sprent, J. et al. (2001) "T Cell Death and Memory," Science 293:245-248.
Sprent, J. et al. (2002) "T Cell Memory," Annu. Rev. Immunol. 20:551-579.
Standifer, N.E. et al. (2006) "Identification of Novel HLA-A*0201-Restricted Epitopes in Recent-Onset Type 1 Diabetic Subjects and Antibody-Positive Relatives," Diabetes 55:3061-3067.
Supplemental Notice of Allowability in U.S. Appl. No. 12/044,435, dated Dec. 13, 2012.
'T Hart, B.A. et al. (2004) "Modelling of multiple sclerosis: lessons learned in a non-human primate," Lancet Neurology 3:588-597.
Tait, B.D. et al. (1995) "HLA Antigens and Age at Diagnosis of Insulin-Dependent Diabetes Mellitus," Hum. Immunol. 42:116-124.
Takaki, T. et al. (2006) "HLA-A*0201-Restricted T Cells from Humanized NOD Mice Recognize Autoantigens of Potential Clinical Relevance to Type 1 Diabetes," J. Immunol. 176:3257-3265.
Tan, J.T. et al. (2002) "Interleukin (IL)-15 and IL-7 Jointly Regulate Homeostatic Proliferation of Memory Phenotype CD8(+) Cells but Are Not Required for Memory Phenotype CD4(+) Cells," J. Exp. Med. 195(12):1523-1532.
Toes, R.E.M. (1996) "Peptide vaccination can lead to enhanced tumor growth through specific T-cell tolerance induction," Proc. Natl. Acad. Sci. USA 93:7855-7860.
Toma, A. et al. (2005) "Recognition of a subregion of human proinsulin by class I-restricted T cells in type 1 diabetic patients," Proc. Natl. Acad. Sci. USA 102(30):10581-10586.
Trenttham, D.E. et al. (1993) "Effects of Oral Administration of Type II Collagen on Rheumatoid Arthritis," Science 261:1727-1730.
Trudeau, J.D. et al. (2003) "Prediction of spontaneous autoimmune diabetes in NOD mice by quantification of autoreactive T cells in peripheral blood," J. Clin. Invest. 111:217-223.
Tsai, S. et al. (2010) "Reversal of Autoimmunity by Boosting Memory-like Autoregulatory T Cells," Immunity 32(4):568-580.
Tsuchida, T. et al. (1994) "Autoreactive CD8(+) T-cell responses to human myelin protein-derived peptides," Proc. Natl. Acad. Sci. USA, 91:10859-10863.
Unger, W.W.J. et al. (2007) "Human Clonal CD8 Autoreactivity to an IGRP Islet Epitope Shared between Mice and Men," Ann. N. Y. Acad. Sci. 1103:192-195.
UniProtKB: D4VD94 (2010) from www.uniprot.org/uniprot/D4VD94.
Van Belle, T.L. et al. (2011) "Type 1 Diabetes: Etiology, Immunology, and Therapeutic Strategies," Physiol. Rev. 91:79-118.
Vandenbark, A.A. et al. (2003) "Recombinant TCR ligand induces tolerance to myelin oligodendrocyte glycoprotein 35-55 peptide and reverses clinical and histological signs of chronic experimental autoimmune encephalomyelitis in HLA-DR2 transgenic mice," Journal of Immunology 171(1):127-33.
Verdaguer, J. et al. (1996) "Acceleration of Spontaneous Diabetes in TCR-beta-Transgenic Nonobese Diabetic Mice by beta-Cell Cytotoxic CD8(+) T Cells Expressing Identical Endogenous TCR-alpha Changes," The Journal of Immunology 157:4726-4735.
Verdaguer, J. et al. (1997) "Spontaneous Autoimmune Diabetes in Monoclonal T Cell Nonobese Diabetic Mice," J. Exp. Med. 186(10):1663-1676.
Verdu, E.F. et al. (2000) "Oral administration of antigens from intestinal flora anaerobic bacteria reduces the severity of experimental acute colitis in BALB/c mice," Clin Exp Immunol. 120:46-50.
Vincent, M.S. et al. (2003) "Understanding the function of CD1-restricted T cells," Nat. Immunol. 4(6):517-523.
Wainwright, S.D. et al. (2000) "HLA-F Is a Predominantly Empty, Intracellular, TAP-Associated MHC Class lb Protein with a Restricted Expression Pattern," J. Immunol. 164(1):319-328.
Walter, U. et al. (2005) "CD8(+) T cells in autoimmunity," Curr. Opin. Immunol. 17:624-631.
Wang, X. et al. (2007) "Induction of Potent CD8( ) T-Cell Responses by Novel Biodegradable Nanoparticles Carrying Human Immunodeficiency Virus Type 1 gp120," Journal of Virology 81(18)10009-10016.
Warnock, G.L. et al. (1991) "Normoglycaemia after transplantation of freshly isolated and cryopreserved pancreatic islets in Type 1 (insulin-dependent) diabetes mellitus," Diabetologia 34:55-58.
Weiner, H.L. et al. (1993) "Double-Blind Pilot Trial of Oral Tolerization with Myelin Antigens in Multiple Sclerosis," Science 259:1321-1324.
Weiss, G.A. et al. (1996) "Covalent HLA-B27/peptide complex induced by specific recognition of an aziridine mimic of arginine," Proc. Natl. Acad. Sci. USA 93:10945-10948.
Wekerle, H. et al. (2006) "Animal models of multiple sclerosis," Drug Discovery Today: Disease Models 3(4):359-367.
Wen, Z., Nanjing University Press (2007) "3. Surface effect of the nanoparticles," Introduction to Nature Science:373-374.
Williams, M.A. et al. (2006) "Developing and maintaining protective CD8(+) memory T cells," Immunol. Rev. 211:146-153.
Winer, S. et al. (2003) "Autoimmune islet destruction in spontaneous type 1 diabetes is not beta-cell exclusive," Nat. Med. 9(2):198-205.
Wong, F.S. et al. (1999) "Identification of an MHC class I-restricted autoantigen in type 1 diabetes by screening an organ-specific cDNA library," Nat. Med. 5(9):1026-1031.
Wraith, D.C. et al. (1989) "Antigen Recognition in Autoimmune Encephalomyelitis and the Potential for Peptide-Mediated Immunotherapy," Cell 59:247-255.
Wu, W. et al. (2008) "Magnetic Iron Oxide Nanoparticles: Synthesis and Surface Functionalization Strategies," Nanoscale Res Lett. 3:397-415.
Xu, H., Tsinghua University Press (2004) "13.3.3 Relationship between gene transduction and nanoparticle size," Nano Medicine:358.

(56) References Cited

OTHER PUBLICATIONS

Yadav, V. et al. (2012) "Recombinant T-Cell Receptor Ligand (RTL) for Treatment of Multiple Sclerosis: A Double-Blind, Placebo-Controlled, Phase 1, Dose-Escalation Study," Autoimmune Diseases 2012(954739):1-11.
Yamanouchi, J. et al. (2007) "Interleukin-2 gene variation impairs regulatory T cell function and causes autoimmunity," Nat. Genet. 39(3):329-337.
Zajac, A.J. et al. (1998) "Viral Immune Evasion Due to Persistence of Activated T Cells Without Effector Function," J. Exp. Med. 188(12):2205-2213.
Zhang, S. et al. (2010) "HMGB1, an innate alarmin, in the pathogenesis of type 1 diabetes," Int. J. Clin. Exp. Pathol. 3(1):24-38.
Clemente-Casares, X. et al. (2016) "Expanding antigen-specific regulatory networks to treat autoimmunity," Nature 530:434-440.
Van Driel, I.R. et al. (2008) "Role of regulatory T cells in gastrointestinal inflammatory disease," Journal of Gastroenterology and Hepatology 23:171-177.
Notice of Allowance for U.S. Appl. No. 14/684,153, dated Jan. 26, 2017.
Bahcetepe, N. et al. (2013) "The role of HLA antigens in the aetiology of psoriasis," Med Glas (Zenica) 10(2):339-342.
Clemente-Casares, J. (2014) "pMHC-class II Nanovaccine to Treat Autoimmune Diseases," Doctor of Philosophy Thesis, Calgary University, Alberta, Canada, retrieved from http://theses.ucalgary.ca/handle/11023/1589.
Corrigall, V.M. et al. (2002) "Autoantigens and immune pathways in rheumatoid arthritis," Crit Rev Immunol. 22(4):281-293.
Fifis, T. et al. (2004) "Short Peptide Sequences Containing MHC Class I And/Or Class II Epitopes Linked to Nano-Beads Induce Strong Immunity and Inhibition of Growth of Antigen-Specific Tumour Challenge in Mice," Vaccine 23(2):258-266.
Harris, S.J. et al. (1997) "Prediction of murine MHC class I epitopes in a major house dust mite allergen and induction of T1-type CD8 T cell responses," Int Immunol. 9(2):273-280.
Ho, K.T. et al. (2003) "The clinical relevance of autoantibodies in scleroderma," Arthritis Res Ther. 5(2):80-93.
Jarius, S. et al. (2008) "Mechanisms of Disease: aquaporin-4 antibodies in neuromyelitis optica," Nat Clin Pract Neurol. 4(4):202-214.
Kita, H. et al. (2002) "Quantitative and functional analysis of PDC-E2-specific autoreactive cytotoxic T lymphocytes in primary biliary cirrhosis," J Clin Invest. 109(9):1231-12340.
Kyger, M. et al. (2013) "Effective Arrestin-Specific Immunotherapy of Experimental Autoimmune Uveitis with RTL: A Prospect for Treatment of Human Uveitis," Transl Vis Sci Technol. 2(2):1-15.
Longhi, M.S. et al. (2011) "Autoantigen-Specific Regulatory T Cells, a Potential Tool for Immune-Tolerance Reconstitution in Type-2 Autoimmune Hepatitis," Hepatology 53(2):536-547.
Marsh, S.G.E. et al. (2011) "Nomenclature for factors of the HLA system, update Oct. 2010," Human Immunology 72(4):364-369.
Packard, T.A. et al. (2013) "COPD is associated with production of autoantibodies to a broad spectrum of self-antigens, correlative with disease phenotype," Immunol Res. 55(1-3):48-57.
Riemekasten, G. et al. (2005) "Key autoantigens in SLE," Rheumatology (Oxford) 44(8):975-982.
Routsias, J.G. et al. (2010) "Autoimmune response and target autoantigens in Sjogren's syndrome," Eur J Clin Invest. 40(11):1026-1036.
Shao, K. et al. (2015) "Nanoparticle-Based Immunotherapy for Cancer," ACS Nano 9(1):16-30.
Shukla, S. et al. (2016) "Emerging nanotechnologies for cancer immunotherapy," Exp Biol Med (Maywood) 241(10):1116-1126.
Sollid, L.M. et al. (2012) "Nomenclature and listing of celiac disease relevant gluten T-cell epitopes restricted by HLA-DQ molecules," Immunogenetics 64(6):455-460.
Szczerkowska-Dobosz, A. (2005) "Human Leukocyte Antigens as Psoriasis Inheritance and Susceptibility Markers," Arch Immunol Ther Exp (Warsz) 53(5), 428-433.
Tanimura, K. et al. (2015) "Beta2-Glycoprotein I/HLA class II complexes are novel autoantigens in antiphospholipid syndrome," Blood 125(18):2835-2844.
Van Boekel, M.A.M. et al. (2002) "Autoantibody systems in rheumatoid arthritis: specificity, sensitivity and diagnostic value," Arthritis Res. 4(2):87-93.
Wilson, J.T. et al. (2013) "pH-Responsive Nanoparticle Vaccines for Dual-Delivery of Antigens and Immunostimulatory Oligonucleotides," ASC Nano 7(5):3912-3925.
Wucherpfennig, K.W. et al. (1995) "Structural basis for major histocompatibility complex (MHC)-linked susceptibility to autoimmunity: charged residues of a single MHC binding pocket confer selective presentation of self-peptides in pemphigus vulgaris," PNAS 92(25):11935-11939.
Yeste, A. et al. (2012) "Nanoparticle-mediated codelivery of myelin antigen and a tolerogenic small molecule suppresses experimental autoimmune encephalomyelitis," PNAS 109(28):11270-11275.
International Search Report and Written Opinion (ISA/CA) for International Application No. PCT/IB2016/000691, dated Mar. 7, 2017.
Australian Patent Application No. 2016225913 Examination Report No. 1 dated Sep. 22, 2017.
Azuma et al., "T Cell Costimulation and Diseases," Stomatological Journal 67(3):233-239, 2000.
Baker et al., Critical appraisal of animal models of multiple sclerosis. Multiple Sclerosis Journal, 17(6):647-657, 2011.
Bossuyt et al., Serologic markers in inflammatory bowel disease. Clinical Chemistry, 52(2):171-181, 2006.
Bottini et al. "Luminescent Silica Nanobeads: Characterization and Evaluation as Efficient Cytoplasmatic Transporters for T-Lymphocytes," Journal of the American Chemical Society, 129(25):7814-7823, 2007.
China Patent Application No. 201380022126.2 fourth Office Action dated Jul. 24, 2017.
Dieterich et al., Identification of tissue transglutaminase as the autoantigen of celiac disease. Nature Medicine, 3(7):797-801, 1997.
Diwan et al., "Biodegradable nanoparticle mediated antigen delivery to human cord blood derived dendritic cells for induction of primary T cell responses," J. Drug Target 11 (8-1 0):495-507, 2003.
Dominguez, et al. Targeting the tumor microenvironment with anti-neu/anti-CD40 conjugated nanoparticles for the induction of antitumor immune responses, Vaccine, 28(15):1383-1390, 2010.
European Patent Application No. 13856460.4 Extended European Search Report dated Feb. 26, 2016.
Gong, et aL 'Immobilized MHC class I chain-related protein .A synergizes with IL-15 and soluble 4-1BB ligand to expand NK cells with high cytotoxicity ex vivo. Cellular & Molecular Immunology, 7(6):477-484, 2010.
Japanese Patent Application No. 2015-536240 Office Action dated Aug. 16, 2017.
Japanese Patent Application No. 2017-014194 Office Action dated Sep. 13, 2017.
Kamikura et al., "VII. Adhesion, Costimulatory Molecule, Trafficking, Homing: 1. Cancer X Immunotherapy and Costimulatory Molecule," Annual Review, Immunity 162:2-13, 2004.
Komai-Koma. "TIR2 is expressed on activated T cells as a costimulatory receptor," Proceedings of the National Academy of Sciences, 181(9):3829-3834, 2004.
Kwong et al. "Synthesis and characterization of antibody-nanoparticle conjugates for locally sequestered tumor immunotherapy," Abstracts of Papers American Chemical Society, 240: POLY 61, 2010.
Laurence and O'Shea, TH-17 differentiation: of mice and men. Nature Immunology, 8(9):903-905, 2007.
Lee, et at. "Biodegradable nanoparticles containing TLR3 or TLR9 agonists together with antigen enhance MHC-restricted presentation of the antigen," Archives of Pharmacal Research, 33(11):1859-1866,2010.
Lowery et al., "Immunonanoshells for targeted photothermal ablation of tumor cells," Int J Nanomedicine 1 (2):149-154, 2006.
Mestas et al., Of mice and not men: Differences between mouse and human immunology. The Journal of Immunology, 172:2731-2738, 2004.

(56) References Cited

OTHER PUBLICATIONS

Mexican Patent Application No. Mx/a/2013/003559 third Office Action dated Jul. 3, 2017.
Miguel-Sancho et al., Development of stable, water-dispersible, and biofunctionalizable superparamagnetic iron oxide nanoparticles. Chemistry of Materials, 23:2795-2802, 2011.
Patel et al., Cationic nanoparticles for delivery of CpG oligodeoxynucleotide and ovalbumin: in vitro and in vivo assessment. J. Biomed Nanotechnology, 3(1):97-106, 2007.
PCT/EP2011/066994 International Search Report and Written Opinion dated Nov. 21, 2011.
PCT/EP2011/069931 International Search Report and Written Opinion dated Jul. 10, 2012.
PCT/IB2013/003033 International Search Report and Written Opinion dated Jul. 14, 2014.
PCT/IB2013/052352 International Search Report and Written Opinion dated Oct. 2, 2013.
PCT/IB2014/003014 International Search Report and Written Opinion dated May 12, 2015.
PCT/IB2016/000691 International Search Report and Written Opinion dated Mar. 7, 2017.
PCT/US2008/056279 International Search Report and Written Opinion dated Oct. 22, 2008.
Petros, et al. "Antibody conjugation to Print nanoparticles as a cellular targeting strategy," Abstracts of Papers American Chemical Society, 233:COLL 14, 2007.
Purton, et al. "Antiviral CD4 memory T cells are IL-15 dependent," Journal of Experimental Medicine, 204(4):951-961, 2007.
Schneider et al, "The end of the era of generosity? Global health amid economic crisis," Philos Ethic Humanit Med. 4:1, 2009.
Schreiber, et al. "Using carbon 31-33 magnetic nanoparticles to target, track, and manipulate dendritic cells," Journal of Immunological Methods, 365(1-2):47-59, 2010.
Shanks et al., Are animal models predictive for humans? Philosophy, Ethics, and Humanities in Medicine, 4(2):20 pages, 2009.
Takahashi et al., Isolation and characterization of a colonic autoantigen specifically recognized by colon tissue bound immunoglobulin G from idiopathic ulcerative colitis. J.Clinical Invest., 76:311-318, 1985.
Tufveson et al., New immunosuppressants: Testing and development in animal models and the clinic: with special reference to DSG. Immun. Reviews, 136:101-107, 1993.
U.S. Appl. No. 15/348,959 First Action Interview Pilot Program, Pre-Interview Communication dated Apr. 13, 2017.
U.S. Appl. No. 12/044,435 Office Action dated Jun. 8, 2011.
U.S. Appl. No. 12/044,435 Office Action dated May 2, 2012.
U.S. Appl. No. 12/044,435 Office Action dated Nov. 24, 2010.
U.S. Appl. No. 12/848,055 Office Action dated Apr. 4, 2012.
U.S. Appl. No. 12/848,055 Office Action dated Aug. 23, 2012.
U.S. Appl. No. 12/848,055 Office Action dated Dec. 19, 2012.
U.S. Appl. No. 12/848,055 Office Action dated Dec. 24, 2014.
U.S. Appl. No. 12/848,055 Office Action dated Jun. 6, 2014.
U.S. Appl. No. 12/848,055 Office Action dated May 13, 2016.
U.S. Appl. No. 13/249,105 Office Action dated Apr. 3, 2015.
U.S. Appl. No. 13/249,105 Office Action dated Nov. 30, 2015.
U.S. Appl. No. 13/249,105 Office Action dated Sep. 8, 2017.
U.S. Appl. No. 13/294,109 Office Action dated Jan. 12, 2015.
U.S. Appl. No. 13/294,109 Office Action dated Jun. 4, 2013.
U.S. Appl. No. 13/294,109 Office Action dated Nov. 13, 2013.
U.S. Appl. No. 13/712,832 Office Action dated Feb. 27, 2015.
U.S. Appl. No. 13/830,521 Office Action dated Jul. 25, 2014.
U.S. Appl. No. 13/830,521 Office Action dated Jun. 28, 2016.
U.S. Appl. No. 13/830,521 Office Action dated Mar. 5, 2015.
U.S. Appl. No. 13/842,302 Office Action dated Apr. 30, 2014.
U.S. Appl. No. 13/842,302 Office Action dated Feb. 18, 2015.
U.S. Appl. No. 13/842,302 Office Action dated Jul. 6, 2016.
U.S. Appl. No. 13/842,302 Office Action dated May 3, 2017.
U.S. Appl. No. 14/531,707 Office Action dated Oct. 3, 2017.
U.S. Appl. No. 14/684,153 Office Action dated Jun. 30, 2016.
U.S. Appl. No. 14/723,268 Office Action dated Mar. 30, 2016.
U.S. Appl. No. 14/723,268 Office Action dated Oct. 16, 2015.
U.S. Appl. No. 15/433,898 Office Action dated Sep. 28, 2017.
Wang et al., One-pot reaction to synthesize superparamagnetic iron oxide nanoparticles by adding phenol as reducing agent and stabilizer. Journal of Nanoparticle Res., 14:755, 7 pages, 2012.
WO2004078909—Bibliographic data page from EPO webiste showing it was also published as US2007154953, downloaded Nov. 15, 2010, 1 page.
Xie et al., Controlled PEGylation of monodisperse Fe3O4 nanoparticles for reduced non-specific uptake by macrophage cells. Advanced Materials, 19:3163-3166, 2007.
Xie et al., One-pot synthesis of monodisperse iron oxide nanoparticles for potential biomedical applications. Pure Applied Chemicals, 78(5):1003-1014, 2006.
Xu, H. "13.3.3 Relationship between gene transduction and nanoparticle size," Nano Medicine:35S, 2004.
U.S. Appl. No. 15/353,602, filed Nov. 16, 2016, UTI Limited Partnership.
U.S. Appl. No. 15/610,550, filed May 31, 2017, UTI Limited Partnership; The General Hospital Corporation.
Final Office Action in U.S. Appl. No. 13/842,302, dated May 3, 2017.
Frankel, A.E. et al. (2000) "Characterization of diphtheria fusion proteins targeted to the human interleukin-3 receptor," Protein Engineering 13(8):575-581.
Guo, H.H. et al. (2004) "Protein tolerance to random amino acid change," PNAS 101(25):9205-9210.
Pakula, A.A. et al. (1989) "Genetic Analysis of Protein Stability and Function," Annu. Rev. Genet. 23:289-310.
Bacchetta, R. et al. High levels of interleukin 10 production in vivo are associated with tolerance in SCID patients transplanted with HLA mismatched hematopoietic stem cells. J. Exp. Med. 179:493-502, 1994.
Bailey-Bucktrout, S. L. et al. Self-antigen-driven activation induces instability of regulatory T cells during an inflammatory autoimmune response. Immunity 39, 949-962, 2013.
Bakker et al. MHC Multimer Technology: Current Status and Future Prospects. Current Opinion in Immunology, 17(4):428-433, 2005.
Burton, B.R. et al. Sequential transcriptional changes dictate safe and effective antigen-specific immunotherapy. Nature Commun. 5:4741-4747, 2014.
Caruso et al., Protein multilayer formation on colloids through a stepwise self-assembly technique. J.Amer. Chem. Soc., 121(25):6039-6046, 1999.
Chen, et al., IL-2 controls the stability of Foxp3 expression in TGF-beta-induced Foxp3+ T cells in vivo. J. Immunol. 186:6329-6337, 2011.
Davies, Engineered particle surfaces. Advanced Materials, 10(15):1264-1270, 1998.
Gagliani, et al. Coexpression of CD49b and LAG-3 identifies human and mouse T regulatory type 1 cells. Nat. Med. 19:739-746, 2013 (Abstract only).
Hale, et al. Distinct memory CD4+ T cells with commitment to T follicular helper- and T helper 1-cell lineages are generated after acute viral infection. Immunity 38:805-817, 2013.
Jokerst et al., Nanoparticle PEGylation for imaging and therapy. Nanomedicine, 6(4):715-728, 2011.
PCT/IB2016/000691 International Preliminary Report on Patentability dated Nov. 7, 2017.
PCT/IB2017/001508 International Search Report and Written Opinion dated Mar. 26, 2018.
Peng et al. Synthesis and characterization of monodisperse hollow Fe3O4 nanoparticles. Angew Chem 119:4233-4236 (2007).
Santamaria, P. The long and winding road to understanding and conquering type 1 diabetes. Immunity 32, 437-445, 2010.
International Application No. PCT/IB2018/000510 International Search Report and Written Opinion dated Sep. 13, 2018.
U.S. Appl. No. 13/249,105 Office Action dated Apr. 11, 2018.
U.S. Appl. No. 13/842,301 Final Office Action dated Dec. 28, 2108.
U.S. Appl. No. 13/842,302 Office Action dated Apr. 30, 2018.
Xu and Sun, Mini Review: Monodisperse magnetic nanoparticles for biomedical applications. Polymer International 56:821-826, 2007.

(56) References Cited

OTHER PUBLICATIONS

Yang, J. et al. CD4+ T cells from type 1 diabetic and healthy subjects exhibit different thresholds of activation to a naturally processed proinsulin epitope. J. Autoimmun. 31:30-41, 2008.

Yu, et al. Cutting edge: Single-chain trimers of MHC Class 1 molecules form stable structures that potentially stimulate antigen-specific T cells and B cells. J Immunol 168:3145-3149, 2002.

Yanaba, et al.: The Development and Function of Regulatory B Cells Expressing IL-10 (B10 Cells) Requires Antigen Receptor Diversity and TLR Signals; The Journal of Immunology, 182(12), 7459-7472 (2009).

* cited by examiner

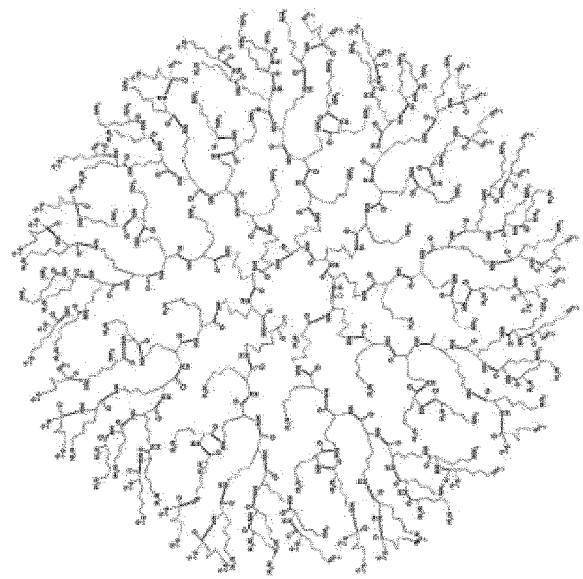
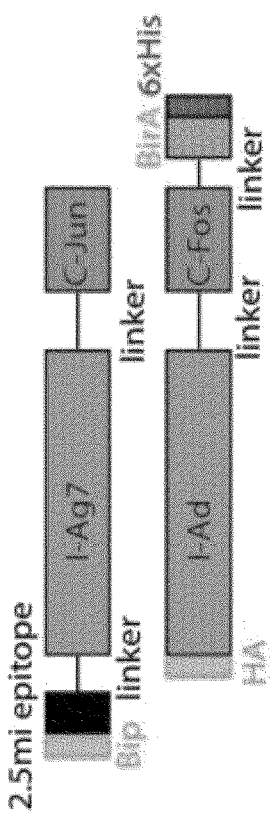
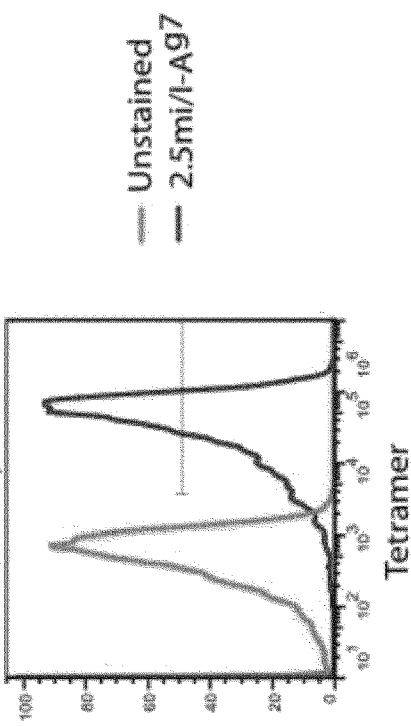
FIG. 3
FIG. 2

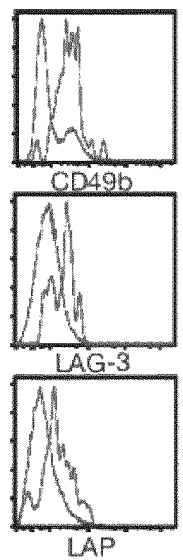
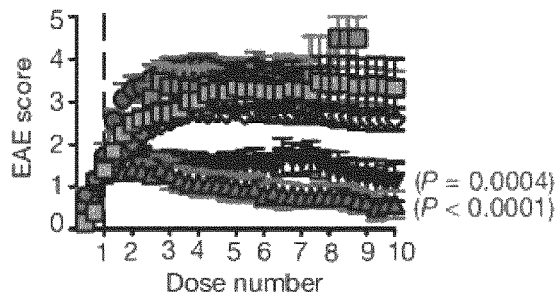
FIG. 10E
FIG. 10F
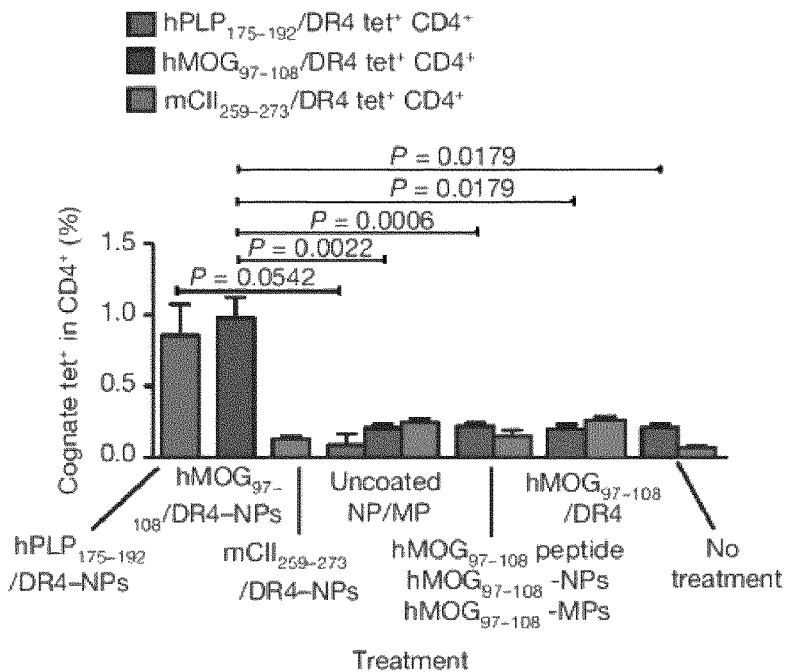
FIG. 10G

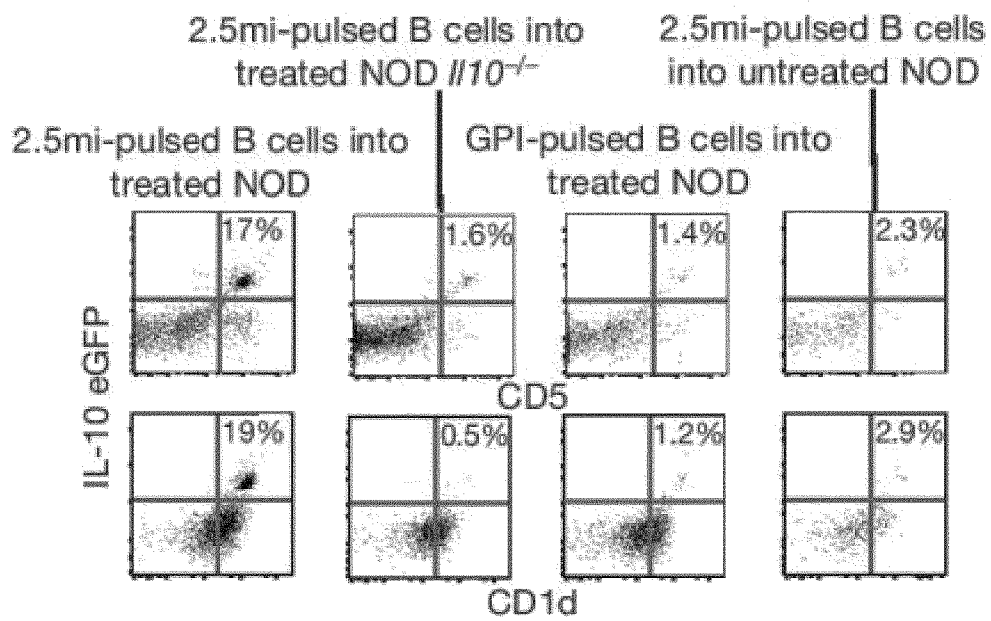
FIG. 11B
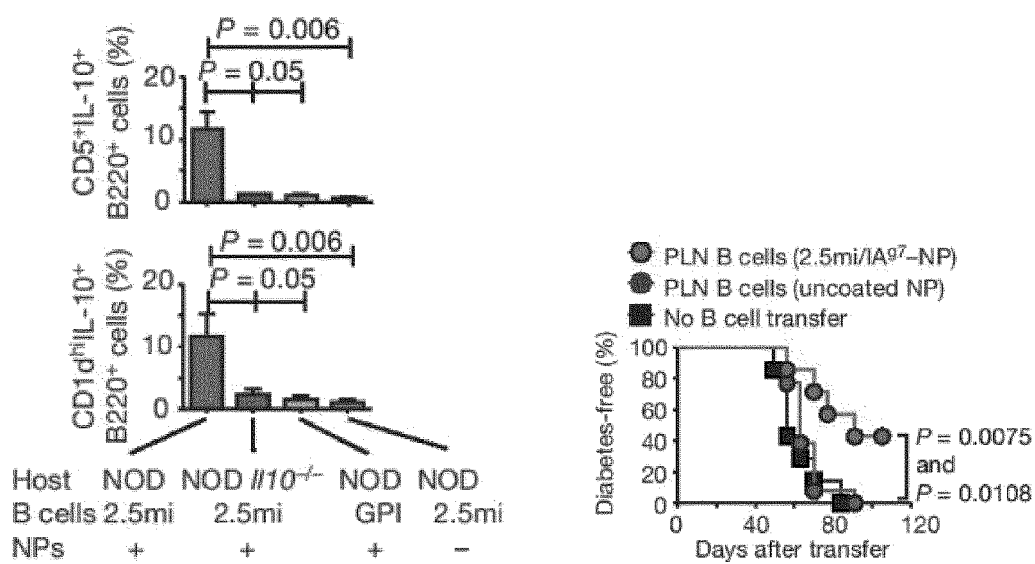
FIG. 11C
FIG. 11D

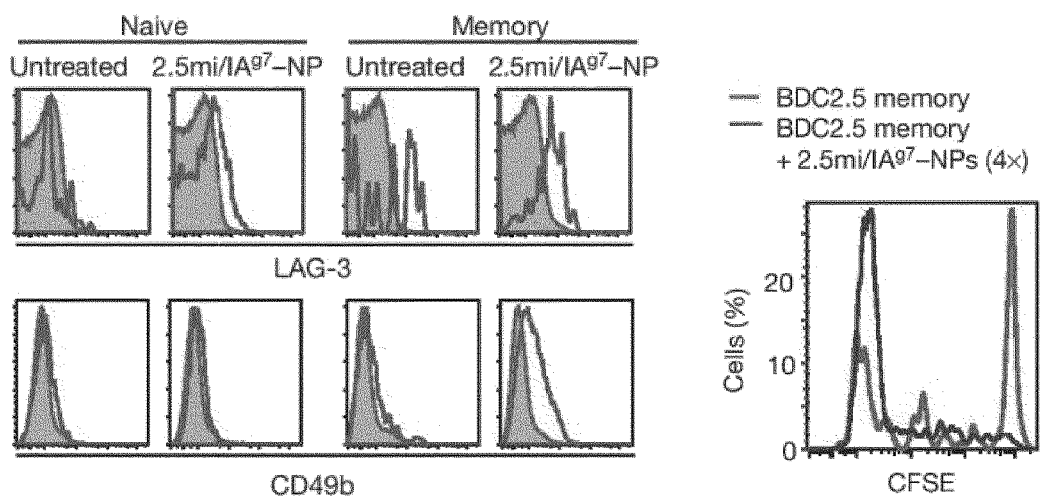
FIG. 12E
FIG. 12F
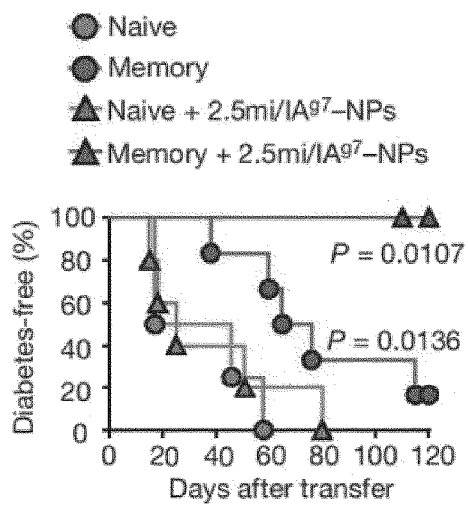
FIG. 12G

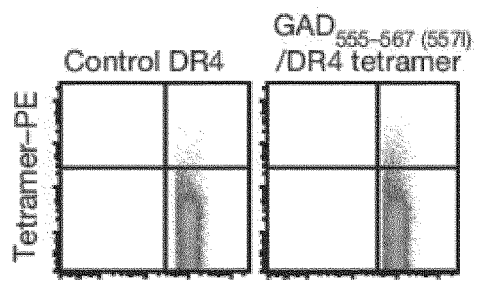
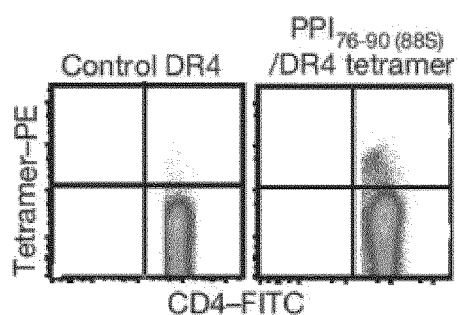
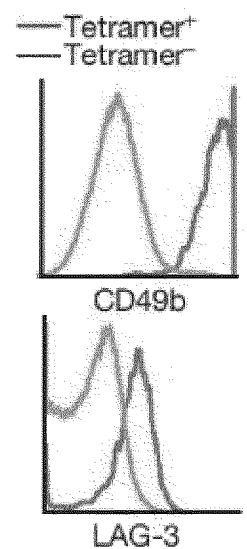
FIG. 13A
FIG. 13B
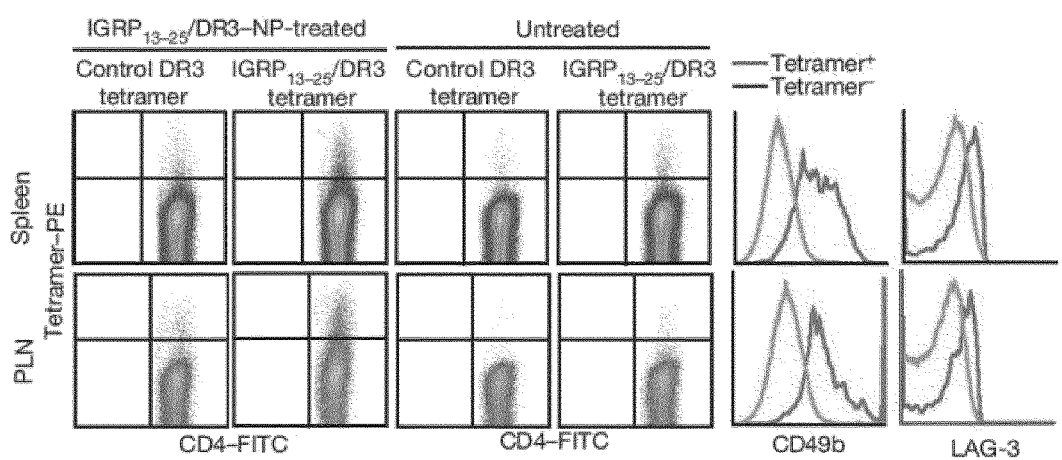
FIG. 13C

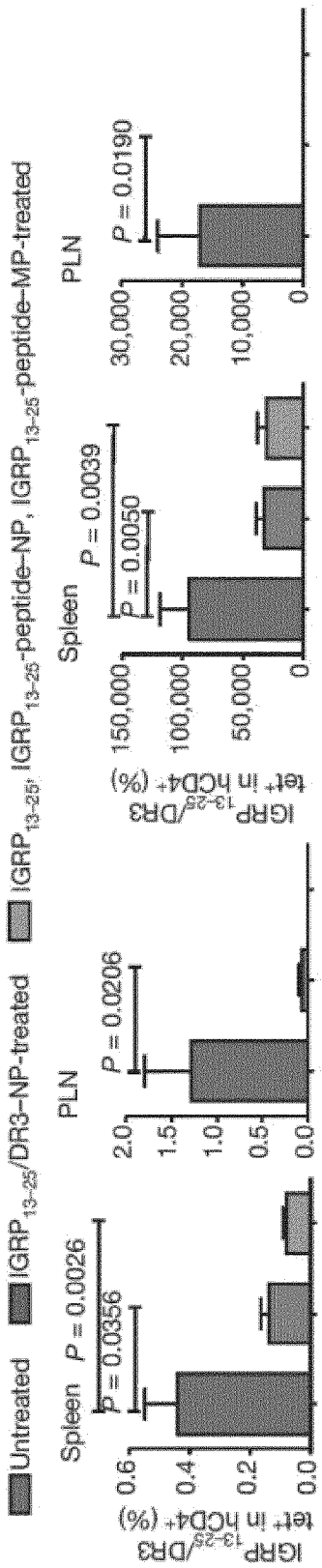
FIG. 13D
FIG. 13E
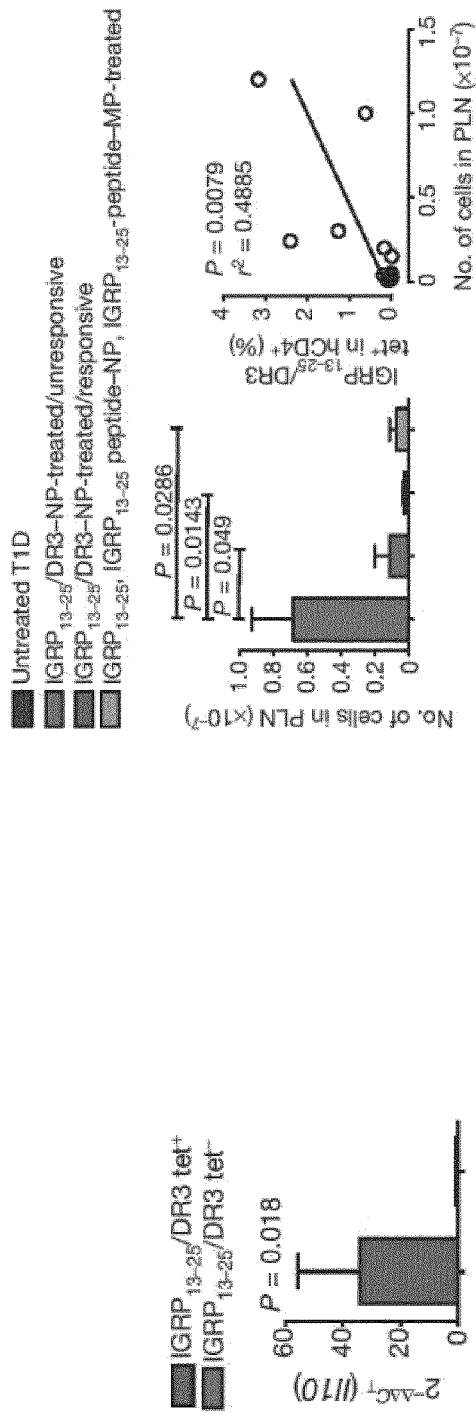
FIG. 13F

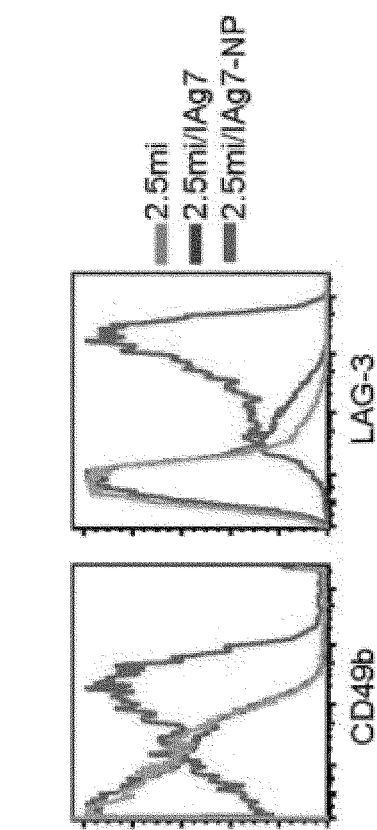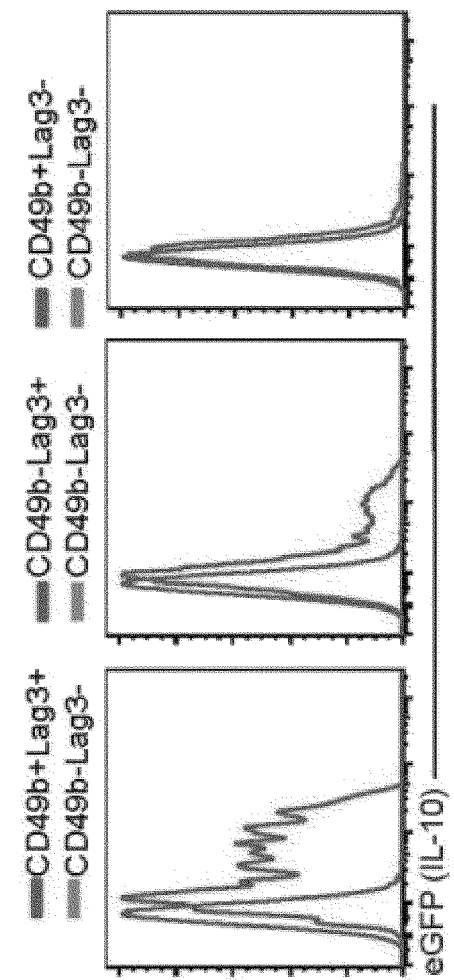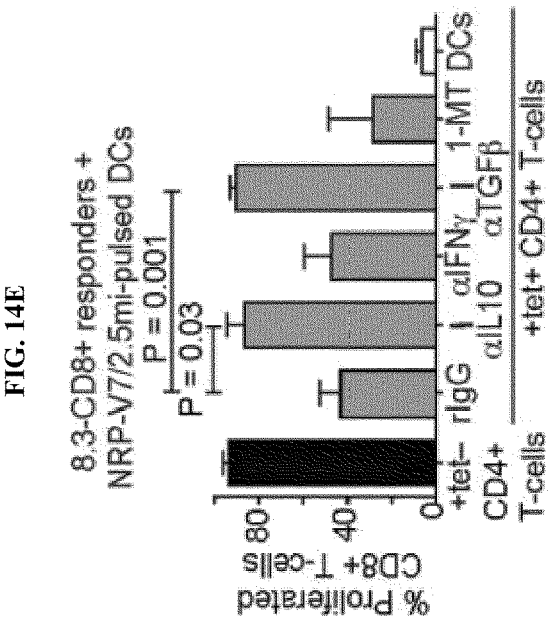
FIG. 14E
FIG. 14G
FIG. 14D
FIG. 14F

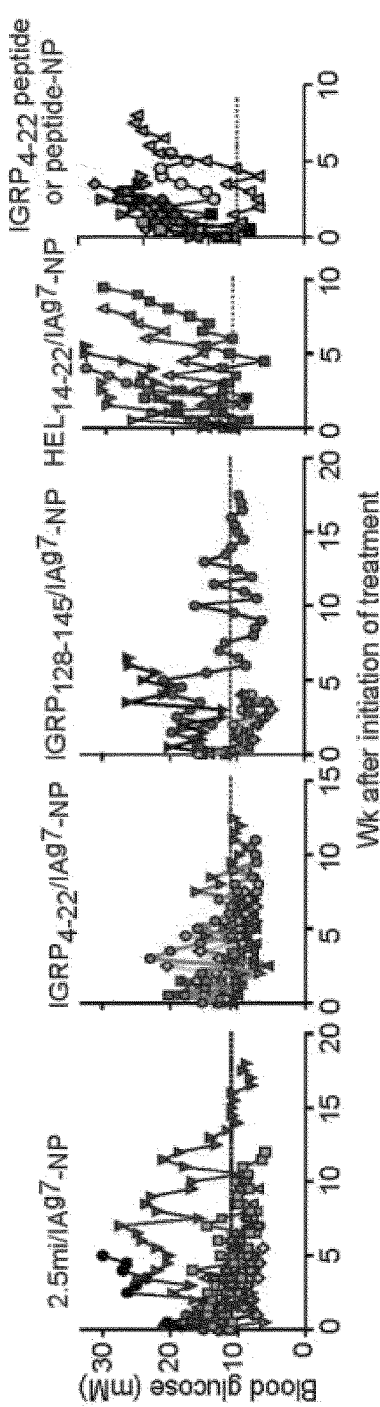
FIG. 14H
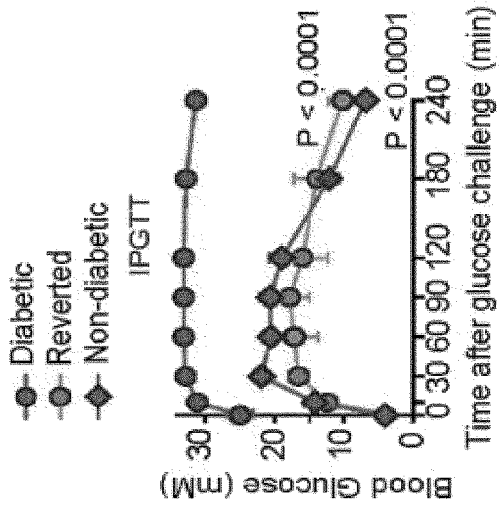
FIG. 14J
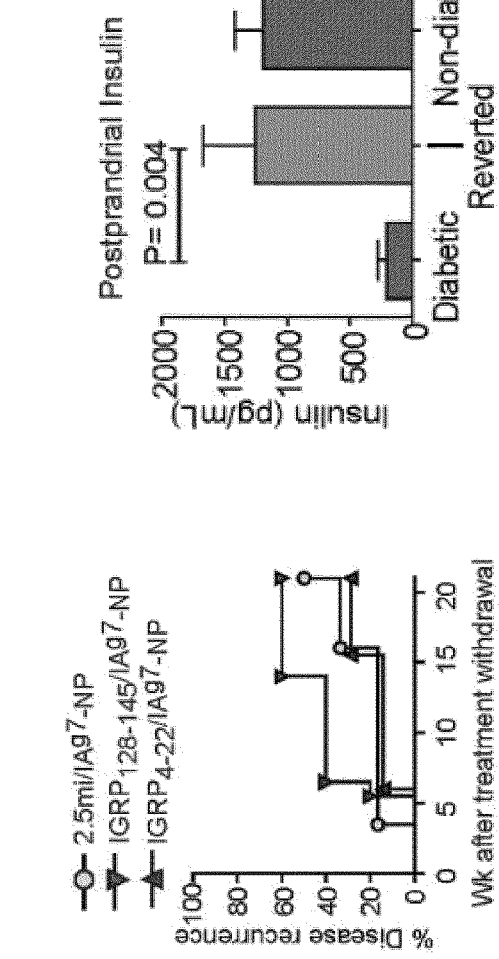
FIG. 14I
FIG. 14K

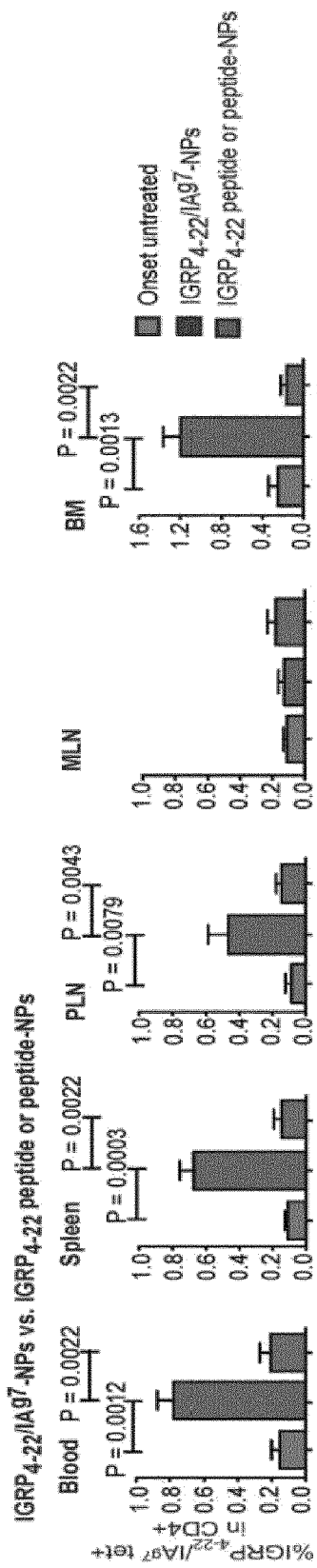
FIG. 15H
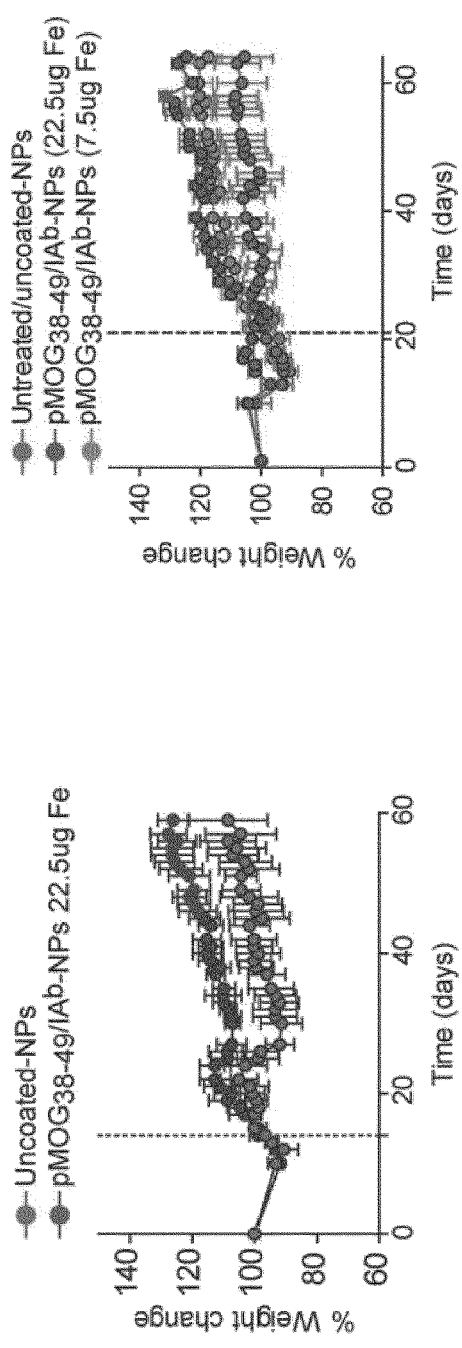
FIG. 16B
FIG. 16A

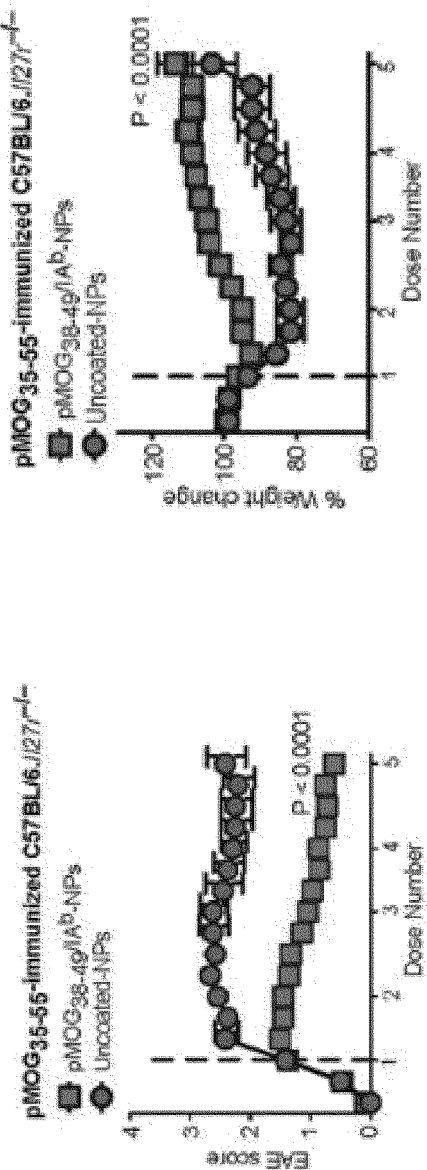
FIG. 18L
FIG. 18K
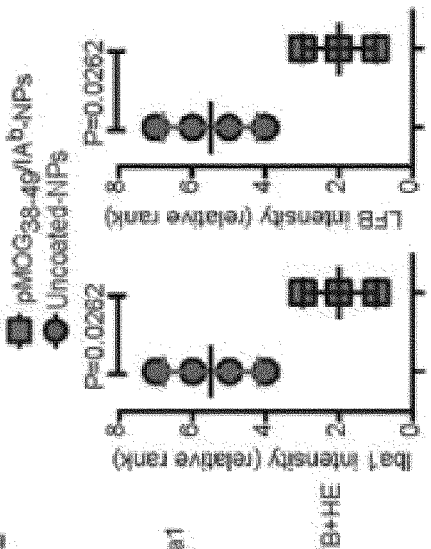
FIG. 18M
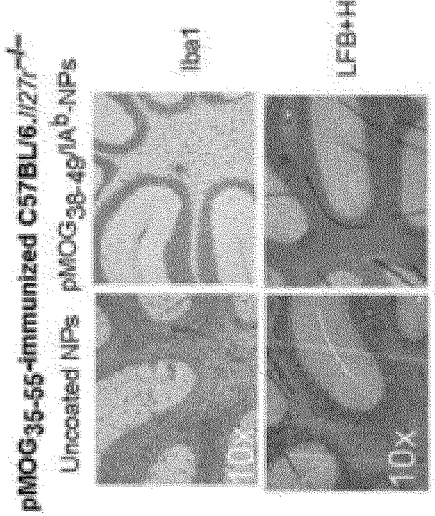

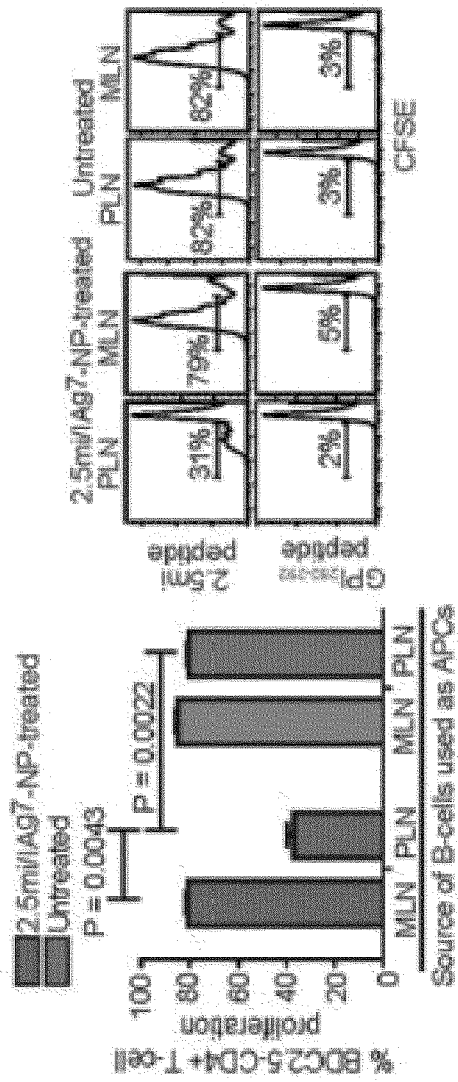
FIG. 18Q
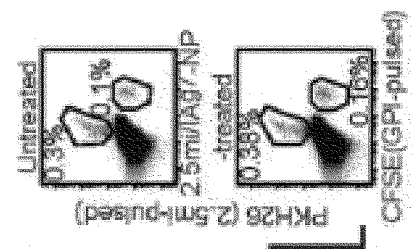
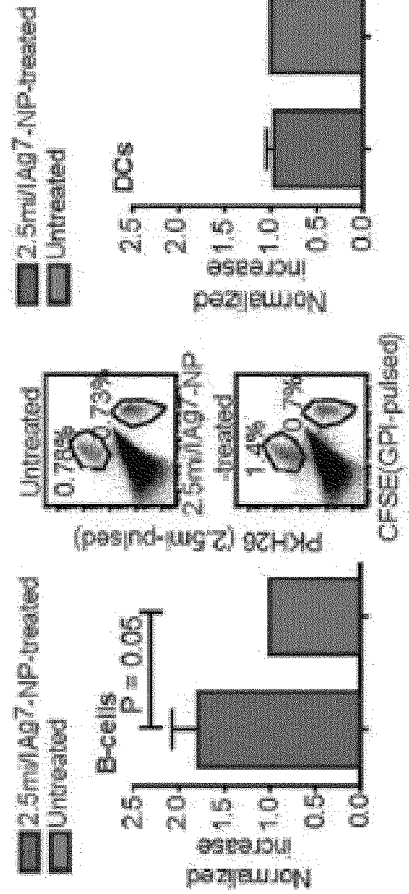
FIG. 18T
FIG. 18S
FIG. 18R

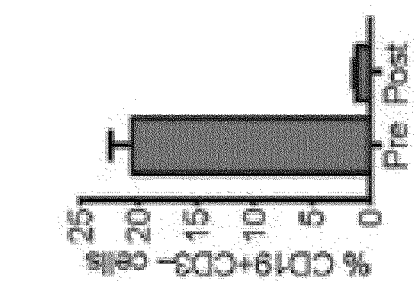
FIG. 18X
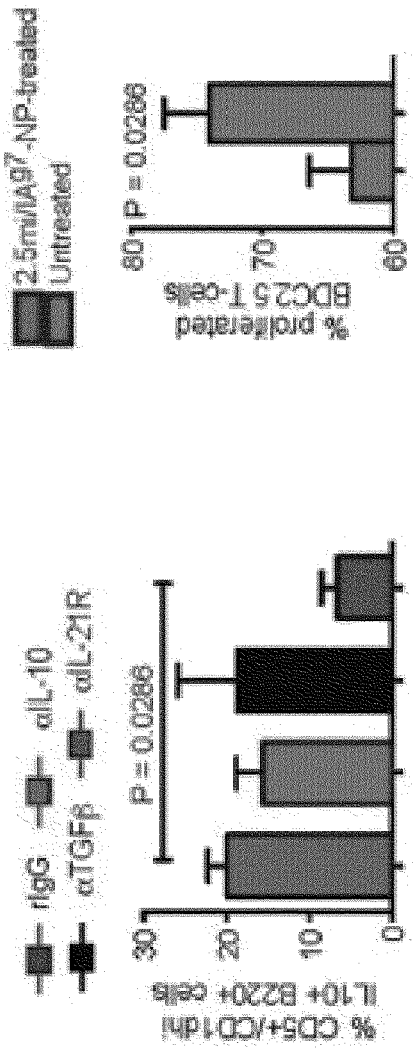
FIG. 18V
FIG. 18U
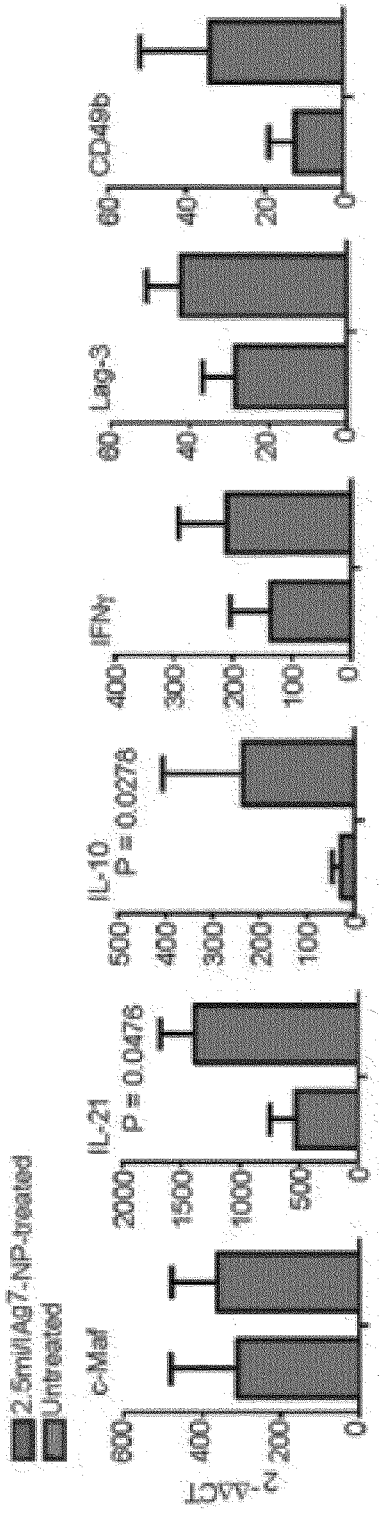
FIG. 18Y

SEQUENCE LISTING

```
<160> NUMBER OF SEQ ID NOS: 504

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 2
<211> LENGTH: 355
<212> TYPE: PRT
<213> ORGANISM: Homo sapiens

<400> SEQUENCE: 2

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
            20                  25                  30

Gly Asp Pro Arg Asn Ile Phe Phe Ile Tyr Phe Pro Leu Cys Phe Gln
        35                  40                  45

Phe Asn Gln Thr Val Gly Thr Lys Met Ile Trp Val Ala Val Ile Gly
    50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
                100                 105                 110

Ser Gly His Ala Met Gly Ala Ser Cys Val Trp Tyr Val Met Val Thr
```

```
                115                 120                 125
Ala Ala Leu Ser His Thr Val Cys Gly Met Asp Lys Phe Ser Ile Thr
        130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190

Phe Glu His Thr Pro Gly Ile Gln Thr Ala Ser Leu Gly Thr Tyr Leu
        195                 200                 205

Lys Thr Asn Leu Phe Leu Phe Leu Phe Ala Val Gly Phe Tyr Leu Leu
210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
            260                 265                 270

Ile Asn Ser Glu Met Phe Leu Leu Ser Cys Arg Gly Asn Asn Tyr
        275                 280                 285

Thr Leu Ser Phe Arg Leu Leu Cys Ala Leu Thr Ser Leu Thr Ile Leu
        290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Ser Gly Lys
            340                 345                 350

Lys Ser Gln
        355

<210> SEQ ID NO 3
<211> LENGTH: 585
<212> TYPE: PRT
<213> ORGANISM: Homo sapiens

<400> SEQUENCE: 3

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
        50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125
```

```
Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                    165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
                260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Arg Met Ser Arg Leu Ser Lys
            515                 520                 525

Val Ala Pro Val Ile Lys Ala Arg Met Met Glu Tyr Gly Thr Thr Met
530                 535                 540

Val Ser Tyr Gln Pro Leu Gly Asp Lys Val Asn Phe Phe Arg Met Val
```

```
                545                 550                 555                 560
Ile Ser Asn Pro Ala Ala Thr His Gln Asp Ile Asp Phe Leu Ile Glu
                    565                 570                 575
Glu Ile Glu Arg Leu Gly Gln Asp Leu
                    580                 585

<210> SEQ ID NO 4
<211> LENGTH: 470
<212> TYPE: PRT
<213> ORGANISM: Homo sapiens

<400> SEQUENCE: 4

Met Ser His His Pro Ser Gly Leu Arg Ala Gly Phe Ser Ser Thr Ser
1               5                   10                  15
Tyr Arg Arg Thr Phe Gly Pro Pro Ser Leu Ser Pro Gly Ala Phe
                20                  25                  30
Ser Tyr Ser Ser Ser Arg Phe Ser Ser Arg Leu Leu Gly Ser
                35                  40                  45
Ala Ser Pro Ser Ser Val Arg Leu Gly Ser Phe Arg Ser Pro Arg
    50                  55                  60
Ala Gly Ala Gly Ala Leu Leu Arg Leu Pro Ser Glu Arg Leu Asp Phe
65                  70                  75                  80
Ser Met Ala Glu Ala Leu Asn Gln Glu Phe Leu Ala Thr Arg Ser Asn
                85                  90                  95
Glu Lys Gln Glu Leu Gln Glu Leu Asn Asp Arg Phe Ala Asn Phe Ile
                100                 105                 110
Glu Lys Val Arg Phe Leu Glu Gln Gln Asn Ala Ala Leu Arg Gly Glu
                115                 120                 125
Leu Ser Gln Ala Arg Gly Gln Glu Pro Ala Arg Ala Asp Gln Leu Cys
            130                 135                 140
Gln Gln Glu Leu Arg Glu Leu Arg Arg Glu Leu Glu Leu Leu Gly Arg
145                 150                 155                 160
Glu Arg Asp Arg Val Gln Val Glu Arg Asp Gly Leu Ala Glu Asp Leu
                165                 170                 175
Ala Ala Leu Lys Gln Arg Leu Glu Glu Glu Thr Arg Lys Arg Glu Asp
                180                 185                 190
Ala Glu His Asn Leu Val Leu Phe Arg Lys Asp Val Asp Asp Ala Thr
                195                 200                 205
Leu Ser Arg Leu Glu Leu Glu Arg Lys Ile Glu Ser Leu Met Asp Glu
            210                 215                 220
Ile Glu Phe Leu Lys Lys Leu His Glu Glu Glu Leu Arg Asp Leu Gln
225                 230                 235                 240
Val Ser Val Glu Ser Gln Gln Val Gln Gln Val Glu Val Glu Ala Thr
                245                 250                 255
Val Lys Pro Glu Leu Thr Ala Ala Leu Arg Asp Ile Arg Ala Gln Tyr
                260                 265                 270
Glu Ser Ile Ala Ala Lys Asn Leu Gln Glu Ala Glu Glu Trp Tyr Lys
                275                 280                 285
Ser Lys Tyr Ala Asp Leu Ser Asp Ala Ala Asn Arg Asn His Glu Ala
            290                 295                 300
Leu Arg Gln Ala Lys Gln Glu Met Asn Glu Ser Arg Arg Gln Ile Gln
305                 310                 315                 320
Ser Leu Thr Cys Glu Val Asp Gly Leu Arg Gly Thr Asn Glu Ala Leu
                325                 330                 335
```

```
Leu Arg Gln Leu Arg Glu Leu Glu Glu Phe Ala Leu Glu Ala Gly
                340                 345                 350

Gly Tyr Gln Ala Gly Ala Ala Arg Leu Glu Glu Leu Arg Gln Leu
            355                 360                 365

Lys Glu Glu Met Ala Arg His Leu Arg Glu Tyr Gln Glu Leu Leu Asn
        370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415

Leu Asn Ile Lys Thr Thr Val Pro Glu Val Glu Pro Pro Gln Asp Ser
            420                 425                 430

His Ser Arg Lys Thr Val Leu Ile Lys Thr Ile Glu Thr Arg Asn Gly
        435                 440                 445

Glu Val Val Thr Glu Ser Gln Lys Glu Gln Arg Ser Glu Leu Asp Lys
    450                 455                 460

Ser Ser Ala His Ser Tyr
465                 470

<210> SEQ ID NO 5
<211> LENGTH: 288
<212> TYPE: PRT
<213> ORGANISM: Homo sapiens

<400> SEQUENCE: 5

Met Lys Thr Phe Leu Ile Leu Ala Leu Leu Ala Ile Val Ala Thr Thr
1               5                   10                  15

Ala Thr Thr Ala Val Arg Val Pro Val Pro Gln Leu Gln Pro Gln Asn
                20                  25                  30

Pro Ser Gln Gln Gln Pro Gln Glu Gln Val Pro Leu Val Gln Gln Gln
            35                  40                  45

Gln Phe Leu Gly Gln Gln Gln Pro Phe Pro Pro Gln Gln Pro Tyr Pro
    50                  55                  60

Gln Pro Gln Pro Phe Pro Ser Gln Gln Pro Tyr Leu Gln Leu Gln Pro
65                  70                  75                  80

Phe Pro Gln Pro Gln Leu Pro Tyr Ser Gln Pro Gln Pro Phe Arg Pro
                85                  90                  95

Gln Gln Pro Tyr Pro Gln Pro Gln Pro Gln Tyr Ser Gln Pro Gln Gln
            100                 105                 110

Pro Ile Ser Gln Gln Gln Gln Gln Gln Gln Gln Gln Gln Gln Gln Gln
        115                 120                 125

Gln Gln Gln Gln Gln Gln Gln Ile Leu Gln Gln Ile Leu Gln Gln Gln
    130                 135                 140

Leu Ile Pro Cys Met Asp Val Val Leu Gln Gln His Asn Ile Ala His
145                 150                 155                 160

Gly Arg Ser Gln Val Leu Gln Gln Ser Thr Tyr Gln Leu Leu Gln Glu
                165                 170                 175

Leu Cys Cys Gln His Leu Trp Gln Ile Pro Glu Gln Ser Gln Cys Gln
            180                 185                 190

Ala Ile His Lys Val Val His Ala Ile Ile Leu His Gln Gln Gln Lys
        195                 200                 205

Gln Gln Gln Gln Pro Ser Ser Gln Val Ser Phe Gln Gln Pro Leu Gln
    210                 215                 220

Gln Tyr Pro Leu Gly Gln Gly Ser Phe Arg Pro Ser Gln Gln Asn Pro
225                 230                 235                 240
```

```
Gln Ala Gln Gly Ser Val Gln Pro Gln Leu Pro Gln Phe Glu Glu
            245                 250                 255

Ile Arg Asn Leu Ala Leu Gln Thr Leu Pro Ala Met Cys Asn Val Tyr
            260                 265                 270

Ile Pro Pro Tyr Cys Thr Ile Thr Pro Phe Gly Ile Phe Gly Thr Asn
            275                 280                 285

<210> SEQ ID NO 6
<211> LENGTH: 268
<212> TYPE: PRT
<213> ORGANISM: Homo sapiens

<400> SEQUENCE: 6

Val Arg Val Pro Val Pro Gln Leu Gln Pro Gln Asn Pro Ser Gln Gln
1               5                   10                  15

Gln Pro Gln Glu Gln Val Pro Leu Val Gln Gln Gln Gln Phe Leu Gly
            20                  25                  30

Gln Gln Gln Pro Phe Pro Pro Gln Gln Pro Tyr Pro Gln Pro Gln Pro
            35                  40                  45

Phe Pro Ser Gln Gln Pro Tyr Leu Gln Leu Gln Pro Phe Pro Gln Pro
        50                  55                  60

Gln Leu Pro Tyr Ser Gln Pro Gln Pro Phe Arg Pro Gln Gln Pro Tyr
65                  70                  75                  80

Pro Gln Pro Gln Pro Gln Tyr Ser Gln Pro Gln Gln Pro Ile Ser Gln
                85                  90                  95

Gln Gln Gln Gln Gln Gln Gln Gln Gln Gln Gln Gln Gln Gln Gln Gln
            100                 105                 110

Gln Gln Gln Ile Leu Gln Gln Ile Leu Gln Gln Gln Leu Ile Pro Cys
            115                 120                 125

Met Asp Val Val Leu Gln Gln His Asn Ile Ala His Gly Arg Ser Gln
        130                 135                 140

Val Leu Gln Gln Ser Thr Tyr Gln Leu Leu Gln Glu Leu Cys Cys Gln
145                 150                 155                 160

His Leu Trp Gln Ile Pro Glu Gln Ser Gln Cys Gln Ala Ile His Lys
                165                 170                 175

Val Val His Ala Ile Ile Leu His Gln Gln Lys Gln Gln Gln Gln
            180                 185                 190

Pro Ser Ser Gln Val Ser Phe Gln Gln Pro Leu Gln Gln Tyr Pro Leu
        195                 200                 205

Gly Gln Gly Ser Phe Arg Pro Ser Gln Gln Asn Pro Gln Ala Gln Gly
    210                 215                 220

Ser Val Gln Pro Gln Gln Leu Pro Gln Phe Glu Glu Ile Arg Asn Leu
225                 230                 235                 240

Ala Leu Gln Thr Leu Pro Ala Met Cys Asn Val Tyr Ile Pro Pro Tyr
                245                 250                 255

Cys Thr Ile Thr Pro Phe Gly Ile Phe Gly Thr Asn
            260                 265

<210> SEQ ID NO 7
<211> LENGTH: 647
<212> TYPE: PRT
<213> ORGANISM: Homo sapiens

<400> SEQUENCE: 7

Met Trp Arg Val Cys Ala Arg Arg Ala Gln Asn Val Ala Pro Trp Ala
1               5                   10                  15
```

```
Gly Leu Glu Ala Arg Trp Thr Ala Leu Gln Glu Val Pro Gly Thr Pro
         20                  25                  30

Arg Val Thr Ser Arg Ser Gly Pro Ala Pro Ala Arg Arg Asn Ser Val
         35                  40                  45

Thr Thr Gly Tyr Gly Val Arg Ala Leu Cys Gly Trp Thr Pro Ser
     50                  55                  60

Ser Gly Ala Thr Pro Arg Asn Arg Leu Leu Gln Leu Leu Gly Ser
65                   70                  75                  80

Pro Gly Arg Arg Tyr Tyr Ser Leu Pro Pro His Gln Lys Val Pro Leu
                 85                  90                  95

Pro Ser Leu Ser Pro Thr Met Gln Ala Gly Thr Ile Ala Arg Trp Glu
             100                 105                 110

Lys Lys Glu Gly Asp Lys Ile Asn Glu Gly Asp Leu Ile Ala Glu Val
         115                 120                 125

Glu Thr Asp Lys Ala Thr Val Gly Phe Glu Ser Leu Glu Glu Cys Tyr
     130                 135                 140

Met Ala Lys Ile Leu Val Ala Glu Gly Thr Arg Asp Val Pro Ile Gly
145                 150                 155                 160

Ala Ile Ile Cys Ile Thr Val Gly Lys Pro Glu Asp Ile Glu Ala Phe
                 165                 170                 175

Lys Asn Tyr Thr Leu Asp Ser Ser Ala Ala Pro Thr Pro Gln Ala Ala
             180                 185                 190

Pro Ala Pro Thr Pro Ala Ala Thr Ala Ser Pro Pro Thr Pro Ser Ala
         195                 200                 205

Gln Ala Pro Gly Ser Ser Tyr Pro Pro His Met Gln Val Leu Leu Pro
     210                 215                 220

Ala Leu Ser Pro Thr Met Thr Met Gly Thr Val Gln Arg Trp Glu Lys
225                 230                 235                 240

Lys Val Gly Glu Lys Leu Ser Glu Gly Asp Leu Leu Ala Glu Ile Glu
                 245                 250                 255

Thr Asp Lys Ala Thr Ile Gly Phe Glu Val Gln Glu Glu Gly Tyr Leu
             260                 265                 270

Ala Lys Ile Leu Val Pro Glu Gly Thr Arg Asp Val Pro Leu Gly Thr
         275                 280                 285

Pro Leu Cys Ile Ile Val Glu Lys Glu Ala Asp Ile Ser Ala Phe Ala
     290                 295                 300

Asp Tyr Arg Pro Thr Glu Val Thr Asp Leu Lys Pro Gln Val Pro Pro
305                 310                 315                 320

Pro Thr Pro Pro Pro Val Ala Ala Val Pro Pro Thr Pro Gln Pro Leu
                 325                 330                 335

Ala Pro Thr Pro Ser Ala Pro Cys Pro Ala Thr Pro Ala Gly Pro Lys
             340                 345                 350

Gly Arg Val Phe Val Ser Pro Leu Ala Lys Lys Leu Ala Val Glu Lys
         355                 360                 365

Gly Ile Asp Leu Thr Gln Val Lys Gly Thr Gly Pro Asp Gly Arg Ile
     370                 375                 380

Thr Lys Lys Asp Ile Asp Ser Phe Val Pro Ser Lys Val Ala Pro Ala
385                 390                 395                 400

Pro Ala Ala Val Val Pro Pro Thr Gly Pro Gly Met Ala Pro Val Pro
                 405                 410                 415

Thr Gly Val Phe Thr Asp Ile Pro Ile Ser Asn Ile Arg Arg Val Ile
             420                 425                 430
```

```
Ala Gln Arg Leu Met Gln Ser Lys Gln Thr Ile Pro His Tyr Tyr Leu
            435                 440                 445

Ser Ile Asp Val Asn Met Gly Glu Val Leu Leu Val Arg Lys Glu Leu
450                 455                 460

Asn Lys Ile Leu Glu Gly Arg Ser Lys Ile Ser Val Asn Asp Phe Ile
465                 470                 475                 480

Ile Lys Ala Ser Ala Leu Ala Cys Leu Lys Val Pro Glu Ala Asn Ser
                485                 490                 495

Ser Trp Met Asp Thr Val Ile Arg Gln Asn His Val Val Asp Val Ser
                500                 505                 510

Val Ala Val Ser Thr Pro Ala Gly Leu Ile Thr Pro Ile Val Phe Asn
            515                 520                 525

Ala His Ile Lys Gly Val Glu Thr Ile Ala Asn Asp Val Val Ser Leu
530                 535                 540

Ala Thr Lys Ala Arg Glu Gly Lys Leu Gln Pro His Glu Phe Gln Gly
545                 550                 555                 560

Gly Thr Phe Thr Ile Ser Asn Leu Gly Met Phe Gly Ile Lys Asn Phe
                565                 570                 575

Ser Ala Ile Ile Asn Pro Pro Gln Ala Cys Ile Leu Ala Ile Gly Ala
                580                 585                 590

Ser Glu Asp Lys Leu Val Pro Ala Asp Asn Glu Lys Gly Phe Asp Val
            595                 600                 605

Ala Ser Met Met Ser Val Thr Leu Ser Cys Asp His Arg Val Val Asp
            610                 615                 620

Gly Ala Val Gly Ala Gln Trp Leu Ala Glu Phe Arg Lys Tyr Leu Glu
625                 630                 635                 640

Lys Pro Ile Thr Met Leu Leu
                645

<210> SEQ ID NO 8
<211> LENGTH: 910
<212> TYPE: PRT
<213> ORGANISM: Homo sapiens

<400> SEQUENCE: 8

Met Asn Trp His Phe Leu Arg Thr Ala Thr Val Leu Leu Ile Phe Leu
1               5                   10                  15

Val Val Val Glu Ile Asn Ser Glu Phe Arg Ile Gln Val Arg Asp Tyr
                20                  25                  30

Asn Thr Lys Asn Gly Thr Ile Lys Trp His Ser Ile Arg Arg Gln Lys
                35                  40                  45

Arg Glu Trp Ile Lys Phe Ala Ala Ala Cys Arg Glu Gly Glu Asp Asn
50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Ile Ile Asn Gln Lys Thr Gly Glu Ile Asn Ile Thr
                100                 105                 110

Ser Ile Val Asp Arg Glu Ile Thr Pro Phe Phe Ile Ile Tyr Cys Arg
            115                 120                 125

Ala Leu Asn Ser Leu Gly Gln Asp Leu Glu Arg Pro Leu Glu Leu Arg
130                 135                 140

Val Arg Val Leu Asp Ile Asn Asp Asn Pro Pro Val Phe Ser Met Ser
145                 150                 155                 160
```

```
Thr Phe Val Gly Gln Ile Glu Glu Asn Ser Asn Ala Asn Thr Leu Val
                165                 170                 175

Met Arg Leu Asn Ala Thr Gly Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
    210                 215                 220

Leu Asp Arg Glu Gln Tyr Ser Gln Tyr Ser Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Pro Ser
                260                 265                 270

Ser His Met Val Arg Ile Glu Glu Asn Ala Leu Ser Gln Asn Leu Val
        275                 280                 285

Glu Ile Arg Val Ile Asp Leu Asp Glu Glu Phe Ser Ala Asn Trp Met
290                 295                 300

Ala Val Ile Phe Phe Ile Ser Gly Asn Glu Gly Gly Trp Phe Asp Ile
305                 310                 315                 320

Glu Met Asn Glu Arg Thr Asn Val Gly Ile Leu Lys Val Ile Lys Pro
                325                 330                 335

Leu Asp Tyr Glu Ala Val Gln Asn Leu Gln Leu Ser Leu Gly Val Arg
                340                 345                 350

Asn Lys Ala Asp Phe His His Ser Ile Met Ser Gln Tyr Lys Val Thr
                355                 360                 365

Ala Thr Ala Ile Ser Val Thr Val Leu Asn Val Ile Glu Gly Ser Val
                370                 375                 380

Phe Arg Pro Gly Ser Lys Thr Tyr Val Val Arg Ser Asp Met Gly Gln
385                 390                 395                 400

Asn Tyr Lys Val Gly Asp Phe Val Ala Thr Asp Leu Asp Thr Gly Leu
                405                 410                 415

Ala Ser Thr Thr Val Arg Tyr Val Met Gly Asn Asn Pro Ala Asn Leu
                420                 425                 430

Leu Asn Val Asp Ser Lys Thr Gly Val Ile Thr Leu Arg Asn Lys Val
                435                 440                 445

Thr Met Glu Gln Tyr Glu Met Leu Asn Gly Lys Tyr Gln Gly Thr Ile
                450                 455                 460

Leu Ser Ile Asp Asp Ala Leu Gln Arg Thr Cys Thr Gly Thr Ile Asn
465                 470                 475                 480

Ile Asp Leu Gln Gly Ser Gly Trp Glu Lys Asp Ser Glu Lys Val Thr
                485                 490                 495

Ser Ser Gln Asn Ser Gly Ser Ser Thr Gly Asp Ser Ser Gly Gly Thr
                500                 505                 510

Gly Gly Gly Gly Arg Glu Asn Pro Ser Glu Gly Asp Thr Thr Thr Asn
                515                 520                 525

Thr Gly Gly Lys Thr Ser Thr Asp Tyr Glu Asp Gly Glu Thr Gln Thr
                530                 535                 540

Gln Ser Asn Asn Asn His Gln Glu Leu Gly Ser Asn Asn Leu Ser Asp
545                 550                 555                 560

Asn Val His Phe Gly Pro Ala Gly Ile Gly Leu Leu Ile Met Gly Phe
                565                 570                 575
```

Leu Val Leu Gly Leu Val Pro Phe Leu Met Cys Cys Asp Cys Gly
                580                 585                 590

Gly Ala Pro Gly Ala Gly Ala Gly Phe Glu Pro Val Pro Glu Cys Ser
        595                 600                 605

Asp Gly Ala Ile His Ser Trp Ala Val Glu Gly Pro Gln Pro Leu Pro
        610                 615                 620

Thr Asp Ala Thr Thr Val Cys Val Pro Pro Ile Pro Ser Asn Asn Ala
625                 630                 635                 640

Asn Val Ile Glu Cys Ile Asp Thr Ser Gly Val Tyr Thr Asn Glu Tyr
                645                 650                 655

Gly Gly Arg Glu Met Gln Asp Leu Gly Gly Glu Arg Thr Thr Gly
                660                 665                 670

Phe Glu Leu Thr Glu Gly Val Lys Thr Ser Gly Val Pro Glu Ile Cys
        675                 680                 685

Gln Glu Tyr Ser Gly Thr Leu Arg Arg Asn Ser Met Arg Glu Cys Arg
        690                 695                 700

Glu Gly Gly Leu Asn Met Asn Phe Met Glu Ser Tyr Phe Cys Gln Lys
705                 710                 715                 720

Ala Tyr Ala Tyr Ala Asp Glu Asp Gly Arg Pro Ser Asn Asp Cys
                725                 730                 735

Leu Leu Ile Tyr Asp Ile Glu Gly Val Gly Ser Pro Ala Gly Ser Val
        740                 745                 750

Gly Cys Cys Ser Phe Ile Gly Glu Asp Leu Asp Asp Ser Phe Leu Asp
        755                 760                 765

Thr Leu Gly Pro Lys Phe Lys Lys Leu Ala Asp Ile Ser Leu Gly Lys
770                 775                 780

Glu Val Glu Pro Asp Pro Ser Trp Pro Pro Glu Ser Thr Glu Pro Ile
785                 790                 795                 800

Cys Pro Gln Gln Gly Thr Glu Pro Ile Ile Gly Gly His Pro Pro Ile
                805                 810                 815

Ser Pro His Phe Gly Thr Thr Thr Val Ile Ser Glu Asn Thr Tyr Pro
                820                 825                 830

Ser Gly Pro Gly Val Gln His Pro Met Pro Ile Pro Asp Pro Leu Gly
        835                 840                 845

Tyr Gly Asn Val Thr Val Thr Glu Ser Tyr Thr Thr Ser Gly Thr Leu
        850                 855                 860

Lys Pro Thr Val His Val His Asp Asn Arg His Ala Ser Asn Val Val
865                 870                 875                 880

Val Thr Glu Arg Val Val Gly Pro Ile Ser Gly Thr Asp Leu His Gly
                885                 890                 895

Met Leu Glu Met Pro Asp Leu Arg Asp Gly Ser Asn Val Ile
                900                 905                 910

<210> SEQ ID NO 9
<211> LENGTH: 999
<212> TYPE: PRT
<213> ORGANISM: Homo sapiens

<400> SEQUENCE: 9

Met Met Gly Leu Phe Pro Arg Thr Gly Ala Leu Ala Ile Phe Val
1               5                   10                  15

Val Val Ile Leu Val His Gly Glu Leu Arg Ile Glu Thr Lys Gly Gln
                20                  25                  30

Tyr Asp Glu Glu Glu Met Thr Met Gln Gln Ala Lys Arg Arg Gln Lys
            35                  40                  45

```
Arg Glu Trp Val Lys Phe Ala Lys Pro Cys Arg Gly Glu Asp Asn
 50                  55                  60

Ser Lys Arg Asn Pro Ile Ala Lys Ile Thr Ser Asp Tyr Gln Ala Thr
 65                  70                  75                  80

Gln Lys Ile Thr Tyr Arg Ile Ser Gly Val Gly Ile Asp Gln Pro Pro
                 85                  90                  95

Phe Gly Ile Phe Val Val Asp Lys Asn Thr Gly Asp Ile Asn Ile Thr
                100                 105                 110

Ala Ile Val Asp Arg Glu Glu Thr Pro Ser Phe Leu Ile Thr Cys Arg
            115                 120                 125

Ala Leu Asn Ala Gln Gly Leu Asp Val Glu Lys Pro Leu Ile Leu Thr
            130                 135                 140

Val Lys Ile Leu Asp Ile Asn Asp Asn Pro Pro Val Phe Ser Gln Gln
145                 150                 155                 160

Ile Phe Met Gly Glu Ile Glu Glu Asn Ser Ala Ser Asn Ser Leu Val
                165                 170                 175

Met Ile Leu Asn Ala Thr Asp Ala Asp Glu Pro Asn His Leu Asn Ser
            180                 185                 190

Lys Ile Ala Phe Lys Ile Val Ser Gln Glu Pro Ala Gly Thr Pro Met
            195                 200                 205

Phe Leu Leu Ser Arg Asn Thr Gly Glu Val Arg Thr Leu Thr Asn Ser
210                 215                 220

Leu Asp Arg Glu Gln Ala Ser Ser Tyr Arg Leu Val Val Ser Gly Ala
225                 230                 235                 240

Asp Lys Asp Gly Glu Gly Leu Ser Thr Gln Cys Glu Cys Asn Ile Lys
                245                 250                 255

Val Lys Asp Val Asn Asp Asn Phe Pro Met Phe Arg Asp Ser Gln Tyr
            260                 265                 270

Ser Ala Arg Ile Glu Glu Asn Ile Leu Ser Ser Glu Leu Leu Arg Phe
            275                 280                 285

Gln Val Thr Asp Leu Asp Glu Glu Tyr Thr Asp Asn Trp Leu Ala Val
            290                 295                 300

Tyr Phe Phe Thr Ser Gly Asn Glu Gly Asn Trp Phe Glu Ile Gln Thr
305                 310                 315                 320

Asp Pro Arg Thr Asn Glu Gly Ile Leu Lys Val Val Lys Ala Leu Asp
                325                 330                 335

Tyr Glu Gln Leu Gln Ser Val Lys Leu Ser Ile Ala Val Lys Asn Lys
            340                 345                 350

Ala Glu Phe His Gln Ser Val Ile Ser Arg Tyr Arg Val Gln Ser Thr
            355                 360                 365

Pro Val Thr Ile Gln Val Ile Asn Val Arg Glu Gly Ile Ala Phe Arg
            370                 375                 380

Pro Ala Ser Lys Thr Phe Thr Val Gln Lys Gly Ile Ser Ser Lys Lys
385                 390                 395                 400

Leu Val Asp Tyr Ile Leu Gly Thr Tyr Gln Ala Ile Asp Glu Asp Thr
                405                 410                 415

Asn Lys Ala Ala Ser Asn Val Lys Tyr Val Met Gly Arg Asn Asp Gly
            420                 425                 430

Gly Tyr Leu Met Ile Asp Ser Lys Thr Ala Glu Ile Lys Phe Val Lys
            435                 440                 445

Asn Met Asn Arg Asp Ser Thr Phe Ile Val Asn Lys Thr Ile Thr Ala
            450                 455                 460
```

```
Glu Val Leu Ala Ile Asp Glu Tyr Thr Gly Lys Thr Ser Thr Gly Thr
465                 470                 475                 480

Val Tyr Val Arg Val Pro Asp Phe Asn Asp Asn Cys Pro Thr Ala Val
                485                 490                 495

Leu Glu Lys Asp Ala Val Cys Ser Ser Ser Pro Ser Val Val Val Ser
            500                 505                 510

Ala Arg Thr Leu Asn Asn Arg Tyr Thr Gly Pro Tyr Thr Phe Ala Leu
            515                 520                 525

Glu Asp Gln Pro Val Lys Leu Pro Ala Val Trp Ser Ile Thr Thr Leu
            530                 535                 540

Asn Ala Thr Ser Ala Leu Leu Arg Ala Gln Glu Gln Ile Pro Pro Gly
545                 550                 555                 560

Val Tyr His Ile Ser Leu Val Leu Thr Asp Ser Gln Asn Asn Arg Cys
                565                 570                 575

Glu Met Pro Arg Ser Leu Thr Leu Glu Val Cys Gln Cys Asp Asn Arg
                580                 585                 590

Gly Ile Cys Gly Thr Ser Tyr Pro Thr Thr Ser Pro Gly Thr Arg Tyr
            595                 600                 605

Gly Arg Pro His Ser Gly Arg Leu Gly Pro Ala Ala Ile Gly Leu Leu
            610                 615                 620

Leu Leu Gly Leu Leu Leu Leu Leu Ala Pro Leu Leu Leu Leu Thr
625                 630                 635                 640

Cys Asp Cys Gly Ala Gly Ser Thr Gly Val Thr Gly Gly Phe Ile
                645                 650                 655

Pro Val Pro Asp Gly Ser Glu Gly Thr Ile His Gln Trp Gly Ile Glu
                660                 665                 670

Gly Ala His Pro Glu Asp Lys Glu Ile Thr Asn Ile Cys Val Pro Pro
            675                 680                 685

Val Thr Ala Asn Gly Ala Asp Phe Met Glu Ser Ser Glu Val Cys Thr
            690                 695                 700

Asn Thr Tyr Ala Arg Gly Thr Ala Val Glu Gly Thr Ser Gly Met Glu
705                 710                 715                 720

Met Thr Thr Lys Leu Gly Ala Ala Thr Glu Ser Gly Gly Ala Ala Gly
                725                 730                 735

Phe Ala Thr Gly Thr Val Ser Gly Ala Ala Ser Gly Phe Gly Ala Ala
                740                 745                 750

Thr Gly Val Gly Ile Cys Ser Ser Gly Gln Ser Gly Thr Met Arg Thr
            755                 760                 765

Arg His Ser Thr Gly Gly Thr Asn Lys Asp Tyr Ala Asp Gly Ala Ile
            770                 775                 780

Ser Met Asn Phe Leu Asp Ser Tyr Phe Ser Gln Lys Ala Phe Ala Cys
785                 790                 795                 800

Ala Glu Glu Asp Asp Gly Gln Glu Ala Asn Asp Cys Leu Leu Ile Tyr
                805                 810                 815

Asp Asn Glu Gly Ala Asp Ala Thr Gly Ser Pro Val Gly Ser Val Gly
            820                 825                 830

Cys Cys Ser Phe Ile Ala Asp Asp Leu Asp Asp Ser Phe Leu Asp Ser
            835                 840                 845

Leu Gly Pro Lys Phe Lys Lys Leu Ala Glu Ile Ser Leu Gly Val Asp
            850                 855                 860

Gly Glu Gly Lys Glu Val Gln Pro Pro Ser Lys Asp Ser Gly Tyr Gly
865                 870                 875                 880

Ile Glu Ser Cys Gly His Pro Ile Glu Val Gln Gln Thr Gly Phe Val
```

-continued

```
                885                 890                 895
Lys Cys Gln Thr Leu Ser Gly Ser Gln Gly Ala Ser Ala Leu Ser Thr
            900                 905                 910

Ser Gly Ser Val Gln Pro Ala Val Ser Ile Pro Asp Pro Leu Gln His
            915                 920                 925

Gly Asn Tyr Leu Val Thr Glu Thr Tyr Ser Ala Ser Gly Ser Leu Val
            930                 935                 940

Gln Pro Ser Thr Ala Gly Phe Asp Pro Leu Leu Thr Gln Asn Val Ile
945                 950                 955                 960

Val Thr Glu Arg Val Ile Cys Pro Ile Ser Ser Val Pro Gly Asn Leu
                965                 970                 975

Ala Gly Pro Thr Gln Leu Arg Gly Ser His Thr Met Leu Cys Thr Glu
            980                 985                 990

Asp Pro Cys Ser Arg Leu Ile
            995

<210> SEQ ID NO 10
<211> LENGTH: 323
<212> TYPE: PRT
<213> ORGANISM: Homo sapiens

<400> SEQUENCE: 10

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125

Gly Ala Gly Ile Leu Tyr Leu Val Thr Pro Pro Ser Val Val Gly Gly
    130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
    210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255
```

```
Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
290                 295                 300

Asp Arg Gly Glu Glu Lys Lys Gly Lys Asp Gln Ser Gly Glu Val Leu
305                 310                 315                 320

Ser Ser Val

<210> SEQ ID NO 11
<211> LENGTH: 277
<212> TYPE: PRT
<213> ORGANISM: Homo sapiens

<400> SEQUENCE: 11

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
        50                  55                  60

Ile His Ala Phe Gln Tyr Val Ile Tyr Gly Thr Ala Ser Phe Phe Phe
65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190

Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275

<210> SEQ ID NO 12
<211> LENGTH: 247
```

```
<212> TYPE: PRT
<213> ORGANISM: Homo sapiens

<400> SEQUENCE: 12

Met Ala Ser Leu Ser Arg Pro Ser Leu Pro Ser Cys Leu Cys Ser Phe
1               5                   10                  15

Leu Leu Leu Leu Leu Leu Gln Val Ser Ser Tyr Ala Gly Gln Phe
            20                  25                  30

Arg Val Ile Gly Pro Arg His Pro Ile Arg Ala Leu Val Gly Asp Glu
            35                  40                  45

Val Glu Leu Pro Cys Arg Ile Ser Pro Gly Lys Asn Ala Thr Gly Met
        50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Glu Ala Ala Met Glu Leu Lys Val
130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Val Gly Leu Ile Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 13
<211> LENGTH: 304
<212> TYPE: PRT
<213> ORGANISM: Homo sapiens

<400> SEQUENCE: 13

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
            35                  40                  45

Ala Asp Ala Asn Gln Asn Asn Gly Thr Ser Ser Gln Asp Thr Ala Val
        50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95
```

```
Arg Asp Ala Pro Gly Arg Glu Asp Asn Thr Phe Lys Asp Arg Pro Ser
            100                 105                 110

Glu Ser Asp Glu Leu Gln Thr Ile Gln Glu Asp Ser Ala Ala Thr Ser
        115                 120                 125

Glu Ser Leu Asp Val Met Ala Ser Gln Lys Arg Pro Ser Gln Arg His
    130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
                180                 185                 190

Asp Ser His His Pro Ala Arg Thr Ala His Tyr Gly Ser Leu Pro Gln
            195                 200                 205

Lys Ser His Gly Arg Thr Gln Asp Glu Asn Pro Val Val His Phe Phe
        210                 215                 220

Lys Asn Ile Val Thr Pro Arg Thr Pro Pro Ser Gln Gly Lys Gly Gly
225                 230                 235                 240

Arg Gly Leu Ser Leu Ser Arg Phe Ser Trp Gly Ala Glu Gly Gln Arg
                245                 250                 255

Pro Gly Phe Gly Tyr Gly Gly Arg Ala Ser Asp Tyr Lys Ser Ala His
                260                 265                 270

Lys Gly Phe Lys Gly Val Asp Ala Gln Gly Thr Leu Ser Lys Ile Phe
            275                 280                 285

Lys Leu Gly Gly Arg Asp Ser Arg Ser Gly Ser Pro Met Ala Arg Arg
        290                 295                 300

<210> SEQ ID NO 14
<211> LENGTH: 963
<212> TYPE: PRT
<213> ORGANISM: Homo sapiens

<400> SEQUENCE: 14

Met Arg Gly Ala Ser Val Thr Val Ala Ala Val Arg Cys Gly Asp Val
1               5                   10                  15

Ala Gly Ser Cys Val Asp Gly Arg Tyr Asn Asp Lys Asp Val Trp Lys
            20                  25                  30

Cys Arg Cys Val Cys Asp Thr Gly Thr Val Cys Asp Asp Cys Asp Val
        35                  40                  45

Lys Asp Cys Ser Gly Cys Cys Cys Thr Asp Ala Thr Ala Ser Gly Gly
    50                  55                  60

Lys Gly Lys Gly Gly Asp Lys Asp Val Gly Lys Gly Gly Ala Gly
65                  70                  75                  80

Gly Arg Gly Asp Arg Gly Asp Lys Gly Lys Gly Ala Gly Arg Gly Arg
                85                  90                  95

Asp Gly Gly Thr Gly Asn Gly Gly Gly Gly Gly Asn Ala Ala
            100                 105                 110

Met Ala Gly Gly Asp Lys Ala Gly Gly Ala Gly Val Met Gly Met Gly
        115                 120                 125

Met Gly Arg Gly Gly Ala Gly Ala Gly Gly Asn Gly Gly Gly Val
    130                 135                 140

Ser Gly Met Gly Arg Gly Gly Lys Gly Asp Asp Gly Ala Gly Lys
145                 150                 155                 160

Gly Lys Ala Gly Arg Gly Gly Ala Arg Gly Thr Gly Gly Val
                165                 170                 175
```

```
Lys Gly His Arg Gly Tyr Gly Asp Gly Ala Lys Gly Ala Gly
        180             185             190

Val Lys Gly Ser Gly Ser Gly Asn Gly Ser Gly Met Gly Arg Gly Gly
        195             200             205

Arg Gly Arg Thr Gly Ala Gly Ala Ala Gly Ala Arg Gly Asn Asp Gly
210             215             220

Gly Ala Gly Gly Val Gly Ala Gly Gly Gly Ala Gly Ala Lys Gly
225             230             235             240

Ala Gly Thr Gly Ala Arg Gly Gly Ala Gly Arg Gly Gly Thr Gly Ser
            245             250             255

Gly Ala Gly Ala Ser Gly Asn Gly Thr Asp Gly Gly Ala Lys Gly Ser
            260             265             270

Ala Gly Ala Gly Ala Gly Gly Arg Gly Gly Ala Thr Gly
            275             280             285

Gly Lys Gly Thr Gly Gly Ala Gly Lys Gly Gly Lys Gly Gly Ala Gly
        290             295             300

Gly Ala Gly Ala Gly Gly Lys Arg Gly Ala Arg Gly Gly Gly Val Gly
305             310             315             320

Gly Gly Arg Gly Ala Gly Asn Arg Gly Gly Asp Gly Ala Gly Lys Gly
            325             330             335

Ala Gly Arg Gly Ser Gly Ala Gly Lys Gly Ala Asn Gly Asp Gly Arg
            340             345             350

Gly Gly Gly Ala Arg Gly Thr Gly Arg Gly Asp Ala Gly Gly Lys Val
            355             360             365

Gly Ser Gly Ala Gly Asp Gly Arg Gly Gly Ala Arg Gly Gly Val
        370             375             380

Met Gly Gly Lys Gly Ala Asn Gly Gly Lys Ala Gly Lys Gly Gly Ala
385             390             395             400

Gly Arg Gly Gly Lys Asp Gly Thr Gly Ala Ala Gly Ala Gly Ala
            405             410             415

Gly Arg Gly Gly Ala Gly Ser Gly Gly Gly Gly Gly Gly Lys Gly
            420             425             430

Asp Gly Val Gly Ala Gly Ala Gly Val Gly Arg Gly Arg Gly Gly Arg
            435             440             445

Gly Ser Gly Ala Gly Gly Arg Gly Gly Thr Gly Thr Asp Gly Lys Gly
            450             455             460

Ala Ser Gly Ala Gly Gly Ala Gly Gly Met Gly Arg Gly Ala Ala
465             470             475             480

Gly Ala Gly Lys Gly Asp Arg Gly Asp Val Gly Lys Gly Gly Ala Gly
            485             490             495

Lys Asp Gly Gly Arg Gly Thr Gly Gly Ala Gly Ala Asn Gly Lys
            500             505             510

Gly Val Gly Gly Ala Gly Ser Ala Gly Ala Arg Gly Ala Gly Arg Gly
        515             520             525

Thr Gly Gly Ala Gly Ala Gly Gly Ala Asp Gly Gly Ala Lys Gly Gly
        530             535             540

Ala Gly Lys Gly Asp Ala Gly Ala Gly Ser Gly Ala Gly Gly Thr
545             550             555             560

Gly Val Thr Gly Lys Gly Ala Arg Gly Ala Gly Ala Thr Gly Gly
            565             570             575

Ala Ala Gly Arg Val Gly Gly Ser Asn Gly Asn Gly Gly Ser Gly
            580             585             590
```

```
Lys Asp Gly Lys Gly Ala Arg Gly Asp Ser Gly Gly Arg Ala Gly
            595                 600                 605

Gly Ala Gly Gly Lys Gly Asp Asp Gly Ser Gly Ala Gly Gly Gly
        610                 615                 620

Ala Gly Arg Gly Val Gly Gly Arg Gly Arg Gly Gly Ser Gly Gly
625                 630                 635                 640

Lys Gly Ala Gly Ala Ser Gly Asp Arg Gly Gly Val Gly Gly Thr Gly
                645                 650                 655

Ala Gly Gly Arg Gly Ser Gly Ala Asp Gly Gly Arg Asp Gly Ala Ala
                660                 665                 670

Gly Val Lys Gly Asp Arg Gly Thr Gly Ala Val Gly Ala Gly Ala Gly
                675                 680                 685

Gly Ser Gly Ala Gly Thr Gly Lys Gly Asp Arg Gly Ala Gly Ala Gly
                690                 695                 700

Met Gly Ser Gly Ala Gly Ala Arg Gly Gly Arg Gly Asp Lys Gly
705                 710                 715                 720

Ala Gly Gly Arg Gly Lys Gly His Arg Gly Thr Gly Gly Gly Ser
                725                 730                 735

Gly Asp Gly Ala Ser Gly Ala Gly Ser Gly Arg Gly Val Gly Ser
        740                 745                 750

Gly Lys Asp Gly Ala Asn Gly Gly Gly Arg Gly Arg Ser Gly Thr
        755                 760                 765

Gly Ala Gly Gly Asn Gly Gly Gly Gly Asp Met Ser Ala Ala Gly
        770                 775                 780

Gly Arg Lys Gly Asp Tyr Met Arg Ala Asp Ala Ala Gly Gly Arg His
785                 790                 795                 800

Asp Ala Val Asp Ala Thr Lys Ser Asn Asn Ser Arg Ser Gly Ser Arg
                805                 810                 815

Lys Asn Ala Arg Thr Cys Arg Asp Lys Cys His Trp Lys Ser Gly Asp
                820                 825                 830

Tyr Trp Asp Asn Gly Cys Thr Asp Ala Met Lys Val Cys Asn Met Thr
                835                 840                 845

Gly Thr Cys Val Tyr Asn Ala Asn Val Lys Lys Asn Trp Trp Ser Ser
850                 855                 860

Lys Ser Lys Lys Lys His Trp Gly Thr Asn Gly Gly His Ser Tyr Gly
865                 870                 875                 880

Asp Asp Asn Ala Asn Thr Ala Asn Val Met Thr Arg Ser Thr Gly Ser
                885                 890                 895

Asn Thr Tyr His Cys Lys Asn Ser Ala Tyr Asp Ala Gly Asn Lys
                900                 905                 910

Lys Ala Gly Ser Asn Asp Val Arg Ala Gly Asn Ser Arg Thr Tyr Thr
                915                 920                 925

Ala Lys Asp Gly Cys Thr Lys His Thr Gly Lys Trp Gly Lys Thr Val
            930                 935                 940

Tyr Arg Ser Lys Thr Ser Arg Asp Ala Met Asp Gly Gly Val Asp
945                 950                 955                 960

Gly Val Cys

<210> SEQ ID NO 15
<211> LENGTH: 1419
<212> TYPE: PRT
<213> ORGANISM: Homo sapiens

<400> SEQUENCE: 15
```

```
Met Ile Arg Leu Gly Ala Pro Gln Ser Leu Val Leu Leu Thr Leu Leu
1               5                   10                  15

Ile Ala Ala Val Leu Arg Cys Gln Gly Gln Asp Ala Arg Lys Leu Gly
            20                  25                  30

Pro Lys Gly Gln Lys Gly Glu Pro Gly Asp Ile Arg Asp Ile Ile Gly
        35                  40                  45

Pro Arg Gly Pro Pro Gly Pro Gln Gly Pro Ala Gly Glu Gln Gly Pro
    50                  55                  60

Arg Gly Asp Arg Gly Asp Lys Gly Glu Lys Gly Ala Pro Gly Pro Arg
65                  70                  75                  80

Gly Arg Asp Gly Glu Pro Gly Thr Pro Gly Asn Pro Gly Pro Ala Gly
                85                  90                  95

Pro Pro Gly Pro Pro Gly Pro Pro Gly Leu Ser Ala Gly Asn Phe Ala
            100                 105                 110

Ala Gln Met Ala Gly Gly Tyr Asp Glu Lys Ala Gly Gly Ala Gln Met
        115                 120                 125

Gly Val Met Gln Gly Pro Met Gly Pro Met Gly Arg Gly Pro Pro
130                 135                 140

Gly Pro Ala Gly Ala Pro Gly Pro Gln Gly Phe Gln Gly Asn Pro Gly
145                 150                 155                 160

Glu Pro Gly Glu Pro Gly Val Ser Gly Pro Met Gly Pro Arg Gly Pro
                165                 170                 175

Pro Gly Pro Ala Gly Lys Pro Gly Asp Asp Gly Glu Ala Gly Lys Pro
            180                 185                 190

Gly Lys Ser Gly Glu Arg Gly Leu Pro Gly Pro Gln Gly Ala Arg Gly
        195                 200                 205

Phe Pro Gly Thr Pro Gly Leu Pro Gly Val Lys Gly His Arg Gly Tyr
    210                 215                 220

Pro Gly Leu Asp Gly Ala Lys Gly Glu Ala Gly Ala Pro Gly Val Lys
225                 230                 235                 240

Gly Glu Ser Gly Ser Pro Gly Glu Asn Gly Ser Pro Gly Pro Met Gly
                245                 250                 255

Pro Arg Gly Leu Pro Gly Glu Arg Gly Arg Thr Gly Pro Ala Gly Ala
            260                 265                 270

Ala Gly Ala Arg Gly Asn Asp Gly Gln Pro Gly Pro Ala Gly Pro Pro
        275                 280                 285

Gly Pro Val Gly Pro Ala Gly Gly Pro Gly Phe Pro Gly Ala Pro Gly
    290                 295                 300

Ala Lys Gly Glu Ala Gly Pro Thr Gly Ala Arg Gly Pro Glu Gly Ala
305                 310                 315                 320

Gln Gly Ser Arg Gly Glu Pro Gly Asn Pro Gly Ser Pro Gly Pro Ala
                325                 330                 335

Gly Ala Ser Gly Asn Pro Gly Thr Asp Gly Ile Pro Gly Ala Lys Gly
            340                 345                 350

Ser Ala Gly Ala Pro Gly Ile Ala Gly Ala Pro Gly Phe Pro Gly Pro
        355                 360                 365

Arg Gly Pro Pro Gly Pro Gln Gly Ala Thr Gly Pro Leu Gly Pro Lys
    370                 375                 380

Gly Gln Ala Gly Glu Pro Gly Ile Ala Gly Phe Lys Gly Asp Gln Gly
385                 390                 395                 400

Pro Lys Gly Glu Thr Gly Pro Ala Gly Pro Gln Gly Ala Pro Gly Pro
                405                 410                 415

Ala Gly Glu Glu Gly Lys Arg Gly Ala Arg Gly Glu Pro Gly Gly Ala
```

420                 425                 430
Gly Pro Ile Gly Pro Pro Gly Glu Arg Gly Ala Pro Gly Asn Arg Gly
            435                 440                 445

Phe Pro Gly Gln Asp Gly Leu Ala Gly Pro Lys Gly Ala Pro Gly Glu
450                 455                 460

Arg Gly Pro Ser Gly Leu Thr Gly Pro Lys Gly Ala Asn Gly Asp Pro
465                 470                 475                 480

Gly Arg Pro Gly Glu Pro Gly Leu Pro Gly Ala Arg Gly Leu Thr Gly
            485                 490                 495

Arg Pro Gly Asp Ala Gly Pro Gln Gly Lys Val Gly Pro Ser Gly Ala
            500                 505                 510

Pro Gly Glu Asp Gly Arg Pro Gly Pro Gly Pro Gln Gly Ala Arg
            515                 520                 525

Gly Gln Pro Gly Val Met Gly Phe Pro Gly Pro Lys Gly Ala Asn Gly
            530                 535                 540

Glu Pro Gly Lys Ala Gly Glu Lys Gly Leu Ala Gly Ala Pro Gly Leu
545                 550                 555                 560

Arg Gly Leu Pro Gly Lys Asp Gly Glu Thr Gly Ala Ala Gly Pro Pro
            565                 570                 575

Gly Pro Ser Gly Pro Ala Gly Glu Arg Gly Glu Gln Gly Ala Pro Gly
            580                 585                 590

Pro Ser Gly Phe Gln Gly Leu Pro Gly Pro Gly Pro Pro Gly Glu
            595                 600                 605

Gly Gly Lys Gln Gly Asp Gln Gly Ile Pro Gly Glu Ala Gly Ala Pro
            610                 615                 620

Gly Leu Val Gly Pro Arg Gly Glu Arg Gly Phe Pro Gly Glu Arg Gly
625                 630                 635                 640

Ser Pro Gly Ala Gln Gly Leu Gln Gly Pro Arg Gly Leu Pro Gly Thr
            645                 650                 655

Pro Gly Thr Asp Gly Pro Lys Gly Ala Ala Gly Pro Asp Gly Pro Pro
            660                 665                 670

Gly Ala Gln Gly Pro Pro Gly Leu Gln Gly Met Pro Gly Glu Arg Gly
            675                 680                 685

Ala Ala Gly Ile Ala Gly Pro Lys Gly Asp Arg Gly Asp Val Gly Glu
            690                 695                 700

Lys Gly Pro Glu Gly Ala Pro Gly Lys Asp Gly Gly Arg Gly Leu Thr
705                 710                 715                 720

Gly Pro Ile Gly Pro Pro Gly Pro Ala Gly Ala Asn Gly Glu Lys Gly
            725                 730                 735

Glu Val Gly Pro Pro Gly Pro Ser Gly Ser Thr Gly Ala Arg Gly Ala
            740                 745                 750

Pro Gly Glu Arg Gly Glu Thr Gly Pro Pro Gly Pro Ala Gly Phe Ala
            755                 760                 765

Gly Pro Pro Gly Ala Asp Gly Gln Pro Gly Ala Lys Gly Asp Gln Gly
            770                 775                 780

Glu Ala Gly Gln Lys Gly Asp Ala Gly Ala Pro Gly Pro Gln Gly Pro
785                 790                 795                 800

Ser Gly Ala Pro Gly Pro Gln Gly Pro Thr Gly Val Thr Gly Pro Lys
            805                 810                 815

Gly Ala Arg Gly Ala Gln Gly Pro Pro Gly Ala Thr Gly Phe Pro Gly
            820                 825                 830

Ala Ala Gly Arg Val Gly Pro Pro Gly Ala Asn Gly Asn Pro Gly Pro
            835                 840                 845

```
Ala Gly Pro Pro Gly Pro Ala Gly Lys Asp Gly Pro Lys Gly Val Arg
    850                 855                 860

Gly Asp Ser Gly Pro Pro Gly Arg Ala Gly Asp Pro Gly Leu Gln Gly
865                 870                 875                 880

Pro Ala Gly Ala Pro Gly Glu Lys Gly Glu Pro Gly Asp Asp Gly Pro
                885                 890                 895

Ser Gly Leu Asp Gly Pro Pro Gly Gln Gly Leu Ala Gly Gln Arg
                900                 905                 910

Gly Ile Val Gly Leu Pro Gly Gln Arg Gly Glu Arg Gly Phe Pro Gly
        915                 920                 925

Leu Pro Gly Pro Ser Gly Glu Pro Gly Lys Gln Gly Ala Pro Gly Ala
    930                 935                 940

Ser Gly Asp Arg Gly Pro Pro Gly Pro Val Gly Pro Pro Gly Leu Thr
945                 950                 955                 960

Gly Pro Ala Gly Glu Pro Gly Arg Glu Gly Ser Pro Gly Ala Asp Gly
                965                 970                 975

Pro Pro Gly Arg Asp Gly Ala Ala Gly Val Lys Gly Asp Arg Gly Glu
                980                 985                 990

Thr Gly Ala Leu Gly Ala Pro Gly  Ala Pro Gly Pro  Gly Ser Pro
        995                 1000                1005

Gly Pro  Ala Gly Pro Thr Gly  Lys Gln Gly Asp Arg  Gly Glu Ala
    1010                 1015                 1020

Gly Ala  Gln Gly Pro Met Gly  Pro Ser Gly Pro Ala  Gly Ala Arg
    1025                 1030                 1035

Gly Ile  Ala Gly Pro Gln Gly  Pro Arg Gly Asp Lys  Gly Glu Ser
    1040                 1045                 1050

Gly Glu  Gln Gly Glu Arg Gly  Leu Lys Gly His Arg  Gly Phe Thr
    1055                 1060                 1065

Gly Leu  Gln Gly Leu Pro Gly  Pro Pro Gly Pro Ser  Gly Asp Gln
    1070                 1075                 1080

Gly Ala  Ser Gly Pro Ala Gly  Pro Ser Gly Pro Arg  Gly Pro Pro
    1085                 1090                 1095

Gly Pro  Val Gly Pro Ser Gly  Lys Asp Gly Ser Asn  Gly Ile Pro
    1100                 1105                 1110

Gly Pro  Ile Gly Pro Pro Gly  Pro Arg Gly Arg Ser  Gly Glu Thr
    1115                 1120                 1125

Gly Pro  Val Gly Pro Pro Gly  Ser Pro Gly Pro Pro  Gly Pro Pro
    1130                 1135                 1140

Gly Pro  Pro Gly Pro Gly Ile  Asp Met Ser Ala Phe  Ala Gly Leu
    1145                 1150                 1155

Gly Gln  Arg Glu Lys Gly Pro  Asp Pro Met Gln Tyr  Met Arg Ala
    1160                 1165                 1170

Asp Glu  Ala Asp Ser Thr Leu  Arg Gln His Asp Val  Glu Val Asp
    1175                 1180                 1185

Ala Thr  Leu Lys Ser Leu Asn  Asn Gln Ile Glu Ser  Ile Arg Ser
    1190                 1195                 1200

Pro Asp  Gly Ser Arg Lys Asn  Pro Ala Arg Thr Cys  Gln Asp Leu
    1205                 1210                 1215

Lys Leu  Cys His Pro Glu Trp  Lys Ser Gly Asp Tyr  Trp Ile Asp
    1220                 1225                 1230

Pro Asn  Gln Gly Cys Thr Leu  Asp Ala Met Lys Val  Phe Cys Asn
    1235                 1240                 1245
```

```
Met Glu Thr Gly Glu Thr Cys Val Tyr Pro Asn Pro Ala Thr Val
1250                1255                1260

Pro Arg Lys Asn Trp Trp Ser Ser Lys Ser Lys Glu Lys Lys His
1265                1270                1275

Ile Trp Phe Gly Glu Thr Met Asn Gly Gly Phe His Phe Ser Tyr
1280                1285                1290

Gly Asp Gly Asn Leu Ala Pro Asn Thr Ala Asn Val Gln Met Thr
1295                1300                1305

Phe Leu Arg Leu Leu Ser Thr Glu Gly Ser Gln Asn Ile Thr Tyr
1310                1315                1320

His Cys Lys Asn Ser Ile Ala Tyr Leu Asp Glu Ala Ala Gly Asn
1325                1330                1335

Leu Lys Lys Ala Leu Leu Ile Gln Gly Ser Asn Asp Val Glu Met
1340                1345                1350

Arg Ala Glu Gly Asn Ser Arg Phe Thr Tyr Thr Ala Leu Lys Asp
1355                1360                1365

Gly Cys Thr Lys His Thr Gly Lys Trp Gly Lys Thr Val Ile Glu
1370                1375                1380

Tyr Arg Ser Gln Lys Thr Ser Arg Leu Pro Ile Ile Asp Ile Ala
1385                1390                1395

Pro Met Asp Ile Gly Gly Ala Glu Gln Glu Phe Gly Val Asp Ile
1400                1405                1410

Gly Pro Val Cys Phe Leu
1415

<210> SEQ ID NO 16
<211> LENGTH: 216
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (47)..(47)
<223> OTHER INFORMATION: Any amino acid

<400> SEQUENCE: 16

Asn Glu Ile Ala Xaa Ala Lys Ile Asp Leu Arg Gln Met Arg Thr Val
1               5                   10                  15

Thr Pro Ile Xaa Met Gln Gly Gly Cys Gly Ser Cys Trp Ala Leu Ser
            20                  25                  30

Gly Val Ala Ala Thr Glu Ser Ala Tyr Leu Ala Tyr Gly Asn Xaa Ser
        35                  40                  45

Leu Asp Leu Ala Glu Gln Glu Leu Val Asp Cys Ala Ser Gln His Gly
    50                  55                  60

Cys His Gly Asp Thr Ile Pro Arg Gly Ile Glu Tyr Ile Gln His Asn
65                  70                  75                  80

Gly Val Val Gln Glu Ser Tyr Tyr Arg Tyr Val Ala Arg Glu Gln Ser
                85                  90                  95

Cys Arg Arg Pro Asn Ala Gln Arg Phe Gly Ile Ser Asn Tyr Cys Gln
            100                 105                 110

Ile Tyr Pro Pro Asn Val Asn Lys Ile Arg Glu Ala Leu Ala Gln Thr
        115                 120                 125
```

```
His Ser Ala Ile Ala Val Ile Ile Gly Ile Lys Asp Leu Asp Ala Phe
    130                 135                 140

Arg His Tyr Asp Gly Arg Thr Ile Ile Gln Arg Asp Asn Gly Tyr Gln
145                 150                 155                 160

Pro Asn Tyr His Ala Val Asn Ile Val Gly Tyr Ser Asn Ala Gln Gly
                165                 170                 175

Val Asp Tyr Trp Ile Val Arg Asn Ser Trp Asp Thr Asn Trp Gly Asp
            180                 185                 190

Asn Gly Tyr Gly Tyr Phe Ala Ala Asn Ile Asp Leu Met Met Ile Glu
        195                 200                 205

Glu Tyr Pro Tyr Val Val Ile Leu
    210                 215

<210> SEQ ID NO 17
<211> LENGTH: 146
<212> TYPE: PRT
<213> ORGANISM: Homo sapiens

<400> SEQUENCE: 17

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 18
<211> LENGTH: 406
<212> TYPE: PRT
<213> ORGANISM: Homo sapiens

<400> SEQUENCE: 18

Met Asp Lys Ile Arg Tyr Arg Leu Val Tyr Asn Arg Gln Asn Thr Leu
1               5                   10                  15

Asn Arg Gln Gly Thr Ala Leu Val Gln Val Glu Ala Tyr Leu Asn Gln
            20                  25                  30

Arg Lys Ile Tyr Leu Lys Thr Asn Val Tyr Leu Lys Pro Glu Cys Trp
        35                  40                  45

Ser Arg Glu Gly Ala Gln Val Ile Asn His Pro Gln Ser Asn Glu Leu
    50                  55                  60

Asn Ile Met Leu Tyr Glu Tyr Ile Leu Tyr Leu Gln Gly Ile Glu Leu
65                  70                  75                  80
```

Gly Tyr Trp Lys Arg Gly Ile Pro Ala Thr Leu Ser Leu Leu Lys Asp
                85                  90                  95

Ala Val Lys Lys Ser Ala Val Asn Ile Ser Phe Ser Thr Phe Ala
            100                 105                 110

Lys Ser Ala Ile Asp Asn Ser Asp Lys Lys Gln Ser Thr Lys Asp Asn
        115                 120                 125

Leu His Ser Thr Leu Ala Val Leu His Asp Phe Arg Ser Gly Leu Asp
    130                 135                 140

Phe Lys Asp Leu Thr Tyr Thr Phe Leu Arg Asp Phe Glu Gln Tyr Leu
145                 150                 155                 160

Arg Glu Lys Gly Asn Ala Val Asn Thr Ile Ala Lys His Met Arg Gln
                165                 170                 175

Leu Arg Thr Leu Val Asn Glu Ala Ile Asn Gln Gly Tyr Met His Ala
            180                 185                 190

Asp Ala Tyr Pro Phe Arg Lys Tyr Lys Ile Lys Gln Glu Lys Gly Arg
        195                 200                 205

His Glu Phe Leu Thr Pro Asp Glu Leu Lys Lys Leu Glu Thr Val Glu
    210                 215                 220

Val Glu Glu Glu Ser Met Arg His Val Leu Asp Ala Phe Leu Phe Cys
225                 230                 235                 240

Cys Tyr Thr Gly Leu Arg Tyr Ser Asp Phe Cys Gln Leu Thr Pro Glu
                245                 250                 255

Asn Phe Ile Arg Ile Asn Gly Lys Arg Trp Leu Tyr Phe Lys Ser Val
            260                 265                 270

Lys Thr Gly Val Glu Ile Arg Leu Pro Leu His Leu Leu Phe Glu Ser
        275                 280                 285

Arg Ala Leu Gly Ile Leu Asp Arg Tyr Pro Asp Ile Gly Ser Phe Ala
290                 295                 300

Ala Leu Pro Cys Asn Ser Glu Val Asn Lys Gln Leu Arg Lys Leu Ala
305                 310                 315                 320

Gly Leu Cys Gly Ile Lys Lys Arg Ile Thr Tyr His Val Ser Arg His
                325                 330                 335

Thr Cys Ala Thr Leu Leu Ile His Gln Gly Val Ala Ile Thr Thr Val
            340                 345                 350

Gln Lys Leu Leu Gly His Thr Ser Val Lys Thr Thr Gln Ile Tyr Ser
        355                 360                 365

Glu Val Leu Ser Ser Thr Ile Val Arg Asp Leu Lys Asn Val Gln Lys
    370                 375                 380

Gly Lys Arg Lys Val Lys Met Phe Pro Asp Lys Gly Leu Arg Thr Ser
385                 390                 395                 400

Asp Phe Ile Asp Asn Arg
                405

<210> SEQ ID NO 19
<211> LENGTH: 459
<212> TYPE: PRT
<213> ORGANISM: Homo sapiens

<400> SEQUENCE: 19

Met Val Val Gln His Asn Leu Arg Ala Met Asn Ser Asn Arg Met Leu
1               5                   10                  15

Gly Ile Thr Gln Gly Ser Leu Asn Lys Ser Thr Glu Lys Leu Ser Ser
            20                  25                  30

Gly Tyr Lys Val Asn Arg Ala Ala Asp Asp Ala Ala Gly Leu Ser Ile

```
                35                  40                  45
Ser Glu Lys Met Arg Lys Gln Ile Arg Gly Leu Ser Gln Ala Ser Leu
 50                  55                  60
Asn Ala Glu Asp Gly Ile Ser Ala Val Gln Thr Ala Glu Gly Ala Leu
 65                  70                  75                  80
Thr Glu Val His Asp Met Leu Gln Arg Met Asn Glu Leu Ala Val Lys
                 85                  90                  95
Ala Ala Asn Gly Thr Asn Ser Thr Ser Asp Arg Gln Thr Ile Gln Asp
                100                 105                 110
Glu Val Asp Gln Leu Leu Thr Glu Ile Asp Arg Val Ala Glu Thr Thr
                115                 120                 125
Lys Phe Asn Glu Leu Tyr Thr Leu Lys Gly Asp Glu Asp Lys Val Thr
130                 135                 140
Arg Tyr Leu Ser Ala His Asp Ala Gly Ile Glu Gly Thr Leu Thr Gln
145                 150                 155                 160
Gly Ala Thr Asn Ala Thr Phe Ser Met Asp Gln Leu Lys Phe Gly Asp
                165                 170                 175
Thr Ile Met Ile Ala Gly Arg Glu Tyr His Ile Ser Gly Thr Lys Ala
                180                 185                 190
Glu Gln Ala Ala Ile Ile Thr Ala Ser Val Lys Ile Gly Gln Gln Val
                195                 200                 205
Thr Ile Asp Gly Ile Met Tyr Thr Cys Ser Ser Val Ser Asn Ala Asp
210                 215                 220
Lys Phe Glu Leu Lys Ser Glu Asp Leu Ile Ala Lys Leu Asp Thr Ser
225                 230                 235                 240
Ser Leu Ser Ile Met Ser Val Asn Gly Lys Thr Tyr Tyr Gly Ala Gly
                245                 250                 255
Ile Thr Asp Asp Arg Thr Val Val Ser Ser Ile Gly Ala Tyr Lys Leu
                260                 265                 270
Ile Gln Lys Glu Leu Gly Leu Ala Ser Ser Ile Gly Ala Asp Gly Ala
                275                 280                 285
Thr Gln Ala Ser Val Asn Ala Gly Val Asp Gly Lys Thr Leu Met Lys
                290                 295                 300
Pro Ser Phe Glu Gly Lys Trp Val Phe Ser Ile Asp Lys Gly Ser Val
305                 310                 315                 320
Gln Val Arg Glu Asp Ile Asp Phe Ser Leu His Val Gly Ala Asp Ala
                325                 330                 335
Asp Met Asn Asn Lys Ile Ala Val Lys Ile Gly Ala Leu Asp Thr Lys
                340                 345                 350
Gly Leu Gly Ile Gln Gly Leu Asn Val Lys Asp Thr Thr Gly Ala Ala
                355                 360                 365
Ala Thr Tyr Ala Ile Asp Ser Ile Ala Asp Ala Val Ala Arg Ile Ser
                370                 375                 380
Ala Gln Arg Ser Leu Leu Gly Ala Val Gln Asn Arg Leu Glu His Thr
385                 390                 395                 400
Ile Asn Asn Leu Asp Asn Val Val Glu Asn Thr Thr Ala Ala Glu Ser
                405                 410                 415
Gln Ile Arg Asp Thr Asp Met Ala Thr Glu Met Val Lys Tyr Ser Asn
                420                 425                 430
Asn Asn Val Leu Ala Gln Ala Gly Gln Ser Met Leu Ala Gln Ser Asn
                435                 440                 445
Gln Ala Asn Gln Gly Val Leu Gln Leu Gln
                450                 455
```

<210> SEQ ID NO 20
<211> LENGTH: 460
<212> TYPE: PRT
<213> ORGANISM: Homo sapiens

<400> SEQUENCE: 20

```
Met Val Val Gln His Asn Leu Arg Ala Met Asn Ser Asn Arg Met Leu
1               5                   10                  15

Gly Ile Thr Gln Gly Ser Leu Asn Lys Ser Thr Glu Lys Leu Ser Ser
            20                  25                  30

Gly Tyr Lys Val Asn Arg Ala Ala Asp Asp Ala Ala Gly Leu Ser Ile
        35                  40                  45

Ser Glu Lys Met Arg Lys Gln Ile Arg Gly Leu Ser Gln Ala Ser Leu
    50                  55                  60

Asn Ala Glu Asp Gly Ile Ser Ala Val Gln Thr Ala Glu Gly Ala Leu
65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Thr Leu Lys Gly Asp Glu Asp Lys Val Thr
    130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Gln Lys
            180                 185                 190

Gln Gln Gly Glu Ile Ile Thr Ser Ser Val Lys Ile Gly Gln Gln Val
        195                 200                 205

Thr Ile Asp Gly Ile Met Tyr Thr Cys Thr Ala Thr Val Ser Asn Ala
    210                 215                 220

Asp Lys Phe Glu Leu Thr Lys Asp Asp Leu Ile Ala Lys Leu Asp Thr
225                 230                 235                 240

Ser Ser Leu Ser Ile Met Ser Val Asn Gly Lys Thr Tyr Tyr Gly Ala
                245                 250                 255

Gly Ile Thr Asp Asp Arg Thr Val Val Ser Ser Ile Gly Ala Tyr Lys
            260                 265                 270

Leu Ile Gln Lys Glu Leu Gly Leu Ala Ser Ser Ile Gly Ala Asp Gly
        275                 280                 285

Ser Thr Gln Ala Ser Val Asn Ala Gly Val Asp Gly Lys Thr Leu Lys
    290                 295                 300

Lys Pro Ser Phe Glu Gly Lys Trp Val Phe Ser Ile Asp Lys Gly Ser
305                 310                 315                 320

Val Gln Val Arg Glu Asp Ile Asp Phe Ser Leu His Val Gly Ala Asp
                325                 330                 335

Ala Asp Met Asn Asn Lys Ile Ala Val Lys Ile Gly Ala Leu Asp Thr
            340                 345                 350

Lys Gly Leu Gly Ile Gln Gly Leu Asn Val Lys Asp Thr Thr Gly Ala
        355                 360                 365

Ala Ala Thr Tyr Ala Ile Asp Ser Ile Ala Asp Ala Val Ala Arg Ile
```

```
                    370                 375                 380
Ser Ala Gln Arg Ser Leu Leu Gly Ala Val Gln Asn Arg Leu Glu His
385                 390                 395                 400

Thr Ile Asn Asn Leu Asp Asn Val Val Glu Asn Thr Thr Ala Ala Glu
                405                 410                 415

Ser Gln Ile Arg Asp Thr Asp Met Ala Thr Glu Met Val Lys Tyr Ser
            420                 425                 430

Asn Asn Asn Val Leu Ala Gln Ala Gly Gln Ser Met Leu Ala Gln Ser
        435                 440                 445

Asn Gln Ala Asn Gln Gly Val Leu Ser Leu Leu Gly
    450                 455                 460

<210> SEQ ID NO 21
<211> LENGTH: 218
<212> TYPE: PRT
<213> ORGANISM: Homo sapiens

<400> SEQUENCE: 21

Met Lys Leu Asn Phe Lys Gly Phe Phe Lys Ala Ala Gly Leu Phe Pro
1               5                   10                  15

Leu Ala Leu Met Leu Ser Gly Cys Ile Ser Tyr Ala Leu Val Ser His
            20                  25                  30

Thr Ala Lys Gly Ser Ser Gly Lys Tyr Gln Ser Gln Ser Asp Thr Ile
        35                  40                  45

Thr Gly Leu Ser Gln Ala Lys Asp Ser Asn Gly Thr Lys Gly Tyr Val
    50                  55                  60

Phe Val Gly Glu Ser Leu Asp Tyr Leu Ile Thr Asp Gly Ala Asp Asp
65                  70                  75                  80

Ile Val Lys Met Leu Asn Asp Pro Ala Leu Asn Arg His Asn Ile Gln
                85                  90                  95

Val Ala Asp Asp Ala Arg Phe Val Leu Asn Ala Gly Lys Lys Lys Phe
            100                 105                 110

Thr Gly Thr Ile Ser Leu Tyr Tyr Tyr Trp Asn Asn Glu Glu Glu Lys
        115                 120                 125

Ala Leu Ala Thr His Tyr Gly Phe Ala Cys Gly Val Gln His Cys Thr
    130                 135                 140

Arg Ser Leu Glu Asn Leu Lys Gly Thr Ile His Glu Lys Asn Lys Asn
145                 150                 155                 160

Met Asp Tyr Ser Lys Val Met Ala Phe Tyr His Pro Phe Lys Val Arg
                165                 170                 175

Phe Tyr Glu Tyr Tyr Ser Pro Arg Gly Ile Pro Asp Gly Val Ser Ala
            180                 185                 190

Ala Leu Leu Pro Val Thr Val Thr Leu Asp Ile Ile Thr Ala Pro Leu
        195                 200                 205

Gln Phe Leu Val Val Tyr Ala Val Asn Gln
    210                 215

<210> SEQ ID NO 22
<211> LENGTH: 412
<212> TYPE: PRT
<213> ORGANISM: Homo sapiens

<400> SEQUENCE: 22

Met Gly Gln Asp Gln Thr Lys Gln Gln Ile Glu Lys Gly Leu Gln Leu
1               5                   10                  15

Tyr Gln Ser Asn Gln Thr Glu Lys Ala Leu Gln Val Trp Thr Lys Val
```

```
                20                  25                  30
Leu Glu Lys Ser Ser Asp Leu Met Gly Arg Phe Arg Val Leu Gly Cys
            35                  40                  45
Leu Val Thr Ala His Ser Glu Met Gly Arg Tyr Lys Glu Met Leu Lys
         50                  55                  60
Phe Ala Val Val Gln Ile Asp Thr Ala Arg Glu Leu Glu Asp Ala Asp
 65                  70                  75                  80
Phe Leu Leu Glu Ser Tyr Leu Asn Leu Ala Arg Ser Asn Glu Lys Leu
                 85                  90                  95
Cys Glu Phe His Lys Thr Ile Ser Tyr Cys Lys Thr Cys Leu Gly Leu
            100                 105                 110
Pro Gly Thr Arg Ala Gly Ala Gln Leu Gly Gly Gln Val Ser Leu Ser
            115                 120                 125
Met Gly Asn Ala Phe Leu Gly Leu Ser Val Phe Gln Lys Ala Leu Glu
        130                 135                 140
Ser Phe Glu Lys Ala Leu Arg Tyr Ala His Asn Asn Asp Asp Ala Met
145                 150                 155                 160
Leu Glu Cys Arg Val Cys Cys Ser Leu Gly Ser Phe Tyr Ala Gln Val
                165                 170                 175
Lys Asp Tyr Glu Lys Ala Leu Phe Phe Pro Cys Lys Ala Ala Glu Leu
            180                 185                 190
Val Asn Asn Tyr Gly Lys Gly Trp Ser Leu Lys Tyr Arg Ala Met Ser
            195                 200                 205
Gln Tyr His Met Ala Val Ala Tyr Arg Leu Leu Gly Arg Leu Gly Ser
        210                 215                 220
Ala Met Glu Cys Cys Glu Glu Ser Met Lys Ile Ala Leu Gln His Gly
225                 230                 235                 240
Asp Arg Pro Leu Gln Ala Leu Cys Leu Leu Cys Phe Ala Asp Ile His
                245                 250                 255
Arg Ser Arg Gly Asp Leu Glu Thr Ala Phe Pro Arg Tyr Asp Ser Ala
            260                 265                 270
Met Ser Ile Met Thr Glu Ile Gly Asn Arg Leu Gly Gln Val Gln Ala
            275                 280                 285
Leu Leu Gly Val Ala Lys Cys Trp Val Ala Arg Lys Ala Leu Asp Lys
        290                 295                 300
Ala Leu Asp Ala Ile Glu Arg Ala Gln Asp Leu Ala Glu Glu Val Gly
305                 310                 315                 320
Asn Lys Leu Ser Gln Leu Lys Leu His Cys Leu Ser Glu Ser Ile Tyr
                325                 330                 335
Arg Ser Lys Gly Leu Gln Arg Glu Leu Arg Ala His Val Val Arg Phe
            340                 345                 350
His Glu Cys Val Glu Glu Thr Glu Leu Tyr Cys Gly Leu Cys Gly Glu
            355                 360                 365
Ser Ile Gly Glu Lys Asn Ser Arg Leu Gln Ala Leu Pro Cys Ser His
        370                 375                 380
Ile Phe His Leu Arg Cys Leu Gln Asn Asn Gly Thr Arg Ser Cys Pro
385                 390                 395                 400
Asn Cys Arg Arg Ser Ser Met Lys Pro Gly Phe Val
                405                 410

<210> SEQ ID NO 23
<211> LENGTH: 493
<212> TYPE: PRT
<213> ORGANISM: Homo sapiens
```

<400> SEQUENCE: 23

Met Ala Arg Ala Pro Leu Gly Val Leu Leu Leu Gly Leu Leu Gly
1               5                   10                  15

Arg Gly Val Gly Lys Asn Glu Glu Leu Arg Leu Tyr His His Leu Phe
            20                  25                  30

Asn Asn Tyr Asp Pro Gly Ser Arg Pro Val Arg Glu Pro Glu Asp Thr
            35                  40                  45

Val Thr Ile Ser Leu Lys Val Thr Leu Thr Asn Leu Ile Ser Leu Asn
    50                  55                  60

Glu Lys Glu Glu Thr Leu Thr Thr Ser Val Trp Ile Gly Ile Asp Trp
65                  70                  75                  80

Gln Asp Tyr Arg Leu Asn Tyr Ser Lys Asp Asp Phe Gly Gly Ile Glu
                85                  90                  95

Thr Leu Arg Val Pro Ser Glu Leu Val Trp Leu Pro Glu Ile Val Leu
            100                 105                 110

Glu Asn Asn Ile Asp Gly Gln Phe Gly Val Ala Tyr Asp Ala Asn Val
            115                 120                 125

Leu Val Tyr Glu Gly Gly Ser Val Thr Trp Leu Pro Pro Ala Ile Tyr
    130                 135                 140

Arg Ser Val Cys Ala Val Glu Val Thr Tyr Phe Pro Phe Asp Trp Gln
145                 150                 155                 160

Asn Cys Ser Leu Ile Phe Arg Ser Gln Thr Tyr Asn Ala Glu Glu Val
                165                 170                 175

Glu Phe Thr Phe Ala Val Asp Asn Asp Gly Lys Thr Ile Asn Lys Ile
            180                 185                 190

Asp Ile Asp Thr Glu Ala Tyr Thr Glu Asn Gly Glu Trp Ala Ile Asp
            195                 200                 205

Phe Cys Pro Gly Val Ile Arg Arg His His Gly Gly Ala Thr Asp Gly
    210                 215                 220

Pro Gly Glu Thr Asp Val Ile Tyr Ser Leu Ile Ile Arg Arg Lys Pro
225                 230                 235                 240

Leu Phe Tyr Val Ile Asn Ile Ile Val Pro Cys Val Leu Ile Ser Gly
                245                 250                 255

Leu Val Leu Leu Ala Tyr Phe Leu Pro Ala Gln Ala Gly Gly Gln Lys
            260                 265                 270

Cys Thr Val Ser Ile Asn Val Leu Leu Ala Gln Thr Val Phe Leu Phe
            275                 280                 285

Leu Ile Ala Gln Lys Ile Pro Glu Thr Ser Leu Ser Val Pro Leu Leu
    290                 295                 300

Gly Arg Phe Leu Ile Phe Val Met Val Val Ala Thr Leu Ile Val Met
305                 310                 315                 320

Asn Cys Val Ile Val Leu Asn Val Ser Gln Arg Thr Pro Thr Thr His
                325                 330                 335

Ala Met Ser Pro Arg Leu Arg His Val Leu Leu Glu Leu Leu Pro Arg
            340                 345                 350

Leu Leu Gly Ser Pro Pro Pro Glu Ala Pro Arg Ala Ala Ser Pro
            355                 360                 365

Pro Arg Arg Ala Ser Ser Val Gly Leu Leu Leu Arg Ala Glu Glu Leu
            370                 375                 380

Ile Leu Lys Lys Pro Arg Ser Glu Leu Val Phe Glu Gly Gln Arg His
385                 390                 395                 400

Arg Gln Gly Thr Trp Thr Ala Ala Phe Cys Gln Ser Leu Gly Ala Ala

```
            405                 410                 415
Ala Pro Glu Val Arg Cys Cys Val Asp Ala Val Asn Phe Val Ala Glu
            420                 425                 430

Ser Thr Arg Asp Gln Glu Ala Thr Gly Glu Glu Val Ser Asp Trp Val
            435                 440                 445

Arg Met Gly Asn Ala Leu Asp Asn Ile Cys Phe Trp Ala Ala Leu Val
        450                 455                 460

Leu Phe Ser Val Gly Ser Ser Leu Ile Phe Leu Gly Ala Tyr Phe Asn
465                 470                 475                 480

Arg Val Pro Asp Leu Pro Tyr Ala Pro Cys Ile Gln Pro
                485                 490
```

<210> SEQ ID NO 24
<211> LENGTH: 482
<212> TYPE: PRT
<213> ORGANISM: Homo sapiens

<400> SEQUENCE: 24

```
Met Glu Pro Trp Pro Leu Leu Leu Phe Ser Leu Cys Ser Ala Gly
1               5                   10                  15

Leu Val Leu Gly Ser Glu His Glu Thr Arg Leu Val Ala Lys Leu Phe
            20                  25                  30

Lys Asp Tyr Ser Ser Val Val Arg Pro Val Glu Asp His Arg Gln Val
        35                  40                  45

Val Glu Val Thr Val Gly Leu Gln Leu Ile Gln Leu Ile Asn Val Asp
    50                  55                  60

Glu Val Asn Gln Ile Val Thr Thr Asn Val Arg Leu Lys Gln Gly Asp
65                  70                  75                  80

Met Val Asp Leu Pro Arg Pro Ser Cys Val Thr Leu Gly Val Pro Leu
                85                  90                  95

Phe Ser His Leu Gln Asn Glu Gln Trp Val Asp Tyr Asn Leu Lys Trp
            100                 105                 110

Asn Pro Asp Asp Tyr Gly Gly Val Lys Lys Ile His Ile Pro Ser Glu
        115                 120                 125

Lys Ile Trp Arg Pro Asp Leu Val Leu Tyr Asn Asn Ala Asp Gly Asp
    130                 135                 140

Phe Ala Ile Val Lys Phe Thr Lys Val Leu Leu Gln Tyr Thr Gly His
145                 150                 155                 160

Ile Thr Trp Thr Pro Pro Ala Ile Phe Lys Ser Tyr Cys Glu Ile Ile
                165                 170                 175

Val Thr His Phe Pro Phe Asp Glu Gln Asn Cys Ser Met Lys Leu Gly
            180                 185                 190

Thr Trp Thr Tyr Asp Gly Ser Val Val Ala Ile Asn Pro Glu Ser Asp
        195                 200                 205

Gln Pro Asp Leu Ser Asn Phe Met Glu Ser Gly Glu Trp Val Ile Lys
    210                 215                 220

Glu Ser Arg Gly Trp Lys His Ser Val Thr Tyr Ser Cys Cys Pro Asp
225                 230                 235                 240

Thr Pro Tyr Leu Asp Ile Thr Tyr His Phe Val Met Gln Arg Leu Pro
                245                 250                 255

Leu Tyr Phe Ile Val Asn Val Ile Ile Pro Cys Leu Leu Phe Ser Phe
            260                 265                 270

Leu Thr Gly Leu Val Phe Tyr Leu Pro Thr Asp Ser Gly Glu Lys Met
        275                 280                 285
```

```
Thr Leu Ser Ile Ser Val Leu Leu Ser Leu Thr Val Phe Leu Leu Val
    290                 295                 300

Ile Val Glu Leu Ile Pro Ser Thr Ser Ser Ala Val Pro Leu Ile Gly
305                 310                 315                 320

Lys Tyr Met Leu Phe Thr Met Val Phe Val Ile Ala Ser Ile Ile Ile
                325                 330                 335

Thr Val Ile Val Ile Asn Thr His His Arg Ser Pro Ser Thr His Val
            340                 345                 350

Met Pro Asn Trp Val Arg Lys Val Phe Ile Asp Thr Ile Pro Asn Ile
        355                 360                 365

Met Phe Phe Ser Thr Met Lys Arg Pro Ser Arg Glu Lys Gln Asp Lys
    370                 375                 380

Lys Ile Phe Thr Glu Asp Ile Asp Ile Ser Asp Ile Ser Gly Lys Pro
385                 390                 395                 400

Gly Pro Pro Pro Met Gly Phe His Ser Pro Leu Ile Lys His Pro Glu
                405                 410                 415

Val Lys Ser Ala Ile Glu Gly Ile Lys Tyr Ile Ala Glu Thr Met Lys
            420                 425                 430

Ser Asp Gln Glu Ser Asn Asn Ala Ala Ala Glu Trp Lys Tyr Val Ala
        435                 440                 445

Met Val Met Asp His Ile Leu Leu Gly Val Phe Met Leu Val Cys Ile
    450                 455                 460

Ile Gly Thr Leu Ala Val Phe Ala Gly Arg Leu Ile Glu Leu Asn Gln
465                 470                 475                 480

Gln Gly

<210> SEQ ID NO 25
<211> LENGTH: 517
<212> TYPE: PRT
<213> ORGANISM: Homo sapiens

<400> SEQUENCE: 25

Met His Gly Gly Gln Gly Pro Leu Leu Leu Leu Leu Leu Leu Ala Val
1               5                   10                  15

Cys Leu Gly Ala Gln Gly Arg Asn Gln Glu Gly Arg Leu Leu Ala Asp
                20                  25                  30

Leu Met Gln Asn Tyr Asp Pro Asn Leu Arg Pro Ala Glu Arg Asp Ser
            35                  40                  45

Asp Val Val Asn Val Ser Leu Lys Leu Thr Leu Thr Asn Leu Ile Ser
50                  55                  60

Leu Asn Glu Arg Glu Glu Ala Leu Thr Thr Asn Val Trp Ile Glu Met
65                  70                  75                  80

Gln Trp Cys Asp Tyr Arg Leu Arg Trp Asp Pro Arg Asp Tyr Glu Gly
                85                  90                  95

Leu Trp Val Leu Arg Val Pro Ser Thr Met Val Trp Arg Pro Asp Ile
                100                 105                 110

Val Leu Glu Asn Asn Val Asp Gly Val Phe Glu Val Ala Leu Tyr Cys
            115                 120                 125

Asn Val Leu Val Ser Pro Asp Gly Cys Ile Tyr Trp Leu Pro Pro Ala
130                 135                 140

Ile Phe Arg Ser Ala Cys Ser Ile Ser Val Thr Tyr Phe Pro Phe Asp
145                 150                 155                 160

Trp Gln Asn Cys Ser Leu Ile Phe Gln Ser Gln Thr Tyr Ser Thr Asn
                165                 170                 175
```

```
Glu Ile Asp Leu Gln Leu Ser Gln Glu Asp Gly Gln Thr Ile Glu Trp
            180                 185                 190
Ile Phe Ile Asp Pro Glu Ala Phe Thr Glu Asn Gly Glu Trp Ala Ile
            195                 200                 205
Gln His Arg Pro Ala Lys Met Leu Leu Asp Pro Ala Ala Pro Ala Gln
            210                 215                 220
Glu Ala Gly His Gln Lys Val Val Phe Tyr Leu Leu Ile Gln Arg Lys
225                 230                 235                 240
Pro Leu Phe Tyr Val Ile Asn Ile Ile Ala Pro Cys Val Leu Ile Ser
                245                 250                 255
Ser Val Ala Ile Leu Ile His Phe Leu Pro Ala Lys Ala Gly Gly Gln
                260                 265                 270
Lys Cys Thr Val Ala Ile Asn Val Leu Leu Ala Gln Thr Val Phe Leu
                275                 280                 285
Phe Leu Val Ala Lys Lys Val Pro Glu Thr Ser Gln Ala Val Pro Leu
            290                 295                 300
Ile Ser Lys Tyr Leu Thr Phe Leu Leu Val Val Thr Ile Leu Ile Val
305                 310                 315                 320
Val Asn Ala Val Val Val Leu Asn Val Ser Leu Arg Ser Pro His Thr
                325                 330                 335
His Ser Met Ala Arg Gly Val Arg Lys Val Phe Leu Arg Leu Leu Pro
                340                 345                 350
Gln Leu Leu Arg Met His Val Arg Pro Leu Ala Pro Ala Ala Val Gln
                355                 360                 365
Asp Thr Gln Ser Arg Leu Gln Asn Gly Ser Ser Gly Trp Ser Ile Thr
            370                 375                 380
Thr Gly Glu Glu Val Ala Leu Cys Leu Pro Arg Ser Glu Leu Leu Phe
385                 390                 395                 400
Gln Gln Trp Gln Arg Gln Gly Leu Val Ala Ala Leu Glu Lys Leu
                405                 410                 415
Glu Lys Gly Pro Glu Leu Gly Leu Ser Gln Phe Cys Gly Ser Leu Lys
            420                 425                 430
Gln Ala Ala Pro Ala Ile Gln Ala Cys Val Glu Ala Cys Asn Leu Ile
            435                 440                 445
Ala Cys Ala Arg His Gln Gln Ser His Phe Asp Asn Gly Asn Glu Glu
450                 455                 460
Trp Phe Leu Val Gly Arg Val Leu Asp Arg Val Cys Phe Leu Ala Met
465                 470                 475                 480
Leu Ser Leu Phe Ile Cys Gly Thr Ala Gly Ile Phe Leu Met Ala His
                485                 490                 495
Tyr Asn Arg Val Pro Ala Leu Pro Phe Pro Gly Asp Pro Arg Pro Tyr
            500                 505                 510
Leu Pro Ser Pro Asp
            515

<210> SEQ ID NO 26
<211> LENGTH: 501
<212> TYPE: PRT
<213> ORGANISM: Homo sapiens

<400> SEQUENCE: 26

Met Thr Pro Gly Ala Leu Leu Met Leu Leu Gly Ala Leu Gly Ala Pro
1               5                   10                  15
Leu Ala Pro Gly Val Arg Gly Ser Glu Ala Glu Gly Arg Leu Arg Glu
            20                  25                  30
```

```
Lys Leu Phe Ser Gly Tyr Asp Ser Val Arg Pro Ala Arg Glu Val
         35                  40                  45
Gly Asp Arg Val Arg Val Ser Val Gly Leu Ile Leu Ala Gln Leu Ile
 50                  55                  60
Ser Leu Asn Glu Lys Asp Glu Glu Met Ser Thr Lys Val Tyr Leu Asp
 65                  70                  75                  80
Leu Glu Trp Thr Asp Tyr Arg Leu Ser Trp Asp Pro Ala Glu His Asp
                 85                  90                  95
Gly Ile Asp Ser Leu Arg Ile Thr Ala Glu Ser Val Trp Leu Pro Asp
                100                 105                 110
Val Val Leu Leu Asn Asn Asn Asp Gly Asn Phe Asp Val Ala Leu Asp
                115                 120                 125
Ile Ser Val Val Ser Ser Asp Gly Ser Val Arg Trp Gln Pro Pro
                130                 135                 140
Gly Ile Tyr Arg Ser Ser Cys Ser Ile Gln Val Thr Tyr Phe Pro Phe
145                 150                 155                 160
Asp Trp Gln Asn Cys Thr Met Val Phe Ser Ser Tyr Ser Tyr Asp Ser
                165                 170                 175
Ser Glu Val Ser Leu Gln Thr Gly Leu Gly Pro Asp Gly Gln Gly His
                180                 185                 190
Gln Glu Ile His Ile His Glu Gly Thr Phe Ile Glu Asn Gly Gln Trp
                195                 200                 205
Glu Ile Ile His Lys Pro Ser Arg Leu Ile Gln Pro Pro Gly Asp Pro
                210                 215                 220
Arg Gly Gly Arg Glu Gly Gln Arg Gln Glu Val Ile Phe Tyr Leu Ile
225                 230                 235                 240
Ile Arg Arg Lys Pro Leu Phe Tyr Leu Val Asn Val Ile Ala Pro Cys
                245                 250                 255
Ile Leu Ile Thr Leu Leu Ala Ile Phe Val Phe Tyr Leu Pro Pro Asp
                260                 265                 270
Ala Gly Glu Lys Met Gly Leu Ser Ile Phe Ala Leu Leu Thr Leu Thr
                275                 280                 285
Val Phe Leu Leu Leu Leu Ala Asp Lys Val Pro Glu Thr Ser Leu Ser
                290                 295                 300
Val Pro Ile Ile Ile Lys Tyr Leu Met Phe Thr Met Val Leu Val Thr
305                 310                 315                 320
Phe Ser Val Ile Leu Ser Val Val Leu Asn Leu His His Arg Ser
                325                 330                 335
Pro His Thr His Gln Met Pro Leu Trp Val Arg Gln Ile Phe Ile His
                340                 345                 350
Lys Leu Pro Leu Tyr Leu Arg Leu Lys Arg Pro Lys Pro Glu Arg Asp
                355                 360                 365
Leu Met Pro Glu Pro Pro His Cys Ser Ser Pro Gly Ser Gly Trp Gly
370                 375                 380
Arg Gly Thr Asp Glu Tyr Phe Ile Arg Lys Pro Pro Ser Asp Phe Leu
385                 390                 395                 400
Phe Pro Lys Pro Asn Arg Phe Gln Pro Glu Leu Ser Ala Pro Asp Leu
                405                 410                 415
Arg Arg Phe Ile Asp Gly Pro Asn Arg Ala Val Ala Leu Leu Pro Glu
                420                 425                 430
Leu Arg Glu Val Val Ser Ser Ile Ser Tyr Ile Ala Arg Gln Leu Gln
                435                 440                 445
```

```
Glu Gln Glu Asp His Asp Ala Leu Lys Glu Asp Trp Gln Phe Val Ala
450                 455                 460

Met Val Val Asp Arg Leu Phe Leu Trp Thr Phe Ile Ile Phe Thr Ser
465                 470                 475                 480

Val Gly Thr Leu Val Ile Phe Leu Asp Ala Thr Tyr His Leu Pro Pro
                485                 490                 495

Pro Asp Pro Phe Pro
            500

<210> SEQ ID NO 27
<211> LENGTH: 517
<212> TYPE: PRT
<213> ORGANISM: Homo sapiens

<400> SEQUENCE: 27

Met Glu Gly Pro Val Leu Thr Leu Gly Leu Leu Ala Ala Leu Ala Val
1               5                   10                  15

Cys Gly Ser Trp Gly Leu Asn Glu Glu Glu Arg Leu Ile Arg His Leu
                20                  25                  30

Phe Gln Glu Lys Gly Tyr Asn Lys Glu Leu Arg Pro Val Ala His Lys
            35                  40                  45

Glu Glu Ser Val Asp Val Ala Leu Ala Leu Thr Leu Ser Asn Leu Ile
50                  55                  60

Ser Leu Lys Glu Val Glu Glu Thr Leu Thr Thr Asn Val Trp Ile Glu
65                  70                  75                  80

His Gly Trp Thr Asp Asn Arg Leu Lys Trp Asn Ala Glu Glu Phe Gly
                85                  90                  95

Asn Ile Ser Val Leu Arg Leu Pro Pro Asp Met Val Trp Leu Pro Glu
            100                 105                 110

Ile Val Leu Glu Asn Asn Asn Asp Gly Ser Phe Gln Ile Ser Tyr Ser
        115                 120                 125

Cys Asn Val Leu Val Tyr His Tyr Gly Phe Val Tyr Trp Leu Pro Pro
130                 135                 140

Ala Ile Phe Arg Ser Ser Cys Pro Ile Ser Val Thr Tyr Phe Pro Phe
145                 150                 155                 160

Asp Trp Gln Asn Cys Ser Leu Lys Phe Ser Ser Leu Lys Tyr Thr Ala
                165                 170                 175

Lys Glu Ile Thr Leu Ser Leu Lys Gln Asp Ala Lys Glu Asn Arg Thr
            180                 185                 190

Tyr Pro Val Glu Trp Ile Ile Ile Asp Pro Glu Gly Phe Thr Glu Asn
        195                 200                 205

Gly Glu Trp Glu Ile Val His Arg Pro Ala Arg Val Asn Val Asp Pro
210                 215                 220

Arg Ala Pro Leu Asp Ser Pro Ser Arg Gln Asp Ile Thr Phe Tyr Leu
225                 230                 235                 240

Ile Ile Arg Arg Lys Pro Leu Phe Tyr Ile Ile Asn Ile Leu Val Pro
                245                 250                 255

Cys Val Leu Ile Ser Phe Met Val Asn Leu Val Phe Tyr Leu Pro Ala
            260                 265                 270

Asp Ser Gly Glu Lys Thr Ser Val Ala Ile Ser Val Leu Leu Ala Gln
        275                 280                 285

Ser Val Phe Leu Leu Leu Ile Ser Lys Arg Leu Pro Ala Thr Ser Met
290                 295                 300

Ala Ile Pro Leu Ile Gly Lys Phe Leu Leu Phe Gly Met Val Leu Val
305                 310                 315                 320
```

```
Thr Met Val Val Val Ile Cys Val Ile Val Leu Asn Ile His Phe Arg
                325                 330                 335

Thr Pro Ser Thr His Val Leu Ser Glu Gly Val Lys Lys Leu Phe Leu
                340                 345                 350

Glu Thr Leu Pro Glu Leu Leu His Met Ser Arg Pro Ala Glu Asp Gly
                355                 360                 365

Pro Ser Pro Gly Ala Leu Val Arg Arg Ser Ser Leu Gly Tyr Ile
        370                 375                 380

Ser Lys Ala Glu Glu Tyr Phe Leu Leu Lys Ser Arg Ser Asp Leu Met
385                 390                 395                 400

Phe Glu Lys Gln Ser Glu Arg His Gly Leu Ala Arg Arg Leu Thr Thr
                405                 410                 415

Ala Arg Arg Pro Pro Ala Ser Ser Glu Gln Ala Gln Gln Glu Leu Phe
                420                 425                 430

Asn Glu Leu Lys Pro Ala Val Asp Gly Ala Asn Phe Ile Val Asn His
                435                 440                 445

Met Arg Asp Gln Asn Asn Tyr Asn Glu Glu Lys Asp Ser Trp Asn Arg
        450                 455                 460

Val Ala Arg Thr Val Asp Arg Leu Cys Leu Phe Val Val Thr Pro Val
465                 470                 475                 480

Met Val Val Gly Thr Ala Trp Ile Phe Leu Gln Gly Val Tyr Asn Gln
                485                 490                 495

Pro Pro Pro Gln Pro Phe Pro Gly Asp Pro Tyr Ser Tyr Asn Val Gln
                500                 505                 510

Asp Lys Arg Phe Ile
        515

<210> SEQ ID NO 28
<211> LENGTH: 933
<212> TYPE: PRT
<213> ORGANISM: Homo sapiens

<400> SEQUENCE: 28

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
                20                  25                  30

Lys Pro Glu Glu Ser Arg Val Ser Val Leu Glu Ser Lys Arg
                35                  40                  45

Leu Val Asp Thr Ala Met Tyr Ala Thr Met Gln Arg Asn Leu Lys Lys
    50                  55                  60

Arg Gly Ile Leu Ser Pro Ala Gln Leu Leu Ser Phe Ser Lys Leu Pro
65                  70                  75                  80

Glu Pro Thr Ser Gly Val Ile Ala Arg Ala Ala Glu Ile Met Glu Thr
                85                  90                  95

Ser Ile Gln Ala Met Lys Arg Lys Val Asn Leu Lys Thr Gln Gln Ser
                100                 105                 110

Gln His Pro Thr Asp Ala Leu Ser Glu Asp Leu Leu Ser Ile Ile Ala
                115                 120                 125

Asn Met Ser Gly Cys Leu Pro Tyr Met Leu Pro Lys Cys Pro Asn
        130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
```

```
                165                 170                 175
Leu Pro Pro Val Tyr Glu Asp Gly Phe Ser Gln Pro Arg Gly Trp Asn
                180                 185                 190
Pro Gly Phe Leu Tyr Asn Gly Phe Pro Leu Pro Pro Val Arg Glu Val
                195                 200                 205
Thr Arg His Val Ile Gln Val Ser Asn Glu Val Val Thr Asp Asp Asp
                210                 215                 220
Arg Tyr Ser Asp Leu Leu Met Ala Trp Gly Gln Tyr Ile Asp His Asp
225                 230                 235                 240
Ile Ala Phe Thr Pro Gln Ser Thr Ser Lys Ala Ala Phe Gly Gly Gly
                245                 250                 255
Ala Asp Cys Gln Met Thr Cys Glu Asn Gln Asn Pro Cys Phe Pro Ile
                260                 265                 270
Gln Leu Pro Glu Glu Ala Arg Pro Ala Ala Gly Thr Ala Cys Leu Pro
                275                 280                 285
Phe Tyr Arg Ser Ser Ala Ala Cys Gly Thr Gly Asp Gln Gly Ala Leu
                290                 295                 300
Phe Gly Asn Leu Ser Thr Ala Asn Pro Arg Gln Gln Met Asn Gly Leu
305                 310                 315                 320
Thr Ser Phe Leu Asp Ala Ser Thr Val Tyr Gly Ser Ser Pro Ala Leu
                325                 330                 335
Glu Arg Gln Leu Arg Asn Trp Thr Ser Ala Glu Gly Leu Leu Arg Val
                340                 345                 350
His Ala Arg Leu Arg Asp Ser Gly Arg Ala Tyr Leu Pro Phe Val Pro
                355                 360                 365
Pro Arg Ala Pro Ala Ala Cys Ala Pro Glu Pro Gly Ile Pro Gly Glu
                370                 375                 380
Thr Arg Gly Pro Cys Phe Leu Ala Gly Asp Gly Arg Ala Ser Glu Val
385                 390                 395                 400
Pro Ser Leu Thr Ala Leu His Thr Leu Trp Leu Arg Glu His Asn Arg
                405                 410                 415
Leu Ala Ala Ala Leu Lys Ala Leu Asn Ala His Trp Ser Ala Asp Ala
                420                 425                 430
Val Tyr Gln Glu Ala Arg Lys Val Val Gly Ala Leu His Gln Ile Ile
                435                 440                 445
Thr Leu Arg Asp Tyr Ile Pro Arg Ile Leu Gly Pro Glu Ala Phe Gln
                450                 455                 460
Gln Tyr Val Gly Pro Tyr Glu Gly Tyr Asp Ser Thr Ala Asn Pro Thr
465                 470                 475                 480
Val Ser Asn Val Phe Ser Thr Ala Ala Phe Arg Phe Gly His Ala Thr
                485                 490                 495
Ile His Pro Leu Val Arg Arg Leu Asp Ala Ser Phe Gln Glu His Pro
                500                 505                 510
Asp Leu Pro Gly Leu Trp Leu His Gln Ala Phe Phe Ser Pro Trp Thr
                515                 520                 525
Leu Leu Arg Gly Gly Gly Leu Asp Pro Leu Ile Arg Gly Leu Leu Ala
                530                 535                 540
Arg Pro Ala Lys Leu Gln Val Gln Asp Gln Leu Met Asn Glu Glu Leu
545                 550                 555                 560
Thr Glu Arg Leu Phe Val Leu Ser Asn Ser Ser Thr Leu Asp Leu Ala
                565                 570                 575
Ser Ile Asn Leu Gln Arg Gly Arg Asp His Gly Leu Pro Gly Tyr Asn
                580                 585                 590
```

-continued

```
Glu Trp Arg Glu Phe Cys Gly Leu Pro Arg Leu Glu Thr Pro Ala Asp
            595                 600                 605

Leu Ser Thr Ala Ile Ala Ser Arg Val Ala Asp Lys Ile Leu Asp
610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
                645                 650                 655

Ile Gly Lys Gln Met Lys Ala Leu Arg Asp Gly Asp Trp Phe Trp Trp
            660                 665                 670

Glu Asn Ser His Val Phe Thr Asp Ala Gln Arg Glu Leu Glu Lys
            675                 680                 685

His Ser Leu Ser Arg Val Ile Cys Asp Asn Thr Gly Leu Thr Arg Val
            690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
                725                 730                 735

Pro Gln Asp Asp Lys Cys Gly Phe Pro Glu Ser Val Glu Asn Gly Asp
            740                 745                 750

Phe Val His Cys Glu Glu Ser Gly Arg Arg Val Leu Val Tyr Ser Cys
            755                 760                 765

Arg His Gly Tyr Glu Leu Gln Gly Arg Glu Gln Leu Thr Cys Thr Gln
            770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
                805                 810                 815

Thr Lys Gly Gly Phe Gln Cys Leu Cys Ala Asp Pro Tyr Glu Leu Gly
            820                 825                 830

Asp Asp Gly Arg Thr Cys Val Asp Ser Gly Arg Leu Pro Arg Val Thr
            835                 840                 845

Trp Ile Ser Met Ser Leu Ala Ala Leu Leu Ile Gly Gly Phe Ala Gly
850                 855                 860

Leu Thr Ser Thr Val Ile Cys Arg Trp Thr Arg Thr Gly Thr Lys Ser
865                 870                 875                 880

Thr Leu Pro Ile Ser Glu Thr Gly Gly Gly Thr Pro Glu Leu Arg Cys
                885                 890                 895

Gly Lys His Gln Ala Val Gly Thr Ser Pro Gln Arg Ala Ala Ala Gln
            900                 905                 910

Asp Ser Glu Gln Glu Ser Ala Gly Met Glu Gly Arg Asp Thr His Arg
            915                 920                 925

Leu Pro Arg Ala Leu
    930

<210> SEQ ID NO 29
<211> LENGTH: 764
<212> TYPE: PRT
<213> ORGANISM: Homo sapiens

<400> SEQUENCE: 29

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
```

```
                    20                  25                  30
Gln Glu Glu Asp Phe Arg Val Thr Cys Lys Asp Ile Gln Arg Ile Pro
                35                  40                  45
Ser Leu Pro Pro Ser Thr Gln Thr Leu Lys Leu Ile Glu Thr His Leu
            50                  55                  60
Arg Thr Ile Pro Ser His Ala Phe Ser Asn Leu Pro Asn Ile Ser Arg
65                  70                  75                  80
Ile Tyr Val Ser Ile Asp Val Thr Leu Gln Gln Leu Glu Ser His Ser
                85                  90                  95
Phe Tyr Asn Leu Ser Lys Val Thr His Ile Glu Ile Arg Asn Thr Arg
            100                 105                 110
Asn Leu Thr Tyr Ile Asp Pro Asp Ala Leu Lys Glu Leu Pro Leu Leu
            115                 120                 125
Lys Phe Leu Gly Ile Phe Asn Thr Gly Leu Lys Met Phe Pro Asp Leu
            130                 135                 140
Thr Lys Val Tyr Ser Thr Asp Ile Phe Phe Ile Leu Glu Ile Thr Asp
145                 150                 155                 160
Asn Pro Tyr Met Thr Ser Ile Pro Val Asn Ala Phe Gln Gly Leu Cys
                165                 170                 175
Asn Glu Thr Leu Thr Leu Lys Leu Tyr Asn Asn Gly Phe Thr Ser Val
            180                 185                 190
Gln Gly Tyr Ala Phe Asn Gly Thr Lys Leu Asp Ala Val Tyr Leu Asn
            195                 200                 205
Lys Asn Lys Tyr Leu Thr Val Ile Asp Lys Asp Ala Phe Gly Gly Val
            210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                245                 250                 255
Thr Trp Thr Leu Lys Lys Leu Pro Leu Ser Leu Ser Phe Leu His Leu
            260                 265                 270
Thr Arg Ala Asp Leu Ser Tyr Pro Ser His Cys Cys Ala Phe Lys Asn
            275                 280                 285
Gln Lys Lys Ile Arg Gly Ile Leu Glu Ser Leu Met Cys Asn Glu Ser
            290                 295                 300
Ser Met Gln Ser Leu Arg Gln Arg Lys Ser Val Asn Ala Leu Asn Ser
305                 310                 315                 320
Pro Leu His Gln Glu Tyr Glu Glu Asn Leu Gly Asp Ser Ile Val Gly
                325                 330                 335
Tyr Lys Glu Lys Ser Lys Phe Gln Asp Thr His Asn Asn Ala His Tyr
            340                 345                 350
Tyr Val Phe Phe Glu Glu Gln Glu Asp Glu Ile Ile Gly Phe Gly Gln
            355                 360                 365
Glu Leu Lys Asn Pro Gln Glu Glu Thr Leu Gln Ala Phe Asp Ser His
            370                 375                 380
Tyr Asp Tyr Thr Ile Cys Gly Asp Ser Glu Asp Met Val Cys Thr Pro
385                 390                 395                 400
Lys Ser Asp Glu Phe Asn Pro Cys Glu Asp Ile Met Gly Tyr Lys Phe
                405                 410                 415
Leu Arg Ile Val Val Trp Phe Val Ser Leu Leu Ala Leu Leu Gly Asn
            420                 425                 430
Val Phe Val Leu Leu Ile Leu Leu Thr Ser His Tyr Lys Leu Asn Val
            435                 440                 445
```

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
                500                 505                 510

Thr Val Ile Thr Leu Glu Arg Trp Tyr Ala Ile Thr Phe Ala Met Arg
            515                 520                 525

Leu Asp Arg Lys Ile Arg Leu Arg His Ala Cys Ala Ile Met Val Gly
    530                 535                 540

Gly Trp Val Cys Cys Phe Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
                580                 585                 590

Ala Phe Val Ile Val Cys Cys Cys Tyr Val Lys Ile Tyr Ile Thr Val
            595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
                660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
    690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
                740                 745                 750

Gly Gln Ile Ser Glu Glu Tyr Met Gln Thr Val Leu
            755                 760

<210> SEQ ID NO 30
<211> LENGTH: 770
<212> TYPE: PRT
<213> ORGANISM: Homo sapiens

<400> SEQUENCE: 30

Pro Arg Val Pro Trp Lys Met Arg Pro Ala Asp Leu Leu Gln Leu Val
1               5                   10                  15

Leu Leu Leu Asp Leu Pro Arg Asp Leu Gly Gly Met Gly Cys Ser Ser
                20                  25                  30

Pro Pro Cys Glu Cys His Gln Glu Glu Asp Phe Arg Val Thr Cys Lys
            35                  40                  45

Asp Ile Gln Arg Ile Pro Ser Leu Pro Pro Ser Thr Gln Thr Leu Lys

```
            50                  55                  60
Leu Ile Glu Thr His Leu Arg Thr Ile Pro Ser His Ala Phe Ser Asn
 65                  70                  75                  80

Leu Pro Asn Ile Ser Arg Ile Tyr Val Ser Ile Asp Val Thr Leu Gln
                     85                  90                  95

Gln Leu Glu Ser His Ser Phe Tyr Asn Leu Ser Lys Val Thr His Ile
                    100                 105                 110

Glu Ile Arg Asn Thr Arg Asn Leu Thr Tyr Ile Asp Pro Asp Ala Leu
                    115                 120                 125

Lys Glu Leu Pro Leu Leu Lys Phe Leu Gly Ile Phe Asn Thr Gly Leu
                    130                 135                 140

Lys Met Phe Pro Asp Leu Thr Lys Val Tyr Ser Thr Asp Ile Phe Phe
145                 150                 155                 160

Ile Leu Glu Ile Thr Asp Asn Pro Tyr Met Thr Ser Ile Pro Val Asn
                    165                 170                 175

Ala Phe Gln Gly Leu Cys Asn Glu Thr Leu Thr Leu Lys Leu Tyr Asn
                    180                 185                 190

Asn Gly Phe Thr Ser Val Gln Gly Tyr Ala Phe Asn Gly Thr Lys Leu
                    195                 200                 205

Asp Ala Val Tyr Leu Asn Lys Asn Lys Tyr Leu Thr Val Ile Asp Lys
                    210                 215                 220

Asp Ala Phe Gly Gly Val Tyr Ser Gly Pro Ser Leu Leu Asp Val Ser
225                 230                 235                 240

Gln Thr Ser Val Thr Ala Leu Pro Ser Lys Gly Leu Glu His Leu Lys
                    245                 250                 255

Glu Leu Ile Ala Arg Asn Thr Trp Thr Leu Lys Lys Leu Pro Leu Ser
                    260                 265                 270

Leu Ser Phe Leu His Leu Thr Arg Ala Asp Leu Ser Tyr Pro Ser His
                    275                 280                 285

Cys Cys Ala Phe Lys Asn Gln Lys Lys Ile Arg Gly Ile Leu Glu Ser
                    290                 295                 300

Leu Met Cys Asn Glu Ser Ser Met Gln Ser Leu Arg Gln Arg Lys Ser
305                 310                 315                 320

Val Asn Ala Leu Asn Ser Pro Leu His Gln Glu Tyr Glu Glu Asn Leu
                    325                 330                 335

Gly Asp Ser Ile Val Gly Tyr Lys Glu Lys Ser Lys Phe Gln Asp Thr
                    340                 345                 350

His Asn Asn Ala His Tyr Tyr Val Phe Phe Glu Glu Gln Glu Asp Glu
                    355                 360                 365

Ile Ile Gly Phe Gly Gln Glu Leu Lys Asn Pro Gln Glu Glu Thr Leu
                    370                 375                 380

Gln Ala Phe Asp Ser His Tyr Asp Tyr Thr Ile Cys Gly Asp Ser Glu
385                 390                 395                 400

Asp Met Val Cys Thr Pro Lys Ser Asp Glu Phe Asn Pro Cys Glu Asp
                    405                 410                 415

Ile Met Gly Tyr Lys Phe Leu Arg Ile Val Val Trp Phe Val Ser Leu
                    420                 425                 430

Leu Ala Leu Leu Gly Asn Val Phe Val Leu Leu Ile Leu Leu Thr Ser
                    435                 440                 445

His Tyr Lys Leu Asn Val Pro Arg Phe Leu Met Cys Asn Leu Ala Phe
                    450                 455                 460

Ala Asp Phe Cys Met Gly Met Tyr Leu Leu Leu Ile Ala Ser Val Asp
465                 470                 475                 480
```

```
Leu Tyr Thr His Ser Glu Tyr Asn His Ala Ile Asp Trp Gln Thr
                485                 490                 495

Gly Pro Gly Cys Asn Thr Ala Gly Phe Phe Thr Val Phe Ala Ser Glu
            500                 505                 510

Leu Ser Val Tyr Thr Leu Thr Val Ile Thr Leu Glu Arg Trp Tyr Ala
            515                 520                 525

Ile Thr Phe Ala Met Arg Leu Asp Arg Lys Ile Arg Leu Arg His Ala
            530                 535                 540

Cys Ala Ile Met Val Gly Gly Trp Val Cys Cys Phe Leu Leu Ala Leu
545                 550                 555                 560

Leu Pro Leu Val Gly Ile Ser Ser Tyr Ala Lys Val Ser Ile Cys Leu
            565                 570                 575

Pro Met Asp Thr Glu Thr Pro Leu Ala Leu Ala Tyr Ile Val Phe Val
            580                 585                 590

Leu Thr Leu Asn Ile Val Ala Phe Val Ile Cys Cys Cys Tyr Val
            595                 600                 605

Lys Ile Tyr Ile Thr Val Arg Asn Pro Gln Tyr Asn Pro Gly Asp Lys
            610                 615                 620

Asp Thr Lys Ile Ala Lys Arg Met Ala Val Leu Ile Phe Thr Asp Phe
625                 630                 635                 640

Ile Cys Met Ala Pro Ile Ser Phe Tyr Ala Leu Ser Ala Ile Leu Asn
            645                 650                 655

Lys Pro Leu Ile Thr Val Ser Asn Ser Lys Ile Leu Leu Val Leu Phe
            660                 665                 670

Tyr Pro Leu Asn Ser Cys Ala Asn Pro Phe Leu Tyr Ala Ile Phe Thr
            675                 680                 685

Lys Ala Phe Gln Arg Asp Val Phe Ile Leu Leu Ser Lys Phe Gly Ile
            690                 695                 700

Cys Lys Arg Gln Ala Gln Ala Tyr Arg Gly Gln Arg Val Pro Pro Lys
705                 710                 715                 720

Asn Ser Thr Asp Ile Gln Val Gln Lys Val Thr His Asp Met Arg Gln
            725                 730                 735

Gly Leu His Asn Met Glu Asp Val Tyr Glu Leu Ile Glu Asn Ser His
            740                 745                 750

Leu Thr Pro Lys Lys Gln Gly Gln Ile Ser Glu Glu Tyr Met Gln Thr
            755                 760                 765

Val Leu
770

<210> SEQ ID NO 31
<211> LENGTH: 411
<212> TYPE: PRT
<213> ORGANISM: Homo sapiens

<400> SEQUENCE: 31

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
            50                  55                  60

Arg Ile Val Val Trp Phe Val Ser Leu Leu Ala Leu Leu Gly Asn Val
```

```
            65                  70                  75                  80
    Phe Val Leu Leu Ile Leu Leu Thr Ser His Tyr Lys Leu Asn Val Pro
                        85                  90                  95

Arg Phe Leu Met Cys Asn Leu Ala Phe Ala Asp Phe Cys Met Gly Met
                        100                 105                 110

Tyr Leu Leu Leu Ile Ala Ser Val Asp Leu Tyr Thr His Ser Glu Tyr
                        115                 120                 125

Tyr Asn His Ala Ile Asp Trp Gln Thr Gly Pro Gly Cys Asn Thr Ala
                        130                 135                 140

Gly Phe Phe Thr Val Phe Ala Ser Glu Leu Ser Val Tyr Thr Leu Thr
    145                 150                 155                 160

Val Ile Thr Leu Glu Arg Trp Tyr Ala Ile Thr Phe Ala Met Arg Leu
                        165                 170                 175

Asp Arg Lys Ile Arg Leu Arg His Ala Cys Ala Ile Met Val Gly Gly
                        180                 185                 190

Trp Val Cys Cys Phe Leu Leu Ala Leu Leu Pro Leu Val Gly Ile Ser
                        195                 200                 205

Ser Tyr Ala Lys Val Ser Ile Cys Leu Pro Met Asp Thr Glu Thr Pro
            210                 215                 220

Leu Ala Leu Ala Tyr Ile Val Phe Val Leu Thr Leu Asn Ile Val Ala
    225                 230                 235                 240

Phe Val Ile Val Cys Cys Cys Tyr Val Lys Ile Tyr Ile Thr Val Arg
                        245                 250                 255

Asn Pro Gln Tyr Asn Pro Gly Asp Lys Asp Thr Lys Ile Ala Lys Arg
                        260                 265                 270

Met Ala Val Leu Ile Phe Thr Asp Phe Ile Cys Met Ala Pro Ile Ser
                        275                 280                 285

Phe Tyr Ala Leu Ser Ala Ile Leu Asn Lys Pro Leu Ile Thr Val Ser
                        290                 295                 300

Asn Ser Lys Ile Leu Leu Val Leu Phe Tyr Pro Leu Asn Ser Cys Ala
    305                 310                 315                 320

Asn Pro Phe Leu Tyr Ala Ile Phe Thr Lys Ala Phe Gln Arg Asp Val
                        325                 330                 335

Phe Ile Leu Leu Ser Lys Phe Gly Ile Cys Lys Arg Gln Ala Gln Ala
                        340                 345                 350

Tyr Arg Gly Gln Arg Val Pro Pro Lys Asn Ser Thr Asp Ile Gln Val
                        355                 360                 365

Gln Lys Val Thr His Glu Met Arg Gln Gly Leu His Asn Met Glu Asp
            370                 375                 380

Val Tyr Glu Leu Ile Glu Asn Ser His Leu Thr Pro Lys Lys Gln Gly
    385                 390                 395                 400

Gln Ile Ser Glu Glu Tyr Met Gln Thr Val Leu
                        405                 410

<210> SEQ ID NO 32
<211> LENGTH: 345
<212> TYPE: PRT
<213> ORGANISM: Homo sapiens

<400> SEQUENCE: 32

Met Ile Ser Pro Val Leu Ile Leu Phe Ser Ser Phe Leu Cys His Val
1               5                   10                  15

Ala Ile Ala Gly Arg Thr Cys Pro Lys Pro Asp Asp Leu Pro Phe Ser
            20                  25                  30
```

Thr Val Val Pro Leu Lys Thr Phe Tyr Glu Pro Gly Glu Ile Thr
              35                  40                  45

Tyr Ser Cys Lys Pro Gly Tyr Val Ser Arg Gly Gly Met Arg Lys Phe
 50                  55                  60

Ile Cys Pro Leu Thr Gly Leu Trp Pro Ile Asn Thr Leu Lys Cys Thr
 65                  70                  75                  80

Pro Arg Val Cys Pro Phe Ala Gly Ile Leu Glu Asn Gly Ala Val Arg
                 85                  90                  95

Tyr Thr Thr Phe Glu Tyr Pro Asn Thr Ile Ser Phe Ser Cys Asn Thr
            100                 105                 110

Gly Phe Tyr Leu Asn Gly Ala Asp Ser Ala Lys Cys Thr Glu Glu Gly
        115                 120                 125

Lys Trp Ser Pro Glu Leu Pro Val Cys Ala Pro Ile Ile Cys Pro Pro
130                 135                 140

Pro Ser Ile Pro Thr Phe Ala Thr Leu Arg Val Tyr Lys Pro Ser Ala
145                 150                 155                 160

Gly Asn Asn Ser Leu Tyr Arg Asp Thr Ala Val Phe Glu Cys Leu Pro
                165                 170                 175

Gln His Ala Met Phe Gly Asn Asp Thr Ile Thr Cys Thr Thr His Gly
            180                 185                 190

Asn Trp Thr Lys Leu Pro Glu Cys Arg Glu Val Lys Cys Pro Phe Pro
        195                 200                 205

Ser Arg Pro Asp Asn Gly Phe Val Asn Tyr Pro Ala Lys Pro Thr Leu
210                 215                 220

Tyr Tyr Lys Asp Lys Ala Thr Phe Gly Cys His Asp Gly Tyr Ser Leu
225                 230                 235                 240

Asp Gly Pro Glu Glu Ile Glu Cys Thr Lys Leu Gly Asn Trp Ser Ala
                245                 250                 255

Met Pro Ser Cys Lys Ala Ser Cys Lys Val Pro Val Lys Lys Ala Thr
            260                 265                 270

Val Val Tyr Gln Gly Glu Arg Val Lys Ile Gln Glu Lys Phe Lys Asn
        275                 280                 285

Gly Met Leu His Gly Asp Lys Val Ser Phe Phe Cys Lys Asn Lys Glu
290                 295                 300

Lys Lys Cys Ser Tyr Thr Glu Asp Ala Gln Cys Ile Asp Gly Thr Ile
305                 310                 315                 320

Glu Val Pro Lys Cys Phe Lys Glu His Ser Ser Leu Ala Phe Trp Lys
                325                 330                 335

Thr Asp Ala Ser Asp Val Lys Pro Cys
            340                 345

<210> SEQ ID NO 33
<211> LENGTH: 102
<212> TYPE: PRT
<213> ORGANISM: Homo sapiens

<400> SEQUENCE: 33

Ser Gly Arg Gly Lys Gly Gly Lys Gly Leu Gly Lys Gly Gly Ala Lys
 1               5                  10                  15

Arg His Arg Lys Val Leu Arg Asp Asn Ile Gln Gly Ile Thr Lys Pro
                 20                  25                  30

Ala Ile Arg Arg Leu Ala Arg Arg Gly Gly Val Lys Arg Ile Ser Gly
            35                  40                  45

Leu Ile Tyr Glu Glu Thr Arg Gly Val Leu Lys Val Phe Leu Glu Asn
 50                  55                  60

```
Val Ile Arg Asp Ala Val Thr Tyr Thr Glu His Ala Lys Arg Lys Thr
 65                  70                  75                  80

Val Thr Ala Met Asp Val Val Tyr Ala Leu Lys Arg Gln Gly Arg Thr
                 85                  90                  95

Leu Tyr Gly Phe Gly Gly
            100

<210> SEQ ID NO 34
<211> LENGTH: 125
<212> TYPE: PRT
<213> ORGANISM: Homo sapiens

<400> SEQUENCE: 34

Pro Glu Pro Ala Lys Ser Ala Pro Ala Pro Lys Lys Gly Ser Lys Lys
 1               5                  10                  15

Ala Val Thr Lys Ala Gln Lys Lys Asp Gly Lys Lys Arg Lys Arg Ser
                20                  25                  30

Arg Lys Glu Ser Tyr Ser Val Tyr Val Tyr Lys Val Leu Lys Gln Val
            35                  40                  45

His Pro Asp Thr Gly Ile Ser Ser Lys Ala Met Gly Ile Met Asn Ser
        50                  55                  60

Phe Val Asn Asp Ile Phe Glu Arg Ile Ala Ser Glu Ala Ser Arg Leu
 65                  70                  75                  80

Ala His Tyr Asn Lys Arg Ser Thr Ile Thr Ser Arg Glu Ile Gln Thr
                 85                  90                  95

Ala Val Arg Leu Leu Leu Pro Gly Glu Leu Ala Lys His Ala Val Ser
            100                 105                 110

Glu Gly Thr Lys Ala Val Thr Lys Tyr Thr Ser Ser Lys
        115                 120                 125

<210> SEQ ID NO 35
<211> LENGTH: 194
<212> TYPE: PRT
<213> ORGANISM: Homo sapiens

<400> SEQUENCE: 35

Met Thr Glu Asn Ser Thr Ser Ala Pro Ala Ala Lys Pro Lys Arg Ala
 1               5                  10                  15

Lys Ala Ser Lys Lys Ser Thr Asp His Pro Lys Tyr Ser Asp Met Ile
                20                  25                  30

Val Ala Ala Ile Gln Ala Glu Lys Asn Arg Ala Gly Ser Ser Arg Gln
            35                  40                  45

Ser Ile Gln Lys Tyr Ile Lys Ser His Tyr Lys Val Gly Glu Asn Ala
        50                  55                  60

Asp Ser Gln Ile Lys Leu Ser Ile Lys Arg Leu Val Thr Thr Gly Val
 65                  70                  75                  80

Leu Lys Gln Thr Lys Gly Val Gly Ala Ser Gly Ser Phe Arg Leu Ala
                 85                  90                  95

Lys Gly Asp Glu Pro Lys Arg Ser Val Ala Phe Lys Lys Thr Lys Lys
            100                 105                 110

Glu Val Lys Lys Val Ala Thr Pro Lys Lys Ala Ala Lys Pro Lys Lys
        115                 120                 125

Ala Ala Ser Lys Ala Pro Ser Lys Lys Pro Lys Ala Thr Pro Val Lys
        130                 135                 140

Lys Ala Lys Lys Lys Pro Ala Ala Thr Pro Lys Lys Ala Lys Lys Pro
145                 150                 155                 160
```

Lys Val Val Lys Val Lys Pro Val Lys Ala Ser Lys Pro Lys Ala
                165                 170                 175

Lys Thr Val Lys Pro Lys Ala Lys Ser Ser Ala Lys Arg Ala Ser Lys
                180                 185                 190

Lys Lys

<210> SEQ ID NO 36
<211> LENGTH: 4505
<212> TYPE: PRT
<213> ORGANISM: Homo sapiens

<400> SEQUENCE: 36

Met Gly Pro Arg Lys Pro Ala Leu Arg Thr Pro Leu Leu Leu Leu Phe
1               5                   10                  15

Leu Leu Leu Phe Leu Asp Thr Ser Val Trp Ala Gln Asp Glu Val Leu
                20                  25                  30

Glu Asn Leu Ser Phe Ser Cys Pro Lys Asp Ala Thr Arg Phe Lys His
                35                  40                  45

Leu Arg Lys Tyr Val Tyr Asn Tyr Glu Ala Glu Ser Ser Ser Gly Val
50                  55                  60

Gln Gly Thr Ala Asp Ser Arg Ser Ala Thr Lys Ile Asn Cys Lys Val
65                  70                  75                  80

Glu Leu Glu Val Pro Gln Ile Cys Gly Phe Ile Met Arg Thr Asn Gln
                85                  90                  95

Cys Thr Leu Lys Glu Val Tyr Gly Phe Asn Pro Glu Gly Lys Ala Leu
                100                 105                 110

Met Lys Lys Thr Lys Asn Ser Glu Glu Phe Ala Ala Ala Met Ser Arg
                115                 120                 125

Tyr Glu Leu Lys Leu Ala Ile Pro Glu Gly Lys Gln Ile Val Leu Tyr
                130                 135                 140

Pro Asp Lys Asp Glu Pro Lys Tyr Ile Leu Asn Ile Lys Arg Gly Ile
145                 150                 155                 160

Ile Ser Ala Leu Leu Val Pro Pro Glu Thr Glu Glu Asp Gln Gln Glu
                165                 170                 175

Leu Phe Leu Asp Thr Val Tyr Gly Asn Cys Ser Thr Gln Val Thr Val
                180                 185                 190

Asn Ser Arg Lys Gly Thr Val Pro Thr Glu Met Ser Thr Glu Arg Asn
                195                 200                 205

Leu Gln Gln Cys Asp Gly Phe Gln Pro Ile Ser Thr Ser Val Ser Pro
                210                 215                 220

Leu Ala Leu Ile Lys Gly Leu Val His Pro Leu Ser Thr Leu Ile Ser
225                 230                 235                 240

Ser Ser Gln Thr Cys Gln Tyr Thr Leu Asp Pro Lys Arg Lys His Val
                245                 250                 255

Ser Glu Ala Val Cys Asp Glu Gln His Leu Phe Leu Pro Phe Ser Tyr
                260                 265                 270

Lys Asn Lys Tyr Gly Ile Met Thr Arg Val Thr Gln Lys Leu Ser Leu
                275                 280                 285

Glu Asp Thr Pro Lys Ile Asn Ser Arg Phe Phe Ser Glu Gly Thr Asn
                290                 295                 300

Arg Met Gly Leu Ala Phe Glu Ser Thr Lys Thr Ser Ser Pro Lys
305                 310                 315                 320

Gln Ala Asp Ala Val Leu Lys Thr Leu Gln Glu Leu Lys Lys Leu Ser
                325                 330                 335

```
Ile Ser Glu Gln Asn Ala Gln Arg Ala Asn Leu Phe Asn Lys Leu Val
            340                 345                 350

Thr Glu Leu Arg Gly Leu Thr Gly Glu Ala Ile Thr Ser Leu Leu Pro
            355                 360                 365

Gln Leu Ile Glu Val Ser Ser Pro Ile Thr Leu Gln Ala Leu Val Gln
            370                 375                 380

Cys Gly Gln Pro Gln Cys Tyr Thr His Ile Leu Gln Trp Leu Lys Thr
385                 390                 395                 400

Glu Lys Ala His Pro Leu Leu Val Asp Ile Val Thr Tyr Leu Met Ala
            405                 410                 415

Leu Ile Pro Asn Pro Ser Thr Gln Arg Leu Gln Glu Ile Phe Asn Thr
            420                 425                 430

Ala Lys Glu Gln Gln Ser Arg Ala Thr Leu Tyr Ala Leu Ser His Ala
            435                 440                 445

Val Asn Ser Tyr Phe Asp Val Asp His Ser Arg Ser Pro Val Leu Gln
            450                 455                 460

Asp Ile Ala Gly Tyr Leu Leu Lys Gln Ile Asp Asn Glu Cys Thr Gly
465                 470                 475                 480

Asn Glu Asp His Thr Phe Leu Ile Leu Arg Val Ile Gly Asn Met Gly
            485                 490                 495

Arg Thr Met Glu Gln Val Met Pro Ala Leu Lys Ser Ser Val Leu Ser
            500                 505                 510

Cys Val Arg Ser Thr Lys Pro Ser Leu Leu Ile Gln Lys Ala Ala Leu
            515                 520                 525

Gln Ala Leu Arg Lys Met Glu Leu Glu Asp Glu Val Arg Thr Ile Leu
            530                 535                 540

Phe Asp Thr Phe Val Asn Gly Val Ala Pro Val Glu Lys Arg Leu Ala
545                 550                 555                 560

Ala Tyr Leu Leu Leu Met Lys Asn Pro Ser Ser Ser Asp Ile Asn Lys
            565                 570                 575

Ile Ala Gln Leu Leu Gln Trp Glu Gln Ser Glu Gln Val Lys Asn Phe
            580                 585                 590

Val Ala Ser His Ile Ala Asn Ile Leu Asn Ser Glu Glu Leu Tyr Val
            595                 600                 605

Gln Asp Leu Lys Val Leu Ile Lys Asn Ala Leu Glu Asn Ser Gln Phe
            610                 615                 620

Pro Thr Ile Met Asp Phe Arg Lys Phe Ser Arg Asn Tyr Gln Ile Ser
625                 630                 635                 640

Lys Ser Ala Ser Leu Pro Met Phe Asp Pro Val Ser Val Lys Ile Glu
            645                 650                 655

Gly Asn Leu Ile Phe Asp Pro Ser Ser Tyr Leu Pro Arg Glu Ser Leu
            660                 665                 670

Leu Lys Thr Thr Leu Thr Val Phe Gly Leu Ala Ser Leu Asp Leu Phe
            675                 680                 685

Glu Ile Gly Leu Glu Gly Lys Gly Phe Glu Pro Thr Leu Glu Ala Leu
            690                 695                 700

Phe Gly Lys Gln Gly Phe Phe Pro Asp Ser Val Asn Lys Ala Leu Tyr
705                 710                 715                 720

Trp Val Asn Gly Arg Val Pro Asp Gly Val Ser Lys Val Leu Val Asp
            725                 730                 735

His Phe Gly Tyr Thr Thr Asp Gly Lys His Glu Gln Asp Met Val Asn
            740                 745                 750
```

Gly Ile Met Pro Ile Val Asp Lys Leu Ile Lys Asp Leu Lys Ser Lys
              755                 760                 765

Glu Ile Pro Glu Ala Arg Ala Tyr Leu Arg Ile Leu Gly Lys Glu Leu
    770                 775                 780

Ser Phe Val Arg Leu Gln Asp Leu Gln Val Leu Gly Lys Leu Leu Leu
785                 790                 795                 800

Ser Gly Ala Gln Thr Leu Gln Gly Ile Pro Gln Met Val Val Gln Ala
              805                 810                 815

Ile Arg Glu Gly Ser Lys Asn Asp Leu Phe Leu His Tyr Ile Phe Met
              820                 825                 830

Asp Asn Ala Phe Glu Leu Pro Thr Gly Ala Gly Leu Gln Leu Gln Val
              835                 840                 845

Ser Ser Ser Gly Val Phe Thr Pro Gly Ile Lys Ala Gly Val Arg Leu
850                 855                 860

Glu Leu Ala Asn Ile Gln Ala Glu Leu Val Ala Lys Pro Ser Val Ser
865                 870                 875                 880

Leu Glu Phe Val Thr Asn Met Gly Ile Ile Pro Asp Phe Ala Lys
              885                 890                 895

Ser Ser Val Gln Met Asn Thr Asn Phe Phe His Glu Ser Gly Leu Glu
              900                 905                 910

Ala Arg Val Ala Leu Lys Ala Gly Gln Leu Lys Val Ile Ile Pro Ser
              915                 920                 925

Pro Lys Arg Pro Val Lys Leu Phe Ser Gly Ser Asn Thr Leu His Leu
              930                 935                 940

Val Ser Thr Thr Lys Thr Glu Val Ile Pro Pro Leu Val Glu Asn Arg
945                 950                 955                 960

Gln Ser Trp Ser Thr Cys Lys Pro Leu Phe Thr Gly Met Asn Tyr Cys
              965                 970                 975

Thr Thr Gly Ala Tyr Ser Asn Ala Ser Ser Thr Glu Ser Ala Ser Tyr
              980                 985                 990

Tyr Pro Leu Thr Gly Asp Thr Arg Tyr Glu Leu Gly Leu Arg Pro Thr
              995                 1000                1005

Gly Glu Val Glu Gln Tyr Ser Ala Thr Ala Thr Tyr Glu Leu Leu
    1010                1015                1020

Lys Glu Asp Lys Ser Leu Val Asp Thr Leu Lys Phe Leu Val Gln
    1025                1030                1035

Ala Glu Gly Val Gln Gln Ser Glu Ala Thr Val Leu Phe Lys Tyr
    1040                1045                1050

Asn Arg Arg Ser Arg Thr Leu Ser Ser Glu Val Leu Ile Pro Gly
    1055                1060                1065

Phe Asp Val Asn Phe Gly Thr Ile Leu Arg Val Asn Asp Glu Ser
    1070                1075                1080

Ala Lys Asp Lys Asn Thr Tyr Lys Leu Ile Leu Asp Ile Gln Asn
    1085                1090                1095

Lys Lys Ile Thr Glu Val Ser Leu Val Gly His Leu Ser Tyr Asp
    1100                1105                1110

Lys Lys Gly Asp Gly Lys Ile Lys Gly Val Val Ser Ile Pro Arg
    1115                1120                1125

Leu Gln Ala Glu Ala Arg Ser Glu Val His Thr His Trp Ser Ser
    1130                1135                1140

Thr Lys Leu Leu Phe Gln Met Asp Ser Ser Ala Thr Ala Tyr Gly
    1145                1150                1155

Ser Thr Ile Ser Lys Arg Val Thr Trp Arg Tyr Asp Asn Glu Ile

```
            1160               1165               1170

Ile Glu Phe Asp Trp Asn Thr Gly Thr Asn Val Asp Thr Lys Lys
    1175               1180               1185

Val Ala Ser Asn Phe Pro Val Asp Leu Ser His Tyr Pro Arg Met
    1190               1195               1200

Leu His Glu Tyr Ala Asn Gly Leu Leu Asp His Arg Val Pro Gln
    1205               1210               1215

Thr Asp Val Thr Phe Arg Asp Met Gly Ser Lys Leu Ile Val Ala
    1220               1225               1230

Thr Asn Thr Trp Leu Gln Met Ala Thr Arg Gly Leu Pro Tyr Pro
    1235               1240               1245

Gln Thr Leu Gln Asp His Leu Asn Ser Leu Ser Glu Leu Asn Leu
    1250               1255               1260

Leu Lys Met Gly Leu Ser Asp Phe His Ile Pro Asp Asn Leu Phe
    1265               1270               1275

Leu Lys Thr Asp Gly Arg Val Lys Tyr Thr Met Asn Arg Asn Lys
    1280               1285               1290

Ile Asn Ile Asp Ile Pro Leu Pro Leu Gly Gly Lys Ser Ser Lys
    1295               1300               1305

Asp Leu Lys Met Pro Glu Ser Val Arg Thr Pro Ala Leu Asn Phe
    1310               1315               1320

Lys Ser Val Gly Phe His Leu Pro Ser Arg Glu Val Gln Val Pro
    1325               1330               1335

Thr Phe Thr Ile Pro Lys Thr His Gln Leu Gln Val Pro Leu Leu
    1340               1345               1350

Gly Val Leu Asp Leu Ser Thr Asn Val Tyr Ser Asn Leu Tyr Asn
    1355               1360               1365

Trp Ser Ala Ser Tyr Thr Gly Gly Asn Thr Ser Arg Asp His Phe
    1370               1375               1380

Ser Leu Gln Ala Gln Tyr Arg Met Lys Thr Asp Ser Val Val Asp
    1385               1390               1395

Leu Phe Ser Tyr Ser Val Gln Gly Ser Gly Glu Thr Thr Tyr Asp
    1400               1405               1410

Ser Lys Asn Thr Phe Thr Leu Ser Cys Asp Gly Ser Leu His His
    1415               1420               1425

Lys Phe Leu Asp Ser Lys Phe Lys Val Ser His Val Glu Lys Phe
    1430               1435               1440

Gly Asn Ser Pro Val Ser Lys Gly Leu Leu Thr Phe Glu Thr Ser
    1445               1450               1455

Ser Ala Leu Gly Pro Gln Met Ser Ala Thr Val His Leu Asp Ser
    1460               1465               1470

Lys Lys Lys Gln His Leu Tyr Val Lys Asp Ile Lys Val Asp Gly
    1475               1480               1485

Gln Phe Arg Ala Ser Ser Phe Tyr Ala Gln Gly Lys Tyr Gly Leu
    1490               1495               1500

Ser Cys Glu Arg Asp Val Thr Thr Gly Gln Leu Ser Gly Glu Ser
    1505               1510               1515

Asn Met Arg Phe Asn Ser Thr Tyr Phe Gln Gly Thr Asn Gln Ile
    1520               1525               1530

Val Gly Met Tyr Gln Asp Gly Ala Leu Ser Ile Thr Ser Thr Ser
    1535               1540               1545

Asp Leu Gln Asp Gly Ile Phe Lys Asn Thr Ala Ser Leu Lys Tyr
    1550               1555               1560
```

-continued

```
Glu Asn Tyr Glu Leu Thr Leu Lys Ser Asp Ser Ser Gly Gln Tyr
1565                1570                1575

Glu Asn Phe Ala Ala Ser Asn Lys Leu Asp Val Thr Phe Ser Thr
1580                1585                1590

Gln Ser Ala Leu Leu Arg Ser Glu His Gln Ala Asn Tyr Lys Ser
1595                1600                1605

Leu Arg Leu Val Thr Leu Leu Ser Gly Ser Leu Thr Ser Gln Gly
1610                1615                1620

Val Glu Leu Asn Ala Asp Ile Leu Gly Thr Asp Lys Ile Asn Thr
1625                1630                1635

Gly Ala His Lys Ala Thr Leu Lys Ile Ala Arg Asp Gly Leu Ser
1640                1645                1650

Thr Ser Ala Thr Thr Asn Leu Lys Tyr Ser Pro Leu Leu Leu Glu
1655                1660                1665

Asn Glu Leu Asn Ala Glu Leu Gly Leu Ser Gly Ala Ser Met Lys
1670                1675                1680

Leu Ser Thr Asn Gly Arg Phe Lys Glu His His Ala Lys Phe Ser
1685                1690                1695

Leu Asp Gly Arg Ala Ala Leu Thr Glu Val Ser Leu Gly Ser Ile
1700                1705                1710

Tyr Gln Ala Met Ile Leu Gly Ala Asp Ser Lys Asn Ile Phe Asn
1715                1720                1725

Phe Lys Leu Ser Arg Glu Gly Leu Arg Leu Ser Asn Asp Leu Met
1730                1735                1740

Gly Ser Tyr Ala Glu Met Lys Leu Asp His Thr His Ser Leu Asn
1745                1750                1755

Ile Ala Gly Leu Ser Leu Asp Phe Phe Ser Lys Met Asp Asn Ile
1760                1765                1770

Tyr Ser Gly Asp Lys Phe Tyr Lys Gln Asn Phe Asn Leu Gln Leu
1775                1780                1785

Gln Pro Tyr Ser Phe Ile Thr Thr Leu Ser Asn Asp Leu Arg Tyr
1790                1795                1800

Gly Ala Leu Asp Leu Thr Asn Asn Gly Arg Phe Arg Leu Glu Pro
1805                1810                1815

Leu Lys Leu Asn Val Gly Gly Asn Phe Lys Gly Thr Tyr Gln Asn
1820                1825                1830

Asn Glu Leu Lys His Ile Tyr Thr Ile Ser Tyr Thr Asp Leu Val
1835                1840                1845

Val Ala Ser Tyr Arg Ala Asp Thr Val Ala Lys Val Gln Gly Val
1850                1855                1860

Glu Phe Ser His Arg Leu Asn Ala Asp Ile Glu Gly Leu Thr Ser
1865                1870                1875

Ser Val Asp Val Thr Thr Ser Tyr Asn Ser Asp Pro Leu His Phe
1880                1885                1890

Asn Asn Val Phe His Phe Ser Leu Ala Pro Phe Thr Leu Gly Ile
1895                1900                1905

Asp Thr His Thr Ser Gly Asp Gly Lys Leu Ser Phe Trp Gly Glu
1910                1915                1920

His Thr Gly Gln Leu Tyr Ser Lys Phe Leu Leu Lys Ala Glu Pro
1925                1930                1935

Leu Ala Leu Ile Val Ser His Asp Tyr Lys Gly Ser Thr Ser His
1940                1945                1950
```

-continued

Ser Leu Pro Tyr Glu Ser Ser Ile Ser Thr Ala Leu Glu His Thr
1955                    1960                    1965

Val Ser Ala Leu Leu Thr Pro Ala Glu Gln Thr Ser Thr Trp Lys
1970                    1975                    1980

Phe Lys Thr Lys Leu Asn Asp Lys Val Tyr Ser Gln Asp Phe Glu
1985                    1990                    1995

Ala Tyr Asn Thr Lys Asp Lys Ile Gly Val Glu Leu Ser Gly Arg
2000                    2005                    2010

Ala Asp Leu Ser Gly Leu Tyr Ser Pro Ile Lys Leu Pro Phe Phe
2015                    2020                    2025

Tyr Ser Glu Pro Val Asn Val Leu Asn Gly Leu Glu Val Asn Asp
2030                    2035                    2040

Ala Val Asp Lys Pro Gln Glu Phe Thr Ile Ile Ala Val Val Lys
2045                    2050                    2055

Tyr Asp Lys Asn Gln Asp Val His Thr Ile Asn Leu Pro Phe Phe
2060                    2065                    2070

Lys Ser Leu Pro Asp Tyr Leu Glu Arg Asn Arg Arg Gly Met Ile
2075                    2080                    2085

Ser Leu Leu Glu Ala Met Arg Gly Glu Leu Gln Arg Leu Ser Val
2090                    2095                    2100

Asp Gln Phe Val Arg Lys Tyr Arg Ala Ala Leu Ser Arg Leu Pro
2105                    2110                    2115

Gln Gln Ile His His Tyr Leu Asn Ala Ser Asp Trp Glu Arg Gln
2120                    2125                    2130

Val Ala Gly Ala Lys Glu Lys Ile Thr Ser Phe Met Glu Asn Tyr
2135                    2140                    2145

Arg Ile Thr Asp Asn Asp Val Leu Ile Ala Ile Asp Ser Ala Lys
2150                    2155                    2160

Ile Asn Phe Asn Glu Lys Leu Ser Gln Leu Glu Thr Tyr Ala Ile
2165                    2170                    2175

Gln Phe Asp Gln Tyr Ile Lys Asp Asn Tyr Asp Pro His Asp Leu
2180                    2185                    2190

Lys Arg Thr Ile Ala Glu Ile Ile Asp Arg Ile Ile Glu Lys Leu
2195                    2200                    2205

Lys Ile Leu Asp Glu Gln Tyr His Ile Arg Val Asn Leu Ala Lys
2210                    2215                    2220

Ser Ile His Asn Leu Tyr Leu Phe Val Glu Asn Val Asp Leu Asn
2225                    2230                    2235

Gln Val Ser Ser Ser Asn Thr Ser Trp Ile Gln Asn Val Asp Ser
2240                    2245                    2250

Asn Tyr Gln Val Arg Ile Gln Ile Gln Glu Lys Leu Gln Gln Leu
2255                    2260                    2265

Arg Thr Gln Ile Gln Asn Ile Asp Ile Gln Gln Leu Ala Ala Glu
2270                    2275                    2280

Val Lys Arg Gln Met Asp Ala Ile Asp Val Thr Met His Leu Asp
2285                    2290                    2295

Gln Leu Arg Thr Ala Ile Leu Phe Gln Arg Ile Ser Asp Ile Ile
2300                    2305                    2310

Asp Arg Val Lys Tyr Phe Val Met Asn Leu Ile Glu Asp Phe Lys
2315                    2320                    2325

Val Thr Glu Lys Ile Asn Thr Phe Arg Val Ile Val Arg Glu Leu
2330                    2335                    2340

Ile Glu Lys Tyr Glu Val Asp Gln His Ile Gln Val Leu Met Asp

```
                2345                2350                2355

Lys Ser Val Glu Leu Ala His Arg Tyr Ser Leu Ser Glu Pro Leu
        2360                2365                2370

Gln Lys Leu Ser Asn Val Leu Gln Arg Ile Glu Ile Lys Asp Tyr
        2375                2380                2385

Tyr Glu Lys Leu Val Gly Phe Ile Asp Asp Thr Val Glu Trp Leu
        2390                2395                2400

Lys Ala Leu Ser Phe Lys Asn Thr Ile Glu Glu Leu Asn Arg Leu
        2405                2410                2415

Thr Asp Met Leu Val Lys Lys Leu Lys Ala Phe Asp Tyr His Gln
        2420                2425                2430

Phe Val Asp Lys Thr Asn Ser Lys Ile Arg Glu Met Thr Gln Arg
        2435                2440                2445

Ile Asn Ala Glu Ile Gln Ala Leu Lys Leu Pro Gln Lys Met Glu
        2450                2455                2460

Ala Leu Lys Leu Leu Val Glu Asp Phe Lys Thr Thr Val Ser Asn
        2465                2470                2475

Ser Leu Glu Arg Leu Lys Asp Thr Lys Val Thr Val Ile Asp
        2480                2485                2490

Trp Leu Gln Asp Ile Leu Thr Gln Met Lys Asp His Phe Gln Asp
        2495                2500                2505

Thr Leu Glu Asp Val Arg Asp Arg Ile Tyr Gln Met Asp Ile Gln
        2510                2515                2520

Arg Glu Leu Glu His Phe Leu Ser Leu Val Asn Gln Val Tyr Ser
        2525                2530                2535

Thr Leu Val Thr Tyr Met Ser Asp Trp Trp Thr Leu Thr Ala Lys
        2540                2545                2550

Asn Ile Thr Asp Phe Ala Glu Gln Tyr Ser Ile Gln Asn Trp Ala
        2555                2560                2565

Glu Ser Ile Lys Val Leu Val Glu Gln Gly Phe Ile Val Pro Glu
        2570                2575                2580

Met Gln Thr Phe Leu Trp Thr Met Pro Ala Phe Glu Val Ser Leu
        2585                2590                2595

Arg Ala Leu Gln Glu Gly Asn Phe Gln Thr Pro Val Phe Ile Val
        2600                2605                2610

Pro Leu Thr Asp Leu Arg Ile Pro Ser Ile Arg Ile Asn Phe Lys
        2615                2620                2625

Met Leu Lys Asn Ile Lys Ile Pro Leu Arg Phe Ser Thr Pro Glu
        2630                2635                2640

Phe Thr Leu Leu Asn Thr Phe His Val His Ser Phe Thr Ile Asp
        2645                2650                2655

Leu Leu Glu Ile Lys Ala Lys Ile Ile Arg Thr Ile Asp Gln Ile
        2660                2665                2670

Leu Ser Ser Glu Leu Gln Trp Pro Leu Pro Glu Met Tyr Leu Arg
        2675                2680                2685

Asp Leu Asp Val Val Asn Ile Pro Leu Ala Arg Leu Thr Leu Pro
        2690                2695                2700

Asp Phe His Val Pro Glu Ile Thr Ile Pro Glu Phe Thr Ile Pro
        2705                2710                2715

Asn Val Asn Leu Lys Asp Leu His Val Pro Asp Leu His Ile Pro
        2720                2725                2730

Glu Phe Gln Leu Pro His Leu Ser His Thr Ile Glu Ile Pro Ala
        2735                2740                2745
```

```
Phe Gly Lys Leu His Ser Ile Leu Lys Ile Gln Ser Pro Leu Phe
    2750            2755            2760

Ile Leu Asp Ala Asn Ala Asn Ile Gln Asn Val Thr Thr Ser Gly
    2765            2770            2775

Asn Lys Ala Glu Ile Val Ala Ser Val Thr Ala Lys Gly Glu Ser
    2780            2785            2790

Gln Phe Glu Ala Leu Asn Phe Asp Phe Gln Ala Gln Ala Gln Phe
    2795            2800            2805

Leu Glu Leu Asn Pro His Pro Pro Val Leu Lys Glu Ser Met Asn
    2810            2815            2820

Phe Ser Ser Lys His Val Arg Met Glu His Glu Gly Glu Ile Val
    2825            2830            2835

Phe Asp Gly Lys Ala Ile Glu Gly Lys Ser Asp Thr Val Ala Ser
    2840            2845            2850

Leu His Thr Glu Lys Asn Glu Val Glu Phe Asn Asn Gly Met Thr
    2855            2860            2865

Val Lys Val Asn Asn Gln Leu Thr Leu Asp Ser His Thr Lys Tyr
    2870            2875            2880

Phe His Lys Leu Ser Val Pro Arg Leu Asp Phe Ser Ser Lys Ala
    2885            2890            2895

Ser Leu Asn Asn Glu Ile Lys Thr Leu Leu Glu Ala Gly His Val
    2900            2905            2910

Ala Leu Thr Ser Ser Gly Thr Gly Ser Trp Asn Trp Ala Cys Pro
    2915            2920            2925

Asn Phe Ser Asp Glu Gly Ile His Ser Ser Gln Ile Ser Phe Thr
    2930            2935            2940

Val Asp Gly Pro Ile Ala Phe Val Gly Leu Ser Asn Asn Ile Asn
    2945            2950            2955

Gly Lys His Leu Arg Val Ile Gln Lys Leu Thr Tyr Glu Ser Gly
    2960            2965            2970

Phe Leu Asn Tyr Ser Lys Phe Glu Val Glu Ser Lys Val Glu Ser
    2975            2980            2985

Gln His Val Gly Ser Ser Ile Leu Thr Ala Asn Gly Arg Ala Leu
    2990            2995            3000

Leu Lys Asp Ala Lys Ala Glu Met Thr Gly Glu His Asn Ala Asn
    3005            3010            3015

Leu Asn Gly Lys Val Ile Gly Thr Leu Lys Asn Ser Leu Phe Phe
    3020            3025            3030

Ser Ala Gln Pro Phe Glu Ile Thr Ala Ser Thr Asn Asn Glu Gly
    3035            3040            3045

Asn Leu Lys Val Gly Phe Pro Leu Lys Leu Thr Gly Lys Ile Asp
    3050            3055            3060

Phe Leu Asn Asn Tyr Ala Leu Phe Leu Ser Pro Arg Ala Gln Gln
    3065            3070            3075

Ala Ser Trp Gln Ala Ser Thr Arg Phe Asn Gln Tyr Lys Tyr Asn
    3080            3085            3090

Gln Asn Phe Ser Ala Ile Asn Asn Glu His Asn Ile Glu Ala Ser
    3095            3100            3105

Ile Gly Met Asn Gly Asp Ala Asn Leu Asp Phe Leu Asn Ile Pro
    3110            3115            3120

Leu Thr Ile Pro Glu Ile Asn Leu Pro Tyr Thr Glu Phe Lys Thr
    3125            3130            3135
```

-continued

| | | | | | | | | | | |
|---|---|---|---|---|---|---|---|---|---|---|
|Pro|Leu|Leu|Lys|Asp|Phe|Ser|Ile|Trp|Glu|Glu|Thr|Gly|Leu|Lys|
| |3140| | | |3145| | | |3150| | | | | |
|Glu|Phe|Leu|Lys|Thr|Thr|Lys|Gln|Ser|Phe|Asp|Leu|Ser|Val|Lys|
| |3155| | | |3160| | | |3165| | | | | |
|Ala|Gln|Tyr|Lys|Lys|Asn|Ser|Asp|Lys|His|Ser|Ile|Val|Val|Pro|
| |3170| | | |3175| | | |3180| | | | | |
|Leu|Gly|Met|Phe|Tyr|Glu|Phe|Ile|Leu|Asn|Asn|Val|Asn|Ser|Trp|
| |3185| | | |3190| | | |3195| | | | | |
|Asp|Arg|Lys|Phe|Glu|Lys|Val|Arg|Asn|Asn|Ala|Leu|His|Phe|Leu|
| |3200| | | |3205| | | |3210| | | | | |
|Thr|Thr|Ser|Tyr|Asn|Glu|Ala|Lys|Ile|Lys|Val|Asp|Lys|Tyr|Lys|
| |3215| | | |3220| | | |3225| | | | | |
|Thr|Glu|Asn|Ser|Leu|Asn|Gln|Pro|Ser|Gly|Thr|Phe|Gln|Asn|His|
| |3230| | | |3235| | | |3240| | | | | |
|Gly|Tyr|Thr|Ile|Pro|Val|Val|Asn|Ile|Glu|Val|Ser|Pro|Phe|Ala|
| |3245| | | |3250| | | |3255| | | | | |
|Val|Glu|Thr|Leu|Ala|Ser|Ser|His|Val|Ile|Pro|Thr|Ala|Ile|Ser|
| |3260| | | |3265| | | |3270| | | | | |
|Thr|Pro|Ser|Val|Thr|Ile|Pro|Gly|Pro|Asn|Ile|Met|Val|Pro|Ser|
| |3275| | | |3280| | | |3285| | | | | |
|Tyr|Lys|Leu|Val|Leu|Pro|Pro|Leu|Glu|Leu|Pro|Val|Phe|His|Gly|
| |3290| | | |3295| | | |3300| | | | | |
|Pro|Gly|Asn|Leu|Phe|Lys|Phe|Phe|Leu|Pro|Asp|Phe|Lys|Gly|Phe|
| |3305| | | |3310| | | |3315| | | | | |
|Asn|Thr|Ile|Asp|Asn|Ile|Tyr|Ile|Pro|Ala|Met|Gly|Asn|Phe|Thr|
| |3320| | | |3325| | | |3330| | | | | |
|Tyr|Asp|Phe|Ser|Phe|Lys|Ser|Ser|Val|Ile|Thr|Leu|Asn|Thr|Asn|
| |3335| | | |3340| | | |3345| | | | | |
|Ala|Gly|Leu|Tyr|Asn|Gln|Ser|Asp|Ile|Val|Ala|His|Phe|Leu|Ser|
| |3350| | | |3355| | | |3360| | | | | |
|Ser|Ser|Ser|Phe|Val|Thr|Asp|Ala|Leu|Gln|Tyr|Lys|Leu|Glu|Gly|
| |3365| | | |3370| | | |3375| | | | | |
|Thr|Ser|Arg|Leu|Met|Arg|Lys|Arg|Gly|Leu|Lys|Leu|Ala|Thr|Ala|
| |3380| | | |3385| | | |3390| | | | | |
|Val|Ser|Leu|Thr|Asn|Lys|Phe|Val|Lys|Gly|Ser|His|Asp|Ser|Thr|
| |3395| | | |3400| | | |3405| | | | | |
|Ile|Ser|Leu|Thr|Lys|Lys|Asn|Met|Glu|Ala|Ser|Val|Arg|Thr|Thr|
| |3410| | | |3415| | | |3420| | | | | |
|Ala|Asn|Leu|His|Ala|Pro|Ile|Phe|Ser|Met|Asn|Phe|Lys|Gln|Glu|
| |3425| | | |3430| | | |3435| | | | | |
|Leu|Asn|Gly|Asn|Thr|Lys|Ser|Lys|Pro|Thr|Val|Ser|Ser|Ser|Ile|
| |3440| | | |3445| | | |3450| | | | | |
|Glu|Leu|Asn|Tyr|Asp|Phe|Asn|Ser|Ser|Lys|Leu|His|Ser|Thr|Ala|
| |3455| | | |3460| | | |3465| | | | | |
|Thr|Gly|Gly|Ile|Asp|His|Lys|Phe|Ser|Leu|Glu|Ser|Leu|Thr|Ser|
| |3470| | | |3475| | | |3480| | | | | |
|Tyr|Phe|Ser|Ile|Glu|Ser|Phe|Thr|Lys|Gly|Asn|Ile|Lys|Ser|Ser|
| |3485| | | |3490| | | |3495| | | | | |
|Phe|Leu|Ser|Gln|Glu|Tyr|Ser|Gly|Ser|Val|Ala|Asn|Glu|Ala|Asn|
| |3500| | | |3505| | | |3510| | | | | |
|Val|Tyr|Leu|Asn|Ser|Lys|Gly|Thr|Arg|Ser|Ser|Val|Arg|Leu|Gln|
| |3515| | | |3520| | | |3525| | | | | |
|Gly|Ala|Ser|Lys|Val|Asp|Gly|Ile|Trp|Asn|Val|Glu|Val|Gly|Glu|

-continued

```
            3530               3535               3540

Asn Phe Ala Gly Glu Ala Thr Leu Gln Arg Ile Tyr Thr Thr Trp
    3545               3550               3555

Glu His Asn Met Lys Asn His Leu Gln Val Tyr Ser Tyr Phe Phe
    3560               3565               3570

Thr Lys Gly Lys Gln Thr Cys Arg Ala Thr Leu Glu Leu Ser Pro
    3575               3580               3585

Trp Thr Met Ser Thr Leu Leu Gln Val His Val Ser Gln Leu Ser
    3590               3595               3600

Ser Leu Leu Asp Leu His His Phe Asp Gln Glu Val Ile Leu Lys
    3605               3610               3615

Ala Asn Thr Lys Asn Gln Lys Ile Ser Trp Lys Gly Gly Val Gln
    3620               3625               3630

Val Glu Ser Arg Val Leu Gln His Asn Ala Gln Phe Ser Asn Asp
    3635               3640               3645

Gln Glu Glu Ile Arg Leu Asp Leu Ala Gly Ser Leu Asp Gly Gln
    3650               3655               3660

Leu Trp Asp Leu Glu Ala Ile Phe Leu Pro Val Tyr Gly Lys Ser
    3665               3670               3675

Leu Gln Glu Leu Leu Gln Met Asp Gly Lys Arg Gln Tyr Leu Gln
    3680               3685               3690

Ala Ser Thr Ser Leu Leu Tyr Thr Lys Asn Pro Asn Gly Tyr Leu
    3695               3700               3705

Leu Ser Leu Pro Val Gln Glu Leu Ala Asp Arg Phe Ile Ile Pro
    3710               3715               3720

Gly Ile Lys Leu Asn Asp Phe Ser Gly Val Lys Ile Tyr Lys Lys
    3725               3730               3735

Leu Ser Thr Ser Pro Phe Ala Leu Asn Leu Thr Met Leu Pro Lys
    3740               3745               3750

Val Lys Phe Pro Gly Ile Asp Leu Leu Thr Gln Tyr Ser Thr Pro
    3755               3760               3765

Glu Gly Ser Ser Val Pro Ile Phe Glu Ala Thr Ile Pro Glu Ile
    3770               3775               3780

His Leu Thr Val Ser Gln Phe Thr Leu Pro Lys Ser Leu Pro Val
    3785               3790               3795

Gly Asn Thr Val Phe Asp Leu Asn Lys Leu Ala Asn Met Ile Ala
    3800               3805               3810

Asp Val Asp Leu Pro Ser Val Thr Leu Pro Glu Gln Thr Ile Val
    3815               3820               3825

Ile Pro Pro Leu Glu Phe Ser Val Pro Ala Gly Ile Phe Ile Pro
    3830               3835               3840

Phe Phe Gly Glu Leu Thr Ala Arg Ala Gly Met Ala Ser Pro Leu
    3845               3850               3855

Tyr Asn Val Thr Trp Ser Ala Gly Trp Lys Thr Lys Ala Asp His
    3860               3865               3870

Val Glu Thr Phe Leu Asp Ser Met Cys Thr Ser Thr Leu Gln Phe
    3875               3880               3885

Leu Glu Tyr Ala Leu Lys Val Val Glu Thr His Lys Ile Glu Glu
    3890               3895               3900

Asp Leu Leu Thr Tyr Asn Ile Lys Gly Thr Leu Gln His Cys Asp
    3905               3910               3915

Phe Asn Val Glu Tyr Asn Glu Asp Gly Leu Phe Lys Gly Leu Trp
    3920               3925               3930
```

```
Asp Trp Gln Gly Glu Ala His Leu Asp Ile Thr Ser Pro Ala Leu
3935                3940                3945

Thr Asp Phe His Leu Tyr Tyr Lys Glu Asp Lys Thr Ser Leu Ser
3950                3955                3960

Ala Ser Ala Ala Ser Ser Thr Ile Gly Thr Val Gly Leu Asp Ser
3965                3970                3975

Ser Thr Asp Asp Gln Ser Val Glu Leu Asn Val Tyr Phe His Pro
3980                3985                3990

Gln Ser Pro Pro Glu Lys Lys Leu Ser Ile Phe Lys Thr Glu Trp
3995                4000                4005

Arg Tyr Lys Glu Ser Asp Gly Glu Arg Tyr Ile Lys Ile Asn Trp
4010                4015                4020

Glu Glu Glu Ala Ala Ser Arg Leu Leu Gly Ser Leu Lys Ser Asn
4025                4030                4035

Val Pro Lys Ala Ser Lys Ala Ile Tyr Asp Tyr Ala Asn Lys Tyr
4040                4045                4050

His Leu Glu Tyr Val Ser Ser Glu Leu Arg Lys Ser Leu Gln Val
4055                4060                4065

Asn Ala Glu His Ala Arg Arg Met Val Asp Glu Met Asn Met Ser
4070                4075                4080

Phe Gln Arg Val Ala Arg Asp Thr Tyr Gln Asn Leu Tyr Glu Glu
4085                4090                4095

Met Leu Ala Gln Lys Ser Leu Ser Ile Pro Glu Asn Leu Lys Lys
4100                4105                4110

Arg Val Leu Asp Ser Ile Val His Val Thr Gln Lys Tyr His Met
4115                4120                4125

Ala Val Met Trp Leu Met Asp Ser Phe Ile His Phe Leu Lys Phe
4130                4135                4140

Asn Arg Val Gln Phe Pro Gly Tyr Ala Gly Thr Tyr Thr Val Asp
4145                4150                4155

Glu Leu Tyr Thr Ile Val Met Lys Glu Thr Lys Lys Ser Leu Ser
4160                4165                4170

Gln Leu Phe Asn Gly Leu Gly Asn Leu Leu Ser Tyr Val Gln Asn
4175                4180                4185

Gln Val Glu Lys Ser Arg Leu Ile Asn Asp Ile Thr Phe Lys Cys
4190                4195                4200

Pro Phe Phe Ser Lys Pro Cys Lys Leu Lys Asp Leu Ile Leu Ile
4205                4210                4215

Phe Arg Glu Glu Leu Asn Ile Leu Ser Asn Ile Gly Gln Gln Asp
4220                4225                4230

Ile Lys Phe Thr Thr Ile Leu Ser Ser Leu Gln Gly Phe Leu Glu
4235                4240                4245

Arg Val Leu Asp Ile Ile Glu Glu Gln Ile Lys Cys Leu Lys Asp
4250                4255                4260

Asn Glu Ser Thr Cys Val Ala Asp His Ile Asn Met Val Phe Lys
4265                4270                4275

Ile Gln Val Pro Tyr Ala Phe Lys Ser Leu Arg Glu Asp Ile Tyr
4280                4285                4290

Phe Val Leu Gly Glu Phe Asn Asp Phe Leu Gln Ser Ile Leu Gln
4295                4300                4305

Glu Gly Ser Tyr Lys Leu Gln Gln Val His Gln Tyr Met Lys Ala
4310                4315                4320
```

Leu Arg Glu Glu Tyr Phe Asp Pro Ser Met Val Gly Trp Thr Val
4325                4330                4335

Lys Tyr Tyr Glu Ile Glu Asn Met Val Glu Leu Ile Lys Thr
4340                4345                4350

Leu Leu Val Ser Phe Arg Asp Val Tyr Ser Glu Tyr Ser Val Thr
4355                4360                4365

Ala Ala Asp Phe Ala Ser Lys Met Ser Thr Gln Val Glu Gln Phe
4370                4375                4380

Val Ser Arg Asp Ile Arg Glu Tyr Leu Ser Met Leu Thr Asp Ile
4385                4390                4395

Asn Gly Lys Trp Met Glu Lys Ile Ala Glu Leu Ser Ile Val Ala
4400                4405                4410

Lys Glu Thr Met Lys Ser Trp Val Thr Ala Val Ala Lys Ile Met
4415                4420                4425

Ser Asp Tyr Pro Gln Gln Phe His Ser Asn Leu Gln Asp Phe Ser
4430                4435                4440

Asp Gln Leu Ser Ser Tyr Tyr Glu Lys Phe Val Gly Glu Ser Thr
4445                4450                4455

Arg Leu Ile Asp Leu Ser Ile Gln Asn Tyr His Val Phe Leu Arg
4460                4465                4470

Tyr Ile Thr Glu Leu Leu Arg Lys Leu Gln Val Ala Thr Ala Asn
4475                4480                4485

Asn Val Ser Pro Tyr Ile Lys Leu Ala Gln Gly Glu Leu Met Ile
4490                4495                4500

Thr Phe
4505

<210> SEQ ID NO 37
<211> LENGTH: 317
<212> TYPE: PRT
<213> ORGANISM: Homo sapiens

<400> SEQUENCE: 37

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
                20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

```
Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315

<210> SEQ ID NO 38
<211> LENGTH: 1480
<212> TYPE: PRT
<213> ORGANISM: Homo sapiens

<400> SEQUENCE: 38

Met Lys Pro Arg Ala Glu Cys Cys Ser Pro Lys Phe Trp Leu Val Leu
1               5                   10                  15

Ala Val Leu Ala Val Ser Gly Ser Arg Ala Arg Ser Gln Lys Ser Pro
            20                  25                  30

Pro Ser Ile Gly Ile Ala Val Ile Leu Val Gly Thr Ser Asp Glu Val
        35                  40                  45

Ala Ile Lys Asp Ala His Glu Lys Asp Asp Phe His His Leu Ser Val
    50                  55                  60

Val Pro Arg Val Glu Leu Val Ala Met Asn Glu Thr Asp Pro Lys Ser
65                  70                  75                  80

Ile Ile Thr Arg Ile Cys Asp Leu Met Ser Asp Arg Lys Ile Gln Gly
                85                  90                  95

Val Val Phe Ala Asp Asp Thr Asp Gln Glu Ala Ile Ala Gln Ile Leu
            100                 105                 110

Asp Phe Ile Ser Ala Gln Thr Leu Thr Pro Ile Leu Gly Ile His Gly
        115                 120                 125

Gly Ser Ser Met Ile Met Ala Asp Lys Asp Glu Ser Ser Met Phe Phe
    130                 135                 140

Gln Phe Gly Pro Ser Ile Glu Gln Gln Ala Ser Val Met Leu Asn Ile
145                 150                 155                 160

Met Glu Glu Tyr Asp Trp Tyr Ile Phe Ser Ile Val Thr Thr Tyr Phe
                165                 170                 175

Pro Gly Tyr Gln Asp Phe Val Asn Lys Ile Arg Ser Thr Ile Glu Asn
            180                 185                 190

Ser Phe Val Gly Trp Glu Leu Glu Glu Val Leu Leu Leu Asp Met Ser
        195                 200                 205

Leu Asp Asp Gly Asp Ser Lys Ile Gln Asn Gln Leu Lys Lys Leu Gln
    210                 215                 220

Ser Pro Ile Ile Leu Leu Tyr Cys Thr Lys Glu Glu Ala Thr Tyr Ile
```

```
            225                 230                 235                 240
        Phe Glu Val Ala Asn Ser Val Gly Leu Thr Gly Tyr Gly Tyr Thr Trp
                        245                 250                 255

Ile Val Pro Ser Leu Val Ala Gly Asp Thr Asp Thr Val Pro Ala Glu
                        260                 265                 270

Phe Pro Thr Gly Leu Ile Ser Val Ser Tyr Asp Glu Trp Asp Tyr Gly
                        275                 280                 285

Leu Pro Ala Arg Val Arg Asp Gly Ile Ala Ile Ile Thr Thr Ala Ala
                        290                 295                 300

Ser Asp Met Leu Ser Glu His Ser Phe Ile Pro Glu Pro Lys Ser Ser
        305                 310                 315                 320

Cys Tyr Asn Thr His Glu Lys Arg Ile Tyr Gln Ser Asn Met Leu Asn
                        325                 330                 335

Arg Tyr Leu Ile Asn Val Thr Phe Glu Gly Arg Asn Leu Ser Phe Ser
                        340                 345                 350

Glu Asp Gly Tyr Gln Met His Pro Lys Leu Val Ile Ile Leu Leu Asn
                        355                 360                 365

Lys Glu Arg Lys Trp Glu Arg Val Gly Lys Trp Lys Asp Lys Ser Leu
                        370                 375                 380

Gln Met Lys Tyr Tyr Val Trp Pro Arg Met Cys Pro Glu Thr Glu Glu
        385                 390                 395                 400

Gln Glu Asp Asp His Leu Ser Ile Val Thr Leu Glu Glu Ala Pro Phe
                        405                 410                 415

Val Ile Val Glu Ser Val Asp Pro Leu Ser Gly Thr Cys Met Arg Asn
                        420                 425                 430

Thr Val Pro Cys Gln Lys Arg Ile Val Thr Glu Asn Lys Thr Asp Glu
                        435                 440                 445

Glu Pro Gly Tyr Ile Lys Lys Cys Cys Lys Gly Phe Cys Ile Asp Ile
                        450                 455                 460

Leu Lys Lys Ile Ser Lys Ser Val Lys Phe Thr Tyr Asp Leu Tyr Leu
        465                 470                 475                 480

Val Thr Asn Gly Lys His Gly Lys Lys Ile Asn Gly Thr Trp Asn Gly
                        485                 490                 495

Met Ile Gly Glu Val Val Met Lys Arg Ala Tyr Met Ala Val Gly Ser
                        500                 505                 510

Leu Thr Ile Asn Glu Glu Arg Ser Glu Val Val Asp Phe Ser Val Pro
                        515                 520                 525

Phe Ile Glu Thr Gly Ile Ser Val Met Val Ser Arg Ser Asn Gly Thr
                        530                 535                 540

Val Ser Pro Ser Ala Phe Leu Glu Pro Phe Ser Ala Asp Val Trp Val
        545                 550                 555                 560

Met Met Phe Val Met Leu Leu Ile Val Ser Ala Val Ala Val Phe Val
                        565                 570                 575

Phe Glu Tyr Phe Ser Pro Val Gly Tyr Asn Arg Cys Leu Ala Asp Gly
                        580                 585                 590

Arg Glu Pro Gly Gly Pro Ser Phe Thr Ile Gly Lys Ala Ile Trp Leu
                        595                 600                 605

Leu Trp Gly Leu Val Phe Asn Asn Ser Val Pro Val Gln Asn Pro Lys
                        610                 615                 620

Gly Thr Thr Ser Lys Ile Met Val Ser Val Trp Ala Phe Phe Ala Val
        625                 630                 635                 640

Ile Phe Leu Ala Ser Tyr Thr Ala Asn Leu Ala Ala Phe Met Ile Gln
                        645                 650                 655
```

```
Glu Glu Tyr Val Asp Gln Val Ser Gly Leu Ser Asp Lys Lys Phe Gln
            660                 665                 670

Arg Pro Asn Asp Phe Ser Pro Pro Phe Arg Phe Gly Thr Val Pro Asn
            675                 680                 685

Gly Ser Thr Glu Arg Asn Ile Arg Asn Asn Tyr Ala Glu Met His Ala
            690                 695                 700

Tyr Met Gly Lys Phe Asn Gln Arg Gly Val Asp Asp Ala Leu Leu Ser
705                 710                 715                 720

Leu Lys Thr Gly Lys Leu Asp Ala Phe Ile Tyr Asp Ala Ala Val Leu
            725                 730                 735

Asn Tyr Met Ala Gly Arg Asp Glu Gly Cys Lys Leu Val Thr Ile Gly
            740                 745                 750

Ser Gly Lys Val Phe Ala Ser Thr Gly Tyr Gly Ile Ala Ile Gln Lys
            755                 760                 765

Asp Ser Gly Trp Lys Arg Gln Val Asp Leu Ala Ile Leu Gln Leu Phe
            770                 775                 780

Gly Asp Gly Glu Met Glu Glu Leu Glu Ala Leu Trp Leu Thr Gly Ile
785                 790                 795                 800

Cys His Asn Glu Lys Asn Glu Val Met Ser Ser Gln Leu Asp Ile Asp
            805                 810                 815

Asn Met Ala Gly Val Phe Tyr Met Leu Gly Ala Ala Met Ala Leu Ser
            820                 825                 830

Leu Ile Thr Phe Ile Cys Glu His Leu Phe Tyr Trp Gln Phe Arg His
            835                 840                 845

Cys Phe Met Gly Val Cys Ser Gly Lys Pro Gly Met Val Phe Ser Ile
            850                 855                 860

Ser Arg Gly Ile Tyr Ser Cys Ile His Gly Val Ala Ile Glu Glu Arg
865                 870                 875                 880

Gln Ser Val Met Asn Ser Pro Thr Ala Thr Met Asn Asn Thr His Ser
            885                 890                 895

Asn Ile Leu Arg Leu Leu Arg Thr Ala Lys Asn Met Ala Asn Leu Ser
            900                 905                 910

Gly Val Asn Gly Ser Pro Gln Ser Ala Leu Asp Phe Ile Arg Arg Glu
            915                 920                 925

Ser Ser Val Tyr Asp Ile Ser Glu His Arg Arg Ser Phe Thr His Ser
            930                 935                 940

Asp Cys Lys Ser Tyr Asn Asn Pro Pro Cys Glu Glu Asn Leu Phe Ser
945                 950                 955                 960

Asp Tyr Ile Ser Glu Val Glu Arg Thr Phe Gly Asn Leu Gln Leu Lys
            965                 970                 975

Asp Ser Asn Val Tyr Gln Asp His Tyr His His His Arg Pro His
            980                 985                 990

Ser Ile Gly Ser Ala Ser Ser Ile Asp Gly Leu Tyr Asp Cys Asp Asn
            995                 1000                1005

Pro Pro Phe Thr Thr Gln Ser Arg Ser Ile Ser Lys Lys Pro Leu
       1010                1015                1020

Asp Ile Gly Leu Pro Ser Ser Lys His Ser Gln Leu Ser Asp Leu
       1025                1030                1035

Tyr Gly Lys Phe Ser Phe Lys Ser Asp Arg Tyr Ser Gly His Asp
       1040                1045                1050

Asp Leu Ile Arg Ser Asp Val Ser Asp Ile Ser Thr His Thr Val
       1055                1060                1065
```

```
Thr Tyr Gly Asn Ile Glu Gly Asn Ala Ala Lys Arg Arg Lys Gln
1070             1075                 1080

Gln Tyr Lys Asp Ser Leu Lys Arg Pro Ala Ser Ala Lys Ser
1085             1090                 1095

Arg Arg Glu Phe Asp Glu Ile Glu Leu Ala Tyr Arg Arg Pro
1100             1105                 1110

Pro Arg Ser Pro Asp His Lys Arg Tyr Phe Arg Asp Lys Glu Gly
1115             1120                 1125

Leu Arg Asp Phe Tyr Leu Asp Gln Phe Arg Thr Glu Asn Ser Pro
1130             1135                 1140

His Trp Glu His Val Asp Leu Thr Asp Ile Tyr Lys Glu Arg Ser
1145             1150                 1155

Asp Asp Phe Lys Arg Asp Ser Val Ser Gly Gly Pro Cys Thr
1160             1165                 1170

Asn Arg Ser His Ile Lys His Gly Thr Gly Asp Lys His Gly Val
1175             1180                 1185

Val Ser Gly Val Pro Ala Pro Trp Glu Lys Asn Leu Thr Asn Val
1190             1195                 1200

Glu Trp Glu Asp Arg Ser Gly Gly Asn Phe Cys Arg Ser Cys Pro
1205             1210                 1215

Ser Lys Leu His Asn Tyr Ser Thr Thr Val Thr Gly Gln Asn Ser
1220             1225                 1230

Gly Arg Gln Ala Cys Ile Arg Cys Glu Ala Cys Lys Lys Ala Gly
1235             1240                 1245

Asn Leu Tyr Asp Ile Ser Glu Asp Asn Ser Leu Gln Glu Leu Asp
1250             1255                 1260

Gln Pro Ala Ala Pro Val Ala Val Thr Ser Asn Ala Ser Thr Thr
1265             1270                 1275

Lys Tyr Pro Gln Ser Pro Thr Asn Ser Lys Ala Gln Lys Lys Asn
1280             1285                 1290

Arg Asn Lys Leu Arg Arg Gln His Ser Tyr Asp Thr Phe Val Asp
1295             1300                 1305

Leu Gln Lys Glu Glu Ala Leu Ala Pro Arg Ser Val Ser Leu Lys
1310             1315                 1320

Asp Lys Gly Arg Phe Met Asp Gly Ser Pro Tyr Ala His Met Phe
1325             1330                 1335

Glu Met Ser Ala Gly Glu Ser Thr Phe Ala Asn Asn Lys Ser Ser
1340             1345                 1350

Val Pro Thr Ala Gly His His His His Asn Asn Pro Gly Gly Gly
1355             1360                 1365

Tyr Leu Ser Lys Ser Leu Tyr Pro Asp Arg Val Thr Gln Asn Pro
1370             1375                 1380

Phe Ile Pro Thr Phe Gly Asp Asp Gln Cys Leu Leu His Gly Ser
1385             1390                 1395

Lys Ser Tyr Phe Phe Arg Gln Pro Thr Val Ala Gly Ala Ser Lys
1400             1405                 1410

Ala Arg Pro Asp Phe Arg Ala Leu Val Thr Asn Lys Pro Val Ser
1415             1420                 1425

Ala Leu His Gly Ala Val Pro Ala Arg Phe Gln Lys Asp Ile Cys
1430             1435                 1440

Ile Gly Asn Gln Ser Asn Pro Cys Val Pro Asn Asn Lys Asn Pro
1445             1450                 1455

Arg Ala Phe Asn Gly Ser Ser Asn Gly His Val Tyr Glu Lys Leu
```

Ser Ser Ile Glu Ser Asp Val
    1475            1480

<210> SEQ ID NO 39
<211> LENGTH: 653
<212> TYPE: PRT
<213> ORGANISM: Homo sapiens

<400> SEQUENCE: 39

Met Glu Val Ala Met Val Ser Ala Glu Ser Ser Gly Cys Asn Ser His
1               5                   10                  15

Met Pro Tyr Gly Tyr Ala Ala Gln Ala Arg Ala Arg Glu Arg Glu Arg
            20                  25                  30

Leu Ala His Ser Arg Ala Ala Ala Ala Ala Val Ala Ala Ala Thr
        35                  40                  45

Ala Ala Val Glu Gly Ser Gly Gly Ser Gly Gly Gly Ser His His His
    50                  55                  60

His Gln Ser Arg Gly Ala Cys Thr Ser His Asp Pro Gln Ser Ser Arg
65                  70                  75                  80

Gly Ser Arg Arg Arg Arg Gln Arg Ser Glu Lys Lys Lys Ala His
                85                  90                  95

Tyr Arg Gln Ser Ser Phe Pro His Cys Ser Asp Leu Met Pro Ser Gly
            100                 105                 110

Ser Glu Glu Lys Ile Leu Arg Glu Leu Ser Glu Glu Glu Asp Glu
        115                 120                 125

Glu Glu Glu Glu Glu Glu Glu Gly Arg Phe Tyr Tyr Ser Glu
    130                 135                 140

Asp Asp His Gly Asp Glu Cys Ser Tyr Thr Asp Leu Leu Pro Gln Asp
145                 150                 155                 160

Glu Gly Gly Gly Gly Tyr Ser Ser Val Arg Tyr Ser Asp Cys Cys Glu
                165                 170                 175

Arg Val Val Ile Asn Val Ser Gly Leu Arg Phe Glu Thr Gln Met Lys
            180                 185                 190

Thr Leu Ala Gln Phe Pro Glu Thr Leu Leu Gly Asp Pro Glu Lys Arg
        195                 200                 205

Thr Gln Tyr Phe Asp Pro Leu Arg Asn Glu Tyr Phe Phe Asp Arg Asn
    210                 215                 220

Arg Pro Ser Phe Asp Ala Ile Leu Tyr Tyr Tyr Gln Ser Gly Gly Arg
225                 230                 235                 240

Leu Lys Arg Pro Val Asn Val Pro Phe Asp Ile Phe Thr Glu Glu Val
                245                 250                 255

Lys Phe Tyr Gln Leu Gly Glu Glu Ala Leu Leu Lys Phe Arg Glu Asp
            260                 265                 270

Glu Gly Phe Val Arg Glu Glu Asp Arg Ala Leu Pro Glu Asn Glu
        275                 280                 285

Phe Lys Lys Gln Ile Trp Leu Leu Phe Glu Tyr Pro Glu Ser Ser Ser
    290                 295                 300

Pro Ala Arg Gly Ile Ala Ile Val Ser Val Leu Val Ile Leu Ile Ser
305                 310                 315                 320

Ile Val Ile Phe Cys Leu Glu Thr Leu Pro Glu Phe Arg Asp Asp Arg
                325                 330                 335

Asp Leu Val Met Ala Leu Ser Ala Gly Gly His Gly Gly Leu Leu Asn
            340                 345                 350

```
Asp Thr Ser Ala Pro His Leu Glu Asn Ser Gly His Thr Ile Phe Asn
                355                 360                 365

Asp Pro Phe Phe Ile Val Glu Thr Val Cys Ile Val Trp Phe Ser Phe
            370                 375                 380

Glu Phe Val Val Arg Cys Phe Ala Cys Pro Ser Gln Ala Leu Phe Phe
385                 390                 395                 400

Lys Asn Ile Met Asn Ile Ile Asp Ile Val Ser Ile Leu Pro Tyr Phe
                405                 410                 415

Ile Thr Leu Gly Thr Asp Leu Ala Gln Gln Gly Gly Gly Asn Gly
                420                 425                 430

Gln Gln Gln Gln Ala Met Ser Phe Ala Ile Leu Arg Ile Ile Arg Leu
            435                 440                 445

Val Arg Val Phe Arg Ile Phe Lys Leu Ser Arg His Ser Lys Gly Leu
450                 455                 460

Gln Ile Leu Gly His Thr Leu Arg Ala Ser Met Arg Glu Leu Gly Leu
465                 470                 475                 480

Leu Ile Phe Phe Leu Phe Ile Gly Val Ile Leu Phe Ser Ser Ala Val
                485                 490                 495

Tyr Phe Ala Glu Ala Asp Glu Pro Thr Thr His Phe Gln Ser Ile Pro
            500                 505                 510

Asp Ala Phe Trp Trp Ala Val Val Thr Met Thr Thr Val Gly Tyr Gly
            515                 520                 525

Asp Met Lys Pro Ile Thr Val Gly Gly Lys Ile Val Gly Ser Leu Cys
            530                 535                 540

Ala Ile Ala Gly Val Leu Thr Ile Ala Leu Pro Val Pro Val Ile Val
545                 550                 555                 560

Ser Asn Phe Asn Tyr Phe Tyr His Arg Glu Thr Glu Asn Glu Glu Gln
                565                 570                 575

Thr Gln Leu Thr Gln Asn Ala Val Ser Cys Pro Tyr Leu Pro Ser Asn
            580                 585                 590

Leu Leu Lys Lys Phe Arg Ser Ser Thr Ser Ser Ser Leu Gly Asp Lys
            595                 600                 605

Ser Glu Tyr Leu Glu Met Glu Glu Gly Val Lys Glu Ser Leu Cys Ala
610                 615                 620

Lys Glu Glu Lys Cys Gln Gly Lys Gly Asp Asp Ser Glu Thr Asp Lys
625                 630                 635                 640

Asn Asn Cys Ser Asn Ala Lys Ala Val Glu Thr Asp Val
                645                 650

<210> SEQ ID NO 40
<211> LENGTH: 786
<212> TYPE: PRT
<213> ORGANISM: Homo sapiens

<400> SEQUENCE: 40

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80
```

Ala Phe Pro Ala Val Thr Phe Pro Gly Ala Leu Val Pro Gly Gly Val
                    85                  90                  95

Ala Asp Ala Ala Ala Tyr Lys Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
    275                 280                 285

Ile Pro Gly Ile Gly Gly Ile Ala Gly Val Gly Thr Pro Ala Ala Ala
    290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
    355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Ala Ala Gly Ala Gly Val Leu Gly Gly Leu Val
    450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Lys Ala Ala Ala Lys
            485                 490                 495

```
Ala Ala Gln Phe Gly Leu Val Pro Gly Val Gly Val Ala Pro Gly Val
            500                 505                 510

Gly Val Ala Pro Gly Val Gly Val Ala Pro Gly Val Gly Leu Ala Pro
        515                 520                 525

Gly Val Gly Val Ala Pro Gly Val Gly Val Ala Pro Gly Val Gly Val
    530                 535                 540

Ala Pro Gly Ile Gly Pro Gly Val Ala Ala Ala Lys Ser Ala
545                 550                 555                 560

Ala Lys Val Ala Ala Lys Ala Gln Leu Arg Ala Ala Gly Leu Gly
            565                 570                 575

Ala Gly Ile Pro Gly Leu Gly Val Gly Val Pro Gly Leu Gly
        580                 585                 590

Val Gly Ala Gly Val Pro Gly Leu Gly Val Gly Ala Gly Val Pro Gly
        595                 600                 605

Phe Gly Ala Gly Ala Asp Glu Gly Val Arg Arg Ser Leu Ser Pro Glu
        610                 615                 620

Leu Arg Glu Gly Asp Pro Ser Ser Gln His Leu Pro Ser Thr Pro
625                 630                 635                 640

Ser Ser Pro Arg Val Pro Gly Ala Leu Ala Ala Ala Lys Ala Ala Lys
            645                 650                 655

Tyr Gly Ala Ala Val Pro Gly Val Leu Gly Gly Leu Gly Ala Leu Gly
            660                 665                 670

Gly Val Gly Ile Pro Gly Gly Val Val Gly Ala Gly Pro Ala Ala Ala
        675                 680                 685

Ala Ala Ala Ala Lys Ala Ala Lys Ala Ala Gln Phe Gly Leu Val
        690                 695                 700

Gly Ala Ala Gly Leu Gly Gly Leu Gly Val Gly Gly Leu Gly Val Pro
705                 710                 715                 720

Gly Val Gly Gly Leu Gly Gly Ile Pro Pro Ala Ala Ala Lys Ala
                725                 730                 735

Ala Lys Tyr Gly Ala Ala Gly Leu Gly Gly Val Leu Gly Ala Gly
            740                 745                 750

Gln Phe Pro Leu Gly Gly Val Ala Ala Arg Pro Gly Phe Gly Leu Ser
        755                 760                 765

Pro Ile Phe Pro Gly Gly Ala Cys Leu Gly Lys Ala Cys Gly Arg Lys
        770                 775                 780

Arg Lys
785

<210> SEQ ID NO 41
<211> LENGTH: 405
<212> TYPE: PRT
<213> ORGANISM: Homo sapiens

<400> SEQUENCE: 41

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
            20                  25                  30

Arg Asp Tyr Ile Asp His Val Ser Gln Val Gln Pro Val Asp Gly Val
        35                  40                  45

Val Leu Val Asp Pro Asp Leu Val Lys Gly Lys Val Tyr Val Thr
    50                  55                  60

Leu Thr Cys Ala Phe Arg Tyr Gly Gln Glu Asp Ile Asp Val Ile Gly
65                  70                  75                  80
```

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
    130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
    210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270

Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
    290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Glu Leu Thr Ser Ser Glu Val Ala
            340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 42
<211> LENGTH: 1976
<212> TYPE: PRT
<213> ORGANISM: Homo sapiens

<400> SEQUENCE: 42

Met Ala Gln Arg Thr Gly Leu Glu Asp Pro Glu Arg Tyr Leu Phe Val
1               5                   10                  15

Asp Arg Ala Val Ile Tyr Asn Pro Ala Thr Gln Ala Asp Trp Thr Ala
            20                  25                  30

Lys Lys Leu Val Trp Ile Pro Ser Glu Arg His Gly Phe Glu Ala Ala

```
                35                  40                  45
Ser Ile Lys Glu Glu Arg Gly Asp Glu Val Met Val Glu Leu Ala Glu
 50                  55                  60

Asn Gly Lys Lys Ala Met Val Asn Lys Asp Asp Ile Gln Lys Met Asn
 65                  70                  75                  80

Pro Pro Lys Phe Ser Lys Val Glu Asp Met Ala Glu Leu Thr Cys Leu
                 85                  90                  95

Asn Glu Ala Ser Val Leu His Asn Leu Lys Asp Arg Tyr Tyr Ser Gly
            100                 105                 110

Leu Ile Tyr Thr Tyr Ser Gly Leu Phe Cys Val Val Ile Asn Pro Tyr
        115                 120                 125

Lys Asn Leu Pro Ile Tyr Ser Glu Asn Ile Ile Glu Met Tyr Arg Gly
130                 135                 140

Lys Lys Arg His Glu Met Pro Pro His Ile Tyr Ala Ile Ser Glu Ser
145                 150                 155                 160

Ala Tyr Arg Cys Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala His Val Ala Ser Ser His Lys Gly Arg Lys Asp His
        195                 200                 205

Asn Ile Pro Gly Glu Leu Glu Arg Gln Leu Leu Gln Ala Asn Pro Ile
210                 215                 220

Leu Glu Ser Phe Gly Asn Ala Lys Thr Val Lys Asn Asp Asn Ser Ser
225                 230                 235                 240

Arg Phe Gly Lys Phe Ile Arg Ile Asn Phe Asp Val Thr Gly Tyr Ile
                245                 250                 255

Val Gly Ala Asn Ile Glu Thr Tyr Leu Leu Glu Lys Ser Arg Ala Val
            260                 265                 270

Arg Gln Ala Lys Asp Glu Arg Thr Phe His Ile Phe Tyr Gln Leu Leu
        275                 280                 285

Ser Gly Ala Gly Glu His Leu Lys Ser Asp Leu Leu Leu Glu Gly Phe
290                 295                 300

Asn Asn Tyr Arg Phe Leu Ser Asn Gly Tyr Ile Pro Ile Pro Gly Gln
305                 310                 315                 320

Gln Asp Lys Asp Asn Phe Gln Glu Thr Met Glu Ala Met His Ile Met
                325                 330                 335

Gly Phe Ser His Glu Glu Ile Leu Ser Met Leu Lys Val Val Ser Ser
            340                 345                 350

Val Leu Gln Phe Gly Asn Ile Ser Phe Lys Lys Glu Arg Asn Thr Asp
        355                 360                 365

Gln Ala Ser Met Pro Glu Asn Thr Val Ala Gln Lys Leu Cys His Leu
370                 375                 380

Leu Gly Met Asn Val Met Glu Phe Thr Arg Ala Ile Leu Thr Pro Arg
385                 390                 395                 400

Ile Lys Val Gly Arg Asp Tyr Val Gln Lys Ala Gln Thr Lys Glu Gln
                405                 410                 415

Ala Asp Phe Ala Val Glu Ala Leu Ala Lys Ala Thr Tyr Glu Arg Leu
            420                 425                 430

Phe Arg Trp Leu Val His Arg Ile Asn Lys Ala Leu Asp Arg Thr Lys
        435                 440                 445

Arg Gln Gly Ala Ser Phe Ile Gly Ile Leu Asp Ile Ala Gly Phe Glu
450                 455                 460
```

```
Ile Phe Glu Leu Asn Ser Phe Glu Gln Leu Cys Ile Asn Tyr Thr Asn
465                 470                 475                 480

Glu Lys Leu Gln Gln Leu Phe Asn His Thr Met Phe Ile Leu Glu Gln
                485                 490                 495

Glu Glu Tyr Gln Arg Glu Gly Ile Glu Trp Asn Phe Ile Asp Phe Gly
            500                 505                 510

Leu Asp Leu Gln Pro Cys Ile Asp Leu Ile Glu Arg Pro Ala Asn Pro
            515                 520                 525

Pro Gly Val Leu Ala Leu Leu Asp Glu Glu Cys Trp Phe Pro Lys Ala
        530                 535                 540

Thr Asp Lys Thr Phe Val Glu Lys Leu Val Gln Glu Gln Gly Ser His
545                 550                 555                 560

Ser Lys Phe Gln Lys Pro Arg Gln Leu Lys Asp Lys Ala Asp Phe Cys
                565                 570                 575

Ile Ile His Tyr Ala Gly Lys Val Asp Tyr Lys Ala Asp Glu Trp Leu
            580                 585                 590

Met Lys Asn Met Asp Pro Leu Asn Asp Asn Val Ala Thr Leu Leu His
            595                 600                 605

Gln Ser Ser Asp Arg Phe Val Ala Glu Leu Trp Lys Asp Val Asp Arg
610                 615                 620

Ile Val Gly Leu Asp Gln Val Thr Gly Met Thr Glu Thr Ala Phe Gly
625                 630                 635                 640

Ser Ala Tyr Lys Thr Lys Lys Gly Met Phe Arg Thr Val Gly Gln Leu
                645                 650                 655

Tyr Lys Glu Ser Leu Thr Lys Leu Met Ala Thr Leu Arg Asn Thr Asn
                660                 665                 670

Pro Asn Phe Val Arg Cys Ile Ile Pro Asn His Glu Lys Arg Ala Gly
                675                 680                 685

Lys Leu Asp Pro His Leu Val Leu Asp Gln Leu Arg Cys Asn Gly Val
            690                 695                 700

Leu Glu Gly Ile Arg Ile Cys Arg Gln Gly Phe Pro Asn Arg Ile Val
705                 710                 715                 720

Phe Gln Glu Phe Arg Gln Arg Tyr Glu Ile Leu Thr Pro Asn Ala Ile
                725                 730                 735

Pro Lys Gly Phe Met Asp Gly Lys Gln Ala Cys Glu Arg Met Ile Arg
                740                 745                 750

Ala Leu Glu Leu Asp Pro Asn Leu Tyr Arg Ile Gly Gln Ser Lys Ile
            755                 760                 765

Phe Phe Arg Ala Gly Val Leu Ala His Leu Glu Glu Glu Arg Asp Leu
            770                 775                 780

Lys Ile Thr Asp Ile Ile Phe Phe Gln Ala Val Cys Arg Gly Tyr
785                 790                 795                 800

Leu Ala Arg Lys Ala Phe Ala Lys Gln Gln Gln Leu Ser Ala Leu
                805                 810                 815

Lys Val Leu Gln Arg Asn Cys Ala Ala Tyr Leu Lys Leu Arg His Trp
                820                 825                 830

Gln Trp Trp Arg Val Phe Thr Lys Val Lys Pro Leu Leu Gln Val Thr
            835                 840                 845

Arg Gln Glu Glu Glu Leu Gln Ala Lys Asp Glu Glu Leu Leu Lys Val
    850                 855                 860

Lys Glu Lys Gln Thr Lys Val Glu Gly Glu Leu Glu Glu Met Glu Arg
865                 870                 875                 880
```

```
Lys His Gln Gln Leu Leu Glu Glu Lys Asn Ile Leu Ala Glu Gln Leu
            885                 890                 895

Gln Ala Glu Thr Glu Leu Phe Ala Glu Ala Glu Glu Met Arg Ala Arg
            900                 905                 910

Leu Ala Ala Lys Lys Gln Glu Leu Glu Glu Ile Leu His Asp Leu Glu
            915                 920                 925

Ser Arg Val Glu Glu Glu Glu Arg Asn Gln Ile Leu Gln Asn Glu
        930                 935                 940

Lys Lys Lys Met Gln Ala His Ile Gln Asp Leu Glu Glu Gln Leu Asp
945                 950                 955                 960

Glu Glu Glu Gly Ala Arg Gln Lys Leu Gln Leu Glu Lys Val Thr Ala
                965                 970                 975

Glu Ala Lys Ile Lys Lys Met Glu Glu Glu Ile Leu Leu Leu Glu Asp
                980                 985                 990

Gln Asn Ser Lys Phe Ile Lys Glu Lys Lys Leu Met Glu Asp Arg Ile
            995                 1000                1005

Ala Glu Cys Ser Ser Gln Leu Ala Glu Glu Glu Lys Ala Lys
        1010                1015                1020

Asn Leu Ala Lys Ile Arg Asn Lys Gln Glu Val Met Ile Ser Asp
        1025                1030                1035

Leu Glu Glu Arg Leu Lys Lys Glu Glu Lys Thr Arg Gln Glu Leu
        1040                1045                1050

Glu Lys Ala Lys Arg Lys Leu Asp Gly Glu Thr Thr Asp Leu Gln
        1055                1060                1065

Asp Gln Ile Ala Glu Leu Gln Ala Gln Ile Asp Glu Leu Lys Leu
        1070                1075                1080

Gln Leu Ala Lys Lys Glu Glu Leu Gln Gly Ala Leu Ala Arg
        1085                1090                1095

Gly Asp Asp Glu Thr Leu His Lys Asn Asn Ala Leu Lys Val Val
        1100                1105                1110

Arg Glu Leu Gln Ala Gln Ile Ala Glu Leu Gln Glu Asp Phe Glu
        1115                1120                1125

Ser Glu Lys Ala Ser Arg Asn Lys Ala Glu Lys Gln Lys Arg Asp
        1130                1135                1140

Leu Ser Glu Glu Leu Glu Ala Leu Lys Thr Glu Leu Glu Asp Thr
        1145                1150                1155

Leu Asp Thr Thr Ala Ala Gln Gln Glu Leu Arg Thr Lys Arg Glu
        1160                1165                1170

Gln Glu Val Ala Glu Leu Lys Lys Ala Leu Glu Glu Glu Thr Lys
        1175                1180                1185

Asn His Glu Ala Gln Ile Gln Asp Met Arg Gln Arg His Ala Thr
        1190                1195                1200

Ala Leu Glu Glu Leu Ser Glu Gln Leu Glu Gln Ala Lys Arg Phe
        1205                1210                1215

Lys Ala Asn Leu Glu Lys Asn Lys Gln Gly Leu Glu Thr Asp Asn
        1220                1225                1230

Lys Glu Leu Ala Cys Glu Val Lys Val Leu Gln Gln Val Lys Ala
        1235                1240                1245

Glu Ser Glu His Lys Arg Lys Lys Leu Asp Ala Gln Val Gln Glu
        1250                1255                1260

Leu His Ala Lys Val Ser Glu Gly Asp Arg Leu Arg Val Glu Leu
        1265                1270                1275

Ala Glu Lys Ala Ser Lys Leu Gln Asn Glu Leu Asp Asn Val Ser
```

-continued

```
              1280              1285              1290
Thr Leu Leu Glu Glu Ala Glu Lys Lys Gly Ile Lys Phe Ala Lys
              1295              1300              1305

Asp Ala Ala Ser Leu Glu Ser Gln Leu Gln Asp Thr Gln Glu Leu
              1310              1315              1320

Leu Gln Glu Glu Thr Arg Gln Lys Leu Asn Leu Ser Ser Arg Ile
              1325              1330              1335

Arg Gln Leu Glu Glu Glu Lys Asn Ser Leu Gln Glu Gln Gln Glu
              1340              1345              1350

Glu Glu Glu Glu Ala Arg Lys Asn Leu Glu Lys Gln Val Leu Ala
              1355              1360              1365

Leu Gln Ser Gln Leu Ala Asp Thr Lys Lys Lys Val Asp Asp Asp
              1370              1375              1380

Leu Gly Thr Ile Glu Ser Leu Glu Glu Ala Lys Lys Lys Leu Leu
              1385              1390              1395

Lys Asp Ala Glu Ala Leu Ser Gln Arg Leu Glu Glu Lys Ala Leu
              1400              1405              1410

Ala Tyr Asp Lys Leu Glu Lys Thr Lys Asn Arg Leu Gln Gln Glu
              1415              1420              1425

Leu Asp Asp Leu Thr Val Asp Leu Asp His Gln Arg Gln Val Ala
              1430              1435              1440

Ser Asn Leu Glu Lys Lys Gln Lys Lys Phe Asp Gln Leu Leu Ala
              1445              1450              1455

Glu Glu Lys Ser Ile Ser Ala Arg Tyr Ala Glu Arg Asp Arg
              1460              1465              1470

Ala Glu Ala Glu Ala Arg Glu Lys Glu Thr Lys Ala Leu Ser Leu
              1475              1480              1485

Ala Arg Ala Leu Glu Glu Ala Leu Glu Ala Lys Glu Glu Phe Glu
              1490              1495              1500

Arg Gln Asn Lys Gln Leu Arg Ala Asp Met Glu Asp Leu Met Ser
              1505              1510              1515

Ser Lys Asp Asp Val Gly Lys Asn Val His Glu Leu Glu Lys Ser
              1520              1525              1530

Lys Arg Ala Leu Glu Gln Gln Val Glu Glu Met Arg Thr Gln Leu
              1535              1540              1545

Glu Glu Leu Glu Asp Glu Leu Gln Ala Thr Glu Asp Ala Lys Leu
              1550              1555              1560

Arg Leu Glu Val Asn Met Gln Ala Met Lys Ala Gln Phe Glu Arg
              1565              1570              1575

Asp Leu Gln Thr Arg Asp Glu Gln Asn Glu Glu Lys Lys Arg Leu
              1580              1585              1590

Leu Ile Lys Gln Val Arg Glu Leu Glu Ala Glu Leu Glu Asp Glu
              1595              1600              1605

Arg Lys Gln Arg Ala Leu Ala Val Ala Ser Lys Lys Lys Met Glu
              1610              1615              1620

Ile Asp Leu Lys Asp Leu Glu Ala Gln Ile Glu Ala Ala Asn Lys
              1625              1630              1635

Ala Arg Asp Glu Val Ile Lys Gln Leu Arg Lys Leu Gln Ala Gln
              1640              1645              1650

Met Lys Asp Tyr Gln Arg Glu Leu Glu Glu Ala Arg Ala Ser Arg
              1655              1660              1665

Asp Glu Ile Phe Ala Gln Ser Lys Glu Ser Glu Lys Lys Leu Lys
              1670              1675              1680
```

Ser Leu Glu Ala Glu Ile Leu Gln Leu Gln Glu Glu Leu Ala Ser
    1685                1690                1695

Ser Glu Arg Ala Arg Arg His Ala Glu Gln Glu Arg Asp Glu Leu
    1700                1705                1710

Ala Asp Glu Ile Thr Asn Ser Ala Ser Gly Lys Ser Ala Leu Leu
    1715                1720                1725

Asp Glu Lys Arg Arg Leu Glu Ala Arg Ile Ala Gln Leu Glu Glu
    1730                1735                1740

Glu Leu Glu Glu Glu Gln Ser Asn Met Glu Leu Leu Asn Asp Arg
    1745                1750                1755

Phe Arg Lys Thr Thr Leu Gln Val Asp Thr Leu Asn Ala Glu Leu
    1760                1765                1770

Ala Ala Glu Arg Ser Ala Ala Gln Lys Ser Asp Asn Ala Arg Gln
    1775                1780                1785

Gln Leu Glu Arg Gln Asn Lys Glu Leu Lys Ala Lys Leu Gln Glu
    1790                1795                1800

Leu Glu Gly Ala Val Lys Ser Lys Phe Lys Ala Thr Ile Ser Ala
    1805                1810                1815

Leu Glu Ala Lys Ile Gly Gln Leu Glu Glu Gln Leu Glu Gln Glu
    1820                1825                1830

Ala Lys Glu Arg Ala Ala Ala Asn Lys Leu Val Arg Arg Thr Glu
    1835                1840                1845

Lys Lys Leu Lys Glu Ile Phe Met Gln Val Glu Asp Glu Arg Arg
    1850                1855                1860

His Ala Asp Gln Tyr Lys Glu Gln Met Glu Lys Ala Asn Ala Arg
    1865                1870                1875

Met Lys Gln Leu Lys Arg Gln Leu Glu Glu Ala Glu Glu Glu Ala
    1880                1885                1890

Thr Arg Ala Asn Ala Ser Arg Arg Lys Leu Gln Arg Glu Leu Asp
    1895                1900                1905

Asp Ala Thr Glu Ala Asn Glu Gly Leu Ser Arg Glu Val Ser Thr
    1910                1915                1920

Leu Lys Asn Arg Leu Arg Arg Gly Gly Pro Ile Ser Phe Ser Ser
    1925                1930                1935

Ser Arg Ser Gly Arg Arg Gln Leu His Leu Glu Gly Ala Ser Leu
    1940                1945                1950

Glu Leu Ser Asp Asp Asp Thr Glu Ser Lys Thr Ser Asp Val Asn
    1955                1960                1965

Glu Thr Gln Pro Pro Gln Ser Glu
    1970                1975

<210> SEQ ID NO 43
<211> LENGTH: 1939
<212> TYPE: PRT
<213> ORGANISM: Homo sapiens

<400> SEQUENCE: 43

Met Thr Asp Ala Gln Met Ala Asp Phe Gly Ala Ala Ala Gln Tyr Leu
1               5                   10                  15

Arg Lys Ser Glu Lys Glu Arg Leu Glu Ala Gln Thr Arg Pro Phe Asp
                20                  25                  30

Ile Arg Thr Glu Cys Phe Val Pro Asp Asp Lys Glu Glu Phe Val Lys
            35                  40                  45

Ala Lys Ile Leu Ser Arg Glu Gly Gly Lys Val Ile Ala Glu Thr Glu

```
              50                  55                  60
    Asn Gly Lys Thr Val Thr Val Lys Glu Asp Gln Val Leu Gln Asn
    65                  70                  75                  80

Pro Pro Lys Phe Asp Lys Ile Glu Asp Met Ala Met Leu Thr Phe Leu
                        85                  90                  95

His Glu Pro Ala Val Leu Phe Asn Leu Lys Glu Arg Tyr Ala Ala Trp
                    100                 105                 110

Met Ile Tyr Thr Tyr Ser Gly Leu Phe Cys Val Thr Val Asn Pro Tyr
                115                 120                 125

Lys Trp Leu Pro Val Tyr Asn Ala Glu Val Val Ala Ala Tyr Arg Gly
            130                 135                 140

Lys Lys Arg Ser Glu Ala Pro Pro His Ile Phe Ser Ile Ser Asp Asn
    145                 150                 155                 160

Ala Tyr Gln Tyr Met Leu Thr Asp Arg Glu Asn Gln Ser Ile Leu Ile
                    165                 170                 175

Thr Gly Glu Ser Gly Ala Gly Lys Thr Val Asn Thr Lys Arg Val Ile
                180                 185                 190

Gln Tyr Phe Ala Ser Ile Ala Ala Ile Gly Asp Arg Gly Lys Lys Asp
                195                 200                 205

Asn Ala Asn Ala Asn Lys Gly Thr Leu Glu Asp Gln Ile Ile Gln Ala
    210                 215                 220

Asn Pro Ala Leu Glu Ala Phe Gly Asn Ala Lys Thr Val Arg Asn Asp
    225                 230                 235                 240

Asn Ser Ser Arg Phe Gly Lys Phe Ile Arg Ile His Phe Gly Ala Thr
                    245                 250                 255

Gly Lys Leu Ala Ser Ala Asp Ile Glu Thr Tyr Leu Leu Glu Lys Ser
                260                 265                 270

Arg Val Ile Phe Gln Leu Lys Ala Glu Arg Asn Tyr His Ile Phe Tyr
                275                 280                 285

Gln Ile Leu Ser Asn Lys Lys Pro Glu Leu Leu Asp Met Leu Leu Val
                290                 295                 300

Thr Asn Asn Pro Tyr Asp Tyr Ala Phe Val Ser Gln Gly Glu Val Ser
    305                 310                 315                 320

Val Ala Ser Ile Asp Asp Ser Glu Glu Leu Met Ala Thr Asp Ser Ala
                    325                 330                 335

Phe Asp Val Leu Gly Phe Thr Ser Glu Glu Lys Ala Gly Val Tyr Lys
                340                 345                 350

Leu Thr Gly Ala Ile Met His Tyr Gly Asn Met Lys Phe Lys Gln Lys
                355                 360                 365

Gln Arg Glu Glu Gln Ala Glu Pro Asp Gly Thr Glu Asp Ala Asp Lys
    370                 375                 380

Ser Ala Tyr Leu Met Gly Leu Asn Ser Ala Asp Leu Leu Lys Gly Leu
    385                 390                 395                 400

Cys His Pro Arg Val Lys Val Gly Asn Glu Tyr Val Thr Lys Gly Gln
                    405                 410                 415

Ser Val Gln Gln Val Tyr Tyr Ser Ile Gly Ala Leu Ala Lys Ala Val
                420                 425                 430

Tyr Glu Lys Met Phe Asn Trp Met Val Thr Arg Ile Asn Ala Thr Leu
                435                 440                 445

Glu Thr Lys Gln Pro Arg Gln Tyr Phe Ile Gly Val Leu Asp Ile Ala
    450                 455                 460

Gly Phe Glu Ile Phe Asp Phe Asn Ser Phe Glu Gln Leu Cys Ile Asn
    465                 470                 475                 480
```

```
Phe Thr Asn Glu Lys Leu Gln Gln Phe Phe Asn His Met Phe Val
                485                 490                 495

Leu Glu Gln Glu Glu Tyr Lys Lys Glu Gly Ile Glu Trp Thr Phe Ile
            500                 505                 510

Asp Phe Gly Met Asp Leu Gln Ala Cys Ile Asp Leu Ile Glu Lys Pro
            515                 520                 525

Met Gly Ile Met Ser Ile Leu Glu Glu Glu Cys Met Phe Pro Lys Ala
    530                 535                 540

Thr Asp Met Thr Phe Lys Ala Lys Leu Tyr Asp Asn His Leu Gly Lys
545                 550                 555                 560

Ser Asn Asn Phe Gln Lys Pro Arg Asn Ile Lys Gly Lys Pro Glu Ala
                565                 570                 575

His Phe Ser Leu Ile His Tyr Ala Gly Thr Val Asp Tyr Asn Ile Leu
            580                 585                 590

Gly Trp Leu Glu Lys Asn Lys Asp Pro Leu Asn Glu Thr Val Val Gly
        595                 600                 605

Leu Tyr Gln Lys Ser Ser Leu Lys Leu Met Ala Thr Leu Phe Ser Ser
    610                 615                 620

Tyr Ala Thr Ala Asp Thr Gly Asp Ser Gly Lys Ser Lys Gly Gly Lys
625                 630                 635                 640

Lys Lys Gly Ser Ser Phe Gln Thr Val Ser Ala Leu His Arg Glu Asn
                645                 650                 655

Leu Asn Lys Leu Met Thr Asn Leu Arg Thr Thr His Pro His Phe Val
            660                 665                 670

Arg Cys Ile Ile Pro Asn Glu Arg Lys Ala Pro Gly Val Met Asp Asn
        675                 680                 685

Pro Leu Val Met His Gln Leu Arg Cys Asn Gly Val Leu Glu Gly Ile
    690                 695                 700

Arg Ile Cys Arg Lys Gly Phe Pro Asn Arg Ile Leu Tyr Gly Asp Phe
705                 710                 715                 720

Arg Gln Arg Tyr Arg Ile Leu Asn Pro Val Ala Ile Pro Glu Gly Gln
                725                 730                 735

Phe Ile Asp Ser Arg Lys Gly Ala Glu Lys Leu Leu Ser Ser Leu Asp
            740                 745                 750

Ile Asp His Asn Gln Tyr Lys Phe Gly His Thr Lys Val Phe Phe Lys
        755                 760                 765

Ala Gly Leu Leu Gly Leu Leu Glu Glu Met Arg Asp Glu Arg Leu Ser
    770                 775                 780

Arg Ile Ile Thr Arg Ile Gln Ala Gln Ala Arg Gly Gln Leu Met Arg
785                 790                 795                 800

Ile Glu Phe Lys Lys Ile Val Glu Arg Arg Asp Ala Leu Leu Val Ile
                805                 810                 815

Gln Trp Asn Ile Arg Ala Phe Met Gly Val Lys Asn Trp Pro Trp Met
            820                 825                 830

Lys Leu Tyr Phe Lys Ile Lys Pro Leu Leu Lys Ser Ala Glu Thr Glu
    835                 840                 845

Lys Glu Met Ala Thr Met Lys Glu Glu Phe Gly Arg Ile Lys Glu Thr
    850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                885                 890                 895
```

```
Gln Asp Asn Leu Asn Asp Ala Glu Glu Arg Cys Asp Gln Leu Ile Lys
            900                 905                 910

Asn Lys Ile Gln Leu Glu Ala Lys Val Lys Glu Met Asn Glu Arg Leu
        915                 920                 925

Glu Asp Glu Glu Glu Met Asn Ala Glu Leu Thr Ala Lys Lys Arg Lys
    930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
            965                 970                 975

Val Lys Asn Leu Thr Glu Glu Met Ala Gly Leu Asp Glu Ile Ile Ala
        980                 985                 990

Lys Leu Thr Lys Glu Lys Lys Ala Leu Gln Glu Ala His Gln Gln Ala
    995                 1000                1005

Leu Asp Asp Leu Gln Ala Glu Glu Asp Lys Val Asn Thr Leu Ser
    1010                1015                1020

Lys Ser Lys Val Lys Leu Glu Gln Gln Val Asp Asp Leu Glu Gly
    1025                1030                1035

Ser Leu Glu Gln Glu Lys Lys Val Arg Met Asp Leu Glu Arg Ala
    1040                1045                1050

Lys Arg Lys Leu Glu Gly Asp Leu Lys Leu Thr Gln Glu Ser Ile
    1055                1060                1065

Met Asp Leu Glu Asn Asp Lys Leu Gln Leu Glu Glu Lys Leu Lys
    1070                1075                1080

Lys Lys Glu Phe Asp Ile Asn Gln Gln Asn Ser Lys Ile Glu Asp
    1085                1090                1095

Glu Gln Val Leu Ala Leu Gln Leu Gln Lys Lys Leu Lys Glu Asn
    1100                1105                1110

Gln Ala Arg Ile Glu Glu Leu Glu Glu Glu Leu Glu Ala Glu Arg
    1115                1120                1125

Thr Ala Arg Ala Lys Val Glu Lys Leu Arg Ser Asp Leu Ser Arg
    1130                1135                1140

Glu Leu Glu Glu Ile Ser Glu Arg Leu Glu Glu Ala Gly Gly Ala
    1145                1150                1155

Thr Ser Val Gln Ile Glu Met Asn Lys Lys Arg Glu Ala Glu Phe
    1160                1165                1170

Gln Lys Met Arg Arg Asp Leu Glu Glu Ala Thr Leu Gln His Glu
    1175                1180                1185

Ala Thr Ala Ala Ala Leu Arg Lys Lys His Ala Asp Ser Val Ala
    1190                1195                1200

Glu Leu Gly Glu Gln Ile Asp Asn Leu Gln Arg Val Lys Gln Lys
    1205                1210                1215

Leu Glu Lys Glu Lys Ser Glu Phe Lys Leu Glu Leu Asp Asp Val
    1220                1225                1230

Thr Ser Asn Met Glu Gln Ile Ile Lys Ala Lys Ala Asn Leu Glu
    1235                1240                1245

Lys Val Ser Arg Thr Leu Glu Asp Gln Ala Asn Glu Tyr Arg Val
    1250                1255                1260

Lys Leu Glu Glu Ala Gln Arg Ser Leu Asn Asp Phe Thr Thr Gln
    1265                1270                1275

Arg Ala Lys Leu Gln Thr Glu Asn Gly Glu Leu Ser Arg Gln Leu
    1280                1285                1290

Glu Glu Lys Glu Ala Leu Ile Ser Gln Leu Thr Arg Gly Lys Leu
```

```
             1295                1300                1305

Ser Tyr Thr Gln Gln Met Glu Asp Leu Lys Arg Gln  Leu Glu Glu
    1310                1315                1320

Glu Gly Lys Ala Lys Asn Ala Leu Ala His Ala Leu  Gln Ser Ala
    1325                1330                1335

Arg His Asp Cys Asp Leu Leu Arg Glu Gln Tyr Glu  Glu Glu Thr
    1340                1345                1350

Glu Ala Lys Ala Glu Leu Gln Arg Val Leu Ser Lys  Ala Asn Ser
    1355                1360                1365

Glu Val Ala Gln Cys Arg Thr Lys Tyr Glu Thr Asp  Ala Ile Gln
    1370                1375                1380

Arg Thr Glu Glu Leu Glu Glu Ala Lys Lys Lys Leu  Ala Gln Arg
    1385                1390                1395

Leu Gln Asp Ala Glu Glu Ala Val Glu Ala Val Asn  Ala Lys Cys
    1400                1405                1410

Ser Ser Leu Glu Lys Thr Lys His Arg Leu Gln Asn  Glu Ile Glu
    1415                1420                1425

Asp Leu Met Val Asp Val Glu Arg Ser Asn Ala Ala  Ala Ala Ala
    1430                1435                1440

Leu Asp Lys Lys Gln Arg Asn Phe Asp Lys Ile Leu  Ala Glu Trp
    1445                1450                1455

Lys Gln Lys Tyr Glu Glu Ser Gln Ser Glu Leu Glu  Ser Ser Gln
    1460                1465                1470

Lys Glu Ala Arg Ser Leu Ser Thr Glu Leu Phe Lys  Leu Lys Asn
    1475                1480                1485

Ala Tyr Glu Glu Ser Leu Glu His Leu Glu Thr Phe  Lys Arg Glu
    1490                1495                1500

Asn Lys Asn Leu Gln Glu Glu Ile Ser Asp Leu Thr  Glu Gln Leu
    1505                1510                1515

Gly Glu Gly Gly Lys Asn Val His Glu Leu Glu Lys  Val Arg Lys
    1520                1525                1530

Gln Leu Glu Val Glu Lys Leu Glu Leu Gln Ser Ala  Leu Glu Glu
    1535                1540                1545

Ala Glu Ala Ser Leu Glu His Glu Glu Gly Lys Ile  Leu Arg Ala
    1550                1555                1560

Gln Leu Glu Phe Asn Gln Ile Lys Ala Glu Ile Glu  Arg Lys Leu
    1565                1570                1575

Ala Glu Lys Asp Glu Glu Met Glu Gln Ala Lys Arg  Asn His Gln
    1580                1585                1590

Arg Val Val Asp Ser Leu Gln Thr Ser Leu Asp Ala  Glu Thr Arg
    1595                1600                1605

Ser Arg Asn Glu Val Leu Arg Val Lys Lys Lys Met  Glu Gly Asp
    1610                1615                1620

Leu Asn Glu Met Glu Ile Gln Leu Ser His Ala Asn  Arg Met Ala
    1625                1630                1635

Ala Glu Ala Gln Lys Gln Val Lys Ser Leu Gln Ser  Leu Leu Lys
    1640                1645                1650

Asp Thr Gln Ile Gln Leu Asp Asp Ala Val Arg Ala  Asn Asp Asp
    1655                1660                1665

Leu Lys Glu Asn Ile Ala Ile Val Glu Arg Arg Asn  Asn Leu Leu
    1670                1675                1680

Gln Ala Glu Leu Glu Glu Leu Arg Ala Val Val Glu  Gln Thr Glu
    1685                1690                1695
```

```
Arg Ser Arg Lys Leu Ala Asp Arg Glu Leu Ile Glu Thr Ser Glu
    1700            1705                1710

Arg Val Gln Leu Leu His Ser Gln Asn Thr Ser Leu Ile Asn Gln
    1715            1720                1725

Lys Lys Lys Met Asp Ala Asp Leu Ser Gln Leu Gln Ser Glu Val
    1730            1735                1740

Glu Glu Ala Val Gln Glu Cys Arg Asn Ala Glu Lys Ala Lys
    1745            1750                1755

Lys Ala Ile Thr His Ala Ala Met Met Ala Glu Leu Lys Lys
    1760            1765                1770

Glu Gln Asp Thr Ser Ala His Leu Glu Arg Met Lys Lys Asn Met
    1775            1780                1785

Glu Gln Thr Ile Lys Asp Leu Gln His Arg Leu Asp Glu Ala Glu
    1790            1795                1800

Gln Ile Ala Leu Lys Gly Gly Lys Lys Gln Leu Gln Lys Leu Glu
    1805            1810                1815

Ala Arg Val Arg Glu Leu Glu Gly Glu Leu Glu Ala Glu Gln Lys
    1820            1825                1830

Arg Asn Ala Glu Ser Val Lys Gly Met Arg Lys Ser Glu Arg Arg
    1835            1840                1845

Ile Lys Glu Leu Thr Tyr Gln Thr Glu Glu Asp Lys Lys Asn Leu
    1850            1855                1860

Leu Arg Leu Gln Asp Leu Val Asp Lys Leu Gln Leu Lys Val Lys
    1865            1870                1875

Ala Tyr Lys Arg Gln Ala Glu Glu Ala Glu Glu Gln Ala Asn Thr
    1880            1885                1890

Asn Leu Ser Lys Phe Arg Lys Val Gln His Glu Leu Asp Glu Ala
    1895            1900                1905

Glu Glu Arg Ala Asp Ile Ala Glu Ser Gln Val Asn Lys Leu Arg
    1910            1915                1920

Ala Lys Ser Arg Asp Ile Gly Ala Lys Gln Lys Met His Asp Glu
    1925            1930                1935

Glu

<210> SEQ ID NO 44
<211> LENGTH: 573
<212> TYPE: PRT
<213> ORGANISM: Homo sapiens

<400> SEQUENCE: 44

Met Leu Arg Leu Pro Thr Val Phe Arg Gln Met Arg Pro Val Ser
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ala Gly Asp Gly
                100                 105                 110
```

```
Thr Thr Thr Ala Thr Val Leu Ala Arg Ser Ile Ala Lys Glu Gly Phe
        115                 120                 125
Glu Lys Ile Ser Lys Gly Ala Asn Pro Val Glu Ile Arg Arg Gly Val
        130                 135                 140
Met Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                165                 170                 175
Asn Gly Asp Lys Glu Ile Gly Asn Ile Ile Ser Asp Ala Met Lys Lys
                180                 185                 190
Val Gly Arg Lys Gly Val Ile Thr Val Lys Asp Gly Lys Thr Leu Asn
        195                 200                 205
Asp Glu Leu Glu Ile Ile Glu Gly Met Lys Phe Asp Arg Gly Tyr Ile
        210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                245                 250                 255
Ile Val Pro Ala Leu Glu Ile Ala Asn Ala His Arg Lys Pro Leu Val
            260                 265                 270
Ile Ile Ala Glu Asp Val Asp Gly Glu Ala Leu Ser Thr Leu Val Leu
        275                 280                 285
Asn Arg Leu Lys Val Gly Leu Gln Val Val Ala Val Lys Ala Pro Gly
        290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                325                 330                 335
Val Gln Pro His Asp Leu Gly Lys Val Gly Glu Val Ile Val Thr Lys
            340                 345                 350
Asp Asp Ala Met Leu Leu Lys Gly Lys Gly Asp Lys Ala Gln Ile Glu
        355                 360                 365
Lys Arg Ile Gln Glu Ile Ile Glu Gln Leu Asp Val Thr Thr Ser Glu
        370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                405                 410                 415
Lys Lys Asp Arg Val Thr Asp Ala Leu Asn Ala Thr Arg Ala Ala Val
            420                 425                 430
Glu Glu Gly Ile Val Leu Gly Gly Cys Ala Leu Leu Arg Cys Ile
        435                 440                 445
Pro Ala Leu Asp Ser Leu Thr Pro Ala Asn Glu Asp Gln Lys Ile Gly
        450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
            500                 505                 510
Met Val Glu Lys Gly Ile Ile Asp Pro Thr Lys Val Val Arg Thr Ala
        515                 520                 525
```

```
Leu Leu Asp Ala Ala Gly Val Ala Ser Leu Leu Thr Thr Ala Glu Val
            530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570
```

<210> SEQ ID NO 45
<211> LENGTH: 15
<212> TYPE: PRT
<213> ORGANISM: Homo sapiens

<400> SEQUENCE: 45

```
Lys Ile Ser Val Ser Leu Pro Leu Ser Leu Ser Gln Ser Val Cys
1               5                   10                  15
```

<210> SEQ ID NO 46
<211> LENGTH: 14
<212> TYPE: PRT
<213> ORGANISM: Homo sapiens

<400> SEQUENCE: 46

```
Gln Leu Ser Lys Asp Thr Ser Val Leu Thr Phe Thr Phe Cys
1               5                   10
```

<210> SEQ ID NO 47
<211> LENGTH: 17
<212> TYPE: PRT
<213> ORGANISM: Homo sapiens

<400> SEQUENCE: 47

```
Cys Ser Asp Ala His Pro Gly Asp Ser Ser Gly Asp Ser Ser Gly Leu
1               5                   10                  15

Asn
```

<210> SEQ ID NO 48
<211> LENGTH: 15
<212> TYPE: PRT
<213> ORGANISM: Homo sapiens

<400> SEQUENCE: 48

```
Arg Gly Glu Val Arg Gln Phe Thr Leu Arg His Trp Leu Lys Val
1               5                   10                  15
```

<210> SEQ ID NO 49
<211> LENGTH: 13
<212> TYPE: PRT
<213> ORGANISM: Homo sapiens

<400> SEQUENCE: 49

```
Gly Asp Tyr Leu Asn Asp Glu Ala Leu Trp Asn Lys Cys
1               5                   10
```

<210> SEQ ID NO 50
<211> LENGTH: 15
<212> TYPE: PRT
<213> ORGANISM: Homo sapiens

<400> SEQUENCE: 50

```
Gly Lys Val Ile Asp Asp Asn Asp His Leu Ser Gln Glu Ile Cys
1               5                   10                  15
```

<210> SEQ ID NO 51

```
<211> LENGTH: 14
<212> TYPE: PRT
<213> ORGANISM: Homo sapiens

<400> SEQUENCE: 51

Leu Met Ala Asn Ser Thr Trp Gly Tyr Pro Phe His Asp Gly
1               5                   10

<210> SEQ ID NO 52
<211> LENGTH: 14
<212> TYPE: PRT
<213> ORGANISM: Homo sapiens

<400> SEQUENCE: 52

Leu Asn Val Val Pro Trp Asn Leu Thr Leu Phe Ser Ile Leu
1               5                   10

<210> SEQ ID NO 53
<211> LENGTH: 12
<212> TYPE: PRT
<213> ORGANISM: Homo sapiens

<400> SEQUENCE: 53

Thr His Ser Phe Thr Ala Phe Lys Arg His Val Cys
1               5                   10

<210> SEQ ID NO 54
<211> LENGTH: 13
<212> TYPE: PRT
<213> ORGANISM: Homo sapiens

<400> SEQUENCE: 54

Asn Leu Ser Leu Pro Pro Ser Leu Ser Leu Ser Ile Cys
1               5                   10

<210> SEQ ID NO 55
<211> LENGTH: 16
<212> TYPE: PRT
<213> ORGANISM: Homo sapiens

<400> SEQUENCE: 55

Glu Arg Pro Ser Ser Val Leu Thr Ile Tyr Asp Ile Gly Ile Gln Cys
1               5                   10                  15

<210> SEQ ID NO 56
<211> LENGTH: 15
<212> TYPE: PRT
<213> ORGANISM: Homo sapiens

<400> SEQUENCE: 56

Cys Tyr Gln Gln Tyr Thr Asn Leu Gln Glu Arg Pro Ser Ser Val
1               5                   10                  15

<210> SEQ ID NO 57
<211> LENGTH: 15
<212> TYPE: PRT
<213> ORGANISM: Homo sapiens

<400> SEQUENCE: 57

Thr Val Glu Pro Glu Thr Gly Asp Pro Val Thr Leu Arg Leu Cys
1               5                   10                  15

<210> SEQ ID NO 58
<211> LENGTH: 17
<212> TYPE: PRT
```

```
<213> ORGANISM: Homo sapiens

<400> SEQUENCE: 58

Cys Ser Arg Lys Lys Arg Ala Asp Lys Lys Glu Asn Gly Thr Lys Leu
1               5                   10                  15

Leu

<210> SEQ ID NO 59
<211> LENGTH: 9
<212> TYPE: PRT
<213> ORGANISM: Homo sapiens

<400> SEQUENCE: 59

Phe Leu Leu Val Leu Gly Phe Ile Ile
1               5

<210> SEQ ID NO 60
<211> LENGTH: 9
<212> TYPE: PRT
<213> ORGANISM: Homo sapiens

<400> SEQUENCE: 60

Val Leu Pro Ser Val Ala Met Phe Leu
1               5

<210> SEQ ID NO 61
<211> LENGTH: 9
<212> TYPE: PRT
<213> ORGANISM: Homo sapiens

<400> SEQUENCE: 61

Leu Val Leu Gly Phe Ile Ile Ala Leu
1               5

<210> SEQ ID NO 62
<211> LENGTH: 9
<212> TYPE: PRT
<213> ORGANISM: Homo sapiens

<400> SEQUENCE: 62

Lys Val Val Thr Ser Ser Phe Val Val
1               5

<210> SEQ ID NO 63
<211> LENGTH: 9
<212> TYPE: PRT
<213> ORGANISM: Homo sapiens

<400> SEQUENCE: 63

Leu Val Pro Gly Thr Lys Phe Tyr Ile
1               5

<210> SEQ ID NO 64
<211> LENGTH: 9
<212> TYPE: PRT
<213> ORGANISM: Homo sapiens

<400> SEQUENCE: 64

Leu Leu Pro Ile Arg Thr Leu Pro Leu
1               5

<210> SEQ ID NO 65
<211> LENGTH: 9
<212> TYPE: PRT
```

-continued

```
<213> ORGANISM: Homo sapiens

<400> SEQUENCE: 65

Tyr Leu Val Lys Lys Gly Thr Ala Thr
1               5

<210> SEQ ID NO 66
<211> LENGTH: 9
<212> TYPE: PRT
<213> ORGANISM: Homo sapiens

<400> SEQUENCE: 66

Ser Leu Phe Ala Glu Thr Ile Trp Val
1               5

<210> SEQ ID NO 67
<211> LENGTH: 9
<212> TYPE: PRT
<213> ORGANISM: Homo sapiens

<400> SEQUENCE: 67

Met Leu Ile Ala Met Tyr Phe Tyr Thr
1               5

<210> SEQ ID NO 68
<211> LENGTH: 9
<212> TYPE: PRT
<213> ORGANISM: Homo sapiens

<400> SEQUENCE: 68

Leu Met Trp Thr Leu Pro Val Met Leu
1               5

<210> SEQ ID NO 69
<211> LENGTH: 9
<212> TYPE: PRT
<213> ORGANISM: Homo sapiens

<400> SEQUENCE: 69

Met Leu Ile Val Tyr Ile Phe Glu Cys
1               5

<210> SEQ ID NO 70
<211> LENGTH: 9
<212> TYPE: PRT
<213> ORGANISM: Homo sapiens

<400> SEQUENCE: 70

Tyr Ile Phe Glu Cys Ala Ser Cys Ile
1               5

<210> SEQ ID NO 71
<211> LENGTH: 9
<212> TYPE: PRT
<213> ORGANISM: Homo sapiens

<400> SEQUENCE: 71

Leu Val Leu Met Leu Ile Val Tyr Ile
1               5

<210> SEQ ID NO 72
<211> LENGTH: 9
<212> TYPE: PRT
<213> ORGANISM: Homo sapiens
```

<400> SEQUENCE: 72

Ala Leu Cys Arg Arg Arg Ser Met Val
1               5

<210> SEQ ID NO 73
<211> LENGTH: 9
<212> TYPE: PRT
<213> ORGANISM: Homo sapiens

<400> SEQUENCE: 73

Leu Leu Ser Gly Leu Ser Leu Phe Ala
1               5

<210> SEQ ID NO 74
<211> LENGTH: 9
<212> TYPE: PRT
<213> ORGANISM: Homo sapiens

<400> SEQUENCE: 74

Phe Leu Leu Val Val Gly Leu Ile Val
1               5

<210> SEQ ID NO 75
<211> LENGTH: 9
<212> TYPE: PRT
<213> ORGANISM: Homo sapiens

<400> SEQUENCE: 75

Leu Val Val Gly Leu Ile Val Ala Leu
1               5

<210> SEQ ID NO 76
<211> LENGTH: 9
<212> TYPE: PRT
<213> ORGANISM: Homo sapiens

<400> SEQUENCE: 76

Lys Val Val Lys Ser Asp Phe Val Val
1               5

<210> SEQ ID NO 77
<211> LENGTH: 9
<212> TYPE: PRT
<213> ORGANISM: Homo sapiens

<400> SEQUENCE: 77

Thr Leu Pro Val Gln Thr Leu Pro Leu
1               5

<210> SEQ ID NO 78
<211> LENGTH: 9
<212> TYPE: PRT
<213> ORGANISM: Homo sapiens

<400> SEQUENCE: 78

Asp Leu His Val Ile Ser Asn Asp Val
1               5

<210> SEQ ID NO 79
<211> LENGTH: 9
<212> TYPE: PRT
<213> ORGANISM: Homo sapiens

<400> SEQUENCE: 79

```
Val Leu Val His Pro Gln Trp Val Leu
1               5
```

<210> SEQ ID NO 80
<211> LENGTH: 9
<212> TYPE: PRT
<213> ORGANISM: Homo sapiens

<400> SEQUENCE: 80

```
Phe Leu Arg Pro Gly Asp Asp Ser Ser
1               5
```

<210> SEQ ID NO 81
<211> LENGTH: 9
<212> TYPE: PRT
<213> ORGANISM: Homo sapiens

<400> SEQUENCE: 81

```
Ala Leu Gly Thr Thr Cys Tyr Ala Ser
1               5
```

<210> SEQ ID NO 82
<211> LENGTH: 9
<212> TYPE: PRT
<213> ORGANISM: Homo sapiens

<400> SEQUENCE: 82

```
Lys Leu Gln Cys Val Asp Leu His Val
1               5
```

<210> SEQ ID NO 83
<211> LENGTH: 9
<212> TYPE: PRT
<213> ORGANISM: Homo sapiens

<400> SEQUENCE: 83

```
Glu Leu Ala His Tyr Asp Val Leu Leu
1               5
```

<210> SEQ ID NO 84
<211> LENGTH: 9
<212> TYPE: PRT
<213> ORGANISM: Homo sapiens

<400> SEQUENCE: 84

```
Asn Leu Asn Gly Ala Gly Asp Pro Leu
1               5
```

<210> SEQ ID NO 85
<211> LENGTH: 9
<212> TYPE: PRT
<213> ORGANISM: Homo sapiens

<400> SEQUENCE: 85

```
Thr Leu Arg Val Asp Cys Thr Pro Leu
1               5
```

<210> SEQ ID NO 86
<211> LENGTH: 9
<212> TYPE: PRT
<213> ORGANISM: Homo sapiens

<400> SEQUENCE: 86

```
Met Met Asn Asp Gln Leu Met Phe Leu
1               5
```

```
<210> SEQ ID NO 87
<211> LENGTH: 9
<212> TYPE: PRT
<213> ORGANISM: Homo sapiens

<400> SEQUENCE: 87

Ala Leu Phe Asp Ile Glu Ser Lys Val
1               5

<210> SEQ ID NO 88
<211> LENGTH: 9
<212> TYPE: PRT
<213> ORGANISM: Homo sapiens

<400> SEQUENCE: 88

Leu Leu His Glu Thr Asp Ser Ala Val
1               5

<210> SEQ ID NO 89
<211> LENGTH: 9
<212> TYPE: PRT
<213> ORGANISM: Homo sapiens

<400> SEQUENCE: 89

Val Leu Ala Lys Glu Leu Lys Phe Val
1               5

<210> SEQ ID NO 90
<211> LENGTH: 9
<212> TYPE: PRT
<213> ORGANISM: Homo sapiens

<400> SEQUENCE: 90

Ile Leu Leu Trp Gln Pro Ile Pro Val
1               5

<210> SEQ ID NO 91
<211> LENGTH: 9
<212> TYPE: PRT
<213> ORGANISM: Homo sapiens

<400> SEQUENCE: 91

Asp Leu Phe Gly Ile Trp Ser Lys Val
1               5

<210> SEQ ID NO 92
<211> LENGTH: 9
<212> TYPE: PRT
<213> ORGANISM: Homo sapiens

<400> SEQUENCE: 92

Pro Leu Glu Arg Phe Ala Glu Leu Val
1               5

<210> SEQ ID NO 93
<211> LENGTH: 9
<212> TYPE: PRT
<213> ORGANISM: Homo sapiens

<400> SEQUENCE: 93

Lys Gln Gly Asn Phe Asn Ala Trp Val
1               5
```

```
<210> SEQ ID NO 94
<211> LENGTH: 9
<212> TYPE: PRT
<213> ORGANISM: Homo sapiens

<400> SEQUENCE: 94

Asn Leu Leu Arg Arg Met Trp Val Thr
1               5

<210> SEQ ID NO 95
<211> LENGTH: 9
<212> TYPE: PRT
<213> ORGANISM: Homo sapiens

<400> SEQUENCE: 95

Asn Leu Phe Glu Thr Pro Ile Leu Ala
1               5

<210> SEQ ID NO 96
<211> LENGTH: 9
<212> TYPE: PRT
<213> ORGANISM: Homo sapiens

<400> SEQUENCE: 96

Asn Leu Phe Glu Thr Pro Val Glu Ala
1               5

<210> SEQ ID NO 97
<211> LENGTH: 9
<212> TYPE: PRT
<213> ORGANISM: Homo sapiens

<400> SEQUENCE: 97

Gly Leu Gln His Trp Val Pro Glu Leu
1               5

<210> SEQ ID NO 98
<211> LENGTH: 9
<212> TYPE: PRT
<213> ORGANISM: Homo sapiens

<400> SEQUENCE: 98

Val Gln Phe Val Ala Ser Tyr Lys Val
1               5

<210> SEQ ID NO 99
<211> LENGTH: 9
<212> TYPE: PRT
<213> ORGANISM: Homo sapiens

<400> SEQUENCE: 99

Arg Leu Leu Ala Ala Leu Cys Gly Ala
1               5

<210> SEQ ID NO 100
<211> LENGTH: 9
<212> TYPE: PRT
<213> ORGANISM: Homo sapiens

<400> SEQUENCE: 100

Leu Leu Leu Leu Thr Val Leu Thr Val
1               5

<210> SEQ ID NO 101
<211> LENGTH: 9
```

<212> TYPE: PRT
<213> ORGANISM: Homo sapiens

<400> SEQUENCE: 101

Leu Leu Leu Thr Val Leu Thr Val Val
1               5

<210> SEQ ID NO 102
<211> LENGTH: 9
<212> TYPE: PRT
<213> ORGANISM: Homo sapiens

<400> SEQUENCE: 102

Phe Leu Ser Phe His Ile Ser Asn Leu
1               5

<210> SEQ ID NO 103
<211> LENGTH: 9
<212> TYPE: PRT
<213> ORGANISM: Homo sapiens

<400> SEQUENCE: 103

Leu Leu Val Leu Val Cys Val Leu Val
1               5

<210> SEQ ID NO 104
<211> LENGTH: 9
<212> TYPE: PRT
<213> ORGANISM: Homo sapiens

<400> SEQUENCE: 104

Ala Leu Leu Val Leu Val Cys Val Leu
1               5

<210> SEQ ID NO 105
<211> LENGTH: 9
<212> TYPE: PRT
<213> ORGANISM: Homo sapiens

<400> SEQUENCE: 105

Ser Leu Ser Tyr Thr Asn Pro Ala Val
1               5

<210> SEQ ID NO 106
<211> LENGTH: 9
<212> TYPE: PRT
<213> ORGANISM: Homo sapiens

<400> SEQUENCE: 106

Asn Leu Thr Ile Ser Asp Val Ser Val
1               5

<210> SEQ ID NO 107
<211> LENGTH: 9
<212> TYPE: PRT
<213> ORGANISM: Homo sapiens

<400> SEQUENCE: 107

Ala Leu Ala Ser Thr Ala Pro Pro Val
1               5

<210> SEQ ID NO 108
<211> LENGTH: 9
<212> TYPE: PRT
<213> ORGANISM: Homo sapiens

<400> SEQUENCE: 108

Ala Ile Leu Cys Trp Thr Phe Trp Val
1               5

<210> SEQ ID NO 109
<211> LENGTH: 9
<212> TYPE: PRT
<213> ORGANISM: Homo sapiens

<400> SEQUENCE: 109

Phe Ile Leu Met Phe Ile Val Tyr Ala
1               5

<210> SEQ ID NO 110
<211> LENGTH: 9
<212> TYPE: PRT
<213> ORGANISM: Homo sapiens

<400> SEQUENCE: 110

Leu Thr Ala Glu Cys Ile Phe Phe Val
1               5

<210> SEQ ID NO 111
<211> LENGTH: 9
<212> TYPE: PRT
<213> ORGANISM: Homo sapiens

<400> SEQUENCE: 111

Met Leu Gln Asp Asn Cys Cys Gly Val
1               5

<210> SEQ ID NO 112
<211> LENGTH: 9
<212> TYPE: PRT
<213> ORGANISM: Homo sapiens

<400> SEQUENCE: 112

Ile Leu Cys Trp Thr Phe Trp Val Leu
1               5

<210> SEQ ID NO 113
<211> LENGTH: 9
<212> TYPE: PRT
<213> ORGANISM: Homo sapiens

<400> SEQUENCE: 113

Lys Ile Leu Leu Ala Tyr Phe Ile Leu
1               5

<210> SEQ ID NO 114
<211> LENGTH: 9
<212> TYPE: PRT
<213> ORGANISM: Homo sapiens

<400> SEQUENCE: 114

Phe Val Gly Ile Cys Leu Phe Cys Leu
1               5

<210> SEQ ID NO 115
<211> LENGTH: 9
<212> TYPE: PRT
<213> ORGANISM: Homo sapiens

<400> SEQUENCE: 115

Val Leu Leu Ser Val Ala Met Phe Leu
1               5

<210> SEQ ID NO 116
<211> LENGTH: 9
<212> TYPE: PRT
<213> ORGANISM: Homo sapiens

<400> SEQUENCE: 116

Leu Leu Ser Val Ala Met Phe Leu Leu
1               5

<210> SEQ ID NO 117
<211> LENGTH: 9
<212> TYPE: PRT
<213> ORGANISM: Homo sapiens

<400> SEQUENCE: 117

Ile Leu Gly Ser Leu Pro Phe Phe Leu
1               5

<210> SEQ ID NO 118
<211> LENGTH: 9
<212> TYPE: PRT
<213> ORGANISM: Homo sapiens

<400> SEQUENCE: 118

Ile Leu Asn Ala Tyr Leu Val Arg Val
1               5

<210> SEQ ID NO 119
<211> LENGTH: 9
<212> TYPE: PRT
<213> ORGANISM: Homo sapiens

<400> SEQUENCE: 119

Phe Leu Leu Val Gly Phe Ala Gly Ala
1               5

<210> SEQ ID NO 120
<211> LENGTH: 9
<212> TYPE: PRT
<213> ORGANISM: Homo sapiens

<400> SEQUENCE: 120

Asn Leu Gln Pro Gln Leu Ala Ser Val
1               5

<210> SEQ ID NO 121
<211> LENGTH: 9
<212> TYPE: PRT
<213> ORGANISM: Homo sapiens

<400> SEQUENCE: 121

Cys Met Phe Asp Ser Lys Glu Ala Leu
1               5

<210> SEQ ID NO 122
<211> LENGTH: 9
<212> TYPE: PRT
<213> ORGANISM: Homo sapiens

<400> SEQUENCE: 122

Tyr Leu Tyr Val Leu Val Asp Ser Ala

<210> SEQ ID NO 123
<211> LENGTH: 9
<212> TYPE: PRT
<213> ORGANISM: Homo sapiens

<400> SEQUENCE: 123

Tyr Met Asp Gly Thr Met Ser Gln Val
1               5

<210> SEQ ID NO 124
<211> LENGTH: 9
<212> TYPE: PRT
<213> ORGANISM: Homo sapiens

<400> SEQUENCE: 124

Lys Met Ala Arg Phe Ser Tyr Ser Val
1               5

<210> SEQ ID NO 125
<211> LENGTH: 9
<212> TYPE: PRT
<213> ORGANISM: Homo sapiens

<400> SEQUENCE: 125

Gly Leu Val Met Asp Glu His Leu Val
1               5

<210> SEQ ID NO 126
<211> LENGTH: 9
<212> TYPE: PRT
<213> ORGANISM: Homo sapiens

<400> SEQUENCE: 126

Phe Leu Pro Gly Cys Asp Gly Leu Val
1               5

<210> SEQ ID NO 127
<211> LENGTH: 9
<212> TYPE: PRT
<213> ORGANISM: Homo sapiens

<400> SEQUENCE: 127

Cys Met Leu Gly Ser Phe Cys Ala Cys
1               5

<210> SEQ ID NO 128
<211> LENGTH: 9
<212> TYPE: PRT
<213> ORGANISM: Homo sapiens

<400> SEQUENCE: 128

Tyr Leu Ala Phe Arg Asp Asp Ser Ile
1               5

<210> SEQ ID NO 129
<211> LENGTH: 9
<212> TYPE: PRT
<213> ORGANISM: Homo sapiens

<400> SEQUENCE: 129

Trp Leu Pro Lys Lys Cys Ser Leu Cys
1               5

```
<210> SEQ ID NO 130
<211> LENGTH: 9
<212> TYPE: PRT
<213> ORGANISM: Homo sapiens

<400> SEQUENCE: 130

Cys Leu Asn Gly Gly Thr Cys Met Leu
1               5

<210> SEQ ID NO 131
<211> LENGTH: 9
<212> TYPE: PRT
<213> ORGANISM: Homo sapiens

<400> SEQUENCE: 131

Met Leu Val Gly Ile Cys Leu Ser Ile
1               5

<210> SEQ ID NO 132
<211> LENGTH: 9
<212> TYPE: PRT
<213> ORGANISM: Homo sapiens

<400> SEQUENCE: 132

Phe Glu Leu Gly Leu Val Ala Gly Leu
1               5

<210> SEQ ID NO 133
<211> LENGTH: 9
<212> TYPE: PRT
<213> ORGANISM: Homo sapiens

<400> SEQUENCE: 133

Lys Met Val Arg Phe Ser Tyr Ser Val
1               5

<210> SEQ ID NO 134
<211> LENGTH: 9
<212> TYPE: PRT
<213> ORGANISM: Homo sapiens

<400> SEQUENCE: 134

Cys Leu Asn Glu Gly Thr Cys Met Leu
1               5

<210> SEQ ID NO 135
<211> LENGTH: 9
<212> TYPE: PRT
<213> ORGANISM: Homo sapiens

<400> SEQUENCE: 135

Met Leu Ala Gly Ile Cys Leu Ser Ile
1               5

<210> SEQ ID NO 136
<211> LENGTH: 9
<212> TYPE: PRT
<213> ORGANISM: Homo sapiens

<400> SEQUENCE: 136

Arg Leu Leu Phe Phe Leu Leu Phe Leu
1               5

<210> SEQ ID NO 137
```

```
<211> LENGTH: 9
<212> TYPE: PRT
<213> ORGANISM: Homo sapiens

<400> SEQUENCE: 137

Thr Leu Ala Tyr Leu Ile Phe Cys Leu
1               5

<210> SEQ ID NO 138
<211> LENGTH: 9
<212> TYPE: PRT
<213> ORGANISM: Homo sapiens

<400> SEQUENCE: 138

Leu Leu Phe Leu Thr Pro Met Glu Val
1               5

<210> SEQ ID NO 139
<211> LENGTH: 9
<212> TYPE: PRT
<213> ORGANISM: Homo sapiens

<400> SEQUENCE: 139

Lys Leu Met Ser Pro Lys Leu Tyr Val
1               5

<210> SEQ ID NO 140
<211> LENGTH: 9
<212> TYPE: PRT
<213> ORGANISM: Homo sapiens

<400> SEQUENCE: 140

Leu Leu Phe Phe Leu Leu Phe Leu Val
1               5

<210> SEQ ID NO 141
<211> LENGTH: 9
<212> TYPE: PRT
<213> ORGANISM: Homo sapiens

<400> SEQUENCE: 141

Ser Leu Phe Leu Gly Ile Leu Ser Val
1               5

<210> SEQ ID NO 142
<211> LENGTH: 9
<212> TYPE: PRT
<213> ORGANISM: Homo sapiens

<400> SEQUENCE: 142

Ala Ile Ser Gly Met Ile Leu Ser Ile
1               5

<210> SEQ ID NO 143
<211> LENGTH: 9
<212> TYPE: PRT
<213> ORGANISM: Homo sapiens

<400> SEQUENCE: 143

Phe Ile Arg Ala His Thr Pro Tyr Ile
1               5

<210> SEQ ID NO 144
<211> LENGTH: 9
<212> TYPE: PRT
```

```
<213> ORGANISM: Homo sapiens

<400> SEQUENCE: 144

Ser Leu Asn Phe Ile Arg Ala His Thr
1               5

<210> SEQ ID NO 145
<211> LENGTH: 9
<212> TYPE: PRT
<213> ORGANISM: Homo sapiens

<400> SEQUENCE: 145

Leu Lys Met Glu Ser Leu Asn Phe Ile
1               5

<210> SEQ ID NO 146
<211> LENGTH: 9
<212> TYPE: PRT
<213> ORGANISM: Homo sapiens

<400> SEQUENCE: 146

Ser His Phe Leu Lys Met Glu Ser Leu
1               5

<210> SEQ ID NO 147
<211> LENGTH: 9
<212> TYPE: PRT
<213> ORGANISM: Homo sapiens

<400> SEQUENCE: 147

Tyr Leu Phe Leu Gly Ile Leu Ser Val
1               5

<210> SEQ ID NO 148
<211> LENGTH: 9
<212> TYPE: PRT
<213> ORGANISM: Homo sapiens

<400> SEQUENCE: 148

His Leu Val Glu Ala Leu Tyr Leu Val
1               5

<210> SEQ ID NO 149
<211> LENGTH: 9
<212> TYPE: PRT
<213> ORGANISM: Homo sapiens

<400> SEQUENCE: 149

Leu Asn Ile Asp Leu Leu Trp Ser Val
1               5

<210> SEQ ID NO 150
<211> LENGTH: 9
<212> TYPE: PRT
<213> ORGANISM: Homo sapiens

<400> SEQUENCE: 150

Val Leu Phe Gly Leu Gly Phe Ala Ile
1               5

<210> SEQ ID NO 151
<211> LENGTH: 9
<212> TYPE: PRT
<213> ORGANISM: Homo sapiens
```

```
<400> SEQUENCE: 151

Val Tyr Leu Lys Thr Asn Val Phe Leu
1               5

<210> SEQ ID NO 152
<211> LENGTH: 9
<212> TYPE: PRT
<213> ORGANISM: Homo sapiens

<400> SEQUENCE: 152

Val Tyr Leu Lys Thr Asn Leu Phe Leu
1               5

<210> SEQ ID NO 153
<211> LENGTH: 9
<212> TYPE: PRT
<213> ORGANISM: Homo sapiens

<400> SEQUENCE: 153

Lys Tyr Asn Lys Ala Asn Ala Phe Leu
1               5

<210> SEQ ID NO 154
<211> LENGTH: 9
<212> TYPE: PRT
<213> ORGANISM: Homo sapiens

<400> SEQUENCE: 154

Lys Tyr Asn Ile Ala Asn Val Phe Leu
1               5

<210> SEQ ID NO 155
<211> LENGTH: 9
<212> TYPE: PRT
<213> ORGANISM: Homo sapiens

<400> SEQUENCE: 155

Lys Tyr Asn Lys Ala Asn Val Phe Leu
1               5

<210> SEQ ID NO 156
<211> LENGTH: 9
<212> TYPE: PRT
<213> ORGANISM: Homo sapiens

<400> SEQUENCE: 156

Phe Gln Asp Glu Asn Tyr Leu Tyr Leu
1               5

<210> SEQ ID NO 157
<211> LENGTH: 9
<212> TYPE: PRT
<213> ORGANISM: Homo sapiens

<400> SEQUENCE: 157

Leu Tyr Leu Val Cys Gly Glu Arg Gly
1               5

<210> SEQ ID NO 158
<211> LENGTH: 15
<212> TYPE: PRT
<213> ORGANISM: Homo sapiens

<400> SEQUENCE: 158
```

```
Ser Leu Gln Pro Leu Ala Leu Glu Gly Ser Leu Gln Ser Arg Gly
1               5                   10                  15

<210> SEQ ID NO 159
<211> LENGTH: 13
<212> TYPE: PRT
<213> ORGANISM: Homo sapiens

<400> SEQUENCE: 159

Gln His Leu Gln Lys Asp Tyr Arg Ala Tyr Tyr Thr Phe
1               5                   10

<210> SEQ ID NO 160
<211> LENGTH: 13
<212> TYPE: PRT
<213> ORGANISM: Homo sapiens

<400> SEQUENCE: 160

Asn Phe Phe Arg Met Val Ile Ser Asn Pro Ala Ala Thr
1               5                   10

<210> SEQ ID NO 161
<211> LENGTH: 13
<212> TYPE: PRT
<213> ORGANISM: Homo sapiens

<400> SEQUENCE: 161

Asn Phe Ile Arg Met Val Ile Ser Asn Pro Ala Ala Thr
1               5                   10

<210> SEQ ID NO 162
<211> LENGTH: 13
<212> TYPE: PRT
<213> ORGANISM: Homo sapiens

<400> SEQUENCE: 162

Tyr Thr Phe Leu Asn Phe Met Ser Asn Val Gly Asp Pro
1               5                   10

<210> SEQ ID NO 163
<211> LENGTH: 13
<212> TYPE: PRT
<213> ORGANISM: Homo sapiens

<400> SEQUENCE: 163

Phe Phe Tyr Thr Pro Lys Thr Arg Arg Glu Ala Glu Asp
1               5                   10

<210> SEQ ID NO 164
<211> LENGTH: 15
<212> TYPE: PRT
<213> ORGANISM: Homo sapiens

<400> SEQUENCE: 164

Ser Leu Gln Pro Leu Ala Leu Glu Gly Ser Leu Gln Lys Arg Gly
1               5                   10                  15

<210> SEQ ID NO 165
<211> LENGTH: 9
<212> TYPE: PRT
<213> ORGANISM: Homo sapiens

<400> SEQUENCE: 165

Leu Tyr Leu Val Cys Gly Glu Arg Ile
1               5
```

<210> SEQ ID NO 166
<211> LENGTH: 9
<212> TYPE: PRT
<213> ORGANISM: Homo sapiens

<400> SEQUENCE: 166

Lys Tyr Gln Ala Val Thr Thr Thr Leu
1               5

<210> SEQ ID NO 167
<211> LENGTH: 9
<212> TYPE: PRT
<213> ORGANISM: Homo sapiens

<400> SEQUENCE: 167

Lys Tyr Cys Leu Ile Thr Ile Phe Leu
1               5

<210> SEQ ID NO 168
<211> LENGTH: 9
<212> TYPE: PRT
<213> ORGANISM: Homo sapiens

<400> SEQUENCE: 168

Ala Leu Trp Met Arg Leu Leu Pro Leu
1               5

<210> SEQ ID NO 169
<211> LENGTH: 9
<212> TYPE: PRT
<213> ORGANISM: Homo sapiens

<400> SEQUENCE: 169

Leu Trp Met Arg Leu Leu Pro Leu Leu
1               5

<210> SEQ ID NO 170
<211> LENGTH: 9
<212> TYPE: PRT
<213> ORGANISM: Homo sapiens

<400> SEQUENCE: 170

Arg Leu Leu Pro Leu Leu Ala Leu Leu
1               5

<210> SEQ ID NO 171
<211> LENGTH: 10
<212> TYPE: PRT
<213> ORGANISM: Homo sapiens

<400> SEQUENCE: 171

His Leu Cys Gly Ser His Leu Val Glu Ala
1               5                   10

<210> SEQ ID NO 172
<211> LENGTH: 9
<212> TYPE: PRT
<213> ORGANISM: Homo sapiens

<400> SEQUENCE: 172

Ala Leu Tyr Leu Val Cys Gly Glu Arg
1               5

<210> SEQ ID NO 173
<211> LENGTH: 10
<212> TYPE: PRT
<213> ORGANISM: Homo sapiens

<400> SEQUENCE: 173

Leu Tyr Leu Val Cys Gly Glu Arg Gly Phe
1               5                   10

<210> SEQ ID NO 174
<211> LENGTH: 9
<212> TYPE: PRT
<213> ORGANISM: Homo sapiens

<400> SEQUENCE: 174

Leu Val Cys Gly Glu Arg Gly Phe Phe
1               5

<210> SEQ ID NO 175
<211> LENGTH: 10
<212> TYPE: PRT
<213> ORGANISM: Homo sapiens

<400> SEQUENCE: 175

Val Cys Gly Glu Arg Gly Phe Phe Tyr Thr
1               5                   10

<210> SEQ ID NO 176
<211> LENGTH: 8
<212> TYPE: PRT
<213> ORGANISM: Homo sapiens

<400> SEQUENCE: 176

Gly Glu Arg Gly Phe Phe Tyr Thr
1               5

<210> SEQ ID NO 177
<211> LENGTH: 9
<212> TYPE: PRT
<213> ORGANISM: Homo sapiens

<400> SEQUENCE: 177

Glu Arg Gly Phe Phe Tyr Thr Pro Lys
1               5

<210> SEQ ID NO 178
<211> LENGTH: 9
<212> TYPE: PRT
<213> ORGANISM: Homo sapiens

<400> SEQUENCE: 178

Phe Tyr Thr Pro Lys Thr Arg Arg Glu
1               5

<210> SEQ ID NO 179
<211> LENGTH: 11
<212> TYPE: PRT
<213> ORGANISM: Homo sapiens

<400> SEQUENCE: 179

Thr Pro Lys Thr Arg Arg Glu Ala Glu Asp Leu
1               5                   10

<210> SEQ ID NO 180
<211> LENGTH: 9

<212> TYPE: PRT
<213> ORGANISM: Homo sapiens

<400> SEQUENCE: 180

Ser Leu Gln Pro Leu Ala Leu Glu Gly
1               5

<210> SEQ ID NO 181
<211> LENGTH: 9
<212> TYPE: PRT
<213> ORGANISM: Homo sapiens

<400> SEQUENCE: 181

Ala Leu Glu Gly Ser Leu Gln Lys Arg
1               5

<210> SEQ ID NO 182
<211> LENGTH: 10
<212> TYPE: PRT
<213> ORGANISM: Homo sapiens

<400> SEQUENCE: 182

Ser Leu Gln Lys Arg Gly Ile Val Glu Gln
1               5                   10

<210> SEQ ID NO 183
<211> LENGTH: 10
<212> TYPE: PRT
<213> ORGANISM: Homo sapiens

<400> SEQUENCE: 183

Gly Ile Val Glu Gln Cys Cys Thr Ser Ile
1               5                   10

<210> SEQ ID NO 184
<211> LENGTH: 9
<212> TYPE: PRT
<213> ORGANISM: Homo sapiens

<400> SEQUENCE: 184

Ile Val Glu Gln Cys Cys Thr Ser Ile
1               5

<210> SEQ ID NO 185
<211> LENGTH: 9
<212> TYPE: PRT
<213> ORGANISM: Homo sapiens

<400> SEQUENCE: 185

Ser Leu Tyr Gln Leu Glu Asn Tyr Cys
1               5

<210> SEQ ID NO 186
<211> LENGTH: 21
<212> TYPE: PRT
<213> ORGANISM: Homo sapiens

<400> SEQUENCE: 186

Met Glu Val Gly Trp Tyr Arg Ser Pro Phe Ser Arg Val Val His Leu
1               5                   10                  15

Tyr Arg Asn Gly Lys
            20

<210> SEQ ID NO 187

```
<211> LENGTH: 20
<212> TYPE: PRT
<213> ORGANISM: Homo sapiens

<400> SEQUENCE: 187

Glu Val Gly Trp Tyr Arg Ser Pro Phe Ser Arg Val Val His Leu Tyr
1               5                   10                  15

Arg Asn Gly Lys
            20

<210> SEQ ID NO 188
<211> LENGTH: 9
<212> TYPE: PRT
<213> ORGANISM: Homo sapiens

<400> SEQUENCE: 188

Ser Leu Leu Leu Glu Leu Glu Glu Val
1               5

<210> SEQ ID NO 189
<211> LENGTH: 9
<212> TYPE: PRT
<213> ORGANISM: Homo sapiens

<400> SEQUENCE: 189

Leu Met Trp Ala Lys Ile Gly Pro Val
1               5

<210> SEQ ID NO 190
<211> LENGTH: 9
<212> TYPE: PRT
<213> ORGANISM: Homo sapiens

<400> SEQUENCE: 190

Val Leu Phe Ser Ser Asp Phe Arg Ile
1               5

<210> SEQ ID NO 191
<211> LENGTH: 9
<212> TYPE: PRT
<213> ORGANISM: Homo sapiens

<400> SEQUENCE: 191

Ser Leu Ser Arg Phe Ser Trp Gly Ala
1               5

<210> SEQ ID NO 192
<211> LENGTH: 9
<212> TYPE: PRT
<213> ORGANISM: Homo sapiens

<400> SEQUENCE: 192

Lys Val Glu Asp Pro Phe Tyr Trp Val
1               5

<210> SEQ ID NO 193
<211> LENGTH: 10
<212> TYPE: PRT
<213> ORGANISM: Homo sapiens

<400> SEQUENCE: 193

Arg Thr Phe Asp Pro His Phe Leu Arg Val
1               5                   10
```

<210> SEQ ID NO 194
<211> LENGTH: 9
<212> TYPE: PRT
<213> ORGANISM: Homo sapiens

<400> SEQUENCE: 194

Phe Leu Arg Val Pro Cys Trp Lys Ile
1               5

<210> SEQ ID NO 195
<211> LENGTH: 10
<212> TYPE: PRT
<213> ORGANISM: Homo sapiens

<400> SEQUENCE: 195

Lys Ile Thr Leu Phe Val Ile Val Pro Val
1               5                   10

<210> SEQ ID NO 196
<211> LENGTH: 9
<212> TYPE: PRT
<213> ORGANISM: Homo sapiens

<400> SEQUENCE: 196

Val Leu Gly Pro Leu Val Ala Leu Ile
1               5

<210> SEQ ID NO 197
<211> LENGTH: 9
<212> TYPE: PRT
<213> ORGANISM: Homo sapiens

<400> SEQUENCE: 197

Thr Leu Phe Val Ile Val Pro Val Leu
1               5

<210> SEQ ID NO 198
<211> LENGTH: 10
<212> TYPE: PRT
<213> ORGANISM: Homo sapiens

<400> SEQUENCE: 198

Arg Leu Ala Gly Gln Phe Leu Glu Glu Leu
1               5                   10

<210> SEQ ID NO 199
<211> LENGTH: 9
<212> TYPE: PRT
<213> ORGANISM: Homo sapiens

<400> SEQUENCE: 199

Phe Leu Tyr Gly Ala Leu Leu Leu Ala
1               5

<210> SEQ ID NO 200
<211> LENGTH: 13
<212> TYPE: PRT
<213> ORGANISM: Homo sapiens

<400> SEQUENCE: 200

Thr Cys Phe Phe Arg Asp His Ser Tyr Gln Glu Glu Ala
1               5                   10

<210> SEQ ID NO 201
<211> LENGTH: 13

```
<212> TYPE: PRT
<213> ORGANISM: Homo sapiens

<400> SEQUENCE: 201

Thr Cys Phe Phe Arg Asp His Ser Tyr Gln Ser Glu Ala
1               5                   10

<210> SEQ ID NO 202
<211> LENGTH: 13
<212> TYPE: PRT
<213> ORGANISM: Homo sapiens

<400> SEQUENCE: 202

Val His Phe Phe Lys Asn Ile Val Thr Pro Arg Thr Pro
1               5                   10

<210> SEQ ID NO 203
<211> LENGTH: 18
<212> TYPE: PRT
<213> ORGANISM: Homo sapiens

<400> SEQUENCE: 203

Tyr Ile Tyr Phe Asn Thr Trp Thr Thr Cys Gln Ser Ile Ala Phe Pro
1               5                   10                  15

Ser Lys

<210> SEQ ID NO 204
<211> LENGTH: 15
<212> TYPE: PRT
<213> ORGANISM: Homo sapiens

<400> SEQUENCE: 204

Gly Ala Val Arg Gln Ile Phe Gly Asp Tyr Lys Thr Thr Ile Cys
1               5                   10                  15

<210> SEQ ID NO 205
<211> LENGTH: 13
<212> TYPE: PRT
<213> ORGANISM: Homo sapiens

<400> SEQUENCE: 205

Pro Val Val His Phe Phe Lys Asn Ile Val Thr Pro Arg
1               5                   10

<210> SEQ ID NO 206
<211> LENGTH: 15
<212> TYPE: PRT
<213> ORGANISM: Homo sapiens

<400> SEQUENCE: 206

Asn Tyr Gln Asp Tyr Glu Tyr Leu Ile Asn Val Ile His Ala Phe
1               5                   10                  15

<210> SEQ ID NO 207
<211> LENGTH: 15
<212> TYPE: PRT
<213> ORGANISM: Homo sapiens

<400> SEQUENCE: 207

Ala Thr Leu Val Ser Leu Leu Thr Phe Met Ile Ala Ala Thr Tyr
1               5                   10                  15

<210> SEQ ID NO 208
<211> LENGTH: 15
```

```
<212> TYPE: PRT
<213> ORGANISM: Homo sapiens

<400> SEQUENCE: 208

Leu Val Leu Leu Ala Val Leu Pro Val Leu Leu Leu Gln Ile Thr
1               5                   10                  15

<210> SEQ ID NO 209
<211> LENGTH: 15
<212> TYPE: PRT
<213> ORGANISM: Homo sapiens

<400> SEQUENCE: 209

Phe Leu Arg Val Pro Cys Trp Lys Ile Thr Leu Phe Val Ile Val
1               5                   10                  15

<210> SEQ ID NO 210
<211> LENGTH: 15
<212> TYPE: PRT
<213> ORGANISM: Homo sapiens

<400> SEQUENCE: 210

Arg His Pro Ile Arg Ala Leu Val Gly Asp Glu Val Glu Leu Pro
1               5                   10                  15

<210> SEQ ID NO 211
<211> LENGTH: 15
<212> TYPE: PRT
<213> ORGANISM: Homo sapiens

<400> SEQUENCE: 211

Arg Val Pro Cys Trp Lys Ile Thr Leu Phe Val Ile Val Pro Val
1               5                   10                  15

<210> SEQ ID NO 212
<211> LENGTH: 15
<212> TYPE: PRT
<213> ORGANISM: Homo sapiens

<400> SEQUENCE: 212

Thr Leu Val Ser Leu Leu Thr Phe Met Ile Ala Ala Thr Tyr Asn
1               5                   10                  15

<210> SEQ ID NO 213
<211> LENGTH: 20
<212> TYPE: PRT
<213> ORGANISM: Homo sapiens

<400> SEQUENCE: 213

Lys Tyr Leu Ala Thr Ala Ser Thr Met Asp His Ala Arg His Gly Phe
1               5                   10                  15

Leu Pro Arg His
            20

<210> SEQ ID NO 214
<211> LENGTH: 17
<212> TYPE: PRT
<213> ORGANISM: Homo sapiens

<400> SEQUENCE: 214

Glu Asn Pro Val Val His Phe Phe Lys Asn Ile Val Thr Pro Arg Thr
1               5                   10                  15

Pro
```

<210> SEQ ID NO 215
<211> LENGTH: 19
<212> TYPE: PRT
<213> ORGANISM: Homo sapiens

<400> SEQUENCE: 215

Leu Ser Arg Phe Ser Trp Gly Ala Glu Gly Gln Arg Pro Gly Phe Gly
1               5                   10                  15

Tyr Gly Gly

<210> SEQ ID NO 216
<211> LENGTH: 25
<212> TYPE: PRT
<213> ORGANISM: Homo sapiens

<400> SEQUENCE: 216

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 217
<211> LENGTH: 15
<212> TYPE: PRT
<213> ORGANISM: Homo sapiens

<400> SEQUENCE: 217

Ala Leu Ile Ile Cys Tyr Asn Trp Leu His Arg Arg Leu Ala Gly
1               5                   10                  15

<210> SEQ ID NO 218
<211> LENGTH: 15
<212> TYPE: PRT
<213> ORGANISM: Homo sapiens

<400> SEQUENCE: 218

Ile Gly Pro Arg His Pro Ile Arg Ala Leu Val Gly Asp Glu Val
1               5                   10                  15

<210> SEQ ID NO 219
<211> LENGTH: 15
<212> TYPE: PRT
<213> ORGANISM: Homo sapiens

<400> SEQUENCE: 219

Ala Glu Gly Phe Tyr Thr Thr Gly Ala Val Arg Gln Ile Phe Gly
1               5                   10                  15

<210> SEQ ID NO 220
<211> LENGTH: 16
<212> TYPE: PRT
<213> ORGANISM: Homo sapiens

<400> SEQUENCE: 220

His Cys Leu Gly Lys Trp Leu Gly His Pro Asp Lys Phe Val Gly Ile
1               5                   10                  15

<210> SEQ ID NO 221
<211> LENGTH: 12
<212> TYPE: PRT
<213> ORGANISM: Homo sapiens

<400> SEQUENCE: 221

```
Gln Leu Gln Pro Phe Pro Gln Pro Glu Leu Pro Tyr
1               5                   10
```

<210> SEQ ID NO 222
<211> LENGTH: 11
<212> TYPE: PRT
<213> ORGANISM: Homo sapiens

<400> SEQUENCE: 222

```
Pro Gln Pro Glu Leu Pro Tyr Pro Gln Pro Glu
1               5                   10
```

<210> SEQ ID NO 223
<211> LENGTH: 13
<212> TYPE: PRT
<213> ORGANISM: Homo sapiens

<400> SEQUENCE: 223

```
Ser Gly Glu Gly Ser Phe Gln Pro Ser Gln Gln Asn Pro
1               5                   10
```

<210> SEQ ID NO 224
<211> LENGTH: 14
<212> TYPE: PRT
<213> ORGANISM: Homo sapiens

<400> SEQUENCE: 224

```
Gly Asp Leu Ile Ala Glu Val Glu Thr Asp Lys Ala Thr Val
1               5                   10
```

<210> SEQ ID NO 225
<211> LENGTH: 14
<212> TYPE: PRT
<213> ORGANISM: Homo sapiens

<400> SEQUENCE: 225

```
Gly Asp Leu Leu Ala Glu Ile Glu Thr Asp Lys Ala Thr Ile
1               5                   10
```

<210> SEQ ID NO 226
<211> LENGTH: 15
<212> TYPE: PRT
<213> ORGANISM: Homo sapiens

<400> SEQUENCE: 226

```
Gly Asp Leu Leu Ala Glu Ile Glu Thr Asp Lys Ala Thr Ile Gly
1               5                   10                  15
```

<210> SEQ ID NO 227
<211> LENGTH: 15
<212> TYPE: PRT
<213> ORGANISM: Homo sapiens

<400> SEQUENCE: 227

```
Ala Gln Trp Leu Ala Glu Phe Arg Lys Tyr Leu Glu Lys Pro Ile
1               5                   10                  15
```

<210> SEQ ID NO 228
<211> LENGTH: 15
<212> TYPE: PRT
<213> ORGANISM: Homo sapiens

<400> SEQUENCE: 228

```
Arg Leu Leu Leu Gln Leu Leu Gly Ser Pro Gly Arg Arg Tyr Tyr
1               5                   10                  15
```

<210> SEQ ID NO 229
<211> LENGTH: 15
<212> TYPE: PRT
<213> ORGANISM: Homo sapiens

<400> SEQUENCE: 229

Gly Arg Val Phe Val Ser Pro Leu Ala Lys Lys Leu Ala Val Glu
1               5                   10                  15

<210> SEQ ID NO 230
<211> LENGTH: 15
<212> TYPE: PRT
<213> ORGANISM: Homo sapiens

<400> SEQUENCE: 230

Asp Ile Pro Ile Ser Asn Ile Arg Arg Val Ile Ala Gln Arg Leu
1               5                   10                  15

<210> SEQ ID NO 231
<211> LENGTH: 15
<212> TYPE: PRT
<213> ORGANISM: Homo sapiens

<400> SEQUENCE: 231

Ser Pro Gly Arg Arg Tyr Tyr Ser Leu Pro Pro His Gln Lys Val
1               5                   10                  15

<210> SEQ ID NO 232
<211> LENGTH: 15
<212> TYPE: PRT
<213> ORGANISM: Homo sapiens

<400> SEQUENCE: 232

Glu Thr Ile Ala Asn Asp Val Val Ser Leu Ala Thr Lys Ala Arg
1               5                   10                  15

<210> SEQ ID NO 233
<211> LENGTH: 14
<212> TYPE: PRT
<213> ORGANISM: Homo sapiens

<400> SEQUENCE: 233

Gly Glu Ile Arg Thr Met Asn Asn Phe Leu Asp Arg Glu Ile
1               5                   10

<210> SEQ ID NO 234
<211> LENGTH: 15
<212> TYPE: PRT
<213> ORGANISM: Homo sapiens

<400> SEQUENCE: 234

Phe Gly Ile Phe Val Val Asp Lys Asn Thr Gly Asp Ile Asn Ile
1               5                   10                  15

<210> SEQ ID NO 235
<211> LENGTH: 15
<212> TYPE: PRT
<213> ORGANISM: Homo sapiens

<400> SEQUENCE: 235

Cys Glu Cys Asn Ile Lys Val Lys Asp Val Asn Asp Asn Phe Pro
1               5                   10                  15

```
<210> SEQ ID NO 236
<211> LENGTH: 15
<212> TYPE: PRT
<213> ORGANISM: Homo sapiens

<400> SEQUENCE: 236

Asn Lys Ala Glu Phe His Gln Ser Val Ile Ser Arg Tyr Arg Val
1               5                   10                  15

<210> SEQ ID NO 237
<211> LENGTH: 15
<212> TYPE: PRT
<213> ORGANISM: Homo sapiens

<400> SEQUENCE: 237

Asp Ser Thr Phe Ile Val Asn Lys Thr Ile Thr Ala Glu Val Leu
1               5                   10                  15

<210> SEQ ID NO 238
<211> LENGTH: 15
<212> TYPE: PRT
<213> ORGANISM: Homo sapiens

<400> SEQUENCE: 238

Ser Ile Thr Thr Leu Asn Ala Thr Ser Ala Leu Leu Arg Ala Gln
1               5                   10                  15

<210> SEQ ID NO 239
<211> LENGTH: 15
<212> TYPE: PRT
<213> ORGANISM: Homo sapiens

<400> SEQUENCE: 239

Ile Leu Ser Ser Glu Leu Leu Arg Phe Gln Val Thr Asp Leu Asp
1               5                   10                  15

<210> SEQ ID NO 240
<211> LENGTH: 15
<212> TYPE: PRT
<213> ORGANISM: Homo sapiens

<400> SEQUENCE: 240

Glu Gly Ile Leu Lys Val Val Lys Ala Leu Asp Tyr Glu Gln Leu
1               5                   10                  15

<210> SEQ ID NO 241
<211> LENGTH: 15
<212> TYPE: PRT
<213> ORGANISM: Homo sapiens

<400> SEQUENCE: 241

Ser Thr Pro Val Thr Ile Gln Val Ile Asn Val Arg Glu Gly Ile
1               5                   10                  15

<210> SEQ ID NO 242
<211> LENGTH: 15
<212> TYPE: PRT
<213> ORGANISM: Homo sapiens

<400> SEQUENCE: 242

Ala Ile Phe Val Val Val Ile Leu Val His Gly Glu Leu Arg Ile
1               5                   10                  15

<210> SEQ ID NO 243
<211> LENGTH: 15
```

```
<212> TYPE: PRT
<213> ORGANISM: Homo sapiens

<400> SEQUENCE: 243

Arg Thr Asn Glu Gly Ile Leu Lys Val Val Lys Ala Leu Asp Tyr
1               5                   10                  15

<210> SEQ ID NO 244
<211> LENGTH: 15
<212> TYPE: PRT
<213> ORGANISM: Homo sapiens

<400> SEQUENCE: 244

Asp Ser Lys Thr Ala Glu Ile Lys Phe Val Lys Asn Met Asn Arg
1               5                   10                  15

<210> SEQ ID NO 245
<211> LENGTH: 15
<212> TYPE: PRT
<213> ORGANISM: Homo sapiens

<400> SEQUENCE: 245

Lys Arg Glu Trp Ile Lys Phe Ala Ala Ala Cys Arg Glu Gly Glu
1               5                   10                  15

<210> SEQ ID NO 246
<211> LENGTH: 15
<212> TYPE: PRT
<213> ORGANISM: Homo sapiens

<400> SEQUENCE: 246

Met Phe Ile Ile Asn Arg Asn Thr Gly Glu Ile Arg Thr Met Asn
1               5                   10                  15

<210> SEQ ID NO 247
<211> LENGTH: 15
<212> TYPE: PRT
<213> ORGANISM: Homo sapiens

<400> SEQUENCE: 247

Ser Gln Tyr Lys Leu Lys Ala Ser Ala Ile Ser Val Thr Val Leu
1               5                   10                  15

<210> SEQ ID NO 248
<211> LENGTH: 15
<212> TYPE: PRT
<213> ORGANISM: Homo sapiens

<400> SEQUENCE: 248

Trp Ser Phe Phe Arg Val Val Ala Met Leu Phe Ile Phe Leu Val
1               5                   10                  15

<210> SEQ ID NO 249
<211> LENGTH: 15
<212> TYPE: PRT
<213> ORGANISM: Homo sapiens

<400> SEQUENCE: 249

Ser Lys Ile Ala Phe Lys Ile Ile Arg Gln Glu Pro Ser Asp Ser
1               5                   10                  15

<210> SEQ ID NO 250
<211> LENGTH: 15
<212> TYPE: PRT
<213> ORGANISM: Homo sapiens
```

<400> SEQUENCE: 250

Thr Asn Val Gly Ile Leu Lys Val Val Lys Pro Leu Asp Tyr Glu
1               5                   10                  15

<210> SEQ ID NO 251
<211> LENGTH: 15
<212> TYPE: PRT
<213> ORGANISM: Homo sapiens

<400> SEQUENCE: 251

Met Asp Trp Ser Phe Phe Arg Val Val Ala Met Leu Phe Ile Phe
1               5                   10                  15

<210> SEQ ID NO 252
<211> LENGTH: 15
<212> TYPE: PRT
<213> ORGANISM: Homo sapiens

<400> SEQUENCE: 252

Lys Asn Gly Thr Ile Lys Trp His Ser Ile Arg Arg Gln Lys Arg
1               5                   10                  15

<210> SEQ ID NO 253
<211> LENGTH: 15
<212> TYPE: PRT
<213> ORGANISM: Homo sapiens

<400> SEQUENCE: 253

Arg Thr Asn Val Gly Ile Leu Lys Val Val Lys Pro Leu Asp Tyr
1               5                   10                  15

<210> SEQ ID NO 254
<211> LENGTH: 15
<212> TYPE: PRT
<213> ORGANISM: Homo sapiens

<400> SEQUENCE: 254

Gly Ala Gly Ile Leu Tyr Leu Val Thr Pro Pro Ser Val Val Gly
1               5                   10                  15

<210> SEQ ID NO 255
<211> LENGTH: 15
<212> TYPE: PRT
<213> ORGANISM: Homo sapiens

<400> SEQUENCE: 255

Arg Ser Gln Val Glu Thr Asp Asp Leu Ile Leu Lys Pro Gly Val
1               5                   10                  15

<210> SEQ ID NO 256
<211> LENGTH: 14
<212> TYPE: PRT
<213> ORGANISM: Homo sapiens

<400> SEQUENCE: 256

Glu Lys Pro Leu Pro Val Asp Met Val Leu Ile Ser Leu Cys
1               5                   10

<210> SEQ ID NO 257
<211> LENGTH: 15
<212> TYPE: PRT
<213> ORGANISM: Homo sapiens

<400> SEQUENCE: 257

```
Thr Ala Glu Phe Leu Ala Met Leu Ile Phe Val Leu Leu Ser Leu
1               5                   10                  15
```

<210> SEQ ID NO 258
<211> LENGTH: 15
<212> TYPE: PRT
<213> ORGANISM: Homo sapiens

<400> SEQUENCE: 258

```
Leu Arg Gln Met Arg Thr Val Thr Pro Ile Arg Met Gln Gly Gly
1               5                   10                  15
```

<210> SEQ ID NO 259
<211> LENGTH: 15
<212> TYPE: PRT
<213> ORGANISM: Homo sapiens

<400> SEQUENCE: 259

```
Ala Val Asn Ile Val Gly Tyr Ser Asn Ala Gln Gly Val Asp Tyr
1               5                   10                  15
```

<210> SEQ ID NO 260
<211> LENGTH: 15
<212> TYPE: PRT
<213> ORGANISM: Homo sapiens

<400> SEQUENCE: 260

```
Arg Phe Gly Ile Ser Asn Tyr Cys Gln Ile Tyr Pro Pro Asn Val
1               5                   10                  15
```

<210> SEQ ID NO 261
<211> LENGTH: 15
<212> TYPE: PRT
<213> ORGANISM: Homo sapiens

<400> SEQUENCE: 261

```
Pro Cys Ile Ile His Arg Gly Lys Pro Phe Gln Leu Glu Ala Val
1               5                   10                  15
```

<210> SEQ ID NO 262
<211> LENGTH: 15
<212> TYPE: PRT
<213> ORGANISM: Homo sapiens

<400> SEQUENCE: 262

```
Thr Val Lys Val Met Gly Asp Asp Gly Val Leu Ala Cys Ala Ile
1               5                   10                  15
```

<210> SEQ ID NO 263
<211> LENGTH: 15
<212> TYPE: PRT
<213> ORGANISM: Homo sapiens

<400> SEQUENCE: 263

```
Glu Ala Ile Asn Gln Gly Tyr Met His Ala Asp Ala Tyr Pro Phe
1               5                   10                  15
```

<210> SEQ ID NO 264
<211> LENGTH: 15
<212> TYPE: PRT
<213> ORGANISM: Homo sapiens

<400> SEQUENCE: 264

```
Lys Asp Leu Thr Tyr Thr Phe Leu Arg Asp Phe Glu Gln Tyr Leu
```

```
1               5                   10                  15
```

<210> SEQ ID NO 265
<211> LENGTH: 15
<212> TYPE: PRT
<213> ORGANISM: Homo sapiens

<400> SEQUENCE: 265

```
Arg Gln Leu Arg Thr Leu Val Asn Glu Ala Ile Asn Gln Gly Tyr
1               5                   10                  15
```

<210> SEQ ID NO 266
<211> LENGTH: 15
<212> TYPE: PRT
<213> ORGANISM: Homo sapiens

<400> SEQUENCE: 266

```
Met Asp Lys Ile Arg Tyr Arg Leu Val Tyr Asn Arg Gln Asn Thr
1               5                   10                  15
```

<210> SEQ ID NO 267
<211> LENGTH: 15
<212> TYPE: PRT
<213> ORGANISM: Homo sapiens

<400> SEQUENCE: 267

```
Leu Asn Gln Arg Lys Ile Tyr Leu Lys Thr Asn Val Tyr Leu Lys
1               5                   10                  15
```

<210> SEQ ID NO 268
<211> LENGTH: 15
<212> TYPE: PRT
<213> ORGANISM: Homo sapiens

<400> SEQUENCE: 268

```
Glu Tyr Ile Leu Tyr Leu Gln Gly Ile Glu Leu Gly Tyr Trp Lys
1               5                   10                  15
```

<210> SEQ ID NO 269
<211> LENGTH: 15
<212> TYPE: PRT
<213> ORGANISM: Homo sapiens

<400> SEQUENCE: 269

```
Thr Cys Ala Thr Leu Leu Ile His Gln Gly Val Ala Ile Thr Thr
1               5                   10                  15
```

<210> SEQ ID NO 270
<211> LENGTH: 15
<212> TYPE: PRT
<213> ORGANISM: Homo sapiens

<400> SEQUENCE: 270

```
Ala Lys His Met Arg Gln Leu Arg Thr Leu Val Asn Glu Ala Ile
1               5                   10                  15
```

<210> SEQ ID NO 271
<211> LENGTH: 15
<212> TYPE: PRT
<213> ORGANISM: Homo sapiens

<400> SEQUENCE: 271

```
Ile Arg Tyr Arg Leu Val Tyr Asn Arg Gln Asn Thr Leu Asn Arg
1               5                   10                  15
```

<210> SEQ ID NO 272
<211> LENGTH: 15
<212> TYPE: PRT
<213> ORGANISM: Homo sapiens

<400> SEQUENCE: 272

Glu Asn Phe Ile Arg Ile Asn Gly Lys Arg Trp Leu Tyr Phe Lys
1               5                   10                  15

<210> SEQ ID NO 273
<211> LENGTH: 15
<212> TYPE: PRT
<213> ORGANISM: Homo sapiens

<400> SEQUENCE: 273

Thr Gly Ala Ala Ala Thr Tyr Ala Ile Asp Ser Ile Ala Asp Ala
1               5                   10                  15

<210> SEQ ID NO 274
<211> LENGTH: 15
<212> TYPE: PRT
<213> ORGANISM: Homo sapiens

<400> SEQUENCE: 274

Asn Ala Thr Phe Ser Met Asp Gln Leu Lys Phe Gly Asp Thr Ile
1               5                   10                  15

<210> SEQ ID NO 275
<211> LENGTH: 15
<212> TYPE: PRT
<213> ORGANISM: Homo sapiens

<400> SEQUENCE: 275

Asp Arg Thr Val Val Ser Ser Ile Gly Ala Tyr Lys Leu Ile Gln
1               5                   10                  15

<210> SEQ ID NO 276
<211> LENGTH: 15
<212> TYPE: PRT
<213> ORGANISM: Homo sapiens

<400> SEQUENCE: 276

Met Val Val Gln His Asn Leu Arg Ala Met Asn Ser Asn Arg Met
1               5                   10                  15

<210> SEQ ID NO 277
<211> LENGTH: 15
<212> TYPE: PRT
<213> ORGANISM: Homo sapiens

<400> SEQUENCE: 277

Lys Met Arg Lys Gln Ile Arg Gly Leu Ser Gln Ala Ser Leu Asn
1               5                   10                  15

<210> SEQ ID NO 278
<211> LENGTH: 15
<212> TYPE: PRT
<213> ORGANISM: Homo sapiens

<400> SEQUENCE: 278

Gly Ala Tyr Lys Leu Ile Gln Lys Glu Leu Gly Leu Ala Ser Ser
1               5                   10                  15

<210> SEQ ID NO 279

```
<211> LENGTH: 15
<212> TYPE: PRT
<213> ORGANISM: Homo sapiens

<400> SEQUENCE: 279

Gln His Asn Leu Arg Ala Met Asn Ser Asn Arg Met Leu Gly Ile
1               5                   10                  15

<210> SEQ ID NO 280
<211> LENGTH: 15
<212> TYPE: PRT
<213> ORGANISM: Homo sapiens

<400> SEQUENCE: 280

Tyr Lys Leu Ile Gln Lys Glu Leu Gly Leu Ala Ser Ser Ile Gly
1               5                   10                  15

<210> SEQ ID NO 281
<211> LENGTH: 15
<212> TYPE: PRT
<213> ORGANISM: Homo sapiens

<400> SEQUENCE: 281

Ala Asp Asp Ile Val Lys Met Leu Asn Asp Pro Ala Leu Asn Arg
1               5                   10                  15

<210> SEQ ID NO 282
<211> LENGTH: 15
<212> TYPE: PRT
<213> ORGANISM: Homo sapiens

<400> SEQUENCE: 282

His Asn Ile Gln Val Ala Asp Asp Ala Arg Phe Val Leu Asn Ala
1               5                   10                  15

<210> SEQ ID NO 283
<211> LENGTH: 15
<212> TYPE: PRT
<213> ORGANISM: Homo sapiens

<400> SEQUENCE: 283

Ala Asp Asp Ala Arg Phe Val Leu Asn Ala Gly Lys Lys Lys Phe
1               5                   10                  15

<210> SEQ ID NO 284
<211> LENGTH: 15
<212> TYPE: PRT
<213> ORGANISM: Homo sapiens

<400> SEQUENCE: 284

Gly Cys Ile Ser Tyr Ala Leu Val Ser His Thr Ala Lys Gly Ser
1               5                   10                  15

<210> SEQ ID NO 285
<211> LENGTH: 15
<212> TYPE: PRT
<213> ORGANISM: Homo sapiens

<400> SEQUENCE: 285

Leu Pro Val Thr Val Thr Leu Asp Ile Ile Thr Ala Pro Leu Gln
1               5                   10                  15

<210> SEQ ID NO 286
<211> LENGTH: 15
<212> TYPE: PRT
```

-continued

<213> ORGANISM: Homo sapiens

<400> SEQUENCE: 286

Ser Gly Cys Ile Ser Tyr Ala Leu Val Ser His Thr Ala Lys Gly
1               5                   10                  15

<210> SEQ ID NO 287
<211> LENGTH: 15
<212> TYPE: PRT
<213> ORGANISM: Homo sapiens

<400> SEQUENCE: 287

Asp Ile Val Lys Met Leu Asn Asp Pro Ala Leu Asn Arg His Asn
1               5                   10                  15

<210> SEQ ID NO 288
<211> LENGTH: 15
<212> TYPE: PRT
<213> ORGANISM: Homo sapiens

<400> SEQUENCE: 288

Ala Arg Phe Val Leu Asn Ala Gly Lys Lys Lys Phe Thr Gly Thr
1               5                   10                  15

<210> SEQ ID NO 289
<211> LENGTH: 24
<212> TYPE: PRT
<213> ORGANISM: Homo sapiens

<400> SEQUENCE: 289

Thr Tyr Thr Glu His Ala Lys Arg Lys Thr Val Thr Ala Met Asp Val
1               5                   10                  15

Val Tyr Ala Leu Lys Arg Gln Gly
            20

<210> SEQ ID NO 290
<211> LENGTH: 15
<212> TYPE: PRT
<213> ORGANISM: Homo sapiens

<400> SEQUENCE: 290

Glu His Ala Lys Arg Lys Thr Val Thr Ala Met Asp Val Val Tyr
1               5                   10                  15

<210> SEQ ID NO 291
<211> LENGTH: 15
<212> TYPE: PRT
<213> ORGANISM: Homo sapiens

<400> SEQUENCE: 291

Ala Lys Arg Lys Thr Val Thr Ala Met Asp Val Val Tyr Ala Leu
1               5                   10                  15

<210> SEQ ID NO 292
<211> LENGTH: 15
<212> TYPE: PRT
<213> ORGANISM: Homo sapiens

<400> SEQUENCE: 292

His Ala Lys Arg Lys Thr Val Thr Ala Met Asp Val Val Tyr Ala
1               5                   10                  15

<210> SEQ ID NO 293
<211> LENGTH: 15

```
<212> TYPE: PRT
<213> ORGANISM: Homo sapiens

<400> SEQUENCE: 293

Arg Lys Thr Val Thr Ala Met Asp Val Val Tyr Ala Leu Lys Arg
1               5                   10                  15

<210> SEQ ID NO 294
<211> LENGTH: 14
<212> TYPE: PRT
<213> ORGANISM: Homo sapiens

<400> SEQUENCE: 294

Thr Val Thr Ala Met Asp Val Val Tyr Ala Leu Lys Arg Gln
1               5                   10

<210> SEQ ID NO 295
<211> LENGTH: 15
<212> TYPE: PRT
<213> ORGANISM: Homo sapiens

<400> SEQUENCE: 295

Pro Lys Lys Gly Ser Lys Lys Ala Val Thr Lys Ala Gln Lys Lys
1               5                   10                  15

<210> SEQ ID NO 296
<211> LENGTH: 15
<212> TYPE: PRT
<213> ORGANISM: Homo sapiens

<400> SEQUENCE: 296

Lys Ala Val Thr Lys Ala Gln Lys Lys Asp Gly Lys Lys Arg Lys
1               5                   10                  15

<210> SEQ ID NO 297
<211> LENGTH: 21
<212> TYPE: PRT
<213> ORGANISM: Homo sapiens

<400> SEQUENCE: 297

Ser Thr Asp His Pro Lys Tyr Ser Asp Met Ile Val Ala Ala Ile Gln
1               5                   10                  15

Ala Glu Lys Asn Arg
            20

<210> SEQ ID NO 298
<211> LENGTH: 15
<212> TYPE: PRT
<213> ORGANISM: Homo sapiens

<400> SEQUENCE: 298

Lys Tyr Ser Asp Met Ile Val Ala Ala Ile Gln Ala Glu Lys Asn
1               5                   10                  15

<210> SEQ ID NO 299
<211> LENGTH: 15
<212> TYPE: PRT
<213> ORGANISM: Homo sapiens

<400> SEQUENCE: 299

Ser Gln Glu Tyr Ser Gly Ser Val Ala Asn Glu Ala Asn Val Tyr
1               5                   10                  15

<210> SEQ ID NO 300
```

```
<211> LENGTH: 15
<212> TYPE: PRT
<213> ORGANISM: Homo sapiens

<400> SEQUENCE: 300

Ser His Ser Leu Pro Tyr Glu Ser Ser Ile Ser Thr Ala Leu Glu
1               5                   10                  15

<210> SEQ ID NO 301
<211> LENGTH: 15
<212> TYPE: PRT
<213> ORGANISM: Homo sapiens

<400> SEQUENCE: 301

Thr Gly Ala Tyr Ser Asn Ala Ser Ser Thr Glu Ser Ala Ser Tyr
1               5                   10                  15

<210> SEQ ID NO 302
<211> LENGTH: 15
<212> TYPE: PRT
<213> ORGANISM: Homo sapiens

<400> SEQUENCE: 302

Ser Phe Leu Ser Gln Glu Tyr Ser Gly Ser Val Ala Asn Glu Ala
1               5                   10                  15

<210> SEQ ID NO 303
<211> LENGTH: 20
<212> TYPE: PRT
<213> ORGANISM: Homo sapiens

<400> SEQUENCE: 303

Lys Thr Thr Lys Gln Ser Phe Asp Leu Ser Val Lys Ala Gln Tyr Lys
1               5                   10                  15

Lys Asn Lys His
            20

<210> SEQ ID NO 304
<211> LENGTH: 15
<212> TYPE: PRT
<213> ORGANISM: Homo sapiens

<400> SEQUENCE: 304

Lys Thr Thr Lys Gln Ser Phe Asp Leu Ser Val Lys Ala Gln Tyr
1               5                   10                  15

<210> SEQ ID NO 305
<211> LENGTH: 15
<212> TYPE: PRT
<213> ORGANISM: Homo sapiens

<400> SEQUENCE: 305

Thr Thr Lys Gln Ser Phe Asp Leu Ser Val Lys Ala Gln Tyr Lys
1               5                   10                  15

<210> SEQ ID NO 306
<211> LENGTH: 15
<212> TYPE: PRT
<213> ORGANISM: Homo sapiens

<400> SEQUENCE: 306

Gly Ala Leu Val Pro Gly Val Ala Asp Ala Ala Ala Ala Tyr
1               5                   10                  15
```

```
<210> SEQ ID NO 307
<211> LENGTH: 15
<212> TYPE: PRT
<213> ORGANISM: Homo sapiens

<400> SEQUENCE: 307

Ala Ala Gln Phe Gly Leu Val Gly Ala Ala Gly Leu Gly Gly Leu
1               5                   10                  15

<210> SEQ ID NO 308
<211> LENGTH: 15
<212> TYPE: PRT
<213> ORGANISM: Homo sapiens

<400> SEQUENCE: 308

Ala Pro Arg Pro Gly Val Leu Leu Leu Leu Ser Ile Leu His
1               5                   10                  15

<210> SEQ ID NO 309
<211> LENGTH: 15
<212> TYPE: PRT
<213> ORGANISM: Homo sapiens

<400> SEQUENCE: 309

Gly Gly Val Ala Asp Ala Ala Ala Tyr Lys Ala Ala Lys Ala
1               5                   10                  15

<210> SEQ ID NO 310
<211> LENGTH: 15
<212> TYPE: PRT
<213> ORGANISM: Homo sapiens

<400> SEQUENCE: 310

Val Leu Leu Leu Leu Leu Ser Ile Leu His Pro Ser Arg Pro Gly
1               5                   10                  15

<210> SEQ ID NO 311
<211> LENGTH: 15
<212> TYPE: PRT
<213> ORGANISM: Homo sapiens

<400> SEQUENCE: 311

Ala Ala Lys Ala Ala Gln Phe Gly Leu Val Gly Ala Ala Gly Leu
1               5                   10                  15

<210> SEQ ID NO 312
<211> LENGTH: 15
<212> TYPE: PRT
<213> ORGANISM: Homo sapiens

<400> SEQUENCE: 312

Val Ala Ala Lys Ala Gln Leu Arg Ala Ala Gly Leu Gly Ala
1               5                   10                  15

<210> SEQ ID NO 313
<211> LENGTH: 15
<212> TYPE: PRT
<213> ORGANISM: Homo sapiens

<400> SEQUENCE: 313

Lys Ser Ala Ala Lys Val Ala Ala Lys Ala Gln Leu Arg Ala Ala
1               5                   10                  15

<210> SEQ ID NO 314
<211> LENGTH: 15
```

```
<212> TYPE: PRT
<213> ORGANISM: Homo sapiens

<400> SEQUENCE: 314

Lys Ala Gln Leu Arg Ala Ala Gly Leu Gly Ala Gly Ile Pro
1               5                   10                  15

<210> SEQ ID NO 315
<211> LENGTH: 15
<212> TYPE: PRT
<213> ORGANISM: Homo sapiens

<400> SEQUENCE: 315

Val Pro Gly Ala Leu Ala Ala Lys Ala Ala Lys Tyr Gly Ala
1               5                   10                  15

<210> SEQ ID NO 316
<211> LENGTH: 15
<212> TYPE: PRT
<213> ORGANISM: Homo sapiens

<400> SEQUENCE: 316

Arg Pro Thr Met Asp Gly Asp Pro Asp Thr Pro Lys Pro Val Ser
1               5                   10                  15

<210> SEQ ID NO 317
<211> LENGTH: 15
<212> TYPE: PRT
<213> ORGANISM: Homo sapiens

<400> SEQUENCE: 317

Ser Tyr Lys Glu Ala Val Leu Arg Ala Ile Asp Gly Ile Asn Gln
1               5                   10                  15

<210> SEQ ID NO 318
<211> LENGTH: 15
<212> TYPE: PRT
<213> ORGANISM: Homo sapiens

<400> SEQUENCE: 318

Asn Gln Arg Ser Ser Asp Ala Asn Leu Tyr Arg Leu Leu Asp Leu
1               5                   10                  15

<210> SEQ ID NO 319
<211> LENGTH: 15
<212> TYPE: PRT
<213> ORGANISM: Homo sapiens

<400> SEQUENCE: 319

Lys Arg Ile Val Gln Arg Ile Lys Asp Phe Leu Arg Asn Leu Val
1               5                   10                  15

<210> SEQ ID NO 320
<211> LENGTH: 15
<212> TYPE: PRT
<213> ORGANISM: Homo sapiens

<400> SEQUENCE: 320

Glu Phe Lys Arg Ile Val Gln Arg Ile Lys Asp Phe Leu Arg Asn
1               5                   10                  15

<210> SEQ ID NO 321
<211> LENGTH: 15
<212> TYPE: PRT
<213> ORGANISM: Homo sapiens
```

<400> SEQUENCE: 321

Arg Ile Val Gln Arg Ile Lys Asp Phe Leu Arg Asn Leu Val Pro
1               5                   10                  15

<210> SEQ ID NO 322
<211> LENGTH: 15
<212> TYPE: PRT
<213> ORGANISM: Homo sapiens

<400> SEQUENCE: 322

Arg Phe Ala Leu Leu Gly Asp Phe Phe Arg Lys Ser Lys Glu Lys
1               5                   10                  15

<210> SEQ ID NO 323
<211> LENGTH: 15
<212> TYPE: PRT
<213> ORGANISM: Homo sapiens

<400> SEQUENCE: 323

Gln Arg Ile Lys Asp Phe Leu Arg Asn Leu Val Pro Arg Thr Glu
1               5                   10                  15

<210> SEQ ID NO 324
<211> LENGTH: 15
<212> TYPE: PRT
<213> ORGANISM: Homo sapiens

<400> SEQUENCE: 324

Asp Gly Arg Tyr Val Leu Asn Gly His Trp Val Val Ser Pro Pro
1               5                   10                  15

<210> SEQ ID NO 325
<211> LENGTH: 15
<212> TYPE: PRT
<213> ORGANISM: Homo sapiens

<400> SEQUENCE: 325

Thr His Val Val Tyr Thr Arg Asp Thr Gly Pro Gln Glu Thr Leu
1               5                   10                  15

<210> SEQ ID NO 326
<211> LENGTH: 15
<212> TYPE: PRT
<213> ORGANISM: Homo sapiens

<400> SEQUENCE: 326

Arg Leu Leu His Tyr Cys Gly Ser Asp Phe Val Phe Gln Ala Arg
1               5                   10                  15

<210> SEQ ID NO 327
<211> LENGTH: 15
<212> TYPE: PRT
<213> ORGANISM: Homo sapiens

<400> SEQUENCE: 327

His Asp Leu Leu Leu Gln Val Leu Leu Gln Glu Pro Asn Pro Gly
1               5                   10                  15

<210> SEQ ID NO 328
<211> LENGTH: 15
<212> TYPE: PRT
<213> ORGANISM: Homo sapiens

<400> SEQUENCE: 328

Glu Thr Arg Tyr Glu Val Arg Ile Gln Leu Val Tyr Lys Asn Arg
1               5                   10                  15

<210> SEQ ID NO 329
<211> LENGTH: 15
<212> TYPE: PRT
<213> ORGANISM: Homo sapiens

<400> SEQUENCE: 329

His Arg Asp Tyr Leu Met Ala Val Gln Arg Leu Val Ser Pro Asp
1               5                   10                  15

<210> SEQ ID NO 330
<211> LENGTH: 15
<212> TYPE: PRT
<213> ORGANISM: Homo sapiens

<400> SEQUENCE: 330

Glu Gly His Ala Phe Tyr His Ser Phe Gly Arg Val Leu Asp Gly
1               5                   10                  15

<210> SEQ ID NO 331
<211> LENGTH: 15
<212> TYPE: PRT
<213> ORGANISM: Homo sapiens

<400> SEQUENCE: 331

Arg Asn His Leu Ala Leu Met Gly Gly Asp Gly Arg Tyr Val Leu
1               5                   10                  15

<210> SEQ ID NO 332
<211> LENGTH: 15
<212> TYPE: PRT
<213> ORGANISM: Homo sapiens

<400> SEQUENCE: 332

Asn Pro Gly Ile Glu Phe Glu Phe Trp Leu Pro Arg Glu Arg Tyr
1               5                   10                  15

<210> SEQ ID NO 333
<211> LENGTH: 15
<212> TYPE: PRT
<213> ORGANISM: Homo sapiens

<400> SEQUENCE: 333

Val Gln Arg Val Phe Arg Asp Ala Gly Ala Phe Ala Gly Tyr Trp
1               5                   10                  15

<210> SEQ ID NO 334
<211> LENGTH: 15
<212> TYPE: PRT
<213> ORGANISM: Homo sapiens

<400> SEQUENCE: 334

Gln Leu Val Tyr Lys Asn Arg Ser Pro Leu Arg Ala Arg Glu Tyr
1               5                   10                  15

<210> SEQ ID NO 335
<211> LENGTH: 15
<212> TYPE: PRT
<213> ORGANISM: Homo sapiens

<400> SEQUENCE: 335

Arg Arg Phe Glu Tyr Asp Asp Pro Arg Phe Leu Arg Leu Leu Asp

```
                 1               5                  10                  15

<210> SEQ ID NO 336
<211> LENGTH: 15
<212> TYPE: PRT
<213> ORGANISM: Homo sapiens

<400> SEQUENCE: 336

Thr Pro Val Val Val Leu Asn Gly Leu Ala Ala Val Arg Glu Ala
1               5                  10                  15

<210> SEQ ID NO 337
<211> LENGTH: 15
<212> TYPE: PRT
<213> ORGANISM: Homo sapiens

<400> SEQUENCE: 337

Glu Asn Leu Arg Ile Val Val Ala Asp Leu Phe Ser Ala Gly Met
1               5                  10                  15

<210> SEQ ID NO 338
<211> LENGTH: 20
<212> TYPE: PRT
<213> ORGANISM: Homo sapiens

<400> SEQUENCE: 338

Thr Leu Ala Trp Gly Leu Leu Leu Met Ile Leu His Pro Asp Val Gln
1               5                  10                  15

Arg Arg Val Gln
            20

<210> SEQ ID NO 339
<211> LENGTH: 20
<212> TYPE: PRT
<213> ORGANISM: Homo sapiens

<400> SEQUENCE: 339

Thr Thr Leu Ile Thr Asn Leu Ser Ser Val Leu Lys Asp Glu Ala Val
1               5                  10                  15

Trp Glu Lys Pro
            20

<210> SEQ ID NO 340
<211> LENGTH: 15
<212> TYPE: PRT
<213> ORGANISM: Homo sapiens

<400> SEQUENCE: 340

Asp Pro Arg Phe Leu Arg Leu Leu Asp Leu Ala Gln Glu Gly Leu
1               5                  10                  15

<210> SEQ ID NO 341
<211> LENGTH: 15
<212> TYPE: PRT
<213> ORGANISM: Homo sapiens

<400> SEQUENCE: 341

Arg Met Glu Leu Phe Leu Phe Phe Thr Ser Leu Leu Gln His Phe
1               5                  10                  15

<210> SEQ ID NO 342
<211> LENGTH: 15
<212> TYPE: PRT
<213> ORGANISM: Homo sapiens
```

<400> SEQUENCE: 342

Asp Leu Phe Ser Ala Gly Met Val Thr Thr Ser Thr Thr Leu Ala
1               5                   10                  15

<210> SEQ ID NO 343
<211> LENGTH: 15
<212> TYPE: PRT
<213> ORGANISM: Homo sapiens

<400> SEQUENCE: 343

Glu Leu Phe Leu Phe Phe Thr Ser Leu Leu Gln His Phe Ser Phe
1               5                   10                  15

<210> SEQ ID NO 344
<211> LENGTH: 15
<212> TYPE: PRT
<213> ORGANISM: Homo sapiens

<400> SEQUENCE: 344

Asp Gln Leu Arg Arg Arg Phe Gly Asp Val Phe Ser Leu Gln Leu
1               5                   10                  15

<210> SEQ ID NO 345
<211> LENGTH: 15
<212> TYPE: PRT
<213> ORGANISM: Homo sapiens

<400> SEQUENCE: 345

Glu Gln Arg Arg Phe Ser Val Ser Thr Leu Arg Asn Leu Gly Leu
1               5                   10                  15

<210> SEQ ID NO 346
<211> LENGTH: 20
<212> TYPE: PRT
<213> ORGANISM: Homo sapiens

<400> SEQUENCE: 346

Arg Arg Phe Glu Tyr Asp Asp Pro Arg Phe Leu Arg Leu Leu Asp Leu
1               5                   10                  15

Ala Gln Glu Gly
            20

<210> SEQ ID NO 347
<211> LENGTH: 20
<212> TYPE: PRT
<213> ORGANISM: Homo sapiens

<400> SEQUENCE: 347

Ala Gly Met Val Thr Thr Ser Thr Thr Leu Ala Trp Gly Leu Leu Leu
1               5                   10                  15

Met Ile Leu His
            20

<210> SEQ ID NO 348
<211> LENGTH: 15
<212> TYPE: PRT
<213> ORGANISM: Homo sapiens

<400> SEQUENCE: 348

Gln Arg Arg Phe Ser Val Ser Thr Leu Arg Asn Leu Gly Leu Gly
1               5                   10                  15

```
<210> SEQ ID NO 349
<211> LENGTH: 15
<212> TYPE: PRT
<213> ORGANISM: Homo sapiens

<400> SEQUENCE: 349

Glu Ser Gly Phe Leu Arg Glu Val Leu Asn Ala Val Pro Val Leu
1               5                   10                  15

<210> SEQ ID NO 350
<211> LENGTH: 15
<212> TYPE: PRT
<213> ORGANISM: Homo sapiens

<400> SEQUENCE: 350

Gly Lys Val Leu Arg Phe Gln Lys Ala Phe Leu Thr Gln Leu Asp
1               5                   10                  15

<210> SEQ ID NO 351
<211> LENGTH: 15
<212> TYPE: PRT
<213> ORGANISM: Homo sapiens

<400> SEQUENCE: 351

Asp Ile Glu Val Gln Gly Phe Arg Ile Pro Lys Gly Thr Thr Leu
1               5                   10                  15

<210> SEQ ID NO 352
<211> LENGTH: 15
<212> TYPE: PRT
<213> ORGANISM: Homo sapiens

<400> SEQUENCE: 352

Lys Pro Glu Ala Phe Leu Pro Phe Ser Ala Gly Arg Arg Ala Cys
1               5                   10                  15

<210> SEQ ID NO 353
<211> LENGTH: 15
<212> TYPE: PRT
<213> ORGANISM: Homo sapiens

<400> SEQUENCE: 353

Tyr Lys Lys Leu Leu Lys Glu Arg Lys Glu Met Phe Ser Tyr Leu
1               5                   10                  15

<210> SEQ ID NO 354
<211> LENGTH: 15
<212> TYPE: PRT
<213> ORGANISM: Homo sapiens

<400> SEQUENCE: 354

Asp Glu Leu Arg Thr Asp Leu Lys Ala Val Glu Ala Lys Val Gln
1               5                   10                  15

<210> SEQ ID NO 355
<211> LENGTH: 15
<212> TYPE: PRT
<213> ORGANISM: Homo sapiens

<400> SEQUENCE: 355

Asn Lys Ile Thr Asn Ser Leu Val Leu Asp Ile Ile Lys Leu Ala
1               5                   10                  15

<210> SEQ ID NO 356
<211> LENGTH: 14
```

```
<212> TYPE: PRT
<213> ORGANISM: Homo sapiens

<400> SEQUENCE: 356

Asn Arg Leu Asp Arg Cys Leu Lys Ala Val Arg Lys Glu Arg
1               5                   10

<210> SEQ ID NO 357
<211> LENGTH: 12
<212> TYPE: PRT
<213> ORGANISM: Homo sapiens

<400> SEQUENCE: 357

Leu Ile Gln Gln Gly Ala Arg Val Gly Arg Ile Asp
1               5                   10

<210> SEQ ID NO 358
<211> LENGTH: 15
<212> TYPE: PRT
<213> ORGANISM: Homo sapiens

<400> SEQUENCE: 358

Ser Pro Ser Leu Asp Val Leu Ile Thr Leu Leu Ser Leu Gly Ser
1               5                   10                  15

<210> SEQ ID NO 359
<211> LENGTH: 15
<212> TYPE: PRT
<213> ORGANISM: Homo sapiens

<400> SEQUENCE: 359

Asp Gln Lys Ser Cys Phe Lys Ser Met Ile Thr Ala Gly Phe Glu
1               5                   10                  15

<210> SEQ ID NO 360
<211> LENGTH: 15
<212> TYPE: PRT
<213> ORGANISM: Homo sapiens

<400> SEQUENCE: 360

Tyr Thr Phe Arg Gly Phe Met Ser His Thr Asn Asn Tyr Pro Cys
1               5                   10                  15

<210> SEQ ID NO 361
<211> LENGTH: 15
<212> TYPE: PRT
<213> ORGANISM: Homo sapiens

<400> SEQUENCE: 361

Tyr Asn Glu Arg Leu Leu His Thr Pro His Asn Pro Ile Ser Leu
1               5                   10                  15

<210> SEQ ID NO 362
<211> LENGTH: 15
<212> TYPE: PRT
<213> ORGANISM: Homo sapiens

<400> SEQUENCE: 362

Asp Cys Ile Leu Cys Ile His Ser Thr Thr Ser Cys Phe Ala Pro
1               5                   10                  15

<210> SEQ ID NO 363
<211> LENGTH: 15
<212> TYPE: PRT
<213> ORGANISM: Homo sapiens
```

<400> SEQUENCE: 363

Ser Ser Leu Leu Asn Lys Ile Thr Asn Ser Leu Val Leu Asp Ile
1               5                   10                  15

<210> SEQ ID NO 364
<211> LENGTH: 15
<212> TYPE: PRT
<213> ORGANISM: Homo sapiens

<400> SEQUENCE: 364

Gly Ser Ser Leu Leu Asn Lys Ile Thr Asn Ser Leu Val Leu Asp
1               5                   10                  15

<210> SEQ ID NO 365
<211> LENGTH: 15
<212> TYPE: PRT
<213> ORGANISM: Homo sapiens

<400> SEQUENCE: 365

Asn Asp Ser Phe Ile Gln Glu Ile Ser Lys Met Tyr Pro Gly Arg
1               5                   10                  15

<210> SEQ ID NO 366
<211> LENGTH: 15
<212> TYPE: PRT
<213> ORGANISM: Homo sapiens

<400> SEQUENCE: 366

Lys Glu Met Phe Ser Tyr Leu Ser Asn Gln Ile Lys Lys Leu Ser
1               5                   10                  15

<210> SEQ ID NO 367
<211> LENGTH: 15
<212> TYPE: PRT
<213> ORGANISM: Homo sapiens

<400> SEQUENCE: 367

Ser Thr Leu Glu Leu Phe Leu His Glu Leu Ala Ile Met Asp Ser
1               5                   10                  15

<210> SEQ ID NO 368
<211> LENGTH: 15
<212> TYPE: PRT
<213> ORGANISM: Homo sapiens

<400> SEQUENCE: 368

Asn Ser Leu Val Leu Asp Ile Ile Lys Leu Ala Gly Val His Thr
1               5                   10                  15

<210> SEQ ID NO 369
<211> LENGTH: 15
<212> TYPE: PRT
<213> ORGANISM: Homo sapiens

<400> SEQUENCE: 369

Ser Lys Cys Met His Leu Ile Gln Gln Gly Ala Arg Val Gly Arg
1               5                   10                  15

<210> SEQ ID NO 370
<211> LENGTH: 15
<212> TYPE: PRT
<213> ORGANISM: Homo sapiens

<400> SEQUENCE: 370

```
Arg Ser His Glu His Leu Ile Arg Leu Leu Glu Lys Gly Lys
1               5                   10                  15

<210> SEQ ID NO 371
<211> LENGTH: 15
<212> TYPE: PRT
<213> ORGANISM: Homo sapiens

<400> SEQUENCE: 371

Arg Arg His Tyr Arg Phe Ile His Gly Ile Gly Arg Ser Gly Asp
1               5                   10                  15

<210> SEQ ID NO 372
<211> LENGTH: 15
<212> TYPE: PRT
<213> ORGANISM: Homo sapiens

<400> SEQUENCE: 372

Ser Asn Gly Tyr Lys Lys Leu Leu Lys Glu Arg Lys Glu Met Phe
1               5                   10                  15

<210> SEQ ID NO 373
<211> LENGTH: 16
<212> TYPE: PRT
<213> ORGANISM: Homo sapiens

<400> SEQUENCE: 373

Gln Phe Phe Met Ser Asp Lys Pro Leu His Leu Ala Val Ser Leu Asn
1               5                   10                  15

<210> SEQ ID NO 374
<211> LENGTH: 15
<212> TYPE: PRT
<213> ORGANISM: Homo sapiens

<400> SEQUENCE: 374

Asp Val Ile Gly Leu Thr Phe Arg Arg Asp Leu Tyr Phe Ser Arg
1               5                   10                  15

<210> SEQ ID NO 375
<211> LENGTH: 15
<212> TYPE: PRT
<213> ORGANISM: Homo sapiens

<400> SEQUENCE: 375

Asn Val Val Leu Tyr Ser Ser Asp Tyr Tyr Val Lys Pro Val Ala
1               5                   10                  15

<210> SEQ ID NO 376
<211> LENGTH: 15
<212> TYPE: PRT
<213> ORGANISM: Homo sapiens

<400> SEQUENCE: 376

Ser Ser Val Arg Leu Leu Ile Arg Lys Val Gln His Ala Pro Leu
1               5                   10                  15

<210> SEQ ID NO 377
<211> LENGTH: 15
<212> TYPE: PRT
<213> ORGANISM: Homo sapiens

<400> SEQUENCE: 377

Glu Val Pro Phe Arg Leu Met His Pro Gln Pro Glu Asp Pro Ala
```

-continued

```
1               5                   10                  15

<210> SEQ ID NO 378
<211> LENGTH: 15
<212> TYPE: PRT
<213> ORGANISM: Homo sapiens

<400> SEQUENCE: 378

Lys Lys Ile Lys Ala Phe Val Glu Gln Val Ala Asn Val Val Leu
1               5                   10                  15

<210> SEQ ID NO 379
<211> LENGTH: 15
<212> TYPE: PRT
<213> ORGANISM: Homo sapiens

<400> SEQUENCE: 379

Ser Thr Pro Thr Lys Leu Gln Glu Ser Leu Leu Lys Lys Leu Gly
1               5                   10                  15

<210> SEQ ID NO 380
<211> LENGTH: 15
<212> TYPE: PRT
<213> ORGANISM: Homo sapiens

<400> SEQUENCE: 380

Lys Lys Val Tyr Val Thr Leu Thr Cys Ala Phe Arg Tyr Gly Gln
1               5                   10                  15

<210> SEQ ID NO 381
<211> LENGTH: 15
<212> TYPE: PRT
<213> ORGANISM: Homo sapiens

<400> SEQUENCE: 381

Lys Thr Leu Thr Leu Leu Pro Leu Leu Ala Asn Asn Arg Glu Arg
1               5                   10                  15

<210> SEQ ID NO 382
<211> LENGTH: 16
<212> TYPE: PRT
<213> ORGANISM: Homo sapiens

<400> SEQUENCE: 382

Asn Arg Glu Arg Arg Gly Ile Ala Leu Asp Gly Lys Ile Lys His Glu
1               5                   10                  15

<210> SEQ ID NO 383
<211> LENGTH: 15
<212> TYPE: PRT
<213> ORGANISM: Homo sapiens

<400> SEQUENCE: 383

Glu Ala Ala Trp Gln Phe Phe Met Ser Asp Lys Pro Leu His Leu
1               5                   10                  15

<210> SEQ ID NO 384
<211> LENGTH: 15
<212> TYPE: PRT
<213> ORGANISM: Homo sapiens

<400> SEQUENCE: 384

Gln Phe Phe Met Ser Asp Lys Pro Leu His Leu Ala Val Ser Leu
1               5                   10                  15
```

<210> SEQ ID NO 385
<211> LENGTH: 15
<212> TYPE: PRT
<213> ORGANISM: Homo sapiens

<400> SEQUENCE: 385

Thr Phe Ile Gln Phe Lys Lys Asp Leu Lys Glu Ser Met Lys Cys
1               5                   10                  15

<210> SEQ ID NO 386
<211> LENGTH: 15
<212> TYPE: PRT
<213> ORGANISM: Homo sapiens

<400> SEQUENCE: 386

Asp Thr Gly Ala Leu Asp Val Ile Arg Asn Phe Thr Leu Asp Met
1               5                   10                  15

<210> SEQ ID NO 387
<211> LENGTH: 15
<212> TYPE: PRT
<213> ORGANISM: Homo sapiens

<400> SEQUENCE: 387

Glu Val Ile His Leu Ile Glu Glu His Arg Leu Val Arg Glu His
1               5                   10                  15

<210> SEQ ID NO 388
<211> LENGTH: 15
<212> TYPE: PRT
<213> ORGANISM: Homo sapiens

<400> SEQUENCE: 388

Arg Glu Tyr Arg Lys Lys Met Asp Ile Pro Ala Lys Leu Ile Val
1               5                   10                  15

<210> SEQ ID NO 389
<211> LENGTH: 15
<212> TYPE: PRT
<213> ORGANISM: Homo sapiens

<400> SEQUENCE: 389

Glu Glu Ile Leu Lys Ala Leu Asp Ala Ala Phe Tyr Lys Thr Phe
1               5                   10                  15

<210> SEQ ID NO 390
<211> LENGTH: 15
<212> TYPE: PRT
<213> ORGANISM: Homo sapiens

<400> SEQUENCE: 390

Lys Arg Phe Leu Leu Ala Val Asp Val Ser Ala Ser Met Asn Gln
1               5                   10                  15

<210> SEQ ID NO 391
<211> LENGTH: 15
<212> TYPE: PRT
<213> ORGANISM: Homo sapiens

<400> SEQUENCE: 391

Thr Asp Met Thr Leu Gln Gln Val Leu Met Ala Met Ser Gln Ile
1               5                   10                  15

<210> SEQ ID NO 392

```
<211> LENGTH: 15
<212> TYPE: PRT
<213> ORGANISM: Homo sapiens

<400> SEQUENCE: 392

Glu Val Trp Lys Ala Leu Leu Gln Glu Met Pro Leu Thr Ala Leu
1               5                   10                  15

<210> SEQ ID NO 393
<211> LENGTH: 15
<212> TYPE: PRT
<213> ORGANISM: Homo sapiens

<400> SEQUENCE: 393

Ser His Lys Asp Leu Leu Arg Leu Ser His Leu Lys Pro Ser Ser
1               5                   10                  15

<210> SEQ ID NO 394
<211> LENGTH: 15
<212> TYPE: PRT
<213> ORGANISM: Homo sapiens

<400> SEQUENCE: 394

Tyr Lys Thr Phe Lys Thr Val Glu Pro Thr Gly Lys Arg Phe Leu
1               5                   10                  15

<210> SEQ ID NO 395
<211> LENGTH: 15
<212> TYPE: PRT
<213> ORGANISM: Homo sapiens

<400> SEQUENCE: 395

Glu Thr Glu Lys Leu Leu Lys Tyr Leu Glu Ala Val Glu Lys Val
1               5                   10                  15

<210> SEQ ID NO 396
<211> LENGTH: 15
<212> TYPE: PRT
<213> ORGANISM: Homo sapiens

<400> SEQUENCE: 396

Arg Ile His Pro Phe His Ile Leu Ile Ala Leu Glu Thr Tyr Lys
1               5                   10                  15

<210> SEQ ID NO 397
<211> LENGTH: 15
<212> TYPE: PRT
<213> ORGANISM: Homo sapiens

<400> SEQUENCE: 397

Glu Lys Asp Ser Tyr Val Val Ala Phe Ser Asp Glu Met Val Pro
1               5                   10                  15

<210> SEQ ID NO 398
<211> LENGTH: 15
<212> TYPE: PRT
<213> ORGANISM: Homo sapiens

<400> SEQUENCE: 398

Thr Pro Ala Asp Val Phe Ile Val Phe Thr Asp Asn Glu Thr Phe
1               5                   10                  15

<210> SEQ ID NO 399
<211> LENGTH: 15
<212> TYPE: PRT
```

<213> ORGANISM: Homo sapiens

<400> SEQUENCE: 399

Gln Lys Leu Gly Leu Glu Asn Ala Glu Ala Leu Ile Arg Leu Ile
1               5                   10                  15

<210> SEQ ID NO 400
<211> LENGTH: 15
<212> TYPE: PRT
<213> ORGANISM: Homo sapiens

<400> SEQUENCE: 400

Lys Leu Leu Lys Lys Ala Arg Ile His Pro Phe His Ile Leu Ile
1               5                   10                  15

<210> SEQ ID NO 401
<211> LENGTH: 15
<212> TYPE: PRT
<213> ORGANISM: Homo sapiens

<400> SEQUENCE: 401

Asp Asp Gln Thr Cys Arg Glu Asp Leu His Ile Leu Phe Ser Asn
1               5                   10                  15

<210> SEQ ID NO 402
<211> LENGTH: 15
<212> TYPE: PRT
<213> ORGANISM: Homo sapiens

<400> SEQUENCE: 402

Thr Asp Glu Tyr Lys Asn Asp Val Lys Asn Arg Ser Val Tyr Ile
1               5                   10                  15

<210> SEQ ID NO 403
<211> LENGTH: 15
<212> TYPE: PRT
<213> ORGANISM: Homo sapiens

<400> SEQUENCE: 403

Ser Ile Phe Val Val Phe Asp Ser Ile Glu Ser Ala Lys Lys Phe
1               5                   10                  15

<210> SEQ ID NO 404
<211> LENGTH: 15
<212> TYPE: PRT
<213> ORGANISM: Homo sapiens

<400> SEQUENCE: 404

Thr Asp Leu Leu Ile Leu Phe Lys Asp Tyr Phe Ala Lys Lys
1               5                   10                  15

<210> SEQ ID NO 405
<211> LENGTH: 15
<212> TYPE: PRT
<213> ORGANISM: Homo sapiens

<400> SEQUENCE: 405

His Gln Ile Glu Tyr Tyr Phe Gly Asp Phe Asn Leu Pro Arg Asp
1               5                   10                  15

<210> SEQ ID NO 406
<211> LENGTH: 15
<212> TYPE: PRT
<213> ORGANISM: Homo sapiens

```
<400> SEQUENCE: 406

Lys Glu Gln Ile Lys Leu Asp Glu Gly Trp Val Pro Leu Glu Ile
1               5                   10                  15

<210> SEQ ID NO 407
<211> LENGTH: 15
<212> TYPE: PRT
<213> ORGANISM: Homo sapiens

<400> SEQUENCE: 407

Asp Lys Gly Gln Val Leu Asn Ile Gln Met Arg Arg Thr Leu His
1               5                   10                  15

<210> SEQ ID NO 408
<211> LENGTH: 15
<212> TYPE: PRT
<213> ORGANISM: Homo sapiens

<400> SEQUENCE: 408

Glu Ile Met Ile Lys Phe Asn Arg Leu Asn Arg Leu Thr Thr Asp
1               5                   10                  15

<210> SEQ ID NO 409
<211> LENGTH: 15
<212> TYPE: PRT
<213> ORGANISM: Homo sapiens

<400> SEQUENCE: 409

Arg Asp Lys Phe Leu Lys Glu Gln Ile Lys Leu Asp Glu Gly Trp
1               5                   10                  15

<210> SEQ ID NO 410
<211> LENGTH: 15
<212> TYPE: PRT
<213> ORGANISM: Homo sapiens

<400> SEQUENCE: 410

Ser Glu Asp Lys Thr Lys Ile Arg Arg Ser Pro Ser Lys Pro Leu
1               5                   10                  15

<210> SEQ ID NO 411
<211> LENGTH: 15
<212> TYPE: PRT
<213> ORGANISM: Homo sapiens

<400> SEQUENCE: 411

Gln Val Leu Asn Ile Gln Met Arg Arg Thr Leu His Lys Ala Phe
1               5                   10                  15

<210> SEQ ID NO 412
<211> LENGTH: 15
<212> TYPE: PRT
<213> ORGANISM: Homo sapiens

<400> SEQUENCE: 412

Arg Asn Lys Glu Val Thr Trp Glu Val Leu Glu Gly Glu Val Glu
1               5                   10                  15

<210> SEQ ID NO 413
<211> LENGTH: 15
<212> TYPE: PRT
<213> ORGANISM: Homo sapiens

<400> SEQUENCE: 413
```

```
Asn Arg Leu Thr Thr Asp Phe Asn Val Ile Val Glu Ala Leu Ser
1               5                   10                  15
```

<210> SEQ ID NO 414
<211> LENGTH: 15
<212> TYPE: PRT
<213> ORGANISM: Homo sapiens

<400> SEQUENCE: 414

```
Lys Gly Ser Ile Phe Val Val Phe Asp Ser Ile Glu Ser Ala Lys
1               5                   10                  15
```

<210> SEQ ID NO 415
<211> LENGTH: 15
<212> TYPE: PRT
<213> ORGANISM: Homo sapiens

<400> SEQUENCE: 415

```
Lys Thr Lys Ile Arg Arg Ser Pro Ser Lys Pro Leu Pro Glu Val
1               5                   10                  15
```

<210> SEQ ID NO 416
<211> LENGTH: 15
<212> TYPE: PRT
<213> ORGANISM: Homo sapiens

<400> SEQUENCE: 416

```
Ile Phe Val Val Phe Asp Ser Ile Glu Ser Ala Lys Lys Phe Val
1               5                   10                  15
```

<210> SEQ ID NO 417
<211> LENGTH: 15
<212> TYPE: PRT
<213> ORGANISM: Homo sapiens

<400> SEQUENCE: 417

```
Lys Glu Arg Ile Ala Asn Phe Lys Ile Glu Pro Pro Gly Leu Phe
1               5                   10                  15
```

<210> SEQ ID NO 418
<211> LENGTH: 15
<212> TYPE: PRT
<213> ORGANISM: Homo sapiens

<400> SEQUENCE: 418

```
Gln Gly Ser Ile Lys Tyr Ile Met Leu Asn Pro Ser Ser Arg Ile
1               5                   10                  15
```

<210> SEQ ID NO 419
<211> LENGTH: 15
<212> TYPE: PRT
<213> ORGANISM: Homo sapiens

<400> SEQUENCE: 419

```
Gln Arg Glu Lys Phe Ala Trp Ala Ile Asp Met Ala Asp Glu Asp
1               5                   10                  15
```

<210> SEQ ID NO 420
<211> LENGTH: 15
<212> TYPE: PRT
<213> ORGANISM: Homo sapiens

<400> SEQUENCE: 420

```
Ile Gln Gly Ser Ile Lys Tyr Ile Met Leu Asn Pro Ser Ser Arg
1               5                   10                  15
```

```
<210> SEQ ID NO 421
<211> LENGTH: 15
<212> TYPE: PRT
<213> ORGANISM: Homo sapiens

<400> SEQUENCE: 421

Tyr Asn Ala Ser Ile Thr Leu Gln Gln Leu Lys Glu Leu Thr
1               5                   10                  15

<210> SEQ ID NO 422
<211> LENGTH: 15
<212> TYPE: PRT
<213> ORGANISM: Homo sapiens

<400> SEQUENCE: 422

Glu Gln Leu Met Lys Leu Glu Val Gln Ala Thr Asp Arg Glu Glu
1               5                   10                  15

<210> SEQ ID NO 423
<211> LENGTH: 15
<212> TYPE: PRT
<213> ORGANISM: Homo sapiens

<400> SEQUENCE: 423

Ser Gln Tyr Phe Lys Ala Gln Thr Glu Ala Arg Lys Gln Met Ser
1               5                   10                  15

<210> SEQ ID NO 424
<211> LENGTH: 15
<212> TYPE: PRT
<213> ORGANISM: Homo sapiens

<400> SEQUENCE: 424

Tyr Ile Met Leu Asn Pro Ser Ser Arg Ile Lys Gly Glu Lys Asp
1               5                   10                  15

<210> SEQ ID NO 425
<211> LENGTH: 15
<212> TYPE: PRT
<213> ORGANISM: Homo sapiens

<400> SEQUENCE: 425

Lys Ile Leu Ser Tyr Asn Arg Ala Asn Arg Ala Val Ala Ile Leu
1               5                   10                  15

<210> SEQ ID NO 426
<211> LENGTH: 15
<212> TYPE: PRT
<213> ORGANISM: Homo sapiens

<400> SEQUENCE: 426

Lys Leu Ile Glu Asp Glu Phe Ile Ile Asp Glu Ser Asp Gln Ser
1               5                   10                  15

<210> SEQ ID NO 427
<211> LENGTH: 15
<212> TYPE: PRT
<213> ORGANISM: Homo sapiens

<400> SEQUENCE: 427

Lys Val Tyr Lys Thr Leu Asp Thr Pro Phe Phe Ser Thr Gly Lys
1               5                   10                  15
```

```
<210> SEQ ID NO 428
<211> LENGTH: 15
<212> TYPE: PRT
<213> ORGANISM: Homo sapiens

<400> SEQUENCE: 428

Gln Asp Ile Leu Val Phe Tyr Val Asn Phe Gly Asp Leu Leu Cys
1               5                   10                  15

<210> SEQ ID NO 429
<211> LENGTH: 15
<212> TYPE: PRT
<213> ORGANISM: Homo sapiens

<400> SEQUENCE: 429

Lys Val Met Leu Lys Lys Ile Glu Ile Asp Asn Lys Val Ser Asp
1               5                   10                  15

<210> SEQ ID NO 430
<211> LENGTH: 15
<212> TYPE: PRT
<213> ORGANISM: Homo sapiens

<400> SEQUENCE: 430

Glu Asp Asn Ile Met Thr Ala Gln Asn Val Pro Leu Lys Pro Gln
1               5                   10                  15

<210> SEQ ID NO 431
<211> LENGTH: 15
<212> TYPE: PRT
<213> ORGANISM: Homo sapiens

<400> SEQUENCE: 431

Thr Arg Glu Ile Ile Leu Met Asp Leu Val Arg Pro Gln Asp Thr
1               5                   10                  15

<210> SEQ ID NO 432
<211> LENGTH: 15
<212> TYPE: PRT
<213> ORGANISM: Homo sapiens

<400> SEQUENCE: 432

Thr Ser Val Ser Gln Asn Val Ile Pro Ser Ser Ala Gln Lys Arg
1               5                   10                  15

<210> SEQ ID NO 433
<211> LENGTH: 15
<212> TYPE: PRT
<213> ORGANISM: Homo sapiens

<400> SEQUENCE: 433

Arg Ile Arg Asp Ser Glu Tyr Glu Ile Gln Arg Gln Ala Lys Lys
1               5                   10                  15

<210> SEQ ID NO 434
<211> LENGTH: 15
<212> TYPE: PRT
<213> ORGANISM: Homo sapiens

<400> SEQUENCE: 434

Thr Tyr Gln Phe Phe Val Lys His Gly Glu Leu Lys Val Tyr Lys
1               5                   10                  15

<210> SEQ ID NO 435
<211> LENGTH: 15
```

```
<212> TYPE: PRT
<213> ORGANISM: Homo sapiens

<400> SEQUENCE: 435

Asp Glu Glu Phe Tyr Leu Ser Val Gly Ser Pro Ser Val Leu Leu
1               5                   10                  15

<210> SEQ ID NO 436
<211> LENGTH: 15
<212> TYPE: PRT
<213> ORGANISM: Homo sapiens

<400> SEQUENCE: 436

Arg Glu Ile Ile Leu Met Asp Leu Val Arg Pro Gln Asp Thr Tyr
1               5                   10                  15

<210> SEQ ID NO 437
<211> LENGTH: 15
<212> TYPE: PRT
<213> ORGANISM: Homo sapiens

<400> SEQUENCE: 437

Tyr Gln Phe Phe Val Lys His Gly Glu Leu Lys Val Tyr Lys Thr
1               5                   10                  15

<210> SEQ ID NO 438
<211> LENGTH: 15
<212> TYPE: PRT
<213> ORGANISM: Homo sapiens

<400> SEQUENCE: 438

His Asp Gly Tyr Ser Leu Asp Gly Pro Glu Glu Ile Glu Cys Thr
1               5                   10                  15

<210> SEQ ID NO 439
<211> LENGTH: 15
<212> TYPE: PRT
<213> ORGANISM: Homo sapiens

<400> SEQUENCE: 439

Lys Cys Ser Tyr Thr Glu Asp Ala Gln Cys Ile Asp Gly Thr Ile
1               5                   10                  15

<210> SEQ ID NO 440
<211> LENGTH: 15
<212> TYPE: PRT
<213> ORGANISM: Homo sapiens

<400> SEQUENCE: 440

Gly Tyr Ser Leu Asp Gly Pro Glu Glu Ile Glu Cys Thr Lys Leu
1               5                   10                  15

<210> SEQ ID NO 441
<211> LENGTH: 15
<212> TYPE: PRT
<213> ORGANISM: Homo sapiens

<400> SEQUENCE: 441

Lys Val Ser Phe Phe Cys Lys Asn Lys Glu Lys Cys Ser Tyr Tyr
1               5                   10                  15

<210> SEQ ID NO 442
<211> LENGTH: 15
<212> TYPE: PRT
<213> ORGANISM: Homo sapiens
```

<400> SEQUENCE: 442

Asp Leu Pro Phe Ser Thr Val Val Pro Leu Lys Thr Phe Tyr Glu
1               5                   10                  15

<210> SEQ ID NO 443
<211> LENGTH: 15
<212> TYPE: PRT
<213> ORGANISM: Homo sapiens

<400> SEQUENCE: 443

Glu Cys Leu Pro Gln His Ala Met Phe Gly Asn Asp Thr Ile Thr
1               5                   10                  15

<210> SEQ ID NO 444
<211> LENGTH: 15
<212> TYPE: PRT
<213> ORGANISM: Homo sapiens

<400> SEQUENCE: 444

Cys Lys Val Pro Val Lys Lys Ala Thr Val Val Tyr Gln Gly Glu
1               5                   10                  15

<210> SEQ ID NO 445
<211> LENGTH: 15
<212> TYPE: PRT
<213> ORGANISM: Homo sapiens

<400> SEQUENCE: 445

Tyr Ser Cys Lys Pro Gly Tyr Val Ser Arg Gly Gly Met Arg Lys
1               5                   10                  15

<210> SEQ ID NO 446
<211> LENGTH: 15
<212> TYPE: PRT
<213> ORGANISM: Homo sapiens

<400> SEQUENCE: 446

Lys Lys Ala Thr Val Val Tyr Gln Gly Glu Arg Val Lys Ile Gln
1               5                   10                  15

<210> SEQ ID NO 447
<211> LENGTH: 15
<212> TYPE: PRT
<213> ORGANISM: Homo sapiens

<400> SEQUENCE: 447

Glu Val Pro Lys Cys Phe Lys Glu His Ser Ser Leu Ala Phe Trp
1               5                   10                  15

<210> SEQ ID NO 448
<211> LENGTH: 15
<212> TYPE: PRT
<213> ORGANISM: Homo sapiens

<400> SEQUENCE: 448

Val Pro Lys Cys Phe Lys Glu His Ser Ser Leu Ala Phe Trp Lys
1               5                   10                  15

<210> SEQ ID NO 449
<211> LENGTH: 15
<212> TYPE: PRT
<213> ORGANISM: Homo sapiens

<400> SEQUENCE: 449

Lys Cys Phe Lys Glu His Ser Ser Leu Ala Phe Trp Lys Thr Asp
1               5                   10                  15

<210> SEQ ID NO 450
<211> LENGTH: 15
<212> TYPE: PRT
<213> ORGANISM: Homo sapiens

<400> SEQUENCE: 450

Gln Pro Phe Met Phe Arg Leu Asp Asn Arg Tyr Gln Pro Met Glu
1               5                   10                  15

<210> SEQ ID NO 451
<211> LENGTH: 15
<212> TYPE: PRT
<213> ORGANISM: Homo sapiens

<400> SEQUENCE: 451

Arg Ile Lys Asn Gln Ala Asp Cys Ile Pro Phe Phe Arg Ser Cys
1               5                   10                  15

<210> SEQ ID NO 452
<211> LENGTH: 15
<212> TYPE: PRT
<213> ORGANISM: Homo sapiens

<400> SEQUENCE: 452

Ser Ser Leu Arg Cys Met Val Asp Leu Gly Pro Cys Trp Ala Gly
1               5                   10                  15

<210> SEQ ID NO 453
<211> LENGTH: 15
<212> TYPE: PRT
<213> ORGANISM: Homo sapiens

<400> SEQUENCE: 453

Gln Gln Arg Gln Ala Leu Ala Gln Ile Ser Leu Pro Arg Ile Ile
1               5                   10                  15

<210> SEQ ID NO 454
<211> LENGTH: 15
<212> TYPE: PRT
<213> ORGANISM: Homo sapiens

<400> SEQUENCE: 454

Arg Ser Leu Met Phe Met Gln Trp Gly Gln Leu Leu Asp His Asp
1               5                   10                  15

<210> SEQ ID NO 455
<211> LENGTH: 15
<212> TYPE: PRT
<213> ORGANISM: Homo sapiens

<400> SEQUENCE: 455

Gln Glu Ala Arg Lys Ile Val Gly Ala Met Val Gln Ile Ile Thr
1               5                   10                  15

<210> SEQ ID NO 456
<211> LENGTH: 15
<212> TYPE: PRT
<213> ORGANISM: Homo sapiens

<400> SEQUENCE: 456

Asp Asn Arg Tyr Gln Pro Met Glu Pro Asn Pro Arg Val Pro Leu

```
                1               5                    10                   15
```

<210> SEQ ID NO 457
<211> LENGTH: 15
<212> TYPE: PRT
<213> ORGANISM: Homo sapiens

<400> SEQUENCE: 457

```
Glu Leu Leu Ser Tyr Phe Lys Gln Pro Val Ala Ala Thr Arg Thr
1               5                    10                   15
```

<210> SEQ ID NO 458
<211> LENGTH: 15
<212> TYPE: PRT
<213> ORGANISM: Homo sapiens

<400> SEQUENCE: 458

```
Gln Leu Gly Thr Val Leu Arg Asn Leu Lys Leu Ala Arg Lys Leu
1               5                    10                   15
```

<210> SEQ ID NO 459
<211> LENGTH: 15
<212> TYPE: PRT
<213> ORGANISM: Homo sapiens

<400> SEQUENCE: 459

```
Tyr Leu Pro Leu Val Leu Gly Pro Thr Ala Met Arg Lys Tyr Leu
1               5                    10                   15
```

<210> SEQ ID NO 460
<211> LENGTH: 15
<212> TYPE: PRT
<213> ORGANISM: Homo sapiens

<400> SEQUENCE: 460

```
Leu Gly Thr Val Leu Arg Asn Leu Lys Leu Ala Arg Lys Leu Met
1               5                    10                   15
```

<210> SEQ ID NO 461
<211> LENGTH: 15
<212> TYPE: PRT
<213> ORGANISM: Homo sapiens

<400> SEQUENCE: 461

```
Lys Asn Asn Ile Phe Met Ser Asn Ser Tyr Pro Arg Asp Phe Val
1               5                    10                   15
```

<210> SEQ ID NO 462
<211> LENGTH: 15
<212> TYPE: PRT
<213> ORGANISM: Homo sapiens

<400> SEQUENCE: 462

```
Ser Leu Gln Met Arg Gly Asn Pro Gly Ser His Phe Cys Gly Gly
1               5                    10                   15
```

<210> SEQ ID NO 463
<211> LENGTH: 15
<212> TYPE: PRT
<213> ORGANISM: Homo sapiens

<400> SEQUENCE: 463

```
Thr Arg Val Ala Leu Tyr Val Asp Trp Ile Arg Ser Thr Leu Arg
1               5                    10                   15
```

<210> SEQ ID NO 464
<211> LENGTH: 15
<212> TYPE: PRT
<213> ORGANISM: Homo sapiens

<400> SEQUENCE: 464

Thr Leu Ile His Pro Ser Phe Val Leu Thr Ala Ala His Cys Leu
1               5                   10                  15

<210> SEQ ID NO 465
<211> LENGTH: 15
<212> TYPE: PRT
<213> ORGANISM: Homo sapiens

<400> SEQUENCE: 465

Asn Asp Val Leu Leu Ile Gln Leu Ser Ser Pro Ala Asn Leu Ser
1               5                   10                  15

<210> SEQ ID NO 466
<211> LENGTH: 15
<212> TYPE: PRT
<213> ORGANISM: Homo sapiens

<400> SEQUENCE: 466

Asp Pro Pro Ala Gln Val Leu Gln Glu Leu Asn Val Thr Val Val
1               5                   10                  15

<210> SEQ ID NO 467
<211> LENGTH: 15
<212> TYPE: PRT
<213> ORGANISM: Homo sapiens

<400> SEQUENCE: 467

His Cys Leu Arg Asp Ile Pro Gln Arg Leu Val Asn Val Val Leu
1               5                   10                  15

<210> SEQ ID NO 468
<211> LENGTH: 15
<212> TYPE: PRT
<213> ORGANISM: Homo sapiens

<400> SEQUENCE: 468

Asp Trp Ile Arg Ser Thr Leu Arg Arg Val Glu Ala Lys Gly Arg
1               5                   10                  15

<210> SEQ ID NO 469
<211> LENGTH: 15
<212> TYPE: PRT
<213> ORGANISM: Homo sapiens

<400> SEQUENCE: 469

Arg Pro His Asn Ile Cys Thr Phe Val Pro Arg Arg Lys Ala Gly
1               5                   10                  15

<210> SEQ ID NO 470
<211> LENGTH: 15
<212> TYPE: PRT
<213> ORGANISM: Homo sapiens

<400> SEQUENCE: 470

His Pro Ser Phe Val Leu Thr Ala Ala His Cys Leu Arg Asp Ile
1               5                   10                  15

<210> SEQ ID NO 471

```
<211> LENGTH: 15
<212> TYPE: PRT
<213> ORGANISM: Homo sapiens

<400> SEQUENCE: 471

Asp Val Leu Leu Ile Gln Leu Ser Ser Pro Ala Asn Leu Ser Ala
1               5                   10                  15

<210> SEQ ID NO 472
<211> LENGTH: 15
<212> TYPE: PRT
<213> ORGANISM: Homo sapiens

<400> SEQUENCE: 472

Tyr Val Asp Trp Ile Arg Ser Thr Leu Arg Arg Val Glu Ala Lys
1               5                   10                  15

<210> SEQ ID NO 473
<211> LENGTH: 15
<212> TYPE: PRT
<213> ORGANISM: Homo sapiens

<400> SEQUENCE: 473

Glu Tyr Val Thr Leu Lys Lys Met Arg Glu Ile Ile Gly Trp Pro
1               5                   10                  15

<210> SEQ ID NO 474
<211> LENGTH: 15
<212> TYPE: PRT
<213> ORGANISM: Homo sapiens

<400> SEQUENCE: 474

Asn Phe Phe Arg Met Val Ile Ser Asn Pro Ala Ala Thr His Gln
1               5                   10                  15

<210> SEQ ID NO 475
<211> LENGTH: 15
<212> TYPE: PRT
<213> ORGANISM: Homo sapiens

<400> SEQUENCE: 475

Asp Ser Val Ile Leu Ile Lys Cys Asp Glu Arg Gly Lys Met Ile
1               5                   10                  15

<210> SEQ ID NO 476
<211> LENGTH: 11
<212> TYPE: PRT
<213> ORGANISM: Homo sapiens

<400> SEQUENCE: 476

Ala His His Pro Ile Trp Ala Arg Met Asp Ala
1               5                   10

<210> SEQ ID NO 477
<211> LENGTH: 18
<212> TYPE: PRT
<213> ORGANISM: Homo sapiens

<400> SEQUENCE: 477

Thr Ala Ala Leu Ser Tyr Thr Ile Ser Arg Met Glu Glu Ser Ser Val
1               5                   10                  15

Thr Leu

<210> SEQ ID NO 478
```

```
<211> LENGTH: 19
<212> TYPE: PRT
<213> ORGANISM: Homo sapiens

<400> SEQUENCE: 478

Leu His Arg Ser Gly Val Leu Ile Ile His His Leu Gln Glu Asp Tyr
1               5                   10                  15
Arg Thr Tyr

<210> SEQ ID NO 479
<211> LENGTH: 9
<212> TYPE: PRT
<213> ORGANISM: Homo sapiens

<400> SEQUENCE: 479

Arg His Gly Leu Asp Asn Tyr Arg Gly
1               5

<210> SEQ ID NO 480
<211> LENGTH: 12
<212> TYPE: PRT
<213> ORGANISM: Homo sapiens

<400> SEQUENCE: 480

Gly Trp Tyr Arg Ser Pro Phe Ser Arg Val Val His
1               5                   10

<210> SEQ ID NO 481
<211> LENGTH: 12
<212> TYPE: PRT
<213> ORGANISM: Homo sapiens

<400> SEQUENCE: 481

Thr Cys Phe Phe Arg Asp His Ser Tyr Gln Glu Glu
1               5                   10

<210> SEQ ID NO 482
<211> LENGTH: 15
<212> TYPE: PRT
<213> ORGANISM: Homo sapiens

<400> SEQUENCE: 482

Gly Ile Ala Gly Phe Lys Gly Asp Gln Gly Pro Lys Gly Glu Thr
1               5                   10                  15

<210> SEQ ID NO 483
<211> LENGTH: 11
<212> TYPE: PRT
<213> ORGANISM: Homo sapiens

<400> SEQUENCE: 483

Leu Ser Ile Ala Leu His Val Gly Phe Asp His
1               5                   10

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 484
tcatcattga cctcgtggcc c                                           21
```

<210> SEQ ID NO 485
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 485
atcgtacttc tccacttgca atcc                                          24

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 486
cttgcactac caaagccaca                                               20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 487
gttattgtct tcccggctgt                                               20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 488
agcagttggt gaccatgtcg                                               20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 489
tggagatctc ctgcttgagg                                               20

<210> SEQ ID NO 490
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 490
tgaacgctac acactgcatc ttgg                                          24

```
<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 491
cgactccttt tccgcttcct gag                                              23

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 492
tcccaaatcc ttcgggttac                                                  20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 493
gagctagact ctgcggcgta                                                  20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 494
ccgggtgcta caaaagtcat                                                  20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 495
gtcggccaca ttgaaaaagt                                                  20

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 496
cgtccctgca tcccactact t                                                21

<210> SEQ ID NO 497
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 497
ggacatggcc ccagcatag                                                   19

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 498
tgacccacct ccttttcaag                                                  20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 499
ttagggtcat gcacactgga                                                  20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 500
ctggaacggt gaaggtgaca                                                  20

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
aagggacttc ctgtaacaat gca                                              23

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 502
aagacccaga catcaaggcg                                                  20

<210> SEQ ID NO 503
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 503
aatcgatgac agcgccgtag                                               20

<210> SEQ ID NO 504
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 504

His His His His His His
1               5
```

NANOPARTICLE COMPOSITIONS FOR SUSTAINED THERAPY

CROSS-REFERENCE TO RELATED PATENT APPLICATIONS

This application is a continuation under 35 U.S.C. § 120 of International Application No. PCT/IB2016/000691, filed May 6, 2016, which claims priority under 35 U.S.C. § 119(e) to U.S. Provisional Application Nos. 62/157,933, 62/273,953, and 62/296,032, filed May 6, 2015, Dec. 31, 2015, and Feb. 16, 2016, respectively, the content of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 14, 2016, is named 378701-0711_SL.txt and is 338,444 bytes in size.

BACKGROUND

Throughout and within this disclosure are technical and patent publications, referenced by an identifying citation or by an Arabic number. The full bibliographic citation corresponding to the Arabic number is found in the specification, preceding the claims. The disclosures of all references cited herein are incorporated by reference into the present application to more fully describe the state of the art to which this disclosure pertains.

A wide variety of diseases implicate improper immune function in pathogenesis or exacerbation of symptoms. While a wide variety of immunotherapies exist, they are often coupled with off target effects due to lack of targeting specificity and/or adverse side effects.

Thus a need exists with respect to finding safe and effective therapies for these disorders. This disclosure satisfies this need and provides related advantages as well.

SUMMARY OF THE DISCLOSURE

This disclosure relates to a nanomedicine, which in one aspect, is a complex comprising a nanoparticle core coupled to a plurality of disease-relevant antigen-MHC complexes (abbreviated herein as "pMHCs" or "pMHC complexes"), that are useful for expanding and differentiating T cell populations and treating disease when administered in an effective amount to a subject. The nanoparticle core comprises a variety of compositions or components, as describe in more detail herein. In some aspects, the nanoparticle core has a diameter selected from the group of from about 1 nm to about 100 nm; from about 1 nm to about 75 nm; from about 1 nm to about 50 nm; from about 1 nm to about 25 nm; from about 1 nm to about 25 nm; from about 5 nm to about 100 nm; from about 5 nm to about 50 nm; or from about 5 nm to about 25 nm, or from about 15 nm to about 25 nm, or about 20 nm. In some embodiments, the nanoparticles core has a diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm.

In some aspects, the number of pMHCs per nanoparticle core (referred to herein as the "valency" of the nanoparticle complex) may range between about 1 pMHC complex to 1 nanoparticle core to about 6000 pMHC complexes to 1 nanoparticle core, or alternatively between about 10:1 to about 6000:1, or alternatively between about 11:1 to about 6000:1, or alternatively between about 12:1 to about 6000:1, or alternatively at least 2:1, or alternatively at least 8:1, or alternatively at least 9:1, or alternatively at least 10:1, or alternatively at least 11:1, or alternatively at least 12:1. In some aspects, the number of pMHCs per nanoparticle core is from about 10:1 to about 6000:1, or from about 20:1 to about 5500:1, or alternatively from about 10:1 to about 5000:1, or alternatively from about 10:1 to about 4000:1, or alternatively from about 10:1 to about 3500:1, or alternatively from about 10:1 to about 3000:1, or alternatively from about 10:1 to about 2500:1, or alternatively from about 10:1 to about 2000:1, or alternatively from about 10:1 to about 1500:1, or alternatively from about 10:1 to about 1000:1, or alternatively from about 10:1 to about 500:1, or alternatively from about 10:1 to about 100:1, or alternatively from about 20:1 to about 50:1, or alternatively from about 25:1 to about 60:1; alternatively from about 30:1 to about 50:1, or alternatively from about 35:1 to about 45:1, or alternatively about 40:1.

In some aspects, the nanoparticle core has a defined valency per surface area of the core, also referred to herein as "density." In these aspects, the pMHC density per nanoparticle is from about 0.025 pMHC/100 $nm^2$ to about 100 pMHC/100 $nm^2$ of the surface area of the nanoparticle core, or alternatively from about 0.406 pMHC/100 $nm^2$ to about 50 pMHC/100 $nm^2$; or alternatively from about 0.05 pMHC/100 $nm^2$ to about 25 pMHC/100 $nm^2$. In certain aspects, the pMHC density per nanoparticle is from about 0.4 pMHC/100 $nm^2$ to about 25 pMHC/100 $nm^2$, or from about 0.4 pMHC/100 $nm^2$ to about 20 pMHC/100 $nm^2$, or from about 0.4 pMHC/100 $nm^2$ to about 15 pMHC/100 $nm^2$, or from about 0.4 pMHC/100 $nm^2$ to about 14 pMHC/100 $nm^2$, or from about 0.4 pMHC/100 $nm^2$ to about 13 pMHC/100 $nm^2$, or from about 0.4 pMHC/100 $nm^2$ to about 12 pMHC/100 $nm^2$, or from about 0.4 pMHC/100 $nm^2$ to about 11.6 pMHC/100 $nm^2$, or from about 0.4 pMHC/100 $nm^2$ to about 11.5 pMHC/100 $nm^2$, or from about 0.4 pMHC/100 $nm^2$ to about 11 pMHC/100 $nm^2$, or from about 0.4 pMHC/100 $nm^2$ to about 10 pMHC/100 $nm^2$, or from about 0.4 pMHC/100 $nm^2$ to about 9 pMHC/100 $nm^2$, or from about 0.4 pMHC/100 $nm^2$ to about 8 pMHC/100 $nm^2$, or from about 0.4 pMHC/100 $nm^2$ to about 7 pMHC/100 $nm^2$, or from about 0.4 pMHC/100 $nm^2$ to about 6 pMHC/100 $nm^2$, or from about 0.4 pMHC/100 $nm^2$ to about 5 pMHC/100 $nm^2$, or from about 0.4 pMHC/100 $nm^2$ to about 4 pMHC/100 $nm^2$, or from about 0.4 pMHC/100 $nm^2$ to about 3 pMHC/100 $nm^2$, or from about 0.4 pMHC/100 $nm^2$ to about 2.5 pMHC/100 $nm^2$, or from about 0.4 pMHC/100 $nm^2$ to about 2 pMHC/100 $nm^2$, or from about 0.4 pMHC/100 $nm^2$ to about 1.5 pMHC/100 $nm^2$.

In another aspect, the nanoparticle may have a pMHC density of from about 0.22 pMHC/100 $nm^2$ to about 10 pMHC/100 $nm^2$, or from about 0.22 pMHC/100 $nm^2$ to about 9 pMHC/100 $nm^2$, or from about 0.22 pMHC/100 $nm^2$ to about 8 pMHC/100 $nm^2$, or from about 0.22 pMHC/100 $nm^2$ to about 7 pMHC/100 $nm^2$, or from about 0.22 pMHC/100 $nm^2$ to about 6 pMHC/100 $nm^2$, or from about 0.22 pMHC/100 $nm^2$ to about 5 pMHC/100 $nm^2$, or from about 0.22 pMHC/100 $nm^2$ to about 4 pMHC/100 $nm^2$, or from about 0.22 pMHC/100 $nm^2$ to about 3 pMHC/100 $nm^2$, or from about 0.22 pMHC/100 $nm^2$ to about 2 pMHC/100 $nm^2$, or from about 0.22 pMHC/100 nm$^2$ to about 1.5 pMHC/100 nm$^2$. In some aspects, the nanoparticle has a pMHC density of from about 0.22 pMHC/100 nm$^2$ to about 10 pMHC/100 nm$^2$, or 0.24 pMHC/100 nm$^2$ to about 9 pMHC/100 nm$^2$, or from about 0.26 pMHC/100 nm$^2$ to about 8 pMHC/100 nm$^2$, or from about 0.28 pMHC/100 nm$^2$ to about 7 pMHC/100 nm$^2$, or from about 0.24 pMHC/100 nm$^2$ to about 4 pMHC/100 nm$^2$, or from about 0.5 pMHC/100 nm$^2$ to about 3 pMHC/100 nm$^2$, or from about 0.6 pMHC/100 nm$^2$ to about 1.5 pMHC/100 nm$^2$. In a further aspect, the nanoparticle has a pMHC density of from about 0.4 pMHC/100 nm$^2$ to about 1.3 pMHC/100 nm$^2$, or alternatively from about 0.5 pMHC/100 nm$^2$ to about 0.9 pMHC/100 nm$^2$, or alternatively from about 0.6 pMHC/100 nm$^2$ to about 0.8 pMHC/100 nm$^2$.

In some embodiments, the nanoparticle can have a pMHC density of from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 pMHC/100 nm$^2$. In specific embodiments, the nanoparticle can have a pMHC density of from about 0.4 pMHC/100 nm$^2$ to about 1.5 pMHC/100 nm$^2$ or from about 0.4 pMHC/100 nm$^2$ to about 6 pMHC/100 nm$^2$ or from about 0.4 pMHC/100 nm$^2$ to about 12 pMHC/100 nm$^2$.

In yet another aspect, the nanoparticle has a pMHC density as defined herein of from about 0.4 pMHC/100 nm$^2$ to about 1.3 pMHC/100 nm$^2$, or alternatively from about 0.5 pMHC/100 nm$^2$ to about 0.9 pMHC/100 nm$^2$, or alternatively from about 0.6 pMHC/100 nm$^2$ to about 0.8 pMHC/100 nm$^2$, and further wherein the nanoparticle core has a diameter from about from about 25 nm to about 60 nm, or from about 25 nm to about 50 nm, or from about 20 nm to about 40 nm, or from about 15 nm to about 50 nm, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm.

In some aspects, the nanoparticle core further comprises a plurality of co-stimulatory molecules, co-stimulatory antibodies, inhibitory receptor-blocking antibodies, and/or a plurality of cytokines coupled to the nanoparticle core.

Thus, certain aspects of the disclosure relate to a complex comprising, or alternatively consisting essentially of, or yet further consisting of, nanoparticle cores coupled to a plurality of pMHC complexes, wherein the nanoparticles cores optionally further comprise, or further consist thereof, or alternatively further consist essentially of one or more co-stimulatory molecules and/or one or more cytokines coupled to the nanoparticle core. For these compositions containing a plurality of the complexes, the pMHC complexes on each nanoparticle core are the same or different from each other; and/or the MHC of the pMHC complexes on each nanoparticle core are the same or different from each other; and/or the cytokines on each nanoparticle core are the same or different from each other; and/or the costimulatory molecules on each nanoparticle core are the same or different from each other; and/or the diameters of the nanoparticle cores are the same or different from each other; and/or the valency of the pMHC complexes on each nanoparticle core are the same or different from each other; and/or the density of the pMHC complexes on each nanoparticle core are the same or different from each other; and/or the valency of the co-stimulatory molecules on each nanoparticle core are the same or different from each other; and/or the valency of the cytokines on each nanoparticle core are the same or different from each other.

In certain aspects, provided herein are compositions comprising a plurality of the complexes provided herein. In some embodiments, the compositions further comprise a carrier, optionally a pharmaceutical carrier. In some embodiments, the compositions provided herein may optionally comprise one or more nanoparticle cores coupled to one or more co-stimulatory molecules and/or cytokines. Accordingly, in some embodiments, the compositions comprise, or alternatively consist essentially of, or yet further consist of: 1) a plurality of nanoparticle cores coupled to a plurality of antigen-MHC complexes wherein at least one portion of the nanoparticle cores further comprises one or more co-stimulatory molecules and/or one or more cytokines and a second portion of the nanoparticle cores do not further comprise a co-stimulatory molecule and/or a cytokine, and 2) a plurality of nanoparticle cores coupled to one or more co-stimulatory molecules and/or cytokines.

Further aspects of the disclosure relate to specific disease-relevant antigens, MHCs, and combinations thereof optimized for the treatment or prevention of disease in human patients and animals.

This disclosure also provides compositions and methods of use for any of the above complexes or compositions, each of which is optionally combined with a carrier, for example a pharmaceutically acceptable carrier.

This disclosure also provides methods for differentiating or triggering T-regulatory type 1 ($T_R1$) cell formation in a pMHC dose independent manner. Applicant has discovered that the pMHC density on the nanoparticle core regulates the ability of pMHC on the nanoparticle core to trigger $T_R1$ cell formation in a dose-independent manner, while pMHC dose regulates the magnitude of $T_R1$ cell expansion in a pMHC density-independent manner. Applicant has observed that the pMHC density threshold and the independent effects of pMHC density versus dose on $T_R1$ cell formation versus expansion are unexpected findings that could not have been anticipated based on conventional immunological knowledge in the art. These methods require contacting (in vitro or in vivo) the cognate T cells with an effective amount of a pMHC-NP or a composition disclosed herein. In certain aspects, the density-dependent methods relate to an activated T cell or a memory T cell being differentiated into a IL-10 producing cognate $T_R1$ cell optionally having the marker CD49b and/or Lag3 and/or a B cell being differentiated into a regulatory B cell by contacting the activated T cell or the memory T cell with an effective amount of the complex or composition disclosed herein. In some embodiments, the differentiated $T_R1$ cell binds to a B cell, thereby differentiating the B cell into a regulatory B cell. In certain aspects of the methods, the contacting is performed in vitro or in vivo. In some embodiments, the pMHC-NP or composition containing a plurality of the pMHC-NPs have pMHC-NPs having an average nanoparticle core diameter of from about 25 nm to about 60 nm, or from about 25 nm to about 50 nm, or from about 20 nm to about 40 nm, or from about 15 nm to about 50 nm, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm. In some aspects, the nanoparticle core further comprises an outer coating or layer, wherein the diameter of the core and outer layer have an average diameter of from about 30 nm to about 75 nm, or from about 30 nm to about 70 nm, or from about 30 nm to about 60 nm, or from about 30 nm to about 50 nm, or about 40 nm. In some aspects, the nanoparticle has an average pMHC density of from about 0.4 pMHC/100 nm$^2$ to about 12 pMHC/100 nm$^2$, or from about 0.4 pMHC/100 nm$^2$ to about 11.6 pMHC/100 nm$^2$, or from about 0.4 pMHC/100 nm$^2$ to about 11.5 pMHC/100 nm$^2$, or from about 0.4 pMHC/100 nm$^2$ to about 11 pMHC/100 nm$^2$, or from about 0.4 pMHC/100 nm$^2$ to about 10 pMHC/100 nm$^2$, or from about 0.4 pMHC/100 nm$^2$ to about 9 pMHC/100 nm$^2$, or from about 0.4 pMHC/100 nm$^2$ to about 8 pMHC/100 nm$^2$, or from about 0.4 pMHC/100 nm$^2$ to about 7 pMHC/100 nm$^2$, or from about 0.4 pMHC/100 nm$^2$ to about 6 pMHC/100 nm$^2$, or from about 0.4 pMHC/100 nm$^2$ to about 5 pMHC/100 nm$^2$, or from about 0.4 pMHC/100 nm$^2$ to about 4 pMHC/100 nm$^2$, or from about 0.4 pMHC/100 nm$^2$ to about 3 pMHC/100 nm$^2$, or from about 0.4 pMHC/100 nm$^2$ to about 2.5 pMHC/100 nm$^2$, or from about 0.4 pMHC/100 nm$^2$ to about 2 pMHC/100 nm$^2$, or from about 0.4 pMHC/100 nm$^2$ to about 1.5 pMHC/100 nm$^2$.

Further aspects of the disclosure relate to methods to treat or prevent the relevant disease or conditions as disclosed herein by admininstering an effective amount of a pMHC-NP as disclosed herein. Also disclosed are methods of detecting the presence and efficacy of treatment with the pMHC-NP complexes and compositions as disclosed herein.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1A is a schematic of a single-chain pMHC-class I expression construct (top) and a representative flow cytometric profile of the binding of the corresponding pMHC tetramer (fluorochrome-labeled) to cognate CD8+ T-cells ("6×His" disclosed as SEQ ID NO: 504). FIG. 1B is a schematic showing the linkers and two dimensional structure of NP-complexes. As can be seen, one NP can contain the same antigen complexed to the nanoparticle core through various chemical linkers.

FIG. 2 shows the structure of a typical pMHC class II monomer (top) and a representative FACS profile of cognate CD4+ T-cells stained with the corresponding pMHC tetramer or left unstained ("6×His" disclosed as SEQ ID NO: 504).

FIG. 3 shows the chemical structure of Dendri-Graft Poly-L-Lysines Generation 3 (DGLs G3).

FIGS. 9A and 9B show tetramerstaining profiles (FIG. 9A) and percentages of tetramer$^+$CD4$^+$ T cells (FIG. 9B). Data correspond to pre-diabetic NOD females treated for 5 weeks (blood: n=5, 8 and 6; spleen: n=5, 18 and 6, respectively). Tet, tetramer. FIG. 9J shows EAE scores of mice treated from day 14 (n=4 each). FIG. 9K shows EAE scores of mice treated from day 21 (n=10, 7 and 3 from top). FIG. 9L shows percentage of tetramer$^+$CD4$^+$ T cells in spleen and blood of mice from FIGS. 9J and 9K (n=13, 14 and 5 from top). FIG. 9M shows representative flow profiles of CD4$^+$ T cells from mice in FIGS. 9J and 9K. FIG. 9N shows representative microglial IBA1 stainings and relative rank scores in the cerebellum of mice from FIG. 9K (n=4-5). P values were calculated via Mann-Whitney U-test, log-rank (Mantel-Cox) test or two-way ANOVA. Error bars, s.e.m.

FIGS. 10A-10H show therapeutic effects are disease-specific and dependent on both pMHC and nanoparticles. FIGS. 10A-10F show C57BL/10.M HLA-DR4-IEtransgenic mice immunized with bovine collagen. FIG. 10A, left, shows changes in joint swelling (top) and clinical scores (bottom) in response to uncoated NPs, pMHC-NPs, peptide s.c. (Burton, B. R. et al. (2014) Nature Commun. 5:4741-4747) or peptide-coated MPs i.v (Getts, D. R. et al. (2012) Nature Biotechnol. 30:1217-1224). Treatment was initiated when joint swelling reached 130% of baseline (data normalized to the initiation of treatment (100% value)) (n=4, 4, 4 and 8 from top). Right, percentage increase in joint swelling relative to pre-immunization baseline (100% value). FIG. 10B shows representative haematoxylin and eosin (first row) and O-safranin/fast-green/haematoxylin (second and third rows) knee joint staining images. Third row shows enlarged images of lacunae on the bone and meniscal articular surfaces. 1, panus formation; 2, cellular infiltration of the meniscus; 3, bone erosion; 4, proteoglycan depletion; 5, loss of chondrocyte/lacunnae. FIG. 10C shows average pathology scores (n=3-4 per group). FIG. 10D shows percentage of tetramer$^+$CD4$^+$ T cells. FIG. 10E shows representative flow cytometry profiles for $T_R$1 markers in mCII$_{259-273}$/DR4-NP-treated. FIGS. 10E-10H show C57BL/6IAb$^{null}$ HLA-DR4-IE-transgenic mice immunized with hPLP. FIG. 10F shows changes in EAE scores ((n=5, 4, 13 (4-9 per group), 5, 19 (4-5 per group, see also FIG. 9H), 4 and 5 from top). FIG. 10G shows percentage of tetramer$^+$ CD4$^+$ T cells in the spleen of mice from FIG. 10F (n=4, 5, 4, 6, 15, 3 and 3 from left). FIG. 10H shows representative flow cytometry profiles for $T_R$1 markers. Data were compared using Mann-Whitney U-test or two-way ANOVA. Error bars, s.e.m.

FIGS. 11A-11H show disease reversal involves effects of $T_R$1 cytokines on cognate B cells and local CD11b+ cells, without compromising systemic immunity. FIG. 11A shows blood glucose levels in diabetic NOD mice treated with 2.5 mi/IA$^{g7}$-NPs and blocking antibodies (n=8, 4, 6, 6, 5 and 4 from top to right). FIG. 11B shows expression of IL-10 (eGFP) and upregulation of CD5 and CD1d by eGFP 2.5 mi-pulsed splenic B cells from NOD Il10$^{GFP}$ donors in 2.5 mi/IA$^{g7}$-NP-treated NOD hosts. FIG. 11C shows averaged results from FIG. 11B (n=4, 3, 3 and 7 from left). FIG. 11D shows incidence of diabetes in T-cell-reconstituted NOD scid hosts left alone or transfused with PLN CD19$^+$ cells (n=7, 13 and 7 from top). FIG. 11E shows incidence of diabetes in T-cell-reconstituted NOD scid hosts transfused with CD19+ and/or CD4+ cells (n=7, 6, 3, 7, 8, 11 and 13 from top). FIG. 11F shows cytokine and chemokine profiles of PLN and MLN CD11b$^+$ cells from 2.5 mi/IA$^{g7}$-NP-treated NOD mice in response to LPS (n=3-4 each). FIG. 11G shows percentage of tetramer+CD4+ T cells in the spleens (left), and viral titres in the ovaries (right) of treated compared with untreated NOD mice 4 and 14 days after vaccinia virus infection (n=3 per group). FIG. 11H shows percentages of tetramer$^+$CD4$^+$ T cells in the spleens (left) and serum anti-dinitrophenyl (DNP) antibody titres (right) in treated and untreated NOD mice immunized with keyhole limpet haemocyanin (KLH)-DNP (n=3-5 per group). Data were compared using Mann-Whitney U-test, log-rank test or two-way ANOVA. Error bars, s.e.m.

FIGS. 12A-12G show the $T_R$1-like CD4$^+$ T cells arising in response to pMHCII-NPs are derived from antigen-experienced precursors. FIG. 12A, Percentage of tetramer$^+$ CD4$^+$ T cells in hyperglycaemic NOD G6pc2$^{-/-}$ compared with NOD mice treated with IGRP$_{4-22}$/IA$^{g7}$-(n=4 and 7) or 2.5 mi/IA$^{g7}$-NPs (n=6 and 9). FIG. 12B shows blood glucose levels in hyperglycaemic NOD G6pc2$^{-/-}$ mice in response to pMHC-NP therapy (n=4-6 per group). FIG. 12C shows upregulation of $T_R$1 transcripts by anti-CD3/anti-CD28 mAb-activated eGFP-CD4+ T cells from BDC2.5 NOD Foxp3-eGFP mice in response to different in vitro stimuli (n=4 mice each). FIG. 12D shows changes in $T_R$1-relevant transcripts in naive or memory BDC2.5 CD4$^+$ T cells in response to 2.5 mi/IA$^{g7}$-NPs in vivo (n=6, 6, 5 and 4 from left). FIG. 12E shows LAG-3 and CD49b profiles (blue; compared with isotype control in red) of Thy1$^{b+}$ cells from FIG. 12D. FIG. 12F shows proliferation of CFSE-labelled memory BDC2.5 CD4+ T cells in NOD. Thy1$^a$ hosts in response to 2.5 mi/IAg7-NPs. FIG. 12G shows incidence of diabetes in T-cell-reconstituted NOD scid hosts transfused with naive or memory BDC2.5 CD4$^+$ T cells and treated with bi-weekly doses of 2.5 mi/IA$^{g7}$-NPs (n=4 and 3) or left untreated (n=4 and 6). P values were calculated via Mann-Whitney U-test or log-rank (Mantel-Cox) tests. Error bars, s.e.m.

FIGS. 13A-13I show human T1D-relevant pMHC-NPs expand cognate $T_R$1-like CD4$^+$ T cells in human PBMC-engrafted NSG hosts. FIG. 13A shows expansion of cognate CD4$^+$ T cells by GAD$_{555-567(557I)}$/DR4-NPs (top) or PPI$_{76-90(88S)}$/DR4-NPs (bottom) in NSG mice engrafted with PBMCs from DR4$^+$ T1D patients. FIG. 13B shows CD49b and LAG-3 marker expression on the sample at the bottom of FIG. 13A. FIG. 13C shows expansion of cognate $T_R$1-like CD4$^+$ T cells in NSG mice engrafted with PBMCs from DR3$^+$ T1D patients in response to IGRP$_{13-25}$/DR3-NP-therapy. FIG. 13D shows percentages (left) and numbers (right) of tetramer$^+$CD4$^+$ T cells in mice engrafted with T1D PBMCs in response to treatment (n for spleen and PLN per treatment=9/6, 7/6 and 14/1 from left legend). FIG. 13E shows expression of Il10 mRNA in IGRP$_{13-25}$/DR3 tetramer$^+$CD4$^+$ T cells from mice treated with IGRP$_{13-25}$/DR3-NPs (n=3 each). FIG. 13F shows the PLNs of responder mice contained increased numbers of lymphocytes compared to the other groups (n=6, 3, 4, 3 from top legend). FIGS. 13G and 13H show correlation between the absolute numbers of IGRP$_{13-25}$/DR3 tetramer$^+$ cells in the PLNs (FIG. 13G) or spleen (FIG. 13H) and the percentage or absolute number of PLN or splenic B cells in IGRP$_{13-25}$/DR3-NP-treated mice (n=6 and 7). FIG. 13I shows secretion of IL-10 by LPS-stimulated CD19$^+$ cells (ex vivo, for 24 h) isolated from the PLNs or spleens of hPBMC-engrafted NSG mice treated with IGRP$_{13-25}$/DR3-NPs (n=3 each). P values were calculated by Mann-Whitney U-test or Pearson correlation test. Error bars, s.e.m.

FIG. 14A, top left, shows expansion of cognate CD4$^+$ T cells by 2.5 mi/IA$^{g7}$-NPs in anti-CD25 mAb-treated NOD Foxp3-eGFP mice. Data correspond to 8-week-old mice treated three times a week with 500 µg of a depleting anti-CD25 mAb i.p. or control anti-HPRN mAbs, followed by 10 doses of 2.5 mi/IA$^{g7}$-NPs starting at 10 weeks of age (two doses per week; n=4 mice each). Bottom, the tetramer$^+$ CD4$^+$ T cells from anti-CD25 mAb-treated mice express $T_R$1 markers. Right, percentage of circulating FOXP3$^+$ eGFP$^+$CD4$^+$ (top) and CD25$^+$CD4$^+$ cells (bottom). FIG. 14D shows upregulation of CD49b and LAG-3 on anti-CD3/anti-CD28 mAb-activated BDC2.5 CD4$^+$ T cells from BDC2.5 NOD Foxp3-eGFP mice in response to 2.5 mi/IA$^{g7}$-NP (25 µg pMHC per ml) versus 2.5 mi peptide (10 µg ml$^{-1}$) or 2.5 mi/IA$^{g7}$ monomers (25 µg pMHC per ml). FIG. 14E shows upregulation of eGFP (IL-10) in anti-CD3/anti-CD28 mAb-activated BDC2.5 CD4$^+$ T cells from BDC2.5 NOD Il10$^{GFP}$ mice in response to 2.5 mi/IA$^{g7}$-NP as a function of CD49b and LAG-3 expression. FIG. 14F shows expression of eGFP (IL-10) in the CD4$^+$ T cells of 2.5 mi/IA$^{g7}$-NP-treated NOD Il10$^{GFP}$ mice (2 doses per week for 5 weeks) as a function of CD49b and LAG-3 expression (left, representative profiles; right, eGFP MFI values) (n=8). FIG. 14G shows proliferation of CFSE-labelled 8.3-TCR-transgenic CD8$^+$ T cells (IGRP$_{206-214}$/NRP-V7-specific) in response to 2.5 mi/NRP-V7-peptide-pulsed or unpulsed DCs in the presence of tetramer$^-$ or tetramer$^+$CD4$^+$ T cells from 2.5 mi/IA$^{g7}$-NP-treated mice and in the presence or absence of cytokine-blocking mAbs, rat IgG (negative control) or 1-methyl-1-tryptophan (1-MT; an IDO inhibitor). Data correspond to average of proliferated cells in 3-7 experiments per condition. FIG. 14H shows changes in blood glucose levels of spontaneously hyperglycaemic (>11 mM) female NOD mice treated with 2.5 mi/IA$^{g7}$-NP, IGRP$_{4-22}$/IA$^{g7}$-NP, IGRP$_{128-145}$/IA$^{g7}$-NP or HEL$_{14-22}$/IA$^{g7}$-NP (n=6-9 per group), IGRP$_{4-22}$ peptide or IGRP$_{4-22}$ peptide-NPs (n=9, 4-5 each). Mice received two doses per week until irreversibly hyperglycaemic or normoglycaemic for 4 consecutive weeks, at which point treatment was withdrawn. FIG. 14I shows incidence and timing of disease relapse in hyperglycaemic female NOD mice rendered stably normoglycaemic by treatment with 2.5 mi/IA$^{g7}$-NP, IGRP$_{4-22}$/IA$^{g7}$-NP or IGRP$_{128-145}$/IA$^{g7}$-NPs upon treatment withdrawal (after 4 consecutive weeks of normoglycaemia). Data correspond to responder mice in FIG. 9G. FIG. 14J shows post-prandial serum insulin levels in pMHC-NP-treated mice that reverted to normoglycaemia until 50 weeks of age (n=6) versus newly diabetic (n=12) and non-diabetic age-matched untreated controls (n=10). FIG. 14K shows intra-peritoneal glucose tolerance tests (IPGTT) of the mice in FIG. 14H. FIG. 14N shows proliferation of CFSE-labelled $IGRP_{206-214}$-reactive 8.3-CD8$^+$ T cells in the PLNs compared with MLNs of 2.5 mi/$IA^{g7}$-NP-treated mice that reverted to normoglycaemia until 50 weeks of age, non-diabetic age-matched untreated controls and newly diabetic mice. Left panels show representative FACS profiles. Right panel compares percentages of proliferated cells in the PLNs after subtraction of the background proliferation values in non-draining MLNs (n=6-8 mice per group). P values were calculated by Mann-Whitney U-test, log-rank (Mantel-Cox) test or two-way ANOVA. Data are averages ±s.e.m.

FIGS. 15A-15H show nanoparticles coated with different T1D-relevant pMHCII complexes expand cognate $T_R1$-like CD4$^+$ T cells in vivo to similar extent, regardless of epitope dominance or role of the target T-cell specificity in the disease process. FIG. 15A shows percentage of tetramer$^+$ CD4$^+$ T cells in the PLN, MLN and bone marrow (BM) of 2.5 mi/$IA^{g7}$-NP-treated mice that reverted to normoglycaemia until 50 weeks of age (n=5-6 mice per lymphoid organ) or relapsed (n=1-2) compared with newly diabetic (n=5-6) and non-diabetic age-matched untreated controls (n=4-6). FIG. 15B shows percentage of tetramer$^+$CD4$^+$ T cells in the splenic CD4$^+$ T cells of 2.5 mi/$IA^{g7}$-NP-treated mice that reverted to normoglycaemia until 50 weeks of age or of age-matched non-diabetic untreated mice, stained with two T1D-relevant but non-cognate pMHCII tetramers (n=3-4 per group). FIG. 15C shows percentage of tetramer$^+$CD4$^+$ T cells in blood, spleen, PLN, MLN and bone marrow of $IGRP_{4-22}$/$IA^{g7}$-NP-treated mice that reverted to normoglycaemia until 50 weeks of age (n=5-6 mice per lymphoid organ) compared with newly diabetic (n=5-8) and non-diabetic age-matched untreated controls (n=4-6). FIG. 15D shows percentage of tetramer$^+$CD4$^+$ T cells in blood, spleen, PLN, MLN and bone marrow of $IGRP_{128-145}$/$IA^{g7}$-NP-treated mice that reverted to normoglycaemia until 50 weeks of age (n=5-7 mice per lymphoid organ) compared with newly diabetic (n=4-7) and non-diabetic age-matched untreated controls (n=5-7). FIG. 15E shows representative $IGRP_{4-22}$/$IA^{g7}$, $IGRP_{128-145}$/$IA^{g7}$ and $GPI_{282-292}$/$IA^{g7}$ tetramer staining profiles for splenic CD4$^+$ T cells from $IGRP_{4-22}$/$IA^{g7}$-NP- and $IGRP_{128-145}$/$IA^{g7}$-NP-treated compared with untreated NOD mice. FIG. 15F shows percentages of blood CD4$^+$ T cells of $IGRP_{422}$/$IA^{g7}$-NP- or $IGR_{P128-145}$/$IA^{g7}$-NP-cured, $HEL_{14-22}$/$IA^{g7}$-NP-treated and age-matched non-diabetic untreated mice stained with non-cognate pMHCII tetramers (n=3-7 per group). FIG. 15G shows the tetramer$^+$CD4$^+$ T cells of mice treated with $IGRP_{128-145}$/$IA^{g7}$-NP (top) and $IGRP_{4-22}$/$IA^{g7}$-NP (bottom) proliferate and produce IL-10 specifically in response to stimulation with $IGRP_{4-22}$ or $IGRF_{128-145}$-peptide-pulsed DCs, respectively (n=3 mice each), cpm, counts per minute. FIG. 15H shows percentages of $IGRP_{4-22}$/$IA^{g7}$ tetramer$^+$ CD4$^+$ T cells in blood, spleen, PLN, MLN and bone marrow of NOD mice at the onset of hyperglycaemia or upon treatment with $IGRP_{4-22}$/$IA^{g7}$-NPs, or $IGRP_{4-22}$ peptide or $IGRP_{4-22}$ peptide-coated nanoparticles (n=5-9 mice per organ). P values were calculated by Mann-Whitney U-test. Data are averages ±s.e.m.

FIGS. 16A-16F show EAE-relevant pMHCII-NPs expand cognate IL-10-secreting $T_R1$-like CD4$^+$ T cells and ameliorate established clinical and pathological signs of EAE. FIGS. 16A and 16B show changes in the average weights of C57BL/6 mice immunized with $pMOG_{35-55}$ and treated with $pMOG_{38-49}$/$IA^b$-NPs or uncoated nanoparticles starting on days 14 (FIG. 16A) or 21 (FIG. 16B) after immunization. FIG. 16C shows percentage of $pMOG_{38-49}$/IAb tetramer$^+$ CD4$^+$ T cells in peripheral lymph nodes, bone marrow and central nervous system (CNS) of mice from FIGS. 16A and 16B. FIG. 16D shows the tetramer$^+$CD4$^+$ T cells of $pMOG_{38-49}$/$IA^b$-NP-treated mice proliferate and produce IL-10 and, to a lesser extent, IFNγ in response to stimulation with $pMOG_{38-49}$ peptide-pulsed DCs. FIG. 16E, left and middle, shows representative luxol fast blue (LFB)/H&E cerebellum staining images from untreated and treated mice from FIG. 16B showing presence of inflammatory foci and areas of demyelination (red arrows). Right, average number of inflammatory foci per section. Data corresponds to 4 untreated and 5 treated mice. FIG. 16F shows representative LFB/H&E-stained spinal cord sections from mice in FIG. 16B. Data were compared with Mann-Whitney U-test. Data are averages ±s.e.m.

FIG. 17A shows changes in the average EAE scores of HLA-DR4-IE-transgenic C57BL/6 $IAb^{null}$ mice immunized with $hPLP_{175-192}$ or $hMOG_{97-108}$ and treated with $hPLP_{175-192}$/DR4-IE or $hMOG_{97-108}$/DR4-IE-NPs or uncoated nanoparticles starting on the day when mice reached a score of 1.5 (to synchronize the groups for disease activity) (n=3-4 per group). FIG. 17B shows percentage of tetramer$^+$CD4$^+$ T cells in spleen, blood, cervical and inguinal LNs and CNS of mice from FIG. 17A. Data correspond to 4 pMHC-NP-treated and 6 control-NP-treated mice. FIG. 17C shows changes in the average weights of HLA-DR4-IE-transgenic C57BL/6$IAb^{null}$ mice from FIG. 17A, immunized with $hPLP_{175-192}$ or $hMOG_{97-108}$ and treated with $hPLP_{175-192}$/DR4-IE-NPs, $hMOG_{97-108}$/DR4-IE-NPs or uncoated nanoparticles when the mice reached a score of 1.5. FIG. 17D shows LFB/H&E staining of the cerebellum of HLA-DR4-IE-transgenic C57BL/6 $IAb^{null}$ mice from FIG. 17A showing reductions in inflammation and demyelination in mice treated with $hPLP_{175-192}$/DR4-IE or $hMOG_{97-108}$/DR4-IE-NPs compared with controls. FIG. 17E shows percentage of tetramer$^+$CD4$^+$ T cells in lymph nodes and bone marrow of the mice in FIG. 10A (C57BL/10.M HLA-DR4-IE mice immunized with bovine collagen) at the end of follow-up (10 doses, 5 weeks). FIG. 17F shows changes in the average weights of HLA-DR4-IE-transgenic C57BL/6 $IAb^{null}$ mice immunized with $hPLP_{175-192}$ from FIG. 10F. FIG. 17G shows representative LFB/H&E staining of the cerebellum of HLA-DR4-IE-transgenic C57BL/6$IAb^{null}$ mice immunized with $hPLP_{175-192}$ and treated with $hPLP_{175-192}$/DR4-IE-NPs, $hMOG_{97-108}$/DR4-IE-NPS, $hMOG_{97-108}$ peptide i.v. or s.c. (8 µg per dose), $hMOG_{97-108}$/DR4-IE monomer (25 µg per dose), $hMOG_{97-108}$ peptide-NPs (using the molar equivalent of peptide delivered via pMHC-NPs; 0.68 µg per dose), or $hMOG_{97-108}$ peptide-MPs (15 µg peptide per dose) compared with mice left untreated or treated with uncoated NPs or MPs (at the same NP/MP number). FIG. 17H shows changes in the average EAE scores and body weights of HLA-DR4-IE-transgenic C57BL/6IAb$^{null}$ mice immunized with hPLP$_{175-192}$ in response to treatment with hMOG$_{97-108}$ peptide i.v. or s.c. (8 μg per dose 16), hMOG$_{97-108}$/DR4-IE monomer (25 μg per dose), hMOG$_{97-108}$ peptide-NPs (0.68 μg peptide per dose), hMOG$_{97-108}$ peptide-MPs (15 μg peptide per dose (Getts, D. R. et al. (2012) Nature Biotechnol. 30:1217-1224)), or a single dose of hMOG$_{97-108}$ peptide-MPs (15 μg peptide (Getts, D. R. et al. (2012) Nature Biotechnol. 30:1217-1224)) compared with mice left untreated or treated with uncoated NPs or MPs (at the same NP/MP number) (n=4-5 per group). The cohort of mice treated with one dose had to be terminated after 2.5 weeks, owing to rapid progression of disease. FIG. 17I shows percentages of tetramer+CD4+ T cells in spleen, blood, cervical and inguinal LNs and bone marrow of mice from FIG. 17H (n=3-9 per group). Data were compared with Mann-Whitney U-test or two-way ANOVA. Data are averages ±s.e.m.

FIGS. 18A-18Y show disease reversal by pMHC-NPs is driven by the T$_R$1 cytokines IL-21, IL-10 and TGF-β and involves several downstream cellular targets. FIG. 18A shows changes in blood glucose levels in diabetic NOD mice (>11 mM) treated with IGRP$_{4-22}$/IA$^{g7}$-NPs and blocking anti-IL-10, anti-IFNγ or anti-TGF-β mAbs or anti-HRPN rat-IgG (n=4-6 per group). FIGS. 18B and 18C show percentages of tetramer$^+$CD4$^+$ T cells in the spleens (FIG. 18B), and proliferation of CFSE-labelled 8.3-CD8$^+$ T cells in the PLNs verus MLN of the mice from FIG. 11A at the end of follow up (FIG. 18C). FIGS. 18K and 18L show changes in the average EAE scores (FIG. 18K) and body weights (FIG. 18L) of C57BL/6 Il27r$^{-/-}$ mice immunized with pMOG$_{35-55}$ and treated with pMOG$_{38-49}$/IA$^b$-NPs or uncoated nanoparticles starting on the day when mice reached a score of 1.5 (to synchronize the groups for disease activity) (n=7 and 4, respectively). FIG. 18M shows representative IBA1 and LFB/H&E stainings of the cerebellum and the corresponding relative rank scores of mice from FIG. 18K (n=3 and 4, respectively). FIG. 18Q, left, shows in vitro proliferation of CFSE-labelled BDC2.5 CD4$^+$ T cells against 2.5 mi or GPI$_{282-292}$ peptide-pulsed B cells purified from the PLNs or MLNs of untreated NOD mice or mice treated with 2.5 mi/IA$^{g7}$-NPs (n=5-6 per group). Right, representative CFSE dilution profiles. Briefly, profiles show the extent of CFSE dilution in CFSE-labelled BDC2.5 CD4$^+$ T cells cultured in the presence of 2.5 mi or GPI$_{282-292}$ peptide-pulsed B cells purified from the PLNs or MLNs of untreated or 2.5 mi/IA$^{g7}$-NP-treated NOD mice. FIG. 18R, PLN-derived B cells (10$^5$) from 2.5 mi/IA$^{g7}$-NP-treated mice secrete IL-10 ex vivo in response to LPS (1 μg ml-1). Data correspond to 6 pMHC-treated and 5 untreated NOD mice. FIGS. 18S and 18T, Changes in the percentages of 2.5 mi (PKH26-labelled) compared with GPI$_{282-292}$ peptide-pulsed (CFSE-labelled) B cells (FIG. 18S) or DCs (FIG. 18T) 7 days after transfer (at 1:1 ratio) into untreated or 2.5 mi/IA$^{g7}$-NP-treated NOD mice. Histograms show averaged ratios for each cell type and condition (n=3-4 mice per cell type and condition). FIG. 18U shows percentages of CD5$^+$ CD1d$^{hi}$eGFP$^+$B220$^+$ cells in mice treated as in FIG. 11B plus blocking Abs (n=4 each). FIG. 18V shows LPS-stimulated PLN B cells from NOD mice treated with 10 doses of 2.5 mi/IA$^{g7}$-NPs suppress the proliferation of CFSE-labelled BDC2.5 CD4$^+$ T cells by 2.5 mi peptide-pulsed DCs in vitro, as compared to LPS-stimulated PLN B cells from untreated controls. FIG. 18X shows percentage of CD19$^+$CD3$^-$ cells in blood before and after 3 doses of 250 μg of anti-CD20 mAb (n=4). FIG. 18Y, 2.5 mi/IA$^{g7}$-NP-induced upregulation of IL-21 and IL-10 mRNA in memory eGFP$^-$ BDC2.5 CD4$^+$ T cells from BDC2.5-TCR-transgenic NOD Foxp3-eGFP donors in NOD Thy1$^a$ hosts (n=5). P values were calculated by Pearson correlation, Mann-Whitney U-test or two-way ANOVA. Data are averages ±s.e.m.

FIG. 20A shows FACS profiles (cognate versus control tetramer staining in hCD4$^+$ T cells) of samples from mice identified as responders in Table 2. Numerical data on tetramer$^+$ T cells are presented on Table 2. FIG. 20B shows representative FACS profiles (cognate versus control tetramer staining in splenic hCD4$^+$ T cells) of human healthy control PBMC-engrafted NSG hosts treated with IGRP$_{13-25}$/DR3-NPs (left), or human T1D PBMC-engrafted NSG hosts treated with IGRP$_{13-25}$ peptide, IGRP$_{13-25}$ peptide-coated nanoparticles, IGRP$_{13-25}$ peptide-coated microparticles, or left untreated (right). See FIGS. 13A-13I legend for details.

(FIG. 22A) Percentages of 2.5 mi/IA$^{g7}$ tetramer+ cells in splenic CD4+ T-cells of 10 wk-old NOD mice treated with 10 doses (given over 5 wk) of preparations of 2.5 mi/IA$^{g7}$-PF-M displaying different pMHC valencies. The x axis values correspond to the amounts of pMHC (in ug) given in each dose. Data correspond to net values of tetramer+ cells after subtraction of staining with a negative control tetramer (HEL$_{14-22}$/IA$^{g7}$). (FIG. 22B) $T_R1$ CD4+ Treg expansion potency of 10 doses of 2.5 mi/IA$^{g7}$-PF-M vs. 2.5 mi/IA$^{g7}$-SFP-Z NPs given over 5 wk. Data correspond to preparations carrying 22-45 pMHCs/NP. (FIG. 22C) Percentage increase in the mean fluorescence intensity of the TR1 cell marker CD49b on 2.5 mi/IA$^{g7}$ tetramer-positive cells expanded in vivo by different 2.5 mi/IA$^{g7}$-NP preparations as a function of pMHC density. Such relationship did not exist when CD49b upregulation levels were plotted as a function of pMHC dose.

BRIEF DESCRIPTION OF THE TABLES

Figure 1A:
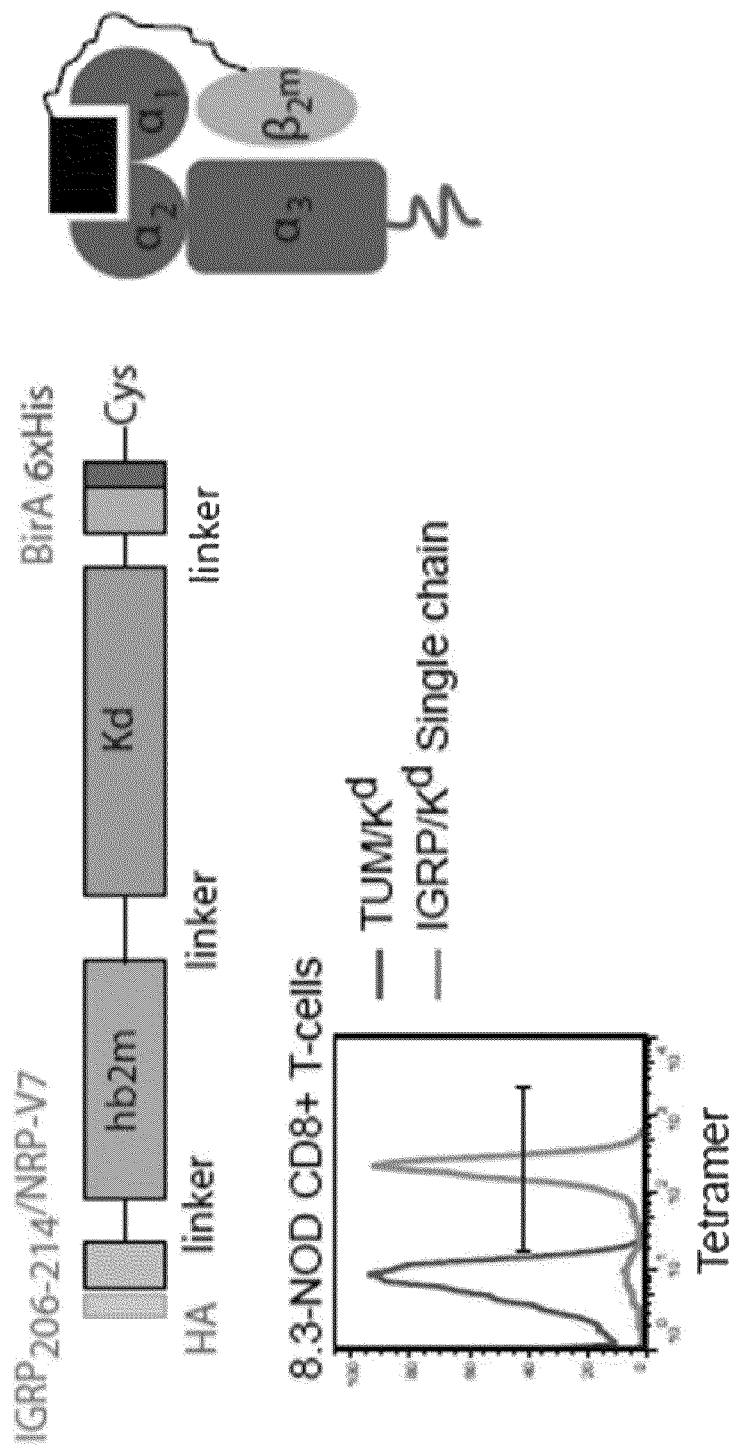
FIGS. 1A-1B show schematics of NP-complexes.
Figure 1B:
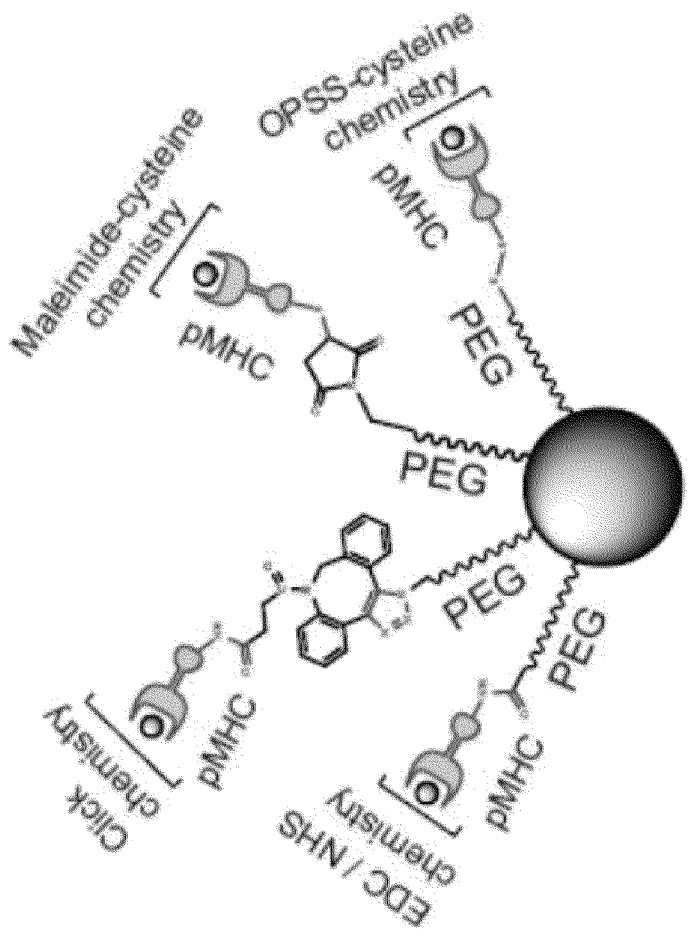
Figure 1B:
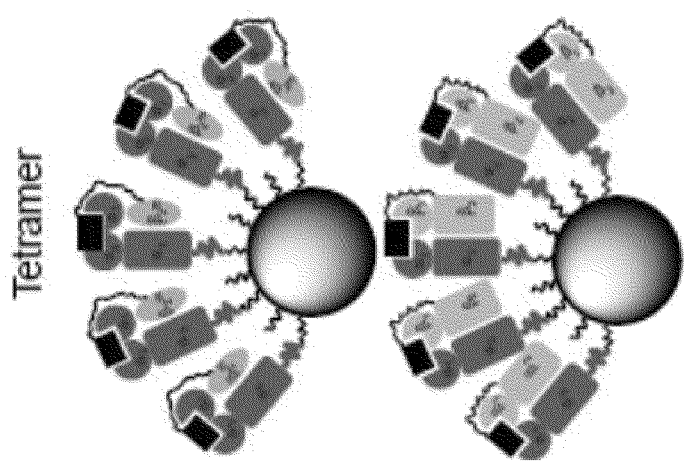

Table 1. Functionalized PEG linkers.

Table 2. Codons.

Tables 3A and 3B. Transcriptional profile of pMHC-NP-expanded CD4+ T-cells. (A) QRT-PCR for a panel of 384 immunological markers in 2.5 mi/IA$^{g7}$ tetramer+ versus tetramer− CD4+ T-cells sorted from NOD mice treated with 10 doses of 2.5 mi/IA$^{g7}$-NPs from 10-15 wk of age (n=3 and 4 samples, respectively). The cells were stimulated in vitro with anti-CD3/anti-CD28 mAb-coated dynabeads before RNA collection. Panel summarizes the most significant differences. (B) QRT-PCR for 8 TR1-relevant markers, including markers that were not represented in the primer set used in (A). Data correspond to four additional 2.5 mi/IA$^{g7}$ tetramer+ and seven tetramer− CD4+ T-cell samples.

Table 4A, 4B, and 4C. Human T1D donors and outcome of pMHC-NP therapy in PBMC-engrafted NSG hosts.

Table 5 is an exemplary list of cancer-relevant antigens for use in this disclosure.

Table 6 is an exemplary list of diabetes-relevant antigens for use in this disclosure.

Table 7 is an exemplary list of multiple sclerosis-relevant antigens for use in this disclosure.

Table 8 is an exemplary list of Celiac Disease-relevant antigens for use in this disclosure.

Table 9 is an exemplary list of primary biliary cirrhosis-relevant antigens for use in this disclosure.

Table 10 is an exemplary list of pemphigus folliaceus-relevant antigens and pemphigus vulgaris-relevant antigens for use in this disclosure.

Table 11 is an exemplary list of neuromyelitis optica spectrum disorder-relevant antigens for use in this disclosure.

Table 12 is an exemplary list of allergic asthma-relevant antigens for use in this disclosure.

Table 13 is an exemplary list of inflammatory bowel disease-relevant antigens for use in this disclosure.

Table 14 is an exemplary list of systemic lupus erythematosus-relevant antigens for use in this disclosure.

Table 15 is an exemplary list of atherosclerosis-relevant antigens for use in this disclosure.

Table 16 is an exemplary list of chronic obstructive pulmonary disease-relevant antigens and emphysema-relevant antigens for use in this disclosure.

Table 17 is an exemplary list of psoriasis-relevant antigens for use in this disclosure.

Table 18 is an exemplary list of autoimmune hepatitis-relevant antigens for use in this disclosure.

Table 19 is an exemplary list of uveitis-relevant antigens for use in this disclosure.

Table 20 is an exemplary list of Sjogren Syndrome-relevant antigens for use in this disclosure.

Table 21 is an exemplary list of scleroderma-relevant antigens for use in this disclosure.

Table 22 is an exemplary list of anti-phospholipid syndrome-relevant antigens for use in this disclosure.

Table 23 is an exemplary list of ANCA-associated vasculitis-relevant antigens for use in this disclosure.

Table 24 is an exemplary list of Stiff Man Syndrome-relevant antigens for use in this disclosure.

DETAILED DESCRIPTION

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "an excipient" includes a plurality of excipients. The term "at least one" intends one or more.

Throughout this application, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (−) 10%, 5%, or 1%.

Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure, such as compositions for treating or preventing multiple sclerosis. "Consisting of" shall mean excluding more than trace elements of other ingredients and substantial method steps. Embodiments defined by each of these transition terms are within the scope of this disclosure.

The terms "inhibiting," "reducing," or "prevention," or any variation of these terms, when used in the claims and/or the specification includes any measurable decrease or complete inhibition to achieve a desired result.

By "biocompatible", it is meant that the components of the delivery system will not cause tissue injury or injury to the human biological system. To impart biocompatibility, polymers and excipients that have had history of safe use in humans or with GRAS (Generally Accepted As Safe) status, will be used preferentially. By biocompatibility, it is meant that the ingredients and excipients used in the composition will ultimately be "bioabsorbed" or cleared by the body with no adverse effects to the body. For a composition to be biocompatible, and be regarded as non-toxic, it must not cause toxicity to cells. Similarly, the term "bioabsorbable" refers to nanoparticles made from materials that undergo bioabsorption in vivo over a period of time such that long term accumulation of the material in the patient is avoided. In a certain embodiment, the biocompatible nanoparticle is bioabsorbed over a period of less than 2 years, preferably less than 1 year and even more preferably less than 6 months. The rate of bioabsorption is related to the size of the particle, the material used, and other factors well recognized by the skilled artisan. A mixture of bioabsorbable, biocompatible materials can be used to form the nanoparticles used in this disclosure. In one embodiment, iron oxide and a biocompatible, bioabsorbable polymer can be combined. For example, iron oxide and PGLA can be combined to form a nanoparticle.

The term "dendrimer," as used herein, refers to a repetitively branched molecule also referred to as an arborol or cascade molecule. With regards to nanoparticle synthesis, the term "dendrimer core" refers to the use of the dendrimer as the central component of a nanoparticle such that it forms the basis of the nanoparticle structure. In some embodiments, the nanoparticle core disclosed herein comprises a dendrimer.

The term "polymeric micelle," as used herein, refers to an amphilic structure that comprises a hydrophobic core and a hydrophilic shell which can be prepared from block copolymers. With regards to nanoparticle synthesis, the term "polymeric micelle core refers to the use of the polymeric micelle as the central component of a nanoparticle such that it forms the basis of the nanoparticle structure. In some embodiments, the nanoparticle core disclosed herein comprises a polymeric micelle.

An antigen-MHC-nanoparticle complex ("NP-complex" or "complex" or pMHC-NP or "nanoparticle complex") refers to presentation of a peptide, carbohydrate, lipid, or other antigenic segment, fragment, or epitope of an antigenic molecule or protein (i.e., self-peptide or autoantigen) on a surface, such as a nanoparticle core.

The "nanoparticle core" is the nanoparticle substrate that does or does not include layers or coatings. The nanoparticle complex comprises the core with at least the antigen-MHC complex coupled to the core.

"Density" when referring to pMHC per nanoparticle is calculated as the surface area of the nanoparticle core with or without outer layers, that can also include linkers. Surface area is the total available surface area of the construct used. In one aspect, when a PEG linker is used, this can increase the total diameter of the nanoparticle core by about 20 nm of the nanoparticle which increases the surface area accordingly of the total available surface area of the nanoparticle. In other words, it is the final surface area of the nanoparticle without the addition of one or more of the pMHC, costimulatory molecules and/or cytokines.

"Antigen" as used herein refers to all, part, fragment, or segment of a molecule that can induce an immune response in a subject or an expansion of an immune cell, preferably a T or B cell.

The term "alkyl" refers to monovalent saturated aliphatic hydrocarbyl groups having from 1 to 10 carbon atoms (i.e., $C_1$-$C_{10}$ alkyl) or 1 to 6 carbon atoms (i.e., $C_1$-$C_6$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

The term "alkoxy" refers to —O-alkyl.

A "mimic" is an analog of a given ligand or peptide, wherein the analog is substantially similar to the ligand. "Substantially similar" means that the analog has a binding profile similar to the ligand except the mimic has one or more functional groups or modifications that collectively accounts for less than about 50%, less than about 40%, less than about 30%, less than about 20%, less than about 10%, or less than about 5% of the molecular weight of the ligand.

"Immune cells" includes, e.g., white blood cells (leukocytes) that are derived from hematopoietic stem cells (HSC) produced in the bone marrow, lymphocytes (T cells, B cells, natural killer (NK) cells) and myeloid-derived cells (neutrophil, eosinophil, basophil, monocyte, macrophage, dendritic cells). As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3, including T-helper cells (CD4+ cells), cytotoxic T-cells (CD8+ cells), natural killer T-cells, T-regulatory cells (Treg) and gamma-delta T cells. A "cytotoxic cell" includes CD8+ T cells, natural-killer (NK) cells, and neutrophils, which cells are capable of mediating cytotoxicity responses.

The term "effector T cells", as used herein, refers to T cells that can specifically bind an antigen and mediate an immune response (effector function) without the need for further differentiation. Examples of effector T cells include CTLs, TH1 cells, TH2 cells, effector memory cells and T helper cells. In contrast to effector T cells, naïve T cells have not encountered their specific antigen: MHC complex, nor responded to it by proliferation and differentiation into an effector T cell. Effector T cells can be resting (in the G0 phase of the cell cycle) or activated (proliferating).

The term "anti-pathogenic autoreactive T cell" refers to a T cell with anti-pathogenic properties (i.e., T cells that counteract an autoimmune disease such as MS, a MS-related disease or disorder, or pre-diabetes). These T cells can include anti-inflammatory T cells, central memory T cells, effector memory T cells, memory T cells, low-avidity T cells, T helper cells, autoregulatory T cells, cytotoxic T cells, natural killer T cells, regulatory T cells, TR1 cells, suppressor T cells, CD4+ T cells, CD8+ T cells and the like.

The term "anti-inflammatory T cell" refers to a T cell that promotes an anti-inflammatory response. The anti-inflammatory function of the T cell may be accomplished through production and/or secretion of anti-inflammatory proteins, cytokines, chemokines, and the like. Anti-inflammatory proteins are also intended to encompass anti-proliferative signals that suppress immune responses. Anti-inflammatory proteins include IL-4, IL-10, IL-13, IL-21, IL-23, IL-27, IFN-α, TGF-β, IL-1ra, G-CSF, and soluble receptors for TNF and IL-6.

The term "differentiated" refers to when a cell of a first type is induced into developing into a cell of a second type. In some embodiments, a cognate T cell is differentiated into a regulatory $T_R1$ cell. In some embodiments, an activated T cell is differentiated into a $T_R1$ cell. In some embodiments, a memory T cell is differentiated into a $T_R1$ cell. In some embodiments, a B cell is differentiated into a regulatory B cell.

As used herein, "knob-in-hole" refers to a polypeptidyl architecture requiring a protuberance (or "knob") at an interface of a first polypeptide and a corresponding cavity (or a "hole") at an interface of a second polypeptide, such that the protuberance can be positioned in the cavity so as to promote heteromultimer formation. Protuberances are constructed by replacing small amino acid side chains from the interface of the first polypeptide with larger side chains (e.g., phenylalanine or tyrosine). Cavities of identical or similar size to the protuberances are created in the interface of the second polypeptide by replacing large amino acid side chains with smaller ones (e.g., alanine or threonine). The protuberances and cavities can be made by synthetic means such as by altering the nucleic acid encoding the polypeptides or by peptide synthesis, using routine methods by one skilled in the art. In some embodiments, the interface of the first polypeptide is located on an Fc domain in the first polypeptide; and the interface of the second polypeptide is located on an Fc domain on the second polypeptide. Knob-in-hole heteromultimers and methods of their preparation and use are disclosed in U.S. Pat. Nos. 5,731,168; 5,807,706; 5,821,333; 7,642,228; 7,695,936; 8,216,805; and 8,679,785, all of which are incorporated by reference herein in their entirety As used herein, "MHC-alpha-Fc/MHC-beta-Fc" refers to heterodimer comprising a first polypeptide and a second polypeptide, wherein the first polypeptide comprises an MHC class II α-chain and an antibody Fc domain; the second polypeptide comprises an MHC class II β-chain and an antibody Fc domain. A knob-in-hole MHC-alpha-Fc/MHC-beta-Fc further requires that the Fc domains of each polypeptide interface with one another through the complementary positioning of a protuberance on one Fc domain within the corresponding cavity on the other Fc domain.

The term "isolated" means separated from constituents, cellular and otherwise, in which the polynucleotide, peptide, polypeptide, protein, antibody, or fragment(s) thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern. A mammalian cell, such as T-cell, is isolated if it is removed from the anatomical site from which it is found in an organism.

An "auto-reactive T cell" is a T cell that recognizes an "auto-antigen", which is a molecule produced and contained by the same individual that contains the T cell.

A "pathogenic T cell" is a T cell that is harmful to a subject containing the T cell. Whereas, a non-pathogenic T cell is not substantially harmful to a subject, and an anti-pathogenic T cells reduces, ameliorates, inhibits, or negates the harm of a pathogenic T cell.

As used herein, the terms regulatory B-cells or B-regulatory cells ("B-regs") intend those cells that are responsible for the anti-inflammatory effect, that is characterized by the expression of CD1d, CD5 and the secretion of IL-10. B-regs are also identified by expression of Tim-1 and can be induced through Tim-1 ligation to promote tolerance. The ability of being B-regs was shown to be driven by many stimulatory factors such as toll-like receptors, CD40-ligand and others. However, full characterization of B-regs is ongoing. B-regs also express high levels of CD25, CD86, and TGF-β. This subset of B cells is able to suppress Th1 proliferation, thus contributing to the maintenance of self-tolerance. The potentiation of B-reg function should become the aim of many immunomodulatory drugs, contributing to a better control of autoimmune diseases. See for example: ncbi.nlm.nih.gov/pubmed/23707422, last accessed on Oct. 31, 2013.

Type-1 T Regulatory ($T_R1$) cells are a subset of CD4+ T cells that have regulatory properties and are able to suppress antigen-specific immune responses in vitro and in vivo. These $T_R1$ cells are defined by their unique profile of cytokine production and make high levels of IL-10 and TGF-beta, but no IL-4 or IL-2. The IL-10 and TGF-beta produced by these cells mediate the inhibition of primary naive T cells in vitro. There is also evidence that $T_R$ cells exist in vivo, and the presence of high IL-10-producing CD4(+) T cells in patients with severe combined immunodeficiency who have received allogeneic stem-cell transplants have been documented. $T_R1$ cells are involved in the regulation of peripheral tolerance and they could potentially be used as a cellular therapy to modulate immune responses in vivo. See for example: ncbi.nlm.nih.gov/pubmed/10887343, last accessed on Oct. 31, 2013.

$T_R1$ cells are defined by their ability to produce high levels of IL-10 and TGF-beta. Tr1 cells specific for a variety of antigens arise in vivo, but may also differentiate from naive CD4+ T cells in the presence of IL-10 in vitro. $T_R1$ cells have a low proliferative capacity, which can be overcome by IL-15. $T_R1$ cells suppress naive and memory T helper type 1 or 2 responses via production of IL-10 and TGF-beta. Further characterization of $T_R1$ cells at the molecular level will define their mechanisms of action and clarify their relationship with other subsets of Tr cells. The use of $T_R1$ cells to identify novel targets for the development of new therapeutic agents, and as a cellular therapy to modulate peripheral tolerance, can be foreseen. See for example, ncbi.nlm.nih.gov/pubmed/11722624, last accessed on Oct. 31, 2013.

An "an effective amount" is an amount sufficient to achieve the intended purpose, non-limiting examples of such include: initiation of the immune response, modulation of the immune response, suppression of an inflammatory response and modulation of T cell activity or T cell populations. In one aspect, the effective amount is one that functions to achieve a stated therapeutic purpose, e.g., a therapeutically effective amount. As described herein in detail, the effective amount, or dosage, depends on the purpose and the composition, and can be determined according to the present disclosure.

An effective amount of therapeutic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

An "MHC multimer" as the term is used herein means a complex of two or more, usually four, up to about fifty or more MHC monomers.

As used herein, a "multimer complex" refers to a complex between a target cell population and one or more pMHC complexes, wherein the MHC protein of the pMHC complex comprises multimeric form of the MHC protein. In some embodiments, the multimeric form of the MHC protein includes a dimer or a trimer.

As used herein, the phrase "immune response" or its equivalent "immunological response" refers to the development of a cell-mediated response (mediated by antigen-specific T cells or their secretion products). A cellular immune response is elicited by the presentation of polypeptide epitopes in association with Class I or Class II MHC molecules, to treat or prevent a viral infection, expand antigen-specific Breg cells, TC1, CD4$^+$ T helper cells and/or CD8+ cytotoxic T cells and/or disease generated, autoregulatory T cell and B cell "memory" cells. The response may also involve activation of other components. In some aspects, the term "immune response" may be used to encompass the formation of a regulatory network of immune cells. Thus, the term "regulatory network formation" may refer to an immune response elicited such that an immune cell, preferably a T cell, more preferably a T regulatory cell, triggers further differentiation of other immune cells, such as but not limited to, B cells or antigen-presenting cells—non limiting examples of which include dendritic cells, monocytes, and macrophages. In certain embodiments, regulatory network formation involves B cells being differentiated into regulatory B cells; in certain embodiments, regulatory network formation involves the formation of tolerogenic antigen-presenting cells.

By "nanosphere," "NP," or "nanoparticle" herein is meant a small discrete particle that is administered singularly or pluraly to a subject, cell specimen or tissue specimen as appropriate. In certain embodiments, the term "nanoparticle" as used herein includes any layers around the nanoparticle core. In certain embodiments, the nanoparticles are substantially spherical in shape. In certain embodiments, the nanoparticle is not a liposome or a viral particle. In further embodiments, the nanoparticle is comprised of any appropriate material, e.g., a solid, a solid core, a metal, a dendrimer, a polymeric micelle, a metal oxide, or a protein or fragment or combinations thereof. The term "substantially spherical," as used herein, means that the shape of the particles does not deviate from a sphere by more than about 10%. Various known antigen or peptide complexes of the disclosure may be applied to the particles. The nanoparticles of this disclosure range in size from about 1 nm to about 1 μm and, preferably, from about 1 nm to about 500 nm or alternatively from about 1 nm to about 100 nm, or alternatively from about 1 nm to about 50 nm or alternatively from about 5 nm to about 100 nm, and in some aspects refers to the average or median diameter of a plurality of nanoparticles when a plurality of nanoparticles are intended. Smaller nanosize particles can be obtained, for example, by the process of fractionation whereby the larger particles are allowed to settle in an aqueous solution. The upper portion of the solution is then recovered by methods known to those of skill in the art. This upper portion is enriched in smaller size particles. The process can be repeated until a desired average size is generated. The term "nanostructure" is used generally to describe structures smaller than about 1 μm.

The terms "inflammatory response" and "inflammation" as used herein indicate the complex biological response of vascular tissues of an individual to harmful stimuli, such as pathogens, damaged cells, or irritants, and includes secretion of cytokines and, more particularly, of pro-inflammatory cytokines, i.e. cytokines which are produced predominantly by activated immune cells and are involved in the amplification of inflammatory reactions. Exemplary pro-inflammatory cytokines include but are not limited to IL-1, IL-6, IL-10, TNF-α, IL-17, IL21, IL23, IL27 and TGF-β. Exemplary inflammations include acute inflammation and chronic inflammation. Acute inflammation indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). Chronic inflammation indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be inhibited in the sense of the present disclosure by affecting and in particular inhibiting any one of the events that form the complex biological response associated with an inflammation in an individual.

As used herein, "CD49b" or "cluster of differentiation 49b" is a protein that is an integrin alpha subunit and makes up about half of the alpha2beta1 integrin duplex. In humans, CD49b is encoded by the CD49 b gene. CD49b can be found on a wide variety of cell types, including T cells, natural killer cells, fibroblasts, and platelets. In some embodiments, the T cell includes a $T_R1$ cell. In some embodiments, the expression of CD49b identifies a $T_R1$ cell. Detection of a cell expressing CD49b can be identified using conventional techniques, such as the use of an anti-CD49b antibody, which are commercially available, e.g., from a vendor such as BioLegend.

As used herein, "Lag3" or "lymphocyte-activation gene 3" or "CD223" or "cluster of differentiation 223" is a protein that is encoded by the Lag3 gene and belongs to the immunoglobulin (Ig) superfamily. Lag 3 is a cell surface protein that is expressed in a variety of cell types, including T cells, natural killer cells, B cells, and plasmacytoid dendritic cells. In some embodiments, the T cell includes a $T_R1$ cell. In some embodiments, the expression of Lag3 identifies a $T_R1$ cell. Detection of a cell expressing Lag3 can be identified using conventional techniques, such as the use of an anti-Lag3 antibody, which are commercially available, e.g., from a vendor such as BioLegend.

As used herein, the term "disease-relevant" antigen intends an antigen or fragment thereof selected to treat a selected disease and is involved in the disease process. For example, a diabetes-relevant antigen is an antigen or fragment thereof that, when presented, produces an immune response that serves to treat diabetes; thus, a diabetes-relevant antigen producing such an effect is selected to treat diabetes. A multiple sclerosis (MS)-relevant antigen is selected to treat MS. A diabetes-relevant antigen would not be selected to treat MS. Similarly, an autoimmunity-related antigen is an antigen that is relevant to an autoimmune disease and would not be selected for the treatment of a disorder or disease other than autoimmunity, e.g., cancer. Non-limiting, exemplary disease-relevant antigens are disclosed herein and further, such antigens may be determined for a particular disease based on techniques, mechanisms, and methods documented in the literature.

"Autoimmune disease or disorder" includes diseases or disorders arising from and directed against an individual's own tissues or organs or manifestation thereof or a condition resulting there from. In one embodiment, it refers to a condition that results from, or is aggravated by, the production by T cells that are reactive with normal body tissues and antigens. Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica spectrum disorder (NMO, also known as Devic's Disease or Devic's Syndrome), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, Type I diabetes, Type II diabetes, latent autoimmune diabetes in adults (or Type 1.5 diabetes) Also contemplated are immune responses associated with acute and delayed hypersensitivity mediated by cytokines and T-lymphocytes, sarcoidosis, granulomatosis including lymphomatoid granulomatosis, Wegener's granulomatosis, agranulocytosis, vasculitides, including vasculitis, large-vessel vasculitis (including polymyalgia rheumatica and gianT cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), Addison's disease, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, anti-phospholipid syndrome, allergic neuritis, Behcet's disease/ syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, autoimmune or immune-mediated thrombocytopenia such as idiopathic thrombocytopenic purpura (ITP) including chronic or acute ITP, acquired thrombocytopenic purpura, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, gianT cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, gianT cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, emphysema, alopecia areata, adipose tissue inflammation/diabetes type II, obesity associated adipose tissue inflammation/insulin resistance, and endometriosis.

In some embodiments, the autoimmune disorder or disease may include, but is not limited to, diabetes melitus Type I and Type II, pre-diabetes, transplantation rejection, multiple sclerosis, a multiple-sclerosis related disorder, premature ovarian failure, scleroderma, Sjogren's disease/syndrome, lupus, vitiligo, alopecia (baldness), polyglandular failure, Grave's disease, hypothyroidism, polymyositits, pemphigus, Crohn's disease, colitis, autoimmune hepatitis, hypopituitarism, myocarditis, Addison's disease, autoimmune skin diseases, uveitis, pernicious anemia, hypoparathyroidism, and/or rheumatoid arthritis. Other indications of interest include, but are not limited to, asthma, allergic asthma, primary biliary cirrhosis, cirrhosis, Neuromyelitis Optica Spectrum Disorder (Devic's disease, opticospinal multiple scleroris (OSMS)), Pemphigus vulgaris, inflammatory bowel disease (IBD), arthritis, Rheumatoid arthritis, systemic lupus erythematosus (SLE), Celiac disease, psoriasis, autoimmune cardiomyopathy, idiopathic dilated cardiomyopathy (IDCM), a Myasthyenia Gravis, Uveitis, Ankylosing Spondylitis, Immune Mediated Myopathies, prostate cancer, anti-phospholipid syndrome (ANCA+), atherosclerosis, dermatomyositis, chronic obstructive pulmonary disease (COPD), emphysema, spinal cord injury, traumatic injury, a tobacco-induced lung destruction, ANCA-associated vasculitis, psoriasis, sclerosing cholangitis, primary sclerosing cholangitis, and diseases of the central and peripheral nervous systems.

In some embodiments, the autoimmune disorder or disease may include, but is not limited to, diabetes, multiple sclerosis, Celiac Disease, primary biliary cirrhosis, pemphigus, pemphigus folliaceus, pemphigus vulgaris, neuromyelitis optica spectrum disorder, arthritis (including rheumatoid arthritis), allergic asthma, inflammatory bowel disease (including Crohn's disease and ulcerative colitis), systemic lupus erythematosus, atherosclerosis, chronic obstructive pulmonary disease, emphysema, psoriasis, autoimmune hepatitis, uveitis, Sjogren's Syndrome, scleroderma, anti-phospholipid syndrome, ANCA-associated vasculitis, and Stiff Man Syndrome.

As used herein, the term "adipose tissue inflammation/diabetes type II" refers to the adipose tissue inflammation exhibited by a subject suffering from type II diabetes. The adipose tissue inflammation contributes to the development of insulin resistance in the subject.

As used herein, the term "obesity associated adipose tissue inflammation/insulin resistance" refers to the adipose tissue inflammation exhibited by a subject suffering from obesity. The adipose tissue inflammation contributes to the insulin resistance of the subject, thereby increasing the likelihood that the adipose tissue inflammation will result in the pathogensis of type II diabetes.

As used herein, the term "canonical sequence" refers to the protein sequence used as a reference for amino acid numbering in the absence of further guidance in the disclosure or the existing art. As is apparent to those of skill in the art, the termini of the antigenic fragments may vary with the reference sequence from which the fragment has been mapped to. Thus, it is to be understood unless specifically stated otherwise that the fragment identifiers are approximate termini.

As used herein, "PPI" refers to all isoforms, variants, and fragments thereof of a protein associated with the name "preproinsulin," a biologically inactive precursor to the biologically active endocrine hormone insulin, or a biological equivalent thereof. The canonical sequence of the isoform PPI is 110 amino acids in length:

```
                                       (SEQ ID NO: 1)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN.
```

As used herein, "IGRP" refers to all isoforms, variants, and fragments thereof of a protein associated with the name "islet-specific glucose-6-phosphatase catalytic subunit-related protein" or "Glucose-6-phosphatase-2" a major autoantigen for autoimmune type 1 diabetes, or a biological equivalent thereof. The canonical sequence of IGRP is 355 amino acids in length:

(SEQ ID NO: 2)
MDFLHRNGVLIIQHLQKDYRAYYTFLNFMSNVGDPRNIFFIYFPLCFQFN

QTVGTKMIWVAVIGDWLNLIFKWILFGHRPYWWVQETQIYPNHSSPCLEQ

FPTTCETGPGSPSGHAMGASCVWYVMVTAALSHTVCGMDKFSITLHRLTW

SFLWSVFWLIQISVCISRVFIATHFPHQVILGVIGGMLVAEAFEHTPGIQ

TASLGTYLKTNLFLFLFAVGFYLLLRVLNIDLLWSVPIAKKWCANPDWIH

IDTTPFAGLVRNLGVLFGLGFAINSEMFLLSCRGGNNYTLSFRLLCALTS

LTILQLYHFLQIPTHEEHLFYVLSFCKSASIPLTVVAFIPYSVHMLMKQS

GKKSQ.

As used herein, "GAD" refers to all isoforms, variants, and fragments thereof of a protein associated with the name "glutamic acid decarboxylase" a diabetes-associated antigen, or a biological equivalent thereof. GAD may optionally refer to GAD1, GAD2, GAD65, GAD67, or any other diabetes relevant glutamic acid decarboxylase. The canonical sequence of the isoform GAD2 is 585 amino acids in length and is disclosed herein below:

(SEQ ID NO: 3)
MASPGSGFWS FGSEDGSGDS ENPGTARAWC QVAQKFTGGI GNKLCALLYG

DAEKPAESGGSQPPRAAARK AACACDQKPC SCSKVDVNYA FLHATDLLPA

CDGERPTLAF LQDVMNILLQYVVKSFDRST KVIDFHYPNE LLQEYNWELA

DQPQNLEEIL MHCQTTLKYA IKTGHPRYFNQLSTGLDMVG LAADWLTSTA

NTNMFTYEIA PVFVLLEYVT LKKMREIIGW PGGSGDGIFSPGGAISNMYA

MMIARFKMFP EVKEKGMAAL PRLIAFTSEH SHFSLKKGAA

ALGIGTDSVILIKCDERGKM IPSDLERRIL EAKQKGFVPF LVSATAGTTV

YGAFDPLLAV ADICKKYKIWMHVDAAWGGG LLMSRKHKWK LSGVERANSV

TWNPHKMMGV PLQCSALLVR EEGLMQNCNQMHASYLFQQD KHYDLSYDTG

DKALQCGRHV DVFKLWLMWR AKGTTGFEAH VDKCLELAEYLYNIIKNREG

YEMVFDGKPQ HTNVCFWYIP PSLRTLEDNE ERMSRLSKVA

PVIKARMMEYGTTMVSYQPL GDKVNFFRMV ISNPAATHQD IDFLIEEIER LGQDL.

As used herein "peripherin" refers to all isoforms, variants, and fragments thereof of a protein associated with that name, or a biological equivalent thereof. A non-limiting exemplary sequence of human peripherin associated with UniProt Reference No. P41219 is disclosed herein below:

(SEQ ID NO: 4)
MSHHPSGLRAGFSSTSYRRTFGPPPSLSPGAFSYSSSSRFSSSRLLGSAS

PSSSVRLGSFRSPRAGAGALLRLPSERLDFSMAEALNQEFLATRSNEKQE

LQELNDRFANFIEKVRFLEQQNAALRGELSQARGQEPARADQLCQQELRE

LRRELELLGRERDRVQVERDGLAEDLAALKQRLEEETRKREDAEHNLVLF

RKDVDDATLSRLELERKIESLMDEIEFLKKLHEEELRDLQVSVESQQVQQ

VEVEATVKPELTAALRDIRAQYESIAAKNLQEAEEWYKSKYADLSDAANR

NHEALRQAKQEMNESRRQIQSLTCEVDGLRGTNEALLRQLRELEEQFALE

AGGYQAGAARLEEELRQLKEEMARHLREYQELLNVKMALDIEIATYRKLL

EGEESRISVPVHSFASLNIKTTVPEVEPPQDSHSRKTVLIKTIETRNGEV

VTESQKEQRSELDKSSAHSY.

As used herein, "aGlia" refers to all isoforms, variants, and fragments thereof of a protein associated with the name "Alpha/beta-gliadin," derived from a member of the wheat family or another celiac-related allergen, or a biological equivalent thereof. A non-limiting exemplary sequence of alpha-gliadin expressed in wheat associated with GenBank Accession No. CAA10257.1 is:

(SEQ ID NO: 5)
MKTFLILALLAIVATTATTAVRVPVPQLQPQNPSQQQPQEQVPLVQQQQF

LGQQQPFPPQQPYPQPQPFPSQQPYLQLQPFPQPQLPYSQPQPFRPQQPY

PQPQPQYSQPQQPISQQQQQQQQQQQQQQQQQQQQILQQILQQQLIPCMD

VVLQQHNIAHGRSQVLQQSTYQLLQELCCQHLWQIPEQSQCQAIHKVVHA

IILHQQQKQQQQPSSQVSFQQPLQQYPLGQGSFRPSQQNPQAQGSVQPQQ

LPQFEEIRNLALQTLPAMCNVYIPPYCTITPFGIFGTN.

Another non-limiting exemplary sequence of alpha-gliadin expressed in wheat is disclosed herein below:

(SEQ ID NO: 6)
VRVPVPQLQPQNPSQQQPQEQVPLVQQQQFLGQQQPFPPQQPYPQPQPFP

SQQPYLQLQPFPQPQLPYSQPQPFRPQQPYPQPQPQYSQPQQPISQQQQ

QQQQQQQQQQQQILQQILQQQLIPCMDVVLQQHNIAHGRSQVLQQST

YQLLQELCCQHLWQIPEQSQCQAIHKVVHAIILHQQQKQQQQPSSQVSFQ

QPLQQYPLGQGSFRPSQQNPQAQGSVQPQQLPQFEEIRNLALQTLPAMCN

VYIPPYCTITPFGIFGTN.

As used herein, "PDC-E2" refers to all isoforms, variants, and fragments thereof of a protein associated with the name "dihydrolipoamide S-acetyltransferase" or "DLAT," an autoantigen of primary biliary cirrhosis, or a biological equivalent thereof. The canonical sequence of PDC-E2 is 647 amino acids in length and is disclosed herein below:

```
                                        (SEQ ID NO: 7)
MWRVCARRAQ NVAPWAGLEA RWTALQEVPG TPRVTSRSGP

APARRNSVTT GYGGVRALCG WTPSSGATPR NRLLLQLLGS

PGRRYYSLPP HQKVPLPSLS PTMQAGTIAR WEKKEGDKIN

EGDLIAEVET DKATVGFESL EECYMAKILV AEGTRDVPIG

AIICITVGKP EDIEAFKNYT LDSSAAPTPQ AAPAPTPAAT

ASPPTPSAQA PGSSYPPHMQ VLLPALSPTM

TMGTVQRWEK KVGEKLSEGD LLAEIETDKA TIGFEVQEEG

YLAKILVPEG TRDVPLGTPL CIIVEKEADI SAFADYRPTE

VTDLKPQVPP PTPPPVAAVP PTPQPLAPTP SAPCPATPAG

PKGRVFVSPL AKKLAVEKGI DLTQVKGTGP DGRITKKDID

SFVPSKVAPA PAAVVPPTGP GMAPVPTGVF TDIPISNIRR

VIAQRLMQSK QTIPHYYLSI DVNMGEVLLV RKELNKILEG

RSKISVNDFI IKASALACLK VPEANSSWMD TVIRQNHVVD

VSVAVSTPAG LITPIVFNAH IKGVETIANDV VSLATKARE

GKLQPHEFQG GTFTISNLGM FGIKNFSAII NPPQACILAI

GASEDKLVPA DNEKGFDVAS MMSVTLSCDH RVVDGAVGAQ

WLAEFRKYLE KPITMLL.
```

As used herein, "Insulin" refers to all isoforms, variants, and fragments thereof of a protein associated with that name, or a biological equivalent thereof. A non-limiting exemplary sequence of human insulin associated with UniProt Reference No. P01308 is disclosed herein below:

```
                                        (SEQ ID NO: 1)
MALWMRLLPL LALLALWGPD PAAAFVNQHL CGSHLVEALY LVCGERGFFY

TPKTRREAED LQVGQVELGG GPGAGSLQPL ALEGSLQKRG IVEQCCTSIC

SLYQLENYCN.
```

As used herein, "DG1EC2" refers to all isoforms, variants, and fragments thereof of a protein associated with the name "desmosomal glycoprotein 1," or a biological equivalent thereof. The canonical sequence of DG1EC2 is 1054 amino acids in length and is disclosed herein below:

```
                                        (SEQ ID NO: 8)
MNWHFLRTAT VLLIFLVVVE INSEFRIQVR DYNTKNGTIK

WHSIRRQKRE WIKFAAACREGEDNSKRNPI AKIHSDCAAN

QQVTYRISGV GIDQPPYGIF IINQKTGEIN

ITSIVDREIT PFFIIYCRAL NSLGQDLERP LELRVRVLDI

NDNPPVFSMS TFVGQIEENS NANTLVMRLN ATGADEPNNL

NSKIAFKIIR QEPSDSPMFI INRNTGEIRT MNNFLDREQY

SQYSLAVRGS DRDGGADGMS AECECNIKIL DVNDNIPYME

PSSHMVRIEE NALSQNLVEI RVIDLDEEFS ANWMAVIFFI

SGNEGGWFDI EMNERTNVGI LKVIKPLDYE AVQNLQLSLG

VRNKADFHHS IMSQYKVTAT AISVTVLNVI EGSVFRPGSK

TYVVRSDMGQ NYKVGDFVAT DLDTGLASTT VRYVMGNNPA

NLLNVDSKTG VITLRNKVTM EQYEMLNGKY QGTILSIDDA

LQRTCTGTIN IDLQGSGWEK DSEKVTSSQN SGSSTGDSSG

GTGGGGRENP SEGDTTTNTG GKTSTDYEDG ETQTQSNNNH

QELGSNNLSD NVHFGPAGIG LLIMGFLVLG LVPFLLMCCD

CGGAPGAGAG FEPVPECSDG AIHSWAVEGP QPLPTDATTV

CVPPIPSNNA NVIECIDTSG VYTNEYGGREM QDLGGGERT

TGFELTEGVK TSGVPEICQE YSGTLRRNSM RECREGGLNM

NFMESYFCQK AYAYADEDEG RPSNDCLLIY DIEGVGSPAG

SVGCCSFIGE DLDDSFLDTL GPKFKKLADI SLGKEVEPDP

SWPPESTEPI CPQQGTEPII GGHPPISPHF GTTTVISENT

YPSGPGVQHP MPIPDPLGYG NVTVTESYTT SGTLKPTVHV

HDNRHASNVV VTERVVGPIS GTDLHGMLEM PDLRDGSNVI.
```

As used herein, "DG3" refers to all isoforms, variants, and fragments thereof of a protein associated with the name "desmoglein 3", or a biological equivalent thereof. A non-limiting exemplary sequence of human desmoglein 3 associated with UniProt Reference No. P32926-1 is disclosed herein below:

```
                                        (SEQ ID NO: 9)
MMGLFPRTTGALAIFVVVILVHGELRIETKGQYDEEEMTMQQAKRRQKRE

WVKFAKPCREGEDNSKRNPIAKITSDYQATQKITYRISGVGIDQPPFGIF

VVDKNTGDINITAIVDREETPSFLITCRALNAQGLDVEKPLILTVKILDI

NDNPPVFSQQIFMGEIEENSASNSLVMILNATDADEPNHLNSKIAFKIVS

QEPAGTPMFLLSRNTGEVRTLTNSLDREQASSYRLVVSGADKDGEGLSTQ

CECNIKVKDVNDNFPMFRDSQYSARIEENILSSELLRFQVTDLDEEYTDN

WLAVYFFTSGNEGNWFEIQTDPRTNEGILKVVKALDYEQLQSVKLSIAVK

NKAEFHQSVISRYRVQSTPVTIQVINVREGIAFRPASKTFTVQKGISSKK

LVDYILGTYQAIDEDTNKAASNVKYVMGRNDGGYLMIDSKTAEIKFVKNM

NRDSTFIVNKTITAEVLAIDEYTGKTSTGTVYVRVPDFNDNCPTAVLEKD

AVCSSSPSVVVSARTLNNRYTGPYTFALEDQPVKLPAVWSITTLNATSAL

LRAQEQIPPGVYHISLVLTDSQNNRCEMPRSLTLEVCQCDNRGICGTSYP

TTSPGTRYGRPHSGRLGPAAIGLLLLGLLLLLLAPLLLLTCDCGAGSTGG

VTGGFIPVPDGSEGTIHQWGIEGAHPEDKEITNICVPPVTANGADFMESS

EVCTNTYARGTAVEGTSGMEMTTKLGAATESGGAAGFATGTVSGAASGFG
```

```
AATGVGICSSGQSGTMRTRHSTGGTNKDYADGAISMNFLDSYFSQKAFAC

AEEDDGQEANDCLLIYDNEGADATGSPVGSVGCCSFIADDLDDSFLDSLG

PKFKKLAEISLGVDGEGKEVQPPSKDSGYGIESCGHPIEVQQTGFVKCQT

LSGSQGASALSTSGSVQPAVSIPDPLQHGNYLVTETYSASGSLVQPSTAG

FDPLLTQNVIVTERVICPISSVPGNLAGPTQLRGSHTMLCTEDPCSRLI.
```

As used herein, "AQP4" refers to all isoforms, variants, and fragments thereof of a protein associated with the name "aquaporin 4," which belongs to the aquaporin family of integral membrane proteins that conduct water through the cell membrane and is the primary autoimmune target of neuromyelitis optica spectrum disorder, or a biological equivalent thereof. The canonical sequence of AQP4 is 323 amino acids in length and is disclosed herein below:

```
                                        (SEQ ID NO: 10)
MSDRPTARRWGKCGPLCTRENIMVAFKGVWTQAFWKAVTAEFLAMLIFVL

LSLGSTINWGGTEKPLPVDMVLISLCFGLSIATMVQCFGHISGGHINPAV

TVAMVCTRKISIAKSVFYIAAQCLGAIIGAGILYLVTPPSVVGGLGVTMV

HGNLTAGHGLLVELIITFQLVFTIFASCDSKRTDVTGSIALAIGFSVAIG

HLFAINYTGASMNPARSFGPAVIMGNWENHWIYWVGPIIGAVLAGGLYEY

VFCPDVEFKRRFKEAFSKAAQQTKGSYMEVEDNRSQVETDDLILKPGVVH

VIDVDRGEEKKGKDQSGEVLSSV.
```

As used herein, "PLP" refers to all isoforms, variants, and fragments thereof of a protein associated with the name "myelin proteolipid protein", or a biological equivalent thereof. A non-limiting exemplary sequence of human myelin proteolipid protein associated with UniProt Reference No. P60201 is disclosed herein below:

```
                                        (SEQ ID NO: 11)
MGLLECCARCLVGAPFASLVATGLCFFGVALFCGCGHEALTGTEKLIETY

FSKNYQDYEYLINVIHAFQYVIYGTASFFFLYGALLLAEGFYTTGAVRQI

FGDYKTTICGKGLSATVTGGQKGRGSRGQHQAHSLERVCHCLGKWLGHPD

KFVGITYALTVVWLLVFACSAVPVYIYFNTWTTCQSIAFPSKTSASIGSL

CADARMYGVLPWNAFPGKVCGSNLLSICKTAEFQMTFHLFIAAFVGAAAT

LVSLLTFMIAATYNFAVLKLMGRGTKF.
```

As used herein, "MOG" refers to all isoforms, variants, and fragments thereof of a protein associated with the name "Myelin Oligodendrocyte Glycoprotein," or a biological equivalent thereof. A non-limiting exemplary sequence of human myelin oligodendrocyte glycoprotein associated with UniProt Reference No. Q16653 is disclosed herein below:

```
                                        (SEQ ID NO: 12)
MASLSRPSLPSCLCSFLLLLLLQVSSSYAGQFRVIGPRHPIRALVGDEVE

LPCRISPGKNATGMEVGWYRPPFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLIFLCLQYRLRGKLRAEIENLHRTFDPH

FLRVPCWKITLFVIVPVLGPLVALIICYNWLHRRLAGQFLEELRNPF.
```

As used herein "MBP" refers to all isoforms, variants, and fragments thereof of a protein associated with the name "myelin basic protein", or a biological equivalent thereof. A non-limiting exemplary sequence of human myelin basic protein associated with UniProt Reference No. P02686 is disclosed herein below:

```
                                        (SEQ ID NO: 13)
MGNHAGKRELNAEKASTNSETNRGESEKKRNLGELSRTTSEDNEVFGEAD

ANQNNGTSSQDTAVTDSKRTADPKNAWQDAHPADPGSRPHLIRLFSRDAP

GREDNTFKDRPSESDELQTIQEDSAATSESLDVMASQKRPSQRHGSKYLA

TASTMDHARHGFLPRHRDTGILDSIGRFFGGDRGAPKRGSGKDSHHPART

AHYGSLPQKSHGRTQDENPVVHFFKNIVTPRTPPPSQGKGRGLSLSRFSW

GAEGQRPGFGYGGRASDYKSAHKGFKGVDAQGTLSKIFKLGGRDSRSGSP

MARR.
```

As used herein, "CII" refers to all isoforms, variants, and fragments thereof of a protein associated with the name "native collagen type II", a high molecular-weight fibrillar molecule implicated in chronic polyarthritis, or a biological equivalent thereof. A non-limiting exemplary consensus sequence of human collagen II is disclosed herein below:

```
                                        (SEQ ID NO: 14)
MRGASVTVAAVRCGDVAGSCVDGRYNDKDVWKCRCVCDTGTVCDDCDVKD

CSGCCCTDATASGGKGKGGDKDVGKGGGAGGRGDRGDKGKGAGRGRDGGT

GNGGGGGGNAAMAGGDKAGGAGVMGMGMGRGGAGAGGGNGGGVSGMGRG

GGKGDDGAGKGKAGRGGGARGGTGGVKGHRGYGDGAKGAGAGVKGSGSGN

GSGMGRGGRGRTGAGAAGARGNDGGAGGVGAGGGGAGAKGAGTGARGGAG

RGGTGSGAGASGNGTDGGAKGSAGAGAGAGGRGGGATGGKGTGGAGKGGK

GGAGGAGAGGKRGARGGGVGGGRGAGNRGGDGAGKGAGRGSGAGKGANGD

GRGGGARGTGRGDAGGKVGSGAGDGRGGGARGGVMGGKGANGGKAGKGGA

GRGGKDGTGAAGGAGAGRGGAGSGGGGGGGKGDGVGAGAGVGRGRGGRGS

GAGGRGGTGTDGKGASGAGGAGGGMGRGAAGAGKGDRGDVGKGGAGKDGG

RGTGGGAGANGKGVGGAGSAGARGAGRGTGGAGAGGADGGAKGGAGKGDA

GAGGSGAGGTGVTGKGARGAGGATGGAAGRVGGSNGNGGGSGKDGKGARG

DSGGRAGGGAGGKGGDDGSGAGGGAGRGVGGRGRGGGSGGKGAGASGDRG

GVGGTGAGGRGSGADGGRDGAAGVKGDRGTGAVGAGAGGSGAGTGKGDRG

AGAGMGSGAGARGGGRGDKGAGGRGKGHRGTGGGGSGDGASGAGSGRGGV

GSGKDGANGGGRGRSGTGAGGNGGGGDMSAAGGRKGDYMRADAAGGRH

DAVDATKSNNSRSGSRKNARTCRDKCHWKSGDYWDNGCTDAMKVCNMTGT

CVYNANVKKNWWSSKSKKKHWGTNGGHSYGDDNANTANVMTRSTGSNTYH

CKNSAYDAAGNKKAGSNDVRAGNSRTYTAKDGCTKHTGKWGKTVYRSKTS

RDAMDGGGVDGVC.
```

Another non-limiting exemplary sequence of murine collagen II is disclosed herein below:

```
                                        (SEQ ID NO: 15)
MIRLGAPQSL VLLTLLIAAV LRCQGQDARK LGPKGQKGEP

GDIRDIIGPR GPPGPQGPAGEQGPRGDRGD KGEKGAPGPR
```

```
GRDGEPGTPG NPGPAGPPGP PGPPGLSAGN

FAAQMAGGYDEKAGGAQMGV MQGPMGPMGP RGPPGPAGAP

GPQGFQGNPG EPGEPGVSGP MGPRGPPGPAGKPGDDGEAG

KPGKSGERGL PGPQGARGFP GTPGLPGVKG HRGYPGLDGA

KGEAGAPGVKGESGSPGENG SPGPMGPRGL PGERGRTGPA

GAAGARGNDG QPGPAGPPGP VGPAGGPGFP GAPGAKGEAG

PTGARGPEGA QGSRGEPGNP GSPGPAGASG NPGTDGIPGA

KGSAGAPGIAGAPGFPGPRG PPGPQGATGP LGPKGQAGEP

GIAGFKGDQG PKGETGPAGP QGAPGPAGEEGKRGARGEPG

GAGPIGPPGE RGAPGNRGFP GQDGLAGPKG APGERGPSGL

TGPKGANGDPGRPGEPGLPG ARGLTGRPGD AGPQGKVGPS

GAPGEDGRPG PPGPQGARGQ PGVMGFPGPKGANGEPGKAG

EKGLAGAPGL RGLPGKDGET GAAGPPGPSG PAGERGEQGA

PGPSGFQGLP GPPGPPGEGG KQGDQGIPGE AGAPGLVGPR

GERGFPGERG SPGAQGLQGP RGLPGTPGTDGPKGAAGPDG

PPGAQGPPGL QGMPGERGAA GIAGPKGDRG DVGEKGPEGA

PGKDGGRGLTGPIGPPGPAG ANGEKGEVGP PGPSGSTGAR

GAPGERGETG PPGPAGFAGP PGADGQPGAKGDQGEAGQKG

DAGAPGPQGP SGAPGPQGPT GVTGPKGARG AQGPPGATGF

PGAAGRVGPPGANGNPGPAG PPGPAGKDGP KGVRGDSGPP

GRAGDPGLQG PAGAPGEKGE PGDDGPSGLD GPPGPQGLAG

QRGIVGLPGQ RGERGFPGLP GPSGEPGKQG APGASGDRGP

PGPVGPPGLTGPAGEPGREG SPGADGPPGR DGAAGVKGDR

GETGALGAPG APGPPGSPGP AGPTGKQGDRGEAGAQGPMG

PSGPAGARGI AGPQGPRGDK GESGEQGERG LKGHRGFTGL

QGLPGPPGPSGDQGASGPAG PSGPRGPPGP VGPSGKDGSN

GIPGPIGPPG PRGRSGETGP VGPPGSPGPPGPPGPGI

DMSAFAGLGQ REKGPDPMQY MRADEADSTL RQHDVEVDAT

LKSLNNQIES IRSPDGSRKN PARTCQDLKL CHPEWKSGDY

WIDPNQGCTL DAMKVFCNME TGETCVYPNPATVPRKNWWS

SKSKEKKHIW FGETMNGGFH FSYGDGNLAP NTANVQMTFL

RLLSTEGSQNITYHCKNSIA YLDEAAGNLK KALLIQGSND

VEMRAEGNSR FTYTALKDGC TKHTGKWGKTVIEYRSQKTS

RLPIIDIAPM DIGGAEQEFG VDIGPVCFL.
```

As used herein, "DERP1" refers to all isoforms, variants, and fragments thereof of a protein associated with the name "Dermatophagoides pteronyssius p1" and known to cause an allergic reaction in humans, or a biological equivalent thereof. A non-limiting exemplary consensus sequence of DERP1 is disclosed herein below:

```
                                        (SEQ ID NO: 16)
NEIAXAKIDLRQMRTVTPIXMQGGCGSCWALSGVAATESAYLAYGNXSLD

LAEQELVDCASQHGCHGDTIPRGIEYIQHNGVVQESYYRYVAREQSCRRP

NAQRFGISNYCQIYPPNVNKIREALAQTHSAIAVIIGIKDLDAFRHYDGR

TIIQRDNGYQPNYHAVNIVGYSNAQGVDYWIVRNSWDTNWGDNGYGYFAA

NIDLMMIEEYPYVVIL.
```

As used herein, "DERP2" refers to all isoforms, variants, and fragments thereof of a protein associated with the name "Dermatophagoides pteronyssius p2" and known to cause an allergic reaction in humans, or a biological equivalent thereof. A non-limiting exemplary consensus sequence of DERP2 is disclosed herein below:

```
                                        (SEQ ID NO: 17)
MMYKILCLSLLVAAVARDQVDVKDCANHEIKKVLVPGCHGSEPCIIHRGK

PFQLEAVFEANQNTKTAKIEIKASIDGLEVDVPGIDPNACHYMKCPLVKG

QQYDIKYTWNVPKIAPKSENVVVTVKVMGDDGVLACAIATHAKIRD.
```

As used herein, "OVA" refers to all isoforms, variants, and fragments thereof of a protein associated with the name "ovalbumin" for use in generating allergic response in mice, or a biological equivalent thereof.

As used herein "BacInt" or "bacteroides integrase" refers to all isoforms, variants, and fragments thereof of a protein associated with that name, or a biological equivalent thereof. The canonical sequence of BacInt is 406 amino acids in length and disclosed herein below:

```
                                        (SEQ ID NO: 18)
MDKIRYRLVYNRQNTLNRQGTALVQVEAYLNQRKIYLKTNVYLKPECWSR

EGAQVINHPQSNELNIMLYEYILYLQGIELGYWKRGIPATLSLLKDAVKK

KSAVNISFSTFAKSAIDNSDKKQSTKDNLHSTLAVLHDFRSGLDFKDLTY

TFLRDFEQYLREKGNAVNTIAKHMRQLRTLVNEAINQGYMHADAYPFRKY

KIKQEKGRHEFLTPDELKKLETVEVEEESMRHVLDAFLFCCYTGLRYSDF

CQLTPENFIRINGKRWLYFKSVKTGVEIRLPLHLLFESRALGILDRYPDI

GSFAALPCNSEVNKQLRKLAGLCGIKKRITYHVSRHTCATLLIHQGVAIT

TVQKLLGHTSVKTTQIYSEVLSSTIVRDLKNVQKGKRKVKMFPDKGLRTS

DFIDNR.
```

As used herein, "CBir," "Fla-X," and/or "Fla-2" refers to all isoforms, variants, and fragments thereof of a protein associated with of one or more bacterial flagellins implicated in colitis, or a biological equivalent thereof. A non-limiting exemplary sequence of Fla-X is disclosed herein below:

```
                                        (SEQ ID NO: 19)
MVVQHNLRAMNSNRMLGITQGSLNKSTEKLSSGYKVNRAADDAAGLSISE

KMRKQIRGLSQASLNAEDGISAVQTAEGALTEVHDMLQRMNELAVKAANG

TNSTSDRQTIQDEVDQLLTEIDRVAETTKFNELYTLKGDEDKVTRYLSAH

DAGIEGTLTQGATNATFSMDQLKFGDTIMIAGREYHISGTKAEQAAIITA

SVKIGQQVTIDGIMYTCSSVSNADKFELKSEDLIAKLDTSSLSLMSVNGK

TYYGAGITDDRTVVSSIGAYKLIQKELGLASSIGADGATQASVNAGVDGK

TLMKPSFEGKWVFSIDKGSVQVREDIDFSLHVGADADMNNKIAVKIGALD
```

TKGLGIQGLNVKDTTGAAATYAIDSIADAVARISAQRSLLGAVQNRLEHT

INNLDNVVENTTAAESQIRDTDMATEMVKYSNNNVLAQAGQSMLAQSNQA

NQGVLQLLQ.

A non-limiting exemplary sequence of Fla-2 is disclosed herein below:

(SEQ ID NO: 20)
MVVQHNLRAMNSNRMLGITQGSLNKSTEKLSSGYKVNRAADDAAGLSISE

KMRKQIRGLSQASLNAEDGISAVQTAEGALTEVHDMLQRMNELAVKAANG

TNSTSDRQTIQDEVDQLLTEIDRVAETTKFNELYTLKGDEDKVTRYLSAH

DAGIEGTLTQGATNATFSMDQLKFGDTIMIAGREYHISGTQKQQGEIITS

SVKIGQQVTIDGIMYTCTATVSNADKFELTKDDLIAKLDTSSLSIMSVNG

KTYYGAGITDDRTVVSSIGAYKLIQKELGLASSIGADGSTQASVNAGVDG

KTLKKPSFEGKWVFSIDKGSVQVREDIDFSLHVGADADMNNKIAVKIGAL

DTKGLGIQGLNVKDTTGAAATYAIDSIADAVARTSAQRSLLGAVQNRLEH

TINNLDNVVENTTAAESQIRDTDMATEMVKYSNNNVLAQAGQSMLAQSNQ

ANQGVLSLLG.

As used herein, "YIDX" refers to all isoforms, variants, and fragments thereof of a protein associated with that name, is of bacterial origin, and is implicated in immune related disease pathogenesis, or a biological equivalent thereof. A non-limiting exemplary sequence of YIDX is disclosed herein below:

(SEQ ID NO: 21)
MKLNFKGFFKAAGLFPLALMLSGCISYALVSHTAKGSSGKYQSQSDTITG

LSQAKDSNGTKGYVFVGESLDYLITDGADDIVKMLNDPALNRHNIQVADD

ARFVLNAGKKKFTGTISLYYYWNNEEEKALATHYGFACGVQHCTRSLENL

KGTIHEKNKNMDYSKVMAFYHPFKVRFYEYYSPRGIPDGVSAALLPVTVT

LDIITAPLQFLVVYAVNQ.

Another non-limiting exemplary sequence of YIDX is disclosed herein below:

(SEQ ID NO: 21)
MKLNFKGFFKAAGLFPLALMLSGCISYALVSHTAKGSSGKYQSQSDTITG

LSQAKDSNGTKGYVFVGESLDYLITDGADDIVKMLNDPALNRHNIQVADD

ARFVLNAGKKKFTGTISLYYYWNNEEEKALATHYGFACGVQHCTRSLENL

KGTIHEKNKNMDYSKVMAFYHPFKVRFYEYYSPRGTPDGVSAALLPVTVT

LDIITAPLQFLVVYAVNQ.

As used herein, "AChR" refers to all isoforms, variants, and fragments thereof of a protein associated with that name, or a biological equivalent thereof.

A non-limiting exemplary sequence of acetylcholine receptor associated with UniProt Reference No. Q13702-1 is disclosed herein below:

(SEQ ID NO: 22)
MGQDQTKQQIEKGLQLYQSNQTEKALQVWTKVLEKSSDLMGRFRVLGCLV

TAHSEMGRYKEMLKFAVVQIDTARELEDADFLLESYLNLARSNEKLCEFH

KTISYCKTCLGLPGTRAGAQLGGQVSLSMGNAFLGLSVFQKALESFEKAL

RYAHNNDDAMLECRVCCSLGSFYAQVKDYEKALFFPCKAAELVNNYGKGW

SLKYRAMSQYHMAVAYRLLGRLGSAMECCEESMKIALQHGDRPLQALCLL

CFADIHRSRGDLETAFPRYDSAMSIMTEIGNRLGQVQALLGVAKCWVARK

ALDKALDAIERAQDLAEEVGNKLSQLKLHCLSESIYRSKGLQRELRAHVV

RFHECVEETELYCGLCGESIGEKNSRLQALPCSHIFHLRCLQNNGTRSCP

NCRRSSMKPGFV.

A non-limiting exemplary sequence of acetylcholine receptor associated with UniProt Reference No. Q04844-1 is disclosed herein below:

(SEQ ID NO: 23)
MARAPLGVLLLLGLLGRGVGKNEELRLYHHLFNNYDPGSRPVREPEDTVT

ISLKVTLTNLISLNEKEETLTTSVWIGIDWQDYRLNYSKDDFGGIETLRV

PSELVWLPEIVLENNIDGQFGVAYDANVLVYEGGSVTWLPPAIYRSVCAV

EVTYFPFDWQNCSLIFRSQTYNAEEVEFTFAVDNDGKTINKIDIDTEAYT

ENGEWAIDFCPGVIRRHHGGATDGPGETDVIYSLIIRRKPLFYVINIIVP

CVLISGLVLLAYFLPAQAGGQKCTVSINVLLAQTVFLFLIAQKIPETSLS

VPLLGRFLIFVMVVATLIVMNCVIVLNVSQRTPTTHAMSPRLRHVLLELL

PRLLGSPPPPEAPRAASPPRRASSVGLLLRAEELILKKPRSELVFEGQRH

RQGTWTAAFCQSLGAAAPEVRCCVDAVNFVAESTRDQEATGEEVSDWVRM

GNALDNICFWAALVLFSVGSSLIFLGAYFNRVPDLPYAPCIQP.

A non-limiting exemplary sequence of acetylcholine receptor associated with UniProt Reference No. P02708-1 is disclosed herein below:

(SEQ ID NO: 24)
MEPWPLLLLFSLCSAGLVLGSEHETRLVAKLFKDYSSVVRPVEDHRQVVE

VTVGLQLIQLINVDEVNQIVTTNVRLKQGDMVDLPRPSCVTLGVPLFSHL

QNEQWVDYNLKWNPDDYGGVKKIHIPSEKIWRPDLVLYNNADGDFAIVKF

TKVLLQYTGHITWTPPAIFKSYCEIIVTHFPFDEQNCSMKLGTWTYDGSV

VAINPESDQPDLSNFMESGEWVIKESRGWKHSVTYSCCPDTPYLDITYHF

VMQRLPLYFIVNVIIPCLLFSFLTGLVFYLPTDSGEKMTLSISVLLSLTV

FLLVIVELIPSTSSAVPLIGKYMLFTMVFVIASIIITVIVINTHHRSPST

HVMPNWVRKVFIDTIPNIMFFSTMKRPSREKQDKKIFTEDIDISDISGKP

GPPPMGFHSPLIKHPEVKSAIEGIKYIAETMKSDQESNNAAAEWKYVAMV

MDHILLGVFMLVCIIGTLAVFAGRLIELNQQG.

A non-limiting exemplary sequence of acetylcholine receptor associated with UniProt Reference No. P07510-1 is disclosed herein below:

(SEQ ID NO: 25)
MHGGQGPLLLLLLLAVCLGAQGRNQEERLLADLMQNYDPNLRPAERDSDV

VNVSLKLTLTNLISLNEREEALTTNVWIEMQWCDYRLRWDPRDYEGLWVL

-continued

RVPSTMVWRPDIVLENNVDGVFEVALYCNVLVSPDGCIYWLPPAIFRSAC

SISVTYFPFDWQNCSLIFQSQTYSTNEIDLQLSQEDGQTIEWIFIDPEAF

TENGEWAIQHRPAKMLLDPAAPAQEAGHQKVVFYLLIQRKPLFYVINIIA

PCVLISSVAILIHFLPAKAGGQKCTVAINVLLAQTVFLFLVAKKVPETSQ

AVPLISKYLTFLLVVTILIVVNAVVVLNVSLRSPHTHSMARGVRKVFLRL

LPQLLRMHVRPLAPAAVQDTQSRLQNGSSGWSITTGEEVALCLPRSELLF

QQWQRQGLVAAALEKLEKGPELGLSQFCGSLKQAAPAIQACVEACNLIAC

ARHQQSHFDNGNEEWFLVGRVLDRVCFLAMLSLFICGTAGIFLMAHYNRV

PALPFPGDPRPYLPSPD.

A non-limiting exemplary sequence of acetylcholine receptor associated with UniProt Reference No. P11230-1 is disclosed herein below:

(SEQ ID NO: 26)
MTPGALLMLLGALGAPLAPGVRGSEAEGRLREKLFSGYDSSVRPAREVGD

RVRVSVGLILAQLISLNEKDEEMSTKVYLDLEWTDYRLSWDPAEHDGIDS

LRITAESVWLPDVVLLNNNDGNFDVALDISVVVSSDGSVRWQPPGIYRSS

CSIQVTYFPFDWQNCTMVFSSYSYDSSEVSLQTGLGPDGQGHQEIHIHEG

TFIENGQWEIIHKPSRLIQPPGDPRGGREGQRQEVIFYLIIRRKPLFYLV

NVIAPCILITLLAIFVFYLPPDAGEKMGLSIFALLTLTVFLLLLADKVPE

TSLSVPIIIKYLMFTMVLVTFSVILSVVVLNLHHRSPHTHQMPLWVRQIF

IHKLPLYLRLKRPKPERDLMPEPPHCSSPGSGWGRGTDEYFIRKPPSDFL

FPKPNRFQPELSAPDLRRFIDGPNRAVALLPELREVVSSISYIARQLQEQ

EDHDALKEDWQFVAMVVDRLFLWTFIIFTSVGTLVIFLDATYHLPPPDPF

P

A non-limiting exemplary sequence of acetylcholine receptor associated with UniProt Reference No. Q07001-1 is disclosed herein below:

(SEQ ID NO: 27)
MEGPVLTLGLLAALAVCGSWGLNEEERLIRHLFQEKGYNKELRPVAHKEE

SVDVALALTLSNLISLKEVEETLTTNVWIEHGWTDNRLKWNAEEFGNISV

LRLPPDMVWLPEIVLENNNDGSFQISYSCNVLVYHYGFVYWLPPAIFRSS

CPISVTYFPFDWQNCSLKFSSLKYTAKEITLSLKQDAKENRTYPVEWIII

DPEGFTENGEWEIVHRPARVNVDPRAPLDSPSRQDITFYLIIRRKPLFYI

INILVPCVLISFMVNLVFYLPADSGEKTSVAISVLLAQSVFLLLISKRLP

ATSMAIPLIGKFLLFGMVLVTMVVVICVIVLNIHFRTPSTHVLSEGVKKL

FLETLPELLHMSRPAEDGPSPGALVRRSSSLGYISKAEEYFLLKSRSDLM

FEKQSERHGLARRLTTARRPPASSEQAQQELFNELKPAVDGANFIVNHMR

DQNNYNEEKDSWNRVARTVDRLCLFVVTPVMVVGTAWIFLQGVYNQPPPQ

PFPGDPYSYNVQDKRFI.

As used herein, "thyroid peroxidase" refers to all isoforms, variants, and fragments thereof of a protein associated with that name, or a biological equivalent thereof. A non-limiting exemplary sequence of human thyroid peroxidase associated with UniProt Reference No. P07202 is disclosed herein below:

(SEQ ID NO: 28)
MRALAVLSVTLVMACTEAFFPFISRGKELLWGKPEESRVSSVLEESKRLV

DTAMYATMQRNLKKRGILSPAQLLSFSKLPEPTSGVIARAAEIMETSIQA

MKRKVNLKTQQSQHPTDALSEDLLSIIANMSGCLPYMLPPKCPNTCLANK

YRPITGACNNRDHPRWGASNTALARWLPPVYEDGFSQPRGWNPGFLYNGF

PLPPVREVTRHVIQVSNEVVTDDDRYSDLLMAWGQYIDHDIAFTPQSTSK

AAFGGGADCQMTCENQNPCFPIQLPEEARPAAGTACLPFYRSSAACGTGD

QGALFGNLSTANPRQQMNGLTSFLDASTVYGSSPALERQLRNWTSAEGLL

RVHARLRDSGRAYLPFVPPRAPAACAPEPGIPGETRGPCFLAGDGRASEV

PSLTALHTLWLREHNRLAAALKALNAHWSADAVYQEARKVVGALHQIITL

RDYIPRILGPEAFQQYVGPYEGYDSTANPTVSNVFSTAAFRFGHATIHPL

VRRLDASFQEHPDLPGLWLHQAFFSPWTLLRGGGLDPLIRGLLARPAKLQ

VQDQLMNEELTERLFVLSNSSTLDLASINLQRGRDHGLPGYNEWREFCGL

PRLETPADLSTAIASRSVADKILDLYKHPDNIDVWLGGLAENFLPRARTG

PLFACLIGKQMKALRDGDWFWWENSHVFTDAQRRELEKHSLSRVICDNTG

LTRVPMDAFQVGKFPEDFESCDSITGMNLEAWRETFPQDDKCGFPESVEN

GDFVHCEESGRRVLVYSCRHGYELQGREQLTCTQEGWDFQPPLCKDVNEC

ADGAHPPCHASARCRNTKGGFQCLCADPYELGDDGRTCVDSGRLPRVTWI

SMSLAALLIGGFAGLTSTVICRWTRTGTKSTLPISETGGGTPELRCGKHQ

AVGTSPQRAAAQDSEQESAGMEGRDTHRLPRAL.

As used herein, "thyroid receptor" refers to all isoforms, variants, and fragments thereof of a protein associated with that name, or a biological equivalent thereof. In some embodiments, "thyroid receptor" includes "thyroid stimulating hormone receptor." A non-limiting exemplary sequence of thyroid stimulating hormone receptor associated with UniProt Reference No. P16473-1 is disclosed herein below:

(SEQ ID NO: 29)
MRPADLLQLVLLLDLPRDLGGMGCSSPPCECHQEEDFRVTCKDIQRIPSL

PPSTQTLKLIETHLRTIPSHAFSNLPNISRIYVSIDVTLQQLESHSFYNL

SKVTHIEIRNTRNLTYIDPDALKELPLLKFLGIFNTGLKMFPDLTKVYST

DIFFILEITDNPYMTSIPVNAFQGLCNETLTLKLYNNGFTSVQGYAFNGT

KLDAVYLNKNKYLTVIDKDAFGGVYSGPSLLDVSQTSVTALPSKGLEHLK

ELIARNTWTLKKLPLSLSFLHLTRADLSYPSHCCAFKNQKKIRGILESLM

CNESSMQSLRQRKSVNALNSPLHQEYEENLGDSIVGYKEKSKFQDTHNNA

HYYVFFEEQEDEIIGFGQELKNPQEETLQAFDSHYDYTICGDSEDMVCTP

KSDEFNPCEDIMGYKFLRIVVWFVSLLALLGNVFVLLILLTSHYKLNVPR

FLMCNLAFADFCMGMYLLLIASVDLYTHSEYYNHAIDWQTGPGCNTAGFF

TVFASELSVYTLTVITLERWYAITFAMRLDRKIRLRHACAIMVGGWVCCF

LLALLPLVGISSYAKVSICLPMDTETPLALAYIVFVLTLNIVAFVIVCCC

-continued
YVKIYITVRNPQYNPGDKDTKIAKRMAVLIFTDFICMAPISFYALSAILN

KPLITVSNSKILLVLFYPLNSCANPFLYAIFTKAFQRDVFILLSKFGICK

RQAQAYRGQRVPPKNSTDIQVQKVTHDMRQGLHNMEDVYELIENSHLTPK

KQGQISEEYMQTVL.

A non-limiting exemplary sequence of thyroid stimulating hormone receptor associated with UniProt Reference No. Q59GA2-1 is disclosed herein below:

(SEQ ID NO: 30)
PRVPWKMRPADLLQLVLLLDLPRDLGGMGCSSPPCECHQEEDFRVTCKDI

QRIPSLPPSTQTLKLIETHLRTIPSHAFSNLPNISRIYVSIDVTLQQLES

HSFYNLSKVTHIEIRNTRNLTYIDPDALKELPLLKFLGIFNTGLKMFPDL

TKVYSTDIFFILEITDNPYMTSIPVNAFQGLCNETLTLKLYNNGFTSVQG

YAFNGTKLDAVYLNKNKYLTVIDKDAFGGVYSGPSLLDVSQTSVTALPSK

GLEHLKELIARNTWTLKKLPLSLSFLHLTRADLSYPSHCCAFKNQKKIRG

ILESLMCNESSMQSLRQRKSVNALNSPLHQEYEENLGDSIVGYKEKSKFQ

DTHNNAHYYVFFEEQEDEIIGFGQELKNPQEETLQAFDSHYDYTICGDSE

DMVCTPKSDEFNPCEDIMGYKFLRIVVWFVSLLALLGNVFVLLILLTSHY

KLNVPRFLMCNLAFADFCMGMYLLLIASVDLYTHSEYYNHAIDWQTGPGC

NTAGFFTVFASELSVYTLTVITLERWYAITFAMRLDRKIRLRHACAIMVG

GWVCCFLLALLPLVGISSYAKVSICLPMDTETPLALAYIVFVLTLNIVAF

VIVCCCYVKIYITVRNPQYNPGDKDTKIAKRMAVLIFTDFICMAPISFYA

LSAILNKPLITVSNSKILLVLFYPLNSCANPFLYAIFTKAFQRDVFILLS

KFGICKRQAQAYRGQRVPPKNSTDIQVQKVTHDMRQGLHNMEDVYELIEN

SHLTPKKQGQISEEYMQTVL.

A non-limiting exemplary sequence of thyroid stimulating hormone receptor associated with UniProt Reference No. B4E0H2-1 is disclosed herein below:

(SEQ ID NO: 31)
MRPADLLQLVLLLDLPRDLGGMGCSSPPCECHQEEDFRVTCKDIQRIPSL

PPSTQTLKLIETHLRIVVWFVSLLALLGNVFVLLILLTSHYKLNVPRFLM

CNLAFADFCMGMYLLLIASVDLYTHSEYYNHAIDWQTGPGCNTAGFFTVF

ASELSVYTLTVITLERWYAITFAMRLDRKIRLRHACAIMVGGWVCCFLLA

LLPLVGISSYAKVSICLPMDTETPLALAYIVFVLTLNIVAFVIVCCCYVK

IYITVRNPQYNPGDKDTKIAKRMAVLIFTDFICMAPISFYALSAILNKPL

ITVSNSKILLVLFYPLNSCANPFLYAIFTKAFQRDVFILLSKFGICKRQA

QAYRGQRVPPKNSTDIQVQKVTHEMRQGLHNMEDVYELIENSHLTPKKQG

QISEEYMQTVL.

As used herein, "phospholipid antigen" refers to all isoforms, variants, and fragments thereof of a protein associated with that name, or a biological equivalent thereof. One non-limiting example of a phospholipid antigen is "beta2-glycoprotein I", whose sequence is disclosed herein below:

(SEQ ID NO: 32)
MISPVLILFSSFLCHVAIAGRTCPKPDDLPFSTVVPLKTFYEPGEEITYS

CKPGYVSRGGMRKFICPLTGLWPINTLKCTPRVCPFAGILENGAVRYTTF

EYPNTISFSCNTGFYLNGADSAKCTEEGKWSPELPVCAPIICPPPSIPTF

ATLRVYKPSAGNNSLYRDTAVFECLPQHAMFGNDTITCTTHGNWTKLPEC

REVKCPFPSRPDNGFVNYPAKPTLYYKDKATFGCHDGYSLDGPEEIECTK

LGNWSAMPSCKASCKVPVKKATVVYQGERVKIQEKFKNGMLHGDKVSFFC

KNKEKKCSYTEDAQCIDGTIEVPKCFKEHSSLAFWKTDASDVKPC

As used herein, "H4" refers to all isoforms, variants, and fragments thereof of a protein associated with the name "histone H4", or a biological equivalent thereof. The canonical sequence H4 is is disclosed herein below:

(SEQ ID NO: 33)
SGRGKGGKGLGKGGAKRHRKVLRDNIQGITKPAIRRLARRGGVKRISGLI

YEETRGVLKVFLENVIRDAVTYTEHAKRKTVTAMDVVYALKRQGRTLYGF

GG.

As used herein, "H2B" refers to all isoforms, variants, and fragments thereof of a protein associated with the name "histone H2B", or a biological equivalent thereof. The canonical sequence of H2B is is disclosed herein below:

(SEQ ID NO: 34)
PEPAKSAPAPKKGSKKAVTKAQKKDGKKRKRSRKESYSVYVYKVLKQVHP

DTGISSKAMGIMNSFVNDIFERIASEASRLAHYNKRSTITSREIQTAVRL

LLPGELAKHAVSEGTKAVTKYTSSK.

As used herein, "H1" refers to all isoforms, variants, and fragments thereof of a protein associated with the name "histone H1", or a biological equivalent thereof. The canonical sequence of H1 is disclosed herein below:

(SEQ ID NO: 35)
MTENSTSAPAAKPKRAKASKKSTDHPKYSDMIVAAIQAEKNRAGSSRQSI

QKYIKSHYKVGENADSQIKLSIKRLVTTGVLKQTKGVGASGSFRLAKGDE

PKRSVAFKKTKKEVKKVATPKKAAKPKKAASKAPSKKPKATPVKKAKKKP

AATPKKAKKPKVVKVKPVKASKPKKAKTVKPKAKSSAKRASKKK.

As used herein, "ApoB" refers to all isoforms, variants, and fragments thereof of a protein associated with the name "apolipoprotein B", or a biological equivalent thereof. The canonical sequence of ApoB is disclosed herein below:

(SEQ ID NO: 36)
MGPRKPALRTPLLLLFLLLFLDTSVWAQDEVLENLSFSCPKDATRFKHLR

KYVYNYEAESSSGVQGTADSRSATKINCKVELEVPQICGFIMRTNQCTLK

EVYGFNPEGKALMKKTKNSEEFAAAMSRYELKLAIPEGKQIVLYPDKDEP

KYILNIKRGIISALLVPPETEEDQQELFLDTVYGNCSTQVTVNSRKGTVP

TEMSTERNLQQCDGFQPISTSVSPLALIKGLVHPLSTLISSSQTCQYTLD

PKRKHVSEAVCDEQHLFLPFSYKNKYGIMTRVTQKLSLEDTPKINSRFFS

EGTNRMGLAFESTKSTSSPKQADAVLKTLQELKKLSISEQNAQRANLFNK

-continued

LVTELRGLTGEAITSLLPQLIEVSSPITLQALVQCGQPQCYTHILQWLKT
EKAHPLLVDIVTYLMALIPNPSTQRLQEIFNTAKEQQSRATLYALSHAVN
SYFDVDHSRSPVLQDIAGYLLKQIDNECTGNEDHTFLILRVIGNMGRTME
QVMPALKSSVLSCVRSTKPSLLIQKAALQALRKMELEDEVRTILFDTFVN
GVAPVEKRLAAYLLLMKNPSSSDINKIAQLLQWEQSEQVKNFVASHIANI
LNSEELYVQDLKVLIKNALENSQFPTIMDFRKFSRNYQISKSASLPMFDP
VSVKIEGNLIFDPSSYLPRESLLKTTLTVFGLASLDLFEIGLEGKGFEPT
LEALFGKQGFFPDSVNKALYWVNGRVPDGVSKVLVDHFGYTTDGKHEQDM
VNGIMPIVDKLIKDLKSKEIPEARAYLRILGKELSFVRLQDLQVLGKLLL
SGAQTLQGIPQMVVQAIREGSKNDLFLHYIFMDNAFELPTGAGLQLQVSS
SGVFTPGIKAGVRLELANIQAELVAKPSVSLEFVTNMGIIIPDFAKSSVQ
MNTNFFHESGLEARVALKAGQLKVIIPSPKRPVKLFSGSNTLHLVSTTKT
EVIPPLVENRQSWSTCKPLFTGMNYCTTGAYSNASSTESASYYPLTGDTR
YELELRPTGEVEQYSATATYELLKEDKSLVDTLKFLVQAEGVQQSEATVL
FKYNRRSRTLSSEVLIPGFDVNFGTILRVNDESAKDKNTYKLILDIQNKK
ITEVSLVGHLSYDKKGDGKIKGVVSIPRLQAEARSEVHTHWSSTKLLFQM
DSSATAYGSTISKRVTWRYDNEIIEFDWNTGTNVDTKKVASNFPVDLSHY
PRMLHEYANGLLDHRVPQTDVTFRDMGSKLIVATNTWLQMATRGLPYPQT
LQDHLNSLSELNLLKMGLSDFHIPDNLFLKTDGRVKYTMNRNKINIDIPL
PLGGKSSKDLKMPESVRTPALNFKSVGFHLPSREVQVPTFTIPKTHQLQV
PLLGVLDLSTNVYSNLYNWSASYTGGNTSRDHFSLQAQYRMKTDSVVDLF
SYSVQGSGETTYDSKNTFTLSCDGSLHHKFLDSKFKVSHVEKFGNSPVSK
GLLTFETSSALGPQMSATVHLDSKKKQHLYVKDIKVDGQFRASSFYAQGK
YGLSCERDVTTGQLSGESNMRFNSTYFQGTNQIVGMYQDGALSITSTSDL
QDGIFKNTASLKYENYELTLKSDSSGQYENFAASNKLDVTFSTQSALLRS
EHQANYKSLRLVTLLSGSLTSQGVELNADILGTDKINTGAHKATLKIARD
GLSTSATTNLKYSPLLLENELNAELGLSGASMKLSTNGRFKEHHAKFSLD
GRAALTEVSLGSIYQAMILGADSKNIFNFKLSREGLRLSNDLMGSYAEMK
LDHTHSLNIAGLSLDFFSKMDNIYSGDKFYKQNFNLQLQPYSFITTLSND
LRYGALDLTNNGRFRLEPLKLNVGGNFKGTYQNNELKHIYTISYTDLVVA
SYRADTVAKVQGVEFSHRLNADIEGLTSSVDVTTSYNSDPLHFNNVFHFS
LAPFTLGIDTHTSGDGKLSFWGEHTGQLYSKFLLKAEPLALIVSHDYKGS
TSHSLPYESSISTALEHTVSALLTPAEQTSTWKFKTKLNDKVYSQDFEAY
NTKDKIGVELSGRADLSGLYSPIKLPFFYSEPVNVLNGLEVNDAVDKPQE
FTHAVVKYDKNQDVHTINLPFFKSLPDYLERNRRGMISLLEAMRGELQRL
SVDQFVRKYRAALSRLPQQIHHYLNASDWERQVAGAKEKITSFMENYRIT
DNDVLIAIDSAKINFNEKLSQLETYAIQFDQYIKDNYDPHDLKRTIAEII
DRIIEKLKILDEQYHIRVNLAKSIHNLYLFVENVDLNQVSSSNTSWIQNV
DSNYQVRIQIQEKLQQLRTQIQNIDIQQLAAEVKRQMDAIDVTMHLDQLR
TAILFQRISDIIDRVKYFVMNLIEDFKVTEKINTFRVIVRELIEKYEVDQ
HIQVLMDKSVELAHRYSLSEPLQKLSNVLQRIEIKDYYEKLVGFIDDTVE

-continued

WLKALSFKNTIEELNRLTDMLVKKLKAFDYHQFVDKTNSKIREMTQRINA
EIQALKLPQKMEALKLLVEDFKTTVSNSLERLKDTKVTVVIDWLQDILTQ
MKDHFQDTLEDVRDRIYQMDIQRELEHFLSLVNQVYSTTVTYMSDWWTTT
AKNTTDFAFQYSTQNWAFSTKVTVFQGFTVPPFMQTFTWTMPAFEVSLRAL
QEGNFQTPVFIVPLTDLRIPSIRINFKMLKNIKIPLRFSTPEFTLLNTFH
VHSFTIDLLEIKAKIIRTIDQILSSELQWPLPEMYLRDLDVVNIPLARLT
LPDFHVPEITIPEFTIPNVNLKDLHVPDLHIPEFQLPHLSHTIEIPAFGK
LHSILKIQSPLFILDANANIQNVTTSGNKAEIVASVTAKGESQFEALNFD
FQAQAQFLELNPHPPVLKESMNFSSKHVRMEHEGEIVFDGKAIEGKSDTV
ASLHTEKNEVEFNNGMTVKVNNQLTLDSHTKYFHKLSVPRLDFSSKASLN
NEIKTLLEAGHVALTSSGTGSWNWACPNFSDEGIHSSQISFTVDGPIAFV
GLSNNINGKHLRVIQKLTYESGFLNYSKFEVESKVESQHVGSSILTANGR
ALLKDAKAEMTGEHNANLNGKVIGTLKNSLFFSAQPFEITASTNNEGNLK
VGFPLKLTGKIDFLNNYALFLSPRAQQASWQASTRFNQYKYNQNFSAINN
EHNIEASIGMNGDANLDFLNIPLTIPEINLPYTEFKTPLLKDFSIWEETG
LKEFLKTTKQSFDLSVKAQYKKNSDKHSIVVPLGMFYEFILNNVNSWDRK
FEKVRNNALHFLTTSYNEAKIKVDKYKTENSLNQPSGTFQNHGYTIPVVN
IEVSPFAVETLASSHVIPTAISTPSVTIPGPNIMVPSYKLVLPPLELPVF
HGPGNLFKFFLPDFKGFNTIDNIYIPAMGNFTYDFSFKSSVITLNTNAGL
YNQSDIVAHFLSSSSFVTDALQYKLEGTSRLMRKRGLKLATAVSLTNKFV
KGSHDSTISLTKKNMEASVRTTANLHAPIFSMNFKQELNGNTKSKPTVSS
SIELNYDFNSSKLHSTATGGIDHKFSLESLTSYFSIESFTKGNIKSSFLS
QEYSGSVANEANVYLNSKGTRSSVRLQGASKVDGIWNVEVGENFAGEATL
QRIYTTWEHNMKNHLQVYSYFFTKGKQTCRATLELSPWTMSTLLQVHVSQ
LSSLLDLHHFDQEVILKANTKNQKISWKGGVQVESRVLQHNAQFSNDQEE
IRLDLAGSLDGQLWDLEAIFLPVYGKSLQELLQMDKRQYLQASTSLLYT
KNPNGYLLSLPVQELADRFIIPGIKLNDFSGVKIYKKLSTSPFALNLTML
PKVKFPGIDLLTQYSTPEGSSVPIFEATIPEIHLTVSQFTLPKSLPVGNT
VFDLNKLANMIADVDLPSVTLPEQTIVIPPLEFSVPAGIFIPFFGELTAR
AGMASPLYNVTWSAGWKTKADHVETFLDSMCTSTLQFLEYALKVVETHKI
EEDLLTYNIKGTLQHCDFNVEYNEDGLFKGLWDWQGEAHLDITSPALTDF
HLYYKEDKTSLSASAASSTIGTVGLDSSTDDQSVELNVYFHPQSPPEKKL
SIFKTEWRYKESDGERYIKINWEEEAASRLLGSLKSNVPKASKAIYDYAN
KYHLEYVSSELRKSLQVNAEHARRMVDEMNMSFQRVARDTYQNLYEEMLA
QKSLSIPENLKKRVLDSIVHVTQKYHMAVMWLMDSFIHFLKFNRVQFPGY
AGTYTVDELYTIVMKETKKSLSQLFNGLGNLLSYVQNQVEKSRLINDITF
KCPFFSKPCKLKDLILIFREELNILSNIGQQDIKFTTILSSLQGFLERVL
DIIEEQIKCLKDNESTCVADHINMVFKIQVPYAFKSLREDIYFVLGEFND
FLQSILQEGSYKLQQVHQYMKALREEYFDPSMVGWTVKYYEIEENMVELI
KTLLVSFRDVYSEYSVTAADFASKMSTQVEQFVSRDIREYLSMLTDINGK

```
WMEKIAELSIVAKETMKSWVTAVAKIMSDYPQQFHSNLQDFSDQLSSYYE

KFVGESTRLIDLSIQNYHVFLRYITELLRKLQVATANNVSPYIKLAQGEL

MITF.
```

As used herein, "ApoE" refers to all isoforms, variants, and fragments thereof of a protein associated with the name "apolipoprotein E", or a biological equivalent thereof. A non-limiting exemplary sequence of human apoE associated with UniProt Reference No. P02649 is disclosed herein below:

```
                                              (SEQ ID NO: 37)
MKVLWAALLVTFLAGCQAKVEQAVETEPEPELRQQTEWQSGQRWELALGR

FWDYLRWVQTLSEQVQEELLSSQVTQELRALMDETMKELKAYKSELEEQL

TPVAEETRARLSKELQAAQARLGADMEDVCGRLVQYRGEVQAMLGQSTEE

LRVRLASHLRKLRKRLLRDADDLQKRLAVYQAGAREGAERGLSAIRERLG

PLVEQGRVRAATVGSLAGQPLQERAQAWGERLRARMEEMGSRTRDRLDEV

KEQVAEVRAKLEEQAQQIRLQAEAFQARLKSWFEPLVEDMQRQWAGLVEK

VQAAVGTSAAPVPSDNH.
```

As used herein, "NMDAR" refers to all isoforms, variants, and fragments thereof of a protein associated with the name "N-methyl-D-aspartate receptor", or a biological equivalent thereof. A non-limiting exemplary sequence of N-methyl-D-asparate receptor associated with UniProt Reference No. Q13224-1 is disclosed herein below:

```
                                              (SEQ ID NO: 38)
MKPRAECCSPKFWLVLAVLAVSGSRARSQKSPPSIGIAVILVGTSDEVAI

KDAHEKDDFHHLSVVPRVELVAMNETDPKSIITRICDLMSDRKIQGVVFA

DDTDQEAIAQILDFISAQTLTPILGIHGGSSMIMADKDESSMFFQFGPSI

EQQASVMLNIMEEYDWYIFSIVTTYFPGYQDFVNKIRSTIENSFVGWELE

EVLLLDMSLDDGDSKIQNQLKKLQSPIILLYCTKEEATYIFEVANSVGLT

GYGYTWIVPSLVAGDTDTVPAEFPTGLISVSYDEWDYGLPARVRDGIAII

TTAASDMLSEHSFIPEPKSSCYNTHEKRIYQSNMLNRYLINVTFEGRNLS

FSEDGYQMHPKLVIILLNKERKWERVGKWKDKSLQMKYYVWPRMCPETEE

QEDDHLSIVTLEEAPFVIVESVDPLSGTCMRNTVPCQKRIVTENKTDEEP

GYIKKCCKGFCIDILKKISKSVKFTYDLYLVTNGKHGKKINGTWNGMIGE

VVMKRAYMAVGSLTINEERSEVVDFSVPFIETGISVMVSRSNGTVSPSAF

LEPFSADVWVMMFVMLLIVSAVAVFVFEYFSPVGYNRCLADGREPGGPSF

TIGKAIWLLWGLVFNNSVPVQNPKGTTSKIMVSVWAFFAVIFLASYTANL

AAFMIQEEYVDQVSGLSDKKFQRPNDFSPPFRFGTVPNGSTERNIRNNYA

EMHAYMGKFNQRGVDDALLSLKTGKLDAFIYDAAVLNYMAGRDEGCKLVT

IGSGKVFASTGYGIAIQKDSGWKRQVDLAILQLFGDGEMEELEALWLTGI

CHNEKNEVMSSQLDIDNMAGVFYMLGAAMALSLITFICEHLFYWQFRHCF

MGVCSGKPGMVFSISRGIYSCIHGVAIEERQSVMNSPTATMNNTHSNILR

LLRTAKNMANLSGVNGSPQSALDFIRRESSVYDISEHRRSFTHSDCKSYN

NPPCEENLFSDYISEVERTFGNLQLKDSNVYQDHYHHHHRPHSIGSASSI

DGLYDCDNPPFTTQSRSISKKPLDIGLPSSKHSQLSDLYGKFSFKSDRYS

GHDDLIRSDVSDISTHTVTYGNIEGNAAKRRKQQYKDSLKKRPASAKSRR

EFDEIELAYRRRPPRSPDHKRYFRDKEGLRDFYLDQFRTENSPHWEHVDL

TDIYKERSDDFKRDSVSGGGPCTNRSHIKHGTGDKHGVVSGVPAPWEKNL

TNVEWEDRSGGNFCRSCPSKLHNYSTTVTGQNSGRQACIRCEACKKAGNL

YDISEDNSLQELDQPAAPVAVTSNASTTKYPQSPTNSKAQKKNRNKLRRQ

HSYDTFVDLQKEEALAPRSVSLKDKGRFMDGSPYAHMFEMSAGESTFANN

KSSVPTAGHHHHNNPGGGYLSKSLYPDRVTQNPFIPTFGDDQCLLHGSKS

YFFRQPTVAGASKARPDFRALVTNKPVSALHGAVPARFQKDICIGNQSNP

CVPNNKNPRAFNGSSNGHVYEKLSSIESDV.
```

As used herein, "voltage-gated potassium channel" refers generally to a transmembrane channel specific for potassium and sensitive to voltage changes in a cell's membrane potential. During action potentials, said channels play a crucial role in returning the depolarized cell to a resting state. A non-limiting exemplary sequence of voltage-gated potassium channel associated with UniProt Reference No. P22459-1 is disclosed herein below:

```
                                              (SEQ ID NO: 39)
MEVAMVSAESSGCNSHMPYGYAAQARARERERLAHSRAAAAAAVAAATAA

VEGSGGSGGGSHHHHQSRGACTSHDPQSSRGSRRRRRQRSEKKKAHYRQS

SFPHCSDLMPSGSEEKILRELSEEEEDEEEEEEEEEGRFYYSEDDHGDE

CSYTDLLPQDEGGGGYSSVRYSDCCERVVINVSGLRFETQMKTLAQFPET

LLGDPEKRTQYFDPLRNEYFFDRNRPSFDAILYYYQSGGRLKRPVNVPFD

IFTEEVKFYQLGEEALLKFREDEGFVREEEDRALPENEFKKQIWLLFEYP

ESSSPARGIAIVSVLVILISIVIFCLETLPEFRDDRDLVMALSAGGHGGL

LNDTSAPHLENSGHTIFNDPFFIVETVCIVWFSFEFVVRCFACPSQALFF

KNIMNIIDIVSILPYFITLGTDLAQQQGGGNGQQQQAMSFAILRIIRLVR

VFRIFKLSRHSKGLQILGHTLRASMRELGLLIFFLFIGVILFSSAVYFAE

ADEPTTHFQSIPDAFWWAVVTMTTVGYGDMKPITVGGKIVGSLCAIAGVL

TIALPVPVIVSNFNYFYHRETENEEQTQLTQNAVSCPYLPSNLLKKFRSS

TSSSLGDKSEYLEMEEGVKESLCAKEEKCQGKGDDSETDKNNCSNAKAVE

TDV.
```

As used herein, "Elastin" refers to all isoforms, variants, and fragments thereof of a protein associated with that name, or a biological equivalent thereof. The canonical sequence of elastin is 786 amino acids in length and is disclosed herein below:

```
                                              (SEQ ID NO: 40)
   MAGLTAAAPR PGVLLLLLSI LHPSRPGGVP GAIPGGVPGG

VFYPGAGLGA LGGGALGPGGKPLKPVPGGL AGAGLGAGLG

AFPAVTFPGA LVPGGVADAA AAYKAAKAGA GLGGVPGVGG

LGVSAGAVVP QPGAGVKPGK VPGVGLPGVY PGGVLPGARF

PGVGVLPGVP TGAGVKPKAPGVGGAFAGIP GVGPFGGPQP
```

-continued

```
GVPLGYPIKA PKLPGGYGLP YTTGKLPYGY GPGGVAGAAG

KAGYPTGTGV GPQAAAAAAA KAAAKFGAGA AGVLPGVGGA

GVPGVPGAIP GIGGIAGVGT PAAAAAAAAA AKAAKYGAAA

GLVPGGPGFG PGVVGVPGAG VPGVGVPGAG IPVVPGAGIP

GAAVPGVVSP EAAAKAAAKA AKYGARPGVG VGGIPTYGVG

AGGFPGFGVG VGGIPGVAGV PGVGGVPGVG GVPGVGISPE

AQAAAAAKAA KYGAAGAGVL GGLVPGPQAA VPGVPGTGGV

PGVGTPAAAA AKAAAKAAQF GLVPGVGVAP GVGVAPGVGV

APGVGLAPGV GVAPGVGVAP GVGVAPGIGP GGVAAAAKSA

AKVAAKAQLR AAAGLGAGIP GLGVGVGVPG LGVGAGVPGL

GVGAGVPGFG AGADEGVRRS LSPELREGDP SSSQHLPSTP

SSPRVPGALA AAKAAKYGAA VPGVLGGLGA LGGVGIPGGV

VGAGPAAAAA AAKAAAKAAQ FGLVGAAGLG GLGVGGLGVP

GVGGLGGIPP AAAAKAAKYG AAGLGGVLGG AGQFPLGGVA

ARPGFGLSPI FPGGACLGKA CGRKRK.
```

As used herein, "IRBP" refers to all isoforms, variants, and fragments thereof of a protein associated with the name "interphotoreceptor retinoid binding protein", or a biological equivalent thereof.

As used herein, "arresting human retinal S antigen" refers to all isoforms, variants, and fragments thereof of a protein associated with that name, or a biological equivalent thereof. One non-limiting exemplary sequence is disclosed herein below:

```
(SEQ ID NO: 41)
MAASGKTSKSEPNHVIFKKISRDKSVTIYLGNRDYIDHVSQVQPVDGVVL

VDPDLVKGKKVYVTLTCAFRYGQEDIDVIGLTFRRDLYFSRVQVYPPVGA

ASTPTKLQESLLKKLGSNTYPFLLTFPDYLPCSVMLQPAPQDSGKSCGVD

FEVKAFATDSTDAEEDKIPKKSSVRLLIRKVQHAPLEMGPQPRAEAAWQF

FMSDKPLHLAVSLNKEIYFHGEPIPVTVTVTNNTEKTVKKIKAFVEQVAN

VVLYSSDYYVKPVAMEEAQEKVPPNSTLTKTLTLLPLLANNRERRGIALD

GKIKHEDTNLASSTIIKEGIDRTVLGILVSYQIKVKLTVSGFLGELTSSE

VATEVPFRLMHPQPEDPAKESYQDANLVFEEFARHNLKDAGEAEEGKRDK

NDVDE
```

As used herein, "myosin" refers to all isoforms, variants, and fragments thereof of a protein associated with that name, or a biological equivalent thereof. A non-limiting exemplary sequence of myosin associated with UniProt Reference No. P35580-1 is disclosed herein below:

```
(SEQ ID NO: 42)
MAQRTGLEDPERYLFVDRAVIYNPATQADWTAKKLVWIPSERHGFEAASI

KEERGDEVMVELAENGKKAMVNKDDIQKMNPPKFSKVEDMAELTCLNEAS

VLHNLKDRYYSGLIYTYSGLFCVVINPYKNLPIYSENIIEMYRGKKRHEM

PPHIYAISESAYRCMLQDREDQSILCTGESGAGKTENTKKVIQYLAHVAS

SHKGRKDHNIPGELERQLLQANPILESFGNAKTVKNDNSSRFGKFIRINF

DVTGYIVGANIETYLLEKSRAVRQAKDERTFHIFYQLLSGAGEHLKSDLL

LEGFNNYRFLSNGYIPIPGQQDKDNFQETMEAMHIMGFSHEEILSMLKVV

SSVLQFGNISFKKERNTDQASMPENTVAQKLCHLLGMNVMEFTRAILTPR

IKVGRDYVQKAQTKEQADFAVEALAKATYERLFRWLVHRINKALDRTKRQ

GASFIGILDIAGFEIFELNSFEQLCINYTNEKLQQLFNHTMFILEQEEYQ

REGIEWNFIDFGLDLQPCIDLIERPANPPGVLALLDEECWFPKATDKTFV

EKLVQEQGSHSKFQKPRQLKDKADFCIIHYAGKVDYKADEWLMKNMDPLN

DNVATLLHQSSDRFVAELWKDVDRIVGLDQVTGMTETAFGSAYKTKKGMF

RTVGQLYKESLTKLMATLRNTNPNFVRCIIPNHEKRAGKLDPHLVLDQLR

CNGVLEGIRICRQGFPNRIVFQEFRQRYEILTPNAIPKGFMDGKQACERM

IRALELDPNLYRIGQSKIFFRAGVLAHLEEERDLKITDIIIFFQAVCRGY

LARKAFAKKQQQLSALKVLQRNCAAYLKLRHWQWWRVFTKVKPLLQVTRQ

EEELQAKDEELLKVKEKQTKVEGELEEMERKHQQLLEEKNILAEQLQAET

ELFAEAEEMRARLAAKKQELEEILHDLESRVEEEEERNQILQNEKKKMQA

HIQDLEEQLDEEEGARQKLQLEKVTAEAKIKKMEEEILLLEDQNSKFIKE

KKLMEDRIAECSSQLAEEEEKAKNLAKIRNKQEVMISDLEERLKKEEKTR

QELEKAKRKLDGETTDLQDQIAELQAQIDELKLQLAKKEEELQGALARGD

DETLHKNNALKVVRELQAQIAELQEDFESEKASRNKAEKQKRDLSEELEA

LKTELEDTLDTTAAQQELRTKREQEVAELKKALEEETKNHEAQIQDMRQR

HATALEELSEQLEQAKRFKANLEKNKQGLETDNKELACEVKVLQQVKAES

EHKRKKLDAQVQELHAKVSEGDRLRVELAEKASKLQNELDNVSTLLEEAE

KKGIKFAKDAASLESQLQDTQELLQEETRQKLNLSSRIRQLEEEKNSLQE

QQEEEEEARKNLEKQVLALQSQLADTKKKVDDDLGTIESLEEAKKKLLKD

AEALSQRLEEKALAYDKLEKTKNRLQQELDDLTVDLDHQRQVASNLEKKQ

KKFDQLLAEEKSISARYAEERDRAEAEAREKETKALSLARALEEALEAKE

EFERQNKQLRADMEDLMSSKDDVGKNVHELEKSKRALEQQVEEMRTQLEE

LEDELQATEDAKLRLEVNMQAMKAQFERDLQTRDEQNEEKKRLLIKQVRE

LEAELEDERKQRALAVASKKKMEIDLKDLEAQIEAANKARDEVIKQLRKL

QAQMKDYQRELEEARASRDEIFAQSKESEKKLKSLEAEILQLQEELASSE

RARRHAEQERDELADEITNSASGKSALLDEKRRLEARIAQLEEELEEEQS

NMELLNDRFRKTTLQVDTLNAELAAERSAAQKSDNARQQLERQNKELKAK

LQELEGAVKSKFKATISALEAKIGQLEEQLEQEAKERAAANKLVRRTEKK

LKEIFMQVEDERRHADQYKEQMEKANARMKQLKRQLEEAEEEATRANASR

RKLQRELDDATEANEGLSREVSTLKNRLRRGGPISFSSSRSGRRQLHLEG

ASLELSDDDTESKTSDVNETQPPQSE.
```

Another non-limiting exemplary sequence of myosin is disclosed herein below:

(SEQ ID NO: 43)
```
MTDAQMADFG AAAQYLRKSE KERLEAQTRP FDIRTECFVP DDKEEFVKAK

ILSREGGKVIAETENGKTVT VKEDQVLQQN PPKFDKIEDM AMLTFLHEPA

VLFNLKERYA AWMIYTYSGLFCVTVNPYKW LPVYNAEVVA AYRGKKRSEA

PPHIFSISDN AYQYMLTDRE NQSILITGESGAGKTVNTKR VIQYFASIAA

IGDRGKKDNANANKGTLEDQI IQANPALEAFGNAKTVRNDNSSRFGKFIRIHFGATG

KLASADIETYLLEKSRVIFQLKAERNYHIFYQILSNKKPELLDMLLVTNNPYDYAFVS

QGEVS VASIDDSEEL MATDSAFDVL GFTSEEKAGV

YKLTGAIMHYGNMKFKQKQR EEQAEPDGTE DADKSAYLMG LNSADLLKGL

CHPRVKVGNE YVTKGQSVQQ

VYYSIGALAK AVYEKMFNWM VTRINATLET KQPRQYFIGV LDIAGFEIFD

FNSFEQLCINFTNEKLQQFF NHHMFVLEQE EYKKEGIEWT FIDFGMDLQA

CIDLIEKPMG IMSILEEECMFPKATDMTFK AKLYDNHLGK SNNFQKPRNI

KGKPEAHFSL IHYAGTVDYN ILGWLEKNKDPLNETVVGLY QKSSLKLMAT

LFSSYATADT GDSGKSKGGK KKGSSFQTVS ALHRENLNKLMTNLRTTHPH

FVRCIIPNER KAPGVMDNPL VMHQLRCNGV LEGIRICRKG FPNRILYGDF

RQRYRILNPV AIPEGQFIDS RKGAEKLLSS LDIDHNQYKF GHTKVFFKAG

LLGLLEEMRDERLSRIITRI QAQARGQLMR IEFKKIVERR DALLVIQWNI

RAFMGVKNWP WMKLYFKIKPLLKSAETEKE MATMKEEFGR IKETLEKSEA

RRKELEEKMV SLLQEKNDLQ LQVQAEQDNLNDAEERCDQL IKNKIQLEAK

VKEMNERLED EEEMNAELTA KKRKLEDECS ELKKDIDDLELTLAKVEKEK

HATENKVKNL TEEMAGLDEI IAKLTKEKKA LQEAHQQALD DLQAEEDKVN

TLSKSKVKLE QQVDDLEGSL EQEKKVRMDL ERAKRKLEGD LKLTQESIMD

LENDKLQLEEKLKKKEFDIN QQNSKIEDEQ VLALQLQKKL KENQARIEEL

EEELEAERTA RAKVEKLRSDLSRELEEISE RLEEAGGATS VQIEMNKKRE

AEFQKMRRDL EEATLQHEAT AAALRKKHADSVAELGEQID NLQRVKQKLE

KEKSEFKLEL DDVTSNMEQI IKAKANLEKV SRTLEDQANEYRVKLEEAQR

SLNDFTTQRA KLQTENGELS RQLEEKEALI SQLTRGKLSY TQQMEDLKRQ

LEEEGKAKNA LAHALQSARH DCDLLREQYE EETEAKAELQ RVLSKANSEV

AQCRTKYETDAIQRTEELEE AKKKLAQRLQ DAEEAVEAVN AKCSSLEKTK

HRLQNEIEDL MVDVERSNAAAAALDKKQRN FDKILAEWKQ KYEESQSELE

SSQKEARSLS TELFKLKNAY EESLEHLETFKRENKNLQEE ISDLTEQLGE

GGKNVHELEK VRKQLEVEKL ELQSALEEAE ASLEHEEGKILRAQLEFNQI

KAEIERKLAE KDEEMEQAKR NHQRVVDSLQ TSLDAETRSR NEVLRVKKKM

EGDLNEMEIQ LSHANRMAAE AQKQVKSLQS LLKDTQIQLD DAVRANDDLK

ENIAIVERRNNLLQAELEEL RAVVEQTERS RKLADRELIE TSERVQLLHS

QNTSLINQKK KMDADLSQLQSEVEEAVQEC RNAEEKAKKA ITHAAMMAEE

LKKEQDTSAH LERMKKNMEQ TIKDLQHRLDEAEQIALKGG KKQLQKLEAR
```

```
VRELEGELEA EQKRNAESVK GMRKSERRIK ELTYQTEEDKKNLLRLQDLV

DKLQLKVKAY KRQAEEAEEQ ANTNLSKFRK VQHELDEAEE RADIAESQVN

KLRAKSRDIG AKQKMHDEE.
```

As used herein, "CD1d-binding lipid antigens" refers generally to lipid antigens that bind to the non-classical MHC CD1d.

As used herein, "HSP" refers to all isoforms, variants, and fragments thereof of a protein associated with the name "heat shock protein", or a biological equivalent thereof. In some embodiments, heat shock proteins includes heat shock protein 60. A non-limiting exemplary sequence of heat shock protein 60 associated with UniProt Reference No. P10809-1 is disclosed herein below:

```
                                               (SEQ ID NO: 44)
MLRLPTVFRQMRPVSRVLAPHLTRAYAKDVKFGADARALMLQGVDLLADA

VAVTMGPKGRTVIIEQSWGSPKVTKDGVTVAKSIDLKDKYKNIGAKLVQD

VANNTNEEAGDGTTTATVLARSIAKEGFEKISKGANPVEIRRGVMLAVDA

VIAELKKQSKPVTTPEEIAQVATISANGDKEIGNIISDAMKKVGRKGVIT

VKDGKTLNDELEIIEGMKFDRGYISPYFINTSKGQKCEFQDAYVLLSEKK

ISSIQSIVPALEIANAHRKPLVIIAEDVDGEALSTLVLNRLKVGLQVVAV

KAPGFGDNRKNQLKDMAIATGGAVFGEEGLTLNLEDVQPHDLGKVGEVIV

TKDDAMLLKGKGDKAQIEKRIQEIIEQLDVTTSEYEKEKLNERLAKLSDG

VAVLKVGGTSDVEVNEKKDRVTDALNATRAAVEEGIVLGGGCALLRCIPA

LDSLTPANEDQKIGIEIIKRTLKIPAMTIAKNAGVEGSLIVEKIMQSSSE

VGYDAMAGDFVNMVEKGIIDPTKVVRTALLDAAGVASLLTTAEVVVTEIP

KEEKDPGMGAMGGMGGGMGGGMF.
```

Multiple sclerosis (MS) is also known as "disseminated sclerosis," "encephalomyelitis disseminate," or "allergic encephalomyelitis." MS is an inflammatory disease in which the fatty myelin sheaths around the axons of the brain and spinal cord are damaged, leading to demyelination and scarring as well as a broad spectrum of signs and symptoms. Multiple sclerosis-related disorders include, for example, neuromyelitis optica spectrum disorder (NMO), uveitis, neuropathis pain, and the like.

"Myelin Oligodendrocyte Glycoprotein" (MOG) is a glycoprotein believed to be important in the process of myelinization of nerves in the central nervous system (CNS). In humans this protein is encoded by the MOG gene. It is speculated to serve as a necessary "adhesion molecule" to provide structural integrity to the myelin sheath and is known to develop late on the oligodendrocyte. The GenBank accession numbers NM 001008228.2 and NP 001008229.1 represent the mRNA and protein sequence, respectively, of the MOG gene. The sequence associated with each of these GenBank accession numbers is incorporated by reference for all purposes.

As used herein, the terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia and metastases thereof. A "metastasis" intends the transference of disease-producing organisms or of malignant or cancerous cells to other parts of the body by way of the blood or lymphatic vessels or membranous surfaces. Non-limiting examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, the term "diabetes" intends a variable disorder of carbohydrate metabolism caused by a combination of hereditary and environmental factors and is usually characterized by inadequate secretion or utilization of insulin, by excessive urine production, by excessive amounts of sugar in the blood and urine, and by thirst, hunger, and loss of weight. Diabetes is characterized by Type 1 diabetes and Type 2 diabetes. The nonobese diabetic ("NOD") mouse is an accepted animal model for the study and treatment of diabetes. Type 1 Diabetes (T1D) in mice is associated with autoreactive CD8+ T-cells. Nonobese diabetic (NOD) mice develop a form of T1D, closely resembling human T1D, that results from selective destruction of pancreatic kens by T-cells recognizing a growing list of autoantigens. Although initiation of T1D clearly requires the contribution of CD4+ cells, there is compelling evidence that T1D is CD8+ T-cell-dependent. It has been discovered that a significant fraction of islet-associated CD8+ cells in NOD mice use CDR3-invariant V$\alpha$17-J$\alpha$42+ TCRs, referred to as '8.3-TCR-like'. These cells, which recognize the mimotope NRP-A7 (defined using combinatorial peptide libraries) in the context of the MHC molecule $K^d$, are already a significant component of the earliest NOD islet CD8+ infiltrates, are diabetogenic, and target a peptide from islet-specific glucose-6-phosphatase catalytic subunit-related protein (IGRP), a protein of unknown function. The CD8+ cells that recognize this peptide (IGRP$_{206-214}$, similar to NRP-A7) are unusually frequent in the circulation (>1/200 CD8+ cells). Notably, progression of insulitis to diabetes in NOD mice is invariably accompanied by cyclic expansion of the circulating IGRP$_{206-214}$-reactive CD8+ pool, and by avid maturation of its islet-associated counterpart. More recently, it has been shown that islet-associated CD8+ cells in NOD mice recognize multiple IGRP epitopes, indicating that IGRP is a dominant autoantigen for CD8+ cells, at least in murine T1D. NOD islet-associated CD8+ cells, particularly those found early on in the disease process also recognize an insulin epitope (Ins B$_{15-23}$).

As used herein, the term "pre-diabetes" intends an asymptomatic period preceding a diabetic condition characterized by subclinical beta cell damage wherein the patient exhibits normal plasma glucose levels. It is also characterized by the presence of islet cell autoantibodies (ICAs) and, when close to the onset of clinical symptoms, may be accompanied by intolerance to glucose.

As used herein, the term "multiple sclerosis-related disorder" intends a disorder that co-presents with a susceptibility to MS or with MS. Non-limiting examples of such include neuromyelitis optica spectrum disorder (NMO), uveitis, neuropathis pain sclerosis, atherosclerosis, arteriosclerosis, sclerosis disseminata, systemic sclerosis, spinooptical MS, primary progressive MS (PPMS), and relapsing remitting MS (RRMS), progressive systemic sclerosis, and ataxic sclerosis.

The terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-20 amino acids in a unique spatial conformation. Methods of determining spatial conformation of epitopes include, for example, x-ray crystallography and 2-dimensional nuclear magnetic resonance. See, e.g., Glenn E. Morris, Epitope Mapping Protocols (1996). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis., 170:1110-1119, 1994), by antigen-dependent killing (cytotoxic T lymphocyte assay, Tigges et al., J. Immunol., 156(10):3901-3910, 1996) or by cytokine secretion. The presence of a cell-mediated immunological response can be determined by proliferation assays (CD4$^+$ T cells) or CTL (cytotoxic T lymphocyte) assays.

Optionally, an antigen or preferably an epitope of an antigen, can be chemically conjugated to, or expressed as, a fusion protein with other proteins, such as MHC and MHC related proteins.

As used herein, the terms "patient" and "subject" are used synonymously and refer to a mammal. In some embodiments, the patient is a human. In other embodiments, the patient is a mammal in need of veterinary medicine or is a mammal commonly used in a laboratory. In some embodiments, the mammal is a mouse, rat, simian, canine, feline, bovine, equine, or ovine.

As used in this disclosure, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It is also contemplated that a particular polypeptide from a given species may be encoded by nucleic acids containing natural variations that have slightly different nucleic acid sequences but, nonetheless, encode the same or substantially similar protein, polypeptide, or peptide.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively, that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example, those described in Current Protocols in Molecular Biology (Ausubel et al., eds. 1987) Supplement 30, section 7.7.18, Table 7.7.1. Preferably, default parameters are used for alignment. A certain alignment program is BLAST, using default parameters. In particular, certain programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

It is to be inferred without explicit recitation and unless otherwise intended, that when the present disclosure relates to an antigen, polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference antigen, protein, antibody, fragment, polypeptide or nucleic acid, and intends those having minimal homology while still maintaining the desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen-binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a polymerase chain (PC) reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

As used herein, the terms "treating," "treatment" and the like are used herein to mean obtaining a desired pharmacologic and/or physiologic effect. The effect may be therapeutic in terms of a partial or complete cure for a disorder and/or adverse effect attributable to the disorder. In one aspect, treatment indicates a reduction in the signs of the disease using an established scale.

As used herein, the term "treatment" or "treating" as it relates to oncology, means any treatment of a disease or condition or associated disorder, in a patient, including inhibiting the disease or condition, that is, arresting or suppressing the development of clinical symptoms, such as cachexia in cancer; and/or relieving the disease or condition that is causing the regression of clinical symptoms, e.g., increasing overall survival or reducing tumor burden.

In some aspects, the term "treating" refers to an improvement in clinical outcomes. The term "clinical outcome" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect. "Overall Survival" (OS) intends a prolongation in life expectancy as compared to na-ve or untreated individuals or patients. "Progression free survival" (PFS) or "Time to Tumor Progression" (TTP) indicates the length of time during and after treatment that the cancer does not grow. Progression-free survival includes the amount of time patients have experienced a complete response or a partial response, as well as the amount of time patients have experienced stable disease. "Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer. "Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up. "Relative Risk" (RR), in statistics and mathematical epidemiology, refers to the risk of an event (or of developing a disease) relative to exposure. Relative risk is a ratio of the probability of the event occurring in the exposed group versus a non-exposed group.

A "composition" is intended to mean a combination of active agent and another compound or composition, inert (for example, a detectable agent or label) or active, such as an adjuvant. In certain embodiments, the composition does not contain an adjuvant.

A "pharmaceutical composition" is intended to include the combination of an active agent with a carrier, inert or active, making the composition suitable for diagnostic or therapeutic use in vitro, in vivo or ex vivo.

The term "functionally equivalent codon" is used herein to refer to codons that encode the same amino acid, such as the six codons for arginine or serine, and also refers to codons that encode biologically equivalent amino acids (see Table 2).

As used herein, a "protein" or "polypeptide" or "peptide" refers to a molecule comprising at least five amino acid residues.

Other objects, features and advantages of the present disclosure will become apparent from the following detailed description. Additional definitions are also provided therein. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

Descriptive Embodiments

Autoimmune diseases such as type 1 diabetes (T1D), multiple sclerosis and rheumatoid arthritis result from chronic autoimmune responses involving T cells and B cells recognizing numerous antigenic epitopes on incompletely defined lists of autoantigens (Santamaria, P. (2010) Immunity 32:437-445; Babbe, H. et al. (2000) J. Exp. Med. 192:393-404; Firestein, G. S. (2003) Nature 423:356-361). Eliminating or suppressing all polyclonal autoreactive T-cell specificities (known and unknown) in each individual autoimmune disorder without compromising systemic immunity is not currently possible.

Adoptive transfer of polyclonal FOXP3$^+$CD4$^+$CD25$^+$ regulatory T (T$_{reg}$) cells expanded ex vivo has been proposed as an alternative therapeutic approach (Sakaguchi, S. et al. (2006) Immunol. Rev. 212:8-27). The potential for bystander immunosuppression, the lack of effective strategies for expanding antigen-specific T$_{reg}$ cells in vitro, and the lineage instability of FOXP3$^+$ T$_{reg}$ cells, have hindered the clinical translation of this approach (Zhou, X. et al. (2009) Nature Immunol. 10:1000-1007; Komatsu, N. et al. (2014) Nature Med. 20:62-68; Bailey-Bucktrout, S. L. et al. (2013) Immunity 39:949-962). T$_R$1 FOXP3 CD4$^+$CD25$^-$ T cells, which produce the cytokines IL-10 and IL-21, and express the surface markers CD49b and LAG-3 and the transcription factor c-Maf 8, constitute another regulatory T-cell subset recently exploited for the treatment of human inflammatory diseases (McLarnon, A. (2012) Nature Rev. Gastroenterol. Hepatol. 9:559; Desreumaux, P. et al. (2012) Gastroenterology 143:1207-1217; Roncarolo, M. G. et al. (2011) Immunol. Rev. 241:145-163). However, as with FOXP3+ Treg cells, there are no pharmacological approaches that can expand autoantigen- or disease-specific T$_R$1-like cells in vivo.

Thus, regulatory T cells hold promise as targets for therapeutic intervention in autoimmunity, but approaches capable of expanding antigen-specific regulatory T cells in vivo are currently not available. Here Applicant shows that systemic delivery of nanoparticles coated with autoimmune-disease-relevant peptides bound to major histocompatibility complex class II (pMHCII) molecules triggers the generation and expansion of antigen-specific regulatory CD4$^+$ T cell type 1 (T$_R$1)-like cells in different mouse models, including mice humanized with lymphocytes from patients, leading to resolution of established autoimmune phenomena. Ten pMHCII-based nanomedicines show similar biological effects, regardless of genetic background, prevalence of the cognate T-cell population or MHC restriction. These nanomedicines promote the differentiation of disease-primed autoreactive T cells into T$_R$1-like cells, which in turn suppress autoantigen-loaded antigen-presenting cells and drive the differentiation of cognate B cells into disease-suppressing regulatory B cells, without compromising systemic immunity. pMHCII-based nanomedicines thus represent a new class of drugs, potentially useful for treating a broad spectrum of autoimmune conditions in a disease-specific manner.

Applicant previously discovered that systemic delivery of nanoparticles (NPs) coated with T1D-relevant pMHC class I complexes (pMHC-NPs) could blunt the progression of T1D by expanding subsets of CD8$^+$ T cells with regulatory potential but conventional memory-like phenotype (Tsai, S. et al. (2010) Immunity 32:568-580). As the nanoparticles could be coated with different pMHC class I complexes, Applicant reasoned that pMHC-NP therapy may utilize a naturally occurring negative feedback regulatory loop, whereby chronic autoantigenic exposure (and exposure to pMHC-NPs) could trigger the differentiation of autoreactive T cells into regulatory T-cell progeny. By this reasoning, Applicant predicted and has shown herein that NPs coated with disease-relevant pMHCII complexes might be able to expand disease-specific regulatory CD4$^+$ T cells in vivo.

This disclosure builds on those initial observations by providing pMHC-NPs, compositions and methods for making them, as well as their use.

Substrates/Particles

By "particle," "nanoparticle," "microparticle," "bead," "microsphere," and grammatical equivalents herein is meant small discrete particles that are administrable to a subject. In certain embodiments, the particles are substantially spherical in shape. The term "substantially spherical," as used herein, means that the shape of the particles does not deviate from a sphere by more than about 10%. Various known antigen or peptide complexes of the disclosure may be applied to the particles.

The nanoparticle core of the pMHC-NP comprises, or consists essentially of, or yet further consists of a core, for example a solid core, a metal core, a dendrimer core, a polymeric micelle nanoparticle core, a nanorod, a fullerene, a nanoshell, a coreshell, a protein-based nanostructure or a lipid-based nanostructure. In some aspects, the nanoparticle core is bioabsorbable and/or biodegradable. In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle core may comprise, or alternatively consist essentially thereof, or yet further consist of a poly(amidoamine)-based dendrimer or a poly-L-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core comprises, or alternatively consists essentially thereof, or yet further consists of a polymeric micelle produced using polyethylene glycol-diastearoylphosphatidylethanolamine block copolymer. In a further aspect, the nanoparticle core comprises, or alternatively consists essentially of, or yet further consists of a metal. In another aspect, the nanoparticle core is not a liposome. Additional examples of core materials include but are not limited to, standard and specialty glasses, silica, polystyrene, polyester, polycarbonate, acrylic polymers, polyacrylamide, polyacrylonitrile, polyamide, fluoropolymers, silicone, celluloses, silicon, metals (e.g., iron, gold, silver), minerals (e.g., ruby), nanoparticles (e.g., gold nanoparticles, colloidal particles, metal oxides, metal sulfides, metal selenides, and magnetic materials such as iron oxide), and composites thereof. In some embodiments, an iron oxide nanoparticle core comprises iron (II, III) oxide. The core could be of homogeneous composition, or a composite of two or more classes of material depending on the properties desired. In certain aspects, metal nanoparticles will be used. These metal particles or nanoparticles can be formed from Au, Pt, Pd, Cu, Ag, Co, Fe, Ni, Mn, Sm, Nd, Pr, Gd, Ti, Zr, Si, and In, precursors, their binary alloys, their ternary alloys and their intermetallic compounds. See U.S. Pat. No. 6,712,997, which is incorporated herein by reference in its entirety. In certain embodiments, the compositions of the core and layers (described below) may vary provided that the nanoparticles are biocompatible and bioabsorbable. The core could be of homogeneous composition, or a composite of two or more classes of material depending on the properties desired. In certain aspects, metal nanospheres will be used. These metal nanoparticles can be formed from Fe, Ca, Ga and the like. In certain embodiments, the nanoparticle comprises, or alternatively consists essentially of, or yet further consists of a core comprising metal or metal oxide such as gold or iron oxide.

The particles typically consist of a substantially spherical core and optionally one or more layers or coatings. The core may vary in size and composition as described herein. In addition to the core, the particle may have one or more layers to provide functionalities appropriate for the applications of interest. The thicknesses of layers, if present, may vary depending on the needs of the specific applications. For example, layers may impart useful optical properties.

Layers may also impart chemical or biological functionalities, referred to herein as chemically active or biologically active layers. These layers typically are applied on the outer surface of the particle and can impart functionalities to the pMHC-NPs. The layer or layers may typically range in thickness from about 0.001 micrometers (1 nanometer) to about 10 micrometers or more (depending on the desired particle diameter) or from about 1 nm to 5 nm, or alternatively from about 1 nm to about 10 nm, or alternatively from about 1 nm to about 40 nm, or from about 15 nm to about 25 nm, or about 20 nm, and ranges in between.

The layer or coating may comprise, or alternatively consist essentially of, or yet further consist of a biodegradable sugar or other polymer. Examples of biodegradable layers include but are not limited to dextran; poly(ethylene glycol); poly(ethylene oxide); mannitol; poly(esters) based on polylactide (PLA), polyglycolide (PGA), polycaprolactone (PCL); poly(hydroxyalkanoate) of the PHB-PHV class; and other modified poly(saccharides) such as starch, cellulose and chitosan. Additionally, the nanoparticle may include a layer with suitable surfaces for attaching chemical functionalities for chemical binding or coupling sites.

Layers can be produced on the nanoparticles in a variety of ways known to those skilled in the art. Examples include sol-gel chemistry techniques such as described in Iler, Chemistry of Silica, John Wiley & Sons, 1979; Brinker and Scherer, Sol-gel Science, Academic Press, (1990). Additional approaches to producing layers on nanoparticles include surface chemistry and encapsulation techniques such as described in Partch and Brown, J. Adhesion, 67:259-276, 1998; Pekarek et al., Nature, 367:258, (1994); Hanprasopwattana, Langmuir, 12:3173-3179, (1996); Davies, Advanced Materials, 10:1264-1270, (1998); and references therein. Vapor deposition techniques may also be used; see, for example, Golman and Shinohara, Trends Chem. Engin., 6:1-6, (2000); and U.S. Pat. No. 6,387,498. Still other approaches include layer-by-layer self-assembly techniques such as described in Sukhorukov et al., Polymers Adv. Tech., 9(10-11):759-767, (1998); Caruso et al., Macromolecules, 32(7):2317-2328, (1998); Caruso et al., J. Amer. Chem. Soc., 121(25):6039-6046, (1999); U.S. Pat. No. 6,103,379 and references cited therein.

In some aspects, the nanoparticle core is a dendrimer nanoparticle core comprising, or alternatively consisting essentially thereof, or yet further consisting of a highly branched macromolecule having a tree-like structure growing from a core. In further aspects, the dendrimer nanoparticle may comprise, or alternatively consist essentially thereof, or yet further consist of a poly(amidoamine)-based dendrimer or a poly-L-lysine-based dendrimer. In certain aspects, the nanoparticle core is a polymeric micelle core comprising, or alternatively consisting essentially thereof, or yet further consisting of an amphiphilic block co-polymer assembled into a nano-scaled core-shell structure. In further aspects, the polymeric micelle core may comprise, or alternatively consist essentially thereof, or yet further consist of a polymeric micelle produced using polyethylene glycol-diastearoylphosphatidylethanolamine block copolymer. The dendrimer core or polymeric micelle core may further comprise an outer coating or layer as described herein.

In certain embodiments, specific means of synthesis of dendrimer nanoparticles or nanoparticles with a dendrimer nanoparticle core may require that metal ions are extracted into the interior of dendrimers and then subsequently chemically reduced to yield nearly size-monodispersed particles having dimensions of less than 3 nm, such as the method disclosed in Crooks et al., "Synthesis, Characterization, and Applications of Dendrimer-Encapsulated Nanoparticles". The Journal of Physical Chemistry B (109): 692-704 (2005), wherein the resulting dendrimer core component serves not only as a template for preparing the nanoparticle but also to stabilize the nanoparticle, making it possible to tune solubility, and provides a means for immobilization of the nanoparticle on solid supports.

The size of the nanoparticle core can range from about 1 nm to about 1 μm. In certain embodiments, the nanoparticle core is less than about 1 μm in diameter. In other embodiments, the nanoparticle core is less than about 500 nm, less than about 400 nm, less than about 300 nm, less than about 200 nm, less than about 100 nm, or less than about 50 nm in diameter. In further embodiments, the nanoparticle core is from about 1 nm to about 10 nm, 15 nm, 20 nm, 25 nm, 30 nm, 40 nm, 50 nm, 75 nm, or 100 nm in diameter. In specific embodiments, the nanoparticle core has a diameter of from about 1 nm to about 100 nm; from about 1 nm to about 75 nm; from about 1 nm to about 50 nm; from about 1 nm to about 25 nm; from about 1 nm to about 25 nm; from about 5 nm to about 100 nm; from about 5 nm to about 50 nm; or from about 5 nm to about 25 nm, or from about 15 nm to about 25 nm, or about 20 nm. In some embodiments, the nanoparticles core has a diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm or about 30 nm, or about 35 nm, or about 40 nm.

The size of the pMHC-NP, with or without the layer, can range from about 5 nm to about 1 μm in diameter. In certain embodiments, the pMHC-NP complex is less than about 1 µm or alternatively less than 100 nm in diameter. In other embodiments, the pMHC-NP complex is less than about 500 nm, less than about 400 nm, less than about 300 nm, less than about 200 nm, less than about 100 nm, or less than about 50 nm in diameter. In further embodiments, the complex is from about 5 nm or 10 nm to about 50 nm, or from about 5 nm to about 75 nm, or from about 5 nm to about 50 nm, or from about 5 nm to about 60 nm, or from about 10 nm to about 50 nm, or from about 10 nm to about 60 nm, or from about 10 nm to about 70 nm, or from about 10 nm to about 75 nm, or from about 20 nm to about 50 nm, or from about 20 nm to about 60 nm, or from about 20 nm to about 70 nm, or from about 20 nm to about 75 nm, or from about 30 nm to about 50 nm, or from about 30 nm to about 60 nm, or from about 30 nm to about 70 nm, or from about 30 nm to about 75 nm, or in one aspect about 55 nm in diameter. In specific embodiments, the pMHC-NP complex is from about 35 nm to about 60 nm, or from about 35 nm to about 70 nm, or from about 35 nm to about 75 nm in diameter. In one aspect, the pMHC-NP complex is from about 30 nm to about 50 nm in diameter.

Antigen-MHC Complexes

The nanoparticle complexes of this disclosure comprise a nanoparticle core, with or without a layer, coupled to an antigen-MHC (pMHC) complex. The selection of antigen will depend on the disease or condition to be treated, as noted above. The individual polypeptide (e.g., MHC) and the antigenic (e.g., peptide) components form a complex through covalent or non-covalent binding (e.g. through hydrogen bonds, ionic bonds, or hydrophobic bonds). The preparation of such complexes may require varying degrees of manipulation and such methods are well known in the literature. In some aspects, antigenic components can be associated non-covalently with the pocket portion of the MHC component by, for instance, mixing the MHC and antigenic components; this relies on the natural binding affinity between an MHC and an antigen. Alternatively, in some aspects, the MHC component may be covalently bound to the antigenic component using standard procedures, such as, but not limited to, the introduction of known coupling agents or photo affinity labelling (see e.g., Hall et al., Biochemistry 24:5702-5711 (1985)). In certain aspects, an antigenic component may be operatively coupled to the MHC component via peptide linkages or other methods discussed in the literature, including but not limited to, attachment via carbohydrate groups on the glycoproteins, including, e.g., the carbohydrate moieties of the alpha- and/or beta-chains. In particular embodiments, the antigenic component may be attached to the N-terminal or C-terminal end of an appropriate MHC molecule. Alternatively, in certain embodiments, the MHC complex may be recombinantly formed by incorporating the sequence of the antigenic component into a sequence encoding an MHC, such that both retain their functional properties.

Multiple antigen-MHC complexes may be coupled to the same nanoparticle core; these complexes, MHCs, and/or antigens may be the same or different from one another.

Valency is defined as the number of pMHC complexes per nanoparticle core. In certain embodiments the valency of the nanoparticle may range between about 1 pMHC complex to 1 nanoparticle core to about 6000 pMHC complexes to 1 nanoparticle core, or alternatively between about 10:1 to about 6000:1, or alternatively between about 11:1 to about 6000:1, or alternatively between about 12:1 to about 6000:1, or alternatively at least 2:1, or alternatively at least 8:1, or alternatively at least 9:1, or alternatively at least 10:1, or alternatively at least 11:1, or alternatively at least 12:1.

In some aspects, the valency is from about 10:1 to about 6000:1, or from about 20:1 to about 5500:1, or alternatively from about 10:1 to about 5000:1, or alternatively from about 10:1 to about 4000:1, or alternatively from about 10:1 to about 3500:1, or alternatively from about 10:1 to about 3000:1, or alternatively from about 10:1 to about 2500:1, or alternatively from about 10:1 to about 2000:1, or alternatively from about 10:1 to about 1500:1, or alternatively from about 10:1 to about 1000:1, or alternatively from about 10:1 to about 500:1, or alternatively from about 10:1 to about 100:1, or alternatively from about 20:1 to about 50:1, or alternatively from about 25:1 to about 60:1; alternatively from about 30:1 to about 50:1, or alternatively from about 35:1 to about 45:1, or alternatively about 40:1.

Applicant has discovered that pMHC density on the nanoparticle regulates the ability of the pMHC-NPs to trigger or differentiate $T_R1$ cell formation in a dose-independent manner. Density is calculated as the number of complexes per unit surface area of the nanoparticle. The surface area of the nanoparticle may be determined with or without the layers, including, but not limited to, linkers that conjugate the pMHC complex to the nanoparticle. For the purposes of calculating density, the relevant surface area value is based on the final diameter of the particle construct without the pMHC complex, with or without the outer layer on the nanoparticle core.

It is determined and disclosed herein that the density of the pMHC complexes on the nanoparticle contributes to the therapeutic benefit in a dose-independent manner. Thus, as disclosed herein, the nanoparticle can have a defined pMHC density in the range of from about 0.01 pMHC, or alternatively 0.025 pMHC, molecules per 100 $nm^2$ of surface area of the nanoparticle including the layer or complex, assuming at least 2 MHC molecules, or alternatively at least 8, or alternatively at least 9, or alternatively at least 10, or alternatively at least 11, or alternatively at least 12, pMHC molecules complexed to the nanoparticle to about 100 pMHC molecules per 100 $nm^2$ of surface area. In one aspect, the nanoparticle has a density of pMHC from about 0.05 pMHC per 100 $nm^2$ to about 76 pMHC/100 $nm^2$, or alternatively from 0.1 pMHC/100 $nm^2$ to about 50 pMHC/100 $nm^2$, or alternatively from about 0.3 pMHC/100 $nm^2$ to about 25 pMHC/100 $nm^2$, or alternatively from about 0.35 pMHC/100 $nm^2$ to about 25 pMHC/100 $nm^2$, or alternatively from about 0.4 pMHC/100 $nm^2$ to about 50 pMHC/100 $nm^2$, or alternatively from about 0.4 pMHC/100 $nm^2$ to about 25 pMHC/100 $nm^2$, or alternatively from about 0.4 pMHC/100 $nm^2$ to about 20 pMHC/100 $nm^2$, 0.4 pMHC/100 $nm^2$ to about 10 pMHC/100 $nm^2$, 0.4 pMHC/100 $nm^2$ to about 5 pMHC/100 $nm^2$, or alternatively from about 0.5 pMHC/100 $nm^2$ to about 20 pMHC/100 $nm^2$, or alternatively from about 0.5 pMHC/100 $nm^2$ to about 10 pMHC/100 $nm^2$, or alternatively from about 0.6 pMHC/100 $nm^2$ to about 20 pMHC/100 $nm^2$, or alternatively from about 1.0 pMHC/100 $nm^2$ to about 20 pMHC/100 $nm^2$, or alternatively from about 10 pMHC/100 $nm^2$ to about 20 pMHC/100 $nm^2$, or alternatively at least about 0.4, or alternatively at least about 0.406, or alternatively at least about 0.5, or alternatively at least about 1.0, or alternatively at least about 5.0, or alternatively at least about 10.0, or alternatively at least about 15.0 pMHC/100 $nm^2$, or alternatively less than about 76 pMHC/100 $nm^2$, or alternatively less than about 50 pMHC/100 $nm^2$, or alternatively less than about 47.75 pMHC/100 $nm^2$ or alternatively less than about 25 pMHC/100 $nm^2$, or alternatively less than about 20 pMHC/100 $nm^2$.

In certain embodiments, the pMHC density per nanoparticle is from about 0.4 pMHC/100 nm² to about 25 pMHC/100 nm², or from about 0.4 pMHC/100 nm² to about 20 pMHC/100 nm², or from about 0.4 pMHC/100 nm² to about 15 pMHC/100 nm², or from about 0.4 pMHC/100 nm² to about 14 pMHC/100 nm², or from about 0.4 pMHC/100 nm² to about 13 pMHC/100 nm², or from about 0.4 pMHC/100 nm² to about 12 pMHC/100 nm², or from about 0.4 pMHC/100 nm² to about 11.6 pMHC/100 nm², or from about 0.4 pMHC/100 nm² to about 11.5 pMHC/100 nm², or from about 0.4 pMHC/100 nm² to about 11 pMHC/100 nm², or from about 0.4 pMHC/100 nm² to about 10 pMHC/100 nm², or from about 0.4 pMHC/100 nm² to about 9 pMHC/100 nm², or from about 0.4 pMHC/100 nm² to about 8 pMHC/100 nm², or from about 0.4 pMHC/100 nm² to about 7 pMHC/100 nm², or from about 0.4 pMHC/100 nm² to about 6 pMHC/100 nm², or from about 0.4 pMHC/100 nm² to about 5 pMHC/100 nm², or from about 0.4 pMHC/100 nm² to about 4 pMHC/100 nm², or from about 0.4 pMHC/100 nm² to about 3 pMHC/100 nm², or from about 0.4 pMHC/100 nm² to about 2.5 pMHC/100 nm², or from about 0.4 pMHC/100 nm² to about 2 pMHC/100 nm², or from about 0.4 pMHC/100 nm² to about 1.5 pMHC/100 nm².

In yet further embodiments, the nanoparticle may have a pMHC density of from about 0.22 pMHC/100 nm² to about 10 pMHC/100 nm², or from about about 0.22 pMHC/100 nm² to about 9 pMHC/100 nm², or from about about 0.22 pMHC/100 nm² to about 8 pMHC/100 nm², or from about about 0.22 pMHC/100 nm² to about 7 pMHC/100 nm², or from about about 0.22 pMHC/100 nm² to about 6 pMHC/100 nm², or from about about 0.22 pMHC/100 nm² to about 5 pMHC/100 nm², or from about about 0.22 pMHC/100 nm² to about 4 pMHC/100 nm², or from about about 0.22 pMHC/100 nm² to about 3 pMHC/100 nm², or from about about 0.22 pMHC/100 nm² to about 2 pMHC/100 nm², or from about about 0.22 pMHC/100 nm² to about 1.5 pMHC/100 nm². In some aspects, the nanoparticle has a pMHC density of from about 0.22 pMHC/100 nm² to about 10 pMHC/100 nm², or 0.24 pMHC/100 nm² to about 9 pMHC/100 nm², or from about 0.26 pMHC/100 nm² to about 8 pMHC/100 nm², or from about 0.28 pMHC/100 nm² to about 7 pMHC/100 nm², or from about 0.24 pMHC/100 nm² to about 4 pMHC/100 nm², or from about 0.5 pMHC/100 nm² to about 3 pMHC/100 nm², or from about 0.6 pMHC/100 nm² to about 1.5 pMHC/100 nm². In some embodiments, the nanoparticle has a pMHC density of from about 0.4 pMHC/100 nm² to about 1.3 pMHC/100 nm², or alternatively from about 0.5 pMHC/100 nm² to about 0.9 pMHC/100 nm², or alternatively from about 0.6 pMHC/100 nm² to about 0.8 pMHC/100 nm².

In yet further embodiments, the nanoparticle can have a density of from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, or 12.0 pMHC/100 nm². In specific embodiments, the nanoparticle has a density of from about 0.4 pMHC/100 nm² to about 1.5 pMHC/100 nm² or from about 0.4 pMHC/100 nm² to about 6 pMHC/100 nm² or from about 0.4 pMHC/100 nm² to about 11 pMHC/100 nm².

In some aspects, provided herein is a complex comprising a nanoparticle core, wherein a plurality of disease-relevant antigen-MHC (pMHC) complexes are coupled to the core; the diameter of the core is from about 15 nm to about 25 nm; and wherein the pMHC density on the nanoparticle is from about 0.4 pMHC/100 nm² to about 6 pMHC/100 nm² of the surface area of the nanoparticle. In some embodiments, the complex further comprises an outer layer on the nanoparticle core, wherein the pMHC complex is coupled to the nanoparticle core and/or the outer layer, and wherein the diameter of the nanoparticle core and the outer layer is from about 35 nm to about 45 nm.

The term "operatively coupled" or "coated" as used herein, refers to a situation where individual polypeptide (e.g., MHC) and antigenic (e.g., peptide) components are combined to form the active complex prior to binding at the target site, for example, an immune cell. This includes the situation where the individual polypeptide complex components are synthesized or recombinantly expressed and subsequently isolated and combined to form a complex, in vitro, prior to administration to a subject; the situation where a chimeric or fusion polypeptide (i.e., each discrete protein component of the complex is contained in a single polypeptide chain) is synthesized or recombinantly expressed as an intact complex. Typically, polypeptide complexes are added to the nanoparticles to yield nanoparticles with adsorbed or coupled polypeptide complexes having a ratio of number of molecules:number of nanoparticle from about, at least about or at most about 0.1, 0.5, 1, 3, 5, 7, 10, 15, 20, 25, 30, 35, 40, 50, 100, 125, 150, 175, 200, 225, 250, 275, 300, 325, 350, 375, 400, 425, 450, 475, 500, 600, 700, 800, 900, 1000, 1500 or more to: 1, more typically 0.1:1, 1:1 to 50:1 or 300:1, and ranges therebetween where the ratios provide the selected endpoints of each range. The polypeptide content of the nanoparticles can be determined using standard techniques.

MHC Molecules

As used herein and unless specifically noted, the term MHC in the context of an pMHC complex intends a classical or a non-classical MHC class I protein and/or or classical or non-classical MHC class II protein, any loci of HLA DR, HLA DQ, HLA DP, HLA-A, HLA-B, HLA-C, HLA-E, CD1d, or a fragment or biological equivalent thereof, dual or single chain constructs, dimers (Fc fusions), tetramers, multimeric forms, and a polymeric form of MHCI or MHCII. In some embodiments, the pMHC can be a single chain construct. In some embodiments, the pMHC can be a dual-chain construct.

In some embodiments, the MHC protein can be a dimer or a multimer.

In some embodiments, the MHC protein may comprise a knob-in-hole based MHC-alpha-Fc/MHC-beta-Fc heterodimer or multimer.

As noted above, "knob-in-hole" is a polypeptidyl architecture requiring a protuberance (or "knob") at an interface of a first polypeptide and a corresponding cavity (or a "hole") at an interface of a second polypeptide, such that the protuberance can be positioned in the cavity so as to promote heteromultimer formation. Protuberances are constructed by replacing small amino acid side chains from the interface of the first polypeptide with larger side chains (e.g., phenylalanine or tyrosine). Cavities of identical or similar size to the protuberances are created in the interface of the second polypeptide by replacing large amino acid side chains with smaller ones (e.g., alanine or threonine). The protuberances and cavities can be made by synthetic means such as by altering the nucleic acid encoding the polypeptides or by peptide synthesis, using routine methods by one skilled in the art. In some embodiments, the interface of the first polypeptide is located on an Fc domain in the first polypeptide; and the interface of the second polypeptide is located on an Fc domain on the second polypeptide.

As noted above, "MHC-alpha-Fc/MHC-beta-Fc" is a heterodimer comprising a first polypeptide and a second polypeptide, wherein the first polypeptide comprises an MHC class II α-chain and an antibody Fc domain; the second polypeptide comprises an MHC class II β-chain and an antibody Fc domain. A knob-in-hole MHC-alpha-Fc/MHC-beta-Fc further requires that the Fc domains of each polypeptide interface with one another through the complementary positioning of a protuberance on one Fc domain within the corresponding cavity on the other Fc domain.

In certain embodiments of the disclosure, a particular antigen is identified and presented in the antigen-MHC-nanoparticle complex in the context of an appropriate MHC class I or II polypeptide. Presentation of antigens to T cells is mediated by two distinct classes of molecules, MHC class I (MHC-I) and MHC class II (MHC-II), which utilize distinct antigen processing pathways. Peptides derived from intracellular antigens are presented to $CD8^+$ T cells by MHC class I molecules, which are expressed on virtually all cells, while extracellular antigen-derived peptides are presented to $CD4^+$ T cells by MHC-II molecules. However, there are certain exceptions to this dichotomy. Several studies have shown that peptides generated from endocytosed particulate or soluble proteins are presented on MHC-I molecules in macrophages as well as in dendritic cells. In certain aspects, the genetic makeup of a subject may be assessed to determine which MHC polypeptide is to be used for a particular patient and a particular set of peptides. In certain embodiments, the MHC class 1 component may comprise, consist essentially of, or alternatively further consist thereof all or part of a HLA-A, HLA-B, HLA-C, HLA-E, HLA-F, HLA-G or CD-1 molecule. In embodiments wherein the MHC component is a MHC class II component, the MHC class II component may comprise, consist essentially of, or alternatively further consist thereof all or a part of a HLA-DR, HLA-DQ, or HLA-DP. In certain embodiments, the MHC may comprise HLA DRB1, HLA DRB3, HLA DRB4, HLA DRB5, HLA DQB1, HLA DQA1, $IAg_7$, I-Ab, I-Ad, HLA-DQ, HLA-DP, HLA-A, HLA-B, HLA-C, HLA-E or CD1d.

Non-classical MHC molecules are also contemplated for use in MHC complexes of the disclosure. In some embodiments, non-classical MHC molecules are non-polymorphic, conserved among species, and possess narrow, deep, hydrophobic ligand binding pockets. These binding pockets are capable of presenting glycolipids and phospholipids to Natural Killer T (NKT) cells. NKT cells represent a unique lymphocyte population that co-express NK cell markers and a semi-invariant T cell receptor (TCR). They are implicated in the regulation of immune responses associated with a broad range of diseases.

As noted above, the term "MHC" may be used interchangeably with the term "human leukocyte antigen" (HLA) when used in reference to human MHC; thus, MHC refers to all HLA subtypes including, but not limited to, the classical MHC genes disclosed above: HLA-A, HLA-B, HLA-C, HLA-DP, HLA-DQ, and HLA-DR, in addition to all variants, isoforms, isotypes, and other biological equivalents thereof.

MHCs for use according to the present disclosure may be produced, isolated, or purified through techniques known in the art. Common protocols for obtaining MI-ICs involve steps such as, but not limited to, electrophoresis or other techniques of charge or size based separation, biotinylation or other tagging methods and purification, or transfection and induction of vector constructs expressing MHC proteins. Purified animal antibodies are also available through commercially available sources, including retailers such as eBioscience, Biolegend, or Tonbo Biosciences.

In certain embodiments, the MHC of the antigen-MHC complexes may be classical MHCI, non-classical MHCI, classical MHCII, non-classical MHCII, dimers (Fc fusions), MHC tetramers, or a polymeric form of MHC. In some embodiments, MHC multimers are generated according to methods well documented in the art, see, e.g., Bakker et al. "MHC Multimer Technology: Current Status and Future Prospects," Current Opinion in Immunology, Vol. 17, No. 4 pp. 428-433 (2005) and references cited therein. Non-limiting exemplary methods include the use of a biotinylating agent such as, but not limited to, streptavidin or avidin, to bind MHC monomers, creating a multimeric structure with the agent as a backbone. MHC dimers, specifically, may alternatively be produced through fusion with antibody constant regions or Fc regions; this may be accomplished through operative coupling directly or through a linker, e.g. a cysteine linker.

Co-Stimulatory Molecule Components

In certain aspects, the NPs additionally comprise, or alternatively consist essentially of, or yet further consist of at least one co-stimulatory molecule. Co-stimulatory molecules are molecules that produce a secondary signal in vivo that serves to activate naive T cells into antigen-specific T cells capable of producing an immune response to cells possessing said specific antigen. The present disclosure is not limited to any specific co-stimulatory molecule. The various co-stimulatory molecules are well-known in the art. Some non-limiting examples of co-stimulatory molecules are 4-IBBL, OX40L, CD40, IL-15/IL-15Ra, CD28, CD80, CD86, CD30L, and ICOSL. Only one specific co-stimulatory molecule may be coupled to one nanoparticle or a variety of co-stimulatory molecules may be coupled to the same nanoparticle. In certain embodiments, the co-stimulatory molecule is a protein such as an antibody that is capable of agonizing a co-stimulatory receptor on a T cell. In this case, the antibody is capable of inducing a co-stimulatory signal that is necessary to activate na-ve T cells and induce an immune response in an antigen-specific manner. Additionally or alternatively, the term "co-stimulatory molecule" as used herein may also refer to an agent capable of generating a co-stimulatory signal by having an agonistic effect on a native co-stimulatory signaling molecule, e.g. anti-CD28 or CD28 ligand generating a CD28 co-stimulatory response.

In specific embodiments, the co-stimulatory molecules of the present disclosure may be any one or more of the following molecules B7-1/CD80, BTLA, B7-2/CD86, CD28, B7-H1/PD-L1, CTLA-4, B7-H2, Gi24/VISTA/B7-H5, B7-H3, ICOS, B7-H4, PD-1, B7-H6, PD-L2/B7-DC, B7-H7, PDCD6, LILRA3/CD85e, LILRB2/CD85d/ILT4, LILRA4/CD85g/ILT7, LILRB3/CD85a/ILT5, LILRB1/CD85j/ILT2, LILRB4/CD85k/ILT3, 4-1BB/TNFRSF9/CD137, GITR Ligand/TNFSF18, 4-1BB Ligand/TNFSF9, HVEM/TNFRSF14, BAFF/BLyS/TNFSF13B, LIGHT/TNFSF14, BAFF R/TNFRSF13C, Lymphotoxin-alpha/TNF-beta, CD27/TNFRSF7, OX40/TNFRSF4, CD27 Ligand/TNFSF7, OX40 Ligand/TNFSF4, CD30/TNFRSF8, RELT/TNFRSF19L, CD30 Ligand/TNFSF8, TACl/TNFRSF13B, CD40/TNFRSF5, TL1A/TNFSF15, CD40 Ligand/TNFSF5, TNF-alpha, DR3/TNFRSF25, TNF RII/TNFRSF1B, GITR/TNFRSF18, 2B4/CD244/SLAMF4, CD84/SLAMF5, BLAME/SLAMF8, CD229/SLAMF3, CD2, CRACC/SLAMF7, CD2F-10/SLAMF9, NTB-A/

SLAMF6, CD48/SLAMF2, SLAM/CD150, CD58/LFA-3, CD7, DPPIV/CD26, CD96, EphB6, CD160, Integrin alpha 4 beta 1, CD200, Integrin alpha 4 beta 7/LPAM-1, CD300a/LMIR1, LAG-3, CRTAM, TIM-1/KIM-1/HAVCR, DAP12, TIM-4, Dectin-1/CLEC7A, TSLP R, ICOSL, and/or biological equivalents thereof.

The co-stimulatory molecule can be coupled to the nanoparticle in the same manner as the pMHC complex. In one embodiment of the present disclosure, the co-stimulatory molecule and the antigen/MHC complex are separately attached to the nanoparticle. In another embodiment of the disclosure, the co-stimulatory molecule and the pMHC complex are first complexed together and are then subsequently complexed to the nanoparticle. Multiple co-stimulatory molecules may be coupled to the nanoparticle; these may be multiple of the same co-stimulatory molecule or multiple different co-stimulatory molecules. Typically, polypeptide complexes are added to the nanoparticles to yield nanoparticles with adsorbed or coupled polypeptide complexes having a ratio of number of co-stimulatory molecules:number of nanoparticles from about 1 to 6000 molecules per nanoparticle, or alternatively at least about or at most about 0.1, 0.5, 1, 10, 100, 500, 1000, 2000, 3000, 4000, 5000, 6000 or more to:1, and ranges in between, typically between about 0.1:1 to about 50:1. In another aspect, the ratio of the co-stimulatory molecule to the pMHC complex can be from about 0.1, 0.5, 1, 2, 5, 10, 50 or more to 1, preferably a ratio of 1:1, 1:2, 1:9, 1:10, 1:100, 2:1, 9:1, 10:1, or 100:1 of co-stimulatory molecule:pMHC complex is obtained. Similarly, density of the co-stimulatory molecules relative to nanoparticle surface area may be calculated according to the same relative formula as the pMHC complexes. In certain embodiments, the density of the co-stimulatory molecule per unit surface area of the nanoparticle is between about 0.0022 co-stimulatory molecules/100 $nm^2$ to about 13.26 co-stimulatory molecules/100 $nm^2$. In some embodiments, the density range of the co-stimulatory molecules may be the same or different from the density range for the pMHC complexes.

In some embodiments, wherein the nanoparticle comprises a one or more co-stimulatory molecules and does not comprise a pMHC complex, the nanoparticle has a co-stimulatory density of about 0.2 co-stimulatory molecule/100 $nm^2$ to about 6.5 co-stimulatory molecule/100 $nm^2$, or from about 0.2 co-stimulatory molecule/100 $nm^2$ to about 6 co-stimulatory molecule/100 $nm^2$, or from about 0.2 co-stimulatory molecule/100 $nm^2$ to about 5.8 co-stimulatory molecule/100 $nm^2$, or from about 0.2 co-stimulatory molecule/100 $nm^2$ to about 5.75 co-stimulatory molecule/100 $nm^2$, or from about 0.2 co-stimulatory molecule/100 $nm^2$ to about 5.5 co-stimulatory molecule/100 $nm^2$, or from about 0.2 co-stimulatory molecule/100 $nm^2$ to about 5 co-stimulatory molecule/100 $nm^2$, or from about 0.2 co-stimulatory molecule/100 $nm^2$ to about 4.5 co-stimulatory molecule/100 $nm^2$, or from about 0.2 co-stimulatory molecule/100 $nm^2$ to about 4 co-stimulatory molecule/100 $nm^2$, or from about 0.2 co-stimulatory molecule/100 $nm^2$ to about 3.5 co-stimulatory molecule/100 $nm^2$, or from about 0.2 co-stimulatory molecule/100 $nm^2$ to about 3 co-stimulatory molecule/100 $nm^2$, or from about 0.2 co-stimulatory molecule/100 $nm^2$ to about 2.5 co-stimulatory molecule/100 $nm^2$, or from about 0.2 co-stimulatory molecule/100 $nm^2$ to about 2 co-stimulatory molecule/100 $nm^2$, or from about 0.2 co-stimulatory molecule/100 $nm^2$ to about 1.5 co-stimulatory molecule/100 $nm^2$, or from about 0.2 co-stimulatory molecule/100 $nm^2$ to about 1.25 co-stimulatory molecule/100 $nm^2$, or from about 0.2 co-stimulatory molecule/100 $nm^2$ to about 1 co-stimulatory molecule/100 $nm^2$, or from about 0.2 co-stimulatory molecule/100 $nm^2$ to about 0.75 co-stimulatory molecule/100 $nm^2$.

In another aspect, the nanoparticle may have a co-stimulatory molecule density of from about 0.11 co-stimulatory molecule/100 $nm^2$ to about 5 co-stimulatory molecule/100 $nm^2$, or from about 0.11 co-stimulatory molecule/100 $nm^2$ to about 4.5 co-stimulatory molecule/100 $nm^2$, or from about 0.11 co-stimulatory molecule/100 $nm^2$ to about 4 co-stimulatory molecule/100 $nm^2$, or from about 0.11 co-stimulatory molecule/100 $nm^2$ to about 3.5 co-stimulatory molecule/100 $nm^2$, or from about 0.11 co-stimulatory molecule/100 $nm^2$ to about 3 co-stimulatory molecule/100 $nm^2$, or from about 0.11 co-stimulatory molecule/100 $nm^2$ to about 2.5 co-stimulatory molecule/100 $nm^2$, or from about 0.11 co-stimulatory molecule/100 $nm^2$ to about 2 co-stimulatory molecule/100 $nm^2$, or from about 0.11 co-stimulatory molecule/100 $nm^2$ to about 1.5 co-stimulatory molecule/100 $nm^2$, or from about 0.11 co-stimulatory molecule/100 $nm^2$ to about 1 pMHC/100 $nm^2$, or from about 0.11 co-stimulatory molecule/100 $nm^2$ to about 0.75 co-stimulatory molecule/100 $nm^2$. In some aspects, the nanoparticle core has a co-stimulatory molecule density of from about 0.11 co-stimulatory molecule/100 $nm^2$ to about 5 co-stimulatory molecule/100 $nm^2$, or 0.12 co-stimulatory molecule/100 $nm^2$ to about 4.5 co-stimulatory molecule/100 $nm^2$, or from about 0.13 co-stimulatory molecule/100 $nm^2$ to about 4 co-stimulatory molecule/100 $nm^2$, or from about 0.14 co-stimulatory molecule/100 $nm^2$ to about 3.5 co-stimulatory molecule/100 $nm^2$, or from about 0.12 co-stimulatory molecule/100 $nm^2$ to about 2 co-stimulatory molecule/100 $nm^2$, or from about 0.25 co-stimulatory molecule/100 $nm^2$ to about 1.5 co-stimulatory molecule/100 $nm^2$, or from about 0.3 co-stimulatory molecule/100 $nm^2$ to about 0.75 co-stimulatory molecule/100 $nm^2$. In a further aspect, the nanoparticle core has a co-stimulatory molecule density of from about 0.2 co-stimulatory molecule/100 $nm^2$ to about 0.65 co-stimulatory molecule/100 $nm^2$, or alternatively from about 0.25 co-stimulatory molecule/100 $nm^2$ to about 0.45 co-stimulatory molecule/100 $nm^2$, or alternatively from about 0.3 co-stimulatory molecule/100 $nm^2$ to about 0.4 co-stimulatory molecule/100 $nm^2$.

In some embodiments, wherein the nanoparticle comprises a pMHC complex and one or more co-stimulatory molecules, the nanoparticle has a co-stimulatory density of about 0.4 co-stimulatory molecule/100 $nm^2$ to about 13 co-stimulatory molecule/100 $nm^2$, or from about 0.4 co-stimulatory molecule/100 $nm^2$ to about 12 co-stimulatory molecule/100 $nm^2$, or from about 0.4 co-stimulatory molecule/100 $nm^2$ to about 11.6 co-stimulatory molecule/100 $nm^2$, or from about 0.4 co-stimulatory molecule/100 $nm^2$ to about 11.5 co-stimulatory molecule/100 $nm^2$, or from about 0.4 co-stimulatory molecule/100 $nm^2$ to about 11 co-stimulatory molecule/100 $nm^2$, or from about 0.4 co-stimulatory molecule/100 $nm^2$ to about 10 co-stimulatory molecule/100 $nm^2$, or from about 0.4 co-stimulatory molecule/100 $nm^2$ to about 9 co-stimulatory molecule/100 $nm^2$, or from about 0.4 co-stimulatory molecule/100 $nm^2$ to about 8 co-stimulatory molecule/100 $nm^2$, or from about 0.4 co-stimulatory molecule/100 $nm^2$ to about 7 co-stimulatory molecule/100 $nm^2$, or from about 0.4 co-stimulatory molecule/100 $nm^2$ to about 6 co-stimulatory molecule/100 $nm^2$, or from about 0.4 co-stimulatory molecule/100 $nm^2$ to about 5 co-stimulatory molecule/100 $nm^2$, or from about 0.4 co-stimulatory molecule/100 $nm^2$ to about 4 co-stimulatory molecule/100 $nm^2$, or from about 0.4 co-stimulatory molecule/100 $nm^2$ to about 3 co-stimulatory molecule/100 $nm^2$, or from about 0.4 co-stimulatory molecule/100 $nm^2$ to about 2.5 co-stimulatory molecule/100 $nm^2$, or from about 0.4 co-stimulatory molecule/100 $nm^2$ to about 2 co-stimulatory molecule/100 $nm^2$, or from about 0.4 co-stimulatory molecule/100 $nm^2$ to about 1.5 co-stimulatory molecule/100 $nm^2$.

In another aspect, the nanoparticle may have a co-stimulatory molecule density of from about 0.22 co-stimulatory molecule/100 $nm^2$ to about 10 co-stimulatory molecule/100 $nm^2$, or from about 0.22 co-stimulatory molecule/100 $nm^2$ to about 9 co-stimulatory molecule/100 $nm^2$, or from about 0.22 co-stimulatory molecule/100 $nm^2$ to about 8 co-stimulatory molecule/100 $nm^2$, or from about 0.22 co-stimulatory molecule/100 $nm^2$ to about 7 co-stimulatory molecule/100 $nm^2$, or from about 0.22 co-stimulatory molecule/100 $nm^2$ to about 6 co-stimulatory molecule/100 $nm^2$, or from about about 0.22 co-stimulatory molecule/100 $nm^2$ to about 5 co-stimulatory molecule/100 $nm^2$, or from about 0.22 co-stimulatory molecule/100 $nm^2$ to about 4 co-stimulatory molecule/100 $nm^2$, or from about 0.22 co-stimulatory molecule/100 $nm^2$ to about 3 co-stimulatory molecule/100 $nm^2$, or from about 0.22 co-stimulatory molecule/100 $nm^2$ to about 2 pMHC/100 $nm^2$, or from about 0.22 co-stimulatory molecule/100 $nm^2$ to about 1.5 co-stimulatory molecule/100 $nm^2$. In some aspects, the nanoparticle core has a co-stimulatory molecule density of from about 0.22 co-stimulatory molecule/100 $nm^2$ to about 10 co-stimulatory molecule/100 $nm^2$, or 0.24 co-stimulatory molecule/100 $nm^2$ to about 9 co-stimulatory molecule/100 $nm^2$, or from about 0.26 co-stimulatory molecule/100 $nm^2$ to about 8 co-stimulatory molecule/100 $nm^2$, or from about 0.28 co-stimulatory molecule/100 $nm^2$ to about 7 co-stimulatory molecule/100 $nm^2$, or from about 0.24 co-stimulatory molecule/100 $nm^2$ to about 4 co-stimulatory molecule/100 $nm^2$, or from about 0.5 co-stimulatory molecule/100 $nm^2$ to about 3 co-stimulatory molecule/100 $nm^2$, or from about 0.6 co-stimulatory molecule/100 $nm^2$ to about 1.5 co-stimulatory molecule/100 $nm^2$. In a further aspect, the nanoparticle has a co-stimulatory molecule density of from about 0.4 co-stimulatory molecule/100 $nm^2$ to about 1.3 co-stimulatory molecule/100 $nm^2$, or alternatively from about 0.5 co-stimulatory molecule/100 $nm^2$ to about 0.9 co-stimulatory molecule/100 $nm^2$, or alternatively from about 0.6 co-stimulatory molecule/100 $nm^2$ to about 0.8 co-stimulatory molecule/100 $nm^2$.

Cytokines

In certain aspect, the NPs further comprise, or alternatively consist essentially of, or yet further consist of at least one cytokine molecule. As used herein, the term "cytokine" encompasses low molecular weight proteins secreted by various cells in the immune system that act as signaling molecules for regulating a broad range of biological processes within the body at the molecular and cellular levels. "Cytokines" include individual immunomodulating proteins that fall within the class of lymphokines, interleukins, or chemokines.

Non limiting examples are disclosed herein: for instance, IL-1A and IL-1B are two distinct members of the human interleukin-1 (IL-1) family. Mature IL-1A is a 18 kDa protein, also known as fibroblast-activating factor (FAF), lymphocyte-activating factor (LAF), B-cell-activating factor (BAF), leukocyte endogenous mediator (LEM), etc. IL-4 is a cytokine that induces T helper-2 (Th2) cell differentiation, and is closely related to and has similar functions to IL-13. IL-5 is produced by Th2 cells and mast cells. It acts to stimulate B cell growth and increase immunoglobulin secretion. It is also involved in eosinophil activation. IL-6 is an interleukin that can act as either a pro-inflammatory or anti-inflammatory cytokine. It is secreted by T cells and macrophages to stimulate immune response to trauma or other tissue damage leading to inflammation. IL-6 is also produced from muscle in response to muscle contraction. IL-8 is a chemokine produced by macrophages and other cell types such as epithelial cells and endothelial cells, and acts as an important mediator of the immune reaction in the innate immune system response. IL-12 is involved in the differentiation of naive T cells to T helper (Th1 or Th2) cells. As a heterodimeric cytokine, IL-12 is formed after two subunits encoded by two separate genes, IL-12A (p35) and IL-12B (p40), dimerize following protein synthesis. IL-12p70 indicates this heterodimeric composition. IL-13, a cytokine secreted by many cell types, especially Th2 cells, is an important mediator of allergic inflammation and disease. IL-17 is a cytokine produced by T helper cells and is induced by IL-23, resulting in destructive tissue damage in delayed-type reactions. IL-17 functions as a pro-inflammatory cytokine that responds to the invasion of the immune system by extracellular pathogens and induces destruction of the pathogen's cellular matrix. IP-10, or Interferon gamma-induced protein 10, is also known as C—X-C motif chemokine 10 (CXCL10) or small-inducible cytokine B10. As a small cytokine belonging to the CXC chemokine family, IP-10 is secreted by several cell types (including monocytes, endothelial cells and fibroblasts) in response to IFN-γ. Macrophage Inflammatory Proteins (MIP) belong to the family of chemokines. There are two major forms of human MIP, MIP-1a and MIP-10, which are also known as chemokine (C—C motif) ligand 3 (CCL3) and CCL4, respectively. Both are produced by macrophages following stimulation with bacterial endotoxins. Granulocyte colony-stimulating factor (G-CSF or GCSF), also known as colony-stimulating factor 3 (CSF 3), is a colony-stimulating factor hormone. G-CSF is a glycoprotein, growth factor, and cytokine produced by a number of different tissues to stimulate the bone marrow to produce granulocytes and stem cells. G-CSF also stimulates the survival, proliferation, differentiation, and function of neutrophil precursors and mature neutrophils. Epidermal growth factor or EGF is a growth factor that plays an important role in the regulation of cell growth, proliferation, and differentiation by binding with high affinity to its receptor EGFR. Vascular endothelial growth factor (VEGF) is a family of growth factors that are important signaling proteins involved in both vasculogenesis (the de novo formation of the embryonic circulatory system) and angiogenesis (the growth of blood vessels from pre-existing vasculature).

The cytokine or cytokines can be coupled to the nanoparticle in the same manner as the pMHC complex. In one embodiment of the present disclosure, the cytokine or cytokines and the pMHC complex are separately attached to the nanoparticle. In another embodiment of the disclosure, the cytokine or cytokines molecule and the pMHC complex are first complexed together and are then subsequently complexed to the nanoparticle. Multiple cytokines may be coupled to the nanoparticle; these may be multiple of the same cytokine or different cytokines.

In some embodiments, the cytokine is complexed to an anti-cytokine antibody to form a cytokine/anti-cytokine antibody complex, which complex is subsequently complexed to the nanoparticle. In some embodiments, the cytokine/anti-cytokine antibody complex includes but is not limited to IL-2/anti-IL-2 complexes. The IL-2/anti-IL-2 complexes can have agonistic properties or antagonistic properties.

In some embodiments, the cytokine is complexed to a cytokine receptor to form a cytokine/cytokine receptor complex, which complex is subsequently complexed to the nanoparaticle. In some embodiments, the cytokine/cytokine receptor complex includes but is not limited to IL15/IL-15Ra and/or IL-1/IL-2Ra. In some embodiments, the IL15/IL-15Ra complex can function as a T-cell co-stimulator.

Typically, polypeptide complexes are added to the nanoparticles to yield nanoparticles with adsorbed or coupled polypeptide complexes having a ratio of number of cytokines:number of nanoparticles from about 1 to 5999 molecules per nanoparticle, or alternatively at least about or at most about 0.1, 0.5, 1, 10, 100, 500, 1000, 2000, 3000, 4000, 5000, 6000 or more to:1, and ranges in between, for example between about 0.1:1 to about 50:1. In other aspects, the ratio of the cytokine to the antigen/MHC complex can be from about 0.1, 0.5, 1, 2, 5, 10, 50 or more to 1, preferably a ratio of 1:1, 1:2, 1:9, 1:10, 1:100, 2:1, 9:1, 10:1, or 100:1 of cytokine:antigen/MHC complex is obtained. Similarly, density of the cytokines relative to nanoparticle surface area may be calculated according to the same relative formula as the antigen/MHC complexes. In certain embodiments, the density of the cytokines per unit surface area of the nanoparticle is between about 0.0022 cytokines/100 $nm^2$ to about 13.26 cytokines/100 $nm^2$. In some embodiments, the density range of the cytokines may be the same or different from the density range for the antigen/MHC complexes.

Antigenic Components

Certain aspects of the disclosure include methods and compositions concerning antigenic compositions including segments, fragments, or epitopes of polypeptides, peptides, nucleic acids, carbohydrates, lipids and other molecules that provoke or induce an antigenic response, generally referred to as antigens. In particular, autoantigens, or antigenic segments or fragments of such autoantigens, which lead to the destruction of a cell via an autoimmune response, can be identified and used in making a peptide-MHC/nanoparticle complex described herein.

Although specific examples of antigens and antigenic components are disclosed herein, the disclosure is not so limited. Unless specifically stated otherwise, included herein are equivalents of the isolated or purified polypeptide antigens, that comprise, or consist essentially of, or yet further consist of, the amino acid sequences as described herein, or a polypeptide having at least about 80% sequence identity, or alternatively at least 85%, or alternatively at least 90%, or alternatively at least 95%, or alternatively at least 98% sequence identity to the amino acid sequences of the antigens, or polypeptides encoded by polynucleotides having at about 80% sequence identity, or alternatively at least 85%, or alternatively at least 90%, or alternatively at least 95%, or alternatively at least 98% sequence identity to the polynucleotide encoding the amino acid sequences of the antigen, or its complement, or a polypeptide encoded by a polynucleotide that hybridizes under conditions of moderate to high stringency to a polynucleotide encoding the amino acid sequence of the antigens, or its complement. Also provided are isolated and purified polynucleotides encoding the antigen polypeptides disclosed herein, or amino acids having at least about 80% sequence identity thereto, or alternatively at least 85%, or alternatively at least 90%, or alternatively at least 95%, or alternatively at least 98% sequence identity to the disclosed sequences, or an equivalent, or a polynucleotide that hybridizes under stringent conditions to the polynucleotide, its equivalent or its complement and isolated or purified polypeptides encoded by these polynucleotides. The polypeptides and polynucleotides can be combined with non-naturally occurring substances with which they are not associated with in nature, e.g., carriers, pharmaceutically acceptable carriers, vectors and MHC molecules.

Modified Peptides and Equivalents Thereto

The antigenic polypeptides, proteins and fragments thereof may be modified by various amino acid deletions, insertions, and/or substitutions. In particular embodiments, modified polypeptides and/or peptides are capable of modulating an immune response in a subject. As used herein, a "protein" or "polypeptide" or "peptide" refers to a molecule comprising at least five amino acid residues. In some embodiments, a wild-type version of a protein or peptide are employed, however, in many embodiments of the disclosure, a modified protein or polypeptide is employed to generate a peptide/MHC/nanoparticle complex. A peptide/MHC/nanoparticle complex can be used to generate an immune response and/or to modify the T cell population of the immune system (i.e., re-educate the immune system). The terms described above may be used interchangeably herein. A "modified protein" or "modified polypeptide" or "modified peptide" refers to a protein or polypeptide whose chemical structure, particularly its amino acid sequence, is altered with respect to the wild-type protein or polypeptide. In some embodiments, a modified protein or polypeptide or peptide has at least one modified activity or function (recognizing that proteins or polypeptides or peptides may have multiple activities or functions). It is specifically contemplated that a modified protein or polypeptide or peptide may be altered with respect to one activity or function yet retain a wild-type activity or function in other respects, such as immunogenicity or ability to interact with other cells of the immune system when in the context of an MHC/nanoparticle complex.

In certain embodiments, the size of a protein or polypeptide (wild-type or modified), including any complex of a protein or peptide of interest and in particular a MHC/peptide fusion, may comprise, but is not limited to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, including any range or value derivable therein, or derivative thereof. In certain aspects, 5, 6, 7, 8, 9, 10 or more contiguous amino acids, including derivatives thereof, and fragments of an autoantigen, such as those amino acid sequences disclosed and referenced herein, can be used as antigens. It is contemplated that polypeptides may be mutated by truncation, rendering them shorter than their corresponding wild-type form, but they might also be altered by fusing or conjugating a heterologous protein sequence with a particular function (e.g., for presentation as a protein complex, for enhanced immunogenicity, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's GenBank and GenPept databases (on the World Wide Web at ncbi.nlm.nih.gov/). The all or part of the coding regions for these genes may be amplified and/or expressed using the techniques disclosed herein or as would be known to those of ordinary skill in the art.

Amino acid sequence variants of autoantigenic epitopes and other polypeptides of these compositions can be substitutional, insertional, or deletion variants. A modification in a polypeptide of the disclosure may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more non-contiguous or contiguous amino acids of a peptide or polypeptide, as compared to wild-type. A peptide or polypeptide that results in an autoimmune response and in particular a pathologic autoimmune response are contemplated for use in methods of the disclosure.

Deletion variants typically lack one or more residues of the native or wild-type amino acid sequence. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected, such as avidity or affinity for a cellular receptor(s). Non-conservative changes typically involve substituting a residue with one that is chemically dissimilar, such as a polar or charged amino acid for a nonpolar or uncharged amino acid, and vice versa.

Proteins of the disclosure may be recombinant, or synthesized in vitro. Alternatively, a recombinant protein may be isolated from bacteria or other host cell.

The term "functionally equivalent codon" is used herein to refer to codons that encode the same amino acid, such as the six codons for arginine or serine, and also refers to codons that encode biologically equivalent amino acids (see Table 2).

It also will be understood that amino acid and nucleic acid sequences may include additional residues, such as additional N- or C-terminal amino acids, or 5' or 3' nucleic acid sequences, respectively, and yet still be essentially as set forth in one of the sequences disclosed herein, so long as the sequence meets the criteria set forth above, including the maintenance of biological protein activity (e.g., immunogenicity). The addition of terminal sequences particularly applies to nucleic acid sequences that may, for example, include various non-coding sequences flanking either of the 5' or 3' portions of the coding region.

Disease-Relevant Antigens

The nanoparticles are useful in the therapeutic methods as described herein. The pMHC complex of the pMHC-NP is selected for use based on the disease to be treated. For example, a diabetes-relevant antigen is an antigen or fragment thereof that is expressed in the cell, tissue or organ targeted in that autoimmune disease and that is exposed to the immune system upon cell, tissue or organ damage caused by the autoimmune response, even if the antigen is not the trigger of the disease process or a key player in its pathogenesis, and when presented, produces an immune response that serves to treat diabetes; thus, a diabetes-relevant antigen meeting this definition is selected to treat diabetes. A MS-relevant antigen is selected to treat MS. A diabetes-relevant antigen would not be selected to treat MS. Non-limiting, exemplary disease-relevant antigens are disclosed herein and further, such antigens may be determined for a particular disease based on techniques, mechanisms, and methods well documented in the literature.

Non-limiting examples of diseases of interest include, but are not limited to, asthma, diabetes mellitus Type I and Type II, pre-diabetes, multiple sclerosis, peripheral neuropathy, allergic asthma, primary biliary cirrhosis, cirrhosis, Neuromyelitis optica spectrum disorder, Autoantibody-associated neurological syndromes such as Stiff Person syndrome, Autoimmune Encephalitis, Narcolepsy, Pemphigus vulgaris, Pemphigus foliaceous, Psoriasis, Sjogren's disease/syndrome, Inflammatory bowel disease (IBD), arthritis, Rheumatoid arthritis, Systemic Lupus Erythematosus (SLE), Scleroderma, ANCA-associated Vasculitis, Goodpasture Syndrome, Kawasaki's Disease, Celiac disease, autoimmune cardiomyopathy, idiopathic dilated cardiomyopathy (IDCM), Myasthyenia Gravis, Autoimmune Uveitis, Ankylosing Spondylitis, Grave's Disease, Immune Mediated Myopathies, anti-phospholipid syndrome (ANCA+), atherosclerosis, Autoimmune Hepatitis, Sclerosing Cholangitis, Primary Sclerosing Cholangitis, Dermatomyositis, Chronic Obstructive Pulmonary Disease, Spinal Cord Injury, traumatic injury, tobacco-induced lung destruction, emphysema, pemphigus, uveitis, any other relevant cancer and/or diseases of the central and peripheral nervous systems.

Cancer/Tumor Relevant Antigens

In certain aspects, the disease-relevant antigen is a cancer relevant antigen. In further aspects, the cancer is carcinoma, sarcoma, myeloma, leukemia, lymphoma, and/or mixed types of metastases from these or other cancers. Exemplary cancer- or tumor-relevant antigens include but are not limited to those disclosed in the following Table 5.

TABLE 5

```
Lys Ile Ser Val Ser Leu Pro Leu Ser Leu Ser Gln Ser Val Cys (SEQ ID NO: 45)

Gln Leu Ser Lys Asp Thr Ser Val Leu Thr Phe Thr Phe Cys (SEQ ID NO: 46)

Cys Ser Asp Ala His Pro Gly Asp Ser Ser Gly Asp Ser Ser Gly Leu Asn (SEQ ID NO: 47)

Arg Gly Glu Val Arg Gln Phe Thr Leu Arg His Trp Leu Lys Val (SEQ ID NO: 48)

Gly Asp Tyr Leu Asn Asp Glu Ala Leu Trp Asn Lys Cys (SEQ ID NO: 49)

Gly Lys Val Ile Asp Asp Asn Asp His Leu Ser Gln Glu Ile Cys (SEQ ID NO: 50)

Leu Met Ala Asn Ser Thr Trp Gly Tyr Pro Phe His Asp Gly (SEQ ID NO: 51)

Leu Asn Val Val Pro Trp Asn Leu Thr Leu Phe Ser Ile Leu (SEQ ID NO: 52)

Thr His Ser Phe Thr Ala Phe Lys Arg His Val Cys (SEQ ID NO: 53)

Asn Leu Ser Leu Pro Pro Ser Leu Ser Leu Ser Ile Cys (SEQ ID NO: 54)

Glu Arg Pro Ser Ser Val Leu Thr Ile Tyr Asp Ile Gly Ile Gln Cys (SEQ ID NO: 55)

Cys Tyr Gln Gln Tyr Thr Asn Leu Gln Glu Arg Pro Ser Ser Val (SEQ ID NO: 56)

Thr Val Glu Pro Glu Thr Gly Asp Pro Val Thr Leu Arg Leu Cys (SEQ ID NO: 57)

Cys Ser Arg Lys Lys Arg Ala Asp Lys Lys Glu Asn Gly Thr Lys Leu Leu (SEQ ID NO: 58)

Phe Leu Leu Val Leu Gly Phe Ile Ile (SEQ ID NO: 59)

Val Leu Pro Ser Val Ala Met Phe Leu (SEQ ID NO: 60)

Leu Val Leu Gly Phe Ile Ile Ala Leu (SEQ ID NO: 61)

Lys Val Val Thr Ser Ser Phe Val Val (SEQ ID NO: 62)

Leu Val Pro Gly Thr Lys Phe Tyr Ile (SEQ ID NO: 63)

Leu Leu Pro Ile Arg Thr Leu Pro Leu (SEQ ID NO: 64)

Tyr Leu Val Lys Lys Gly Thr Ala Thr (SEQ ID NO: 65)

Ser Leu Phe Ala Glu Thr Ile Trp Val (SEQ ID NO: 66)

Met Leu Ile Ala Met Tyr Phe Tyr Thr (SEQ ID NO: 67)

Leu Met Trp Thr Leu Pro Val Met Leu (SEQ ID NO: 68)

Met Leu Ile Val Tyr Ile Phe Glu Cys (SEQ ID NO: 69)

Tyr Ile Phe Glu Cys Ala Ser Cys Ile (SEQ ID NO: 70)

Leu Val Leu Met Leu Ile Val Tyr Ile (SEQ ID NO: 71)

Ala Leu Cys Arg Arg Arg Ser Met Val (SEQ ID NO: 72)
```

TABLE 5-continued

```
Leu Leu Ser Gly Leu Ser Leu Phe Ala  (SEQ ID NO: 73)
Phe Leu Leu Val Val Gly Leu Ile Val  (SEQ ID NO: 74)
Leu Val Val Gly Leu Ile Val Ala Leu  (SEQ ID NO: 75)
Lys Val Val Lys Ser Asp Phe Val Val  (SEQ ID NO: 76)
Thr Leu Pro Val Gln Thr Leu Pro Leu  (SEQ ID NO: 77)
Asp Leu His Val Ile Ser Asn Asp Val  (SEQ ID NO: 78)
Val Leu Val His Pro Gln Trp Val Leu  (SEQ ID NO: 79)
Phe Leu Arg Pro Gly Asp Asp Ser Ser  (SEQ ID NO: 80)
Ala Leu Gly Thr Thr Cys Tyr Ala Ser  (SEQ ID NO: 81)
Lys Leu Gln Cys Val Asp Leu His Val  (SEQ ID NO: 82)
Glu Leu Ala His Tyr Asp Val Leu Leu  (SEQ ID NO: 83)
Asn Leu Asn Gly Ala Gly Asp Pro Leu  (SEQ ID NO: 84)
Thr Leu Arg Val Asp Cys Thr Pro Leu  (SEQ ID NO: 85)
Met Met Asn Asp Gln Leu Met Phe Leu  (SEQ ID NO: 86)
Ala Leu Phe Asp Ile Glu Ser Lys Val  (SEQ ID NO: 87)
Leu Leu His Glu Thr Asp Ser Ala Val  (SEQ ID NO: 88)
Val Leu Ala Lys Glu Leu Lys Phe Val  (SEQ ID NO: 89)
Ile Leu Leu Trp Gln Pro Ile Pro Val  (SEQ ID NO: 90)
Asp Leu Phe Gly Ile Trp Ser Lys Val  (SEQ ID NO: 91)
Pro Leu Glu Arg Phe Ala Glu Leu Val  (SEQ ID NO: 92)
Lys Gln Gly Asn Phe Asn Ala Trp Val  (SEQ ID NO: 93)
Asn Leu Leu Arg Arg Met Trp Val Thr  (SEQ ID NO: 94)
Asn Leu Phe Glu Thr Pro Ile Leu Ala  (SEQ ID NO: 95)
Asn Leu Phe Glu Thr Pro Val Glu Ala  (SEQ ID NO: 96)
Gly Leu Gln His Trp Val Pro Glu Leu  (SEQ ID NO: 97)
Val Gln Phe Val Ala Ser Tyr Lys Val  (SEQ ID NO: 98)
Arg Leu Leu Ala Ala Leu Cys Gly Ala  (SEQ ID NO: 99)
Leu Leu Leu Leu Thr Val Leu Thr Val  (SEQ ID NO: 100)
Leu Leu Leu Thr Val Leu Thr Val Val  (SEQ ID NO: 101)
Phe Leu Ser Phe His Ile Ser Asn Leu  (SEQ ID NO: 102)
Leu Leu Val Leu Val Cys Val Leu Val  (SEQ ID NO: 103)
Ala Leu Leu Val Leu Val Cys Val Leu  (SEQ ID NO: 104)
Ser Leu Ser Tyr Thr Asn Pro Ala Val  (SEQ ID NO: 105)
Asn Leu Thr Ile Ser Asp Val Ser Val  (SEQ ID NO: 106)
Ala Leu Ala Ser Thr Ala Pro Pro Val  (SEQ ID NO: 107)
Ala Ile Leu Cys Trp Thr Phe Trp Val  (SEQ ID NO: 108)
Phe Ile Leu Met Phe Ile Val Tyr Ala  (SEQ ID NO: 109)
Leu Thr Ala Glu Cys Ile Phe Phe Val  (SEQ ID NO: 110)
Met Leu Gln Asp Asn Cys Cys Gly Val  (SEQ ID NO: 111)
Ile Leu Cys Trp Thr Phe Trp Val Leu  (SEQ ID NO: 112)
```

TABLE 5-continued

```
Lys Ile Leu Leu Ala Tyr Phe Ile Leu (SEQ ID NO: 113)

Phe Val Gly Ile Cys Leu Phe Cys Leu (SEQ ID NO: 114)

Val Leu Leu Ser Val Ala Met Phe Leu (SEQ ID NO: 115)

Leu Leu Ser Val Ala Met Phe Leu Leu (SEQ ID NO: 116)

Ile Leu Gly Ser Leu Pro Phe Phe Leu (SEQ ID NO: 117)

Ile Leu Asn Ala Tyr Leu Val Arg Val (SEQ ID NO: 118)

Phe Leu Leu Val Gly Phe Ala Gly Ala (SEQ ID NO: 119)

Asn Leu Gln Pro Gln Leu Ala Ser Val (SEQ ID NO: 120)

Cys Met Phe Asp Ser Lys Glu Ala Leu (SEQ ID NO: 121)

Tyr Leu Tyr Val Leu Val Asp Ser Ala (SEQ ID NO: 122)

Tyr Met Asp Gly Thr Met Ser Gln Val (SEQ ID NO: 123)

Lys Met Ala Arg Phe Ser Tyr Ser Val (SEQ ID NO: 124)

Gly Leu Val Met Asp Glu His Leu Val (SEQ ID NO: 125)

Phe Leu Pro Gly Cys Asp Gly Leu Val (SEQ ID NO: 126)

Cys Met Leu Gly Ser Phe Cys Ala Cys (SEQ ID NO: 127)

Tyr Leu Ala Phe Arg Asp Asp Ser Ile (SEQ ID NO: 128)

Trp Leu Pro Lys Lys Cys Ser Leu Cys (SEQ ID NO: 129)

Cys Leu Asn Gly Gly Thr Cys Met Leu (SEQ ID NO: 130)

Met Leu Val Gly Ile Cys Leu Ser Ile (SEQ ID NO: 131)

Phe Glu Leu Gly Leu Val Ala Gly Leu (SEQ ID NO: 132)

Lys Met Val Arg Phe Ser Tyr Ser Val (SEQ ID NO: 133)

Cys Leu Asn Glu Gly Thr Cys Met Leu (SEQ ID NO: 134)

Met Leu Ala Gly Ile Cys Leu Ser Ile (SEQ ID NO: 135)

Arg Leu Leu Phe Phe Leu Leu Phe Leu (SEQ ID NO: 136)

Thr Leu Ala Tyr Leu Ile Phe Cys Leu (SEQ ID NO: 137)

Leu Leu Phe Leu Thr Pro Met Glu Val (SEQ ID NO: 138)

Lys Leu Met Ser Pro Lys Leu Tyr Val (SEQ ID NO: 139)

Leu Leu Phe Phe Leu Leu Phe Leu Val (SEQ ID NO: 140)

Ser Leu Phe Leu Gly Ile Leu Ser Val (SEQ ID NO: 141)

Ala Ile Ser Gly Met Ile Leu Ser Ile (SEQ ID NO: 142)

Phe Ile Arg Ala His Thr Pro Tyr Ile (SEQ ID NO: 143)

Ser Leu Asn Phe Ile Arg Ala His Thr (SEQ ID NO: 144)

Leu Lys Met Glu Ser Leu Asn Phe Ile (SEQ ID NO: 145)

Ser His Phe Leu Lys Met Glu Ser Leu (SEQ ID NO: 146)

Tyr Leu Phe Leu Gly Ile Leu Ser Val (SEQ ID NO: 147)
```

Other cancer relevant antigens include those summarized in the Tables in the online database found at cancerimmunity.org/peptide/ and incorporated herein by reference, last referenced May 6, 2015.

Autoimmune-Disease Relevant Antigens

In certain aspects, the disease-relevant antigen comprised in the antigen-MHC complex is selected from an autoimmune disease-relevant antigen, an inflammation-relevant antigen, or an allergic disease-relevant antigen. In further aspects, the immune inflammation-relevant antigen is one or more selected from the group of an asthma-relevant antigen, a diabetes-relevant antigen, a pre-diabetes relevant antigen, a multiple sclerosis-relevant antigen, an allergic asthma-relevant antigen, a primary biliary cirrhosis-relevant antigen, a cirrhosis-relevant antigen, a Neuromyelitis optica spectrum disorder (Devic's disease, NMO)-relevant antigen, an autoimmune encephalitis-relevant antigen, an antigen relevant to autoantibody-mediated neurological syndromes, a Stiff Man syndrome-relevant antigen, a paraneoplastic disease-relevant antigen, antigens relevant to other diseases of the central and peripheral nervous systems, a Pemphigus vulgaris-relevant antigen, inflammatory bowel disease (IBD)-relevant antigen, Crohn's disease-relevant antigen, Ulcerative Colitis-relevant antigen, an arthritis-relevant antigen, a Rheumatoid Arthritis-relevant antigen, a systemic lupus erythematosus (SLE)-relevant antigen, a Celiac Disease relevant antigen, a psoriasis-relevant antigen, an Alopecia Areata-relevant antigen, an Acquired Thrombocytopenic Purpura-relevant antigen, an autoimmune cardiomyopathy-relevant antigen, an idiopathic dilated cardiomyopathy (IDCM)-relevant antigen, a Myasthyenia Gravis-relevant antigen, an Uveitis-relevant antigen, an Ankylosing Spondylitis-relevant antigen, a Grave's Disease-relevant antigen, a Hashimoto's thyroiditis-relevant antigen, an Immune Mediated Myopathies-relevant antigen, an antiphospholipid syndrome (ANCA+)-relevant antigen, an atherosclerosis-relevant antigen, a scleroderma-relevant antigen, an autoimmune hepatitis-relevant antigen, a dermatomyositis-relevant antigen, a chronic obstructive pulmonary disease-relevant antigen, a spinal cord injury-relevant antigen, a traumatic injury-relevant antigen, a tobacco-induced lung destruction-relevant antigen, a Chronic Obstructive Pulmonary Disease (COPD)-relevant antigen, a lung emphysema-relevant antigen, a sclerosing cholangitis-relevant antigen, a peripheral neuropathy-relevant antigen, a narcolepsy-relevant antigen, a Goodpasture Syndrome-relevant antigen, a Kawasaki's Disease-relevant antigen, an autoimmune uveitis-relevant antigen, a colitis-relevant antigen, emphysema-relevant antigen, a pemphigus-relevant antigen, a pemphigus folliaceus-relevant antigen, an arthritis-relevant antigen, a Sjogren's Syndrome-relevant antigen, an ANCA-associated vasculitis-relevant antigen, a primary sclerosing cholangitis-relevant antigen, an adipose tissue inflammation/diabetes type II-relevant antigen, or an obesity associated adipose tissue inflammation/insulin resistance-relevant antigen.

In certain aspects, the disease-relevant antigen is derived from one or more of the group: PPI, IGRP, GAD, peripherin, aGlia, PDC-E2, Insulin, DG1EC2, DG3, AQP4, PLP, MOG, MBP, CII, DERP1, DERP2, OVA, BacInt, CBir, Fla-X, Fla-2, YIDX, AChR, Thyroid peroxidase, Thyroid receptor, Phospholipid antigen, H4, H2B, H1, DNA, ApoB, ApoE, NMDAR, Voltage-gated potassium channel, Elastin, Arrestin, PERM HUMAN Myeloperoxidase, PRTN3_HUMAN Myeloblastin, CP2D6_HUMAN Cytochrome P450 2D6, SPCS_HUMAN O-phosphoseryl-tRNA(Sec) selenium transferase, CAMP_HUMAN Cathelicidin antimicrobial peptide, DNA topoisomerase I, CENP-C, APOH_HUMAN Beta-2-glycoprotein 1, RO60_HUMAN 60 kDa SS-A/Ro ribonucleoprotein, LA_HUMAN Lupus La protein, IRBP, myosin, CD1d-binding lipid antigens, Cap18, CP2D6, SPCS, RO60, RO52, LA, APOH, MPO, PRTN3, or HSP.

In some embodiments, the disease-relevant antigen is:
a) a diabetes-relevant antigen and is derived from an antigen selected from one or more of the group: preproinsulin (PPI), islet-specific glucose-6-phosphatase (IGRP), glutamate decarboxylase (GAD), islet cell autoantigen-2 (ICA2), insulin, proinsulin, or a fragment or an equivalent of each thereof;
b) a multiple sclerosis-relevant antigen and is derived from an antigen selected from one or more of the group: myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins, NOGO A, glycoprotein Po, peripheral myelin protein 22, 2'3'-cyclic nucleotide 3'-phosphodiesterase, or a fragment or an equivalent of each thereof;
c) a Celiac Disease-relevant antigen and is derived from gliadin or a fragment or an equivalent thereof;
d) a primary biliary cirrhosis-relevant antigen and is derived from PDC-E2 or a fragment or an equivalent thereof;
e) a pemphigus folliaceus-relevant antigen and/or pemphigus vulgaris-relevant antigen and is derived from an antigen selected from one or more of the group: DG1, DG3, or a fragment or an equivalent of each thereof;
 f) a neuromyelitis optica spectrum disorder-relevant antigen and is derived from AQP4 or a fragment or an equivalent thereof;
g) an arthritis-relevant antigen and is derived from an antigen selected from one or more of the group: heat shock proteins, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, Complement C3, or a fragment or an equivalent of each thereof;
h) an allergic asthma-relevant antigen and is derived from an antigen selected from one or more of the group: DERP1, DERP2, or a fragment or an equivalent of each thereof;
i) an inflammatory bowel disease-relevant antigen and is derived from an antigen selected from one or more of the group: Flagelin, Fla-2, Fla-X, YIDX, bacteroides integrase, or a fragment or an equivalent of each thereof;
j) a systemic lupus erythematosus-relevant antigen and is derived from an antigen selected from one or more of the group: double-stranded (ds)DNA, ribonucleoprotein (RNP), Smith (Sm), Sjögren's-syndrome-related antigen A (SS-A)/Ro, Sjögren's-syndrome-related antigen B (SS-B)/La, RO60, RO52, histones, or a fragment or an equivalent of each thereof;
k) an atherosclerosis-relevant antigen and is derived from an antigen selected from one or more of the group: ApoB, ApoE or a fragment or an equivalent of each thereof;
l) a COPD-relvant antigen and/or emphysema-relevant antigen and is derived from elastin or a fragment or an equivalent thereof;
m) a psoriasis-relevant antigen and is derived from an antigen selected from one or more of the group: Cap18, ADMTSL5, ATL5, or a fragment or an equivalent of each thereof;
n) an autoimmune hepatitis-relevant antigen and is derived from an antigen selected from one or more of the group: CYP2D6, SLA, or a fragment or an equivalent of each thereof;
o) an uveitis-relevant antigen and is derived from arrestin or a fragment or an equivalent thereof;

p) a Sjogren's Syndrome-relevant antigen and is derived from an antigen selected from one or more of the group: (SS-A)/Ro, (SS-B)/La, MR3, RO60, RO52, or a fragment or an equivalent of each thereof;

q) a scleroderma-relevant antigen and is derived from an antigen selected from one or more of the group: CENP-C, TOP 1, RNA polymerase III, or a fragment or an equivalent of each thereof;

r) an anti-phospholipid syndrome-relevant antigen and is derived from APOH or a fragment or an equivalent thereof;

s) an ANCA-associated vasculitis-relevant antigen and is derived from an antigen selected from one or more of the gropu: MPO, PRTN3, or a fragment or an equivalent of each thereof; or t) a Stiff Man Syndrome-relevant antigen and is derived from GAD or a fragment or an equivalent thereof.

Diabetes-Relevant Antigens

Diabetes-relevant antigens include but are not limited to those derived from PPI, IGRP, GAD, islet cell autoantigen-2 (ICA2), and/or insulin. Autoreactive, diabetes-relevant antigenic peptides include, but are not limited to, include those listed in the following Table 6, in addition to the peptides and proteins disclosed in U.S. Publication 2005/0202032, which is incorporated herein by reference in its entirety, as well as equivalents and/or combinations of each thereof,

TABLE 6

| Peptide | | SEQ ID NO: |
|---|---|---|
| hInsB$_{10-18}$ | HLVEALYLV | 148 |
| hIGRP$_{228-236}$ | LNIDLLWSV | 149 |
| hIGRP$_{265-273}$ | VLFGLGFAI | 150 |
| IGRP$_{206-214}$ | VYLKTNVFL | 151 |
| hIGRP$_{206-214}$ | VYLKTNLFL | 152 |
| NRP-A7 | KYNKANAFL | 153 |
| NRP-I4 | KYNIANVFL | 154 |
| NRP-V7 | KYNKANVFL | 155 |
| YAI/D$^b$ | FQDENYLYL | 156 |
| INS B$_{15-23}$ | LYLVCGERG | 157 |
| PPI$_{76-90\ (K88S)}$ | SLQPLALEGSLQSRG | 158 |
| IGRP$_{13-25}$ | QHLQKDYRAYYTF | 159 |
| GAD$_{555-567}$ | NFFRMVISNPAAT | 160 |
| GAD$_{555-567\ (557I)}$ | NFIRMVISNPAAT | 161 |
| IGRP$_{23-35}$ | YTFLNFMSNVGDP | 162 |
| B$_{24}$-C$_{36}$ | FFYTPKTRREAED | 163 |
| PPI$_{76-90}$ | SLQPLALEGSLQKRG | 164 |
| INS-I9 | LYLVCGERI | 165 |
| TUM | KYQAVTTTL | 166 |
| G6Pase | KYCLITIFL | 167 |
| Pro-insulin$_{L2-10}$ | ALWMRLLPL | 168 |
| Pro-insulin$_{L3-11}$ | LWMRLLPLL | 169 |
| Pro-insulin$_{L6-14}$ | RLLPLLALL | 170 |

TABLE 6-continued

| Peptide | | SEQ ID NO: |
|---|---|---|
| Pro-insulin$_{B5-14}$ | HLCGSHLVEA | 171 |
| Pro-insulin$_{B10-18}$ | HLVEALYLV | 148 |
| Pro-insulin$_{B14-22}$ | ALYLVCGER | 172 |
| Pro-insulin$_{B15-24}$ | LYLVCGERGF | 173 |
| Pro-insulin$_{B17-25}$ | LVCGERGFF | 174 |
| Pro-insulin$_{B18-27}$ | VCGERGFFYT | 175 |
| Pro-insulin$_{B20-27}$ | GERGFFYT | 176 |
| Pro-insulin$_{B21-29}$ | ERGFFYTPK | 177 |
| Pro-insulin$_{B25-C1}$ | FYTPKTRRE | 178 |
| Pro-insulin$_{B27-C5}$ | TPKTRREAEDL | 179 |
| Pro-insulin$_{C20-28}$ | SLQPLALEG | 180 |
| Pro-insulin$_{C25-33}$ | ALEGSLQKR | 181 |
| Pro-insulin$_{C29-A5}$ | SLQKRGIVEQ | 182 |
| Pro-insulin$_{41-10}$ | GIVEQCCTSI | 183 |
| Pro-insulin$_{42-10}$ | IVEQCCTSI | 184 |
| Pro-insulin$_{412-20}$ | SLYQLENYC | 185 |

MS-Relevant Antigens

Antigens of the disclosure include antigens related to multiple sclerosis. Such antigens include, for example, those disclosed in U.S. Patent Application Publication No. 2012/0077686, and antigens derived from myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins NOGO A, glycoprotein Po, peripheral myelin protein 22, or 2'3'-cyclic nucleotide 3'-phosphodiesterase. In certain embodiments, the antigen is derived from Myelin Oligodendrocyte Glycoprotein (MOG).

In still further aspects, peptide antigens for the treatment of MS and MS-related disorders include without limitation those listed in Table 7 as well as equivalents and/or combinations of each thereof:

TABLE 7

| Peptide | | SEQ ID NO: |
|---|---|---|
| MOG$_{35-55}$ | MEVGWYRSPFSRVVHLYRNGK | 186 |
| MOG$_{36-55}$ | EVGWYRSPFSRVVHLYRNGK | 187 |
| MAG$_{287-295}$ | SLLLELEEV | 188 |
| MAG$_{509-517}$ | LMWAKIGPV | 189 |
| MAG$_{556-564}$ | VLFSSDFRI | 190 |
| MBP$_{110-118}$ | SLSRFSWGA | 191 |
| MOG$_{114-122}$ | KVEDPFYWV | 192 |
| MOG$_{166-175}$ | RTFDPHFLRV | 193 |

TABLE 7-continued

| Peptide | | SEQ ID NO: |
|---|---|---|
| $MOG_{172-180}$ | FLRVPCWKI | 194 |
| $MOG_{179-188}$ | KITLFVIVPV | 195 |
| $MOG_{188-196}$ | VLGPLVALI | 196 |
| $MOG_{181-189}$ | TLFVIVPVL | 197 |
| $MOG_{205-214}$ | RLAGQFLEEL | 198 |
| $PLP_{80-88}$ | FLYGALLLA | 199 |
| $MAG_{287-295}$ | SLLLELEEV | 188 |
| $MAG_{509-517}$ | LMWAKIGPV | 189 |
| $MAG_{556-564}$ | VLFSSDFRI | 190 |
| $MOG_{97-109}$ | TCFFRDHSYQEEA | 200 |
| $MOG_{97-109\ (E107S)}$ | TCFFRDHSYQEEA | 200 |
| $MOG_{97-109\ (E107S)}$ | TCFFRDHSYQSEA | 201 |
| $MBP_{89-101}$ | VHFFKNIVTPRTP | 202 |
| $PLP_{175-192}$ | YIYFNTWTTCQSIAFPSK | 203 |
| $PLP_{94-108}$ | GAVRQIFGDYKTTIC | 204 |
| $MBP_{86-98}$ | PVVHFFKNIVTPR | 205 |
| $PLP_{54-68}$ | NYQDYEYLINVIHAF | 206 |
| $PLP_{249-263}$ | ATLVSLLTFMIAATY | 207 |
| $MOG_{156-170}$ | LVLLAVLPVLLLQIT | 208 |
| $MOG_{201-215}$ | FLRVPCWKITLFVIV | 209 |
| $MOG_{38-52}$ | RHPIRALVGDEVELP | 210 |
| $MOG_{203-217}$ | RVPCWKITLFVIVPV | 211 |
| $PLP_{250-264}$ | TLVSLLTFMIAATYN | 212 |
| $MPB_{13-32}$ | KYLATASTMDHARHGFLPRH | 213 |
| $MPB_{83-99}$ | ENPVVHFFKNIVTPRTP | 214 |
| $MPB_{111-129}$ | LSRFSWGAEGQRPGFGYGG | 215 |
| $MPB_{146-170}$ | AQGTLSKIFKLGGRDSRSGSPMARR | 216 |
| $MOG_{223-237}$ | ALIICYNWLHRRLAG | 217 |
| $MOG_{6-20}$ | IGPRHPIRALVGDEV | 218 |
| $PLP_{88-102}$ | AEGFYTTGAVRQIFG | 219 |
| $PLP_{139-154}$ | HCLGKWLGHPDKFVGI | 220 |

Celiac Disease (CD) Relevant Antigens

Antigens relevant to celiac disease include, but are not limited to, those derived from gliadin. In some embodiments, non-limiting types of gliadin include alpha/beta gliadin, γ-gliadin, or ω-gliadin. Other non-limiting exemplary celiac disease-relevant antigens include those listed in Table 8 as well as equivalents and/or combinations of each thereof.

TABLE 8

| Peptide | | SEQ ID NO: |
|---|---|---|
| $aGlia_{57-68}$ | QLQPFPQPELPY | 221 |
| $aGlia_{62-72}$ | PQPELPYPQPE | 222 |
| $aGlia_{217-229}$ | SGEGSFQPSQQNP | 223 |

Primary Biliary Cirrhosis (PBC) Relevant Antigens

Antigens relevant to primary biliary cirrhosis include, but are not limited to, those derived from PDC-E2. Non-limiting examples of exemplary antigens include those listed in Table 9 as well as equivalents and/or combinations of each thereof

TABLE 9

| Peptide | | SEQ ID NO: |
|---|---|---|
| $PDC-E2_{122-135}$ | GDLIAEVETDKATV | 224 |
| $PDC-E2_{249-262}$ | GDLLAEIETDKATI | 225 |
| $PDC-E2_{249-263}$ | GDLLAEIETDKATIG | 226 |
| $PDC-E2_{629-643}$ | AQWLAEFRKYLEKPI | 227 |
| $PDC-E2_{72-86}$ | RLLLQLLGSPGRRYY | 228 |
| $PDC-E2_{353-367}$ | GRVFVSPLAKKLAVE | 229 |
| $PDC-E2_{422-436}$ | DIPISNIRRVIAQRL | 230 |
| $PDC-E2_{629-643}$ | AQWLAEFRKYLEKPI | 227 |
| $PDC-E2_{80-94}$ | SPGRRYYSLPPHQKV | 231 |
| $PDC-E2_{353-367}$ | GRVFVSPLAKKLAVE | 229 |
| $PDC-E2_{535-549}$ | ETIANDVVSLATKAR | 232 |

Pemphigus Folliaceus (PF) and Pemphigus Vulgaris (PV) Relevant Antigens

Antigens relevant to PF and PV include, but are not limited to, those derived from desmoglein 3 (DG3) and/or desmoglein 1 (DG1). Non-limiting examples include those listed in Table 10 as well as equivalents and/or combinations of each thereof.

TABLE 10

| Peptide | | SEQ ID NO: |
|---|---|---|
| $DG1_{216-229}$ | GEIRTMNNFLDREI | 233 |
| $DG3_{97-111}$ | FGIFVVDKNTGDINI | 234 |
| $DG3_{251-265}$ | CECNIKVKDVNDNFP | 235 |
| $DG3_{351-365}$ | NKAEFHQSVISRYRV | 236 |
| $DG3_{453-467}$ | DSTFIVNKTITAEVL | 237 |
| $DG3_{540-554}$ | SITTLNATSALLRAQ | 238 |
| $DG3_{280-294}$ | ILSSELLRFQVTDLD | 239 |
| $DG3_{326-340}$ | EGILKVVKALDYEQL | 240 |
| $DG3_{367-381}$ | STPVTIQVINVREGI | 241 |
| $DG3_{13-27}$ | AIFVVVILVHGELRI | 242 |
| $DG3_{323-337}$ | RTNEGILKVVKALDY | 243 |

TABLE 10-continued

| Peptide | | SEQ ID NO: |
|---|---|---|
| DG3$_{438-452}$ | DSKTAEIKFVKNMNR | 244 |
| DG1$_{48-62}$ | KREWIKFAAACREGE | 245 |
| DG1$_{206-222}$ | MFIINRNTGEIRTMN | 246 |
| DG1$_{363-377}$ | SQYKLKASAISVTVL | 247 |
| DG1$_{3-17}$ | WSFFRVVAMLFIFLV | 248 |
| DG1$_{192-206}$ | SKIAFKIIRQEPSDS | 249 |
| DG1$_{326-340}$ | TNVGILKVVKPLDYE | 250 |
| DG1$_{1-15}$ | MDWSFFRVVAMLFIF | 251 |
| DG1$_{35-49}$ | KNGTIKWHSIRRQKR | 252 |
| DG1$_{325-339}$ | RTNVGILKVVKPLDY | 253 |

Neuromyelitis Optica Spectrum Disorder (NMO) Relevant Antigens

Antigens relevant to NMO include, but are not limited to, those derived from AQP4 or aquaporin 4. Non-limiting examples include those listed in Table 11 as well as equivalents and/or combinations of each thereof.

TABLE 11

| Peptide | | SEQ ID NO: |
|---|---|---|
| AQP4$_{129-143}$ | GAGILYLVTPPSVVG | 254 |
| AQP4$_{284-298}$ | RSQVETDDLILKPGV | 255 |
| AQP4$_{63-76}$ | EKPLPVDMVLISLC | 256 |
| AQP4$_{129-143}$ | GAGILYLVTPPSVVG | 254 |
| AQP4$_{39-53}$ | TAEFLAMLIFVLLSL | 257 |

Arthritis-Relevant Antigens

Antigens relevant to arthritis include, but are not limited to, those derived from heat shock proteins, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, Complement C3, or a fragment or an equivalent of each thereof.

Allergic Asthma Relevant Antigens

Antigens relevant to allergic asthma include, but are not limited to, those derived from DERP1 and DERP2. Non-limiting examples include those listed in Table 12 as well as equivalents and/or combinations of each thereof.

TABLE 12

| Peptide | | SEQ ID NO: |
|---|---|---|
| DERP-1$_{16-30}$ | LRQMRTVTPIRMQGG | 258 |
| DERP-1$_{171-185}$ | AVNIVGYSNAQGVDY | 259 |
| DERP-1$_{110-124}$ | RFGISNYCQIYPPNV | 260 |
| DERP-2$_{26-40}$ | PCIIHRGKPFQLEAV | 261 |
| DERP-2$_{107-121}$ | TVKVMGDDGVLACAI | 262 |

Inflammatory Bowel Disease-Relevant Antigens

Antigens relevant to inflammatory bowel disease include but are not limited to Crohn's Disease-relevant antigens and ulcerative colitis-relevant antigens. In some embodiments, inflammatory bowel disease-relevant antigens include, but are not limited to, those derived from bacteroides integrase, flagelin, flagellin 2 (Fla-2/Fla-X), or uncharacterized E. coli protein (YIDX). Non-limiting examples include those listed in Table 13 as well as equivalents and/or combinations of each thereof.

TABLE 13

| Peptide | | SEQ ID NO: |
|---|---|---|
| bacteroides integrase antigen$_{183-197}$ | EAINQGYMHADAYPF | 263 |
| bacteroides integrase antigen$_{146-160}$ | KDLTYTFLRDFEQYL | 264 |
| bacteroides integrase antigen$_{175-189}$ | RQLRTLVNEAINQGY | 265 |
| bacteroides integrase antigen$_{1-15}$ | MDKIRYRLVYNRQNT | 266 |
| bacteroides integrase antigen$_{183-197}$ | EAINQGYMHADAYPF | 263 |
| bacteroides integrase antigen$_{30-44}$ | LNQRKIYLKTNVYLK | 267 |
| bacteroides integrase antigen$_{70-84}$ | EYILYLQGIELGYWK | 268 |
| bacteroides integrase antigen$_{337-351}$ | TCATLLIHQGVAITT | 269 |
| bacteroides integrase antigen$_{171-185}$ | AKHMRQLRTLVNEAI | 270 |
| bacteroides integrase antigen$_{4-18}$ | IRYRLVYNRQNTLNR | 271 |
| bacteroides integrase antigen$_{256-270}$ | ENFIRINGKRWLYFK | 272 |
| Fla-2/Fla-X$_{366-380}$ | TGAAATYAIDSIADA | 273 |
| Fla-2/Fla-X$_{164-178}$ | NATFSMDQLKFGDTI | 274 |
| Fla-2/Fla-X$_{261-275}$ | DRTVVSSIGAYKLIQ | 275 |
| Fla-2/Fla-X$_{1-15}$ | MVVQHNLRAMNSNRM | 276 |
| Fla-2/Fla-X$_{51-65}$ | KMRKQIRGLSQASLN | 277 |
| Fla-2/Fla-X$_{269-283}$ | GAYKLIQKELGLASS | 278 |
| Fla-2/Fla-X$_{4-18}$ | QHNLRAMNSNRMLGI | 279 |
| Fla-2/Fla-X$_{271-285}$ | YKLIQKELGLASSIG | 280 |
| YIDX$_{78-92}$ | ADDIVKMLNDPALNR | 281 |

TABLE 13-continued

| Peptide | | SEQ ID NO: |
|---|---|---|
| YIDX$_{93-107}$ | HNIQVADDARFVLNA | 282 |
| YIDX$_{98-112}$ | ADDARFVLNAGKKKF | 283 |
| YIDX$_{23-37}$ | GCISYALVSHTAKGS | 284 |
| YIDX$_{78-92}$ | ADDIVKMLNDPALNR | 281 |
| YIDX$_{195-209}$ | LPVTVTLDIITAPLQ | 285 |
| YIDX$_{22-36}$ | SGCISYALVSHTAKG | 286 |
| YIDX$_{80-94}$ | DIVKMLNDPALNRHN | 287 |
| YIDX$_{101-115}$ | ARFVLNAGKKKFTGT | 288 |

Systemic Lupus Erythematosus (SLE) Relevant Antigens

Antigens relevant to SLE include, but are not limited to, those derived from H4, H2B, H1', dsDNA, RNP, Smith (Sm), Sjogren's Syndrome-related Antigen A (SS-A)/Ro, Sjogren's Syndrome-related Antigen B (SS-B)/La, and/or histones. In some embodiments, SS-A includes but is not limited to RO60 and RO52. In some embodiments, histones includes but is not limited to H4, H2B, H1'. Non-limiting examples include those listed in Table 14 as well as equivalents and/or combinations of each thereof

TABLE 14

| Peptide | | SEQ ID NO: |
|---|---|---|
| H4$_{71-94}$ | TYTEHAKRKTVTAMDVVYALKRQG | 289 |
| H4$_{74-88}$ | EHAKRKTVTAMDVVY | 290 |
| H4$_{76-90}$ | AKRKTVTAMDVVYAL | 291 |
| H4$_{75-89}$ | HAKRKTVTAMDVVYA | 292 |
| H4$_{78-92}$ | RKTVTAMDVVYALKR | 293 |
| H4$_{80-94}$ | TVTAMDVVYALKRQ | 294 |
| H2B$_{10-24}$ | PKKGSKKAVTKAQKK | 295 |
| H2B$_{16-30}$ | KAVTKAQKKDGKKRK | 296 |
| H1'$_{22-42}$ | STDHPKYSDMIVAAIQAEKNR | 297 |
| H1'$_{27-41}$ | KYSDMIVAAIQAEKN | 298 |

Atherosclerosis Relevant Antigens

Antigens relevant to atherosclerosis include, but are not limited to, those derived from Apolipoprotein B (ApoB) or Apolipoprotein E (ApoE). Non-limiting examples include those listed in Table 15 as well as equivalents and/or combinations of each thereof.

TABLE 15

| Peptide | | SEQ ID NO: |
|---|---|---|
| ApoB$_{3501-3516}$ | SQEYSGSVANEANVY | 299 |
| ApoB$_{1952-1966}$ | SHSLPYESSISTALE | 300 |
| ApoB$_{978-993}$ | TGAYSNASSTESASY | 301 |
| ApoB$_{3498-3513}$ | SFLSQEYSGSVANEA | 302 |

TABLE 15-continued

| Peptide | | SEQ ID NO: |
|---|---|---|
| ApoB$_{210A}$ | KTTKQSFDLSVKAQYKKNKH | 303 |
| ApoB$_{210B}$ | KTTKQSFDLSVKAQY | 304 |
| ApoB$_{210C}$ | TTKQSFDLSVKAQYK | 305 |

Chronic Obstructive Pulmonary Disease (COPD) and/or Emphysema Relevant Antigens

Antigens relevant to COPD and/or emphysema include, but are not limited to, those derived from elastin. Non-limiting examples include those listed in Table 16 as well as equivalents and/or combinations of each thereof.

TABLE 16

| Peptide | | SEQ ID NO: |
|---|---|---|
| elastin$_{89-103}$ | GALVPGGVADAAAAY | 306 |
| elastin$_{698-712}$ | AAQFGLVGAAGLGGL | 307 |
| elastin$_{8-22}$ | APRPGVLLLLLSILH | 308 |
| elastin$_{94-108}$ | GGVADAAAAYKAAKA | 309 |
| elastin$_{13-27}$ | VLLLLLSILHPSRPG | 310 |
| elastin$_{695-709}$ | AAKAAQFGLVGAAGL | 311 |
| elastin$_{563-577}$ | VAAKAQLRAAAGLGA | 312 |
| elastin$_{558-572}$ | KSAAKVAAKAQLRAA | 313 |
| elastin$_{698-712}$ | AAQFGLVGAAGLGGL | 307 |
| elastin$_{566-580}$ | KAQLRAAAGLGAGIP | 314 |
| elastin$_{645-659}$ | VPGALAAAKAAKYGA | 315 |

Psoriasis-Relevant Antigens

Antigens relevant to psoriasis include but are not limited to those listed in the following Table 17, as well as equivalents and/or combinations thereof. Other non-limiting exemplary psoriasis-relevant antigens can be derived from human adamis-like protein 5 (ATL5), cathelicidin antimicrobial peptide (CAP18), and/or ADAMTS-like protein 5 (AD-MTSL5).

TABLE 17

| Peptide | | SEQ ID NO: |
|---|---|---|
| Cap18$_{64-78}$ | RPTMDGDPDTPKPVS | 316 |
| Cap18$_{34-48}$ | SYKEAVLRAIDGINQ | 317 |
| Cap18$_{47-61}$ | NQRSSDANLYRLLDL | 318 |
| Cap18$_{151-165}$ | KRIVQRIKDFLRNLV | 319 |
| Cap18$_{149-163}$ | EFKRIVQRIKDFLRN | 320 |
| Cap18$_{152-166}$ | RIVQRIKDFLRNLVP | 321 |
| Cap18$_{131-145}$ | RFALLGDFFRKSKEK | 322 |
| Cap18$_{24-38}$ | QRIKDFLRNLVPRTE | 323 |
| ADMTSL5$_{245-259}$ | DGRYVLNGHWVVSPP | 324 |
| ADMTSL5$_{267-281}$ | THVVYTRDTGPQETL | 325 |

TABLE 17-continued

| Peptide | | SEQ ID NO: |
|---|---|---|
| ADMTSL5$_{372-386}$ | RLLHYCGSDFVFQAR | 326 |
| ADMTSL5$_{289-303}$ | HDLLLQVLLQEPNPG | 327 |
| ADMTSL5$_{396-410}$ | ETRYEVRIQLVYKNR | 328 |
| ADMTSL5$_{433-447}$ | HRDYLMAVQRLVSPD | 329 |
| ADMTSL5$_{142-156}$ | EGHAFYHSFGRVLDG | 330 |
| ADMTSL5$_{236-250}$ | RNHLALMGGDGRYVL | 331 |
| ADMTSL5$_{301-315}$ | NPGIEFEFWLPRERY | 332 |
| ADMTSL5$_{203-217}$ | VQRVFRDAGAFAGYW | 333 |
| ADMTSL5$_{404-418}$ | QLVYKNRSPLRAREY | 334 |

Autoimmune Hepatitis-Relevant Antigens

Autoimmune hepatitis-relevant antigens include but are not limited to those disclosed in the following Table 18, as well as equivalents and/or combinations thereof. Other non-limiting exemplary autoimmune hepatitis-relevant antigens can be derived from microsomal cytochrome P450IID6 (CYP2D6) and/or soluble liver antigen (SLA).

TABLE 18

| Peptide | | SEQ ID NO: |
|---|---|---|
| CYP2D6$_{193-207}$ | RRFEYDDPRFLRLLD | 335 |
| CYP2D6$_{76-90}$ | TPVVVLNGLAAVREA | 336 |
| CYP2D6$_{293-307}$ | ENLRIVVADLFSAGM | 337 |
| CYP2D6$_{313-332}$ | TLAWGLLLMILHPDVQRRVQ | 338 |
| CYP2D6$_{393-412}$ | TTLITNLSSVLKDEAVWEKP | 339 |
| CYP2D6$_{199-213}$ | DPRFLRLLDLAQEGL | 340 |
| CYP2D6$_{450-464}$ | RMELFLFFTSLLQHF | 341 |
| CYP2D6$_{301-315}$ | DLFSAGMVTTSTTLA | 342 |
| CYP2D6$_{452-466}$ | ELFLFFTSLLQHFSF | 343 |
| CYP2D6$_{59-73}$ | DQLRRRFGDVFSLQL | 344 |
| CYP2D6$_{130-144}$ | EQRRFSVSTLRNLGL | 345 |
| CYP2D6$_{193-212}$ | RRFEYDDPRFLRLLDLAQEG | 346 |
| CYP2D6$_{305-324}$ | AGMVTTSTTLAWGLLLMILH | 347 |
| CYP2D6$_{131-145}$ | QRRFSVSTLRNLGLG | 348 |
| CYP2D6$_{216-230}$ | ESGFLREVLNAVPVL | 349 |
| CYP2D6$_{238-252}$ | GKVLRFQKAFLTQLD | 350 |
| CYP2D6$_{199-213}$ | DPRFLRLLDLAQEGL | 340 |
| CYP2D6$_{235-252}$ | GKVLRFQKAFLTQLD | 350 |
| CYP2D6$_{293-307}$ | ENLRIVVADLFSAGM | 337 |
| CYP2D6$_{381-395}$ | DIEVQGFRIPKGTTL | 351 |
| CYP2D6$_{429-443}$ | KPEAFLPFSAGRRAC | 352 |
| SLA$_{334-348}$ | YKKLLKERKEMFSYL | 353 |
| SLA$_{196-210}$ | DELRTDLKAVEAKVQ | 354 |

TABLE 18-continued

| Peptide | | SEQ ID NO: |
|---|---|---|
| SLA$_{115-129}$ | NKITNSLVLDIIKLA | 355 |
| SLA$_{373-386}$ | NRLDRCLKAVRKER | 356 |
| SLA$_{186-197}$ | LIQQGARVGRID | 357 |
| SLA$_{317-331}$ | SPSLDVLITLLSLGS | 358 |
| SLA$_{171-185}$ | DQKSCFKSMITAGFE | 359 |
| SLA$_{417-431}$ | YTFRGFMSHTNNYPC | 360 |
| SLA$_{359-373}$ | YNERLLHTPHNPISL | 361 |
| SLA$_{215-229}$ | DCILCIHSTTSCFAP | 362 |
| SLA$_{111-125}$ | SSLLNKITNSLVLDI | 363 |
| SLA$_{110-124}$ | GSSLLNKITNSLVLD | 364 |
| SLA$_{299-313}$ | NDSFIQEISKMYPGR | 365 |
| SLA$_{342-356}$ | KEMFSYLSNQIKKLS | 366 |
| SLA$_{49-63}$ | STLELFLHELAIMDS | 367 |
| SLA$_{119-133}$ | NSLVLDIIKLAGVHT | 368 |
| SLA$_{260-274}$ | SKCMHLIQQGARVGR | 369 |
| SLA$_{26-40}$ | RSHEHLIRLLLEKGK | 370 |
| SLA$_{86-100}$ | RRHYRFIHGIGRSGD | 371 |
| SLA$_{331-345}$ | SNGYKKLLKERKEMF | 372 |

Uveitis-Relevant Antigens

Uveitis-relevant antigens include but are not limited to those disclosed in the following Table 19, as well as equivalents and/or combinations thereof. Other non-limiting exemplary uveitis-relevant antigens can be derived from arrestin, human retinal S-antigen, and/or interphotoreceptor retinoid-binding protein (IRBP).

TABLE 19

| Peptide | | SEQ ID NO: |
|---|---|---|
| arrestin$_{199-213}$ | QFFMSDKPLHLAVSLN | 373 |
| arrestin$_{77-91}$ | DVIGLTFRRDLYFSR | 374 |
| arrestin$_{250-264}$ | NVVLYSSDYYVKPVA | 375 |
| arrestin$_{172-186}$ | SSVRLLIRKVQHAPL | 376 |
| arrestin$_{354-368}$ | EVPFRLMHPQPEDPA | 377 |
| arrestin$_{239-253}$ | KKIKAFVEQVANVVL | 378 |
| arrestin$_{102-116}$ | STPTKLQESLLKKLG | 379 |
| arrestin$_{59-73}$ | KKVYVTLTCAFRYGQ | 380 |
| arrestin$_{280-294}$ | KTLTLLPLLANNRER | 381 |
| arrestin$_{291-306}$ | NRERRGIALDGKIKHE | 382 |
| arrestin$_{195-209}$ | EAAWQFFMSDKPLHL | 383 |
| arrestin$_{200-214}$ | QFFMSDKPLHLAVSL | 384 |

Sjogren's Syndrome-Relevant Antigens

Sjogren's Syndrome-relevant antigens include but are not limited to those disclosed in the following Table 20, as well as equivalents and/or combinations thereof. Other non-limiting exemplary Sjogren's Syndrome-relevant antigens can be derived from (SS-A)/Ro, (SS-B)/La, RO60, RO52, and/or muscarinic receptor 3 (MR3).

TABLE 20

| | Peptide | SEQ ID NO: |
|---|---|---|
| RO60$_{127-141}$ | TFIQFKKDLKESMKC | 385 |
| RO60$_{523-537}$ | DTGALDVIRNFTLDM | 386 |
| RO60$_{243-257}$ | EVIHLIEEHRLVREH | 387 |
| RO60$_{484-498}$ | REYRKKMDIPAKLIV | 388 |
| RO60$_{347-361}$ | EEILKALDAAFYKTF | 389 |
| RO60$_{369-383}$ | KRFLLAVDVSASMNQ | 390 |
| RO60$_{426-440}$ | TDMTLQQVLMAMSQI | 391 |
| RO60$_{267-281}$ | EVWKALLQEMPLTAL | 392 |
| RO60$_{178-192}$ | SHKDLLRLSHLKPSS | 393 |
| RO60$_{358-372}$ | YKTFKTVEPTGKRFL | 394 |
| RO60$_{221-235}$ | ETEKLLKYLEAVEKV | 395 |
| RO60$_{318-332}$ | RIHPFHILIALETYK | 396 |
| RO60$_{407-421}$ | EKDSYVVAFSDEMVP | 397 |
| RO60$_{459-473}$ | TPADVFIVFTDNETF | 398 |
| RO60$_{51-65}$ | QKLGLENAEALIRLI | 399 |
| RO60$_{312-326}$ | KLLKKARIHPFHILI | 400 |
| LA$_{241-255}$ | DDQTCREDLHILFSN | 401 |
| LA$_{101-115}$ | TDEYKNDVKNRSVYI | 402 |
| LA$_{153-167}$ | SIFVVFDSIESAKKF | 403 |
| LA$_{178-192}$ | TDLLILFKDDYFAKK | 404 |
| LA$_{19-33}$ | HQIEYYFGDFNLPRD | 405 |
| LA$_{37-51}$ | KEQIKLDEGWVPLEI | 406 |
| LA$_{133-147}$ | DKGQVLNIQMRRTLH | 407 |
| LA$_{50-64}$ | EIMIKFNRLNRLTTD | 408 |
| LA$_{32-46}$ | RDKFLKEQIKLDEGW | 409 |
| LA$_{153-167}$ | SIFVVFDSIESAKKF | 403 |
| LA$_{83-97}$ | SEDKTKIRRSPSKPL | 410 |
| LA$_{136-150}$ | QVLNIQMRRTLHKAF | 411 |
| LA$_{297-311}$ | RNKEVTWEVLEGEVE | 412 |
| LA$_{59-73}$ | NRLTTDFNVIVEALS | 413 |
| LA$_{151-165}$ | KGSIFVVFDSIESAK | 414 |
| LA$_{86-100}$ | KTKIRRSPSKPLPEV | 415 |
| LA$_{154-168}$ | IFVVFDSIESAKKFV | 416 |

Scleroderma-Relevant Antigens

Scleroderma-relevant antigens include but are not limited to those disclosed in the following Table 21, as well as equivalents and/or combinations thereof. Non-limiting exemplary Scleroderma-relevant antigens can be derived from centromere autoantigen centromere protein C (CENP-C), DNA topoisomerase I (TOP1), and/or RNA polymerase III.

TABLE 21

| | Peptide | SEQ ID NO: |
|---|---|---|
| TOP1$_{346-360}$ | KERIANFKIEPPGLF | 417 |
| TOP1$_{420-434}$ | QGSIKYIMLNPSSRI | 418 |
| TOP1$_{750-764}$ | QREKFAWAIDMADED | 419 |
| TOP1$_{419-433}$ | IQGSIKYIMLNPSSR | 420 |
| TOP1$_{591-605}$ | YNASITLQQQLKELT | 421 |
| TOP1$_{695-709}$ | EQLMKLEVQATDREE | 422 |
| TOP1$_{305-319}$ | SQYFKAQTEARKQMS | 423 |
| TOP1$_{346-360}$ | KERIANFKIEPPGLF | 417 |
| TOP1$_{419-433}$ | IQGSIKYIMLNPSSR | 420 |
| TOP1$_{425-439}$ | YIMLNPSSRIKGEKD | 424 |
| TOP1$_{614-628}$ | KILSYNRANRAVAIL | 425 |
| CENP-C$_{297-311}$ | KLIEDEFIIDESDQS | 426 |
| CENP-C$_{857-871}$ | KVYKTLDTPFFSTGK | 427 |
| CENP-C$_{887-901}$ | QDILVFYVNFGDLLC | 428 |
| CENP-C$_{212-226}$ | KVMLKKIEIDNKVSD | 429 |
| CENP-C$_{643-657}$ | EDNIMTAQNVPLKPQ | 430 |
| CENP-C$_{832-846}$ | TREIILMDLVRPQDT | 431 |
| CENP-C$_{167-181}$ | TSVSQNVIPSSAQKR | 432 |
| CENP-C$_{246-260}$ | RIRDSEYEIQRQAKK | 433 |
| CENP-C$_{846-860}$ | TYQFFVKHGELKVYK | 434 |
| CENP-C$_{149-163}$ | DEEFYLSVGSPSVLL | 435 |
| CENP-C$_{833-847}$ | REIILMDLVRPQDTY | 436 |
| CENP-C$_{847-861}$ | YQFFVKHGELKVYKT | 437 |

Anti-Phospholipid Syndrome-Relevant Antigens

Anti-phospholipid syndrome relevant antigens include but are not limited to those disclosed in the following Table 22, as well as equivalents and/or combinations thereof. Non-limiting exemplary anti-phospholipid syndrome-relevant antigens can be derived from beta-2-glycoprotein 1 (BG2P1 or APOH).

TABLE 22

| | Peptide | SEQ ID NO: |
|---|---|---|
| APOH$_{235-249}$ | HDGYSLDGPEEIECT | 438 |
| APOH$_{306-320}$ | KCSYTEDAQCIDGTI | 439 |
| APOH$_{237-251}$ | GYSLDGPEEIECTKL | 440 |
| APOH$_{295-309}$ | KVSFFCKNKEKKCSY | 441 |

TABLE 22-continued

| Peptide | | SEQ ID NO: |
|---|---|---|
| APOH$_{28-42}$ | DLPFSTVVPLKTFYE | 442 |
| APOH$_{173-187}$ | ECLPQHAMFGNDTIT | 443 |
| APOH$_{264-278}$ | CKVPVKKATVVYQGE | 444 |
| APOH$_{295-309}$ | KVSFFCKNKEKKCSY | 441 |
| APOH$_{49-63}$ | YSCKPGYVSRGGMRK | 445 |
| APOH$_{269-283}$ | KKATVVYQGERVKIQ | 446 |
| APOH$_{295-309}$ | KVSFFCKNKEKKCSY | 441 |
| APOH$_{321-355}$ | EVPKCFKEHSSLAFW | 447 |
| APOH$_{322-336}$ | VPKCFKEHSSLAFWK | 448 |
| APOH$_{324-338}$ | KCFKEHSSLAFWKTD | 449 |

ANCA-Associated Vasculitis-Relevant Antigens

ANCA-associated vasculitis-relevant antigens include but are not limited to those disclosed in the following Table 23, as well as equivalents and/or combinations thereof. Non-limiting exemplary ANCA-associated vasculitis-relevant antigens can be derived from myeloperoxidase (MPO), proteinase (PRTN3), or bacterial permeability increasing factor (BPI).

TABLE 23

| Peptide | | SEQ ID NO: |
|---|---|---|
| MPO$_{506-520}$ | QPFMFRLDNRYQPME | 450 |
| MPO$_{302-316}$ | RIKNQADCIPFFRSC | 451 |
| MPO$_{7-21}$ | SSLRCMVDLGPCWAG | 452 |
| MPO$_{689-703}$ | QQRQALAQISLPRII | 453 |
| MPO$_{248-262}$ | RSLMFMQWGQLLDHD | 454 |
| MPO$_{444-458}$ | QEARKIVGAMVQIIT | 455 |
| MPO$_{513-527}$ | DNRYQPMEPNPRVPL | 456 |
| MPO$_{97-111}$ | ELLSYFKQPVAATRT | 457 |
| MPO$_{616-630}$ | QLGTVLRNLKLARKL | 458 |
| MPO$_{462-476}$ | YLPLVLGPTAMRKYL | 459 |
| MPO$_{617-631}$ | LGTVLRNLKLARKLM | 460 |
| MPO$_{714-728}$ | KNNIFMSNSYPRDFV | 461 |
| PRTN3$_{44-58}$ | SLQMRGNPGSHFCGG | 462 |
| PRTN3$_{234-248}$ | TRVALYVDWIRSTLR | 463 |
| PRTN3$_{59-73}$ | TLIHPSFVLTAAHCL | 464 |
| PRTN3$_{117-131}$ | NDVLLIQLSSPANLS | 465 |
| PRTN3$_{164-178}$ | DPPAQVLQELNVTVV | 466 |
| PRTN3$_{71-85}$ | HCLRDIPQRLVNVVL | 467 |
| PRTN3$_{241-255}$ | DWIRSTLRRVEAKGR | 468 |
| PRTN3$_{59-73}$ | TLIHPSFVLTAAHCL | 464 |
| PRTN3$_{183-197}$ | RPHNICTFVPRRKAG | 469 |

TABLE 23-continued

| Peptide | | SEQ ID NO: |
|---|---|---|
| PRTN3$_{62-76}$ | HPSFVLTAAHCLRDI | 470 |
| PRTN3$_{118-132}$ | DVLLIQLSSPANLSA | 471 |
| PRTN3$_{239-253}$ | YVDWIRSTLRRVEAK | 472 |

Stiff Man Syndrome-Relevant Antigens

Stiff Man Syndrome-relevant antigens include but are not limited to those disclosed in the following Table 24, as well as equivalents and/or combinations thereof. Non-limiting exemplary Stiff Man Syndrome-relevant antigens can be derived from glutamate decarboxylase (GAD). In some embodiments, GAD includes but is not limited to GAD65.

TABLE 24

| Peptide | | SEQ ID NO: |
|---|---|---|
| GAD$_{212-226}$ | EYVTLKKMREIIGWP | 473 |
| GAD$_{555-569}$ | NFFRMVISNPAATHQ | 474 |
| GAD$_{297-311}$ | DSVILIKCDERGKMI | 475 |

It is contemplated that in compositions of the disclosure, there is between about 0.001 mg and about 10 mg of total protein per ml in the composition. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100 µg/ml or mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be peptide/MHC/nanoparticle complex.

The present disclosure contemplates the administration of a peptide/MHC/nanoparticle complex to effect a diagnosis, treatment or preventative therapy against the development of a disease or condition associated with autoimmune responses or cancer.

In addition, U.S. Pat. No. 4,554,101 (Hopp), which is incorporated herein by reference, teaches the identification and preparation of epitopes from primary amino acid sequences on the basis of hydrophilicity. Through the methods disclosed in Hopp, one of skill in the art would be able to identify potential epitopes from within an amino acid sequence and confirm their immunogenicity. Numerous scientific publications have also been devoted to the prediction of secondary structure and to the identification of epitopes, from analyses of amino acid sequences (Chou & Fasman, 1974a,b; 1978a,b; 1979). Any of these may be used, if desired, to supplement the teachings of Hopp in U.S. Pat. No. 4,554,101.

Other Antigenic Components

Molecules other than peptides can be used as antigens or antigenic fragments in complex with MHC molecules. Such molecules include, but are not limited to, carbohydrates, lipids, small molecules, and the like. Carbohydrates are major components of the outer surface of a variety of cells.

Certain carbohydrates are characteristic of different stages of differentiation and very often these carbohydrates are recognized by specific antibodies. Expression of distinct carbohydrates can be restricted to specific cell types. Autoantibody responses to endometrial and serum antigens have been shown to be a common feature of endometriosis. There has been described a serum autoantibody response in endometriosis to a number of previously identified antigens, including 2-Heremans Schmidt glycoprotein and carbonic anhydrase, which is specific for a carbohydrate epitope.

Non-Limiting, Exemplary Antigen-MHC Complexes

In certain embodiments, specific combinations of antigen and MHC may be optimized for the treatment of a specific disease. Non-limiting examples include, but are not limited to, the following examples:

For the treatment of type I diabetes, the antigen of the pMHC complex may be derived from an antigen of the group: $PPI_{76-90(K88S)}$, $IGRP_{13-25}$, $GAD_{555-567}$, $GAD_{555-567(557I)}$, $IGRP_{23-35}$, $B_{24}$-$C_{36}$, $PPI_{76-60}$, or a fragment or an equivalent of each thereof, and the MHC of the pMHC complex comprises all or part of a polypeptide of the group: HLA-DRB1*0401/DRA, HLA-DRB1*0301/DRA, or a fragment or an equivalent of each thereof.

In some embodiments, the antigen of the pMHC complex comprises a:

a) a diabetes-relevant antigen and is derived from an antigen selected from one or more of the group: preproinsulin (PPI), islet-specific glucose-6-phosphatase (IGRP), glutamate decarboxylase (GAD), islet cell autoantigen-2 (ICA2), insulin, proinsulin, or a fragment or an equivalent of each thereof;

b) a multiple sclerosis-relevant antigen and is derived from an antigen selected from one or more of the group: myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins, NOGO A, glycoprotein Po, peripheral myelin protein 22, 2'3'-cyclic nucleotide 3'-phosphodiesterase, or a fragment or an equivalent of each thereof;

c) a Celiac Disease-relevant antigen and is derived from gliadin or a fragment or an equivalent thereof;

d) a primary biliary cirrhosis-relevant antigen and is derived from PDC-E2 or a fragment or an equivalent thereof;

e) a pemphigus folliaceus-relevant antigen and/or pemphigus vulgaris-relevant antigen and is derived from an antigen selected from one or more of the group: DG1, DG3, or a fragment or an equivalent of each thereof;

f) a neuromyelitis optica spectrum disorder-relevant antigen and is derived from AQP4 or a fragment or an equivalent thereof;

g) an arthritis-relevant antigen and is derived from an antigen selected from one or more of the group: heat shock proteins, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, Complement C3, or a fragment or an equivalent of each thereof;

h) an allergic asthma-relevant antigen and is derived from an antigen selected from one or more of the group: DERP1, DERP2, or a fragment or an equivalent of each thereof;

i) an inflammatory bowel disease-relevant antigen and is derived from an antigen selected from one or more of the group: Flagelin, Fla-2, Fla-X, YIDX, bacteroides integrase, or a fragment or an equivalent of each thereof;

j) a systemic lupus erythematosus-relevant antigen and is derived from an antigen selected from one or more of the group: double-stranded (ds)DNA, ribonucleoprotein (RNP), Smith (Sm), Sjögren's-syndrome-related antigen A (SS-A)/Ro, Sjögrens-syndrorne-related antigen B (SS-B)/La, RO60, RO52, histones, or a fragment or an equivalent of each thereof;

k) an atherosclerosis-relevant antigen and is derived from an antigen selected from one or more of the group: ApoB, ApoE or a fragment or an equivalent of each thereof;

l) a COPD-relvant antigen and/or emphysema-relevant antigen and is derived from elastin or a fragment or an equivalent thereof;

m) a psoriasis-relevant antigen and is derived from an antigen selected from one or more of the group: Cap18, ADMTSL5, ATL5, or a fragment or an equivalent of each thereof;

n) an autoimmune hepatitis-relevant antigen and is derived from an antigen selected from one or more of the group: CYP2D6, SLA, or a fragment or an equivalent of each thereof;

o) an uveitis-relevant antigen and is derived from arrestin or a fragment or an equivalent thereof;

p) a Sjogren's Syndrome-relevant antigen and is derived from an antigen selected from one or more of the group: (SS-A)/Ro, (SS-B)/La, MR3, RO60, RO52, or a fragment or an equivalent of each thereof;

q) a scleroderma-relevant antigen and is derived from an antigen selected from one or more of the group: CENP-C, TOP 1, RNA polymerase III, or a fragment or an equivalent of each thereof;

r) an anti-phospholipid syndrome-relevant antigen is derived from APOH or a fragment or an equivalent thereof;

s) an ANCA-associated vasculitis-relevant antigen and is derived from an antigen selected from one or more of the group: MPO, PRTN3, or a fragment or an equivalent of each thereof; or t) a Stiff Man Syndrome-relevant antigen and is derived from GAD or a fragment or an equivalent thereof;

In some embodiments, the MHC protein of the pMHC complex comprises all or part of a classical MHC class I protein, non-classical MHC class I protein, classical MHC class II protein, non-classical MHC class II protein, MHC dimers (Fc fusions), MHC tetramers, or a polymeric form of a MHC protein, wherein the MHC protein optionally comprises a knob-in-hole based MHC-alpha-Fc/MHC-beta-Fc heterodimer or multimer.

In some embodiments, the MHC protein of the pMHC complex comprises all or part of a polypeptide of the group: HLA DR, HLA DQ, HLA DP, HLA-A, HLA-B, HLA-C, HLA-E, HLA-F, HLA-G, CD1d, or a fragment or an equivalent of each thereof.

In some embodiments, the MHC protein of the pMHC complex comprises all or part of a polypeptide of the group: HLA-DR, HLA-DQ, HLA-DP, or a fragment or an equivalent of each thereof.

In some embodiments, the MHC protein of the pMHC complex comprises all or part of a polypeptide of the group: HLA-DRB1/DRA, HLA-DRB3/DRA, HLA-DRB4/DRA, HLA-DRB5/DRA, HLA-DQA1/HLA-DQB1, HLA-DPB1/HLA-DPA1, or a fragment or an equivalent of each thereof.

In certain aspects, the pMHC complex comprises:

a) a diabetes-relevant antigen derived from an antigen selected from one or more of the group: $hInsB_{10-18}$, $hIGRP_{228-236}$, $hIGRP_{265-273}$, $IGRP_{206-214}$, $hIGRP_{206-214}$, NRP-A7, NRP-I4, NRP-V7, $YAI/D^b$, $INS\ B_{15-23}$, $PPI_{76-90\ (K88S)}$, $IGRP_{13-25}$, $GAD_{555-567}$, $GAD_{555-567(557I)}$, $IGRP_{23-35}$, $B_{24}\text{-}C_{36}$, $PPI_{76-90}$, INS-I9, TUM, G6Pase, Pro-insulin$_{L2-10}$, Pro-insulin$_{L3-11}$, Pro-insulin$_{L6-14}$, Pro-insulin$_{B5-14}$, Pro-insulin$_{B10-18}$, Pro-insulin$_{B14-22}$, Pro-insulin$_{B15-24}$, Pro-insulin$_{B17-25}$, Pro-insulin$_{B18-27}$, Pro-insulin$_{B20-27}$, Pro-insulin$_{B21-29}$, Pro-insulin$_{B25-C1}$, Pro-insulin$_{B27-C5}$, Pro-insulin$_{C20-28}$, Pro-insulin$_{C25-33}$, Pro-insulin$_{C29-A5}$, Pro-insulin$_{41-10}$, Pro-insulin$_{42-10}$, Pro-insulin$_{412-20}$, or a fragment or an equivalent of each thereof;

b) a multiple sclerosis-relevant antigen derived from an antigen selected from one or more of the group: $MOG_{35-55}$, $MOG_{36-55}$, $MAG_{287-295}$, $MAG_{509-517}$, $MAG_{556-564}$, $MBP_{110-118}$, $MOG_{114422}$, $MOG_{166-175}$, $MOG_{172-180}$, $MOG_{179-188}$, $MOG_{188-196}$, $MOG_{181-189}$, $MOG_{205-214}$, $PLP_{80-88}$, $MAG_{287-295}$, $MAG_{509-517}$, $MAG_{556-564}$, $MOG_{97-109}$, $MOG_{97-109(E107S)}$, $MBP_{89-101}$, $PLP_{175-192}$, $PLP_{94-108}$, $MBP_{86-98}$, $PLP_{54-68}$, $PLP_{249-263}$, $MOG_{156-170}$, $MOG_{201-215}$, $MOG_{38-52}$, $MOG_{203-217}$, $PLP_{250-264}$, $MPB_{13-32}$, $MPB_{83-99}$, $MPB_{111-129}$, $MPB_{146-170}$, $MOG_{223-237}$, $MOG_{6-20}$, $PLP_{88-102}$, $PLP_{136-154}$, or a fragment or an equivalent of each thereof;

c) a Celiac Disease-relevant antigen derived from an antigen selected from one or more of the group: $aGlia_{57-68}$, $aGlia_{62-72}$, $aGlia_{217-229}$, or a fragment or an equivalent of each thereof;

d) a primary biliary cirrhosis-relevant antigen derived from an antigen selected from one or more of the group: $PDC\text{-}E2_{122-135}$, $PDC\text{-}E2_{249-262}$, $PDC\text{-}E2_{249-263}$, $PDC\text{-}E2_{629-643}$, $PDC\text{-}E2_{72-86}$, $PDC\text{-}E2_{353-367}$, $PDC\text{-}E2_{422-436}$, $PDC\text{-}E2_{629-643}$, $PDC\text{-}E2_{80-94}$, $PDC\text{-}E2_{353-367}$, $PDC\text{-}E2_{535-549}$, or a fragment or an equivalent of each thereof;

e) a pemphigus folliaceus-relevant antigen and/or pemphigus vulgaris-relevant antigen, each of which is derived from an antigen selected from one or more of the group: $DG1_{216-229}$, $DG3_{97-111}$, $DG3_{251-265}$, $DG3_{441-455}$, $DG3_{351-365}$, $DG3_{453-467}$, $DG3_{540-554}$, $DG3_{280-294}$, $DG3_{326-340}$, $DG3_{367-381}$, $DG3_{13-27}$, $DG3_{323-337}$, $DG3_{438-452}$, $DG1_{48-62}$, $DG1_{206-222}$, $DG1_{363-377}$, $DG1_{3-17}$, $DG1_{192-206}$, $DG1_{326-340}$, $DG1_{145}$, $DG1_{35-49}$, $DG1_{325-339}$, or a fragment or an equivalent of each thereof;

f) a neuromyelitis optica spectrum disorder-relevant antigen derived from an antigen selected from one or more of the group: $AQP4_{129-143}$, $AQP4_{284-298}$, $AQP4_{63-76}$, $AQP4_{129-143}$, $AQP4_{39-53}$, or a fragment or an equivalent of each thereof;

g) an allergic asthma-relevant antigen derived from an antigen selected from one or more of the group: $DERP1_{16-30}$, $DERP1_{171-185}$, $DERP1_{110-124}$, $DERP\text{-}2_{26-40}$, $DERP\text{-}2_{107-121}$, or a fragment or an equivalent of each thereof;

h) an inflammatory bowel disease-relevant antigen derived from an antigen selected from one or more of the group: bacteroides integrase antigen$_{183-197}$, bacteroides integrase antigen$_{146-160}$, bacteroides integrase antigen$_{175-189}$, bacteroides integrase antigen$_{1-15}$, bacteroides integrase antigen$_{183-197}$, bacteroides integrase antigen$_{30-44}$, bacteroides integrase antigen$_{70-84}$, bacteroides integrase antigen$_{337-351}$, bacteroides integrase antigen$_{171-185}$, bacteroides integrase antigen$_{4-18}$, bacteroides integrase antigen$_{256-270}$, Fla-2/Fla-$X_{366-380}$, Fla-2/Fla-$X_{164-178}$, Fla-2/Fla-$X_{261-275}$, Fla-2/Fla-$X_{1-15}$, Fla-2/Fla-$X_{51-65}$, Fla-2/Fla-$X_{260-283}$, Fla-2/Fla-$X_{4-18}$, Fla-2/Fla-$X_{271-285}$, $YIDX_{78-02}$, $YIDX_{93-107}$, $YIDX_{98-112}$, $YIDX_{23-37}$, $YIDX_{78-92}$, $YIDX_{195-209}$, $YIDX_{22-36}$, $YIDX_{80-94}$, $YIDX_{101-115}$, or a fragment or an equivalent of each thereof;

i) a systemic lupus erythematosus-relevant antigen derived from an antigen selected from one or more of the group: $H4_{71-04}$, $H4_{74-88}$, $H4_{76-90}$, $H4_{75-89}$, $H4_{78-92}$, $H4_{80-94}$, $H2B_{10-24}$, $H2B_{16-30}$, $H1'_{22-42}$, $H1'_{27-41}$, or a fragment or an equivalent of each thereof;

j) an atherosclerosis-relevant antigen derived from an antigen selected from one or more of the group: $ApoB_{3501-3516}$, $ApoB_{1952-1966}$, $ApoB_{978-993}$, $ApoB_{3498-3513}$, $ApoB_{210A}$, $ApoB_{210B}$, $ApoB_{210C}$, or a fragment or an equivalent of each thereof;

k) a COPD-relvant antigen and/or emphysema-relevant antigen, each of which is derived from an antigen selected from one or more of the group: $elastin_{89-103}$, $elastin_{698-712}$, $elastin_{8-22}$, $elastin_{94-108}$, $elastin_{13-27}$, $elastin_{695-709}$, $elastin_{563-577}$, $elastin_{558-572}$, $elastin_{698-712}$, $elastin_{566-580}$, $elastin_{645-659}$, or a fragment or an equivalent of each thereof;

l) a psoriasis-relevant antigen derived from an antigen selected from one or more of the group: $Cap18_{64-78}$, $Cap18_{34-48}$, $Cap18_{47-61}$, $Cap18_{151-165}$, $Cap18_{149-163}$, $Cap18_{152-166}$, $Cap18_{131-145}$, $Cap18_{24-38}$, $ADMTSL5_{245-259}$, $ADMTSL5_{267-281}$, $ADMTSL5_{372-386}$, $ADMTSL5_{289-303}$, $ADMTSL5_{396-410}$, $ADMTSL5_{433-447}$, $ADMTSL5_{142-156}$, $ADMTSL5_{236-250}$, $ADMTSL5_{301-315}$, $ADMTSL5_{203-217}$, $ADMTSL5_{404-418}$, or a fragment or an equivalent of each thereof;

m) an autoimmune hepatitis-relevant antigen derived from an antigen selected from one or more of the group: $(CYP2D6)_{193-207}$, $CYP2D6_{76-90}$, $CYP2D6_{293-307}$, $CYP2D6_{313-332}$, $CYP2D6_{393-412}$, $CYP2D6_{100-213}$, $CYP2D6_{450-464}$, $CYP2D6_{301-315}$, $CYP2D6_{452-466}$, $CYP2D6_{59-73}$, $CYP2D6_{130-144}$, $CYP2D6_{193-212}$, $CYP2D6_{305-324}$, $CYP2D6_{131-145}$, $CYP2D6_{216-230}$, $CYP2D6_{238-252}$, $CYP2D6_{199-213}$, $CYP2D6_{235-252}$, $CYP2D6_{293-307}$, $CYP2D6_{381-395}$, $CYP2D6_{429-443}$, $SLA_{334-348}$, $SLA_{196-210}$, $SLA_{115-129}$, $SLA_{373-386}$, $SLA_{186-197}$, $SLA_{317-331}$, $SLA_{171-185}$, $SLA_{417-431}$, $SLA_{359-373}$, $SLA_{215-229}$, $SLA_{111-125}$, $SLA_{110-124}$, $SLA_{200-313}$, $SLA_{342-356}$, $SLA_{49-63}$, $SLA_{119-133}$, $SLA_{260-274}$, $SLA_{26-40}$, $SLA_{86-100}$, $SLA_{331-345}$, or a fragment or an equivalent of each thereof;

n) an uveitis-relevant antigen derived from an antigen selected from one or more of the group: $arrestin_{199-213}$, $arrestin_{77-91}$, $arrestin_{250-264}$, $arrestin_{172-186}$, $arrestin_{354-368}$, $arrestin_{239-253}$, $arrestin_{102-116}$, $arrestin_{59-73}$, $arrestin_{280-294}$, $arrestin_{291-306}$, $arrestin_{195-209}$, $arrestin_{200-214}$, or a fragment or an equivalent of each thereof;

o) a Sjogren's Syndrome-relevant antigen derived from an antigen selected from one or more of the group: $OR60_{127-141}$, $RO60_{523-537}$, $RO60_{243-257}$, $RO60_{484-498}$, $RO60_{347-361}$, $RO60_{369-383}$, $RO60_{426-440}$, $RO60_{267-281}$, $RO60_{178-192}$, $RO60_{358-372}$, $RO60_{221-235}$, $RO60_{318-332}$, $RO60_{407421}$, $RO60_{459473}$, $RO60_{51-65}$, $RO60_{312-326}$, $LA_{241-255}$, $LA_{101-115}$, $LA_{153-167}$, $LA_{178-192}$, $LA_{19-33}$, $LA_{37-51}$, $LA_{133-147}$, $LA_{50-64}$, $LA_{32-46}$, $LA_{153-167}$, $LA_{83-97}$, $LA_{136-150}$, $LA_{297-311}$, $LA_{59-73}$, $LA_{151-165}$, $LA_{86-100}$, $LA_{154-168}$, or a fragment or an equivalent of each thereof;

p) a scleroderma-relevant antigen derived from an antigen selected from one or more of the group: $TOP1_{346-360}$, $TOP1_{420-434}$, $TOP1_{750-764}$, $TOP1_{419-433}$, $TOP1_{591-605}$, $TOP1_{695-709}$, $TOP1_{305-319}$, $TOP1_{346-360}$, $TOP1_{419-433}$, $TOP1_{425-439}$, $TOP1_{614-628}$, $CENP\text{-}C_{297-311}$, $CENP\text{-}C_{857\text{-}}$ 871, $CENP-C_{887-901}$, $CENP-C_{212-226}$, $CENP-C_{643-657}$, $CENP-C_{832-846}$, $CENP-C_{167-181}$, $CENP-C_{246-260}$, $CENP-C_{846-860}$, $CENP-C_{149-163}$, $CENP-C_{833-847}$, $CENP-C_{847-861}$, or a fragment or an equivalent of each thereof;

q) an anti-phospholipid syndrome-relevant antigen derived from an antigen selected from one or more of the group: $APOH_{235-249}$, $APOH_{306-320}$, $APOH_{237-251}$, $APOH_{295-309}$, $APOH_{28-42}$, $APOH_{173-187}$, $APOH_{264-278}$, $APOH_{295-309}$, $APOH_{49-63}$, $APOH_{269-283}$, $APOH_{295-309}$, $APOH_{321-355}$, $APOH_{322-336}$, $APOH_{324-338}$, or a fragment or an equivalent of each thereof;

r) an ANCA-associated vasculitis-relevant antigen derived from an antigen selected from one or more of the group: $MPO_{506-520}$, $MPO_{302-316}$, $MPO_{7-21}$, $MPO_{689-703}$, $MPO_{248-262}$, $MPO_{444-458}$, $MPO_{513-527}$, $MPO_{97-111}$, $MPO_{616-630}$, $MPO_{462-476}$, $MPO_{617-631}$, $MPO_{714-728}$, $PRTN3_{44-58}$, $PRTN3_{234-248}$, $PRTN3_{59-73}$, $PRTN3_{117-131}$, $PRTN3_{164-178}$, $PRTN3_{71-85}$, $PRTN3_{241-255}$, $PRTN3_{59-73}$, $PRTN3_{183-197}$, $PRTN3_{62-76}$, $PRTN3_{118-132}$, $PRTN3_{239-253}$, or a fragment or an equivalent of each thereof or s) a Stiff Man Syndrome-relevant antigen derived from an antigen selected from one or more of the group: $GAD_{212-226}$, $GAD_{555-569}$, $GAD_{297-311}$, or a fragment or an equivalent of each thereof.

In certain aspects, the pMHC complex comprises:

a) a diabetes-relevant antigen derived from an antigen selected from one or more of the group: $hInsB_{10-18}$, $hIGRP_{228-236}$, $hIGRP_{265-273}$, $IGRP_{206-214}$, $hIGRP_{206-214}$, NRP-A7, NRP-I4, NRP-V7, $YAI/D^b$, $INS\ B_{15-23}$, $PPI_{76-90\ (K88S)}$, $IGRP_{13-25}$, $GAD_{555-567}$, $GAD_{555-567(557I)}$, $IGRP_{23-35}$, $B_{24}$-$C_{36}$, $PPI_{76-90}$, INS-I9, TUM, G6Pase, Pro-insulin$_{L2-10}$, Pro-insulin$_{L3-11}$, Pro-insulin$_{L6-14}$, Pro-insulin$_{B5-14}$, Pro-insulin$_{B10-18}$, Pro-insulin$_{B14-22}$, Pro-insulin$_{B15-24}$, Pro-insulin$_{B17-25}$, Pro-insulin$_{B18-27}$, Pro-insulin$_{B20-27}$, Pro-insulin$_{B21-29}$, Pro-insulin$_{B25-C1}$, Pro-insulin$_{B27-C5}$, Pro-insulin$_{C20-28}$, Pro-insulin$_{C25-33}$, Pro-insulin$_{C29-A}$5, Pro-insulin$_{41-10}$, Pro-insulin$_{42-10}$, Pro-insulin$_{412-20}$, or a fragment or an equivalent of each thereof, and the MHC protein of the pMHC complex comprises all or part of HLA-DR or a fragment or an equivalent thereof;

b) a multiple sclerosis-relevant antigen derived from an antigen selected from one or more of the group: $MOG_{35-55}$, $MOG_{36-55}$, $MAG_{287-295}$, $MAG_{509-517}$, $MAG_{556-564}$, $MBP_{110-118}$, $MOG_{114-122}$, $MOG_{166-175}$, $MOG_{172-180}$, $MOG_{179-188}$, $MOG_{188-196}$, $MOG_{181-189}$, $MOG_{205-214}$, $PLP_{80-88}$, $MAG_{287-295}$, $MAG_{509-517}$, $MAG_{556-564}$, $MOG_{97-109}$ $MOG_{97-109(E107S)}$, $MBP_{89-101}$, $PLP_{175-192}$, $PLP_{94-108}$, $MBP_{86-98}$, $PLP_{54-68}$, $PLP_{249-263}$, $MOG_{156-170}$, $MOG_{201-215}$, $MOG_{38-52}$, $MOG_{203-217}$, $PLP_{250-264}$, $MPB_{13-32}$, $MPB_{83-99}$, $MPB_{111-129}$, $MPB_{146-170}$, $MOG_{223-237}$, $MOG_{6-20}$, $PLP_{88-102}$, $PLP_{139-154}$, or a fragment or an equivalent of each thereof, and the MHC protein of the pMHC complex comprises all or part of HLA-DR or a fragment or an equivalent thereof;

c) a Celiac Disease-relevant antigen derived from an antigen selected from one or more of the group: $aGlia_{57-68}$, $aGlia_{62-72}$, $aGlia_{217-229}$, or a fragment or an equivalent of each thereof, and the MHC protein of the pMHC complex comprises all or part of HLA-DQ or a fragment or an equivalent thereof;

d) a primary biliary cirrhosis-relevant antigen derived from an antigen selected from one or more of the group: $PDC-E2_{122-135}$, $PDC-E2_{249-262}$, $PDC-E2_{249-263}$, $PDC-E2_{629-643}$, $PDC-E2_{72-86}$, $PDC-E2_{353-367}$, $PDC-E2_{422-436}$, $PDC-E2_{629-643}$, $PDC-E2_{80-94}$, $PDC-E2_{353-367}$, $PDC-E2_{535-546}$, or a fragment or an equivalent of each thereof, and the MHC protein of the pMHC complex comprises all or part of HLA-DR or a fragment of an equivalent thereof;

e) a pemphigus folliaceus-relevant antigen and/or pemphigus vulgaris-relevant antigen, each of which is derived from an antigen selected from one or more of the group: $DG1_{216-229}$, $DG3_{97-111}$, $DG3_{251-265}$, $DG3_{441-455}$, $DG3_{351-365}$, $DG3_{453-467}$, $DG3_{540-554}$, $DG3_{280-294}$, $DG3_{326-340}$, $DG3_{367-381}$, $DG3_{13-27}$, $DG3_{323-337}$, $DG3_{438-452}$, $DG1_{48-62}$, $DG1_{206-222}$, $DG1_{363-377}$, $DG1_{3-17}$, $DG1_{192-206}$, $DG1_{326-340}$, $DG1_{1-15}$, $DG1_{35-49}$, $DG1_{325-336}$, or a fragment or an equivalent of each thereof, and the MHC protein of the pMHC complex comprises all or part of HLA-DR or a fragment or an equivalent thereof;

f) a neuromyelitis optica spectrum disorder-relevant antigen derived from an antigen selected from one or more of the group: $AQP4_{129-143}$, $AQP4_{284-298}$, $AQP4_{63-76}$, $AOP4_{129-143}$, $AQP4_{39-53}$, or a fragment or an equivalent of each thereof, and the MHC protein of the pMHC complex comprises all or part of HLA-DR or a fragment or an equivalent thereof;

g) an allergic asthma-relevant antigen derived from an antigen selected from one or more of the group: $DERP1_{16-30}$, $DERP1_{171-185}$, $DERP1_{110-124}$, $DERP-2_{26-40}$, $DERP-2_{107-121}$, or a fragment or an equivalent of each thereof, and the MHC protein of the pMHC complex comprises all or part of a polypeptide of the group: HLA-DR, HLA-DP, or a fragment or an equivalent of each thereof;

h) an inflammatory bowel disease-relevant antigen derived from an antigen selected from one or more of the group: bacteroides integrase antigen$_{183-197}$, bacteroides integrase antigen$_{146-160}$, bacteroides integrase antigen$_{175-180}$, bacteroides integrase antigen$_{1-15}$, bacteroides integrase antigen$_{183-197}$, bacteroides integrase antigen$_{30-44}$, bacteroides integrase antigen$_{70-84}$, bacteroides integrase antigen$_{337-351}$, bacteroides integrase antigen$_{171-185}$, bacteroides integrase antigen$_{4-18}$, bacteroides integrase antigen$_{256-270}$, $Fla-2/Fla-X_{366-380}$, $Fla-2/Fla-X_{164-178}$, $Fla-2/Fla-X_{261-275}$, $Fla-2/Fla-X_{1-15}$, $Fla-2/Fla-X_{51-65}$, $Fla-2/Fla-X_{269-283}$, $Fla-2/Fla-X_{4-18}$, $Fla-2/Fla-X_{271-285}$, $YIDX_{78-92}$, $YIDX_{93-107}$, $YIDX_{98-112}$, $YIDX_{23-37}$, $YIDX_{78-92}$, $YIDX_{195-209}$, $YIDX_{22-36}$, $YIDX_{80-94}$, $YIDX_{101-115}$, or a fragment or an equivalent of each thereof, and the MHC protein of the pMHC complex comprises all or part of HLA-DR or a fragment or an equivalent thereof;

i) a systemic lupus erythematosus-relevant antigen derived from an antigen selected from one or more of the group: $H4_{71-94}$, $H4_{74-88}$, $H4_{76-90}$, $H4_{75-89}$, $H4_{78-92}$, $H4_{80-94}$, $H2B_{10-24}$, $H2B_{16-30}$, $H1'_{22-42}$, $H1'_{27-41}$, or a fragment or an equivalent of each thereof, and the MHC protein of the pMHC complex comprises all or part of a polypeptide of the group: I-$A_d$, HLA-DR, or a fragment or an equivalent of each thereof;

j) an atherosclerosis-relevant antigen derived from an antigen selected from one or more of the group: $ApoB_{3501-3516}$, $ApoB_{1952-1966}$, $ApoB_{978-993}$, $ApoB_{3498-3513}$, $ApoB_{210A}$, $ApoB_{210B}$, $ApoB_{210C}$, or a fragment or an equivalent of each thereof, and the MHC protein of the pMHC complex comprises all or part of I-$A_b$ or a fragment or an equivalent thereof;

k) a COPD-relvant antigen and/or emphysema-relevant antigen, each of which is derived from an antigen selected from one or more of the group: $elastin_{89-103}$, $elastin_{698-712}$, $elastin_{8-22}$, $elastin_{94-108}$, $elastin_{13-27}$, $elastin_{695-709}$, $elastin_{563-577}$, $elastin_{558-572}$, $elastin_{698-712}$, $elastin_{566-580}$, $elastin_{645-659}$, or a fragment or an equivalent of each thereof, and the MHC protein of the pMHC complex comprises all or part of HLA-DR or a fragment or an equivalent thereof;

l) a psoriasis-relevant antigen derived from an antigen selected from one or more of the group: $Cap18_{64-78}$, $Cap18_{34-48}$, $CaP18_{47-61}$, $Cap18_{151-165}$, $Cap18_{149-163}$, $Cap18_{152-166}$, $Cap18_{131-145}$, $Cap18_{24-38}$, $ADMTSL5245_{-259}$, $ADMTSL5_{267-281}$, $ADMTSL5_{372-386}$, $ADMTSL5_{289-303}$, $ADMTSL5_{396-410}$, $ADMTSL5_{433-447}$, $ADMTSL5_{142-156}$, $ADMTSL5_{236-250}$, $ADMTSL5_{301-315}$, $ADMTSL5_{203-217}$, $ADMTSL5_{404-418}$, or a fragment or an equivalent of each thereof, and the MHC protein of the pMHC complex comprises all or part of HLA-DR or a fragment or an equivalent thereof;

m) an autoimmune hepatitis-relevant antigen derived from an antigen selected from one or more of the group: $CYP2D6_{193-207}$, $CYP2D6_{76-90}$, $CYP2D6_{293-307}$, $CYP2D6_{313-332}$, $CYP2D6_{393-412}$, $CYP2D6_{199-213}$, $CYP2D6_{450-464}$, $CYP2D6_{301-315}$, $CYP2D6_{452-466}$, $CYP2D6_{59-73}$, $CYP2D6_{130-144}$, $CYP2D6_{193-212}$, $CYP2D6_{305-324}$, $CYP2D6_{131-145}$, $CYP2D6_{216-230}$, $CYP2D6_{238-252}$, $CYP2D6_{199-213}$, $CYP2D6_{235-252}$, $CYP2D6_{293-307}$, $CYP2D6_{381-395}$, $CYP2D6_{429-443}$, $SLA_{334-348}$, $SLA_{196-210}$, $SLA_{115-129}$, $SLA_{373-386}$, $SLA_{186-197}$, $SLA_{317-331}$, $SLA_{171-185}$, $SLA_{417-431}$, $SLA_{359-373}$, $SLA_{215-229}$, $SLA_{111-125}$, $SLA_{110-124}$, $SLA_{299-313}$, $SLA_{342-356}$, $SLA_{49-63}$, $SLA_{119-133}$, $SLA_{260-274}$, $SLA_{26-40}$, $SLA_{86-100}$, $SLA_{331-345}$, or a fragment or an equivalent of each thereof, and the MHC protein of the pMHC complex comprises all or part of HLA-DR or a fragment or an equivalent thereof;

n) an uveitis-relevant antigen derived from an antigen selected from one or more of the group: $arrestin_{199-213}$, $arrestin_{77-91}$, $arrestin_{250-264}$, $arrestin_{172-186}$, $arrestin_{354-368}$, $arrestin_{239-253}$, $arrestin_{102-116}$, $arrestin_{59-73}$, $arrestin_{280-294}$, $arrestin_{291-306}$, $arrestin_{195-209}$, $arrestin_{200-214}$, or a fragment or an equivalent of each thereof, and the MHC protein of the pMHC complex comprises all or part of HLA-DR or a fragment or an equivalent thereof;

o) a Sjogren's Syndrome-relevant antigen derived from an antigen selected from one or more of the group: $RO60_{127-141}$, $RO60_{523-537}$, $RO60_{243-257}$, $RO60_{484-498}$, $RO60_{347-361}$, $RO60_{369-383}$, $RO60_{426-440}$, $RO60_{267-281}$, $RO60_{178-192}$, $RO60_{358-372}$, $RO60_{221-235}$, $RO60_{318-332}$, $RO60_{407-421}$, $RO60_{459-473}$, $RO60_{51-65}$, $RO60_{312-326}$, $LA_{241-255}$, $LA_{101-115}$, $LA_{153-167}$, $LA_{178-192}$, $LA_{19-33}$, $LA_{37-51}$, $LA_{133-147}$, $LA_{50-64}$, $LA_{32-46}$, $LA_{153-167}$, $LA_{83-97}$, $LA_{136-150}$, $LA_{297-311}$, $LA_{59-73}$, $LA_{151-165}$, $LA_{86-100}$, $LA_{154-168}$, or a fragment or an equivalent of each thereof, and the MHC protein of the pMHC complex comprises all or part of a polypeptide of the group: HLA-DR, HLA-DP, or a fragment or an equivalent of each thereof;

p) a scleroderma-relevant antigen derived from an antigen selected from one or more of the group: $TOP1_{346-360}$, $TOP1_{420-434}$, $TOP1_{750-764}$, $TOP1_{419-433}$, $TOP1_{591-605}$, $TOP1_{695-709}$, $TOP1_{305-319}$, $TOP1_{346-360}$, $TOP1_{419-433}$, $TOP1_{425-439}$, $TOP1_{614-628}$, $CENP-C_{297-311}$, $CENP-C_{857-871}$, $CENP-C_{887-901}$, $CENP-C_{212-226}$, $CENP-C_{643-657}$, $CENP-C_{832-846}$, $CENP-C_{167-181}$, $CENP-C_{246-260}$, $CENP-C_{846-860}$, $CENP-C_{149-163}$, $CENP-C_{833-847}$, $CENP-C_{847-861}$, or a fragment or an equivalent of each thereof, and the MHC protein of the pMHC complex comprises all or part of HLA-DR or a fragment or an equivalent thereof;

q) an anti-phospholipid syndrome-relevant antigen derived from an antigen selected from one or more of the group: $APOH_{235-249}$, $APOH_{306-320}$, $APOH_{237-251}$, $APOH_{295-309}$, $APOH_{28-42}$, $APOH_{173-187}$, $APOH_{264-278}$, $APOH_{295-309}$, $APOH_{49-63}$, $APOH_{269-283}$, $APOH_{295-309}$, $APOH_{321-355}$, $APOH_{322-336}$, $APOH_{324-338}$, or a fragment or an equivalent of each thereof, and the MHC protein of the pMHC complex comprises all or part of HLA-DR or a fragment or an equivalent thereof;

r) an ANCA-associated vasculitis-relevant antigen derived from an antigen selected from one or more of the group: $MPO_{506-520}$, $MPO_{302-316}$, $MPO_{7-21}$, $MPO_{689-703}$, $MPO_{248-262}$, $MPO_{444-458}$, $MPO_{513-527}$, $MPO_{97-111}$, $MPO_{616-630}$, $MPO_{462-476}$, $MPO_{617-631}$, $MPO_{714-728}$, $PRTN3_{44-58}$, $PRTN3_{234-248}$, $PRTN3_{59-73}$, $PRTN3_{117-131}$, $PRTN3_{164-178}$, $PRTN3_{71-85}$, $PRTN3_{241-255}$, $PRTN3_{59-73}$, $PRTN3_{183-197}$, $PRTN3_{62-76}$, $PRTN3_{118-132}$, $PRTN3_{239-253}$, or a fragment or an equivalent of each thereof, and the MHC protein of the pMHC complex comprises all or part of HLA-DR or a fragment or an equivalent thereof; or s) a Stiff Man Syndrome-relevant antigen derived from an antigen selected from one or more of the group: $GAD_{212-226}$, $GAD_{555-569}$, $GAD_{297-311}$, and the MHC protein of the pMHC complex comprises all or part of a polypeptide of the group: HLA-DR, HLA-DQ, or a fragment or an equivalent of each thereof.

In certain aspects, the pMHC complex is for the treatment of:

a) type I diabetes and the pMHC complex is selected from the group of: $PPI_{76-90(K88S)}$-HLA-DRB1*0401/DRA, $IGRP_{13-25}$-HLA-DRB1*0301/DRA, $GAD_{555-567}$-HLA-DRB1*0401/DRA, $GAD_{555-567(557I)}$-HLA-DRB1*0401/DRA, $IGRP_{23-35}$-HLA-DRB1*0401/DRA, $B_{24}$-$C_{36}$-HLA-DRB1*0301/DRA, or $PPI_{76-90}$-HLA-DRB1*0401/DRA;

b) multiple sclerosis and the pMHC complex is selected from the group of: $MBP_{86-98}$-HLA-DRB1*1501/DRA, $MBP_{89-101}$-HLA-DRB5*0101/DRA, $MOG_{38-52}$-HLA-DRB4*0101/DRA, $MOG_{97-109(E107S)}$-HLA-DRB1*0401/DRA, $MOG_{203-217}$-HLA-DRB3*0101/DRA, $PLP_{54-68}$-HLA-DRB3*0101/DRA, $PLP_{94-108}$-HLA-DRB1*0301/DRA, $PLP_{250-264}$-HLA-DRB4*0101/DRA, $MPB_{13-32}$-HLA-DRB5*0101/DRA, $MPB_{83-99}$-HLA-DRB5*0101/DRA, $MPB_{111-129}$-HLA-DRB5*0101/DRA, $MPB_{146-170}$-HLA-DRB5*0101/DRA, $MOG_{223-237}$-HLA-DRB3*0202/DRA, $MOG_{6-20}$-HLA-DRB5*0101/DRA, $PLP_{88-102}$-HLA-DRB3*0202/DRA, or $PLP_{139-154}$-HLA-DRB5*0101/DRA;

c) Celiac Disease and the pMHC complex is selected from the group of: $aGlia_{57-68}$-HLA-DQA1*0501/HLA-DQB1*0201, $aGlia_{62-72}$-HLA-DQA1*0501/HLA-DQB1*0201, $aGlia_{217-229}$-HLA-DQA1*0501/HLA-DQB1*0302, or $aGlia_{217-229}$-HLA-DQA1*03/HLA-DQB1*0302;

d) primary biliary cirrhosis and the pMHC complex is selected from the group of: $PDC-E2_{122-135}$-HLA-DRB4*0101/DRA, $PDC-E2_{249-262}$-HLA-DRB4*0101/DRA, $PDC-E2_{249-263}$-HLA-DRB1*0801/DRA, $PDC-E2_{629-643}$-HLA-DRB1*0801/DRA, $PDC-E2_{72-86}$-HLA-DRB3*0202/DRA, $PDC-E2_{353-367}$-HLA-DRB3*0202/DRA, $PDC-E2_{422-436}$-HLA-DRB3*0202/DRA, $PDC-E2_{629-643}$-HLA-DRB4*0101/DRA, $PDC-E2_{80-94}$-HLA-DRB5*0101/DRA, $PDC-E2_{353-367}$-HLA-DRB5*0101/DRA, or $PDC-E2_{535-549}$-HLA-DRB5*0101/DRA, $mPDC-E2_{166-181}$-I-$A_{g7}$, or $mPDC-E2_{82-96}$-I-$A_{g7}$;

e) pemphigus folliaceus and/or pemphigus vulgaris and the pMHC complex is selected from the group of: $DG1_{216-229}$-HLA-DRB1*0101/DRA, $DG1_{216-229}$-HLA-DRB1*0102/DRA, $DG3_{97-111}$-HLA-DRB1*0402/DRA, $DG3_{251-265}$-HLA-DRB1*0402/DRA, $DG3_{251-265}$-HLA-DRB1*0401/DRA, $DG3_{441-455}$-HLA-DRB1*0402/DRA, $DG3_{351-365}$-HLA-DRB3*0202/DRA, $DG3_{453-467}$-HLA-DRB3*0202/DRA, $DG3_{540-554}$-HLA-DRB3*0202/DRA, $DG3_{280-294}$-HLA-DRB4*0101/DRA, $DG3_{326-340}$-HLA-DRB4*0101/DRA, $DG3_{367-381}$-HLA-DRB4*0101/DRA, $DG3_{13-27}$-HLA-DRB5*0101/DRA, $DG3_{323-337}$-HLA- DRB5*0101/DRA, DG3$_{438-452}$-HLA-DRB5*0101/DRA, DG1$_{48-62}$-HLA-DRB3*0202/DRA, DG1$_{206-222}$-HLA-DRB3*0202/DRA, DG1$_{363-377}$-HLA-DRB3*0202/DRA, DG1$_{347}$-HLA-DRB4*0101/DRA, DG1$_{192-206}$-HLA-DRB4*0101/DRA, DG1$_{326-340}$-HLA-DRB4*0101/DRA, DG1$_{1-15}$-HLA-DRB5*0101/DRA, DG1$_{35-49}$-HLA-DRB5*0101/DRA, or DG1$_{325-339}$-HLA-DRB5*0101/DRA;

f) neuromyelitis optica spectrum disorder and the pMHC complex is selected from the group of: AQP4$_{129-443}$-HLA-DRB1*0101/DRA, AQP4$_{284-298}$-HLA-DRB1*0301/DRA, AQP4$_{63-76}$-HLA-DRB1*0301/DRA, AQP4$_{129-143}$-HLA-DRB1*0401/DRA, or AQP4$_{39-53}$-HLA-DRB1*01501/DRA;

g) allergic asthma and the pMHC complex is selected from the group of: DERP-1$_{16-30}$-HLA-DRB1*0101/DRA, DERP-1$_{16-30}$-HLA-DRB1*1501/DRA, DERP1$_{171-185}$-HLA-DRB 1*1501/DRA, DERP-1$_{110-124}$-HLA-DPB1*0401/DRA, DERP-2$_{26-40}$-HLA-DRB1*0101/DRA; DERP-2$_{26-40}$-HLA-DRB1*1501/DRA, or DERP-2$_{107-121}$-HLA-DRB1*0301/DRA;

h) inflammatory bowel disease and the pMHC complex is selected from the group of: bacteroides integrase antigen$_{183-197}$-HLA-DRB3*0101/DRA, bacteroides integrase antigen$_{146-160}$-HLA-DRB3*0101/DRA, bacteroides integrase antigen$_{175-189}$-HLA-DRB3*0101/DRA, bacteroides integrase antigen$_{1-15}$-HLA-DRB5*0101/DRA, bacteroides integrase antigen$_{183-197}$-HLA-DRB5*0101/DRA, bacteroides integrase antigen$_{183-197}$-HLA-DRB3*0101/DRA, bacteroides integrase antigen$_{30-44}$-HLA-DRB5*0101/DRA, bacteroides integrase antigen$_{70-84}$-HLA-DRB4*0101/DRA, bacteroides integrase antigen$_{337-351}$-HLA-DRB4*0101/DRA, bacteroides integrase antigen$_{171-185}$-HLA-DRB4*0101/DRA, bacteroides integrase antigen$_{4-18}$-HLA-DRB3*0202/DRA, bacteroides integrase antigen$_{171-185}$-HLA-DRB3*0202/DRA, bacteroides integrase antigen$_{256-270}$-HLA-DRB3*0202/DRA, Fla-2/Fla-X$_{366-380}$-HLA-DRB3*0101/DRA, Fla-2/Fla-X$_{164-178}$-HLA-DRB3*0101/DRA, Fla-2/Fla-X$_{261-275}$-HLA-DRB5*0101/DRA, Fla-2/Fla-X$_{1-15}$-HLA-DRB5*0101/DRA, Fla-2/Fla-X$_{51-65}$-HLA-DRB4*0101/DRA, Fla-2/Fla-X$_{269-283}$-HLA-DRB4*0101/DRA, Fla-2/Fla-X$_{4-18}$-HLA-DRB3*0202/DRA, Fla-2/Fla-X$_{261-275}$-HLA-DRB3*0202/DRA, Fla-2/Fla-X$_{271-285}$-HLA-DRB3*0202/DRA, YIDX$_{78-92}$-HLA-DRB3*0101/DRA, YIDX$_{78-92}$-HLA-DRB4*0101/DRA, YIDX$_{93-107}$-HLA-DRB3*0101/DRA, YIDX$_{98-112}$-HLA-DRB5*0101/DRA, YIDX$_{23-37}$-HLA-DRB5*0101/DRA, YIDX$_{78-92}$-HLA-DRB4*0101/DRA, YIDX$_{195-209}$-HLA-DRB4*0101/DRA, YIDX$_{22-36}$-HLA-DRB3*0202/DRA, YIDX$_{80-94}$-HLA-DRB3*0202/DRA, or YIDX$_{101-115}$-HLA-DRB3*0202/DRA;

i) COPD and/or emphysema and the pMHC complex is selected from the group of: elastin$_{89-103}$-HLA-DRB3*0101/DRA, elastin$_{698-712}$-HLA-DRB5*0101/DRA, elastin$_{8-22}$-HLA-DRB5*0101/DRA, elastin$_{94-108}$-HLA-DRB5*0101/DRA, elastin$_{13-27}$-HLA-DRB4*0101/DRA, elastin$_{695-709}$-HLA-DRB4*0101/DRA, elastin$_{563-577}$-HLA-DRB4*0101/DRA, elastin$_{558-572}$-HLA-DRB4*0101/DRA, elastin$_{698-712}$-HLA-DRB5*0101/DRA, elastin$_{566-580}$-HLA-DRB3*0202/DRA, or elastin$_{645-659}$-HLA-DRB3*0202/DRA;

j) psoriasis and the pMHC complex is selected from the group of: Cap18$_{64-78}$-HLA-DRB3*0101/DRA, Cap18$_{34-48}$-HLA-DRB3*0101/DRA, Cap18$_{47-61}$-HLA-DRB3*0101/DRA, Cap18$_{151-165}$-HLA-DRB4*0101/DRA, Cap18$_{149-163}$-HLA-DRB5*0101/DRA, Cap18$_{152-166}$-HLA-DRB5*0101/DRA, Cap18$_{131-145}$-HLA-DRB5*0101/DRA, Cap1824-38-HLA-DRB3*0202/DRA, ADMTSL5$_{245-259}$-HLA-DRB3*0101/DRA, ADMTSL5$_{267-281}$-HLA-DRB3*0101/DRA, ADMTSL5$_{372-386}$-HLA-DRB3*0101/DRA, ADMTSL5$_{289-303}$-HLA-DRB4*0101/DRA, ADMTSL5$_{396-410}$-HLA-DRB4*0101/DRA, ADMTSL5$_{433-447}$-HLA-DRB4*0101/DRA, ADMTSL5$_{142-156}$-HLA-DRB5*0101/DRA, ADMTSL5$_{236-250}$-HLA-DRB5*0101/DRA, ADMTSL5$_{301-315}$-HLA-DRB5*0101/DRA, ADMTSL5$_{2o3-217}$-HLA-DRB3*0202/DRA, ADMTSL5$_{404-418}$-HLA-DRB3*0202/DRA, or ADMTSL5$_{433-447}$-HLA-DRB3*0202/DRA;

k) autoimmune hepatitis and the pMHC complex is selected from the group of: CYP2D6$_{193-207}$-HLA-DRB1*0301/DRA, CYP2D6$_{76-90}$-HLA-DRB1*0301/DRA, CYP2D6$_{293-307}$-HLA-DRB1*0301/DRA, CYP2D6$_{313-332}$-HLA-DRB1*0301/DRA, CYP2D6$_{393-412}$-HLA-DRB1*0301/DRA, CYP2D6$_{199-213}$-HLA-DRB1*0401/DRA, CYP2D6$_{450-464}$-HLA-DRB1*0401/DRA, CYP2D6$_{301-315}$-HLA-DRB1*0401/DRA, CYP2D6$_{452-466}$-HLA-DRB1*0701/DRA, CYP2D6$_{59-73}$-HLA-DRB1*0701/DRA, CYP2D6$_{130-144}$-HLA-DRB1*0701/DRA, CYP2D6$_{193-212}$-HLA-DRB1*0701/DRA, CYP2D6$_{305-324}$-HLA-DRB1*0701/DRA, CYP2D6$_{131-145}$-HLA-DRB3*0202/DRA, CYP2D6$_{216-230}$-HLA-DRB3*0202/DRA, CYP2D6$_{238-252}$-HLA-DRB3*0202/DRA, CYP2D6$_{199-213}$-HLA-DRB4*0101/DRA, CYP2D6$_{235-252}$-HLA-DRB4*0101/DRA, CYP2D6$_{293-307}$-HLA-DRB4*0101/DRA, CYP2D6$_{238-252}$-HLA-DRB5*0101/DRA, CYP2D6$_{381-395}$-HLA-DRB5*0101/DRA, CYP2D6$_{429-443}$-HLA-DRB5*0101/DRA, SLA$_{334-348}$-HLA-DRB1*0301/DRA, SLA$_{196-210}$-HLA-DRB1*0301/DRA, SLA$_{115-129}$-HLA-DRB1*0301/DRA, SLA$_{373-386}$-HLA-DRB1*0301/DRA, SLA$_{186-197}$-HLA-DRB1*0301/DRA, SLA$_{317-331}$-HLA-DRB1*0401/DRA, SLA$_{171-185}$-HLA-DRB1*0401/DRA, SLA$_{417-431}$-HLA-DRB1*0401/DRA, SLA$_{359-373}$-HLA-DRB1*0701/DRA, SLA$_{215-229}$-HLA-DRB1*0701/DRA, SLA$_{111-125}$-HLA-DRB1*0701/DRA, SLA$_{110-124}$-HLA-DRB3*0202/DRA, SLA$_{299-313}$-HLA-DRB3*0202/DRA, SLA$_{342-356}$-HLA-DRB3*0202/DRA, SLA$_{49-63}$-HLA-DRB4*0101/DRA, SLA$_{119-133}$-HLA-DRB4*0101/DRA, SLA$_{260-274}$-HLA-DRB4*0101/DRA, SLA$_{26-40}$-HLA-DRB5*0101/DRA, SLA$_{86-100}$-HLA-DRB5*0101/DRA, or SLA$_{331-345}$-HLA-DRB5*0101/DRA;

l) uveitis and the pMHC complex is selected from the group of: arrestin$_{199-213}$-HLA-DRB3*0101/DRA, arrestin$_{77-91}$-HLA-DRB3*0101/DRA, arrestin$_{250-264}$-HLA-DRB3*0101/DRA, arrestin$_{172-186}$-HLA-DRB4*0101/DRA, arrestin$_{354-368}$-HLA-DRB4*0101/DRA, arrestin$_{239-253}$-HLA-DRB4*0101/DRA, arrestin$_{1o2-116}$-HLA-DRB5*0101/DRA, arrestin$_{59-73}$-HLA-DRB5*0101, arrestin$_{280-294}$-HLA-DRB5*0101, arrestin$_{291-306}$-HLA-DRB1*0301/DRA, arrestin$_{195-209}$-HLA-DRB3*0202/DRA, arrestin$_{199-213}$-HLA-DRB3*0202/DRA, or arrestin$_{no-214}$-HLA-DRB3*0202/DRA;

m) Sjogren Syndrome and the pMHC complex is selected from the group of: RO60$_{127-141}$-HLA-DRB1*0301/DRA, RO60$_{523-537}$-HLA-DRB1*0301/DRA, RO60$_{243-257}$-HLA-DRB1*0301/DRA, RO60$_{484-498}$-HLA-DRB3*0101/DRA, RO60$_{347-361}$-HLA-DRB3*0101/DRA, RO60$_{369-383}$-HLA-DRB3*0101/DRA, RO60$_{426-440}$-HLA-DRB4*0101/DRA, RO60$_{267-281}$-HLA-DRB4*0101/DRA, RO60$_{178-192}$-HLA-DRB4*0101/DRA, RO60$_{358-372}$-HLA-DRB5*0101/DRA, RO60$_{358-372}$-HLA-DRB4*0101/DRA, RO60$_{221-235}$-HLA-DRB5*0101/DRA, RO60$_{221-235}$-HLA-DRB4*0101/DRA, RO60$_{318-332}$-HLA-DRB5*0101/DRA, RO60$_{318-332}$-HLA-DRB4*0101/DRA, RO60$_{407-421}$-HLA-DRB4*0101/DRA, RO60$_{407-421}$-HLA-DQA1*0501/HLA-DQB1*0201, RO60$_{459-473}$-HLA-DRB4*0101/DRA, RO60$_{459-473}$-HLA-DQA1*0501/HLA-DQB1*0201, RO60$_{318-332}$-HLA- DQA1*0501/HLA-DQB1*0201, RO60$_{51-65}$-HLA-DRB3*0202/DRA, RO60$_{312-326}$-HLA-DRB3*0202/DRA, RO60$_{347-361}$-HLA-DRB3*0202/DRA, LA$_{241-255}$-HLA-DRB1*0301/DRA, LA$_{101-115}$-HLA-DRB1*0301/DRA, LA$_{153467}$-HLA-DRB1*0301/DRA, LA$_{178-192}$-HLA-DRB3*0101/DRA, LA$_{19-33}$-HLA-DRB3*0101/DRA, LA$_{37-51}$-HLA-DRB3*0101/DRA, LA$_{133-147}$-HLA-DRB4*0101/DRA, LA$_{50-64}$-HLA-DRB4*0101/DRA, LA$_{32-46}$-HLA-DRB4*0101/DRA, LA$_{153-167}$-HLA-DRB5*0101/DRA, LA$_{83-97}$-HLA-DRB5*0101/DRA, LA$_{136-150}$-HLA-DRB5*0101/DRA, LA$_{297-311}$-DQA1*0501/HLA-DQB1*0201, LA$_{59-73}$-DQA1*0501/HLA-DQB1*0201, LA$_{59-73}$-HLA-DRB4*0101/DRA, LA$_{151-165}$-HLA-DQA1*0501/HLA-DQB1*0201, 1-A$_{151-165}$-HLA-DRB4*0101/DRA, LA$_{297-311}$-HLA-DRB4*0101/DRA, LA$_{50-64}$-HLA-DRB3*0202/DRA, LA$_{86-100}$-HLA-DRB3*0202/DRA, or LA$_{154-168}$-HLA-DRB3*0202/DRA;

n) scleroderma and the pMHC complex is selected from the group of: TOP1$_{346-360}$-HLA-DRB3*0101/DRA, TOP1$_{420-434}$-HLA-DRB3*0101/DRA, TOP1$_{750-764}$-HLA-DRB3*0101/DRA, TOP1$_{419-433}$-HLA-DRB4*0101/DRA, TOP1$_{591-605}$-HLA-DRB4*0101/DRA, TOP1$_{695-709}$-HLA-DRB4*0101/DRA, TOP1$_{305-319}$-HLA-DRB5*0101/DRA, TOP1$_{346-360}$-HLA-DRB5*0101/DRA, TOP1$_{419-433}$-HLA-DRB5*0101/DRA, TOP1$_{420-434}$-HLA-DRB3*0202/DRA, TOP1$_{425-439}$-HLA-DRB3*0202/DRA, TOP1$_{614-628}$-HLA-DRB3*0202/DRA, CENP-C$_{297-311}$-HLA-DRB3*0101/DRA, CENP-C$_{857-871}$-HLA-DRB3*0101/DRA, CENP-C$_{887-901}$-HLA-DRB3*0101/DRA, CENP-C$_{212-226}$-HLA-DRB4*0101/DRA, CENP-C$_{643-657}$-HLA-DRB4*0101/DRA, CENP-C$_{832-846}$-HLA-DRB4*0101/DRA, CENP-C$_{167-181}$-HLA-DRB5*0101/DRA, CENP-C$_{246-263}$-HLA-DRB5*0101/DRA, CENP-C$_{846-860}$-HLA-DRB5*0101/DRA, CENP-C$_{149-163}$-HLA-DRB3*0202/DRA, CENP-C$_{833-847}$-HLA-DRB3*0202/DRA, or CENP-C$_{847-861}$-HLA-DRB3*0202/DRA;

o) anti-phospholipid syndrome and the pMHC complex is selected from the group of: APOH$_{235-249}$-HLA-DRB3*0101/DRA, APOH$_{306-320}$-HLA-DRB3*0101/DRA, APOH$_{237-251}$-HLA-DRB3*0101/DRA, APOH$_{295-309}$-HLA-DRB3*0101/DRA, APOH$_{28-42}$-HLA-DRB4*0101/DRA, APOH$_{173-187}$-HLA-DRB4*0101/DRA, APOH$_{264-278}$-HLA-DRB4*0101/DRA, APOH$_{295-309}$-HLA-DRB4*0101/DRA, APOH$_{49-63}$-HLA-DRB5*0101/DRA, APOH$_{269-283}$-HLA-DRB5*0101/DRA, APOH$_{295-309}$-HLA-DRB5*0101/DRA, APOH$_{321-355}$-HLA-DRB3*0202/DRA, APOH$_{322-336}$-HLA-DRB3*0202/DRA, or APOH$_{324-338}$-HLA-DRB3*0202/DRA;

p) ANCA-associated vasculitis and the pMHC complex is selected from the group of: MPO$_{506-520}$-HLA-DRB3*0101/DRA, MPO$_{302-316}$-HLA-DRB3*0101/DRA, MPO$_{7-21}$-HLA-DRB3*0101/DRA, MPO$_{689-703}$-HLA-DRB4*0101/DRA, MPO$_{248-262}$-HLA-DRB4*0101/DRA, MPO$_{444-458}$-HLA-DRB4*0101/DRA, MPO$_{513-527}$-HLA-DRB5*0101/DRA, MPO$_{97-111}$-HLA-DRB5*0101/DRA, MPO$_{616-630}$-HLA-DRB5*0101/DRA, MPO$_{462-476}$-HLA-DRB3*0202/DRA, MPO$_{617-631}$-HLA-DRB3*0202/DRA, MPO$_{714-728}$-HLA-DRB3*0202/DRA, PRTN3$_{44-58}$-HLA-DRB3*0101/DRA, PRTN3$_{234-248}$-HLA-DRB3*0101/DRA, PRTN3$_{59-73}$-HLA DRB3*0101/DRA, PRTN3$_{59-73}$-HLA-DRB5*0101/DRA, PRTN3$_{117-131}$-HLA-DRB4*0101/DRA, PRTN3$_{164-178}$-HLA-DRB4*0101/DRA, PRTN3$_{71-85}$-HLA-DRB4*0101/DRA, PRTN3$_{241-255}$-HLA-DRB5*0101/DRA, PRTN3$_{183-197}$-HLA-DRB5*0101/DRA, PRTN3$_{62-76}$-HLA-DRB3*0202/DRA, PRTN3$_{118-132}$-HLA-DRB3*0202/DRA, or PRTN3$_{239-253}$-HLA-DRB3*0202/DRA; or q) Stiff Man Syndrome and the pMHC complex is selected from the group of: GAD$_{212-226}$-HLA-DRB1*0801/DRA, GAD$_{555-569}$-HLA-DRB1*0801/DRA, or GAD$_{297-311}$-HLA-DRB1*0301/DRA.

In some aspects, the pMHC complex is for the treatment of:

a) type I diabetes and the pMHC complex is selected from the group of: PPI$_{76-90(K88S)}$-HLA-DRB1*0401/DRA, IGRP$_{13-25}$-HLA-DRB1*0301/DRA, GAD$_{555-567}$-HLA-DRB1*0401/DRA, GAD$_{555-567(557I)}$-HLA-DRB1*0401/DRA, IGRP$_{23-35}$-HLA-DRB1*0401/DRA, or PPI$_{76-90}$-HLA-DRB1*0401/DRA;

b) multiple sclerosis and the pMHC complex is selected from the group of: MBP$_{86-98}$-HLA-DRB1*1501/DRA, MBP$_{89-101}$-HLA-DRB5*0101/DRA, MOG$_{38-52}$-HLA-DRB4*0101/DRA, MOG$_{97-109(E107S)}$-HLA-DRB1*0401/DRA, MOG$_{203-217}$-HLA-DRB3*0101/DRA, PLP$_{54-68}$-HLA-DRB3*0101/DRA, PLP$_{94-108}$-HLA-DRB1*0301/DRA, PLP$_{250-264}$-HLA-DRB4*0101/DRA, MPB$_{13-32}$-HLA-DRB5*0101/DRA, MPB$_{83-99}$-HLA-DRB5*0101/DRA, MPB$_{111-129}$-HLA-DRB5*0101/DRA, MPB$_{146-170}$-HLA-DRB5*0101/DRA, MOG$_{223-237}$-HLA-DRB3*0202/DRA, MOG$_{6-20}$-HLA-DRB5*0101/DRA, PLP$_{88-102}$-HLA-DRB3*0202/DRA, or PLP$_{139-154}$-HLA-DRB5*0101/DRA;

c) Celiac Disease and the pMHC complex is selected from the group of: aGlia$_{57-68}$-HLA-DQA1*0501/HLA-DQB1*0201, aGlia$_{62-72}$-HLA-DQA1*0501/HLA-DQB1*0201, or aGlia$_{217-229}$-HLA-DQA1*0501/HLA-DQB1*0302;

d) primary biliary cirrhosis and the pMHC complex is selected from the group of: PDC-E2$_{122-135}$-HLA-DRB4*0101/DRA, PDC-E2$_{249-262}$-HLA-DRB4*0101/DRA, PDC-E2$_{249-263}$-HLA-DRB1*0801/DRA, PDC-E2$_{629-643}$-HLA-DRB1*0801/DRA, PDC-E2$_{72-86}$-HLA-DRB3*0202/DRA, PDC-E2$_{353-367}$-HLA-DRB3*0202/DRA, PDC-E2$_{422-436}$-HLA-DRB3*0202/DRA, PDC-E2$_{629-643}$-HLA-DRB4*0101/DRA, PDC-E2$_{80-94}$-HLA-DRB5*0101/DRA, PDC-E2$_{353-367}$-HLA-DRB5*0101/DRA, or PDC-E2$_{535-549}$-HLA-DRB5*0101/DRA;

e) pemphigus folliaceus and/or pemphigus vulgaris and the pMHC complex is selected from the group of: DG1$_{216-229}$-HLA-DRB1*0101/DRA, DG3$_{97-111}$-HLA-DRB1*0402/DRA, DG3$_{251-265}$-HLA-DRB1*0401/DRA, DG3$_{441-455}$-HLA-DRB1*0402/DRA, DG3$_{351-365}$-HLA-DRB3*0202/DRA, DG3$_{453-467}$-HLA-DRB3*0202/DRA, DG3$_{540-554}$-HLA-DRB3*0202/DRA, DG3$_{280-294}$-HLA-DRB4*0101/DRA, DG3$_{326-340}$-HLA-DRB4*0101/DRA, DG3$_{367-381}$-HLA-DRB4*0101/DRA, DG3$_{13-27}$-HLA-DRB5*0101/DRA, DG3$_{323-337}$-HLA-DRB5*0101/DRA, DG3$_{438-452}$-HLA-DRB5*0101/DRA, DG1$_{48-62}$-HLA-DRB3*0202/DRA, DG1$_{206-222}$-HLA-DRB3*0202/DRA, DG1$_{363-377}$-HLA-DRB3*0202/DRA, DG1$_{3-17}$-HLA-DRB4*010/DRA, DG1$_{192-206}$-HLA-DRB4*0101/DRA, DG1$_{326-340}$-HLA-DRB4*0101/DRA, DG1$_{1-15}$-HLA-DRB5*0101/DRA, DG1$_{35-49}$-HLA-DRB5*0101/DRA, or DG1$_{325-339}$-HLA-DRB5*0101/DRA;

f) neuromyelitis optica spectrum disorder and the pMHC complex is selected from the group of: AQP4$_{284-298}$-HLA-DRB1*0301/DRA, AQP4$_{63-76}$-HLA-DRB1*0301/DRA, AQP4$_{129-143}$-HLA-DRB1*0401/DRA, or AQP4$_{39-53}$-HLA-DRB1*1501/DRA;

g) allergic asthma and the pMHC complex is selected from the group of: DERP-1$_{16}$-30-HLA-DRB1*0101/DRA, DERP-1$_{16-30}$-HLA-DRB1*1501/DRA, DERP$_{1171-185}$-HLA-DRB 1*1501/DRA, DERP-1$_{110-124}$-HLA- DPB1*0401/DRA, DERP-2$_{26-40}$-HLA-DRB1*0101/DRA; DERP-2$_{26-40}$-HLA-DRB1*1501/DRA, or DERP-2$_{107-121}$-HLA-DRB1*0301/DRA;

h) inflammatory bowel disease and the pMHC complex is selected from the group of: bacteroides integrase antigen$_{1-15}$-HLA-DRB5*0101/DRA, bacteroides integrase antigen$_{183-197}$-HLA-DRB3*0101/DRA, bacteroides integrase antigen$_{70-84}$-HLA-DRB4*0101/DRA, bacteroides integrase antigen$_{4-18}$-HLA-DRB3*0202/DRA, bacteroides integrase antigen$_{171-185}$-HLA-DRB3*0202/DRA, bacteroides integrase antigen$_{256-270}$-HLA-DRB3*0202/DRA, Fla-2/Fla-X$_{366-380}$-HLA-DRB3*0101/DRA, Fla-2/Fla-X$_{261-275}$-HLA-DRB5*0101/DRA, Fla-2/Fla-X$_{51-65}$-HLA-DRB4*0101/DRA, Fla-2/Fla-X$_{4-18}$-HLA-DRB3*0202/DRA, Fla-2/Fla-X$_{261-275}$-HLA-DRB3*0202/DRA, Fla-2/Fla-X$_{271-285}$-HLA-DRB3*0202/DRA, YIDX$_{78-92}$-HLA-DRB3*0101/DRA, YIDX$_{78-92}$-HLA-DRB4*0101/DRA, YIDX$_{98-112}$-HLA-DRB5*0101/DRA, YIDX$_{22-36}$-HLA-DRB3*0202/DRA, YIDX$_{80-94}$-HLA-DRB3*0202/DRA, or YIDX$_{1o1-115}$-HLA-DRB3*0202/DRA;

i) emphysema and the pMHC complex is selected from the group of: elastin$_{89-103}$-HLA-DRB3*0101/DRA, elastin$_{698-712}$-HLA-DRB5*0101/DRA, elastin$_{558-572}$-HLA-DRB4*0101/DRA, elastin$_{566-580}$-HLA-DRB3*0202/DRA, or elastin$_{645-659}$-HLA-DRB3*0202/DRA;

j) psoriasis and the pMHC complex is selected from the group of: Cap18$_{64-78}$-HLA-DRB3*0101/DRA, Cap18$_{34-48}$-HLA-DRB3*0101/DRA, Cap18$_{47-61}$-HLA-DRB3*0101/DRA, Cap18$_{151-165}$-HLA-DRB4*0101/DRA, Cap18$_{149-163}$-HLA-DRB5*0101/DRA, Cap18$_{152-166}$-HLA-DRB5*0101/DRA, Cap18$_{131-145}$-HLA-DRB5*0101/DRA, Cap18$_{24-38}$-HLA-DRB3*0202/DRA, ADMTSL5$_{245-259}$-HLA-DRB3*0101/DRA, ADMTSL5$_{267-281}$-HLA-DRB3*0101/DRA, ADMTSL5$_{372-386}$-HLA-DRB3*0101/DRA, ADMTSL5$_{289-303}$-HLA-DRB4*0101/DRA, ADMTSL5$_{396-410}$-HLA-DRB4*0101/DRA, ADMTSL5$_{433-447}$-HLA-DRB4*0101/DRA, ADMTSL5$_{142-156}$-HLA-DRB5*0101/DRA, ADMTSL5$_{236-250}$-HLA-DRB5*0101/DRA, ADMTSL5$_{301-315}$-HLA-DRB5*0101/DRA, ADMTSL5$_{2o3-217}$-HLA-DRB3*0202/DRA, ADMTSL5$_{4o4-418}$-HLA-DRB3*0202/DRA, or ADMTSL5$_{433-447}$-HLA-DRB3*0202/DRA;

k) autoimmune hepatitis and the pMHC complex is selected from the group of: CYP2D6$_{193-207}$-HLA-DRB1*0301/DRA, CYP2D6$_{76-90}$-HLA-DRB1*0301/DRA, CYP2D6$_{293-307}$-HLA-DRB1*0301/DRA, CYP2D6$_{313-332}$-HLA-DRB1*0301/DRA, CYP2D6$_{393-412}$-HLA-DRB1*0301/DRA, CYP2D6$_{199-213}$-HLA-DRB1*0401/DRA, CYP2D6$_{450-464}$-HLA-DRB1*0401/DRA, CYP2D6$_{301-315}$-HLA-DRB1*0401/DRA, CYP2D6$_{452-466}$-HLA-DRB1*0701/DRA, CYP2D6$_{59-73}$-HLA-DRB1*0701/DRA, CYP2D6$_{130-144}$-HLA-DRB1*0701/DRA, CYP2D6$_{193-212}$-HLA-DRB1*0701/DRA, CYP2D6$_{305-324}$-HLA-DRB1*0701/DRA, CYP2D6$_{131-145}$-HLA-DRB3*0202/DRA, CYP2D6$_{216-230}$-HLA-DRB3*0202/DRA, CYP2D6$_{238-252}$-HLA-DRB3*0202/DRA, CYP2D6$_{199-213}$-HLA-DRB4*0101/DRA, CYP2D6$_{235-252}$-HLA-DRB4*0101/DRA, CYP2D6$_{293-307}$-HLA-DRB4*0101/DRA, CYP2D6$_{238-252}$-HLA-DRB5*0101/DRA, CYP2D6$_{381-395}$-HLA-DRB5*0101/DRA, CYP2D6$_{429-443}$-HLA-DRB5*0101/DRA, SLA$_{334-348}$-HLA-DRB1*0301/DRA, SLA$_{196-210}$-HLA-DRB1*0301/DRA, SLA$_{115-129}$-HLA-DRB1*0301/DRA, SLA$_{373-386}$-HLA-DRB1*0301/DRA, SLA$_{186-197}$-HLA-DRB1*0301/DRA, SLA$_{317-331}$-HLA-DRB1*0401/DRA, SLA$_{171-185}$-HLA-DRB1*0401/DRA, SLA$_{417-431}$-HLA-DRB1*0401/DRA, SLA$_{359-373}$-HLA-DRB1*0701/DRA, SLA$_{215-229}$-HLA-DRB1*0701/DRA, SLA$_{111-125}$-HLA-DRB1*0701/DRA, SLA$_{110-124}$-HLA-DRB3*0202/DRA, SLA$_{299-313}$-HLA-DRB3*0202/DRA, SLA$_{342-356}$-HLA-DRB3*0202/DRA, SLA$_{49-63}$-HLA-DRB4*0101/DRA, SLA$_{119-133}$-HLA-DRB4*0101/DRA, SLA$_{260-274}$-HLA-DRB4*0101/DRA, SLA$_{26-40}$-HLA-DRB5*0101/DRA, SLA$_{86-100}$-HLA-DRB5*0101/DRA, or SLA$_{331-345}$-HLA-DRB5*0101/DRA;

l) uveitis and the pMHC complex is selected from the group of: arrestin$_{199-213}$-HLA-DRB3*0101/DRA, arrestin$_{77-91}$-HLA-DRB3*0101/DRA, arrestin$_{250-264}$-HLA-DRB3*0101/DRA, arrestin$_{172-186}$-HLA-DRB4*0101/DRA, arrestin$_{354-368}$-HLA-DRB4*0101/DRA, arrestin$_{239-253}$-HLA-DRB4*0101/DRA, arrestin$_{102-116}$-HLA-DRB5*0101/DRA, arrestin$_{59-73}$-HLA-DRB5*0101, arrestin$_{280-294}$-HLA-DRB5*0101, arrestin$_{291-306}$-HLA-DRB1*0301/DRA, arrestin$_{195-209}$-HLA-DRB3*0202/DRA, arrestin$_{199-213}$-HLA-DRB3*0202/DRA, or arrestin$_{200-214}$-HLA-DRB3*0202/DRA;

m) Sjogren Syndrome and the pMHC complex is selected from the group of: RO60$_{127-141}$-HLA-DRB1*0301/DRA, RO60$_{523-537}$-HLA-DRB1*0301/DRA, RO60$_{243-257}$-HLA-DRB1*0301/DRA, RO60$_{484-498}$-HLA-DRB3*0101/DRA, RO60$_{347-361}$-HLA-DRB3*0101/DRA, RO60$_{369-383}$-HLA-DRB3*0101/DRA, RO60$_{426-440}$-HLA-DRB4*0101/DRA, RO60$_{267-281}$-HLA-DRB4*0101/DRA, RO60$_{178-192}$-HLA-DRB4*0101/DRA, RO60$_{358-372}$-HLA-DRB5*0101/DRA, RO60$_{221-235}$-HLA-DRB5*0101/DRA, RO60$_{318-332}$-HLA-DRB5*0101/DRA, RO60$_{51-65}$-HLA-DRB3*0202/DRA, RO60$_{312-326}$-HLA-DRB3*0202/DRA, RO60$_{347-361}$-HLA-DRB3*0202/DRA, LA$_{241-255}$-HLA-DRB1*0301/DRA, LA$_{101-115}$-HLA-DRB1*0301/DRA, LA$_{153-167}$-HLA-DRB1*0301/DRA, LA$_{178-192}$-HLA-DRB3*0101/DRA, LA$_{19-33}$-HLA-DRB3*0101/DRA, LA$_{37-51}$-HLA-DRB3*0101/DRA, LA$_{133-447}$-HLA-DRB4*0101/DRA, LA$_{50-64}$-HLA-DRB4*0101/DRA, LA$_{32-46}$-HLA-DRB4*0101/DRA, LA$_{153-167}$-HLA-DRB5*0101/DRA, LA$_{83-97}$-HLA-DRB5*0101/DRA, LA$_{136-150}$-HLA-DRB5*0101/DRA, LA$_{50-64}$-HLA-DRB3*0202/DRA, LA$_{86-100}$-HLA-DRB3*0202/DRA, or LA$_{154-168}$-HLA-DRB3*0202/DRA;

n) scleroderma and the pMHC complex is selected from the group of: TOP1$_{346-360}$-HLA-DRB3*0101/DRA, TOP1$_{420-434}$-HLA-DRB3*0101/DRA, TOP1$_{750-764}$-HLA-DRB3*0101/DRA, TOP1$_{419-433}$-HLA-DRB4*0101/DRA, TOP1$_{591-605}$-HLA-DRB4*0101/DRA, TOP1$_{695-709}$-HLA-DRB4*0101/DRA, TOP1$_{305-319}$-HLA-DRB5*0101/DRA, TOP1$_{346-360}$-HLA-DRB5*0101/DRA, TOP1$_{419-433}$-HLA-DRB5*0101/DRA, TOP1$_{420-434}$-HLA-DRB3*0202/DRA, TOP1$_{425-439}$-HLA-DRB3*0202/DRA, TOP1$_{614-628}$-HLA-DRB3*0202/DRA, CENP-C$_{297-311}$-HLA-DRB3*0101/DRA, CENP-C$_{857-871}$-HLA-DRB3*0101, CENP-C$_{887-901}$-HLA-DRB3*0101, CENP-C$_{212-226}$-HLA-DRB4*0101/DRA, CENP-C$_{643-657}$-HLA-DRB4*0101/DRA, CENP-C$_{832-846}$-HLA-DRB4*0101/DRA, CENP-C$_{167-181}$-HLA-DRB5*0101/DRA, CENP-C$_{246-260}$-HLA-DRB5*0101/DRA, CENP-C$_{846-860}$-HLA-DRB5*0101/DRA, CENP-C$_{149-163}$-HLA-DRB3*0202/DRA, CENP-C$_{833-847}$-HLA-DRB3*0202/DRA, or CENP-C$_{847-861}$-HLA-DRB3*0202/DRA;

o) anti-phospholipid syndrome and the pMHC complex is selected from the group of: APOH$_{235-249}$-HLA-DRB3*0101/DRA, APOH$_{306-320}$-HLA-DRB3*0101/DRA, APOH$_{237-251}$-HLA-DRB3*0101/DRA, APOH$_{295-309}$-HLA-DRB3*0101/DRA, APOH$_{28-42}$-HLA-DRB4*0101/DRA, APOH$_{173-187}$-HLA-DRB4*0101/DRA, APOH$_{264-278}$-HLA-DRB4*0101/DRA, APOH$_{295-309}$-HLA-DRB4*0101/DRA, APOH$_{49-63}$-HLA-DRB5*0101/DRA, APOH$_{269-283}$-HLA- DRB5*0101/DRA, APOH$_{295-309}$-HLA-DRB5*0101/DRA, APOH$_{321-355}$-HLA-DRB3*0202/DRA, APOH$_{322-336}$-HLA-DRB3*0202/DRA, or APOH$_{324-338}$-HLA-DRB3*0202/DRA;

p) ANCA-associated vasculitis and the pMHC complex is selected from the group of: MPO$_{506-520}$-HLA-DRB3*0101/DRA, MPO$_{302-316}$-HLA-DRB3*0101/DRA, MPO$_{7-21}$-HLA-DRB3*0101/DRA, MPO$_{689-703}$-HLA-DRB4*0101/DRA, MPO$_{248-262}$-HLA-DRB4*0101/DRA, MPO$_{444-458}$-HLA-DRB4*0101/DRA, MPO$_{513-527}$-HLA-DRB5*0101/DRA, MPO$_{97-111}$-HLA-DRB5*0101/DRA, MPO$_{616-630}$-HLA-DRB5*0101/DRA, MPO$_{462-476}$-HLA-DRB3*0202/DRA, MPO$_{617-631}$-HLA-DRB3*0202/DRA, MPO$_{714-728}$-HLA-DRB3*0202/DRA, PRTN3$_{44-58}$-HLA-DRB3*0101/DRA, PRTN3$_{234-248}$-HLA-DRB3*0101/DRA, PRTN3$_{59-73}$-HLA DRB3*0101/DRA, PRTN3$_{59-73}$-HLA-DRB5*0101/DRA, PRTN3$_{117-131}$-HLA-DRB4*0101/DRA, PRTN3$_{164-178}$-HLA-DRB4*0101/DRA, PRTN3$_{71-85}$-HLA-DRB4*0101/DRA, PRTN3$_{241-255}$-HLA-DRB5*0101/DRA, PRTN3$_{183-197}$-HLA-DRB5*0101/DRA, PRTN3$_{62-76}$-HLA-DRB3*0202/DRA, PRTN3$_{118-132}$-HLA-DRB3*0202/DRA, or PRTN3$_{239-253}$-HLA-DRB3*0202/DRA; or q) Stiff Man Syndrome and the pMHC complex is selected from the group of: GAD$_{212-226}$-HLA-DRB1*0801/DRA, GAD$_{555-569}$-HLA-DRB1*0801/DRA, or GAD$_{297-311}$-HLA-DRB1*0301/DRA.

Selection of the co-stimulatory molecule or molecules to be coupled to the pMHC/NP complex may also be similarly optimized and will largely depend on the nature of the immune cell population in need of differentiation or expansion. For instance, if the intent is to expand or differentiate T regulatory cell populations, relevant combinations may include, but are not limited to, co-stimulatory molecules and cytokines such as IL15-IL15Ra, IL-2, IL-10, IL-35, ICOS-L, IL2/Anti-IL2 mAb complex, TGF-beta, IL-21, ITE or ICOSL. In contrast, in certain embodiments, such as with certain types of cancers, an expansion and/or differentiation of the T regulatory phenotype may not be the desired response. Thus, alternative co-stimulatory molecules and cytokines would be optimized to the particular treatment.

Methods of Making Nanoparticles and Complexes

MHCs and nanoparticles can be made by a variety of methods. The following are merely exemplary.

MHCs

To make MHC class I complexes, two exemplary methods are provided. The first involves re-folding MHC class I heavy and light chains, which are expressed in bacteria in the presence of peptide, followed by purification via gel filtration and anion exchange chromatography, as described in the literature (Garboczi, D. N. et al. (1992) Proc Natl. Acad Sci USA 89:3429-3433; Altman, J. D. et al. (1996) Science 274:94-96). The second involves expressing MHC class I complexes at high yields in lentiviral-transduced freestyle CHO cells as single chain constructs in which the peptide-coding sequence, the MHC class I light and heavy chains are sequentially tethered with flexible GS linkers (Yu, Y. Y. et al. (2002) J Immunol 168:3145-3149) followed by a carboxyterminal linker encoding a BirA site, a 6×His tag (SEQ ID NO: 504) ending with a free Cys. The secreted proteins are purified from culture supernatants using nickel columns and anion exchange chromatography and are used directly for NP coating or are biotinylated to produce pMHC tetramers using fluorochrome-conjugated streptavidin. Tetramers generated using representative single-chain pMHC complexes encoding the IGRP$_{206-214}$ autoantigenic peptide or its mimic NRP-V7 efficiently bind to cognate monoclonal autoreactive CD8+ T-cells but not to their polyclonal counterparts as determined by flow cytometry.

Recombinant pMHC class II monomers can be purified from *Drosophila* SC2 cells transfected with constructs encoding I-Aβ and I-Aα chains carrying c-Jun or c-Fos leucine zippers, respectively, and a BirA and 6×His tags (SEQ ID NO: 504) as previously described (Stratmann, T. et al. (2000) J Immunol 165:3214-3225, Stratmann, T. et al. (2003) J. Clin. Invest. 112:3214-3225). As the yields of this approach are generally low and time-consuming, Applicant has developed an expression system in freestyle CHO cells transduced with lentiviruses encoding a monocistronic message in which the peptide-IAβ and IAα chains of the complex are separated by the ribosome skipping P2A sequence (Hoist, J. et al. (2006) Nat Protoc 1:406-417). As with the single chain pMHC class I constructs described above, a linker encoding a BirA site, a 6×His tag (SEQ ID NO: 504) and a free Cys is added to the carboxyterminal end of the construct. The self-assembled pMHC class II complexes are purified from the cell culture supernatants by nickel chromatography followed by anion exchange and are used for coating onto NPs or are processed for biotinylation and tetramer formation as described above. pMHC class II tetramers generated using a representative pMHC class II complex encoding the 2.5 mi autoantigenic peptide are specifically and efficiently bound by cognate monoclonal autoreactive CD4+ T-cells, as determined by flow cytometry.

PE-conjugated tetramers can be prepared using biotinylated pMHC monomers as described (Stratmann, T. et al. (2000) J Immunol 165:3214-3225; Stratmann, T. et al. (2003) J. Clin. Invest. 112:3214-3225; Amrani, A. et al. (2000) Nature 406:739-742). Peripheral blood mononuclear cells, splenocytes and lymph node CD8+ or CD4+ T-cells can be stained with tetramer (5 ug/mL) in FACS buffer (0.1% sodium azide and 1% FBS in PBS) for 1 h at 4° C., washed, and incubated with FITC-conjugated anti-CD8α or anti-CD4 (5 μg/mL) and PerCP-conjugated anti-B220 (2 μg/mL; as a 'dumb' gate) for 30 min at 4° C. Cells are washed, fixed in 1% PFA/PBS and analyzed by FACS.

NP Synthesis

Nanoparticles may be formed by contacting an aqueous phase containing the co-stimulatory molecule(s), the pMHC complex and/or cytokine, and a polymer and a nonaqueous phase followed by evaporation of the nonaqueous phase to cause the coalescence of particles from the aqueous phase as taught in U.S. Pat. No. 4,589,330 or 4,818,542. Certain polymers for such preparations are natural or synthetic copolymers or polymers which include gelatin agar, starch, arabinogalactan, albumin, collagen, polyglycolic acid, polylactic acid, glycolide-L(-) lactide poly(episilon-caprolactone), poly(epsilon-caprolactone-CO-lactic acid), poly(epsilon-caprolactone-CO-glycolic acid), poly(β-hydroxy butyric acid), poly(ethylene oxide), polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly, certain polymers are polyesters, such as polyglycolic acid, polylactic acid, glycolide-L(-) lactide poly (episilon-caprolactone), poly(epsilon-caprolactone-CO-lactic acid), and poly(epsilon-caprolactone-CO-glycolic acid). Solvents useful for dissolving the polymer include: water, hexafluoroisopropanol, methylenechloride, tetrahydrofuran, hexane, benzene, or hexafluoroacetone sesquihydrate.

Gold nanoparticles (GNPs) are synthesized using chemical reduction of gold chloride with sodium citrate as described (Perrault, S. D. et al. (2009) Nano Lett 9:1909-1915). Briefly, 2 mL of 1% of HAuCl$_4$ (Sigma Aldrich) is added to 100 mL H$_2$O under vigorous stirring and the solution is heated in an oil bath. Six (for 14 nm GNPs) or two mL (for 40 nm GNPs) of 1% Na Citrate is added to the boiling HAuCl$_4$ solution, which is stirred for an additional 10 min and then is cooled down to room temperature. GNPs are stabilized by the addition of 1 µMol of thiol-PEG linkers (Nanocs, MA) functionalized with —COOH or —NH$_2$ groups as acceptors of MHC. Pegylated GNPs are washed with water to remove free thiol-PEG, concentrated and stored in water for further analysis. NP density is determined via spectrophotometry and calculated according to Beer's law.

The SFP series iron oxide NPs (SFP IONPs) can also be produced by thermal decomposition of iron acetate in organic solvents in the presence of surfactants, then rendered solvent in aqueous buffers by pegylation (Xie, J. et al. (2007) Adv Mater 19:3163; Xie, J. et al. (2006) Pure Appl. Chem. 78:1003-1014; Xu, C. et al. (2007) Polymer International 56:821-826). Briefly, 2 mMol Fe(acac)$_3$ (Sigma Aldrich, Oakville, ON) are dissolved in a mixture of 10 mL benzyl ether and oleylamine and heated to 100° C. for 1 hr followed by 300° C. for 2 hr with reflux under the protection of a nitrogen blanket. Synthesized NPs are precipitated by addition of ethanol and resuspended in hexane. For pegylation of the IONPs, 100 mg of different 3.5 kDa DPA-PEG linkers (Jenkem Tech USA) are dissolved in a mixture of CHCl$_3$ and HCON(CH$_3$)$_2$ (dimethylformamide (DMF)). The NP solution (20 mg Fe) is then added to the DPA-PEG solution and stirred for 4 hr at room temperature. Pegylated SFP NPs are precipitated overnight by addition of hexane and then resuspended in water. Trace amounts of aggregates are removed by high-speed centrifugation (20,000×g, 30 min), and the monodisperse SFP NPs are stored in water for further characterization and pMHC conjugation. The concentration of iron in IONP products is determined by spectrophotometry at A410 in 2N HCL. Based on the molecular structure and diameter of SFP NPs (Fe$_3$O$_4$; 8±1 nm diameter) (Xie, J. et al. (2007) Adv Mater 19:3163; Xie, J. et al. (2006) Pure Appl. Chem. 78:1003-1014), Applicant estimates that SFP solutions containing 1 mg of iron contain $5 \times 10^{14}$ NPs.

The nanoparticles can also be made by thermally decomposing or heating a nanoparticle precursor. In one embodiment, the nanoparticle is a metal or a metal oxide nanoparticle. In one embodiment, the nanoparticle is an iron oxide nanoparticle. In one embodiment, the nanoparticle is a gold nanoparticle. In one embodiment, provided herein are the nanoparticles prepared in accordance with the present technology. In one embodiment, provided herein is a method of making iron oxide nanoparticles comprising a thermal decomposition reaction of iron acetyl acetonate. In one embodiment, the iron oxide nanoparticle obtained is water-soluble. In one aspect, the iron oxide nanoparticle is suitable for protein conjugation. In one embodiment, the method comprises a single-step thermal decomposition reaction.

In one aspect, the thermal decomposition occurs in the presence of functionalized PEG molecules. Certain non-limiting examples of functionalized PEG linkers are shown in Table 1.

In one aspect, the thermal decomposition comprises heating iron acetyl acetonate. In one embodiment, the thermal decomposition comprises heating iron acetyl acetonate in the presence of functionalized PEG molecules. In one embodiment, the thermal decomposition comprises heating iron acetyl acetonate in the presence of benzyl ether and functionalized PEG molecules.

Without being bound by theory, in one embodiment, functionalized PEG molecules are used as reducing reagents and as surfactants. The method of making nanoparticles provided herein simplifies and improves conventional methods, which use surfactants that are difficult to be displaced, or are not displaced to completion, by PEG molecules to render the particles water-soluble. Conventionally, surfactants can be expensive (e.g., phospholipids) or toxic (e.g., Oleic acid or oleilamine). In another aspect, without being bound by theory, the method of making nanoparticles obviates the need to use conventional surfactants, thereby achieving a high degree of molecular purity and water solubility.

In one embodiment, the thermal decomposition involves iron acetyl acetonate and benzyl ether and in the absence of conventional surfactants other than those employed herein.

In one embodiment, the temperature for the thermal decomposition is about 80° C. to about 300° C., or about 80° C. to about 200° C., or about 80° C. to about 150° C., or about 100° C. to about 250° C., or about 100° C. to about 200° C., or about 150° C. to about 250° C., or about 150° C. to about 250° C. In one embodiment, the thermal decomposition occurs at about 1 to about 2 hours of time.

In one embodiment, the method of making the iron oxide nanoparticles comprises a purification step, such as by using Miltenyi Biotec LS magnet column.

In one embodiment, the nanoparticles are stable at about 4° C. in phosphate buffered saline (PBS) without any detectable degradation or aggregation. In one embodiment, the nanoparticles are stable for at least 6 months.

In one aspect, provided herein is a method of making nanoparticle complexes comprising contacting pMHC with iron oxide nanoparticles provided herein. Without being bound by theory, pMHC encodes a Cysteine at its carboxy-terminal end, which can react with the maleimide group in functionalized PEG at about pH 6.2 to about pH 6.5 for about 12 to about 14 hours.

In one aspect, the method of making nanoparticle complexes comprises a purification step, such as by using Miltenyi Biotec LS magnet column.

Coupling to Nanoparticles

In certain aspects, antigen-MHC complex and/or cytokine and/or costimulatory molecule can be coupled to the nanoparticle core by one or more of covalently, non-covalently, or cross-linked and optionally coupled through a linker. In further aspects, the linker may be less than 5 kD in size, and is optionally polyethylene glycol. In aspects involving a linker or linkers, the linkers may be the same or different from each other on a single nanoparticle core.

In order to couple the substrate or particles to the antigen-MHC complex and/or cytokine and/or costimulatory molecule, the following techniques can be applied.

The binding can be generated by chemically modifying the substrate or particle which typically involves the generation of "functional groups" on the surface, said functional groups being capable of binding to an MHC complex, and/or linking the optionally chemically modified surface of the surface or particle with covalently or non-covalently bound so-called "linking molecules," followed by reacting the MHC or MHC complex with the particles obtained.

The term "linking molecule" or "linker" means a substance capable of linking with the substrate or particle and also capable of linking to an MHC complex.

The term "functional groups" as used hereinbefore is not restricted to reactive chemical groups forming covalent bonds, but also includes chemical groups leading to an ionic interaction or hydrogen bonds with the MHC complex.

Moreover, it should be noted that a strict distinction between "functional groups" generated at the surface and linking molecules bearing "functional groups" is not possible, since sometimes the modification of the surface requires the reaction of smaller linking molecules such as ethylene glycol with the particle surface.

The functional groups or the linking molecules bearing them may be selected from amino groups, carbonic acid groups, thiols, thioethers, disulfides, guanidino, hydroxyl groups, amine groups, vicinal diols, aldehydes, alpha-haloacetyl groups, mercury organyles, ester groups, acid halide, acid thioester, acid anhydride, isocyanates, isothiocyanates, sulfonic acid halides, imidoesters, diazoacetates, diazonium salts, 1,2-diketones, phosphonic acids, phosphoric acid esters, sulfonic acids, azolides, imidazoles, indoles, N-maleimides, alpha-beta-unsaturated carbonyl compounds, arylhalogenides or their derivatives.

Non-limiting examples for other linking molecules with higher molecular weights are nucleic acid molecules, polymers, copolymers, polymerizable coupling agents, silica, proteins, and chain-like molecules having a surface with the opposed polarity with respect to the substrate or particle. Nucleic acids can provide a link to affinity molecules containing themselves nucleic acid molecules, though with a complementary sequence with respect to the linking molecule.

In some embodiments, the linking molecule comprises polyethylene glycol. In some embodiments, the linking molecule comprises polyethylene glycol and maleimide. In some embodiments, the polyethylene glycol comprises one or more of a $C_1$-$C_3$ alkoxy group, —$R^{10}$NHC(O)R—, —$R^{10}$C(O)NHR—, —$R^{10}$OC(O)R—, —$R^{10}$C(O)OR—, wherein each R is independently H or $C_1$-$C_6$ alkyl and wherein each $R^{10}$ is independently a bond or $C_1$-$C_6$ alkyl.

As examples for polymerizable coupling agents, diacetylene, styrene butadiene, vinylacetate, acrylate, acrylamide, vinyl compounds, styrene, silicone oxide, boron oxide, phosphorous oxide, borates, pyrrole, polypyrrole and phosphates can be cited.

pMHC complexes can be coupled to nanoparticles by a variety of methods, one non-limiting example includes conjugation to NPs produced with PEG linkers carrying distal —$NH_2$ or —COOH groups that can be achieved via the formation of amide bonds in the presence of 1-Ethyl-3-[3-dimethylaminopropyl]carbodiimide hydrochloride (EDC). NPs with —COOH groups are first dissolved in 20 mM MES buffer, pH 5.5. N-hydroxysulfosuccinimide sodium salt (sulpha-NHS, Thermo scientific, Waltham, Mass., final concentration 10 mM) and EDC (Thermo scientific, Waltham, Mass., final concentration 1 mM) is added to the NP solution. After 20 min of stirring at room temperature, the NP solution is added drop-wise to the solution containing pMHC monomers dissolved in 20 mM borate buffer (pH 8.2). The mixture is stirred for an additional 4 hr. To conjugate MHCs to $NH_2$-functionalized NPs pMHC complexes are first dissolved in 20 mM MES buffer, pH 5.5, containing 100 mM NaCl. Sulpha-NHS (10 mM) and EDC (5 mM) are then added to the MHC solution. The activated MHC molecules are then added to the NP solution in 20 mM borate buffer (pH 8.2), and stirred for 4 hr at room temperature.

To conjugate MHC to maleimide-functionalized NPs, pMHC complexes are first incubated with Tributylphospine (TBP, 1 mM) for 4 hr at room temperature. pMHCs engineered to encode a free carboxyterminal Cys residue are then mixed with NPs in 40 mM phosphate buffer, pH 6.0, containing 2 mM EDTA, 150 mM NaCl, and incubated overnight at room temperature. MHCs of the pMHC complexes are covalently bound with NPs via the formation of a carbon-sulfide bond between meleimide groups and the Cys residue.

Click chemistry can be used to conjugate pMHC or avidin to NPs functionalized with azide groups. For this reaction, MHC or avidin molecules are first incubated with dibenzocyclooctyl (DBCO, Click Chemistry Tools, Scottdale, Ariz.) reagent for 2 hr at room temperature. Free DBCO molecules can be removed by dialysis overnight. MHC- or avidin-DBCO conjugates are then incubated with SFP-Z for 2 hr, resulting in formation of triazole bonds between pMHCs or avidin molecules and NPs.

Unconjugated pMHC complexes in the different MHC-NP conjugating reactions can be removed by extensive dialysis using methods known in the art. A non-limiting example is dialysis against PBS, pH 7.4, at 4° C. though 300 kDa molecular weight cut off membranes (Spectrum labs). Alternatively, pMHC-conjugated IONPs can be purified by magnetic separation. The conjugated NPs can be concentrated by ultrafiltration through Amicon Ultra-15 units (100 kDa MWCO) and stored in PBS.

The surface of the substrate or particle can be chemically modified, for instance by the binding of phosphonic acid derivatives having functional reactive groups. One example of these phosphonic acid or phosphonic acid ester derivates is imino-bis(methylenphosphono) carbonic acid which can be synthesized according to the "Mannich-Moedritzer" reaction. This binding reaction can be performed with a substrate or a particle as directly obtained from the preparation process or after a pre-treatment (for instance with trimethylsilyl bromide). In the first case the phophonic acid (ester) derivative may for instance displace components of the reaction medium which are still bound to the surface. This displacement can be enhanced at higher temperatures. Trimethylsilyl bromide, on the other hand, is believed to dealkylate alkyl group-containing phosphorous-based complexing agents, thereby creating new binding sites for the phosphonic acid (ester) derivative. The phosphonic acid (ester) derivative, or linking molecules bound thereto, may display the same functional groups as given above. A further example of the surface treatment of the substrate or particle involves heating in a diol such as ethylene glycol. It should be noted that this treatment may be redundant if the synthesis already proceeded in a diol. Under these circumstances the synthesis product directly obtained is likely to show the necessary functional groups. This treatment is, however, applicable to a substrate or a particle that was produced in N- or P-containing complexing agents. If such substrate or particle is subjected to an after-treatment with ethylene glycol, ingredients of the reaction medium (e.g. complexing agent) still binding to the surface can be replaced by the diol and/or can be dealkylated.

It is also possible to replace N-containing complexing agents still bound to the particle surface by primary amine derivatives having a second functional group. The surface of the substrate or particle can also be coated with silica. Silica allows a relatively simple chemical conjugation of organic molecules since silica easily reacts with organic linkers, such as triethoxysilane or chlorosilane. The particle surface may also be coated by homo- or copolymers. Examples for polymerizable coupling agents are: N-(3-aminopropyl)-3-mercaptobenzamidine, 3-(trimethoxysilyl)propylhydrazide and 3-trimethoxysilyl)propylmaleimide. Other non-limiting examples of polymerizable coupling agents are mentioned herein. These coupling agents can be used singly or in combination depending on the type of copolymer to be generated as a coating.

Another surface modification technique that can be used with substrates or particles containing oxidic transition metal compounds is conversion of the oxidic transition metal compounds by chlorine gas or organic chlorination agents to the corresponding oxychlorides. These oxychlorides are capable of reacting with nucleophiles, such as hydroxy or amino groups as often found in biomolecules. This technique allows generating a direct conjugation with proteins, for instance, via the amino group of lysine side chains. The conjugation with proteins after surface modification with oxychlorides can also be effected by using a bi-functional linker, such as maleimidopropionic acid hydrazide.

For non-covalent linking techniques, chain-type molecules having a polarity or charge opposite to that of the substrate or particle surface are particularly suitable. Examples for linking molecules which can be non-covalently linked to core/shell nanoparticles involve anionic, cationic or zwitter-ionic surfactants, acid or basic proteins, polyamines, polyamides, polysulfone or polycarboxylic acid. The hydrophobic interaction between substrate or particle and amphiphilic reagent having a functional reactive group can generate the necessary link. In particular, chain-type molecules with amphiphilic character, such as phospholipids or derivatised polysaccharides, which can be crosslinked with each other, are useful. The absorption of these molecules on the surface can be achieved by coincubation. The binding between affinity molecule and substrate or particle can also be based on non-covalent, self-organizing bonds. One example thereof involves simple detection probes with biotin as linking molecule and avidin- or strepdavidin-coupled molecules.

Protocols for coupling reactions of functional groups to biological molecules can be found in the literature, for instance in "Bioconjugate Techniques" (Greg T. Hermanson, Academic Press 1996). The biological molecule (e.g., MHC molecule or derivative thereof) can be coupled to the linking molecule, covalently or non-covalently, in line with standard procedures of organic chemistry such as oxidation, halogenation, alkylation, acylation, addition, substitution or amidation. These methods for coupling the covalently or non-covalently bound linking molecule can be applied prior to the coupling of the linking molecule to the substrate or particle or thereafter. Further, it is possible, by means of incubation, to effect a direct binding of molecules to correspondingly pre-treated substrate or particles (for instance by trimethylsilyl bromide), which display a modified surface due to this pre-treatment (for instance a higher charge or polar surface).

Pharmaceutical Compositions and Administration

Provided herein are pharmaceutical compositions useful for the treatment and prevention of disease. The compositions comprise, or alternatively consist essentially of, or yet further consist of, a nanoparticle complex as described herein and a carrier.

The compositions can be used to induce or modify an immune response against a disease relevant antigen, e.g., a polypeptide, a peptide, a carbohydrate, a lipid or other molecule or molecular fragment and against developing a condition or disease caused by such an autoimmune response or cancer.

Compositions of the disclosure may be conventionally administered parenterally, by injection, for example, intravenously, subcutaneously, or intramuscularly. Additional formulations which are suitable for other modes of administration include oral formulations. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. The preparation of an aqueous composition that contains an antigen-MHC-nanoparticle complex that modifies the subject's immune condition will be known to those of skill in the art in light of the present disclosure. In certain embodiments, a composition may be inhaled (e.g., U.S. Pat. No. 6,651,655, which is specifically incorporated by reference in its entirety). In one embodiment, the antigen-MHC-nanoparticle complex is administered systemically. In specific embodiments, the pMHC-NP complex or the compositions comprising a plurality of pMHC-NP complexes can be administered intravenously.

Typically, compositions of the disclosure are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner. However, suitable dosage ranges are of the order of ten to several hundred nanograms or micrograms of antigen/MHC/nanoparticle complex per administration. Suitable regimes for initial administration and boosters are also variable, but are typified by an initial administration followed by subsequent administrations.

The manner of application may be varied widely. Any of the conventional methods for administration of a vaccine are applicable. These are believed to include oral application on a solid physiologically acceptable base or in a physiologically acceptable dispersion, parenterally, by injection and the like. The dosage of the antigen/MHC/nanoparticle complex will depend on the route of administration and will vary according to the size and health of the subject.

In many instances, it will be desirable to have multiple administrations of a peptide/MHC/nanoparticle complex, about, at least about, or at most about 3, 4, 5, 6, 7, 8, 9, 10 or more administrations. The administrations will normally range from 1, 2, 3, 4, 5, 6, or 7 day to twelve week intervals, more usually from one to two week intervals. Periodic boosters at intervals of every other day, twice a week, weekly, biweekly, monthly, or 0.1, 0.2, 0.3, 0.4, 0.5, 1, 2, 3, 4 or 5 years, usually two years, will be desirable to maintain the condition of the immune system. The course of the administrations may be followed by assays for autoreactive immune responses, cognate $T_R1$ cells, and T cell activity.

In certain aspects, a single dose of the pMHC complex without including the nanoparticle core and any outer layer comprises about 0.001 mg/kg to about 2.0 mg/kg, or about 0.001 mg/kg to about 1.5 mg/kg, or about 0.001 mg/kg to about 1.4 mg/kg, or about 0.001 mg/kg to about 1.3 mg/kg, or about 0.001 mg/kg to about 1.2 mg/kg, or about 0.001 mg/kg to about 1.1 mg/kg, or about 0.001 mg/kg to about 1.0 mg/kg. In some embodiments, the single dose comprises from about 0.004 mg/kg to about 1.014 mg/kg, or from about 0.02 mg/kg to about 0.811 mg/kg, or from about 0.041 mg/kg to about 0.608 mg/kg, or from about 0.061 mg/kg to about 0.507 mg/kg, or from about 0.081 mg/kg to about 0.405 mg/kg, or from about 0.121 mg/kg to about 0.324 mg/kg, or from about 0.162 mg/kg to about 0.243 mg/kg. In some embodiments, the single dose comprises from about 0.004 mg/kg to about 1.015 mg/kg, or from about 0.004 mg/kg to about 1.0 mg/kg, or from about 0.004 mg/kg to about 0.9 mg/kg, or from about 0.004 mg/kg to about 0.8 mg/kg, or from about 0.004 mg/kg to about 0.7 mg/kg, or from about 0.004 mg/kg to about 0.6 mg/kg, or from about 0.004 mg/kg to about 0.5 mg/kg, or from about 0.004 mg/kg to about 0.4 mg/kg, or from about 0.004 mg/kg to about 0.3 mg/kg, or from about 0.004 mg/kg to about 0.2 mg/kg, or from about 0.004 mg/kg to about 0.1 mg/kg.

Combination Therapy

The compositions and related methods of the present disclosure, particularly administration of an antigen/MHC/nanoparticle complex, may also be used in combination with the administration of traditional therapies. These include, but are not limited to, the administration of immunosuppressive or modulating therapies or treatments. Non-limiting examples of certain disease-relevant treatments include Avonex (interferon beta-1a), Betaseron (interferon beta-1b), Copaxone (glatiramer acetate), Novantrone (mitoxantrone), Rebif (interferon beta-1a), Tysabri (natalizumab), Gilenya (fingolimod), Glatiramer, steroids, Cytoxan, Imuran, Baclofen, deep brain stimulation, Ampyra (dalfampridine), acupuncture, and physical therapy. When treating cancer, additional chemotherapeutics, radiation or surgery may be added to augment the therapeutic response of the disclosed compositions and methods.

In one aspect, it is contemplated that an antigen/MHC/nanoparticle complex is used in conjunction with a cytokine treatment. Alternatively, antigen/MHC/nanoparticle complex administration may precede or follow the other treatment by intervals ranging from minutes to weeks. In embodiments where the other agents and/or antigen/MHC/nanoparticle complexes are administered separately, one would generally ensure that a significant period of time did not expire between the time of each delivery, such that the agent and antigen/MHC/nanoparticle complex would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations may be employed, for example antigen/MHC/nanoparticle complex administration is "A" and the additional agent is "B":

| A/B/A | B/A/B | B/B/A | A/A/B | A/B/B | B/A/A |
|---|---|---|---|---|---|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the peptide-MHC complex compositions of the present disclosure to a patient/subject will follow general protocols for the administration of such compounds, taking into account the toxicity, if any. It is expected that the treatment cycles would be repeated as necessary. It is also contemplated that various standard therapies, such as hydration, may be applied in combination with the described therapy.

Pharmaceutical Carriers and Formulations

In some embodiments, pharmaceutical compositions are administered to a subject. Different aspects of the present disclosure involve administering an effective amount of a antigen/MHC/nanoparticle complex composition to a subject. Additionally, such compositions can be administered in combination with modifiers of the immune system. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The active compounds of the present disclosure can be formulated for parenteral administration, e.g., formulated for injection via the intravenous, intramuscular, subcutaneous, or even intraperitoneal routes. The preparation of an aqueous composition that contains a antigen/MHC/nanoparticle complex that modifies the subject's immune condition will be known to those of skill in the art in light of the present disclosure. Typically, such compositions can be prepared as injectables, either as liquid solutions or suspensions; solid forms suitable to prepare solutions or suspensions upon the addition of a liquid prior to injection; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases, the form must be sterile and must be fluid to the extent that it may be easily injected. It should also be stable under the conditions of manufacture and storage and must be preserved against the contaminating action of microorganisms, such as bacteria and fungi.

The compositions may be formulated into a neutral or salt form. Pharmaceutically acceptable salts, including the acid addition salts (formed with the free amino groups of the protein), are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by sterilization. Sterilization of the solution will be done in such a way as to not diminish the therapeutic properties of the antigen-MI-IC-nanoparticle complex. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the certain methods of preparation are vacuum-drying and freeze-drying techniques, which yield a powder of the active ingredient, plus any additional desired ingredient from a previously sterilized solution thereof. One such method of sterilization of the solution is sterile filtration, however, this disclosure is meant to include any method of sterilization that does not significantly decrease the therapeutic properties of the antigen-MHC-nanoparticle complexes. Methods of sterilization that involve intense heat and pressure, such as autoclaving, may compromise the tertiary structure of the complex, thus significantly decreasing the therapeutic properties of the antigen-MHC-nanoparticle complexes.

Administration of the compositions according to the present disclosure will typically be via any common route. This includes, but is not limited to, orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference).

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above. A typical dosing regimen in a mouse model involves the administration of 1 µg-50 µg of total pMHC (NP-coated) and 1-50 µg of total iron per dose which may be translated to a specific unit dosage in humans. In certain embodiments, the dose may range from about 0.1 µg to about 400 µg. However, it is understood that the amount of pMHC per dose can range from as low as 0.1 µg to 100 mg. As an example, in a 60 kg human patient, the amount of pMHC per dose can range from 0.24 mg to 12 mg with the understanding that this corresponds to the 1 µg to 50 µg discussed above. Also as above, this dose can be changed to correspond to 0.1 µg to 100 mg above, corresponding to a human equivalent dose of 0.0004 mg/kg to 405.4 mg/kg and ranges in between depending on the patient being treated, the condition and other parameters decided by the treating physician.

In Vitro or Ex Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject, including administrations.

In certain aspects of the present disclosure, the compositions may be administered either in vitro, ex vivo, or in vivo. In certain in vitro embodiments, autologous T cells are incubated with compositions of this disclosure. The cells can then be used for in vitro analysis, or alternatively for ex vivo administration.

Production of Protein Components

The present disclosure describes polypeptides, peptides, and proteins for use in various embodiments of the present disclosure. For example, specific peptides and their complexes are assayed for their abilities to elicit or modulate an immune response. In specific embodiments, all or part of the peptides or proteins of the disclosure can also be synthesized in solution or on a solid support in accordance with conventional techniques. Various automatic synthesizers are commercially available and can be used in accordance with known protocols.

Alternatively, recombinant DNA technology may be employed wherein a nucleotide sequence which encodes a peptide of the disclosure is inserted into an expression vector, transformed or transfected into an appropriate host cell and cultivated under conditions suitable for expression.

One embodiment of the disclosure includes the use of gene transfer to cells, including microorganisms, for the production of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are known to one skilled in the art and are briefly discussed herein. Examples of mammalian host cell lines include, but are not limited to, Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to, HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Nucleic Acids

The present disclosure may include recombinant polynucleotides encoding the proteins, polypeptides, peptides of the disclosure. The nucleic acid sequences for autoantigens and MHC molecules for presenting the autoantigens, are included and can be used to prepare a peptide/MHC complex.

As used in this disclosure, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be RNA, DNA, analogs thereof, or a combination thereof.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide of the following lengths: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs. It is also contemplated that a particular polypeptide from a given species may be encoded by nucleic acids containing natural variations that having slightly different nucleic acid sequences but, nonetheless, encode the same or substantially similar protein, polypeptide, or peptide.

In particular embodiments, the disclosure concerns isolated nucleic acid segments and recombinant vectors incorporating nucleic acid sequences that encode an autoantigen and/or a MHC molecule. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments used in the present disclosure, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein "heterologous" refers to a polypeptide that is not the same as the modified polypeptide.

Methods of Treatment

Medical and diagnostic methods are also provided. In one aspect, a method is provided for promoting the formation, expansion and recruitment of immune cells, including but not limited to, effector cells, B-regulatory cells and/or $T_R1$ cells (e.g., $T_R1$ and CD4+ cells) or CD8+ cells, in an antigen-specific manner in a subject in need thereof, comprising, or alternatively consisting essentially of, or yet further consisting of, administering to the subject an effective amount of the NP-complex or composition as described herein.

This disclosure also provides methods for differentiating or triggering T-regulatory type 1 ($T_R1$) cell formation in a pMHC dose independent manner. Applicant has discovered that the pMHC density on the nanoparticle core regulates the ability of pMHC on the nanoparticle core to trigger $T_R1$ cell formation in a dose-independent manner, while pMHC dose regulates the magnitude of $T_R1$ cell expansion in a pMHC density-independent manner. Applicant has observed that the pMHC density threshold and the independent effects of pMHC density versus dose on $T_R1$ cell formation versus expansion are unexpected findings that could not have been anticipated based on conventional immunological knowledge in the art. These methods require contacting the cognate T cells with an effective amount of a pMHC-NP or a composition disclosed herein. In certain aspects, the density-dependent methods relate to an activated T cell or a memory T cell being differentiated into a IL-10 producing cognate $T_R1$ cell optionally having the marker CD49b and/or Lag3 and/or a B cell being differentiated into a regulatory B cell by contacting the activated T cell or the memory T cell with an effective amount of the complex or composition disclosed herein. In some embodiments, the differentiated T regulatory cell binds to a B cell, thereby differentiating the B cell into a regulatory B cell. In certain aspects of the methods, the contacting is performed in vitro or in vivo.

Accordingly, aspects of the disclosure relate to a method for differentiating or triggering $T_R1$ cell formation in a pMHC dose independent manner comprising contacting the cognate T cells with an effective amount of the complex or composition disclosed herein. In certain aspects, the contacting may be in vitro or in vivo. In certain aspects, the methods relate to an activated T cell or a memory T cell being differentiated into a IL-10 producing $T_R1$ cell optionally expressing the marker CD49b and/or Lag3 comprising contacting the activated T cell or the memory T cell with an effective amount of the complex or composition disclosed herein. Based on the correlation between relevant cell type for each disease, the corresponding optimized MHC/NP complex and optionally co-stimulatory molecule and/or cytokine is also administered.

With this in mind, Applicant provides a method for differentiating an activated T cell or a memory T cell into a IL-10 producing $T_R1$ cell optionally expressing the marker CD49b and/or Lag3 and/or differentiating a B cell into a regulatory B cell comprising, or alternatively consisting of, or yet further consisting of, contacting the activated T cell or the memory T cell with an effective amount of the complex or composition as described herein. The contacting can be in vitro or in vivo. In some embodiments, the pMHC-NP or composition containing a plurality of the pMHC-NPs have pMHC-NPs having an average nanoparticle core diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm. In some aspects, the nanoparticle core further comprises an outer coating or layer, wherein the diameter of the core and outer layer have an average diameter of from about 30 nm to about 75 nm, or from about 30 nm to about 70 nm, or from about 30 nm to about 60 nm, or from about 30 nm to about 50 nm, or about 40 nm. In some aspects, the nanoparticle has an average pMHC density of from about 0.4 pMHC/100 nm$^2$ to about 12 pMHC/100 nm$^2$, or from about 0.4 pMHC/100 nm$^2$ to about 11.6 pMHC/100 nm$^2$, or from about 0.4 pMHC/100 nm$^2$ to about 11.5 pMHC/100 nm$^2$, or from about 0.4 pMHC/100 nm$^2$ to about 11 pMHC/100 nm$^2$, or from about 0.4 pMHC/100 nm$^2$ to about 10 pMHC/100 nm$^2$, or from about 0.4 pMHC/100 nm$^2$ to about 9 pMHC/100 nm$^2$, or from about 0.4 pMHC/100 nm$^2$ to about 8 pMHC/100 nm$^2$, or from about 0.4 pMHC/100 nm$^2$ to about 7 pMHC/100 nm$^2$, or from about 0.4 pMHC/100 nm$^2$ to about 6 pMHC/100 nm$^2$, or from about 0.4 pMHC/100 nm$^2$ to about 5 pMHC/100 nm$^2$, or from about 0.4 pMHC/100 nm$^2$ to about 4 pMHC/100 nm$^2$, or from about 0.4 pMHC/100 nm$^2$ to about 3 pMHC/100 nm$^2$, or from about 0.4 pMHC/100 nm$^2$ to about 2.5 pMHC/100 nm$^2$, or from about 0.4 pMHC/100 nm$^2$ to about 2 pMHC/100 nm$^2$, or from about 0.4 pMHC/100 nm$^2$ to about 1.5 pMHC/100 nm$^2$.

Also provided are methods for differentiating an activated T cell or a memory T cell into a IL-10 producing $T_R1$ cell optionally expressing the marker CD49b and/or Lag3 and/or differentiating a B cell into a regulatory B cell comprising, or alternatively consisting essentially of, or yet further consisting of, administering to the subject an effective amount of the complex or composition as described herein. As used herein, the subject may include an animal, a mammal, a murine, a bovine, an equine, a canine, a feline, an ovine, or a human. In some embodiments, the pMHC-NP or composition containing a plurality of the pMHC-NPs have pMHC-NPs having an average nanoparticle core diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm. In some aspects, the nanoparticle core further comprises an outer coating or layer, wherein the diameter of the core and outer layer have an average diameter of from about 30 nm to about 75 nm, or from about 30 nm to about 70 nm, or from about 30 nm to about 60 nm, or from about 30 nm to about 50 nm, or about 40 nm. In some aspects, the nanoparticle has an average pMHC density of from about 0.4 pMHC/100 nm$^2$ to about 12 pMHC/100 nm$^2$, or from about 0.4 pMHC/100 nm$^2$ to about 11.6 pMHC/100 nm$^2$, or from about 0.4 pMHC/100 nm$^2$ to about 11.5 pMHC/100 nm$^2$, or from about 0.4 pMHC/100 nm$^2$ to about 11 pMHC/100 nm$^2$, or from about 0.4 pMHC/100 nm$^2$ to about 10 pMHC/100 nm$^2$, or from about 0.4 pMHC/100 nm$^2$ to about 9 pMHC/100 nm$^2$, or from about 0.4 pMHC/100 nm$^2$ to about 8 pMHC/100 nm$^2$, or from about 0.4 pMHC/100 nm$^2$ to about 7 pMHC/100 nm$^2$, or from about 0.4 pMHC/100 nm$^2$ to about 6 pMHC/100 nm$^2$, or from about 0.4 pMHC/100 nm$^2$ to about 5 pMHC/100 nm$^2$, or from about 0.4 pMHC/100 nm$^2$ to about 4 pMHC/100 nm$^2$, or from about 0.4 pMHC/100 nm$^2$ to about 3 pMHC/100 nm$^2$, or from about 0.4 pMHC/100 nm$^2$ to about 2.5 pMHC/100 nm$^2$, or from about 0.4 pMHC/100 nm$^2$ to about 2 pMHC/100 nm$^2$, or from about 0.4 pMHC/100 nm$^2$ to about 1.5 pMHC/100 nm$^2$.

Provided herein are methods of treating an autoimmune disease or disorder in a subject in need thereof comprising administering an effective amount of any of the complexes or compositions disclosed herein to the subject, provided that the complexes and the compositions do not comprise co-stimulatory molecules.

Further provided herein are methods of treating a cancer or a tumor and/or inhibiting the growth of a tumor cell or tissue in a subject in need t hereof comprising administering an effective amount of any of the pMHC-NP complex with one or more co-stimulatory molecules.

Yet further aspects provided herein include a nanoparticle complex having a pMHC density of from about 0.4 pMHC/100 nm$^2$ to about 12 pMHC/100 nm$^2$ for use in promoting a differentiation of activated T cells or memory T cells into IL-10 producing $T_R1$ cells optionally expressing a marker CD49b and/or Lag3. In some embodiments, the pMHC-NP or composition containing a plurality of the pMHC-NPs have pMHC-NPs having an average nanoparticle core diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm. In some aspects, the nanoparticle core further comprises an outer coating or layer, wherein the diameter of the core and outer layer have an average diameter of from about 30 nm to about 75 nm, or from about 30 nm to about 70 nm, or from about 30 nm to about 60 nm, or from about 30 nm to about 50 nm, or about 40 nm. In some aspects, the nanoparticle has an average pMHC density of from about 0.4 pMHC/100 nm$^2$ to about 12 pMHC/100 nm$^2$, or from about 0.4 pMHC/100 nm$^2$ to about 11.6 pMHC/100 nm$^2$, or from about 0.4 pMHC/100 nm$^2$ to about 11.5 pMHC/100 nm$^2$, or from about 0.4 pMHC/100 nm$^2$ to about 11 pMHC/100 nm$^2$, or from about 0.4 pMHC/100 nm$^2$ to about 10 pMHC/100 nm$^2$, or from about 0.4 pMHC/100 nm$^2$ to about 9 pMHC/100 nm$^2$, or from about 0.4 pMHC/100 nm$^2$ to about 8 pMHC/100 nm$^2$, or from about 0.4 pMHC/100 nm$^2$ to about 7 pMHC/100 nm$^2$, or from about 0.4 pMHC/100 nm$^2$ to about 6 pMHC/100 nm$^2$, or from about 0.4 pMHC/100 nm$^2$ to about 5 pMHC/100 nm$^2$, or from about 0.4 pMHC/100 nm$^2$ to about 4 pMHC/100 nm$^2$, or from about 0.4 pMHC/100 nm$^2$ to about 3 pMHC/100 nm$^2$, or from about 0.4 pMHC/100 nm$^2$ to about 2.5 pMHC/100 nm$^2$, or from about 0.4 pMHC/100 nm$^2$ to about 2 pMHC/100 nm$^2$, or from about 0.4 pMHC/100 nm$^2$ to about 1.5 pMHC/100 nm$^2$.

In one aspect, provided herein are methods for differentiating an activated T cell or a memory T cell into a IL-10 producing $T_R1$ cell expressing a marker comprising CD49b and/or LAG3, and/or differentiating a B cell into a regulatory B cell, the method comprising contacting the activated T cell or the memory T cell with an effective amount of a complex comprising: a nanoparticle core, wherein: a plurality of disease-relevant antigen-MHC (pMHC) complexes are coupled to the nanoparticle core; the diameter of the core is from about 15 nm to about 25 nm; and wherein the pMHC density on the nanoparticle is from about 0.4 pMHC/100 nm² to about 12 pMHC/100 nm² of the surface area of the nanoparticle. In some embodiments, the nanoparticle core further comprises an outer layer on the core, wherein the pMHC complex is coupled to the nanoparticle core and/or the outer layer, and wherein the combined diameter of the nanoparticle core and the outer layer is from about 35 nm to about 45 nm. In some embodimens, contacting is in vitro or in vivo.

In another aspect, provided herein is a nanoparticle complex for use in differentiating an activated T cell or a memory T cell into a IL-10 producing $T_R1$ cell expressing a marker comprising CD49b and/or LAG3, and/or differentiating a B cell into a regulatory B cell, wherein the nanoparticle complex comprises a nanoparticle core, wherein: a plurality of disease-relevant antigen-MHC (pMHC) complexes are coupled to the nanoparticle core; the diameter of the core is from about 15 nm to about 25 nm; and wherein the pMHC density on the nanoparticle is from about 0.4 pMHC/100 nm² to about 12 pMHC/100 nm² of the surface area of the nanoparticle.

In another aspect, provided herein is a nanoparticle complex for use in differentiating an activated T cell or a memory T cell into a IL-10 producing $T_R1$ cell expressing a marker comprising CD49b and/or LAG3, and/or differentiating a B cell into a regulatory B cell, wherein the nanoparticle complex comprises a nanoparticle core and an outer layer on the nanoparticle core, wherein: a plurality of disease-relevant antigen-MHC (pMHC) complexes are coupled to the nanoparticle core and/or the outer layer; the combined diameter of the core and the outer layer is from about 25 nm to about 45 nm; and wherein the pMHC density on the nanoparticle is from about 0.4 pMHC/100 nm² to about 12 pMHC/100 nm² of the surface area of the nanoparticle.

In some embodiments, a therapeutic effect comprises about a 0.1% to about a 250% increase in the population of $T_R1$ cells. In some embodiments, the increase comprises about 0.1% to about 225%, or about 0.1% to about 200%, or about 0.1% to about 175%, or about 0.1% to about 150%, or about 0.1% to about 125%, or about 0.1% to about 100%, or about 0.1% to about 75%, or about 0.1% to about 50%, or about 0.1% to about 25%, or about 0.1% to about 20%, or about 0.1% to about 15%, or about 0.1% to about 10%, or about 0.1% to about 9%, or about 0.1% to about 8%, or about 0.1% to about 7%, or about 0.1% to about 6%, or about 0.1% to about 5%, or about 0.1% to about 4%, or about 0.1% to about 3%, or about 0.1% to about 2%, or about 0.1% to about 1%, or about 0.1% to about 0.9%, or about 0.1% to about 0.8%, or about 0.1% to about 0.7%, or about 0.1% to about 0.6%, or about 0.1% to about 0.5%, or about 0.1% to about 0.4%, or about 0.1% to about 0.3%, or about 0.1% to about 0.2% increase in the population of $T_R1$ cells.

For the therapeutic use, the following diseases can be combined with the following antigen-MHC complexes and compositions containing them:

In some embodiments, the antigen of the pMHC complex comprises a:

a) a diabetes-relevant antigen and is derived from antigen selected from one or more of the group: preproinsulin (PPI), islet-specific glucose-6-phosphatase (IGRP), glutamate decarboxylase (GAD), islet cell autoantigen-2 (ICA2), insulin, proinsulin, or a fragment or an equivalent of each thereof;

b) a multiple sclerosis-relevant antigen and is derived from an antigen selected from one or more of the group: myelin basic protein, myelin associated glycoprotein, myelin oligodendrocyte protein, proteolipid protein, oligodendrocyte myelin oligoprotein, myelin associated oligodendrocyte basic protein, oligodendrocyte specific protein, heat shock proteins, oligodendrocyte specific proteins, NOGO A, glycoprotein Po, peripheral myelin protein 22, 2'3'-cyclic nucleotide 3'-phosphodiesterase, or a fragment or an equivalent of each thereof;

c) a Celiac Disease-relevant antigen and is derived from gliadin or a fragment or an equivalent thereof;

d) a primary biliary cirrhosis-relevant antigen and is derived from PDC-E2 or a fragment or an equivalent thereof;

e) a pemphigus folliaceus-relevant antigen and/or pemphigus vulgaris-relevant antigen and is derived from an antigen selected from one or more of the group: DG1, DG3, or a fragment or an equivalent of each thereof;

f) a neuromyelitis optica spectrum disorder-relevant antigen and is derived from AQP4 or a fragment or an equivalent thereof;

g) an arthritis-relevant antigen and is derived from an antigen selected from one or more of the group: heat shock proteins, immunoglobulin binding protein, heterogeneous nuclear RNPs, annexin V, calpastatin, type II collagen, glucose-6-phosphate isomerase, elongation factor human cartilage gp39, mannose binding lectin, citrullinated vimentin, type II collagen, fibrinogen, alpha enolase, anti-carbamylated protein (anti-CarP), peptidyl arginine deiminase type 4 (PAD4), BRAF, fibrinogen gamma chain, inter-alpha-trypsin inhibitor heavy chain H1, alpha-1-antitrypsin, plasma protease C1 inhibitor, gelsolin, alpha 1-B glycoprotein, ceruloplasmin, inter-alpha-trypsin inhibitor heavy chain H4, complement factor H, alpha 2 macroglobulin, serum amyloid, C-reactive protein, serum albumin, fibrogen beta chain, serotransferin, alpha 2 HS glycoprotein, vimentin, Complement C3, or a fragment or an equivalent of each thereof;

h) an allergic asthma-relevant antigen and is derived from an antigen selected from one or more of the group: DERP1, DERP2, or a fragment or an equivalent of each thereof;

i) an inflammatory bowel disease-relevant antigen and is derived from an antigen selected from one or more of the group: Flagelin, Fla-2, Fla-X, YIDX, bacteroides integrase, or a fragment or an equivalent of each thereof;

j) a systemic lupus erythematosus-relevant antigen and is derived from an antigen selected from one or more of the group: double-stranded (ds)DNA, ribonucleoprotein (RNP), Smith (Sm), Sjogreds-syndrome-related antigen A (SS-A)/Ro, Sjögren's-syndrome-related antigen B (SS-B)/La, RO60, RO52, histones, or a fragment or an equivalent of each thereof;

k) an atherosclerosis-relevant antigen and is derived from an antigen selected from one or more of the group: ApoB, ApoE or a fragment or an equivalent of each thereof;

l) a COPD-relvant antigen and/or emphysema-relevant antigen and is derived from elastin or a fragment or an equivalent thereof;

m) a psoriasis-relevant antigen and is derived from an antigen selected from one or more of the group: Cap18, ADMTSL5, ATL5, or a fragment or an equivalent of each thereof;

n) an autoimmune hepatitis-relevant antigen and is derived from an antigen selected from one or more of the group: CYP2D6, SLA, or a fragment or an equivalent of each thereof;

o) an uveitis-relevant antigen and is derived from arrestin or a fragment or an equivalent thereof;

p) a Sjogren's Syndrome-relevant antigen and is derived from an antigen selected from one or more of the group: (SS-A)/Ro, (SS-B)/La, MR3, RO60, RO52, or a fragment or an equivalent of each thereof;

q) a scleroderma-relevant antigen and is derived from an antigen selected from one or more of the group: CENP-C, TOP 1, RNA polymerase III, or a fragment or an equivalent of each thereof;

r) an anti-phospholipid syndrome-relevant antigen and is derived from APOH or a fragment or an equivalent thereof;

s) an ANCA-associated vasculitis-relevant antigen and is derived from an antigen selected from one or more of the gropu: MPO, PRTN3, or a fragment or an equivalent of each thereof; or t) a Stiff Man Syndrome-relevant antigen and is derived from GAD or a fragment or an equivalent thereof.

In some embodiments, the MHC protein of the pMHC complex comprises all or part of a classical MHC class I protein, non-classical MHC class I protein, classical MHC class II protein, non-classical MHC class II protein, MHC dimers (Fc fusions), MHC tetramers, or a polymeric form of a MHC protein, wherein the MHC protein optionally comprises a knob-in-hole based MHC-alpha-Fc/MHC-beta-Fc heterodimer or multimer.

In some embodiments, the MHC protein of the pMHC complex comprises all or part of a polypeptide of the group: HLA DR, HLA DQ, HLA DP, HLA-A, HLA-B, HLA-C, HLA-E, HLA-F, HLA-G, CD1d, or a fragment or an equivalent of each thereof.

In some embodiments, the MHC protein of the pMHC complex comprises all or part of a polypeptide of the group: HLA-DR, HLA-DQ, HLA-DP, or a fragment or an equivalent of each thereof In some embodiments, the MHC protein of the pMHC complex comprises all or part of a polypeptide of the group: HLA-DRB1/DRA, HLA-DRB3/DRA, HLA-DRB4/DRA, HLA-DRB5/DRA, HLA-DQA1/HLA-DQB1, HLA-DPB1/HLA-DPA1, or a fragment or an equivalent of each thereof.

In certain aspects, the pMHC complex comprises:

a) a diabetes-relevant antigen derived from an antigen selected from one or more of the group: $hInsB_{10-18}$, $hIGRP_{228-236}$, $hIGRP_{265-273}$, $IGRP_{206-214}$, $hIGRP_{206-214}$, NRP-A7, NRP-I4, NRP-V7, $YAI/D^b$, $INS\ B_{15-23}$, $PPI_{76-90\ (K88S)}$, $IGRP_{13-25}$, $GAD_{555-567}$, $GAD_{555-567(557I)}$, $IGRP_{23-35}$, $B_{24}$-$C_{36}$, $PP_{176-90}$, INS-I9, TUM, G6Pase, Pro-insulin$_{L2-10}$Pro-insulin$_{L2-11}$, Pro-insulin$_{L6-14}$, Pro-insulin$_{B5-14}$, Pro-insulin$_{B10-18}$, Pro-insulin$_{B14-22}$, Pro-insulin$_{B15-24}$, Pro-insulin$_{B17-25}$, Pro-insulin$_{B18-27}$, Pro-insulin$_{B20-27}$, Pro-insulin$_{B21-29}$, Pro-insulin$_{B25-C1}$, Pro-insulin$_{B27-C5}$, Pro-insulin$_{C20-28}$, Pro-insulin$_{C25-33}$, Pro-insulin$_{C29-A5}$, Pro-insulin$_{A1-10}$, Pro-insulin$_{A2-10}$, Pro-insulin$_{A12-20}$, or a fragment or an equivalent of each thereof;

b) a multiple sclerosis-relevant antigen derived from an antigen selected from one or more of the group: $MOG_{35-55}$, $MOG_{36-55}$, $MAG_{287-295}$, $MAG_{509-517}$, $MAG_{556-564}$, $MBP_{110-118}$, $MOG_{114-122}$, $MOG_{166475}$, $MOG_{172-180}$, $MOG_{179-188}$, $MOG_{188-196}$, $MOG_{181-189}$, $MOG_{205-214}$, $PLP_{80-88}$, $MAG_{287-295}$, $MAG_{509-517}$, $MAG_{556-564}$, $MOG_{97-109}$, $MOG_{97-109(E107S)}$, $MBP_{89-101}$, $PLP_{175-192}$, $PLP_{94-108}$, $MBP_{86-98}$, $PLP_{54-68}$, $PLP_{249-263}$, $MOG_{156-170}$, $MOG_{201-215}$, $MOG_{38-52}$, $MOG_{203-217}$, $PLP_{250-264}$, $MPB_{13-32}$, $MPB_{83-99}$, $MPB_{111-129}$, $MPB_{146-170}$, $MOG_{223-237}$, $MOG_{6-20}$, $PLP_{88-102}$, $PLP_{139-154}$, or a fragment or an equivalent of each thereof;

c) a Celiac Disease-relevant antigen derived from an antigen selected from one or more of the group: $aGlia_{57-68}$, $aGlia_{62-72}$, $aGlia_{217-229}$, or a fragment or an equivalent of each thereof;

d) a primary biliary cirrhosis-relevant antigen derived from an antigen selected from one or more of the group: $PDC-E2_{122-135}$, $PDC-E2_{249-262}$, $PDC-E2_{249-263}$, $PDC-E2_{629-643}$, $PDC-E2_{72-86}$, $PDC-E2_{353-367}$, $PDC-E2_{422-436}$, $PDC-E2_{629-643}$, $PDC-E2_{80-94}$, $PDC-E2_{353-367}$, $PDC-E2_{535-546}$, or a fragment or an equivalent of each thereof;

e) a pemphigus folliaceus-relevant antigen and/or pemphigus vulgaris-relevant antigen, each of which is derived from an antigen selected from one or more of the group: $DG1_{216-229}$, $DG3_{97-111}$, $DG3_{251-265}$, $DG3_{441-455}$, $DG3_{351-365}$, $DG3_{453-467}$, $DG3_{540-554}$, $DG3_{280-294}$, $DG3_{326-340}$, $DG3_{367-381}$, $DG3_{13-27}$, $DG3_{323-337}$, $DG3_{438-452}$, $DG1_{48-62}$, $DG1_{206-222}$, $DG1_{363-377}$, $DG1_{3-17}$, $DG1_{192-206}$, $DG1_{326-340}$, $DG1_{145}$, $DG1_{35-49}$, $DG1_{325-339}$, or a fragment or an equivalent of each thereof;

f) a neuromyelitis optica spectrum disorder-relevant antigen derived from an antigen selected from one or more of the group: $AQP4_{129-143}$, $AQP4_{284-298}$, $AQP4_{63-76}$, $AQP4_{129-143}$, $AQP4_{39-53}$, or a fragment or an equivalent of each thereof;

g) an allergic asthma-relevant antigen derived from an antigen selected from one or more of the group: $DERP1_{16-30}$, $DERP1_{171-185}$, $DERP1_{110-124}$, $DERP-2_{26-40}$, $DERP-2_{107-121}$, or a fragment or an equivalent of each thereof;

h) an inflammatory bowel disease-relevant antigen derived from an antigen selected from one or more of the group: bacteroides integrase antigen$_{183-197}$, bacteroides integrase antigen$_{146-160}$, bacteroides integrase antigen$_{175-189}$, bacteroides integrase antigen$_{1-15}$, bacteroides integrase antigen$_{183-197}$, bacteroides integrase antigen$_{30-44}$, bacteroides integrase antigen$_{70-84}$, bacteroides integrase antigen$_{337-351}$, bacteroides integrase antigen$_{171-185}$, bacteroides integrase antigen$_{4-18}$, bacteroides integrase antigen$_{256-270}$, Fla-2/Fla-$X_{366-380}$, 2/Fla-$X_{164-178}$, Fla-2/Fla-$X_{261-275}$, Fla-2/Fla-$X_{1-15}$, Fla-2/Fla-$X_{51-65}$, Fla-2/Fla-$X_{269-283}$, 2/Fla-$X_{4-18}$, Fla-2/Fla-$X_{271-285}$, $YIDX_{78-92}$, $YIDX_{93-107}$, $YIDX_{98-112}$, $YIDX_{23-37}$, $YIDX_{78-92}$, $YIDX_{195-209}$, $YIDX_{22-36}$, $YIDX_{80-94}$, $YIDX_{101-115}$, or a fragment or an equivalent of each thereof;

i) a systemic lupus erythematosus-relevant antigen derived from an antigen selected from one or more of the group: $H4_{71-94}$, $H4_{74-88}$, $H4_{76-90}$, $H4_{75-89}$, $H4_{78-92}$, $H4_{80-94}$, $H2B_{10-24}$, $H2B_{16-30}$, $H1'_{22-42}$, $H1'_{27-41}$, or a fragment or an equivalent of each thereof;

j) an atherosclerosis-relevant antigen derived from an antigen selected from one or more of the group: $ApO\ B_{3501-3516}$, $ApOB_{1952-1966}$, $ApoB_{978-993}$, $ApoB_{3498-3513}$, $ApoB_{210A}$, $ApoB_{210B}$, $ApoB_{210C}$, or a fragment or an equivalent of each thereof;

k) a COPD-relvant antigen and/or emphysema-relevant antigen, each of which is derived from an antigen selected from one or more of the group: elastin$_{89-103}$, elastin$_{698-712}$, elastin$_{8-22}$, elastin$_{94-108}$, elastin$_{13-27}$, elastin$_{695-709}$, elastin$_{563-577}$, elastin$_{558-572}$, elastin$_{698-712}$, elastin$_{566-580}$, elastin$_{645-659}$, or a fragment or an equivalent of each thereof;

l) a psoriasis-relevant antigen derived from an antigen selected from one or more of the group: $Cap18_{64-78}$, $Cap18_{34-48}$, $Cap18_{47-61}$, $Cap18_{151-165}$, $Cap18_{149-163}$, $Cap1_{152-166}$, $Cap18_{131-145}$, $Cap18_{24-38}$, $ADMTSL5_{245-259}$, $ADMTSL5_{267-281}$, $ADMTSL5_{372-386}$, $ADMTSL5_{289-303}$, $ADMTSL5_{396-410}$, $ADMTSL5_{433-447}$, $ADMTSL5_{142-156}$, $ADMTSL5_{236-250}$, $ADMTSL5_{301-315}$, $ADMTSL5_{203-217}$, $ADMTSL5_{404-418}$, or a fragment or an equivalent of each thereof;

m) an autoimmune hepatitis-relevant antigen derived from an antigen selected from one or more of the group: (CYP2D6)$_{193-207}$, CYP2D6$_{76-90}$, CYP2D6$_{293-307}$, CYP2D6$_{313-332}$, CYP2D6$_{393-412}$, CYP2D6$_{166-213}$, CYP2D6$_{450-464}$, CYP2D6$_{301-315}$, CYP2D6$_{452-466}$, CYP2D6$_{59-73}$, CYP2D6$_{130-144}$, CYP2D6$_{193-212}$, CYP2D6$_{305-324}$, CYP2D6$_{131-145}$, CYP2D6$_{216-230}$, CYP2D6$_{238-252}$, CYP2D6$_{199-213}$, CYP2D6$_{235-252}$, CYP2D6$_{293-307}$, CYP2D6$_{381-395}$, CYP2D6$_{429-443}$, SLA$_{334-348}$, SLA$_{196-210}$, SLA$_{115-126}$, SLA$_{373-386}$, SLA$_{186-167}$, SLA$_{317-331}$, SLA$_{171-185}$, SLA$_{417-431}$, SLA$_{359-373}$, SLA$_{215-226}$, SLA$_{111-125}$, SLA$_{110-124}$, SLA$_{299-313}$, SLA$_{342-356}$, SLA$_{49-63}$, SLA$_{119-133}$, SLA$_{260-274}$, SLA$_{26-40}$, SLA$_{86-100}$, SLA$_{331-345}$, or a fragment or an equivalent of each thereof;

n) an uveitis-relevant antigen derived from an antigen selected from one or more of the group: arrestin$_{100-213}$, arrestin$_{77-91}$, arrestin$_{250-264}$, arrestin$_{172-186}$, arrestin$_{354-368}$, arrestin$_{239-253}$, arrestin$_{102-116}$, arrestin$_{59-73}$, arrestin$_{280-294}$, arrestin$_{291-306}$, arrestin$_{195-209}$, arrestin$_{200-214}$, or a fragment or an equivalent of each thereof;

o) a Sjogren's Syndrome-relevant antigen derived from an antigen selected from one or more of the group: RO60$_{127-141}$, RO60$_{523-537}$, RO60$_{243-257}$, RO60$_{484-498}$, RO60$_{347-361}$, RO60$_{366-383}$, RO60$_{426-440}$, RO60$_{267-281}$, RO60$_{178-162}$, RO60$_{358-372}$, RO60$_{221-235}$, RO60$_{318-332}$, RO60$_{407-421}$, RO60$_{459-473}$, RO60$_{51-65}$, RO60$_{312-326}$, LA$_{241-255}$, LA$_{101-115}$, LA$_{153-167}$, LA$_{178-192}$, LA$_{19-33}$, LA$_{37-51}$, LA$_{133-147}$, LA$_{50-64}$, LA$_{32-46}$, LA$_{153-167}$, LA$_{83-97}$, LA$_{136-150}$, LA$_{297-311}$, LA$_{59-73}$, LA$_{151-165}$, LA$_{86-100}$, LA$_{154-168}$, or a fragment or an equivalent of each thereof;

p) a scleroderma-relevant antigen derived from an antigen selected from one or more of the group: TOP1$_{346-360}$, TOP1$_{420-434}$, TOP1$_{750-764}$, TOP1$_{419-433}$, TOP1$_{591-605}$, TOP1$_{695-709}$, TOP1$_{1305-319}$, TOP1$_{346-360}$, TOP1$_{419-433}$, TOP1$_{425-439}$, TOP1$_{614-628}$, CENP-C$_{297-311}$, CENP-C$_{857-871}$, CENP-C$_{887-901}$, CENP-C$_{212-226}$, CENP-C$_{643-657}$, CENP-C$_{832-846}$, CENP-C$_{167-181}$, CENP-C$_{246-260}$, CENP-C$_{846-860}$, CENP-C$_{149-163}$, CENP-C$_{833-847}$, CENP-C$_{847-861}$, or a fragment or an equivalent of each thereof;

q) an anti-phospholipid syndrome-relevant antigen derived from an antigen selected from one or more of the group: APOH$_{235-249}$, APOH$_{306-320}$, APOH$_{237-251}$, APOH$_{295-309}$, APOH$_{28-42}$, APOH$_{173-187}$, APOH$_{264-278}$, APOH$_{295-309}$, APOH$_{49-63}$, APOH$_{269-283}$, APOH$_{295-309}$, APOH$_{321-355}$, APOH$_{322-336}$, APOH$_{324-338}$, or a fragment or an equivalent of each thereof;

r) an ANCA-associated vasculitis-relevant antigen derived from an antigen selected from one or more of the group: MPO$_{506-520}$, MPO$_{302-316}$, MPO$_{7-21}$, MPO$_{689-703}$, MPO$_{248-262}$, MPO$_{444-458}$, MPO$_{513-527}$, MPO$_{97-111}$, MPO$_{616-630}$, MPO$_{462-476}$, MPO$_{617-631}$, MPO$_{714-728}$, PRTN3$_{44-58}$, PRTN3$_{234-248}$, PRTN3$_{59-73}$, PRTN3$_{117-131}$, PRTN3$_{164-178}$, PRTN3$_{71-85}$, PRTN3$_{241-255}$, PRTN3$_{59-73}$, PRTN3$_{183-197}$, PRTN3$_{62-76}$, PRTN3$_{118-132}$, PRTN3$_{239-253}$, or a fragment or an equivalent of each thereof; or s) a Stiff Man Syndrome-relevant antigen derived from an antigen selected from one or more of the group: GAD$_{212-226}$, GAD$_{555-569}$, GAD$_{297-311}$, or a fragment or an equivalent of each thereof.

In certain aspects, the pMHC complex comprises:

a) a diabetes-relevant antigen derived from an antigen selected from one or more of the group: hInsB$_{10-18}$, hIGRP$_{228-236}$, hIGRP$_{265-273}$, IGRP$_{206-214}$, hIGRP$_{206-214}$, NRP-A7, NRP-I4, NRP-V7, YAI/D$^b$, INS B$_{15-23}$, PPI$_{76-90(K88S)}$, IGRP$_{13-25}$, GAD$_{555-567}$, GAD$_{555-567(557I)}$, IGRP$_{23-35}$, B$_{24}$-C$_{36}$, PPI$_{76-90}$, INS-I9, TUM, G6Pase, Pro-insulin$_{L2-10}$, Pro-insulin$_{L3-11}$, Pro-insulin$_{L6-14}$, Pro-insulin$_{B5-14}$, Pro-insulin$_{B10-18}$, Pro-insulin$_{B14-22}$, Pro-insulin$_{B15-24}$, Pro-insulin$_{B17-25}$, Pro-insulin$_{B18-27}$, Pro-insulin$_{B20-27}$, Pro-insulin$_{B21-29}$, Pro-insulin$_{B25-C1}$, Pro-insulin$_{B27-C5}$, Pro-insulin$_{C20-28}$, Pro-insulin$_{C25-33}$, Pro-insulin$_{C29-A5}$, Pro-insulin$_{41-10}$, Pro-insulin$_{42-10}$, Pro-insulin$_{412-20}$, or a fragment or an equivalent of each thereof, and the MHC protein of the pMHC complex comprises all or part of HLA-DR or a fragment or an equivalent thereof;

b) a multiple sclerosis-relevant antigen derived from an antigen selected from one or more of the group: MOG$_{35-55}$, MOG$_{36-55}$, MAG$_{287-295}$, MAG$_{509-517}$, MAG$_{556-564}$, MBP$_{110-118}$, MOG$_{114-122}$, MOG$_{166-175}$, MOG$_{172-180}$, MOG$_{179-188}$, MOG$_{188-196}$, MOG$_{181-189}$, MOG$_{205-214}$, PLP$_{80-88}$, MAG$_{287-295}$, MAG$_{509-517}$, MAG$_{556-564}$, MOG$_{97-109}$ MOG$_{97-109(E107S)}$, MBP$_{89-101}$, PLP$_{175-192}$, PLP$_{94-108}$, MBP$_{86-98}$, PLP$_{54-68}$, PLP$_{249-263}$, MOG$_{156-170}$, MOG$_{201-215}$, MOG$_{38-52}$, MOG$_{203-217}$, PLP$_{250-264}$, MPB$_{13-32}$, MPB$_{83-99}$, MPB$_{111-129}$, MPB$_{146-170}$, MOG$_{223-237}$, MOG$_{6-20}$, PLP$_{88-102}$, PLP$_{139-154}$, or a fragment or an equivalent of each thereof, and the MHC protein of the pMHC complex comprises all or part of HLA-DR or a fragment or an equivalent thereof;

c) a Celiac Disease-relevant antigen derived from an antigen selected from one or more of the group: aGlia$_{57-68}$, aGlia$_{62-72}$, aGlia$_{217-229}$, or a fragment or an equivalent of each thereof, and the MHC protein of the pMHC complex comprises all or part of HLA-DQ or a fragment or an equivalent thereof;

d) a primary biliary cirrhosis-relevant antigen derived from an antigen selected from one or more of the group: PDC-E2$_{122-135}$, PDC-E2$_{249-262}$, PDC-E2$_{249-263}$, PDC-E2$_{629-643}$, PDC-E2$_{72-86}$, PDC-E2$_{353-367}$, PDC-E2$_{422-436}$, PDC-E2$_{80-94}$, PDC-E2$_{353-367}$, PDC-PDC-E2$_{629-643}$, E2$_{535-549}$, or a fragment or an equivalent of each thereof, and the MHC protein of the pMHC complex comprises all or part of HLA-DR or a fragment of an equivalent thereof;

e) a pemphigus folliaceus-relevant antigen and/or pemphigus vulgaris-relevant antigen, each of which is derived from an antigen selected from one or more of the group: DG1$_{216-229}$, DG3$_{97-111}$, DG3$_{251-265}$, DG3$_{441-455}$, DG3$_{351-365}$, DG3$_{453-467}$, DG3$_{540-554}$, DG3$_{280-294}$, DG3$_{326-340}$, DG3$_{367-381}$, DG3$_{13-27}$, DG3$_{323-337}$, DG3$_{438-452}$, DG1$_{48-62}$, DG1$_{206-222}$, DG1$_{363-377}$, DG1$_{347}$, DG1$_{192-206}$, DG1$_{326-340}$, DG1$_{145}$, DG1$_{35-49}$, DG1$_{325-339}$, or a fragment or an equivalent of each thereof, and the MHC protein of the pMHC complex comprises all or part of HLA-DR or a fragment or an equivalent thereof;

f) a neuromyelitis optica spectrum disorder-relevant antigen derived from an antigen selected from one or more of the group: AQP4$_{129-143}$, AQP4$_{284-298}$, AQP4$_{63-76}$, AQP 4$_{129-143}$, AQP4$_{39-53}$, or a fragment or an equivalent of each thereof, and the MHC protein of the pMHC complex comprises all or part of HLA-DR or a fragment or an equivalent thereof;

g) an allergic asthma-relevant antigen derived from an antigen selected from one or more of the group: DERP1$_{16-30}$, DERP1$_{171-185}$, DERP1$_{110-124}$, DERP-2$_{26-40}$, DERP-2$_{107-121}$, or a fragment or an equivalent of each thereof, and the MHC protein of the pMHC complex comprises all or part of a polypeptide of the group: HLA-DR, HLA-DP, or a fragment or an equivalent of each thereof;

h) an inflammatory bowel disease-relevant antigen derived from an antigen selected from one or more of the group: bacteroides integrase antigen$_{183-197}$, bacteroides integrase antigen$_{146-160}$, bacteroides integrase antigen$_{175-189}$, bacteroides integrase antigen$_{1-15}$, bacteroides integrase antigen$_{183-197}$, bacteroides integrase antigen$_{30-44}$, bacteroides integrase antigen$_{70-84}$, bacteroides integrase antigen$_{337-351}$, bacteroides integrase antigen$_{171-185}$, bacteroides integrase antigen$_{4-18}$, bacteroides integrase antigen$_{256-270}$, Fla-2/Fla-X$_{366-380}$, Fla-2/Fla-X$_{164-178}$, Fla-2/Fla-X$_{261-275}$, Fla-2/Fla-X$_{1-15}$, Fla-2/Fla-X$_{51-65}$, Fla-2/Fla-X$_{269-283}$, Fla-2/Fla-X$_{4-18}$, Fla-2/Fla-X$_{271-285}$, YIDX$_{78-92}$, YIDX$_{93-107}$, YIDX$_{98-112}$, YIDX$_{23-37}$, YIDX$_{78-92}$, YIDX$_{195-209}$, YIDX$_{22-36}$, YIDX$_{80-94}$, YIDX$_{101-115}$, or a fragment or an equivalent of each thereof, and the MHC protein of the pMHC complex comprises all or part of HLA-DR or a fragment or an equivalent thereof;

i) a systemic lupus erythematosus-relevant antigen derived from an antigen selected from one or more of the group: H4$_{71-94}$, H4$_{74-88}$, H4$_{76-90}$, H4$_{75-89}$, H4$_{78-92}$, H4$_{80-94}$, H2B$_{10-24}$, H2B$_{16-30}$, H1'$_{22-42}$, H1'$_{27-41}$, or a fragment or an equivalent of each thereof, and the MHC protein of the pMHC complex comprises all or part of a polypeptide of the group: I-A$_d$, HLA-DR, or a fragment or an equivalent of each thereof;

j) an atherosclerosis-relevant antigen derived from an antigen selected from one or more of the group: Apo B$_{3501-3516}$, ApoB$_{1952-1966}$, ApOB$_{978-993}$, ApOB$_{3498-3513}$, ApoB$_{210A}$, ApoB$_{210B}$, ApoB$_{210C}$, or a fragment or an equivalent of each thereof, and the MHC protein of the pMHC complex comprises all or part of I-A$_b$, or a fragment or an equivalent thereof;

k) a COPD-relvant antigen and/or emphysema-relevant antigen, each of which is derived from an antigen selected from one or more of the group: elastin$_{89-103}$, elastin$_{698-712}$, elastin$_{8-22}$, elastin$_{94-108}$, elastin$_{13-27}$, elastin$_{695-709}$, elastin$_{563-577}$, elastin$_{558-572}$, elastin$_{698-712}$, elastin$_{566-580}$, elastin$_{645-659}$, or a fragment or an equivalent of each thereof, and the MHC protein of the pMHC complex comprises all or part of HLA-DR or a fragment or an equivalent thereof;

l) a psoriasis-relevant antigen derived from an antigen selected from one or more of the group: Cap18$_{64-78}$, Cap18$_{34-48}$, Cap18$_{47-61}$, Cap18$_{151-165}$, Cap18$_{149-163}$, Cap18$_{152-166}$, Cap18$_{131-145}$, Cap$_{1824-38}$, ADMTSL5245$_{-259}$, ADMTSL5$_{267-281}$, ADMTSL5$_{372-386}$, ADMTSL5$_{289-303}$, ADMTSL5$_{396-410}$, ADMTSL5$_{433-447}$, ADMTSL5$_{142-156}$, ADMTSL5$_{236-250}$, ADMTSL5$_{301-315}$, ADMTSL5$_{203-217}$, ADMTSL5$_{404-418}$, or a fragment or an equivalent of each thereof, and the MHC protein of the pMHC complex comprises all or part of HLA-DR or a fragment or an equivalent thereof;

m) an autoimmune hepatitis-relevant antigen derived from an antigen selected from one or more of the group: CYP2D6$_{193-207}$, CYP2D6$_{76-90}$, CYP2D6$_{293-307}$, CYP2D6$_{313-332}$, CYP2D6$_{393-412}$, CYP2D6$_{199-213}$, CYP2D6$_{450-464}$, CYP2D6$_{301-315}$, CYP2D6$_{452-466}$, CYP2D6$_{59-73}$, CYP2D6$_{130-144}$, CYP2D6$_{193-212}$, CYP2D6$_{305-324}$, CYP2D6$_{131-145}$, CYP2D6$_{216-230}$, CYP2D6$_{238-252}$, CYP2D6$_{199-213}$, CYP2D6$_{235-252}$, CYP2D6$_{293-307}$, CYP2D6$_{381-395}$, CYP2D6$_{429-443}$, SLA$_{334-348}$, SLA$_{196-210}$, SLA$_{115-129}$, SLA$_{373-386}$, SLA$_{186-197}$, SLA$_{317-331}$, SLA$_{171-185}$, SLA$_{417-431}$, SLA$_{359-373}$, SLA$_{215-229}$, SLA$_{111-125}$, SLA$_{110-124}$, SLA$_{299-313}$, SLA$_{342-356}$, SLA$_{49-63}$, SLA$_{119-133}$, SLA$_{260-274}$, SLA$_{26-40}$, SLA$_{86-100}$, SLA$_{331-345}$, or a fragment or an equivalent of each thereof, and the MHC protein of the pMHC complex comprises all or part of HLA-DR or a fragment or an equivalent thereof;

n) an uveitis-relevant antigen derived from an antigen selected from one or more of the group: arrestin$_{199-213}$, arrestin$_{77-91}$, arrestin$_{250-264}$, arrestin$_{172486}$, arrestin$_{354-368}$, arrestin$_{239-253}$, arrestin$_{102-116}$, arrestin$_{59-73}$, arrestin$_{280-294}$, arrestin$_{291-306}$, arrestin$_{195-209}$, arrestin$_{200-214}$, or a fragment or an equivalent of each thereof, and the MHC protein of the pMHC complex comprises all or part of HLA-DR or a fragment or an equivalent thereof;

o) a Sjogren's Syndrome-relevant antigen derived from an antigen selected from one or more of the group: RO60$_{127-141}$, RO60$_{523-537}$, RO60$_{243-257}$, RO60$_{484-498}$, RO60$_{347-361}$, RO60$_{369-383}$, RO60$_{426-440}$, RO60$_{267-281}$, RO60$_{178-192}$, RO60$_{358-372}$, RO60$_{221-235}$, RO60$_{318-332}$, RO60$_{407-421}$, RO60$_{459-473}$, RO60$_{51-65}$, RO60$_{312-326}$, LA$_{241-255}$, LA$_{101-115}$, LA$_{153-167}$, LA$_{178-192}$, LA$_{19-33}$, LA$_{37-51}$, LA$_{133-147}$, LA$_{50-64}$, LA$_{32-46}$, LA$_{153-167}$, LA$_{83-97}$, LA$_{136-150}$, LA$_{297-311}$, LA$_{59-73}$, LA$_{151-165}$, LA$_{86-100}$, LA$_{154-168}$, or a fragment or an equivalent of each thereof, and the MHC protein of the pMHC complex comprises all or part of a polypeptide of the group: HLA-DR, HLA-DP, or a fragment or an equivalent of each thereof;

p) a scleroderma-relevant antigen derived from an antigen selected from one or more of the group: TOP1$_{346-360}$, TOP1$_{420-434}$, TOP1$_{750-764}$, TOP1$_{419-433}$, TOP1$_{591-605}$, TOP1$_{695-709}$, TOP1$_{305-319}$, TOP1$_{346-360}$, TOP1$_{419-433}$, TOP1$_{425-439}$, TOP1$_{614-628}$, CENP-C$_{297-311}$, CENP-C$_{857-871}$, CENP-C$_{887-901}$, CENP-C$_{212-226}$, CENP-C$_{643-657}$, CENP-C$_{832-846}$, CENP-C$_{167-181}$, CENP-C$_{246-260}$, CENP-C$_{846-860}$, CENP-C$_{149-163}$, CENP-C$_{833-847}$, CENP-C$_{847-861}$, or a fragment or an equivalent of each thereof, and the MHC protein of the pMHC complex comprises all or part of HLA-DR or a fragment or an equivalent thereof;

q) an anti-phospholipid syndrome-relevant antigen derived from an antigen selected from one or more of the group: APOH$_{235-249}$, APOH$_{306-320}$, APOH$_{237-251}$, APOH$_{295-309}$, APOH$_{28-42}$, APOH$_{173-187}$, APOH$_{264-278}$, APOH$_{295-309}$, APOH$_{49-63}$, APOH$_{269-283}$, APOH$_{295-309}$, APOH$_{321-355}$, APOH$_{322-336}$, APOH$_{324-338}$, or a fragment or an equivalent of each thereof, and the MHC protein of the pMHC complex comprises all or part of HLA-DR or a fragment or an equivalent thereof;

r) an ANCA-associated vasculitis-relevant antigen derived from an antigen selected from one or more of the group: MPO$_{506-520}$, MPO$_{302-316}$, MPO$_{7-21}$, MPO$_{689-703}$, MPO$_{248-262}$, MPO$_{444-458}$, MPO$_{513-527}$, MPO$_{97-111}$, MPO$_{616-630}$, MPO$_{462-476}$, MPO$_{617-631}$, MPO$_{714-728}$, PRTN3$_{44-58}$, PRTN3$_{234-248}$, PRTN3$_{59-73}$, PRTN3$_{117-131}$, PRTN3$_{164-178}$, PRTN3$_{71-85}$, PRTN3$_{241-255}$, PRTN3$_{59-73}$, PRTN3$_{183-197}$, PRTN3$_{62-76}$, PRTN3$_{118-132}$, PRTN3$_{239-253}$, or a fragment or an equivalent of each thereof, and the MHC protein of the pMHC complex comprises all or part of HLA-DR or a fragment or an equivalent thereof; or s) a Stiff Man Syndrome-relevant antigen derived from an antigen selected from one or more of the group: GAD$_{212-226}$, GAD$_{555-569}$, GAD$_{297-311}$- and the MHC protein of the pMHC complex comprises all or part of a polypeptide of the group: HLA-DR, HLA-DQ, or a fragment or an equivalent of each thereof.

In certain aspects, the pMHC complex is for the treatment of:

a) type I diabetes and the pMHC complex is selected from the group of: PPI$_{76-90(K88S)}$-HLA-DRB1*0401/DRA, IGRP$_{13-25}$-HLA-DRB1*0301/DRA, GAD$_{555-567}$-HLA-DRB1*0401/DRA, GAD$_{555-567(557I)}$-HLA-DRB1*0401/DRA, IGRP$_{23-35}$-HLA-DRB1*0401/DRA, B$_{24}$—C$_{36}$-HLA-DRB1*0301/DRA, or PPI$_{76-90}$-HLA-DRB1*0401/DRA;

b) multiple sclerosis and the pMHC complex is selected from the group of: MBP$_{86-98}$-HLA-DRB1*1501/DRA, MBP$_{89-101}$-HLA-DRB5*0101/DRA, MOG$_{38-52}$-HLA-DRB4*0101/DRA, MOG$_{97-109(E107S)}$-HLA-DRB1*0401/DRA, MOG$_{203-217}$-HLA-DRB3*0101/DRA, PLP$_{54-68}$-HLA-DRB3*0101/DRA, PLP$_{94-108}$-HLA-DRB1*0301/

DRA, PLP$_{250-264}$-HLA-DRB4*0101/DRA, MPB$_{13-32}$-HLA-DRB5*0101/DRA, MPB$_{83-99}$-HLA-DRB5*0101/DRA, MPB$_{111-129}$-HLA-DRB5*0101/DRA, MPB$_{146-170}$-HLA-DRB5*0101/DRA, MOG$_{223-237}$-HLA-DRB3*0202/DRA, MOG$_{6-20}$-HLA-DRB5*0101/DRA, PLP$_{88-102}$-HLA-DRB3*0202/DRA, or PLP$_{139-154}$-HLA-DRB5*0101/DRA;

c) Celiac Disease and the pMHC complex is selected from the group of: aGlia$_{57-68}$-HLA-DQA1*0501/HLA-DQB1*0201, aGlia$_{62-72}$-HLA-DQA1*0501/HLA-DQB1*0201, aGlia$_{217-229}$-HLA-DQA1*0501/HLA-DQB1*0302, or aGlia$_{217-229}$-HLA-DQA1*03/HLA-DQB1*0302;

d) primary biliary cirrhosis and the pMHC complex is selected from the group of: PDC-E2$_{122-135}$-HLA-DRB4*0101/DRA, PDC-E2$_{249-262}$-HLA-DRB4*0101/DRA, PDC-E2$_{249-263}$-HLA-DRB1*0801/DRA, PDC-E2$_{629-643}$-HLA-DRB1*0801/DRA, PDC-E2$_{72-86}$-HLA-DRB3*0202/DRA, PDC-E2$_{353-367}$-HLA-DRB3*0202/DRA, PDC-E2$_{422-436}$-HLA-DRB3*0202/DRA, PDC-E2$_{629-643}$-HLA-DRB4*0101/DRA, PDC-E2$_{80-94}$-HLA-DRB5*0101/DRA, PDC-E2$_{353-367}$-HLA-DRB5*0101/DRA, or PDC-E2$_{535-549}$-HLA-DRB5*0101/DRA, mPDC-E2$_{166-181}$-I-A$_{g7}$, or mPDC-E2$_{82-96}$-I-A$_{g7}$;

e) pemphigus folliaceus and/or pemphigus vulgaris and the pMHC complex is selected from the group of: DG1$_{216-229}$-HLA-DRB1*0101/DRA, DG1$_{216-229}$-HLA-DRB1*0102/DRA, DG3$_{97-111}$-HLA-DRB1*0402/DRA, DG3$_{251-265}$-HLA-DRB1*0402/DRA, DG3$_{251-265}$-HLA-DRB1*0401/DRA, DG3$_{441-455}$-HLA-DRB1*0402/DRA, DG3$_{351-365}$-HLA-DRB3*0202/DRA, DG3$_{453-467}$-HLA-DRB3*0202/DRA, DG3$_{540-554}$-HLA-DRB3*0202/DRA, DG3$_{280-294}$-HLA-DRB4*0101/DRA, DG3$_{326-340}$-HLA-DRB4*0101/DRA, DG3$_{367-381}$-HLA-DRB4*0101/DRA, DG3$_{13-27}$-HLA-DRB5*0101/DRA, DG3$_{323-337}$-HLA-DRB5*0101/DRA, DG3$_{438-452}$-HLA-DRB5*0101/DRA, DG1$_{48-62}$-HLA-DRB3*0202/DRA, DG1$_{206-222}$-HLA-DRB3*0202/DRA, DG1$_{363-377}$-HLA-DRB3*0202/DRA, DG1$_{347}$-HLA-DRB4*0101/DRA, DG1$_{192-206}$-HLA-DRB4*0101/DRA, DG1$_{326-340}$-HLA-DRB4*0101/DRA, DG1$_{1-15}$-HLA-DRB5*0101/DRA, DG1$_{35-49}$-HLA-DRB5*0101/DRA, or DG1$_{325-339}$-HLA-DRB5*0101/DRA;

f) neuromyelitis optica spectrum disorder and the pMHC complex is selected from the group of: AQP4$_{129-143}$-HLA-DRB1*0101/DRA, AQP4$_{284-298}$-HLA-DRB1*0301/DRA, AQP4$_{63-76}$-HLA-DRB1*0301/DRA, AQP4$_{129-143}$-HLA-DRB1*0401/DRA, or AQP4$_{39-53}$-HLA-DRB1*1501/DRA;

g) allergic asthma and the pMHC complex is selected from the group of: DERP-1$_{16-30}$-FILA-DRB 1*0101/DRA, DERP-1$_{16-30}$-HLA-DRB1*1501/DRA, DERP1$_{171-185}$-HLA-DRB1*1501/DRA, DERP-1$_{110-124}$-HLA-DPB1*0401/DRA, DERP-2$_{26-40}$-HLA-DRB1*0101/DRA; DERP-2$_{26-40}$-HLA-DRB1*1501/DRA, or DERP-2$_{107-121}$-HLA-DRB1*0301/DRA;

h) inflammatory bowel disease and the pMHC complex is selected from the group of: bacteroides integrase antigen$_{183-197}$ HLA-DRB3*0101/DRA, bacteroides integrase antigen$_{146-160}$-HLA-DRB3*0101/DRA, bacteroides integrase antigen$_{175-189}$-HLA-DRB3*0101/DRA, bacteroides integrase antigen$_{1-15}$-HLA-DRB5*0101/DRA, bacteroides integrase antigen$_{183-197}$-HLA-DRB5*0101/DRA, bacteroides integrase antigen$_{183-197}$-HLA-DRB3*0101/DRA, bacteroides integrase antigen$_{30-44}$-HLA-DRB5*0101/DRA, bacteroides integrase antigen$_{70-84}$-HLA-DRB4*0101/DRA, bacteroides integrase antigen$_{337-351}$-HLA-DRB4*0101/DRA, bacteroides integrase antigen$_{171-185}$-HLA-DRB4*0101/DRA, bacteroides integrase antigen$_{4-18}$-HLA-DRB3*0202/DRA, bacteroides integrase antigen$_{171-185}$-HLA-DRB3*0202/DRA, bacteroides integrase antigen$_{256-270}$-HLA-DRB3*0202/DRA, Fla-2/Fla-X$_{366-380}$-HLA-DRB3*0101/DRA, Fla-2/Fla-X$_{164-178}$-HLA-DRB3*0101/DRA, Fla-2/Fla-X$_{261-275}$-HLA-DRB5*0101/DRA, Fla-2/Fla-X$_{1-15}$-HLA-DRB5*0101/DRA, Fla-2/Fla-X$_{51-65}$-HLA-DRB4*0101/DRA, Fla-2/Fla-X$_{269-283}$-HLA-DRB4*0101/DRA, Fla-2/Fla-X$_{4-18}$-HLA-DRB3*0202/DRA, Fla-2/Fla-X$_{261-275}$-HLA-DRB3*0202/DRA, Fla-2/Fla-X$_{271-285}$-HLA-DRB3*0202/DRA, YIDX$_{78-92}$-HLA-DRB3*0101/DRA, YIDX$_{78-92}$-HLA-DRB4*0101/DRA, YIDX$_{93-107}$-HLA-DRB3*0101/DRA, YIDX$_{98-112}$-HLA-DRB5*0101/DRA, YIDX$_{23-37}$-HLA-DRB5*0101/DRA, YIDX$_{78-92}$-HLA-DRB4*0101/DRA, YIDX$_{195-209}$-HLA-DRB4*0101/DRA, YIDX$_{22-36}$-HLA-DRB3*0202/DRA, YIDX$_{80-94}$-HLA-DRB3*0202/DRA, or YIDX$_{101-115}$-HLA-DRB3*0202/DRA;

i) COPD and/or emphysema and the pMHC complex is selected from the group of: elastin$_{89-103}$-HLA-DRB3*0101/DRA, elastin$_{698-712}$-HLA-DRB5*0101/DRA, elastin$_{8-22}$-HLA-DRB5*0101/DRA, elastin$_{94-108}$-HLA-DRB5*0101/DRA, elastin$_{13-27}$-HLA-DRB4*0101/DRA, elastin$_{695-709}$-HLA-DRB4*0101/DRA, elastin$_{563-577}$-HLA-DRB4*0101/DRA, elastin$_{558-572}$-HLA-DRB4*0101/DRA, elastin$_{698-712}$-HLA-DRB5*0101/DRA, elastin$_{566-580}$-HLA-DRB3*0202/DRA, or elastin$_{645-659}$-HLA-DRB3*0202/DRA;

j) psoriasis and the pMHC complex is selected from the group of: Cap18$_{64-78}$-HLA-DRB3*0101/DRA, Cap18$_{34-48}$-HLA-DRB3*0101/DRA, Cap18$_{47-61}$-HLA-DRB3*0101/DRA, Cap18$_{151-165}$-HLA-DRB4*0101/DRA, Cap18$_{149-163}$-HLA-DRB5*0101/DRA, Cap18$_{152-166}$-HLA-DRB5*0101/DRA, Cap18$_{131-145}$-HLA-DRB5*0101/DRA, Cap$_{1824-38}$-HLA-DRB3*0202/DRA, ADMTSL5$_{245-259}$-HLA-DRB3*0101/DRA, ADMTSL5$_{267-281}$-HLA-DRB3*0101/DRA, ADMTSL5$_{372-386}$-HLA-DRB3*0101/DRA, ADMTSL5$_{289-303}$-HLA-DRB4*0101/DRA, ADMTSL5$_{396-410}$-HLA-DRB4*0101/DRA, ADMTSL5$_{433-447}$-HLA-DRB4*0101/DRA, ADMTSL5$_{142-156}$-HLA-DRB5*0101/DRA, ADMTSL5$_{236-250}$-HLA-DRB5*0101/DRA, ADMTSL5$_{301-315}$-HLA-DRB5*0101/DRA, ADMTSL5$_{203-217}$-HLA-DRB3*0202/DRA, ADMTSL5$_{404-418}$-HLA-DRB3*0202/DRA, or ADMTSL5$_{433-447}$-HLA-DRB3*0202/DRA;

k) autoimmune hepatitis and the pMHC complex is selected from the group of: CYP2D6$_{193-207}$-HLA-DRB1*0301/DRA, CYP2D6$_{76-90}$-HLA-DRB1*0301/DRA, CYP2D6$_{293-307}$-HLA-DRB1*0301/DRA, CYP2D6$_{313-332}$-HLA-DRB1*0301/DRA, CYP2D6$_{393-412}$-HLA-DRB1*0301/DRA, CYP2D6$_{199-213}$-HLA-DRB1*0401/DRA, CYP2D6$_{450-464}$-HLA-DRB1*0401/DRA, CYP2D6$_{301-315}$-HLA-DRB1*0401/DRA, CYP2D6$_{452-466}$-HLA-DRB1*0701/DRA, CYP2D6$_{59-73}$-HLA-DRB1*0701/DRA, CYP2D6$_{130-144}$-HLA-DRB1*0701/DRA, CYP2D6$_{193-212}$-HLA-DRB1*0701/DRA, CYP2D6$_{305-324}$-HLA-DRB1*0701/DRA, CYP2D6$_{131-145}$-HLA-DRB3*0202/DRA, CYP2D6$_{216-230}$-HLA-DRB3*0202/DRA, CYP2D6$_{238-252}$-HLA-DRB3*0202/DRA, CYP2D6$_{199-213}$-HLA-DRB4*0101/DRA, CYP2D6$_{235-252}$-HLA-DRB4*0101/DRA, CYP2D6$_{293-307}$-HLA-DRB4*0101/DRA, CYP2D6$_{238-252}$-HLA-DRB5*0101/DRA, CYP2D6$_{381-395}$-HLA-DRB5*0101/DRA, CYP2D6$_{429-443}$-HLA-DRB5*0101/DRA, SLA$_{334-348}$-HLA-DRB1*0301/DRA, SLA$_{196-210}$-HLA-DRB1*0301/DRA, SLA$_{115-129}$-HLA-DRB1*0301/DRA, SLA$_{373-386}$-HLA-DRB1*0301/DRA, SLA$_{186-197}$-HLA-DRB1*0301/DRA, SLA$_{317-331}$-HLA-DRB1*0401/DRA, SLA$_{171-185}$-HLA-DRB1*0401/DRA, SLA$_{417-431}$-HLA-DRB1*0401/DRA, SLA$_{359-373}$-HLA-DRB1*0701/DRA, SLA$_{215-229}$-

HLA-DRB1*0701/DRA, SLA$_{111-125}$-HLA-DRB1*0701/DRA, SLA$_{110-124}$-HLA-DRB3*0202/DRA, SLA$_{299-313}$-HLA-DRB3*0202/DRA, SLA$_{342-356}$-HLA-DRB3*0202/DRA, SLA$_{49-63}$-HLA-DRB4*0101/DRA, SLA$_{119-133}$-HLA-DRB4*0101/DRA, SLA$_{260-274}$-HLA-DRB4*0101/DRA, SLA$_{26-40}$-HLA-DRB5*0101/DRA, SLA$_{86-100}$-HLA-DRB5*0101/DRA, or SLA$_{331-345}$-HLA-DRB5*0101/DRA;

l) uveitis and the pMHC complex is selected from the group of: arrestin$_{199-213}$-HLA-DRB3*0101/DRA, arrestin$_{77-91}$-HLA-DRB3*0101/DRA, arrestin$_{250-264}$-HLA-DRB3*0101/DRA, arrestin$_{172-186}$-HLA-DRB4*0101/DRA, arrestin$_{354-368}$-HLA-DRB4*0101/DRA, arrestin$_{239-253}$-HLA-DRB4*0101/DRA, arrestin$_{102-116}$-HLA-DRB5*0101/DRA, arrestin$_{59-73}$-HLA-DRB5*0101, arrestin$_{280-294}$-HLA-DRB5*0101, arrestin$_{291-306}$-HLA-DRB1*0301/DRA, arrestin$_{195-209}$-HLA-DRB3*0202/DRA, arrestin$_{199-213}$-HLA-DRB3*0202/DRA, or arrestin$_{200-214}$-HLA-DRB3*0202/DRA;

m) Sjogren Syndrome and the pMHC complex is selected from the group of: RO60$_{127-141}$-HLA-DRB1*0301/DRA, RO60$_{523-537}$-HLA-DRB1*0301/DRA, RO60$_{243-257}$-HLA-DRB1*0301/DRA, RO60$_{484-498}$-HLA-DRB3*0101/DRA, RO60$_{347-361}$-HLA-DRB3*0101/DRA, RO60$_{369-383}$-HLA-DRB3*0101/DRA, RO60$_{426-440}$-HLA-DRB4*0101/DRA, RO60$_{267-281}$-HLA-DRB4*0101/DRA, RO60$_{178-192}$-HLA-DRB4*0101/DRA, RO60$_{358-372}$-HLA-DRB5*0101/DRA, RO60$_{358-372}$-HLA-DRB4*0101/DRA, RO60$_{221-235}$-HLA-DRB5*0101/DRA, RO60$_{221-235}$-HLA-DRB4*0101/DRA, RO60$_{318-332}$-HLA-DRB5*0101/DRA, RO60$_{318-332}$-HLA-DRB4*0101/DRA, RO60$_{407-421}$-HLA-DRB4*0101/DRA, RO60$_{407-421}$-HLA-DQA1*0501/HLA-DQB1*0201, RO60$_{459-473}$-HLA-DRB4*0101/DRA, RO60$_{459-473}$-HLA-DQA1*0501/HLA-DQB1*0201, RO60$_{318-332}$-HLA-DQA1*0501/HLA-DQB1*0201, RO60$_{51-65}$-HLA-DRB3*0202/DRA, RO60$_{312-326}$-HLA-DRB3*0202/DRA, RO60$_{347-361}$-HLA-DRB3*0202/DRA, LA$_{241-255}$-HLA-DRB1*0301/DRA, LA$_{101-115}$-HLA-DRB1*0301/DRA, LA$_{153-167}$-HLA-DRB1*0301/DRA, LA$_{178-192}$-HLA-DRB3*0101/DRA, LA$_{19-33}$-HLA-DRB3*0101/DRA, LA$_{37-51}$-HLA-DRB3*0101/DRA, LA$_{133-147}$-HLA-DRB4*0101/DRA, LA$_{50-64}$-HLA-DRB4*0101/DRA, LA$_{32-46}$-HLA-DRB4*0101/DRA, LA$_{153-167}$-HLA-DRB5*0101/DRA, LA$_{83-97}$-HLA-DRB5*0101/DRA, LA$_{136-150}$-HLA-DRB5*0101/DRA, LA$_{297-311}$-HLA-DQA1*0501/HLA-DQB1*0201, LA$_{59-73}$-HLA-DQA1*0501/HLA-DQB1*0201, LA$_{59-73}$-HLA-DRB4*0101/DRA, LA$_{151-165}$-HLA-DQA1*0501/HLA-DQB1*0201, LA$_{151-165}$-HLA-DRB4*0101/DRA, LA$_{297-311}$-HLA-DRB4*0101/DRA, LA$_{50-64}$-HLA-DRB3*0202/DRA, LA$_{86-100}$-HLA-DRB3*0202/DRA, or LA$_{154-168}$-HLA-DRB3*0202/DRA;

n) scleroderma and the pMHC complex is selected from the group of: TOP1$_{346-360}$-HLA-DRB3*0101/DRA, TOP1$_{420-434}$-HLA-DRB3*0101/DRA, TOP1$_{750-764}$-FILA-DRB3*0101/DRA, TOP1$_{419-433}$-HLA-DRB4*0101/DRA, TOP1$_{591-605}$-HLA-DRB4*0101/DRA, TOP1$_{695-709}$-HLA-DRB4*0101/DRA, TOP1$_{305-319}$-HLA-DRB5*0101/DRA, TOP1$_{346-360}$-HLA-DRB5*0101/DRA, TOP1$_{419-433}$-HLA-DRB5*0101/DRA, TOP1$_{420-434}$-HLA-DRB3*0202/DRA, TOP1$_{425-439}$-HLA-DRB3*0202/DRA, TOP1$_{614-628}$-HLA-DRB3*0202/DRA, CENP-C$_{297-311}$-HLA-DRB3*0101/DRA, CENP-C$_{857-871}$-HLA-DRB3*0101/DRA, CENP-C$_{887-901}$-HLA-DRB3*0101/DRA, CENP-C$_{212-226}$-HLA-DRB4*0101/DRA, CENP-C$_{643-657}$-HLA-DRB4*0101/DRA, CENP-C$_{832-846}$-HLA-DRB4*0101/DRA, CENP-C$_{167-181}$-HLA-DRB5*0101/DRA, CENP-C$_{246-260}$-HLA-DRB5*0101/DRA, CENP-C$_{846-860}$-HLA-DRB5*0101/DRA, CENP-C$_{149-163}$-HLA-DRB3*0202/DRA, CENP-C$_{833-847}$-HLA-DRB3*0202/DRA, or CENP-C$_{847-861}$-HLA-DRB3*0202/DRA;

o) anti-phospholipid syndrome and the pMHC complex is selected from the group of: APOH$_{235-249}$-HLA-DRB3*0101/DRA, APOH$_{306-320}$-HLA-DRB3*0101/DRA, APOH$_{237-251}$-HLA-DRB3*0101/DRA, APOH$_{295-309}$-HLA-DRB3*0101/DRA, APOH$_{28-42}$-HLA-DRB4*0101/DRA, APOH$_{173-187}$-HLA-DRB4*0101/DRA, APOH$_{264-278}$-HLA-DRB4*0101/DRA, APOH$_{295-309}$-HLA-DRB4*0101/DRA, APOH$_{49-63}$-HLA-DRB5*0101/DRA, APOH$_{269-283}$-HLA-DRB5*0101/DRA, APOH$_{295-309}$-HLA-DRB5*0101/DRA, APOH$_{321-355}$-HLA-DRB3*0202/DRA, APOH$_{322-336}$-HLA-DRB3*0202/DRA, or APOH$_{324-338}$-HLA-DRB3*0202/DRA;

p) ANCA-associated vasculitis and the pMHC complex is selected from the group of: MPO$_{506-520}$-HLA-DRB3*0101/DRA, MPO$_{302-316}$-HLA-DRB3*0101/DRA, MPO$_{7-21}$-HLA-DRB3*0101/DRA, MPO$_{689-703}$-HLA-DRB4*0101/DRA, MPO$_{248-262}$-HLA-DRB4*0101/DRA, MPO$_{444-458}$-HLA-DRB4*0101/DRA, MPO$_{513-527}$-HLA-DRB5*0101/DRA, MPO$_{97-111}$-HLA-DRB5*0101/DRA, MPO$_{616-630}$-HLA-DRB5*0101/DRA, MPO$_{462-476}$-HLA-DRB3*0202/DRA, MPO$_{617-631}$-HLA-DRB3*0202/DRA, MPO$_{714-728}$-HLA-DRB3*0202/DRA, PRTN3$_{44-58}$-HLA-DRB3*0101/DRA, PRTN3$_{234-248}$-HLA-DRB3*0101/DRA, PRTN3$_{59-73}$-HLA DRB3*0101/DRA, PRTN3$_{59-73}$-HLA-DRB5*0101/DRA, PRTN3$_{117-131}$-HLA-DRB4*0101/DRA, PRTN3$_{164-178}$-HLA-DRB4*0101/DRA, PRTN3$_{71-85}$-HLA-DRB4*0101/DRA, PRTN3$_{241-255}$-HLA-DRB5*0101/DRA, PRTN3$_{183-197}$-HLA-DRB5*0101/DRA, PRTN3$_{62-76}$-HLA-DRB3*0202/DRA, PRTN3$_{118-132}$-HLA-DRB3*0202/DRA, or PRTN3$_{239-253}$-HLA-DRB3*0202/DRA; or q) Stiff Man Syndrome and the pMHC complex is selected from the group of: GAD$_{212-226}$-HLA-DRB1*0801/DRA, GAD$_{555-569}$-HLA-DRB1*0801/DRA, or GAD$_{297-311}$-HLA-DRB1*0301/DRA.

In some aspects, the pMHC complex is for the treatment of:

a) type I diabetes and the pMHC complex is selected from the group of: PPI$_{76-90(K88S)}$-HLA-DRB1*0401/DRA, IGRP$_{13-25}$-HLA-DRB1*0301/DRA, GAD$_{555-567}$-HLA-DRB1*0401/DRA, GAD$_{555-567(557I)}$-HLA-DRB1*0401/DRA, IGRP$_{23-35}$-HLA-DRB1*0401/DRA, or PPI$_{76-90}$-HLA-DRB1*0401/DRA;

b) multiple sclerosis and the pMHC complex is selected from the group of: MBP$_{86-98}$-HLA-DRB1*1501/DRA, MBP$_{89-101}$-HLA-DRB5*0101/DRA, MOG$_{38-52}$-HLA-DRB4*0101/DRA, MOG$_{97-109(E107S)}$-HLA-DRB1*0401/DRA, MOG$_{203-217}$-HLA-DRB3*0101/DRA, PLP$_{54-68}$-HLA-DRB3*0101/DRA, PLP$_{94-108}$-HLA-DRB1*0301/DRA, PLP$_{250-264}$-HLA-DRB4*0101/DRA, MPB$_{13-32}$-HLA-DRB5*0101/DRA, MPB$_{83-99}$-HLA-DRB5*0101/DRA, MPB$_{111-129}$-HLA-DRB5*0101/DRA, MPB$_{146-170}$-HLA-DRB 5*0101/DRA, MOG$_{223-237}$-HLA-DRB3*0202/DRA, MOG$_{6-20}$-HLA-DRB5*0101/DRA, PLP$_{88-102}$-HLA-DRB3*0202/DRA, or PLP$_{139-154}$-HLA-DRB5*0101/DRA;

c) Celiac Disease and the pMHC complex is selected from the group of: aGlia$_{57-68}$-HLA-DQA1*0501/HLA-DQB1*0201, aGlia$_{62-72}$-HLA-DQA1*0501/HLA-DQB1*0201, or aGlia$_{217-229}$-HLA-DQA1*0501/HLA-DQB1*0302;

d) primary biliary cirrhosis and the pMHC complex is selected from the group of: PDC-E2$_{122-135}$-HLA-DRB4*0101/DRA, PDC-E2$_{249-262}$-HLA-DRB4*0101/DRA, PDC-E2$_{249-263}$-HLA-DRB1*0801/DRA, PDC-E2$_{629-643}$-HLA-DRB1*0801/DRA, PDC-E2$_{72-86}$-HLA- DRB3*0202/DRA, PDC-E2$_{353-367}$-HLA-DRB3*0202/DRA, PDC-E2$_{422-436}$-HLA-DRB3*0202/DRA, PDC-E2$_{629-643}$-HLA-DRB4*0101/DRA, PDC-E2$_{80-94}$-HLA-DRB5*0101/DRA, PDC-E2$_{353-367}$-HLA-DRB5*0101/DRA, or PDC-E2$_{535-549}$-HLA-DRB5*0101/DRA;

e) pemphigus folliaceus and/or pemphigus vulgaris and the pMHC complex is selected from the group of: DG1$_{216-229}$-HLA-DRB1*0101/DRA, DG3$_{97-111}$-HLA-DRB1*0402/DRA, DG3$_{251-265}$-HLA-DRB1*0401/DRA, DG3$_{441-455}$-HLA-DRB1*0402/DRA, DG3$_{351-365}$-HLA-DRB3*0202/DRA, DG3$_{453-467}$-HLA-DRB3*0202/DRA, DG3$_{540-554}$-HLA-DRB3*0202/DRA, DG3$_{280-294}$-HLA-DRB4*0101/DRA, DG3$_{326-340}$-HLA-DRB4*0101/DRA, DG3$_{367-381}$-HLA-DRB4*0101/DRA, DG3$_{13-27}$-HLA-DRB5*0101/DRA, DG3$_{323-337}$-HLA-DRB5*0101/DRA, DG3$_{438-452}$-HLA-DRB5*0101/DRA, DG1$_{48-62}$-HLA-DRB3*0202/DRA, DG1$_{206-222}$-HLA-DRB3*0202/DRA, DG1$_{363-377}$-HLA-DRB3*0202/DRA, DG1$_{3-17}$-HLA-DRB4*0101/DRA, DG1$_{192-206}$-HLA-DRB4*0101/DRA, DG1$_{326-340}$-HLA-DRB4*0101/DRA, DG1$_{1-15}$-HLA-DRB5*0101/DRA, DG1$_{35-49}$-HLA-DRB5*0101/DRA, or DG1$_{325-339}$-HLA-DRB5*0101/DRA;

f) neuromyelitis optica spectrum disorder and the pMHC complex is selected from the group of: AQP4$_{284-298}$-HLA-DRB1*0301/DRA, AQP4$_{63-76}$-HLA-DRB1*0301/DRA, AQP4$_{129-143}$-HLA-DRB1*0401/DRA, or AQP4$_{39-53}$-HLA-DRB1*1501/DRA;

g) allergic asthma and the pMHC complex is selected from the group of: DERP-1$_{16-30}$-FILA-DRB1*0101/DRA, DERP-1$_{16-30}$-HLA-DRB1*1501/DRA, DERP$_{1171-185}$-HLA-DRB1*1501/DRA, DERP-1$_{110-124}$-HLA-DPB1*0401/DRA, DERP-2$_{26-40}$-HLA-DRB1*0101/DRA; DERP-2$_{26-40}$-HLA-DRB1*1501/DRA, or DERP-2$_{107-121}$-HLA-DRB1*0301/DRA;

h) inflammatory bowel disease and the pMHC complex is selected from the group of: bacteroides integrase antigen$_{1-15}$-HLA-DRB5*0101/DRA, bacteroides integrase antigen$_{183-197}$-HLA-DRB3*0101/DRA, bacteroides integrase antigen$_{70-84}$-HLA-DRB4*0101/DRA, bacteroides integrase antigen$_{4-18}$-HLA-DRB3*0202/DRA, bacteroides integrase antigen$_{171-185}$-HLA-DRB3*0202/DRA, bacteroides integrase antigen$_{256-270}$-HLA-DRB3*0202/DRA, Fla-2/Fla-X$_{366-380}$-HLA-DRB3*0101/DRA, Fla-2/Fla-X$_{261-275}$-HLA-DRB5*0101/DRA, Fla-2/Fla-X$_{51-65}$-HLA-DRB4*0101/DRA, Fla-2/Fla-X$_{4-18}$-HLA-DRB3*0202/DRA, Fla-2/Fla-X$_{261-275}$-HLA-DRB3*0202/DRA, Fla-2/Fla-X$_{271-285}$-HLA-DRB3*0202/DRA, YIDX$_{78-92}$-HLA-DRB3*0101/DRA, YIDX$_{78-92}$-HLA-DRB4*0101/DRA, YIDX$_{98-112}$-HLA-DRB5*0101/DRA, YIDX$_{22-36}$-HLA-DRB3*0202/DRA, YIDX$_{80-94}$-HLA-DRB3*0202/DRA, or YIDX$_{101-115}$-HLA-DRB3*0202/DRA;

i) emphysema and the pMHC complex is selected from the group of: elastin$_{89-103}$-HLA-DRB3*0101/DRA, elastin$_{698-712}$-HLA-DRB5*0101/DRA, elastin$_{558-572}$-HLA-DRB4*0101/DRA, elastin$_{566-580}$-HLA-DRB3*0202/DRA, or elastin$_{645-659}$-HLA-DRB3*0202/DRA;

j) psoriasis and the pMHC complex is selected from the group of: Cap18$_{64-78}$-HLA-DRB3*0101/DRA, Cap18$_{34-48}$-HLA-DRB3*0101/DRA, Cap18$_{47-61}$-HLA-DRB3*0101/DRA, Cap18$_{151-165}$-HLA-DRB4*0101/DRA, Cap18$_{149-163}$-HLA-DRB5*0101/DRA, Cap18$_{152-166}$-HLA-DRB5*0101/DRA, Cap18$_{131-145}$-HLA-DRB5*0101/DRA, Cap$_{1824-38}$-HLA-DRB3*0202/DRA, ADMTSL5$_{245-259}$-HLA-DRB3*0101/DRA, ADMTSL5$_{267-281}$-HLA-DRB3*0101/DRA, ADMTSL5$_{372-386}$-HLA-DRB3*0101/DRA, ADMTSL5$_{289-303}$-HLA-DRB4*0101/DRA, ADMTSL5$_{396-410}$-HLA-DRB4*0101/DRA, ADMTSL5$_{433-447}$-HLA-DRB4*0101/DRA, ADMTSL5$_{142-156}$-HLA-DRB5*0101/DRA, ADMTSL5$_{236-250}$-HLA-DRB5*0101/DRA, ADMTSL5$_{301-315}$-HLA-DRB5*0101/DRA, ADMTSL5$_{203-217}$-HLA-DRB3*0202/DRA, ADMTSL5$_{404-418}$-HLA-DRB3*0202/DRA, or ADMTSL5$_{433-447}$-HLA-DRB3*0202/DRA;

k) autoimmune hepatitis and the pMHC complex is selected from the group of: CYP2D6$_{193-207}$-HLA-DRB1*0301/DRA, CYP2D6$_{76-90}$-HLA-DRB1*0301/DRA, CYP2D6$_{293-307}$-HLA-DRB1*0301/DRA, CYP2D6$_{313-332}$-HLA-DRB1*0301/DRA, CYP2D6$_{393-412}$-HLA-DRB1*0301/DRA, CYP2D6$_{199-213}$-HLA-DRB1*0401/DRA, CYP2D6$_{450-464}$-HLA-DRB1*0401/DRA, CYP2D6$_{301-315}$-HLA-DRB1*0401/DRA, CYP2D6$_{452-466}$-HLA-DRB1*0701/DRA, CYP2D6$_{59-73}$-HLA-DRB1*0701/DRA, CYP2D6$_{130-144}$-HLA-DRB1*0701/DRA, CYP2D6$_{193-212}$-HLA-DRB1*0701/DRA, CYP2D6$_{305-324}$-HLA-DRB1*0701/DRA, CYP2D6$_{131-145}$-HLA-DRB3*0202/DRA, CYP2D6$_{216-230}$-HLA-DRB3*0202/DRA, CYP2D6$_{238-252}$-HLA-DRB3*0202/DRA, CYP2D6$_{199-213}$-HLA-DRB4*0101/DRA, CYP2D6$_{235-252}$-HLA-DRB4*0101/DRA, CYP2D6$_{293-307}$-HLA-DRB4*0101/DRA, CYP2D6$_{238-252}$-HLA-DRB5*0101/DRA, CYP2D6$_{381-395}$-HLA-DRB5*0101/DRA, CYP2D6$_{429-443}$-HLA-DRB5*0101/DRA, SLA$_{334-348}$-HLA-DRB1*0301/DRA, SLA$_{196-210}$-HLA-DRB1*0301/DRA, SLA$_{115-129}$-HLA-DRB1*0301/DRA, SLA$_{373-386}$-HLA-DRB1*0301/DRA, SLA$_{186-197}$-HLA-DRB1*0301/DRA, SLA$_{317-331}$-HLA-DRB1*0401/DRA, SLA$_{171-185}$-HLA-DRB1*0401/DRA, SLA$_{417-431}$-HLA-DRB1*0401/DRA, SLA$_{359-373}$-HLA-DRB1*0701/DRA, SLA$_{215-229}$-HLA-DRB1*0701/DRA, SLA$_{111-125}$-HLA-DRB1*0701/DRA, SLA$_{110-124}$-HLA-DRB3*0202/DRA, SLA$_{299-313}$-HLA-DRB3*0202/DRA, SLA$_{342-356}$-HLA-DRB3*0202/DRA, SLA$_{49-63}$-HLA-DRB4*0101/DRA, SLA$_{119-133}$-HLA-DRB4*0101/DRA, SLA$_{260-274}$-HLA-DRB4*0101/DRA, SLA$_{26-40}$-HLA-DRB5*0101/DRA, SLA$_{86-100}$-HLA-DRB5*0101/DRA, or SLA$_{331-345}$-HLA-DRB5*0101/DRA;

l) uveitis and the pMHC complex is selected from the group of: arrestin$_{199-213}$-HLA-DRB3*0101/DRA, arrestin$_{77-91}$-HLA-DRB3*0101/DRA, arrestin$_{250-264}$-HLA-DRB3*0101/DRA, arrestin$_{172-186}$-HLA-DRB4*0101/DRA, arrestin$_{354-368}$-HLA-DRB4*0101/DRA, arrestin$_{239-253}$-HLA-DRB4*0101/DRA, arrestin$_{102-116}$-HLA-DRB5*0101/DRA, arrestin$_{59-73}$-HLA-DRB5*0101, arrestin$_{280-294}$-HLA-DRB5*0101, arrestin$_{291-306}$-HLA-DRB1*0301/DRA, arrestin$_{195-209}$-HLA-DRB3*0202/DRA, arrestin$_{199-213}$-HLA-DRB3*0202/DRA, or arrestin$_{200-214}$-HLA-DRB3*0202/DRA;

m) Sjogren Syndrome and the pMHC complex is selected from the group of: RO60$_{127-141}$-HLA-DRB1*0301/DRA, RO60$_{523-537}$-HLA-DRB1*0301/DRA, RO60$_{243-257}$-HLA-DRB1*0301/DRA, RO60$_{484-498}$-HLA-DRB3*0101/DRA, RO60$_{347-361}$-HLA-DRB3*0101/DRA, RO60$_{369-383}$-HLA-DRB3*0101/DRA, RO60$_{426-440}$-HLA-DRB4*0101/DRA, RO60$_{267-281}$-HLA-DRB4*0101/DRA, RO60$_{178-192}$-HLA-DRB4*0101/DRA, RO60$_{358-372}$-HLA-DRB5*0101/DRA, RO60$_{221-235}$-HLA-DRB5*0101/DRA, RO60$_{318-332}$-HLA-DRB5*0101/DRA, RO60$_{51-65}$-HLA-DRB3*0202/DRA, RO60$_{312-326}$-HLA-DRB3*0202/DRA, RO60$_{347-361}$-HLA-DRB3*0202/DRA, LA$_{241-255}$-HLA-DRB1*0301/DRA, LA$_{101-115}$-HLA-DRB1*0301/DRA, LA$_{153-167}$-HLA-DRB1*0301/DRA, LA$_{178-192}$-HLA-DRB3*0101/DRA, LA$_{19-33}$-HLA-DRB3*0101/DRA, LA$_{37-51}$-HLA-DRB3*0101/DRA, LA$_{133447}$-HLA-DRB4*0101/DRA, LA$_{50-64}$-HLA-DRB4*0101/DRA, LA$_{32-46}$-HLA-DRB4*0101/DRA, LA$_{153-167}$-HLA-DRB5*0101/DRA, LA$_{83-97}$-HLA-DRB5*0101/DRA, LA$_{136-150}$-HLA-DRB5*0101/DRA, LA$_{50-64}$-HLA-DRB3*0202/DRA, LA$_{86-100}$-HLA-DRB3*0202/DRA, or LA$_{154-168}$-HLA-DRB3*0202/DRA;

n) scleroderma and the pMHC complex is selected from the group of: TOP1$_{346-360}$-HLA-DRB3*0101/DRA, TOP1$_{420-434}$-HLA-DRB3*0101/DRA, TOP1$_{750-764}$-HLA-DRB3*0101/DRA, TOP1$_{419-433}$-HLA-DRB4*0101/DRA, TOP1$_{591-605}$-HLA-DRB4*0101/DRA, TOP1$_{695-709}$-HLA-DRB4*0101/DRA, TOP1$_{305-319}$-HLA-DRB5*0101/DRA, TOP1$_{346-360}$-HLA-DRB5*0101/DRA, TOP1$_{419-433}$-HLA-DRB5*0101/DRA, TOP1$_{420-434}$-HLA-DRB3*0202/DRA, TOP1$_{425-439}$-HLA-DRB3*0202/DRA, TOP1$_{614-628}$-HLA-DRB3*0202/DRA, CENP-C$_{297-311}$-HLA-DRB3*0101/DRA, CENP-C$_{857-871}$-HLA-DRB3*0101, CENP-C$_{887-901}$-HLA-DRB3*0101, CENP-C$_{212-226}$-HLA-DRB4*0101/DRA, CENP-C$_{643-657}$-HLA-DRB4*0101/DRA, CENP-C$_{832-846}$-HLA-DRB4*0101/DRA, CENP-C$_{167-181}$-HLA-DRB5*0101/DRA, CENP-C$_{246-260}$-HLA-DRB5*0101/DRA, CENP-C$_{846-860}$-HLA-DRB5*0101/DRA, CENP-C$_{149-163}$-HLA-DRB3*0202/DRA, CENP-C$_{833-847}$-HLA-DRB3*0202/DRA, or CENP-C$_{847-861}$-HLA-DRB3*0202/DRA;

o) anti-phospholipid syndrome and the pMHC complex is selected from the group of: APOH$_{235-249}$-HLA-DRB3*0101/DRA, APOH$_{306-320}$-HLA-DRB3*0101/DRA, APOH$_{237-251}$-HLA-DRB3*0101/DRA, APOH$_{295-309}$-HLA-DRB3*0101/DRA, APOH$_{28-42}$-HLA-DRB4*0101/DRA, APOH$_{173-187}$-HLA-DRB4*0101/DRA, APOH$_{264-278}$-HLA-DRB4*0101/DRA, APOH$_{295-309}$-HLA-DRB4*0101/DRA, APOH$_{49-63}$-HLA-DRB5*0101/DRA, APOH$_{269-283}$-HLA-DRB5*0101/DRA, APOH$_{295-309}$-HLA-DRB5*0101/DRA, APOH$_{321-355}$-HLA-DRB3*0202/DRA, APOH$_{322-336}$-HLA-DRB3*0202/DRA, or APOH$_{324-338}$-HLA-DRB3*0202/DRA;

p) ANCA-associated vasculitis and the pMHC complex is selected from the group of: MPO$_{506-520}$-HLA-DRB3*0101/DRA, MPO$_{302-316}$-HLA-DRB3*0101/DRA, MPO$_{7-21}$-HLA-DRB3*0101/DRA, MPO$_{689-703}$-HLA-DRB4*0101/DRA, MPO$_{248-262}$-HLA-DRB4*0101/DRA, MPO$_{444-458}$-HLA-DRB4*0101/DRA, MPO$_{513-527}$-HLA-DRB5*0101/DRA, MPO$_{97-111}$-HLA-DRB5*0101/DRA, MPO$_{616-630}$-HLA-DRB5*0101/DRA, MPO$_{462-476}$-HLA-DRB3*0202/DRA, MPO$_{617-631}$-HLA-DRB3*0202/DRA, MPO$_{714-728}$-HLA-DRB3*0202/DRA, PRTN3$_{44-58}$-HLA-DRB3*0101/DRA, PRTN3$_{234-248}$-HLA-DRB3*0101/DRA, PRTN3$_{59-73}$-HLA DRB3*0101/DRA, PRTN3$_{59-73}$-HLA-DRB5*0101/DRA, PRTN3$_{117-131}$-HLA-DRB4*0101/DRA, PRTN3$_{164-178}$-HLA-DRB4*0101/DRA, PRTN3$_{371-85}$-HLA-DRB4*0101/DRA, PRTN3$_{241-255}$-HLA-DRB5*0101/DRA, PRTN3$_{183-197}$-HLA-DRB5*0101/DRA, PRTN3$_{62-76}$-HLA-DRB3*0202/DRA, PRTN3$_{118-132}$-HLA-DRB3*0202/DRA, or PRTN3$_{239-253}$-HLA-DRB3*0202/DRA; or q) Stiff Man Syndrome and the pMHC complex is selected from the group of: GAD$_{212-226}$-HLA-DRB1*0801/DRA, GAD$_{555-569}$-HLA-DRB1*0801/DRA, or GAD$_{297-311}$-HLA-DRB1*0301/DRA.

In certain aspects, provided herein are methods to treat type I diabetes in a subject in need thereof comprising administering an effective amount of the complex or composition disclosed herein, wherein the complex and the composition may comprise one or more nanoparticle core coupled to a plurality of pMHC complexes, wherein the antigen of the pMHC complex is a diabetes-relevant antigen, wherein the MHC protein of the pMHC complex comprises a MHC class II protein, wherein the nanoparticle core has a diameter of from about 1 nm to about 100 nm, and wherein the pMHC density per nanoparticle core is from about 0.4 pMHC/100 nm$^2$ to about 11.6 pMHC/100 nm$^2$. In some embodiments, the nanoparticle core has a diameter of from about 1 nm to about 75 nm; from about 1 nm to about 50 nm; from about 1 nm to about 25 nm; from about 1 nm to about 25 nm; from about 5 nm to about 100 nm; from about 5 nm to about 50 nm; or from about 5 nm to about 25 nm, or from about 15 nm to about 25 nm, or about 20 nm. In some embodiments, the nanoparticles core has a diameter of from about 25 nm to about 60 nm, or from about 25 nm to about 50 nm, or from about 20 nm to about 40 nm, or from about 15 nm to about 50 nn, or from about 15 nm to about 40 nm, or from about 15 nm to about 35 nm, or from about 15 nm to about 30 nm, or from about 15 nm to about 25 nm, or alternatively about 15 nm, or about 20 nm, or about 25 nm, or about 30 nm, or about 35 nm, or about 40 nm. In some embodiments, the nanoparticle core has a pMHC density of from about 0.4 pMHC/100 nm$^2$ to about 11.6 pMHC/100 nm$^2$, or from about 0.4 pMHC/100 nm$^2$ to about 11.0 pMHC/100 nm$^2$, or from about 0.4 pMHC/100 nm$^2$ to about 10 pMHC/100 nm$^2$, or from about 0.4 pMHC/100 nm$^2$ to about 9 pMHC/100 nm$^2$, or from about 0.4 pMHC/100 nm$^2$ to about 8 pMHC/100 nm$^2$, or from about 0.4 pMHC/100 nm$^2$ to about 7 pMHC/100 nm$^2$, or from about 0.4 pMHC/100 nm$^2$ to about 6 pMHC/100 nm$^2$, or from about 0.4 pMHC/100 nm$^2$ to about 5 pMHC/100 nm$^2$, or from about 0.4 pMHC/100 nm$^2$ to about 4 pMHC/100 nm$^2$, or from about 0.4 pMHC/100 nm$^2$ to about 3 pMHC/100 nm$^2$, or from about 0.4 pMHC/100 nm$^2$ to about 2 pMHC/100 nm$^2$, or from about 0.4 pMHC/100 nm$^2$ to about 1.5 pMHC/100 nm$^2$. In some embodiments, the nanoparticle core has a pMHC density of from about 0.4 pMHC/100 nm$^2$ to about 6 pMHC/100 nm$^2$ or from about 0.4 pMHC/100 nm$^2$ to about 1.5 pMHC/100 nm$^2$. In some embodiments, the pMHC complex comprises an antigen derived from one or more of IGRP or PPI. In some embodiments, the pMHC complex comprises an antigen selected from one or more of the group: IGRP$_{13-25}$, PPI$_{76-90}$ or PPI$_{76-90(K88S)}$. In some embodiments, the pMHC complex comprises HLA-DR. In some embodiments, the pMHC complex comprises HLA-DR/DRA. In some embodiments, the pMHC complex comprises, or alternatively consists of, or further yet consists essentially of one or more of IGRP$_{13-25}$-HLA-DRB1*0301/DRA, PPI$_{76-90}$-HLA-DRB1*0401/DRA, or PPI$_{76-90(K88S)}$-HLA-DRB1*0401/DRA.

Methods to determine and monitor the therapy are known in the art and are briefly described herein. When delivered in vitro, administration is by contacting the composition with the tissue or cell by any appropriate method, e.g., by administration to cell or tissue culture medium and is useful as a screen to determine if the therapy is appropriate for an individual or to screen for alternative therapies to be used as a substitute or in combination with the disclosed compositions. When administered in vivo, administration is by systemic or local administration. In vivo, the methods can be practiced on a non-human animal to screen alternative therapies to be used as a substitute or in combination with the disclosed compositions prior to human administration. In a human or non-human mammal, they are also useful to treat the disease or disorder.

The above methods require administration of an effective amount of an antigen/MHC complex operatively coupled to a nanoparticle as disclosed herein above, which may optionally further comprise, alternatively consist essentially of, or yet further consist of co-stimulatory molecules and/or cytokines coupled to the same nanoparticle. Disease targets and relevant antigens are disclosed herein above.

Details regarding modes of administration in vitro and in vivo are described herein above.

This disclosure also provides use of the NP-complexes for the preparation of medicaments for the treatment and/or prevention of diseases and disorders as described herein.

Monitoring Therapy and Detection of T Cells

Some aspects of the present disclosure relate to methods of detecting and/or monitoring a population of immune cells, preferably T cells comprising administering a labeled antigen-MHC complex where a subject has received an pMHC-NP or composition as disclosed herein.

In certain aspects, provided herein are methods to detect a population of $T_R1$ cells and/or effector T cells in an antigen specific manner in a subject that has received the complex or the composition disclosed herein. The method comprises, alternatively consists of, or yet further consists essentially of, contacting a sample suspected of comprising the $T_R1$ cells with an effective amount of labeled pMHC complex to form a multimer complex, and detecting any multimer complex, thereby detecting the population of $T_R1$ cells. In some embodiments, the method further comprises, alternatively further consists of, or yet further consists essentially of staining any T cell population using a labeled multimer complex. In some embodiments, the step of detecting the population of $T_R1$ cells comprises flow cytometry to detect any multimer complex. In some embodiments, the method further comprises, or alternatively consists of, or yet further consists essentially of administering the complex or composition to the subject.

In certain aspects, provided herein are methods to detect a population of $T_R1$ cells and/or effector T cells in an antigen specific manner in a subject that has received the complex or the composition disclosed herein The method comprises, alternatively consists of, or yet further consists essentially of any one of the following assays: cytokine ELISPOT assay, a multimer-guided epitope analysis, or a multimer-pulldown assay. In some embodiments, the method further comprises, alternatively further consists of, or yet further consists essentially of administering the complex or the composition disclosed herein.

In other aspects, provided herein are methods to monitor the expansion of a population of antigen-specific $T_R1$ and/or effector T cells in a subject. The method comprises, alternatively consists of, or yet further consists essentially of: a) administering to a subject an effective amount of the complex or the composition disclosed herein, wherein the disease-relevant antigen of the pMHC complex is selected to expand the antigen-specific $T_R1$ and/or effector T cells; b) isolating a suitable sample from the subject suspected of containing the population; c) contacting the sample with an effective amount of labeled pMHC complex to form a multimer complex, and detecting any multimer complex; and d) quantifying the number of antigen-specific $T_R1$ and/or effector T cells in the population. In some embodiments, the method further comprises, alternatively further consists of, or yet further consists essentially of staining any multimer complex. In some embodiments, the step of quantifying the number of antigen-specific $T_R1$ and/or effector T cells comprises flow cytometry and/or ELISA. In some embodiments, the method further comprises, alternatively further consists of, or yet further consists essentially of administering the complex or the composition disclosed herein.

There are many types of immunoassays that can be implemented. Immunoassays encompassed by the present disclosure include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

One method for quantifying the number of circulating antigen-specific immune cells is the tetramer assay. In this assay, a specific epitope is bound to synthetic multimeric forms of fluorescently labeled MHC molecules. Since immune cells recognize antigens in the form of short peptides bound to MHC molecules, cells with the appropriate T cell receptor will bind to the labeled tetramers and can be quantified by flow cytometry. Although this method is less time-consuming than an ELISPOT assay, the multimer assay measures only binding, not function. Not all cells that bind a particular antigen necessarily become activated. However, correlation between ELISPOT, multimer, and cytotoxicity assays has been demonstrated.

Immunoassays generally are binding assays. Certain immunoassays, including the various types of enzyme linked immunosorbent assays (ELISAs), radioimmunoassays (RIA) or bead based assays, such as Luminex® technology, are known in the art. Immunohistochemical detection using tissue sections is also particularly useful.

In one example of ELISA, the antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non-specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label. Variations on ELISA techniques are known to those of skill in the art.

Competition ELISAs are also possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of the antigen or antibody to the well, coating with a non reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

Additionally, flow cytometry may be used to detect and quantitate particular cell subtypes according to cell surface markers. Common means of detection and quantitation via flow cytometry include the use of fluorescent labeled beads that bind to cell surface markers specific to each immune cell subtype, e.g. CD 4 specific beads, to select for CD 4+ T cells, etc.

Kits

Also provided herein are kits comprising the nanoparticle complex as described herein or the compositions as described herein for diagnostic, prognostic or therapeutic use. Additional reagents and/or instructions can further be provided as necessary.

EXAMPLES

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

Example 1. Polymeric and Dendrimer Nanoparticle Cores for Autoimmunity and Immunity The enormous antigenic complexity of autoimmune diseases and other chronic inflammatory phenomena, including allergy, is a barrier to the design of strategies that can purge the immune system of auto- or allergen-reactivity without impairing systemic immunity; current systemic immunosuppressive approaches compromise immunity to infections and cancer.

Thus, in one aspect, the present disclosure establishes that systemic delivery of nanoparticles (NPs) coated with autoimmune or allergic disease-relevant peptide-major histocompatibility complex (pMHC) class II molecules triggers the expansion of cognate T-regulatory type 1 ($T_R1$) CD4+ T-cells in vivo in different disease models and genetic backgrounds, leading to resolution of various autoimmune or allergic phenomena, including spontaneous type 1 diabetes, experimental autoimmune encephalomyelitis and house dust mite-induced asthma. These nanomedicines promote the differentiation of disease-primed autoreactive T-cell precursors into disease-suppressing $T_R1$ cells, which then go on to suppress autoreactive and allergen-specific T-cell responses in the affected tissues by targeting autoantigen- or allergen-loaded antigen-presenting cells (APCs), while sparing non-loaded APCs elsewhere. Suppression of disease does not impair the host's ability to clear viral infections or to mount antibody responses to conventional vaccines; is mediated by local secretion of IL-10 and TGF-beta in response to these cognate $T_R1$-APC interactions; and involves a profound inhibition of the ability of local (but not distal) APCs to secrete pro-inflammatory cytokines and activate other T-cells. Furthermore, it is found that the expanded $T_R1$ cells promote the differentiation of cognate B-lymphocytes into IL-10-producing B-regulatory cells in vivo, which contribute to the remarkable therapeutic activity of this therapeutic platform. Importantly, the examples demonstrate that human type 1 diabetes-relevant nanomedicines can expand human $T_R1$ cells in NSG mice engrafted with peripheral blood mononuclear cells from patients, demonstrating the translational potential of this approach. Thus, pMHC class II-based nanomedicines may represent the long-sought-after antigen-specific therapy for autoimmune and allergic inflammation. Similar results can be achieved with pMHC class I-based nanomedicines for the expansion of the appropriate T cell population.

It was determined that the therapeutic properties of these nanomedicines are primarily a function of MHC density (inter-molecular distance). Mathematical modeling of experimental data indicates that, for any given pMHC valency, small but densely coated NPs will have superior biological and therapeutic activity.

In one aspect, superior results are shown for NP core diameter around ~8-12 nm. The MHC-binding capacity of the pegylated iron oxide NPs lies at ~55 pMHCs on a 68 nm hydrodynamic diameter NP.

By building MHC-based nanomedicines using third generation poly-L-lysine-based dendrimers (DGLs; 7 nm), this limitation is overcome. The ordered structure of the pMHC-acceptor PEGs on these compounds increases the ligand-binding capacity (hence molecular density) several fold (52 pMHCs on 19 nm hydrodynamic diameter pMHC-DGLN vs. 55 pMHCs on 68 nm diameter pMHC-IONP, resulting in a several fold increase in pMHC density, a critical parameter for biological activity).

Dendrimers are highly branched macromolecules having a tree-like structure with branches growing from a core. They are well known for their three-dimensional, monodispersed, highly branched macromolecular nanoscopic architecture with a number of reactive end groups. These features make dendrimers popular instruments for drug, peptide, and gene delivery in addition to many other biomedical applications.

The widely investigated dendrimers are mainly bear primary amine groups on the branched surface, such as poly (amidoamine) (PAMAM) and poly-L-lysine (PLL) based dendrimers. These dendrimers are soluble in water at the physiological pH due to the presence of charged terminal $NH3^+$ groups. However, cationic PAMAM dendrimers exhibit bio-incompatibility, non-degradability and positive-associated cytotoxicity, which limit their wide application in vitro and in vivo.

Cationic PLL are promising new candidates due to their biodegradable properties. A previous study reported that free lysine and larger species (non-dendrimer) appeared in plasma at 1 h postdose of L-lysine capped dendrimers, which indicated the quick degradation of PLL in vivo. (Bailey-Bucktrout, S. L. et al. (2013) Immunity 39:949-962). However, quick degradation is not a benefit for maintaining an effective therapeutic level. Fortunately, it has been reported that fully PEGylated PLL dendrimers had a greater ability to increase plasma stability and circulation time, meanwhile completely masking the positive charge on the surface. PLL-based dendrimers have already been exploited in constructing drug delivery systems. Kaminskas and co-workers conjugated methotrexate (MTX) to a series of PEGylated PLL dendrimers, and demonstrated their potential as long-circulating vectors for the delivery and tumor-targeting of hydrophobic drugs. Others have attached camptothecin (CPT) covalently to PEGylated PLL dendrimers, and demonstrated the significantly prolonged survival in tumor-bearing mice compared to free CPT. However, most of the PLL-based dendrimers used were synthesized by the researchers themselves. The structures of these PLL-based dendrimers are not exactly the same, which significantly limits the prevalence of these dendrimers.

Dendrigraft poly-L-lysines (DGLs), a kind of PLL-based dendrimers, are now commercially available. They are composed of 100% L-lysine, biodegradable, monodispersed, and well-defined, possessing the main properties of PLL-based dendrimers. Current studies are focused on the utility of DGLs for drug or gene delivery. To the best of Applicant's knowledge, DGLs have never been used in the field of presenting pMHC to T cells in blood circulation. In this study, DGLs of generation 3 (G3) (123 amino groups, 7 nm) were used as a scaffold to present pMHC and to evaluate the immunology activity.

Preparation, Purification and Characterization of pMHC-PEG-DGL

In this study, G3 of DGLs with 123 amino groups is selected as the vector material. Its surface is coated with heterobifunctional crosslinker, NHS-PEG$_4$-Azido (MW 388 g/mol) through the specific reaction between primary amino groups and activated NHS ester. The heterobifunctional PEG, maleimide-PEG-alkyne (Mal-PEG-Alkyne, MW 2,000) can conjugate with pMHC molecule via thiol-maleimide reaction. The free alkyne on the end of pMHC-PEG conjugates could react with azido coated DGLs through Click chemistry. The resulting NPs were purified by gel filtration to remove the unconjugated pMHC. The significant charge changes of DGLs before and after coating can be monitored by Z-potential and agarose gel electrophoresis. The resulting NPs can be characterized by DLS, Z-potential, SDS-page and TEM.

Dendri-Graft Poly-L-Lysine Generation 3 (DGLs G3)

In another study, dendri-Graft Poly-L-Lysines Generation 3 (DGLs G3) was purchased from COLCOM in France. DGLs G3 is a synthetic polymer with a structure constituted by nine equivalent dendrons linked to a core. The core is a linear poly-L-lysine with an average of eight monomers. Each dendron looks like the traditional Tam-type dendrons synthesized from Merrifield resins. DGLs G3 is a non-immunogenic carrier with a molecular weight of 22 KDa and 123 terminal primary amino groups (—NH$_2$) for functionalization and conjugation (FIG. 3).

Synthesis of Dendri-Graft Poly-L-Lysines-Azido (—N$_3$) ("DGLN")

DGLs were first functionalized with N-Hydroxysuccinimide-PEG$_4$-Azido (NHS-PEG$_4$-Azido, MW 388.37, purchased from Conju-Probe, Canada) to: 1) enable the conjugation of pMHC; and 2) neutralize the positive surface charge of non-functionalized DGLs.

Figure 4:
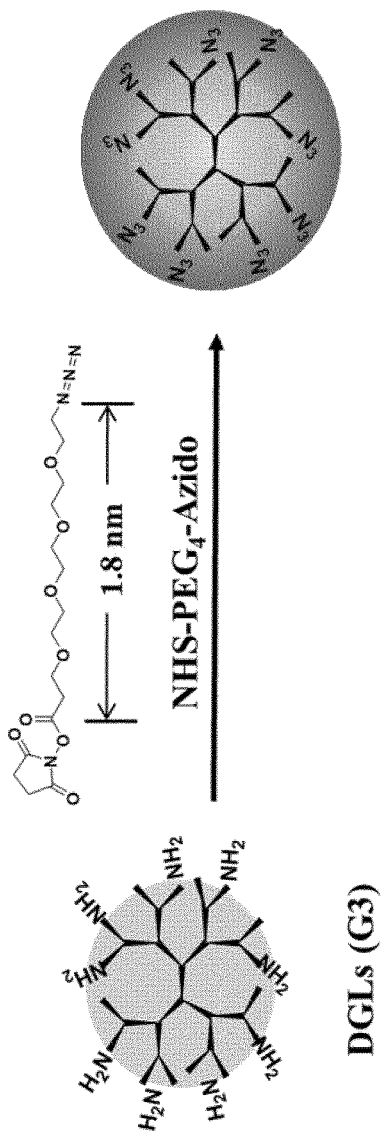
FIG. 4 shows the synthesis of G3 Dendri-Graft Poly-L-Lysines functionalized with PEG-Azido (DGLN).
Figure 5:
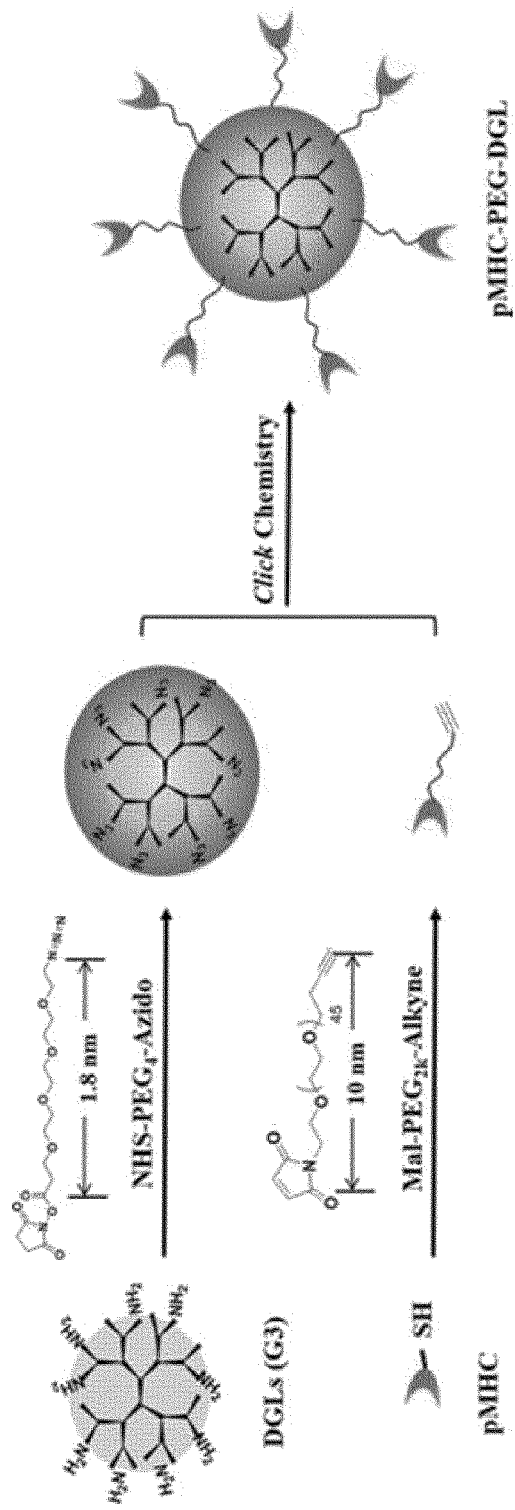
FIG. 5 shows the synthesis of pMHC-DGLN.

The DGLs surface functionalization was achieved by using a heterobifunctional crosslinker, NHS-PEG$_4$-Azido. Activated NHS ester easily reacts with primary amino groups on DGLs in a mild aqueous environment. About 1 mg of DGL-NH$_2$ was dissolved in PBS, at a pH of about 8.0. About 4.3 mg of NHS-PEG$_4$-N$_3$ (—NH$_2$:PEG$_4$=1:2, mol:mol) was added into the solution and reacted at room temperature for about 2 hours. After reaction, the DGL-N$_3$ was washed by ultrafiltration (MW cutoff 3000) with PBS at about pH 7.4 three times to remove unreacted NHS-PEG$_4$-N$_3$ (FIG. 4).

pMHC Conjugation to DGLN (FIG. 5)

To conjugate pMHC monomers to the surface of DGLN, a single-chain NRP-V7/K$^d$ construct engineered to encode a carboxyterminal Cys (—SH) is first pegylated and produced in CHO cells (referred to as V7CHO-Cys). Briefly, a 3.5 mL solution of V7CHO-Cys (3.58 mg/mL) in PBS pH 7.4 was mixed with 24 pt of 500 mM EDTA, 375 uL of 1 M NaCl, 500 μL of 200 mM PB buffer and 1.625 mL ETF water. 4 mg of Malimide-PEG$_{2k}$-Alkyne was then added to the mixture (final reaction volume was 6.0 mL) and allowed to react overnight at R.T. The reaction solution was then dialyzed against PBS pH 7.4 at 4° C. for 48 h.

V7CHO-PEG$_{2k}$-Alkyne solution was next concentrated to a final volume of 3.5 mL in PBS pH 7.4 in a nitrogen athmosphere and added 60 μL of DGLN (5 mg/mL in PBS), 150 μL ascorbic acid (50 mM in PBS) and 175 μL Cu-TBTA, which were allowed to react for 24 h at R.T. After reaction, the nanoparticles were purified via ultrafiltration (MW cutoff 100 KDa) against PBS pH 7.4, 6 times.

Biochemical and Biophysical Analyses of the Conjugates

Figure 6:
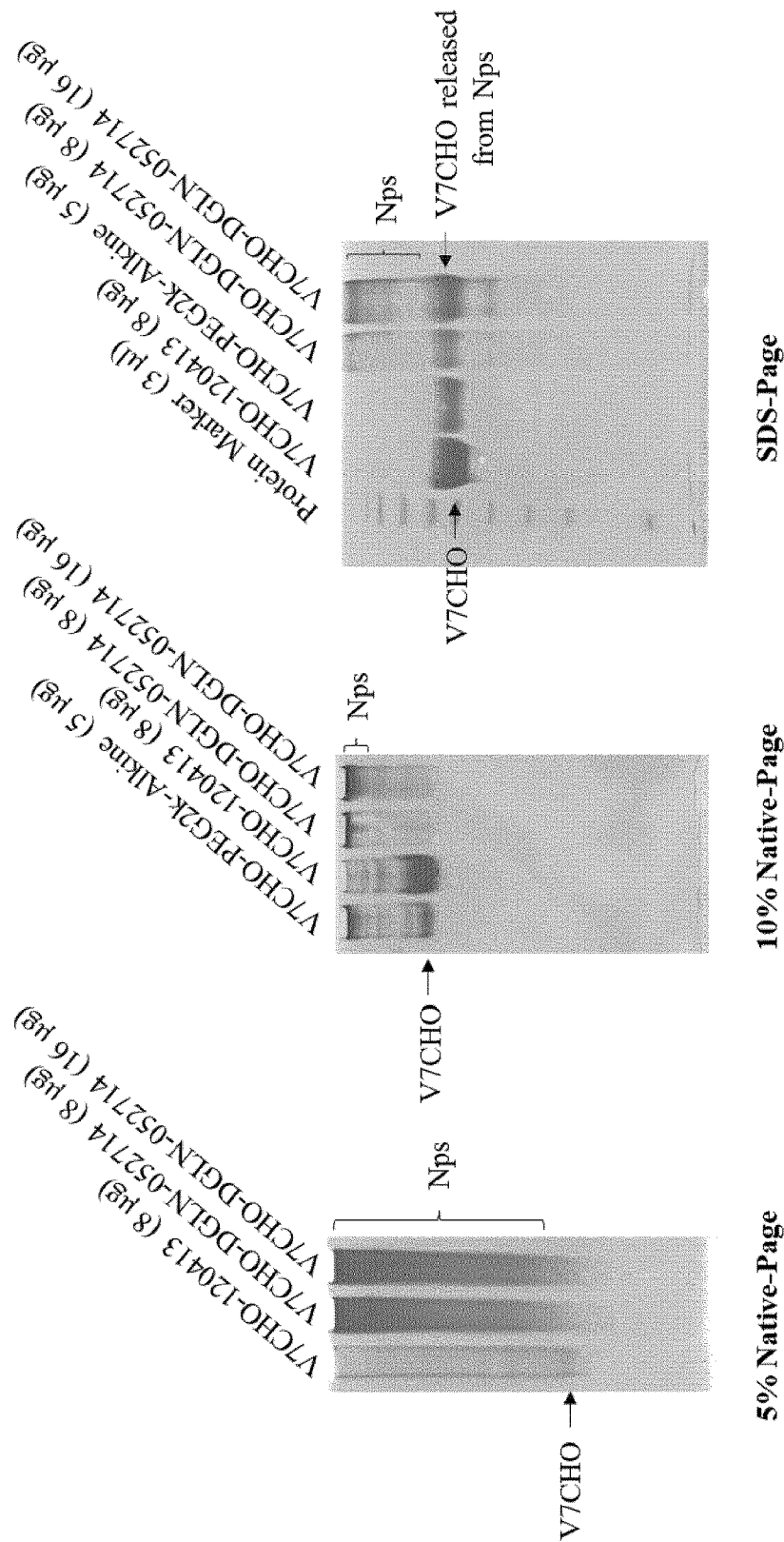
FIG. 6 shows native and denaturing PAGE analysis of pMHC-DGLN conjugates.

The conjugates were analyzed via native and denaturing (SDS) PAGE. FIG. 6 shows the presence of an obvious Coomassie-blue stained smear under native-PAGE conditions (left two panels), detecting pMHC-conjugated DLGN, in the absence of free (unconjugated) V7CHO monomer. Electrophoresis of these compounds under denaturing/reducing conditions revealed the release of V7CHO from the NPs, confirming that pMHC conjugation to DLGN was successful.

Figure 7:
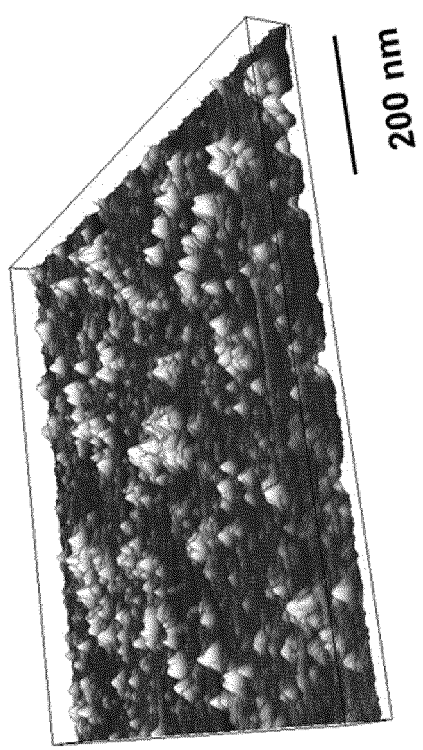
FIG. 7 shows AFM analysis of V7CHO-DGLN.

The biophysical properties of the pMHC-DGLN compound were next ascertained using atomic force microscopy (AFM) (FIG. 7). Briefly, the NP solution was layered on mica and observed under an AFM. V7CHO-DGLN displayed a spherical conformation with an average diameter of 19.95±0.25 nm (AFM measurements). The NPs were distributed well with monodisperity. The polydispersity Index (PI) and the hydrodynamic diameter in aqueous solution was tested by DLS. The concentration used for the AFM sample preparation was 4 μg DGLN/mL (equal to 4.38×10$^{13}$ NPs/mL). Analysis was done using 5 pt of this solution (~2.19× 10$^{11}$ NPs) on a 1 um×1 um scanning area.

Bradford analysis indicated that the pMHC content of the compound described above corresponded to 52 pMHC monomers on each NP.

Figures 8A, 8B:
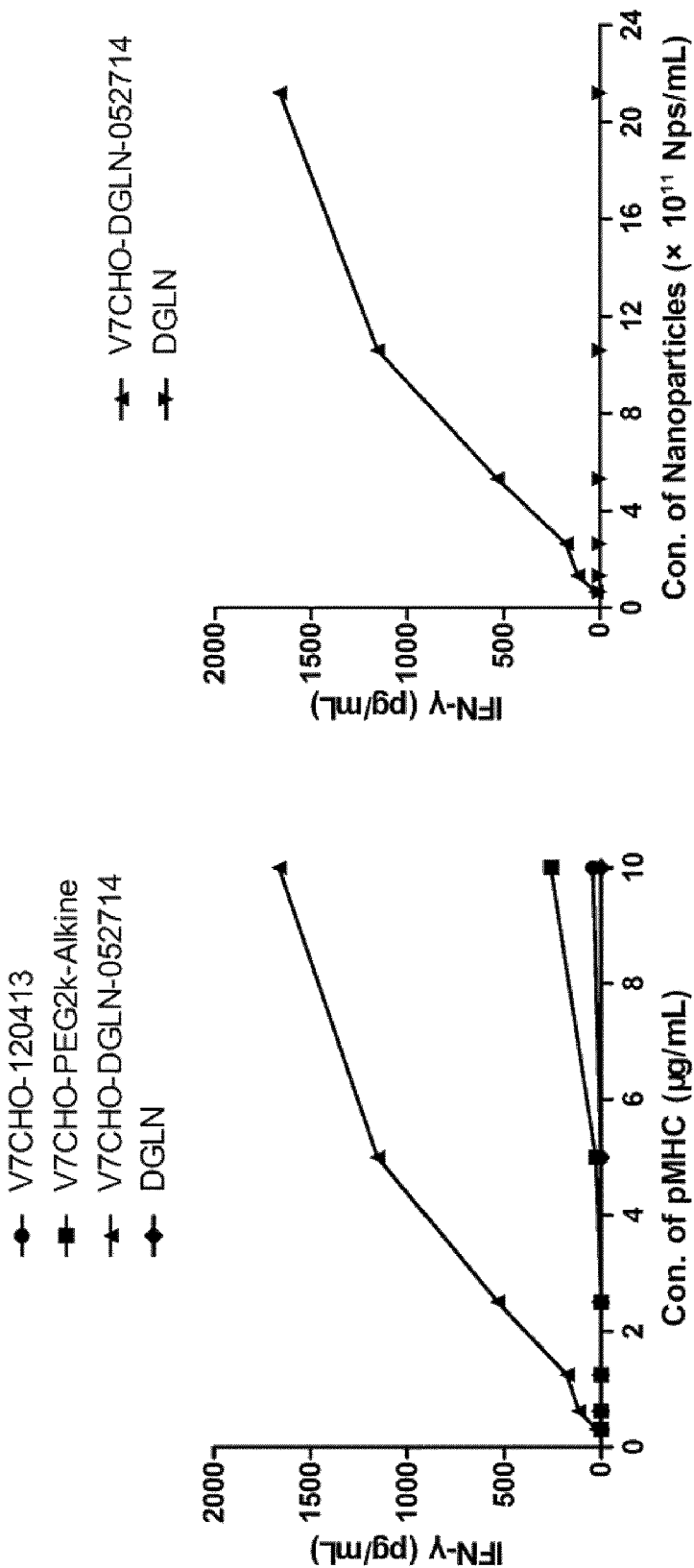
FIGS. 8A-8B show that V7CHO-DGLN have powerful agonistic properties on cognate CD8+ T-cells.

Lastly, to ascertain if this compound had agonistic activity on cognate T-cells, its ability to trigger the secretion of IFNγ by NRP-V7/K$^d$-specific CD8+ T-cells purified from 8.3-TCR-transgenic NOD mice was measured. Briefly, 8.3-CD8+ T-cells were cultured in the presence of free V7CHO protein, pegylated V7CHO, V7CHO-DGLN or DGLN for 48 h. The IFN-γ content was subsequently measured in the supernatants by ELISA. FIGS. 8A-8B show that V7CHO-DGLN and, to a much lesser extent, pegylated V7CHO, had very high, concentration-dependent agonistic activity on these T-cells, demonstrating the functional properties of these compounds.

Preparation, Purification and Characterization of pMHC-PEG-DSPE Micelles.

Amphiphilic block copolymers assemble into nano-scaled core-shell structures, polymeric micelles, which have been of considerable interest for delivering drugs with poor water solubility. Poly(ethylene glycol)-distearoylphosphatidylethanolamine (PEG-DSPE) block copolymers are safe, biocompatible and have been approved by the Food and Drug Administration for clinical applications. DSPE-PEG has been widely used in the preparation of liposomes, polymeric nanoparticles, polymer hybrid nanoparticles, and solid lipid nanoparticles, among others. The amphiphilic copolymers are nanostructures composed by a hydrophobic core (DSPE) and a hydrophilic shell (PEG). The core-shell structure can encapsulate and carry poorly water-soluble drugs to congregate in the core of DSPE, and the PEG shell reduces the in vivo clearance and the adsorption of plasma proteins. Therefore, utilizing DSPE-PEG for the formation of nanostructures could prolong the body circulation. Most importantly, the critical micelle concentration (CMC) of the DSPE-PEG is extremely low ($10^{-5}$ M). This property results in some positive functions of formulated micelles such as greater solubilization of hydrophobic drugs and more thermodynamic stability against dilution with the large volume of the blood following intravenous administration.

To decorate pMHC on the surface of polymeric micelles, DSPE-PEG-maleimide (DSPE-PEG-Mal) were chosen as copolymers. The DSPE-PEG polymeric micelles are prepared by solvent evaporation method as reported in Vakil, R. et al. (2008) Mol Pharm 5: 98-104 and Musacchio, T. et al. (2009) Mol Pharm 6:468-479. In brief, DSPE-PEG-Mal was dissolved in methanol in a round-bottom flask. The organic solvent mixture was evaporated under high vacuum to produce a thin film of copolymers. This film was further dried under vacuum overnight to remove any traces of remaining solvents. Then, the dry polymeric film was dissolved in PBS pH 7.4 to self-assemble into micelles with maleimide groups on the surface. pMHC could be conjugated onto the micellar surfaces through a thiol-maleimide specific reaction. The resulting NPs were purified by gel filtration to remove the unconjugated pMHC. After that, the resulting NPs can be characterized by DLS, Z-potential, SDS-page and TEM.

Example 2

Expansion of Disease-Specific $T_R1$ Cells

Figure 9A:
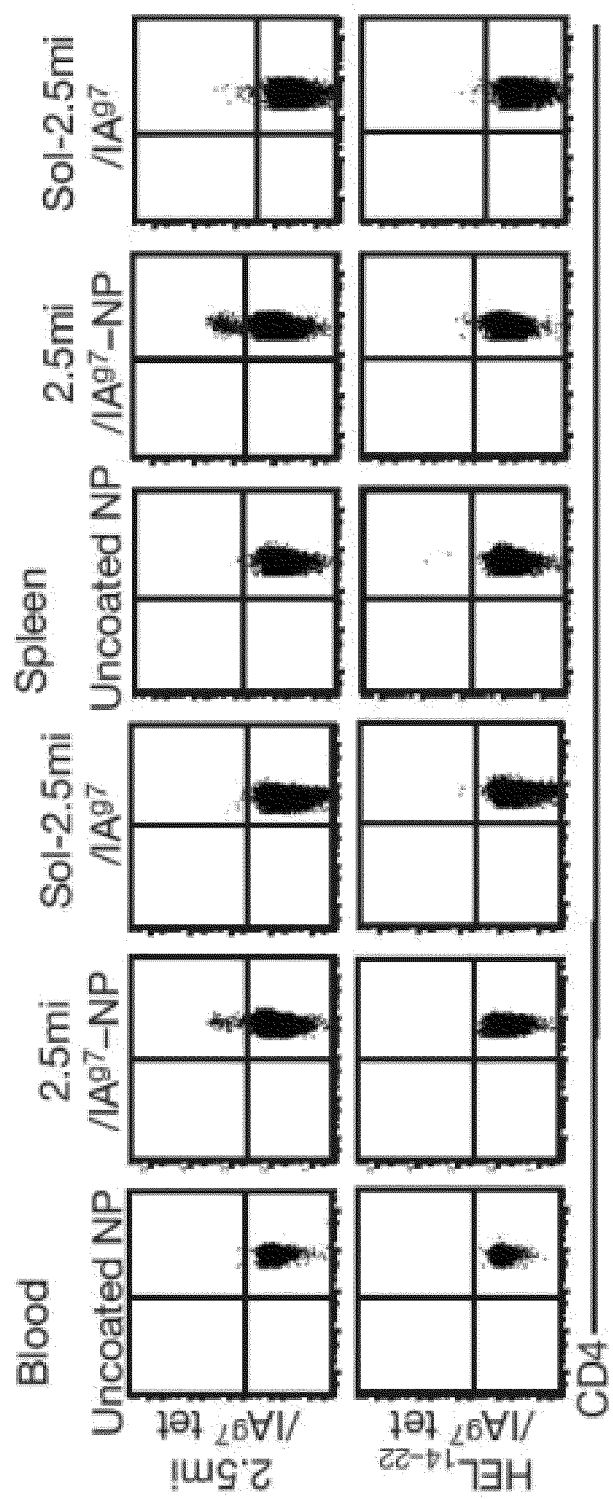
FIGS. 9A-9N show pMHC-NPs relevant for T1D or EAE expand cognate disease-suppressing $T_R$1-like CD4+ T cells in vivo.
Figure 9B:
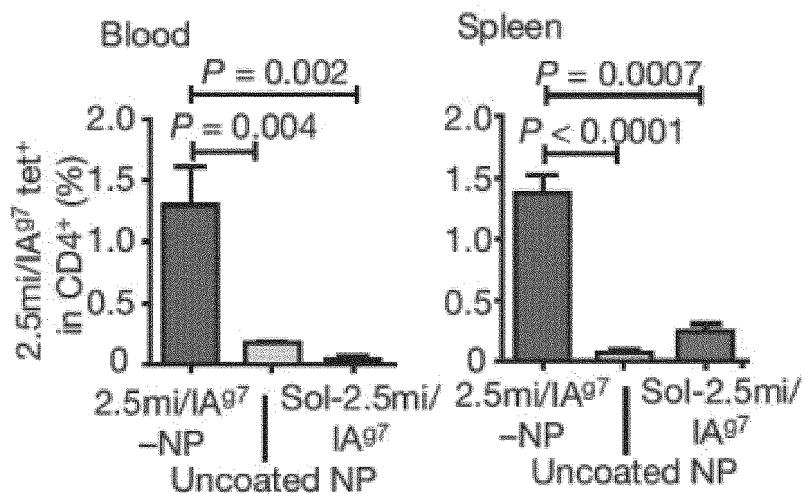
Figure 9C:
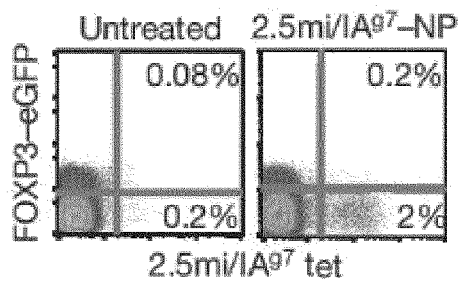
FIG. 9C shows tetramer-staining of splenic CD4$^+$ T cells from treated or untreated NOD Foxp3-eGFP mice.
Figure 9D:
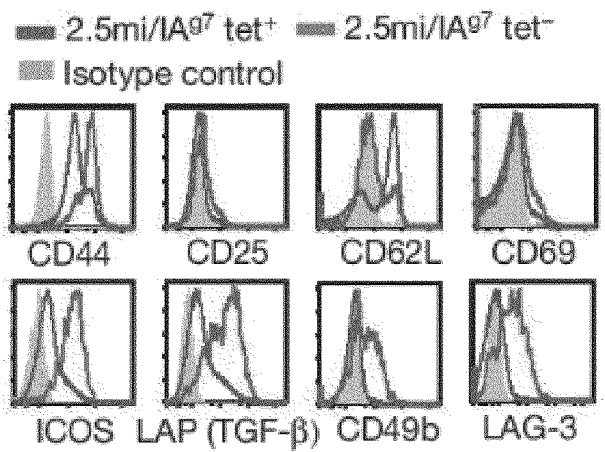
FIG. 9D shows the tetramer$^+$CD4$^+$ T cells of 2.5 mi/IA$^{g7}$-NP-treated mice display a $T_R$1-like phenotype.
Figure 14A:
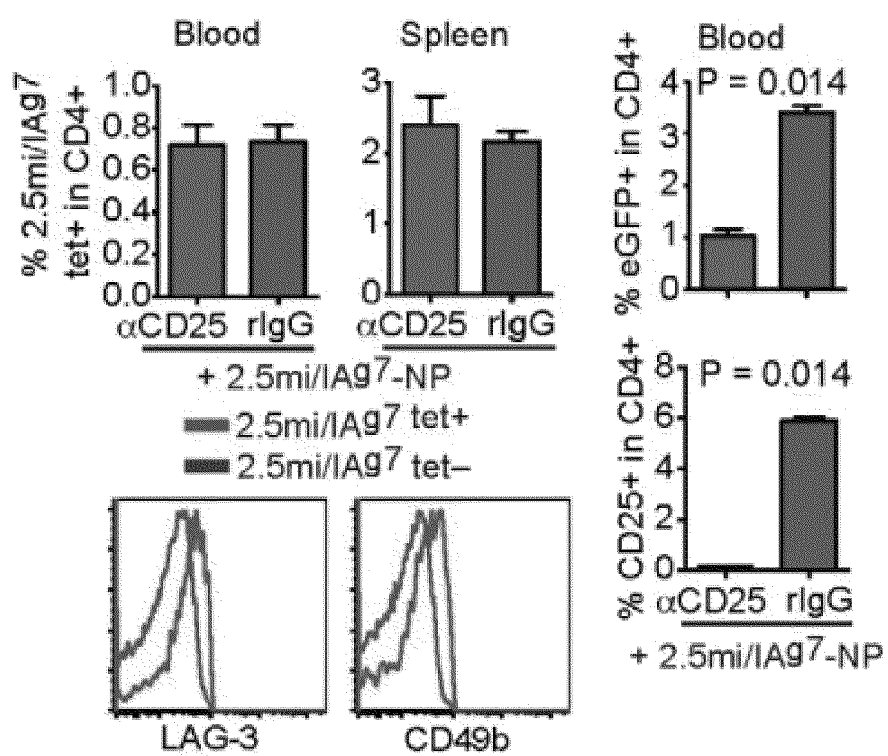
FIGS. 14A-14N show sustained expansion of cognate $T_R$1-like CD4$^+$ T cells by pMHCII-NP therapy restores normal glucose homeostasis in diabetic NOD mice by suppressing antigen presentation and the activation of non-cognate autoreactive T cells in the PLNs and the progression of insulitis.
Figure 14B:
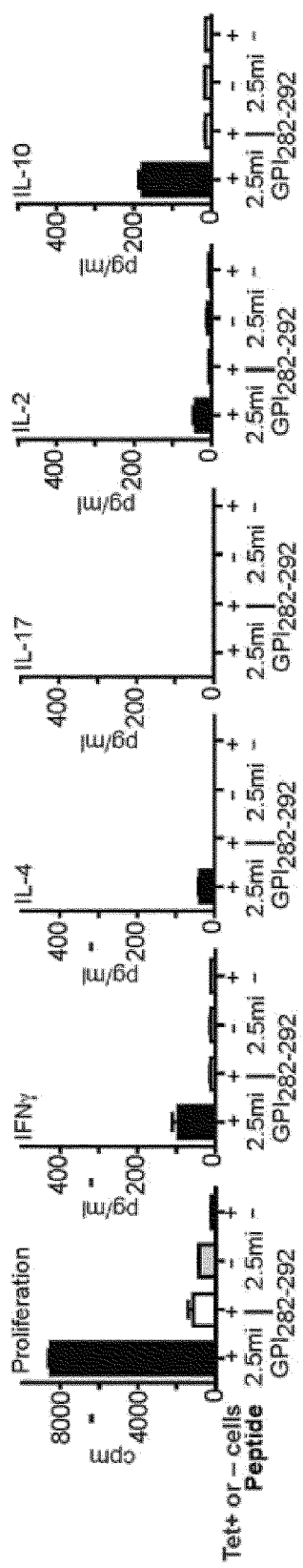
FIG. 14B shows tetramer$^+$CD4$^+$ T cells sorted from 2.5 mi/IA$^{g7}$-NP-treated mice proliferate and produce IL-10 and, to a lesser extent IFNγ in response to stimulation with 2.5 mi peptide-pulsed DCs (n=3 mice).

Applicant treated non-obese diabetic (NOD) and NOD Foxp3-eGFP mice expressing enhanced green fluorescent protein (eGFP) under the control of the mouse Foxp3 promoter) with uncoated nanoparticles or nanoparticles coated with a pMHC, 2.5 mi/IA$^{g7}$ (Stratmann, T. et al. (2003) J. Clin. Invest. 112:902-914), recognized by the diabetogenic BDC2.5-specific T-cell receptor (TCR), or with 2.5 mi/IA$^{g7}$ monomers. Nanoparticles coated in 2.5 mi/IA$^{g7}$ induced expansion of cognate CD4$^+$ T cells in blood and spleens of all mice (FIGS. 9A, 9B). These cells had a memory-like (CD44$^{hi}$CD62L$^{low}$) FOXP3 $T_R1$-like phenotype, expressing ICOS, latent-associated TGF-β and the $T_R1$ markers CD49b and LAG-3 (FIGS. 9C, 9D). A similar outcome was observed in mice treated with 2.5 mi/IA$^{g7}$-NPs upon depletion of CD4$^+$CD25$^+$ T cells (FIG. 14A). Unlike their tetramer counterparts, these cells proliferated and secreted IL-10 and to a lesser extent IFNγ, but not IL-2, IL-4 or IL-17, in response to dendritic cells (DCs) pulsed with the 2.5 mi peptide (FIG. 14B). Real-time reverse-transcription (RT)-PCR analyses confirmed the $T_R1$-like phenotype of these cells (Tables 3A-3B).

Figure 14C:
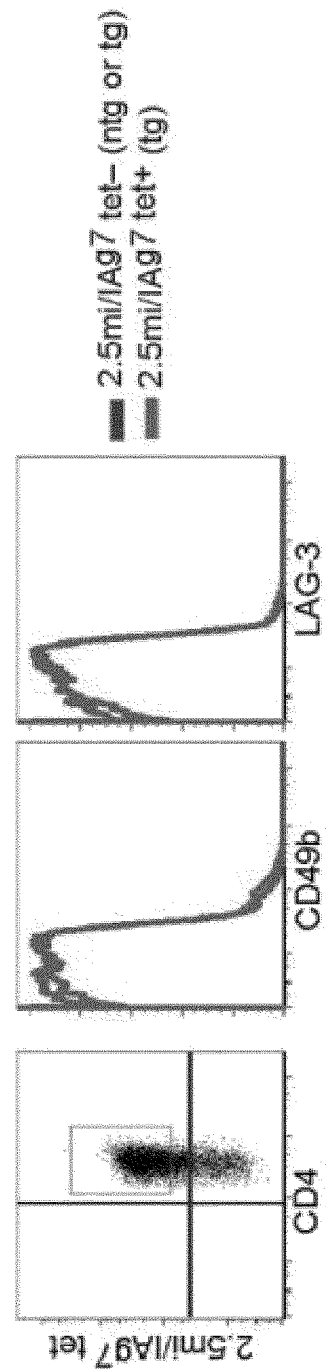
FIG. 14C shows representative cell surface CD49b and LAG-3 profiles on tetramer$^+$ CD4$^+$ T cells from BDC2.5 NOD Foxp3-eGFP mice compared with tetramer-CD4$^+$ T cells from transgenic or wild-type NOD mice (n=4).
Figure 14M:
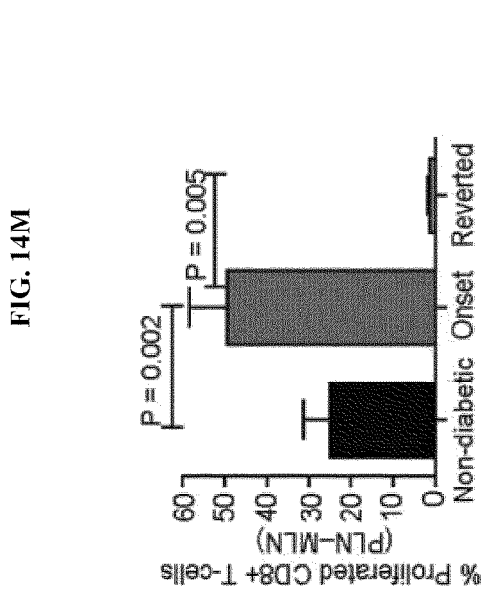
FIG. 14M shows IPGTT serum insulin levels corresponding to the mice in FIG. 14K.
Figure 14L:
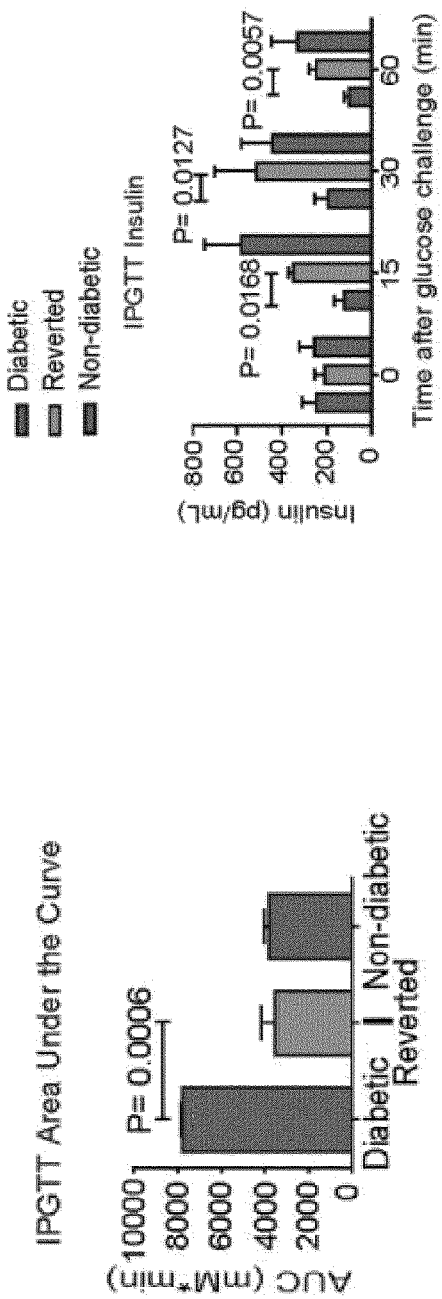
FIG. 14L shows areas under the curve (AUC) in the IPGTTs shown in FIG. 14K.

To determine if pMHCII-NPs could directly trigger $T_R1$ marker and IL-10 expression on cognate CD4$^+$ T cells, Applicant cultured naive and anti-CD3 plus anti-CD28 monoclonal antibody (mAb)-preactivated 2.5 mi/IA$^{g7}$-tetramer$^+$CD4$^+$ T cells from BDC2.5-TCR-transgenic NOD Foxp3-eGFP or NOD Il10$^{GFP}$ mice (carrying an eGFP insertion in the Il10 locus) (Kamanaka, M. et al. (2006) Immunity 25:941-952) in the presence of 2.5 mi/IA$^{g7}$-NPs, 2.5 mi peptide or 2.5 mi/IA$^{g7}$ monomer. Naive T cells expressed neither CD49b nor LAG-3, even after incubation with 2.5 mi/IA$^{g7}$-NPs, 2.5 mi/IA$^{g7}$ monomer or 2.5 mi peptide (FIGS. 14C, 14D). However, preactivated T cells upregulated both markers as well as eGFP (IL-10) only in response to 2.5 mi/IA$^{g7}$-NPs (FIGS. 14D, 14E). In agreement with this, expression of IL-10 in NOD Il10$^{GFP}$ mice treated with 2.5 mi/IA$^{g7}$-NPs was largely restricted to the CD49b$^+$LAG-3$^+$CD4$^+$ subset (FIG. 14F).

Figure 9E:
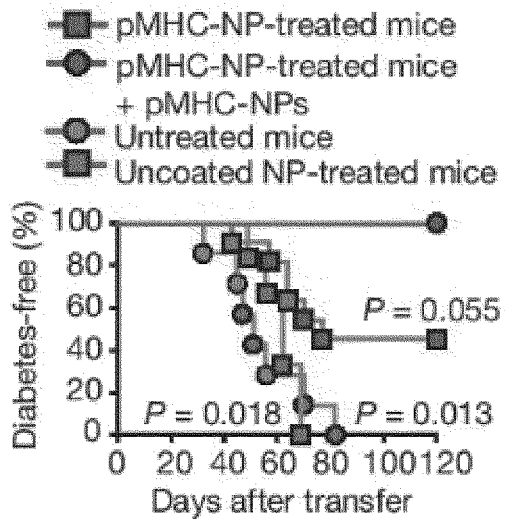
FIG. 9E shows incidence of diabetes in T-cell-reconstituted NOD scid hosts transfused with CD4$^+$ T cells from different donors±2.5 mi/IA$^{g7}$-NPs (n=11, 5, 7 and 6 from top).
Figure 9F:
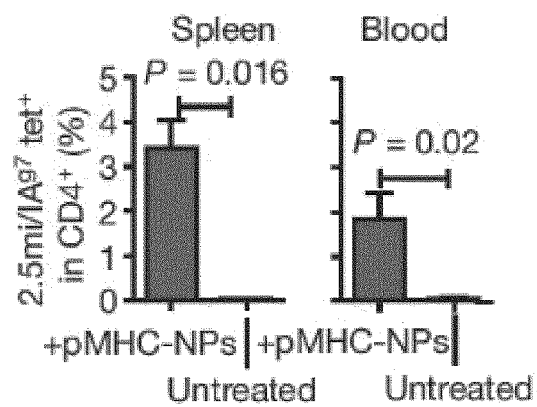
FIG. 9F shows percentages of tetramer+CD4$^+$ T cells in 2.5 mi/IA$^{g7}$-NP-treated or untreated NOD scid hosts (n=4-5 per group).

In vitro, the tetramer$^+$CD4$^+$ T cells of pMHC-NP-treated mice suppressed the proliferation of non-cognate (islet-specific glucose-6-phosphatase catalytic subunit-related protein (IGRP)- or LCMV Gp33-specific) CD8+ T cells in response to peptide-pulsed DCs, in an IL-10- and TGF-β-dependent manner (FIG. 14G). In vivo, splenic CD4+ T cells from donors treated with pMHC-NPs suppressed diabetes development in T-cell-reconstituted NOD scid (also known as NOD Prkdc$^{scid}$) hosts (FIG. 9E), an effect that was potentiated by treating hosts with pMHC-NPs (FIGS. 9E, 9F).

Figure 9G:
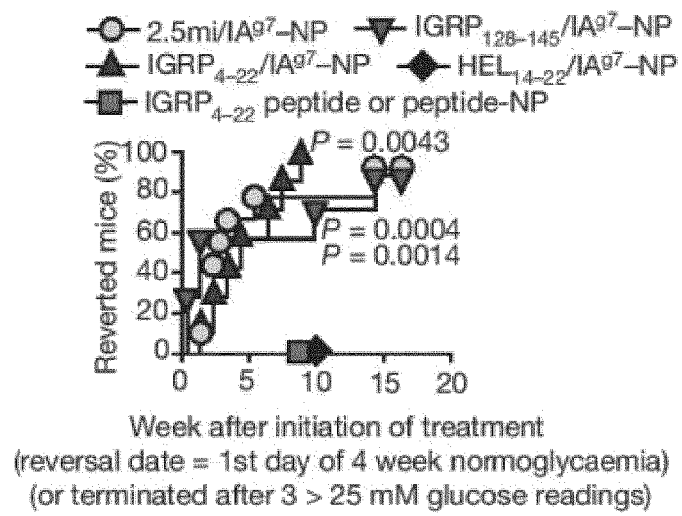
FIG. 9G shows incidence of disease reversal in diabetic mice treated with pMHC-NPs (n=9, 7, 7, 7 from top left to right), or IGRP$_{4-22}$ peptide (Burton, B. R. et al. (2014) Nature Commun. 5:4741-4747) and IGRP$_{4-22}$ peptide-NP (n=9).
Figure 9H:
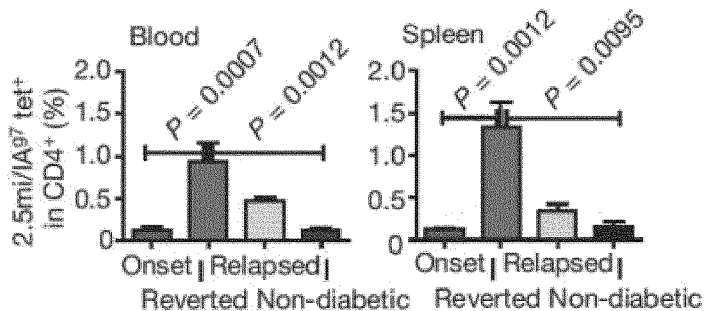
FIG. 9H shows percentage of tetramer$^+$ CD4$^+$ T cells in diabetic mice at onset, in response to 2.5 mi/IA$^{g7}$-NP therapy and age-matched non-diabetic controls (n=8, 6, 2 and 7 from left).
Figure 9I:
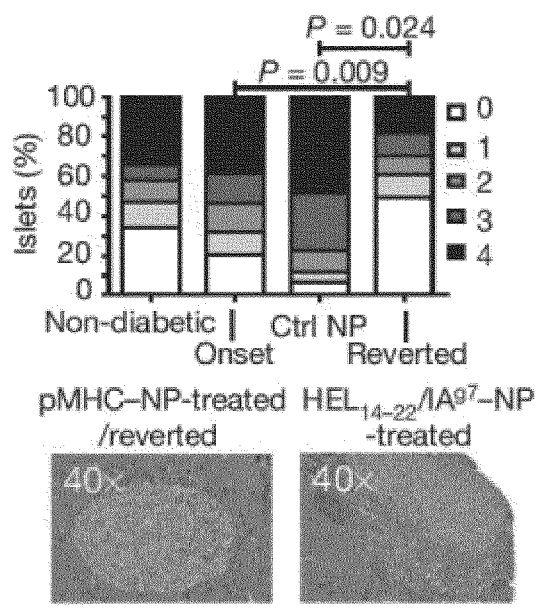
FIG. 9I shows insulitis scores (n=6, 4, 3 and 6 from left). Bottom, representative images.
Figure 14N:
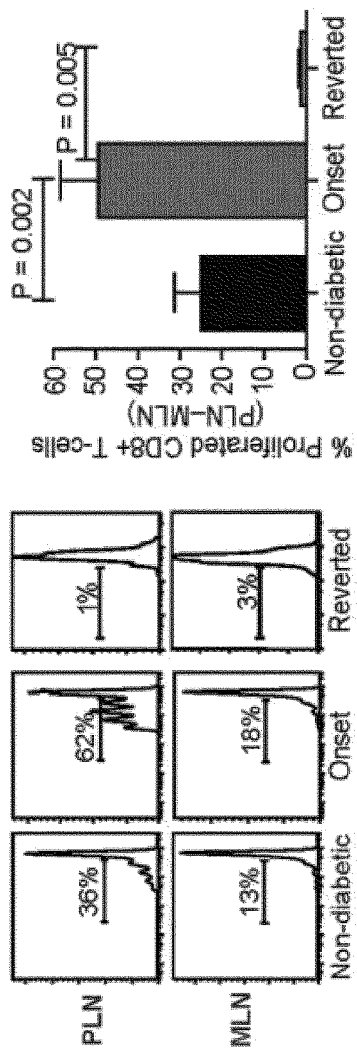
Figure 15A:
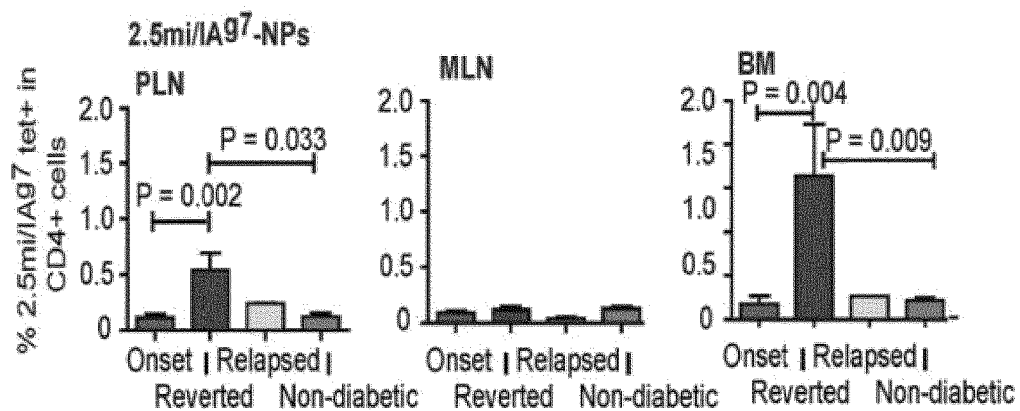
Figure 15B:
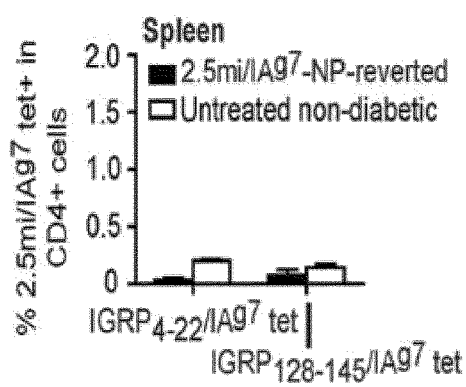
Figure 15C:
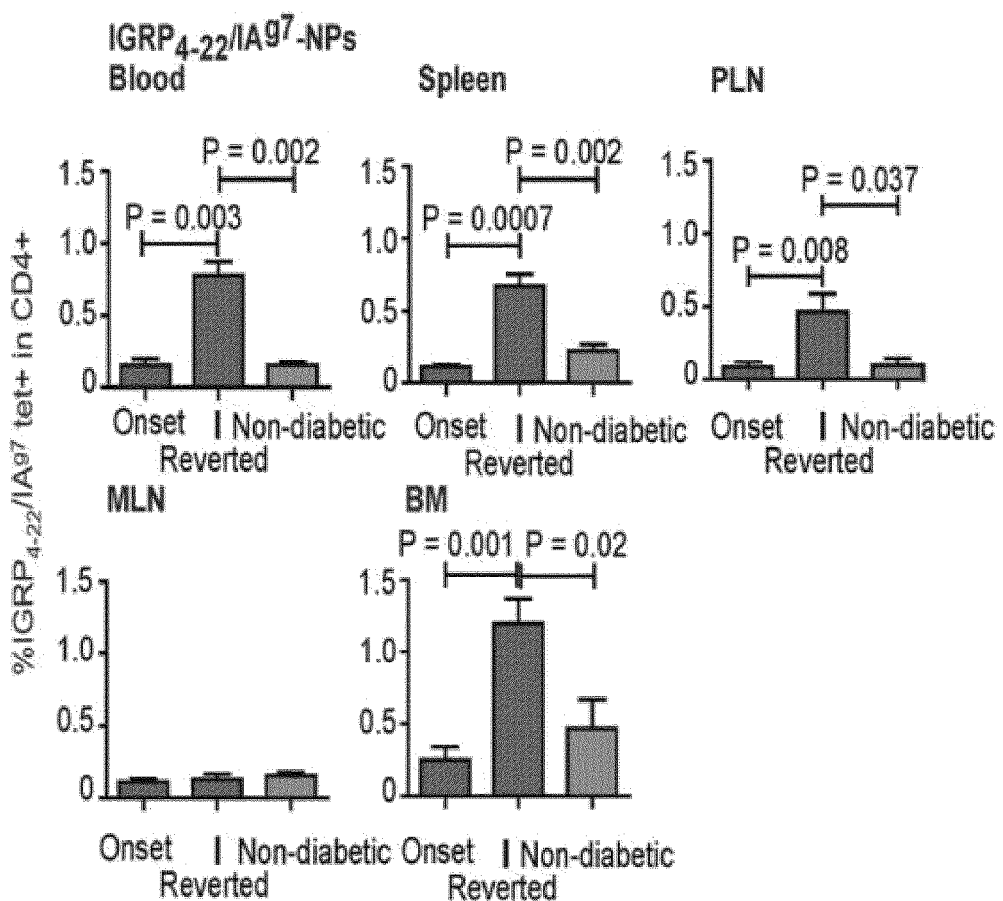
Figure 15D:
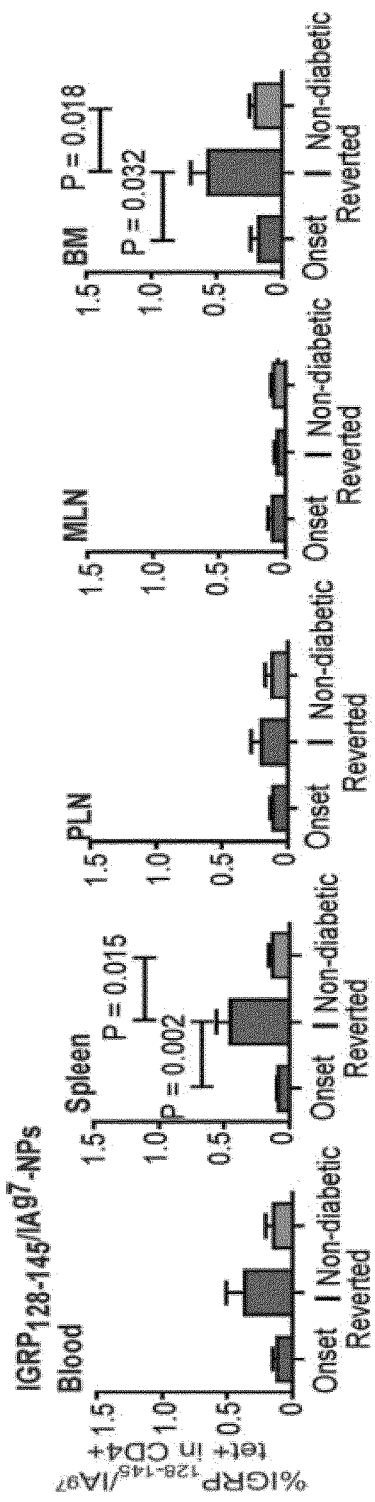
Figure 15E:
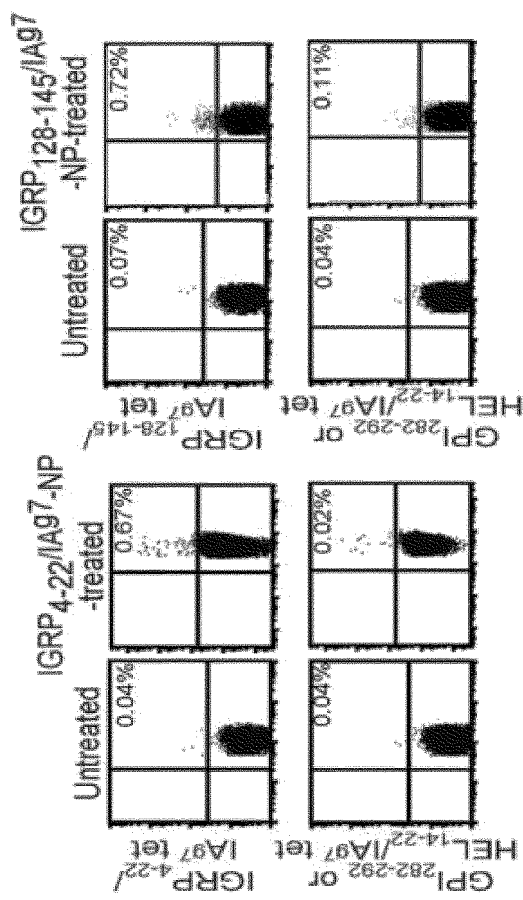
Figure 15F:
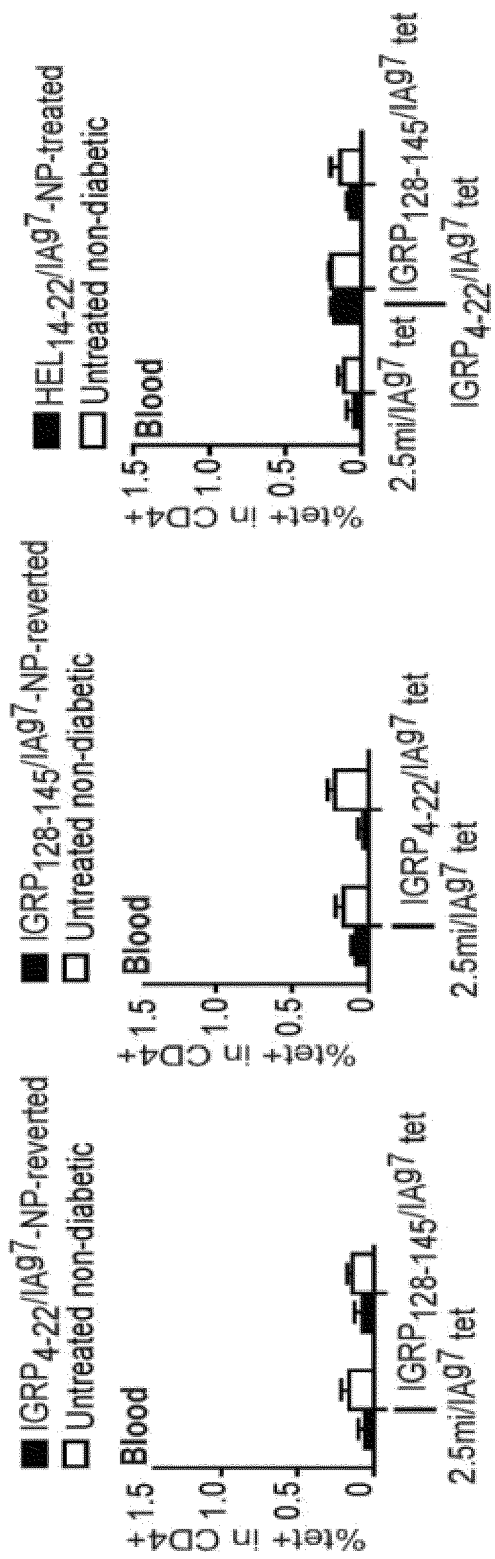
Figure 15G:
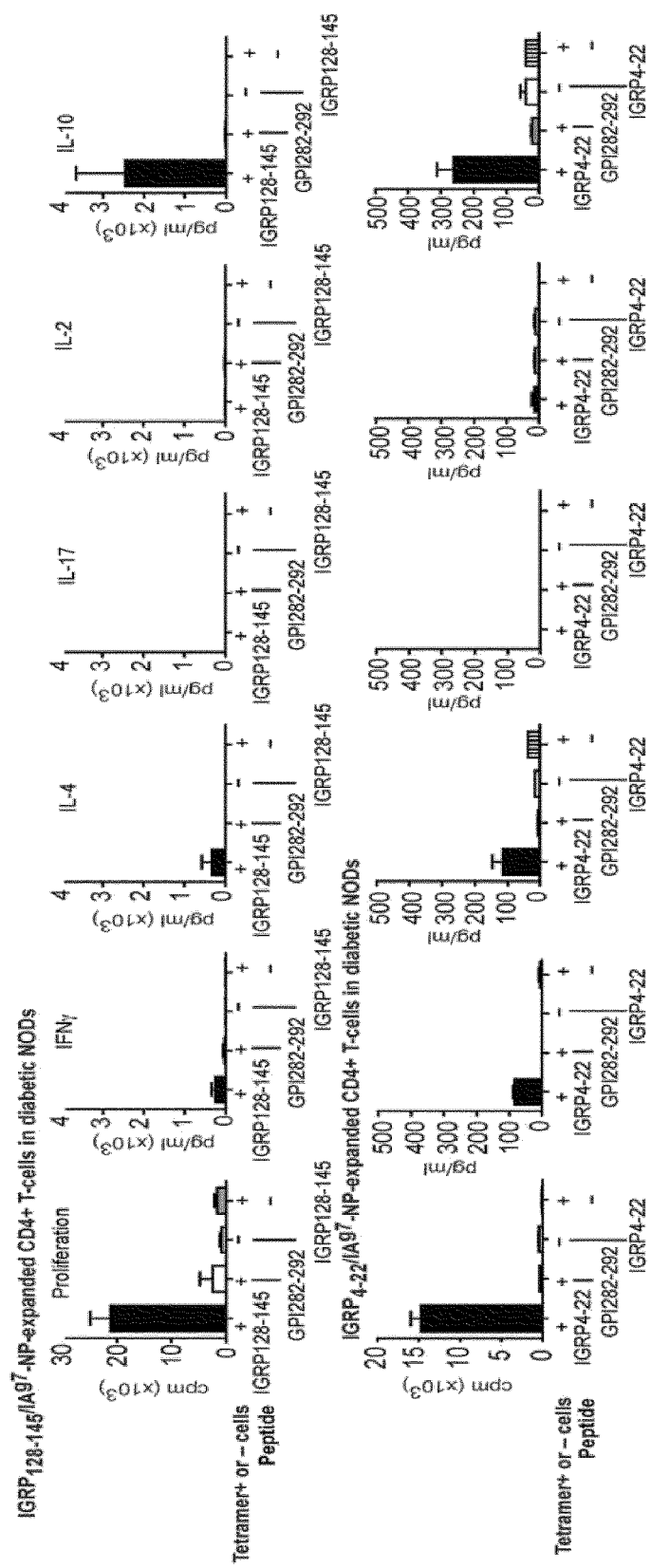
Figure 16C:
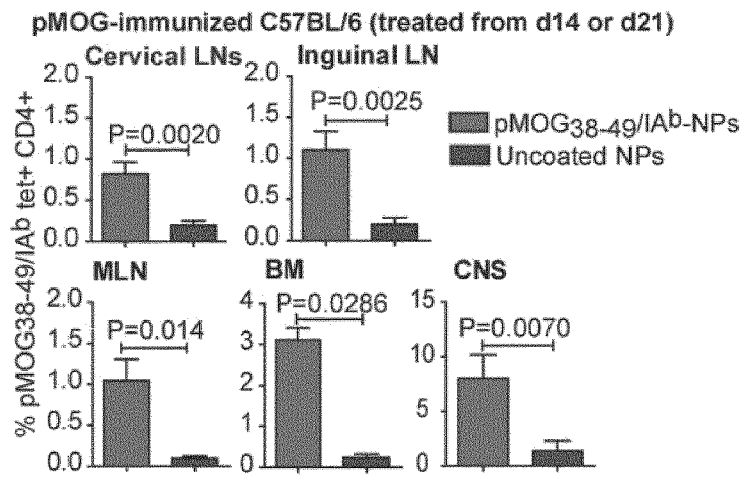
Figure 16D:
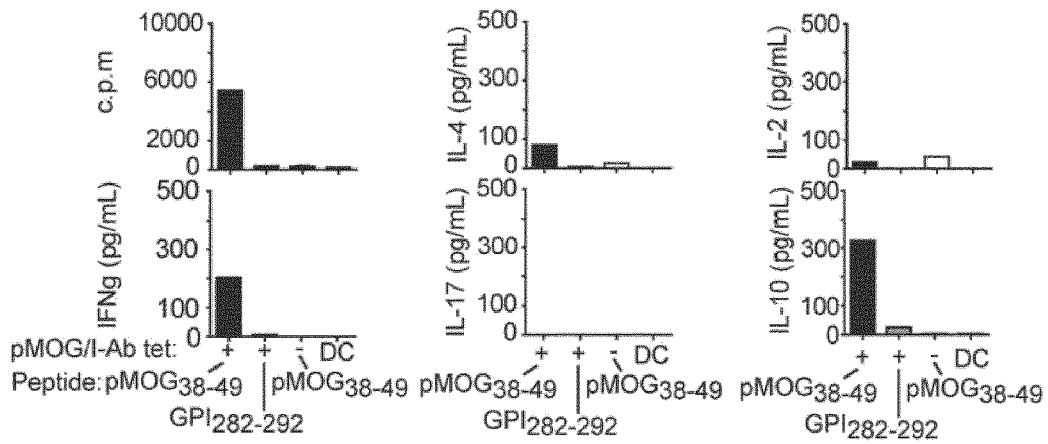
Figure 16E:
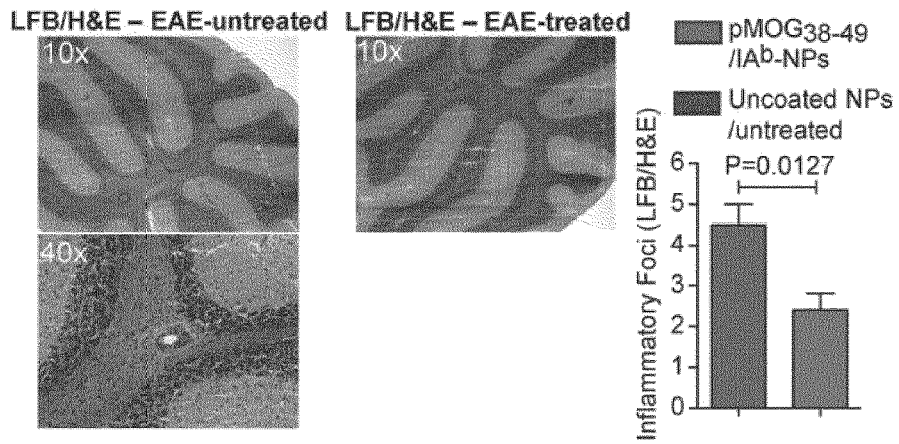
Figure 16F:
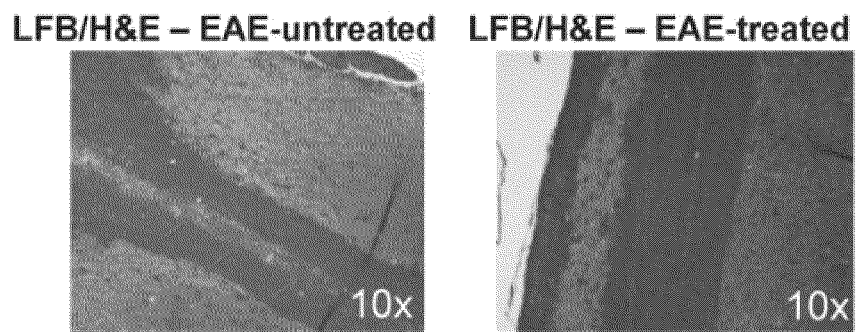

Applicant next investigated whether 2.5 mi/IA$^{g7}$-NPs or NPs coated with IGRP$_{4-22}$/IA$^{g7}$ or IGRP$_{128-145}$/IA$^{g7}$, targeted by sub-dominant pools of autoreactive CD4$^+$ T cells (Mukherjee, R. et al. (2005) J. Immunol. 174:5306-5315), could restore normoglycaemia in diabetic NOD mice. Unlike mice treated with nanoparticles coated with hen egg-white lysozyme (HEL)$_{14-22}$/IA$^{g7}$, 90-100% of the mice that received nanoparticles coated with 2.5 mi/IA$^{g7}$, IGRP$_{4-22}$/IA$^{g7}$ or IGRP$_{128-145}$/IA$^{g7}$ reverted to stable normoglycaemia (FIGS. 9G, 14H) and displayed systemic expansion of cognate $T_R1$-like T cells (FIGS. 1H, 15A-15G). Treatment with peptide (Burton, B. R. et al. (2014) Nature Commun. 5:4741-4747) or peptide-coated nanoparticles but without MHC could not reproduce any of these effects (FIGS. 9G, 14H, 15H). Treatment withdrawal resulted in loss of the normoglycaemic state in 25-60% of mice (FIG. 14I), in association with the loss of the tetramer$^+$CD4$^+$ T-cell pools (FIGS. 9H, 15A). The animals that maintained normoglycaemia had normal postprandial serum insulin levels, fasting glucose tolerance (FIGS. 14J-14M) and reduced insulitis (FIG. 9I). In addition, their pancreatic lymph nodes (PLNs) could not support the proliferation of carboxyfluorescein succinimidyl ester (CFSE)-labelled IGRP$_{206-214}$/K$^d$-specific CD8$^+$ T cells in vivo (FIG. 14N).

Figure 9J:
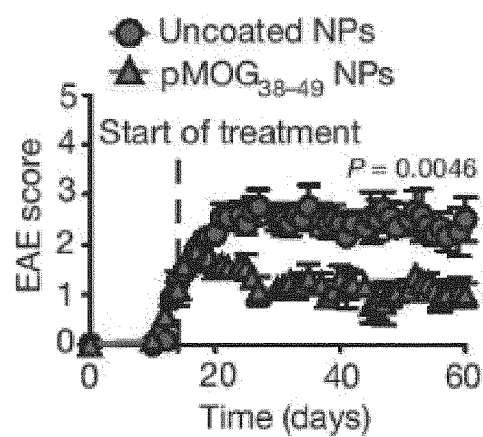
FIGS. 9J-9M show C57BL/6 mice were immunized with pMOG$_{35-55}$.
Figure 9K:
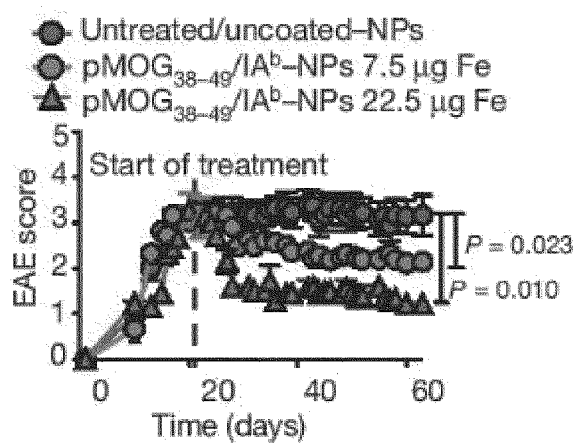
Figure 9L:
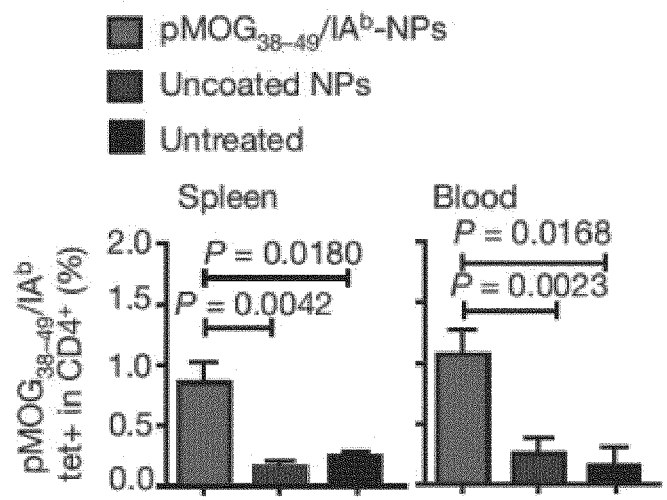
Figure 9M:
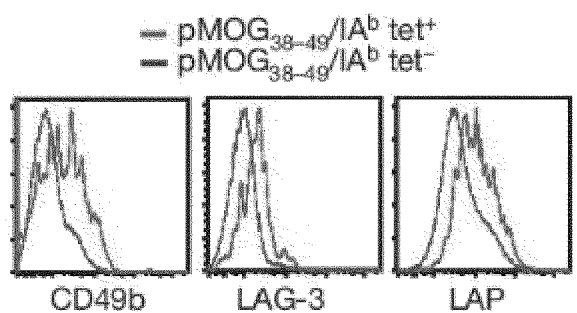
Figure 9N:
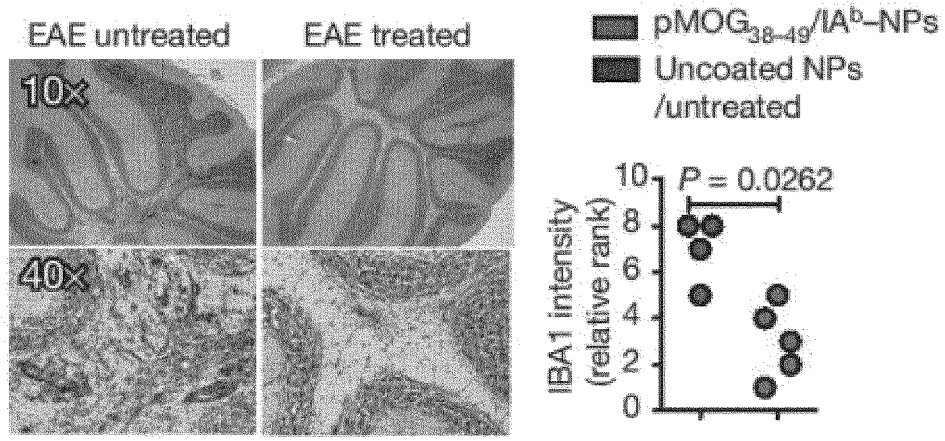

Applicant next tested the ability of nanoparticles coated with myelin oligodendrocyte glycoprotein (pMOG)$_{38-49}$/IA$^b$ to blunt the progression of pMOG$_{35-55}$-induced experimental autoimmune encephalomyelitis (EAE, a model of multiple sclerosis) in C57BL/6 mice. pMOG$_{38-49}$/IA$^b$-NP therapy dampended disease progression when given on day 14 after immunization and restored motor function in paralytic mice when given on day 21 (FIGS. 9J, 9K). These effects were mirrored by weight gain, and were associated with systemic expansion of cognate $T_R1$-like T cells, reductions in activated macrophage/microglia in the cerebellum, fewer inflammatory foci and areas of demyelination in the white matter of the cerebellum and decreased demyelination of the spinal cord (FIGS. 9L-9N, 16A-16F). Similar therapeutic effects were seen in HLA-DR4-IE-transgenic C57BL/6 IAb$^{null}$ mice (MHCII knockout mice expressing a transgenic hybrid MHCII molecule composed of the peptide-binding domain of human HLA-DR4 and the membrane-proximal domain of mouse IE (DR4-IE)) immunized with human (h) proteolipid protein (hPLP)$_{175-192}$ or hMOG$_{97-108}$ peptides and treated with hPLP$_{175-192}$/DR4-IE or hMOG$_{97-108}$/DR4-IE-NPs upon developing limb paralysis (FIGS. 17A-17D).

Disease and Organ Specificity

Figure 10A:
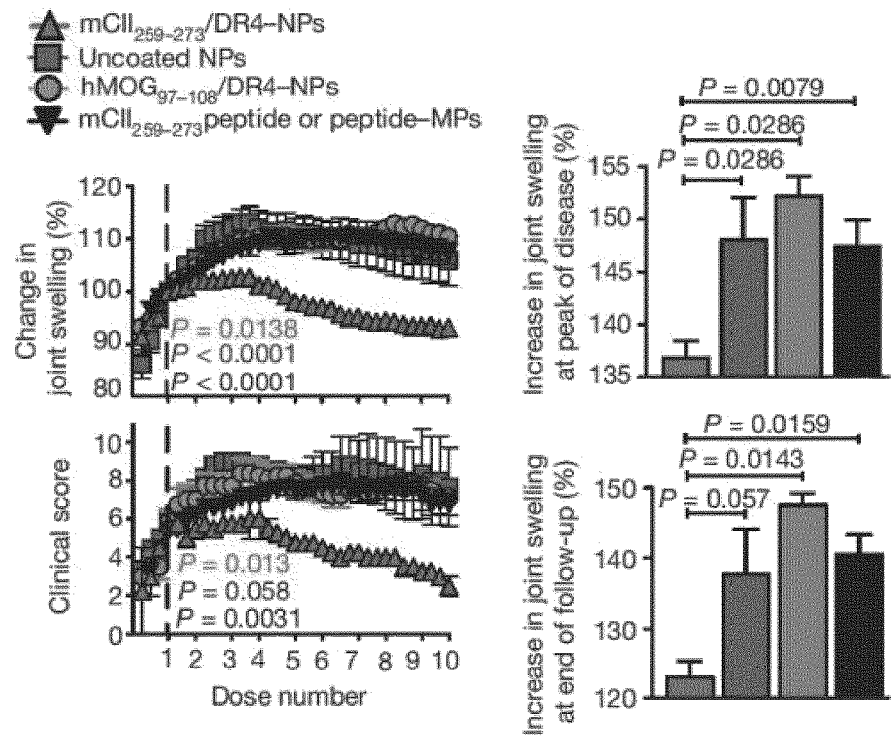
Figure 10B:
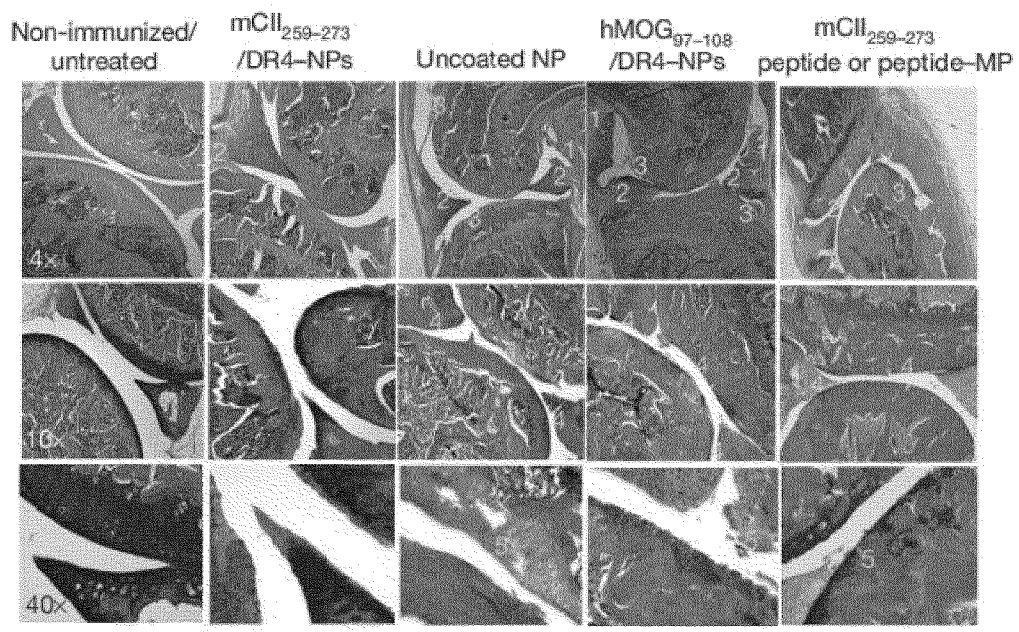
Figure 10C:
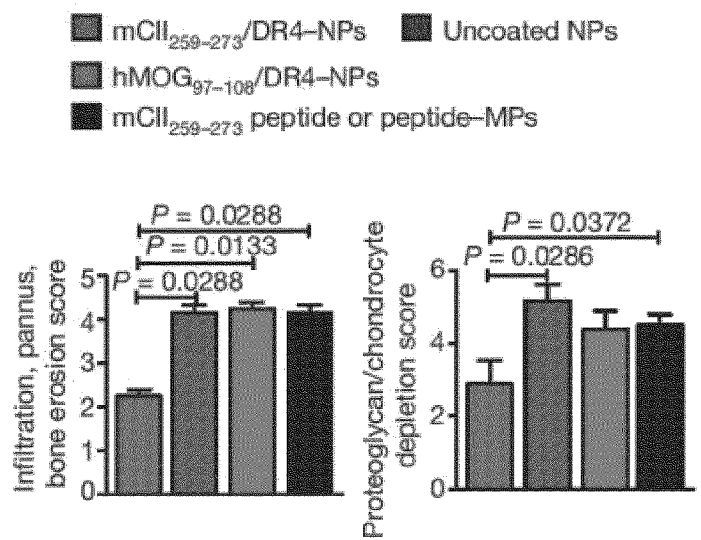
Figure 10D:
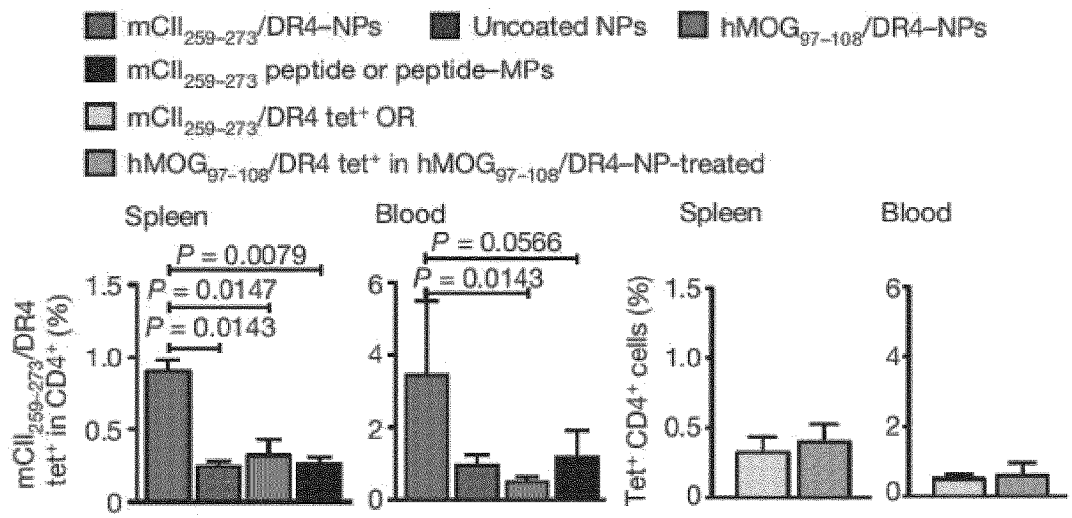

Studies in another autoimmune disease model, collagen-induced arthritis (CIA), showed that nanoparticles displaying mouse collagen (mCII)$_{259-273}$/DR4-IE could reduce joint inflammation in arthritic HLA-DR4-IE-transgenic C57BL/10.M mice in association with systemic expansions of cognate T$_R$1-like T cells (FIGS. 10A-10E, 1E). In contrast, nanoparticles coated with hMOG$_{97-108}$/DR4-IE complexes had no effect (FIGS. 10A-10C).

Figure 10H:
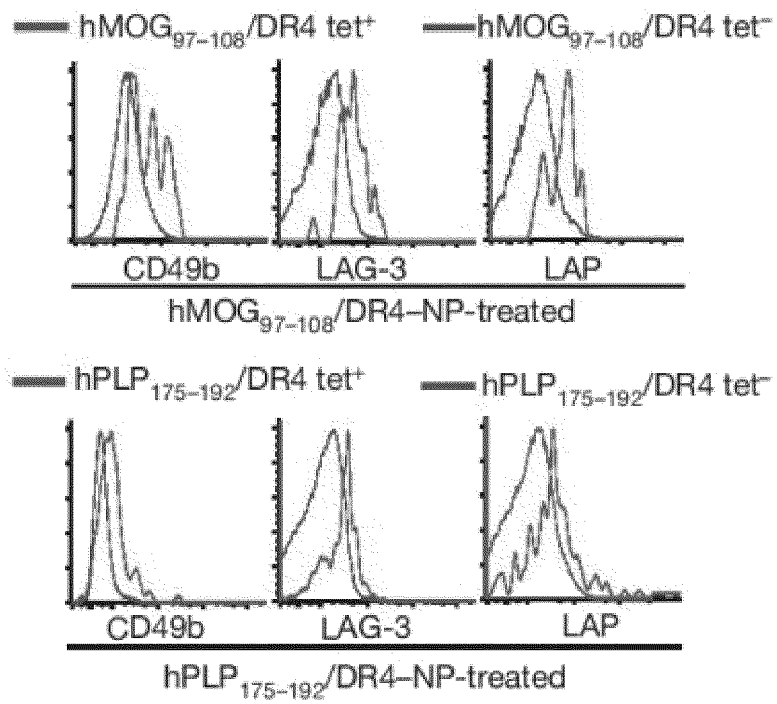
Figure 17A:
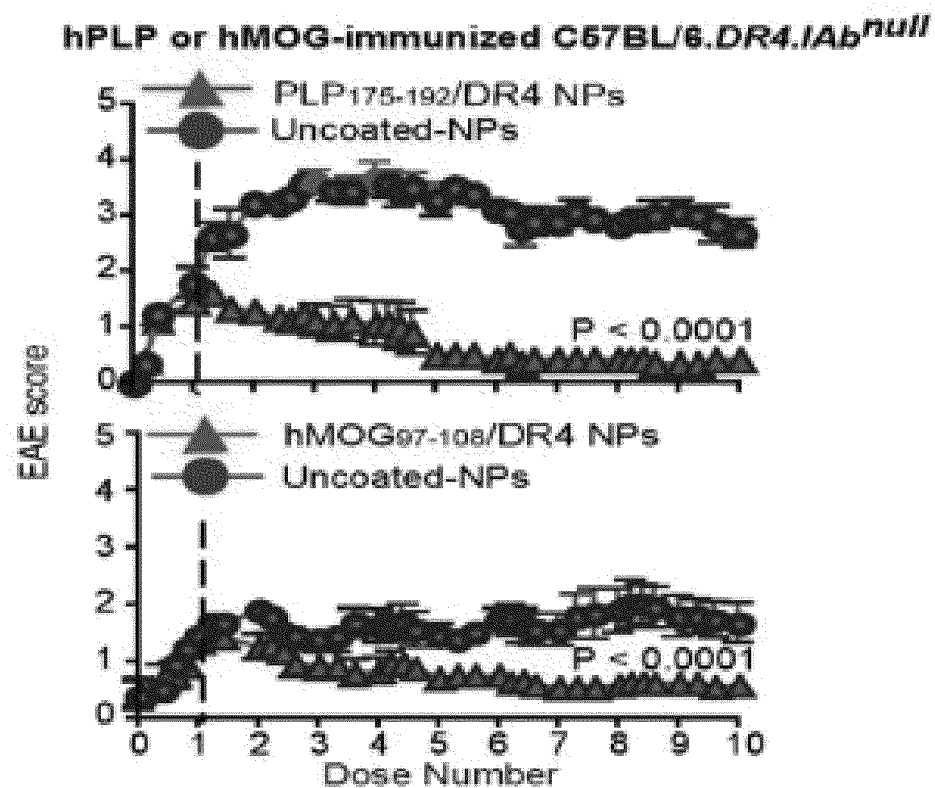
FIGS. 17A-17I show EAE- or CIA-relevant pMHCII-NPs expand cognate $T_R1$-like CD4$^+$ T cells and ameliorate clinical and pathological signs of EAE or CIA in HLA-DR4-IE-transgenic C57BL/6/$IAb^{null}$ or C57BL/10.M mice.
Figure 17B:
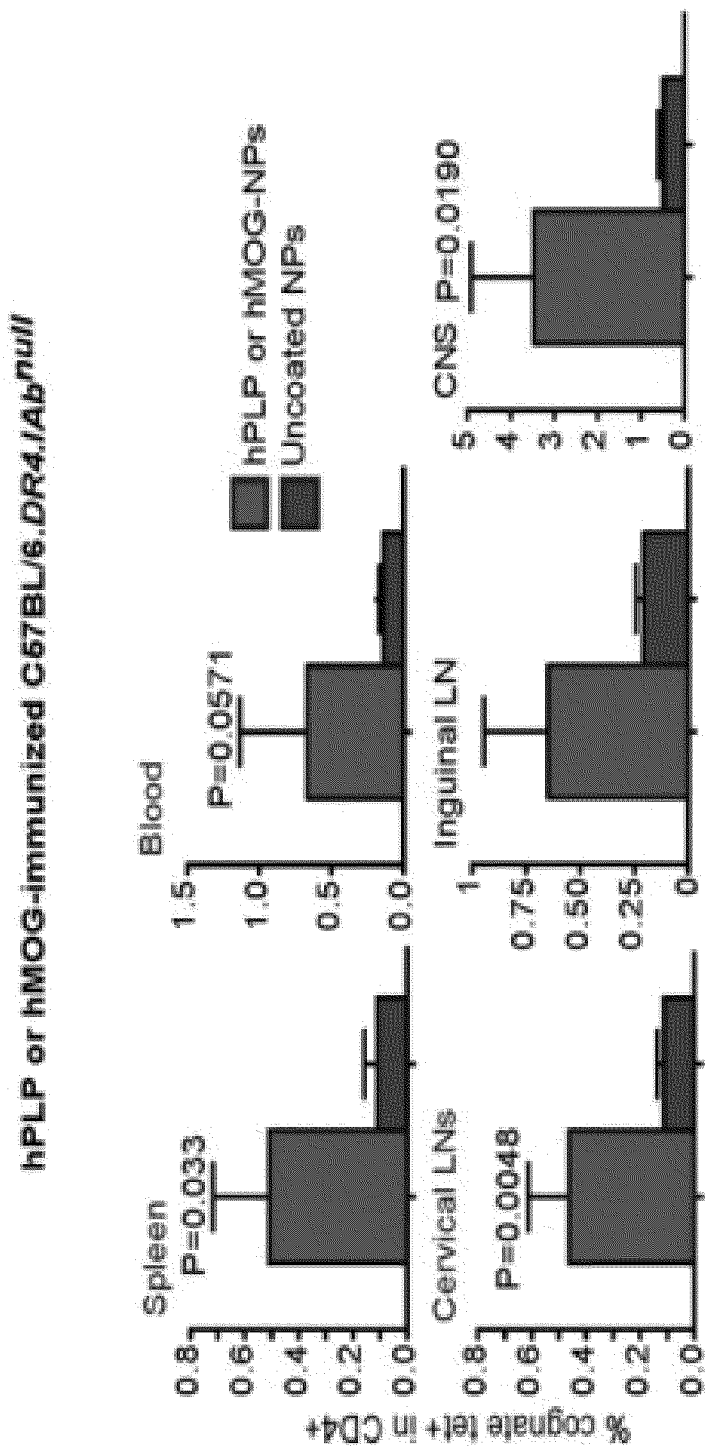
Figure 17C:
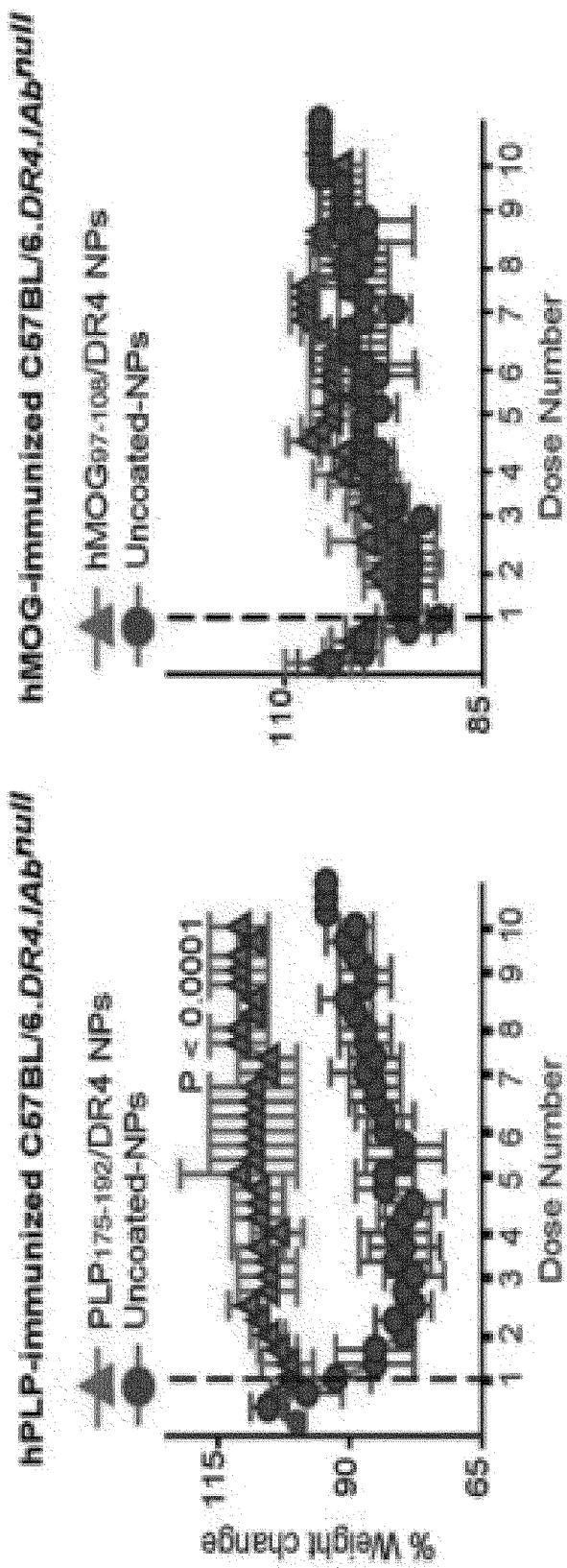
Figure 17D:
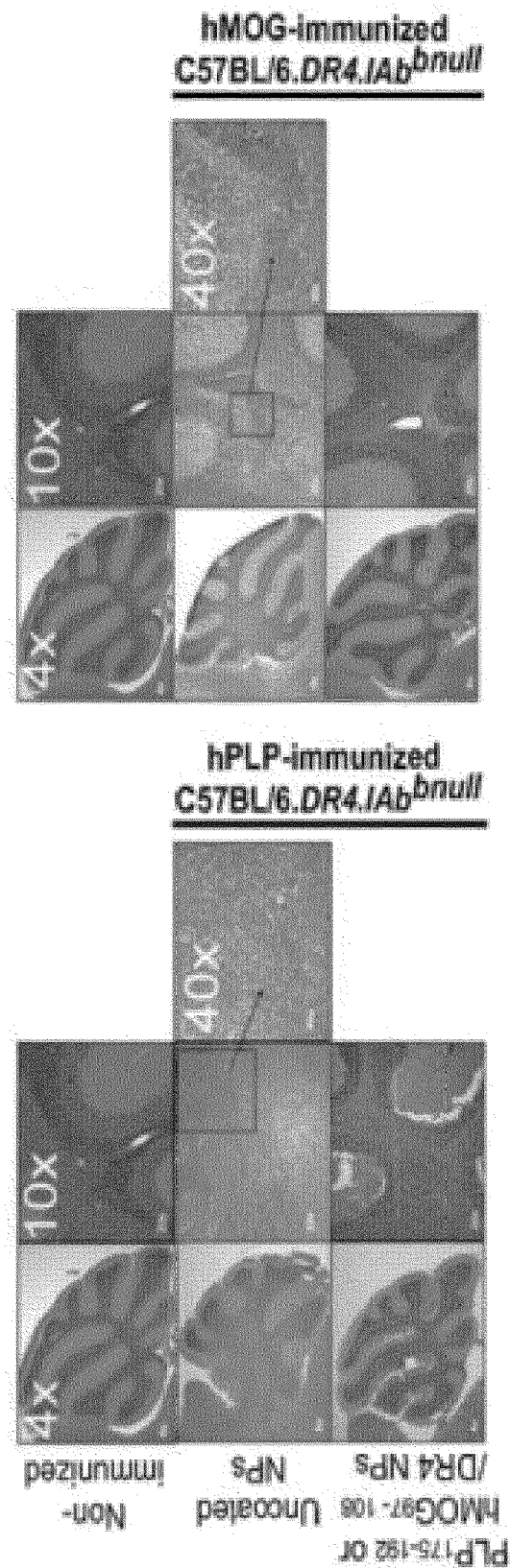
Figure 17E:
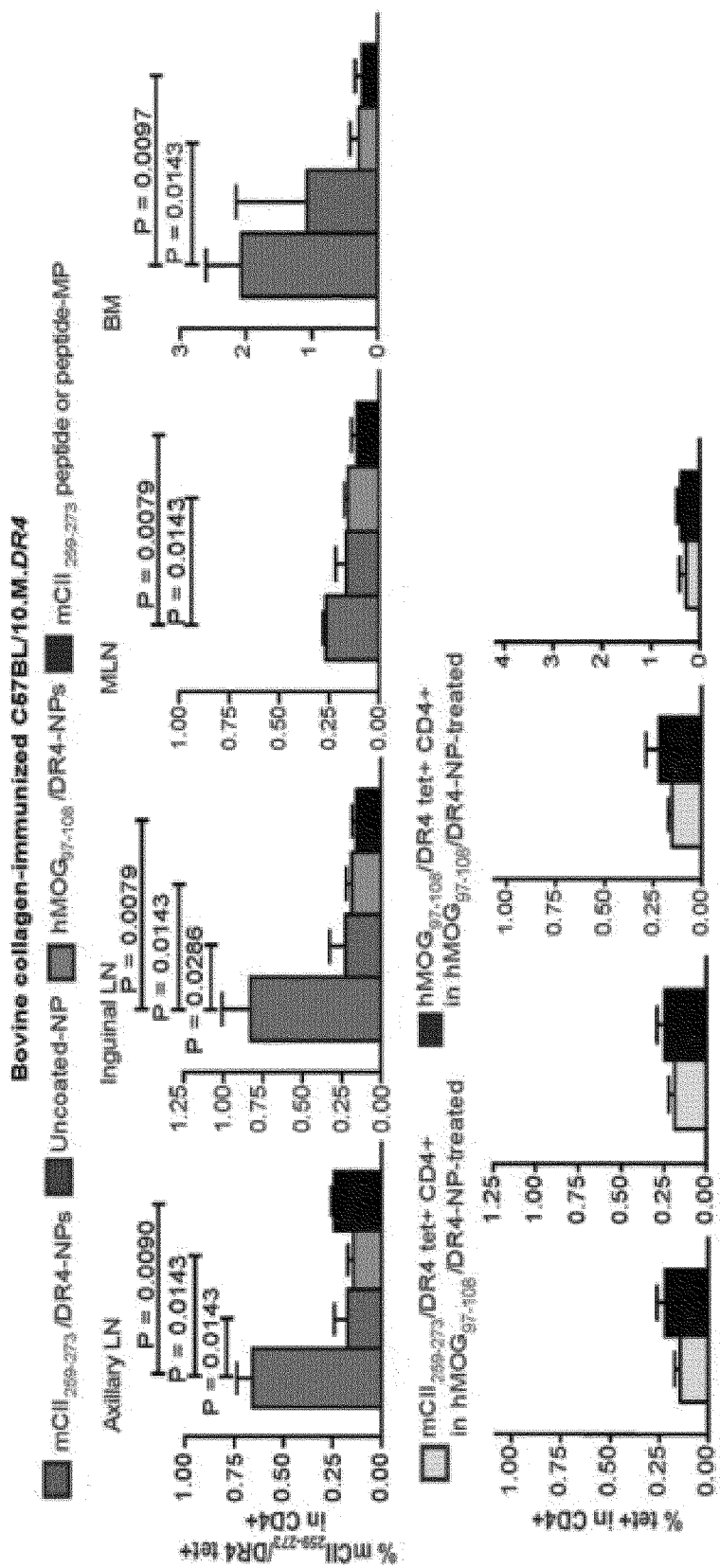
Figure 17F:
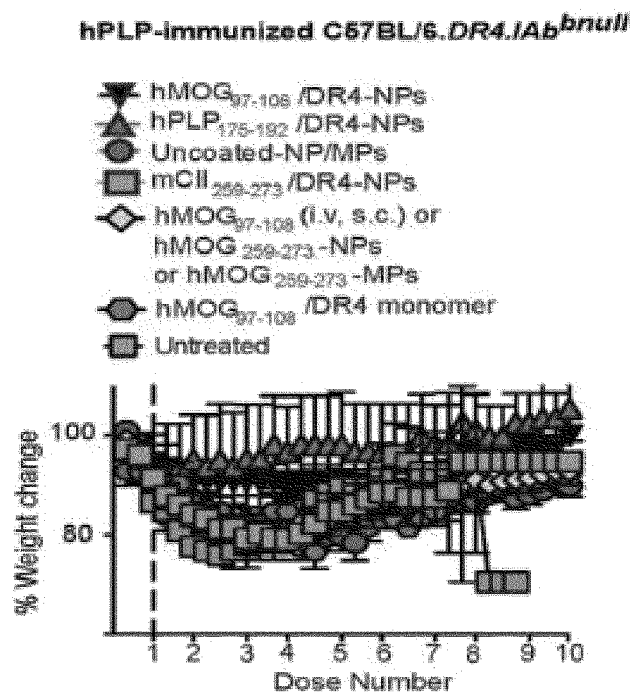
Figure 17G:
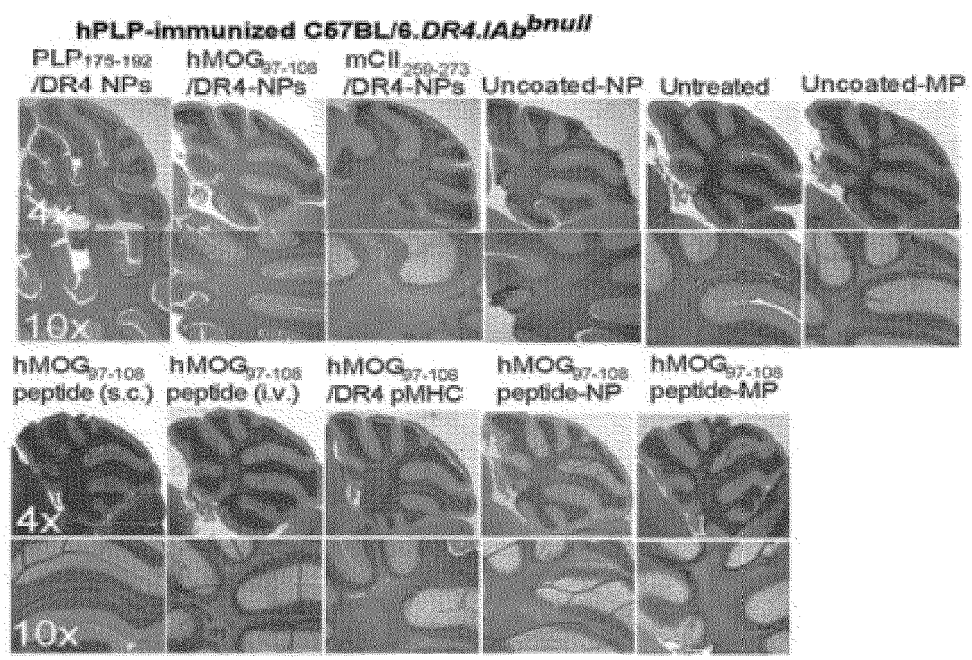

To investigate further the disease-specificity of pMHC-NP therapy, Applicant induced EAE in C57BL/6 IAb$^{null}$ HLA-DR4-IE-transgenic mice by immunization with hPLP$_{175-192}$ and treated diseased mice with hPLP$_{175-192}$/DR4-IE-NPs (positive control), uncoated nanoparticles (negative control), EAE-relevant hMOG$_{97-108}$/DR4-IE-NPs (which display a peptide from a CNS autoantigen other than that used to induce disease), or CIA-relevant mCII$_{259-273}$/DR4-IE-NPs. Whereas hMOG$_{97-108}$/DR4-IE-NPs blunted EAE as efficiently as the positive control, mCII$_{259-273}$/DR4-IE-NPs had no therapeutic activity (FIGS. 10F, 17F, 17G). Here, too, therapeutic activity was associated with systemic expansions of cognate T$_R$1-like T cells (FIGS. 10G, 10H). Administration of mCII$_{259-273}$ peptide (Burton, B. R. et al. (2014) Nature Commun. 5:4741-4747) or of mCII$_{259-273}$-peptide-coated microparticles (MPs) (Getts, D. R. et al. (2012) Nature Biotechnol. 30:1217-1224) to arthritic C57BL/10.M HLA-DR4-IE-transgenic mice (FIGS. 10A-10D, 17E), or of hMOG$_{97-108}$ peptide, hMPG$_{97-108}$/DR4-IE monomers or hMOG$_{97-108}$-coated nanoparticles or microparticles to C57BL/6 IAb$^{null}$ HLA-DR4-IE-transgenic mice failed to both expand cognate T$_R$1-like cells and blunt disease (FIGS. 10F, 10G, 17F-17I). Thus, the biological and therapeutic effects of pMHCII-NPs are disease-specific and dissociated from the pathogenic role of epitopes (disease-triggering versus downstream autoantigenic targets), suggesting that these compounds act on pre-activated autoreactive T cells and can generate T$_R$1-like cell expansions from rare T-cell precursor pools.

Soluble Mediators

Figure 11A:
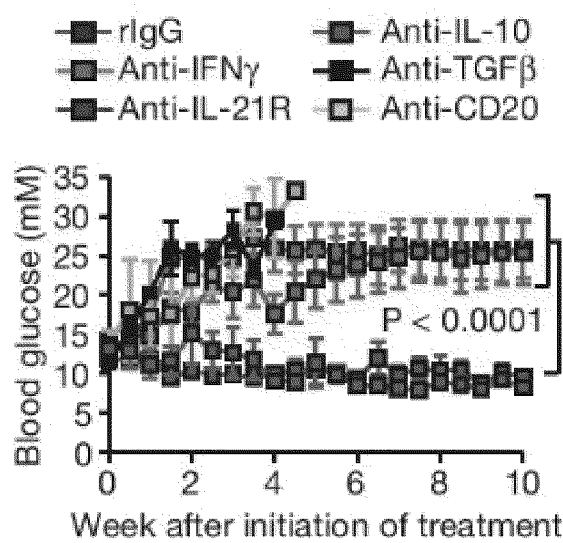
Figures 18A, 18B, 18C:
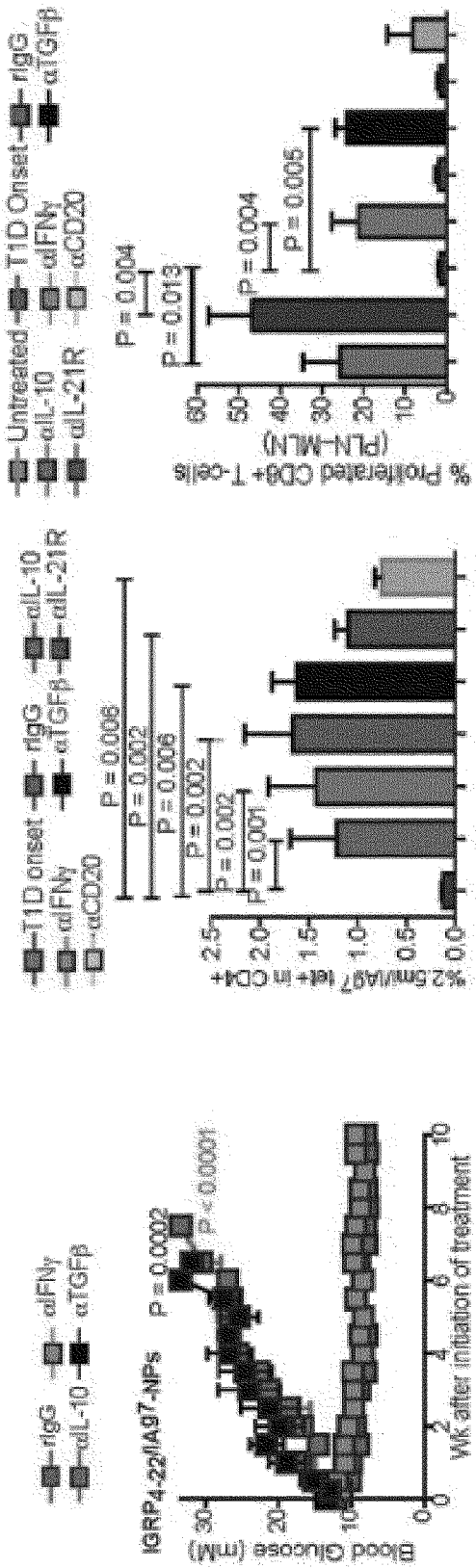
Figure 18F:
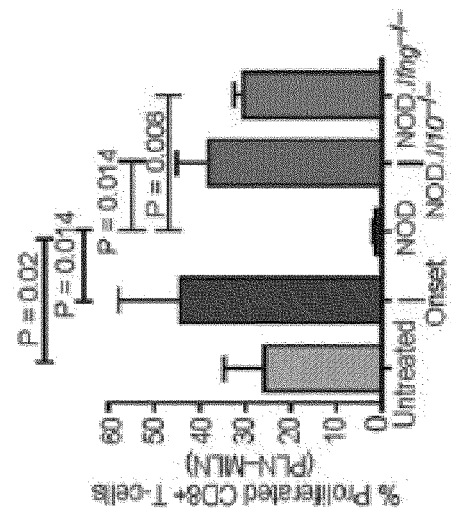
FIGS. 18E and 18F show percentages of tetramer$^+$CD4$^+$ T cells in the spleens (FIG. 18E), and proliferation of CFSE-labelled 8.3-CD8$^+$ T cells in the PLNs versus MLN of the mice from FIG. 18D at the end of follow up (FIG. 18F).
Figure 18E:
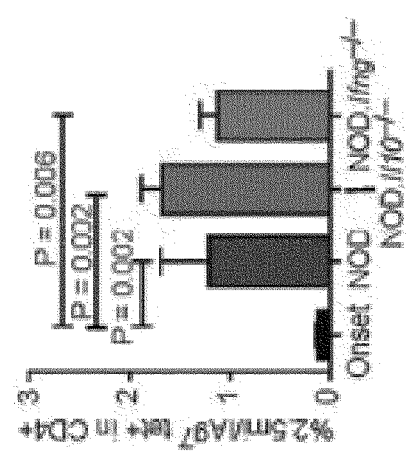
Figure 18D:
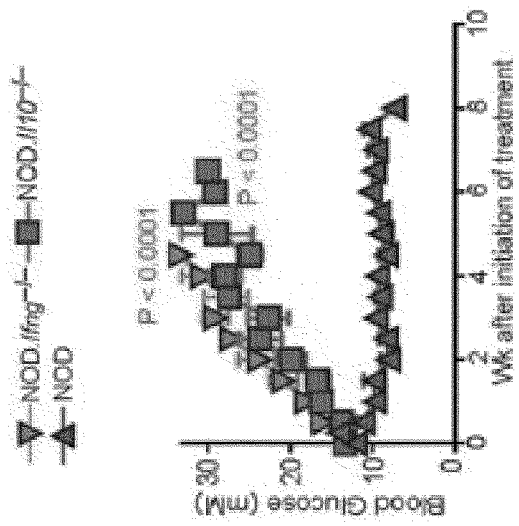
FIG. 18D shows changes in blood glucose in hyperglycaemic NOD, NOD Il10$^{-/-}$ and NOD Ifng$^{-/-}$ mice (n=3-6 per group) in response to 2.5 mi/IA$^{g7}$-NPs.
Figure 18G:
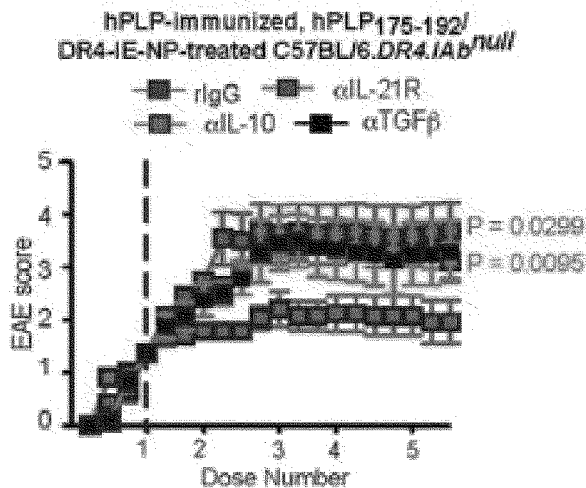
FIG. 18G shows EAE scores of mice treated with pMHC-NPs and rat-IgG or blocking mAbs (n=4 per group).
Figure 18H:
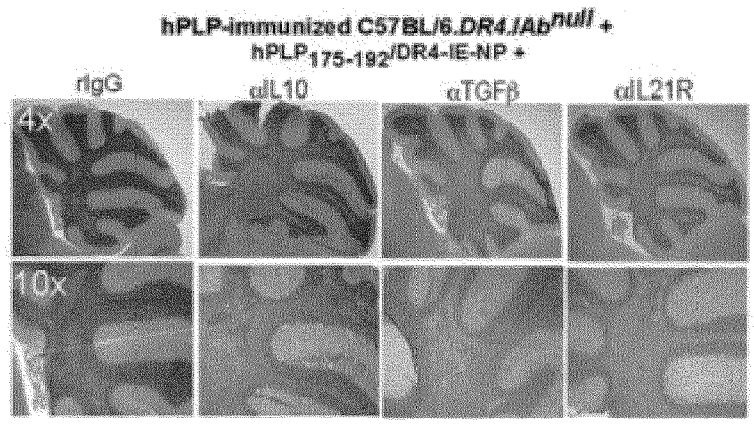
FIG. 18H shows LFB/H&E staining of the cerebellum of HLA-DR4-IE-transgenic C57BL/6 IAb$^{null}$ mice from FIG. 18G, highlighting differences in inflammation and demyelination in mice treated with hPLP$_{175-192}$/DR4-IE-NPs and rat-IgG versus blocking anti-IL-10, anti-TGF-β or anti-IL-21R mAbs.
Figure 18I:
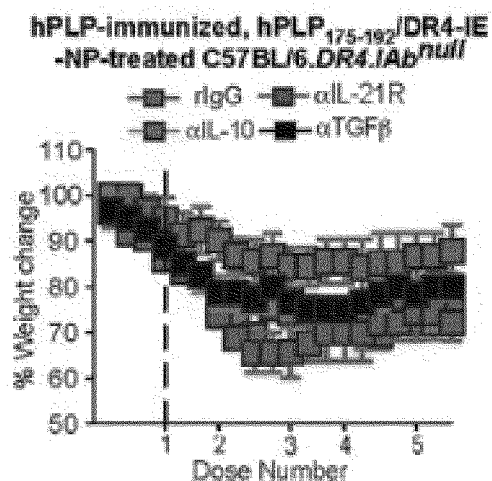
FIG. 18I shows changes in the average body weights of HLA-DR4-IE-transgenic C57BL/6IAb$^{null}$ mice from FIG. 18G.
Figure 18J:
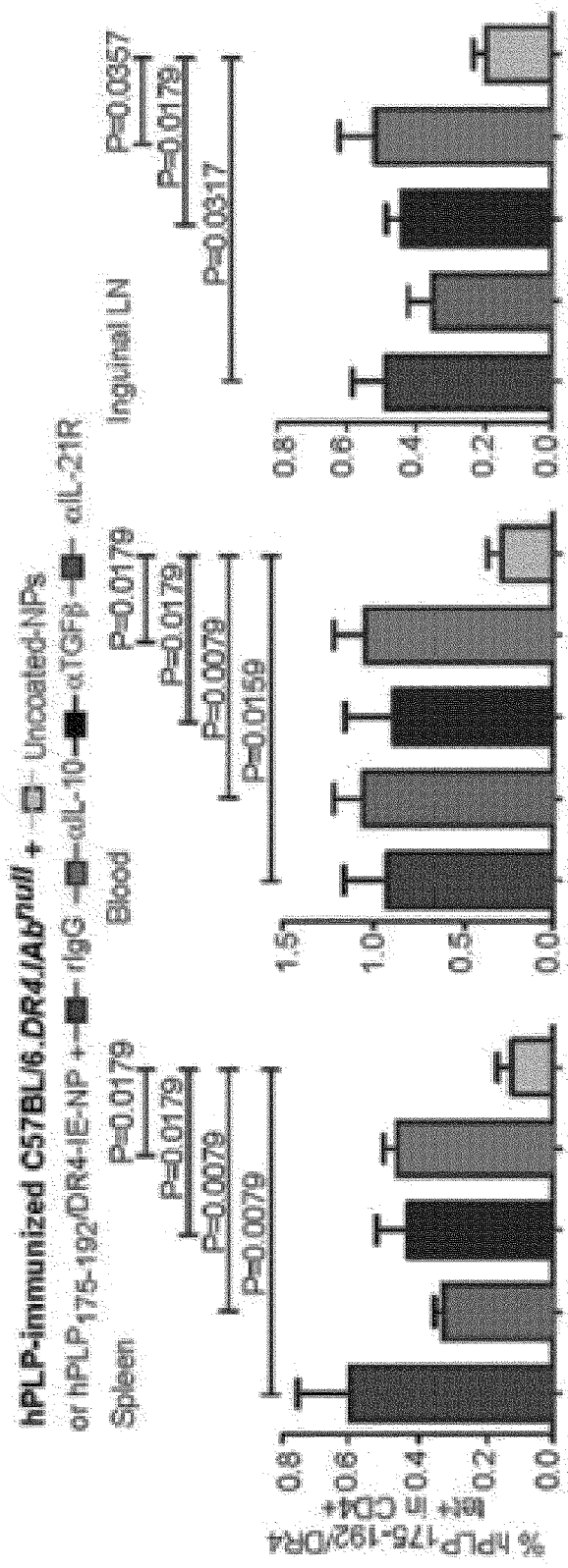
FIG. 18J, Percentage of tetramer$^+$ CD4$^+$ T cells in spleen, blood and inguinal LNs of mice from FIG. 18G (n=4 per group).
Figure 18N:
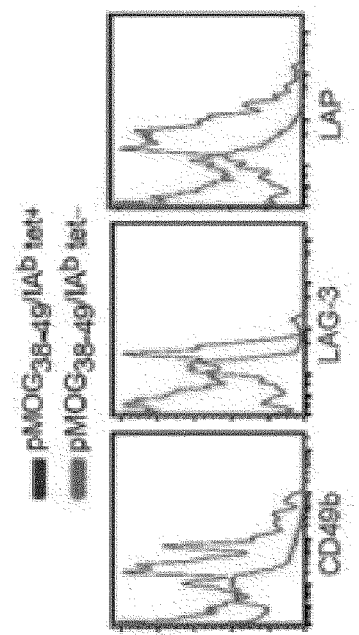
FIG. 18N shows percentage of tetramer$^+$CD4$^+$ T cells in spleen, blood, inguinal LNs and bone marrow of mice from FIG. 18K (left), and representative CD49b and LAG-3 staining profiles of tetramer$^+$ versus tetramer$^-$ cells (right).
Figure 18N:
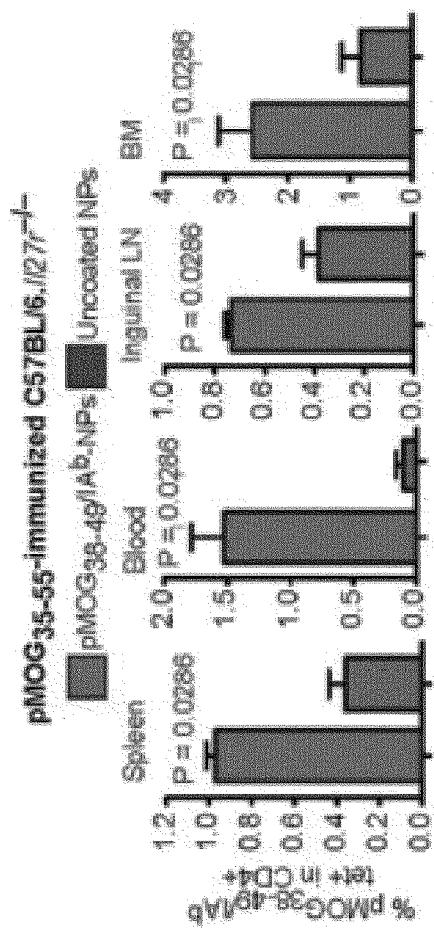
Figure 19:
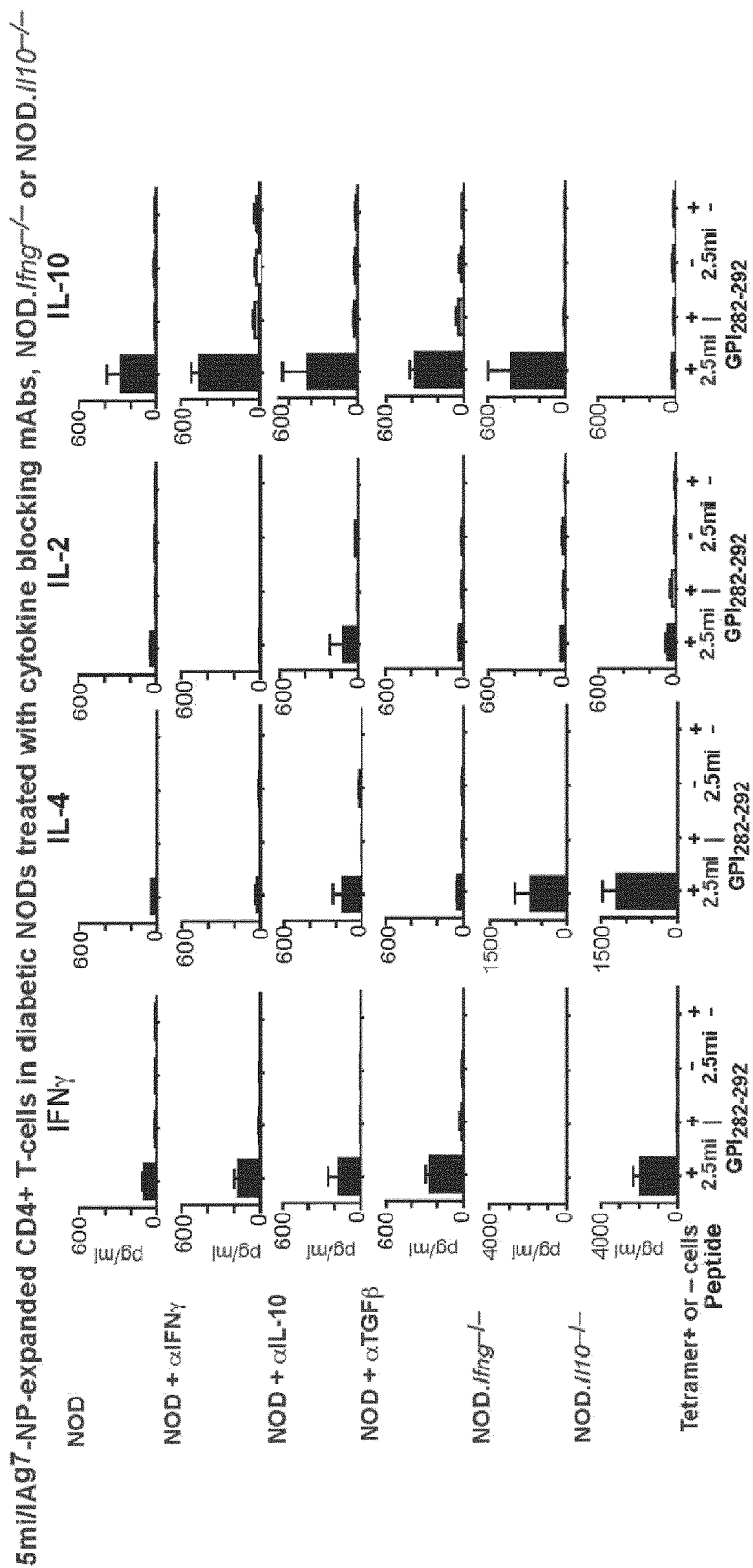
FIG. 19 shows effects of cytokine blockade or genetic deficiency on the cytokine profile of cognate CD4$^+$ T cells expanded by 2.5 mi/IA$^{g7}$-NPs. n=3 mice each. Data are averages ±s.e.m.

Blockade of IL-10, TGF-β and IL-21R (but not IFNγ) abrogated the anti-diabetogenic properties of 2.5 mi/IA$^{g7}$-NPs or IGRP$_{4-22}$/IA$^{g7}$-NPs (FIGS. 11A, 18A). With the exception of IL-21R blockade (known to inhibit CD8$^+$ T-cell activation), these interventions also abrogated the suppression of autoantigen crosspresentation by the pMHC-NP-expanded T$_R$1-like T cells in the PLNs (FIGS. 18B, 18C, 19). Studies using diabetic NOD Ifng$^{-/-}$ and NOD Il10$^{-/-}$ mice revealed that development of the T$_R$1 precursors and/or T$_R$1-like cells that expand in response to therapy requires IFNγ in addition to IL-10 (FIGS. 18D-18F, 19). mAbs against IL-10, TGF-β and IL-21R also abrogated the anti-encephalitogenic activity of hPLP$_{175-192}$/DR4-IE-NPs in C57BL/6 IAb$^{null}$ HLA-DR4-IE-transgenic mice (FIGS. 18G-18J). pMOG$_{35-55}$-immunized C57BL/6 Il27r$^{-/-}$ mice responded to pMOG$_{38-49}$/IA$^b$-NPs like their wild-type counter parts (FIGS. 9J-9N, 18K-18N). Thus, IFNγ and IL-10, but not IL-27 (Pot, C. et al. (2009) J. Immunol. 183:797-801), are necessary for pMHC-NP-induced T$_R$1-like cell development; and autoreactive T$_R$1-like T cells use IL-10, TGF-β and IL-21 (but not IFNγ) to suppress disease.

Downstream Effectors and Network Formation

Figure 18O:
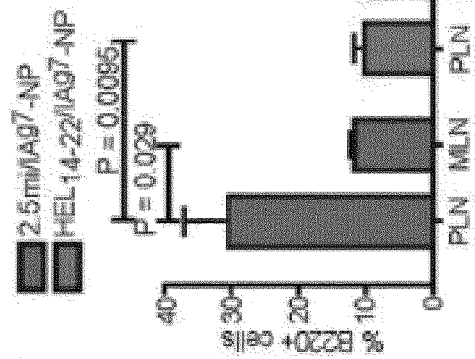
FIG. 18O shows percentage of B220$^+$ cells in the PLNs or MLNs of 2.5 mi/IA$^{g7}$-NP- or HEL$_{14-22}$/IA$^{g7}$-NP-treated mice (n=4 per group).
Figure 18P:
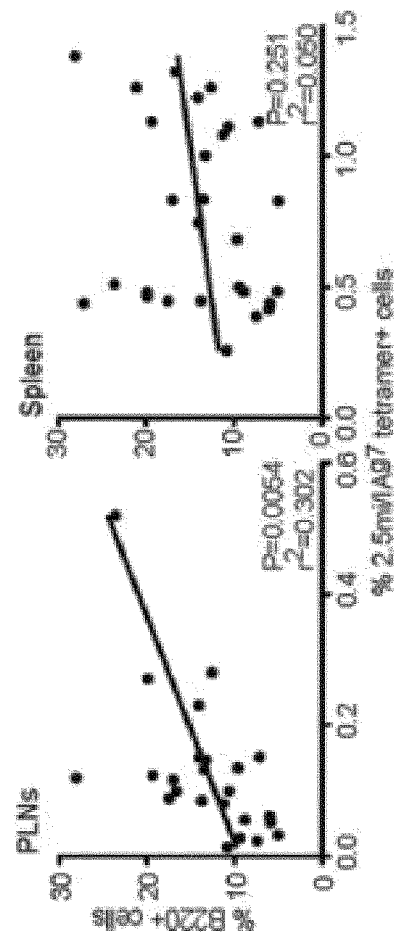
FIG. 18P shows correlation between the percentages of PLN and splenic B220$^+$ cells and 2.5 mi/IA$^{g7}$ tetramer$^+$ CD4$^+$ T cells in additional cohorts of mice treated with 2.5 mi/IA$^{g7}$-NPs, over a range of total pMHC dose (0.75-25 μg of total pMHC)=24-28).

The PLNs (but not the mesenteric lymph nodes (MLNs) or spleens) of pMHC-NP-treated NOD mice harboured increased percentages of B cells compared with the PLNs of mice treated with pMHCII-NPs not relevant for T1D (FIG. 18O). Studies of mice treated with a range of pMHC-NP doses revealed that the sizes of the PLN (but not splenic) B-cell and T$_R$1-like cell pools were correlated (FIG. 18P). Unlike their splenic or MLN counterparts, the PLN B cells of these mice could not effectively present peptide to cognate CD4$^+$ T cells ex vivo (FIG. 18Q). In addition, these cells produced IL-10 in response to lipopolysaccharide (LPS) (FIG. 18R), suggesting that pMHC-NP-induced T$_R$1-like cells might trigger the formation and expansion of regulatory B (B$_{reg}$) cells in the PLNs. In fact, 2.5 mi-pulsed B cells, but not DCs, underwent expansion in 2.5 mi/IA$^{g7}$-NP-treated hosts within a week of transfer (FIGS. 18S, 18T).

To probe this further, Applicant transfused NOD Il10$^{GFP}$ splenic B cells that were either pulsed with 2.5 mi or a negative control peptide (GPI$_{282-292}$), into 2.5 mi/IA$^{g7}$-NP-treated NOD or NOD Il10$^{-/-}$ hosts. Seven days later, the hosts were analysed for the presence of IL-10-producing (eGFP$^+$) CD5$^+$CD1d$^{high}$ B cells. NOD (but not NOD Il10$^{-/-}$) mice treated with 2.5 mi/IA$^{g7}$-NPs efficiently induced formation of B$_{reg}$ cells specifically from 2.5 mi-pulsed B cells, and IL-21R but not IL-10 or TGF-β blockade suppressed this effect (FIGS. 11B, 11C, 18U).

In vitro, the PLN B cells of 2.5 mi/IA$^{g7}$-NP-treated mice had a moderate suppressive effect on the proliferative activity of BDC2.5 CD4$^+$ T cells in response to peptide-pulsed DCs (FIG. 18V). In vivo, these B cells suppressed diabetes development in T-cell-reconstituted NOD scid hosts as compared to PLN B cells from control mice (FIG. 11D). Co-transfer of PLN B cells and bulk or 2.5 mi/IA$^{g7}$-tetramer$^+$ splenic CD4$^+$ T cells from 2.5 mi/IA$^{g7}$-NP-treated mice resulted in >95% suppression, as compared to PLN B cells with or without tetramer$^-$CD4$^+$ T cells from 2.5 mi/IA$^{g7}$-NP-treated mice, to CD4$^+$ T cells with or without MLN B cells from 2.5 mi/IA$^{g7}$-NP-treated mice (~40%), or to CD4+ T cells from untreated or control-NP-treated mice (0%) (FIG. 11E), supporting synergistic effects. In agreement with this, treatment of newly diabetic NOD mice with a B-cell-depleting anti-CD20 mAb abrogated the anti-diabetogenic activity of 2.5 mi/IA$^{g7}$-NPs (FIGS. 11A, 18X).

Figure 11E:
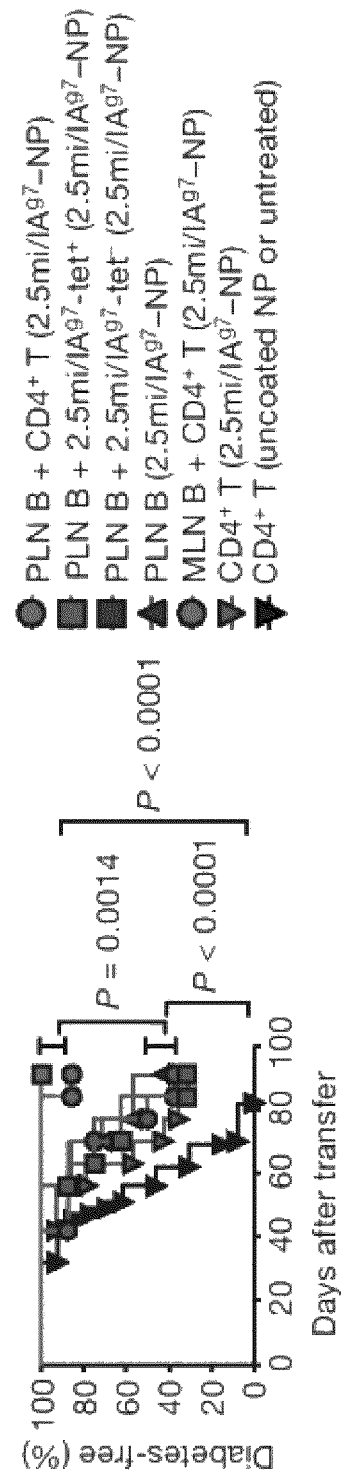
Figure 11F:
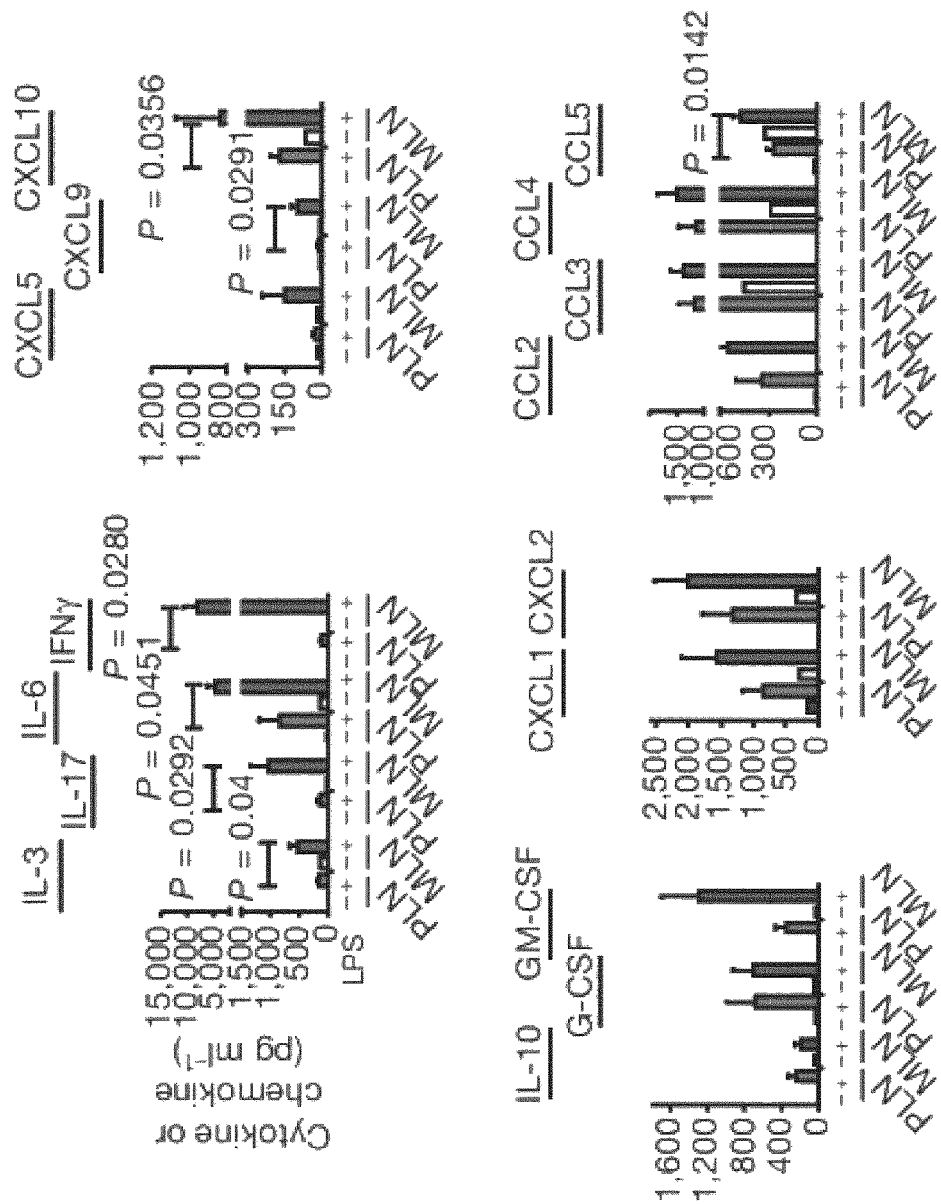
Figure 11G:
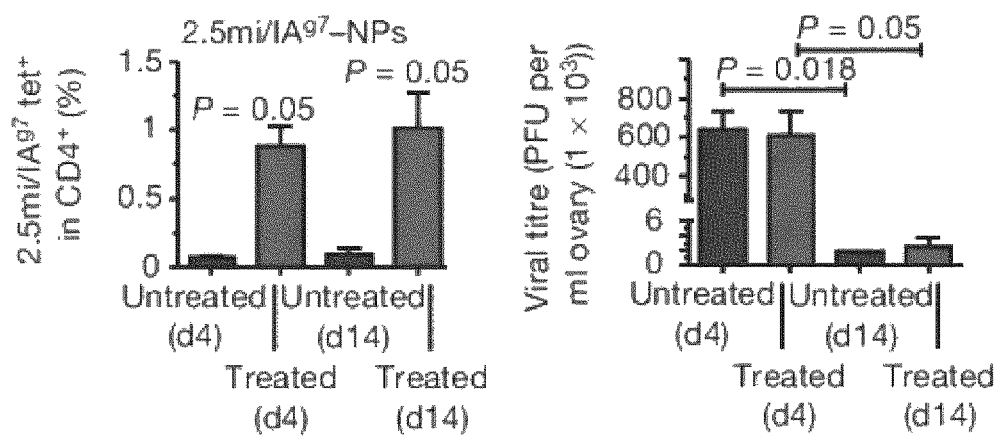
Figure 11H:
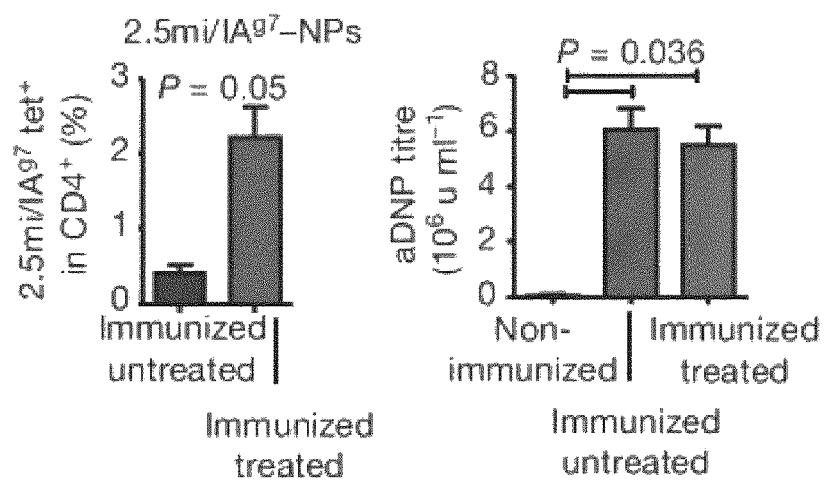

Comparison of the cytokine and chemokine profile of CD11b$^+$ cells derived from the PLN or MLN of pMHC-NP-treated NOD mice further revealed that CD11b$^+$ cells from the PLN produced lower levels of the pro-inflammatory mediators IL-3, IL-17, IL-6, IFNγ, CXCL9 and CXCL10 in response to LPS than their MLN counterparts did (FIG. 11F). Importantly, the effects of pMHC-NP therapy on antigen-presenting cells (APC)s from draining lymph nodes were not associated with impaired systemic immunity because pMHC-NP-treated NOD mice cleared an acute viral infection and mounted antibodies against an exogenous antigen as efficiently as untreated mice (FIGS. 11G, 11H).

Antigen-Experienced T Cells as Targets

Figure 12A:
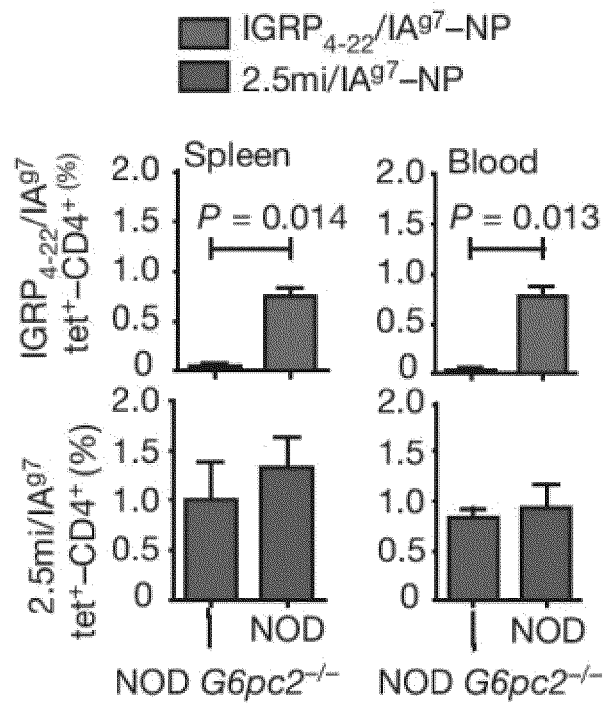
Figure 12B:
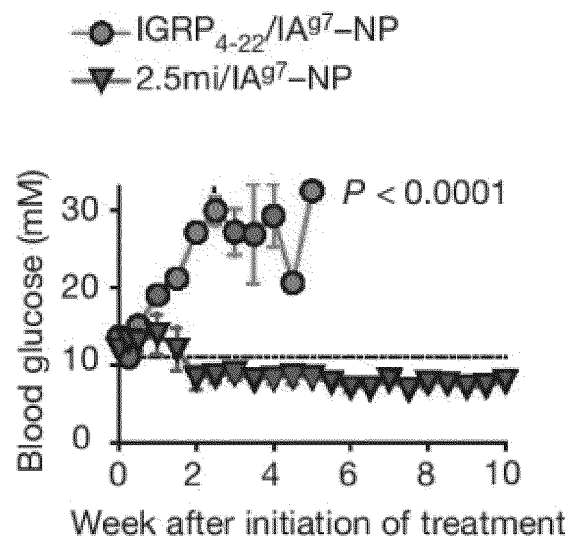
Figure 12C:
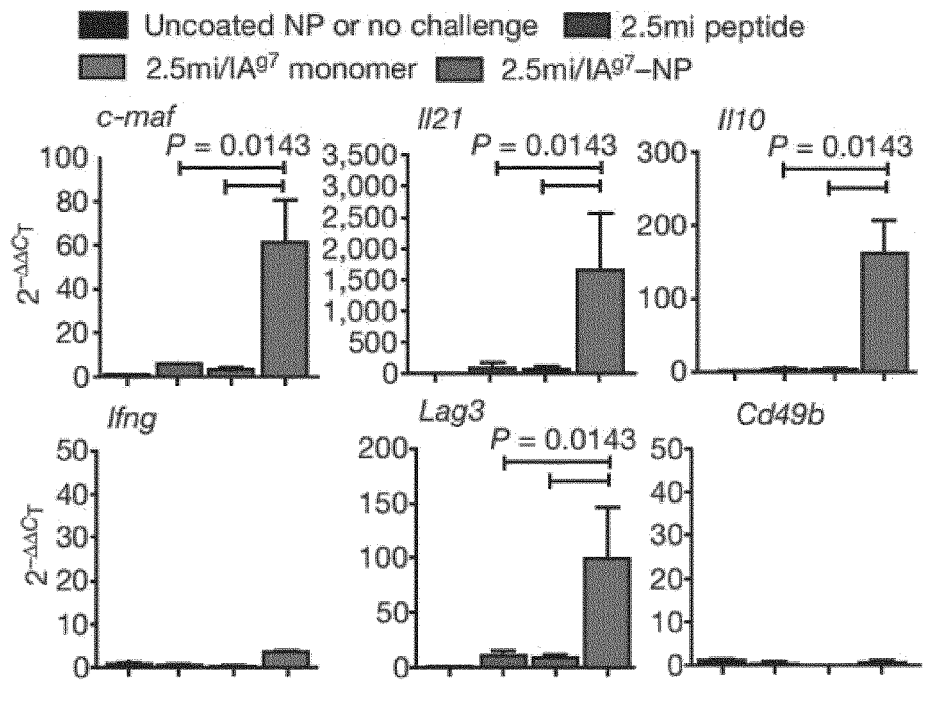

The memory-like phenotype and the upregulation of T-bet mRNA in the expanded T$_R$1-like cells, coupled with the inability of pMHC-NPs to expand cognate T$_R$1-like cells in non-diseased mice or NOD Ifng$^{-/-}$ mice suggested that pMHC-NPs expand pre-existing TR1 cells that arise from antigen-experienced precursors; and/or trigger the differentiation of antigen-experienced T$_H$1 cells into T$_R$1-like cells. Indeed, whereas diabetic NOD G6pc2$^{-/-}$ mice (which lack IGRP) responded to 2.5 mi/IA$^{g7}$-NPs like wild-type NOD mice, they did not respond to IGRP$_{4-22}$/IA$^{g7}$-NPs (FIG. 12A, 12B). In vitro, 2.5 mi/IA$^{g7}$-NPs triggered the expression of CD49b and LAG-3 and the upregulation of c-maf, Il21, Il10 and Lag3 mRNA exclusively in anti-CD3 plus anti-CD28 mAb-activated, but not naive BDC2.5 CD4$^+$ T cells (FIGS. 12C, 14D).

Figure 12D:
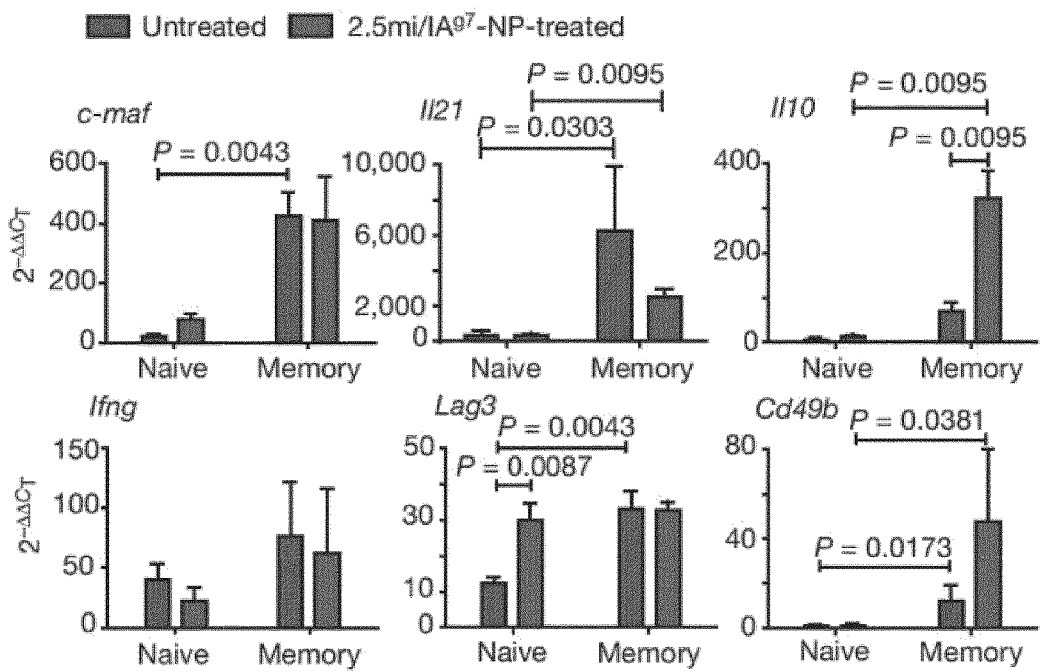

To investigate this further, Applicant transfused naive (CD44$^{low}$CD62L$^{hi}$) or memory-like (CD44$^{hi}$CD62L$^{low}$) BDC2.5 CD4$^+$ T cells into hosts of the congenic NOD. Thy1$^a$ strain and measured changes in their expression of LAG-3 and CD49b protein and c-maf, Il21, Il10, Ifng, Lag3 and Cd49b mRNA, both upon 2.5 mi/IA$^{g7}$-NP therapy and in the absence of therapy. Notably, the memory T cells from pMHC-NP-untreated hosts expressed about one hundred-fold higher levels of c-maf and Il21 and, to a lesser extent, Lag3 and Cd49b, but not Il10 mRNA than their na-ve counterparts (FIG. 12D). This is in accordance with the observed demethylation of Il21 and the c-Maf/IL-10- and IL-21-expression competency of effector/memory CD4$^+$ T cells (Pot, C. et al. (2009) J. Immunol. 183:797-801; Spensieri, F. et al. (2013) Proc. Natl Acad. Sci. USA 110:14330-14335; Hale, J. S. et al. (2013) Immunity 38:805-817; Sato, K. et al. (2011) J. Biol. Chem. 286:14963-14971; Saraiva, M. et al. (2009) Immunity 31:209-219), and suggests that the memory T-cell pool is enriched for uncommitted $T_R1$ precursors, expressing a $T_R1$-poised transcriptional program. Remarkably, whereas pMHC-NP therapy only upregulated Lag3 mRNA and, to a lesser extent, LAG-3 protein in naive BDC2.5 CD4$^+$ T cells, it promoted the upregulation of Il10 mRNA and LAG-3 and CD49b protein, and the proliferation of memory BDC2.5 CD4$^+$ T cells (FIGS. 12D-12F). Similar results were observed using memory eGFP$^-$ (FOXP3$^-$) BDC2.5 CD4$^+$ cells from BDC2.5 NOD Foxp3-eGFP mice (FIG. 18Y).

These effects on antigen-experienced T cells were accompanied by acquisition of anti-diabetogenic properties: whereas pMHC-NP therapy afforded 100% diabetes protection to T-cell-reconstituted NOD scid hosts bearing memory BDC2.5 T cells, therapy was inconsequential in hosts receiving naive BDC2.5 T cells (FIG. 12G). Therefore, pMHC-NP therapy promotes the differentiation (and expansion) of c-Maf-expressing antigen-experienced CD4$^+$ T cells into $T_R1$ progeny.

Translational Potential

Figure 20A:
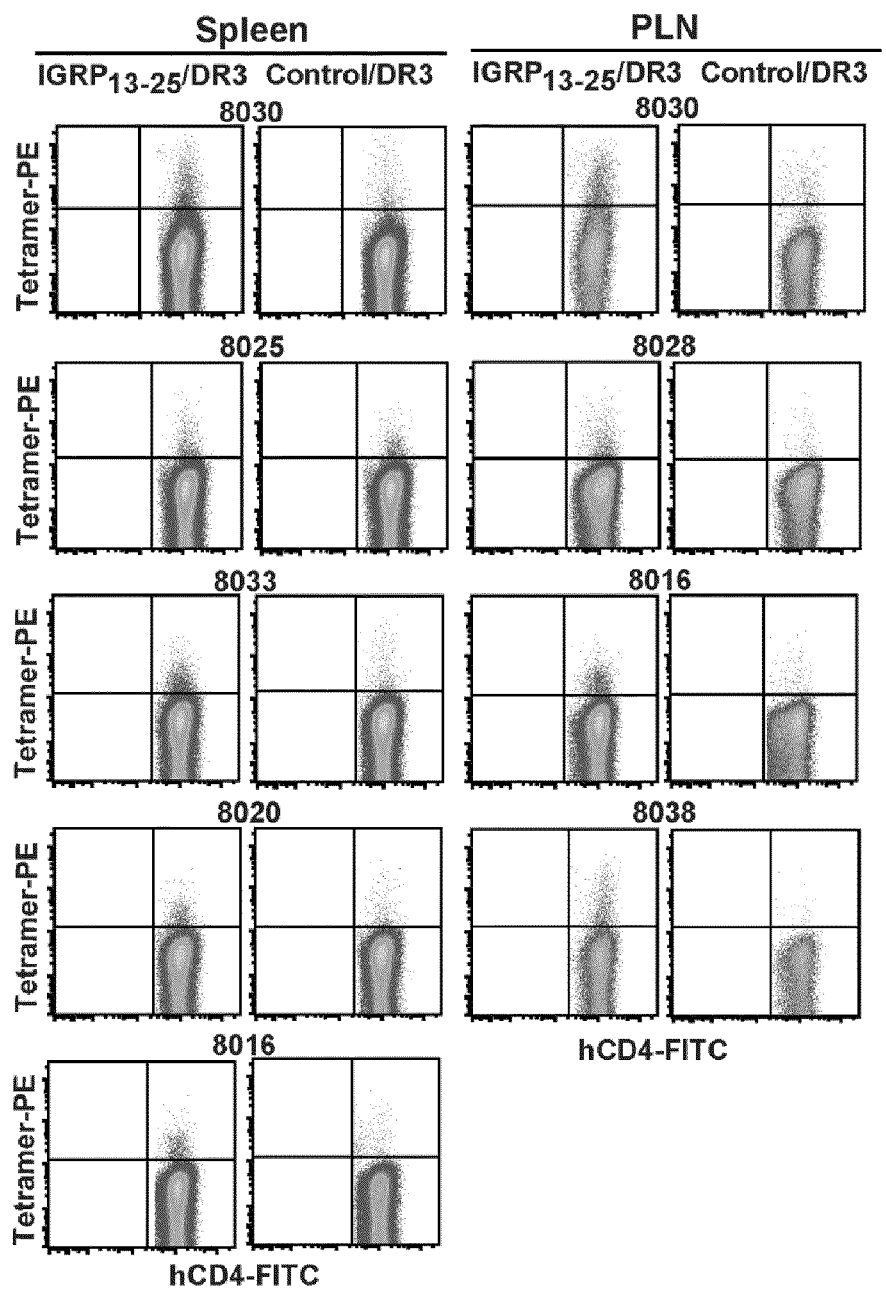
FIGS. 20A and 20B show human T1D-relevant pMHCII-NPs, but not free peptide or peptide-coated nanoparticles or microparticles, expand cognate T$_R$1-like CD4$^+$ T cells in human PBMC-engrafted NSG hosts.
Figure 20B:
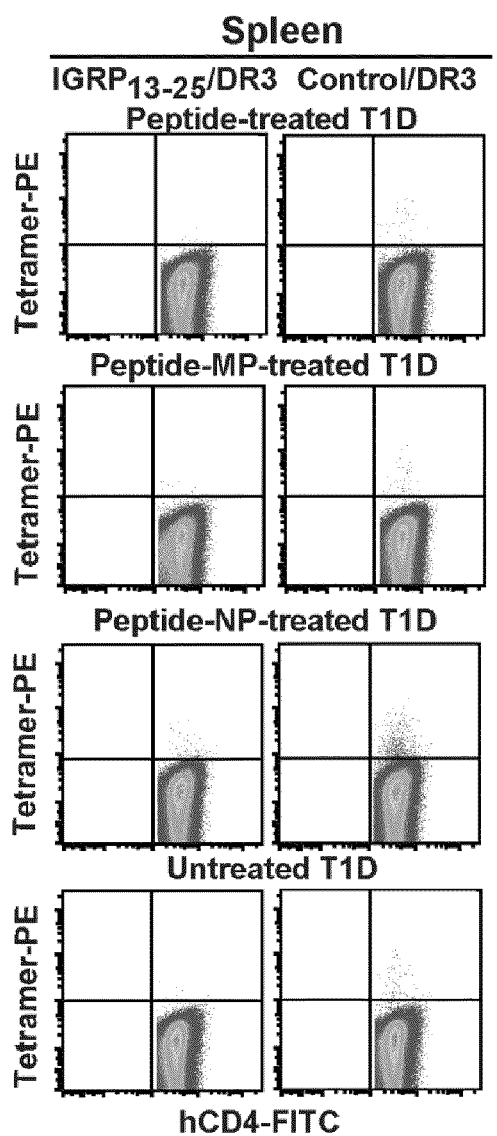

Applicant determined the ability of human T1D-relevant pMHCII-NPs to expand cognate $T_R1$-like T cells in NOD scid Il2rg$^{-/-}$ (NSG) hosts reconstituted with peripheral blood mononuclear cells (PBMCs) from T1D patients (Table 2). Initial assay development focused on NSG hosts reconstituted with PBMCs from five DRB1*0401$^+$ recent-onset T1D patients and treated with nanoparticles coated in either human glutamic acid decarboxylase-65 (GAD65)$_{555-567}$ (F557I)/DR4 or preproinsulin (PPI)76-90(K88S)/DR4 (FIGS. 13A, 13B, Table 2). Applicant then repeated these experiments using NSG hosts reconstituted with PBMCs from 7 DRB1*0301$^+$ T1D patients and a third T1D-relevant pMHC-NP type (hIGRP13-25/DR3-NPs) given at a higher dose. Applicant saw expansion of tetramer$^+$CD49b$^+$LAG-3$^+$CD4$^+$ T cells in the spleen and/or PLNs (endogenous mouse (m)IGRP$_{13-25}$ is highly homologous to hIGRP$_{13-25}$) from all seven pMHC-NP-treated mice and none of the untreated controls (FIGS. 13C, 13D, 20A and Table 2). The average percentage and numbers of tetramer$^+$CD4$^+$ T cells in IGRP13-25/DR3-NP-treated mice were significantly greater than in untreated littermates (FIG. 13D) and expressed Il10 mRNA (FIG. 13E). These responses could not be induced with peptide or peptide-coated nanoparticles or microparticles (FIGS. 13D, 20B and Table 2).

Figure 13G:
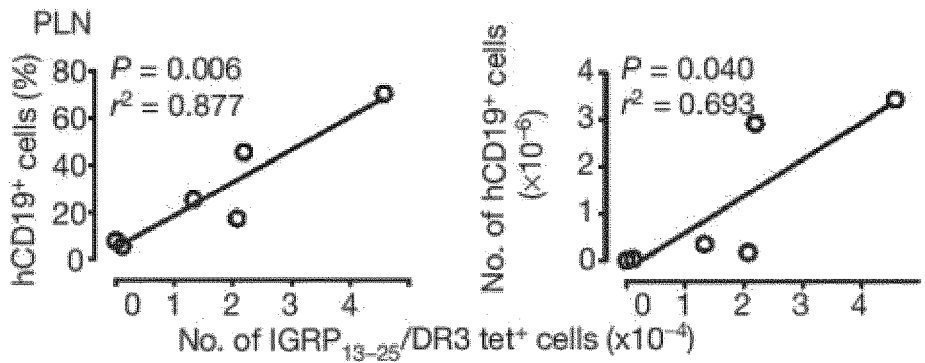
Figure 13H:
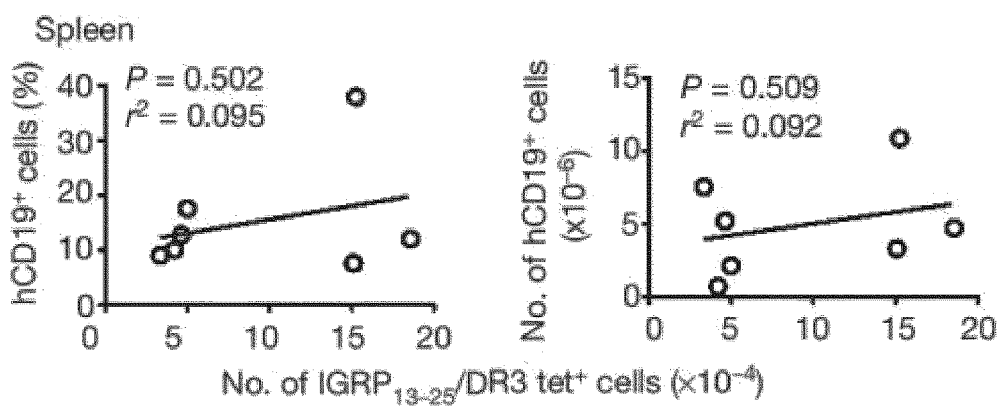
Figure 13I:
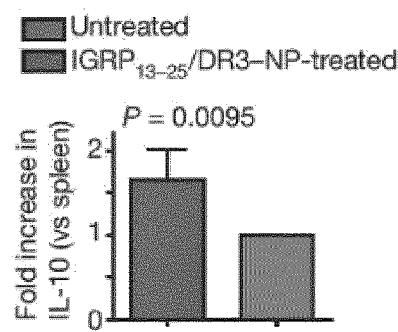

The PLNs of the pMHC-NP-treated mice that harboured increased percentages of tetramer$^+$CD4$^+$ T cells had increased cellularity (FIG. 13F). Furthermore, there were correlations between the number of PLN tetramer$^+$CD4$^+$ T cells and the percentage and absolute number of PLN human B cells, and the PLN B cells, unlike their splenic counterparts, produced IL-10 in response to LPS (FIGS. 13G-13I), suggesting $B_{reg}$ formation and/or recruitment. No such responses were seen in patient hPBMC-reconstituted NSG mice treated with peptide or peptide-NPs/MPs (FIG. 13F).

Discussion

Figure 21:
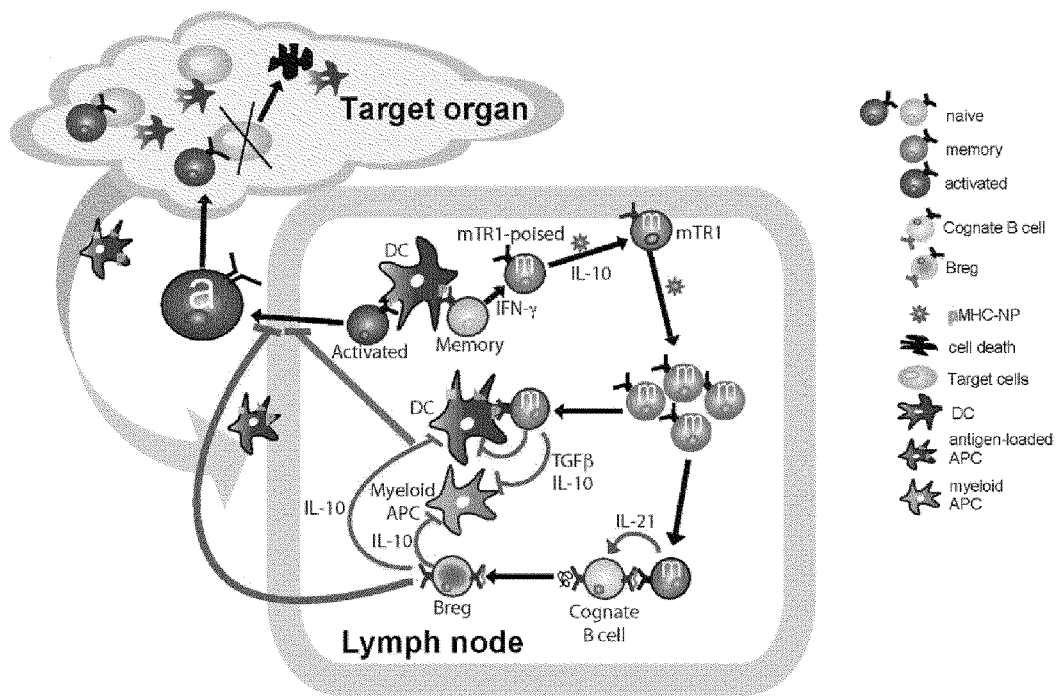
FIG. 21 shows schematic of the proposed mode of operation of pMHCII-based nanomedicines. pMHCII-coated NPs (pMHC-NP, lacking costimulatory molecules) promote the differentiation of disease-primed (antigen-experienced) IFNγ-producing CD4$^+$ T$_H$1-cells into memory T$_R$1-like CD4$^+$ T cells followed by systemic expansion. This differentiation process (but not the subsequent expansion) requires both IFNγ and IL-10, whereas IL-27 is dispensable. The pMHC-NP-expanded (mono-specific) autoreactive T$_R$1-like CD4$^+$ T cells then suppress other autoreactive T-cell responses by secreting IL-21, IL-10 and TGF-β, which act on local APCs (B cells, CD11c$^+$ and CD11b$^+$ cells) that have captured the cognate autoantigen and thus present cognate pMHCII complexes to the expanded T$_R$1-like cells. This interaction inhibits the proinflammatory function of the targeted APCs and blocks their ability to present other pMHC class I and class II complexes to non-pMHC-NP-cognate autoreactive T-cell specificities (note that the local APCs uptake both cognate and non-cognate autoantigens shed into the milieu simultaneously). Suppression of antigen-presentation requires IL-10 and TGF-β but not IFNγ or IL-21. Furthermore, cognate interactions between the pMHC-NP-expanded $T_R1$ CD4+ T cells and autoreactive B cells specific for the cognate autoantigen (able to display the cognate pMHCII complex on the surface) promotes their differentiation into $B_{reg}$ cells in an IL-21-dependent manner, which contribute to promote local immunosuppression, likely by secreting IL-10. Suppression of antigen presentation selectively targets APCs displaying the cognate pMHC, but as local APCs that capture the cognate autoantigen also capture other autoantigens simultaneously, the autoregulatory CD4+ T cells expanded by pMHC-NPs blunt the presentation of other autoantigenic Pmhc complexes to a broad range of autoreactive T cells. This suppression is disease-specific and self-limiting.

Applicant has shown that systemic therapy with nanoparticles coated with autoimmune-disease-relevant pMHC class II complexes triggers the expansion of cognate $T_R1$-like CD4$^+$ T cells, restores normoglycaemia in spontaneously diabetic mice and motor function in paralyzed EAE mice, and resolves joint swelling and destruction in arthritic mice, without compromising systemic immunity. Applicant demonstrates that this outcome is dissociated from genetic background and type of auto immune disease and can be replicated with ten different human or murine autoimmune-disease-relevant pMHC-NP types. The cell surface phenotype, cytokine secretion pattern, transcriptional profile and function of the $T_R1$-like cell pools expanded by pMHCII-based nanomedicines are consistent with those described for murine $T_R1$-like CD4$^+$ T cells and remarkably similar to $T_R1$ cells derived from healthy individuals and autoimmune disease patients (Gagliani, N. et al. (2013) Nature Med. 19:739-746). Applicant demonstrates key roles for prior autoantigenic experience and IFNγ- and IL-10-expression competence in the developmental biology of autoreactive $T_R1$ cells. Applicant shows that pMHCII-NPs promote IL-10 transcription and the upregulation of $T_R1$ markers in $T_R1$-poised, antigen-experienced CD4$^+$ T cells in an APC and IL-27-independent manner, followed by systemic expansion. The need for IFNγ, the expression of the $T_H1$ transcription factor T-bet, the c-Maf/IL-10- and IL-21-expression competency of effector and memory CD4$^+$ T cells (Pot, C. et al. (2009) J. Immunol. 183:797-801; Spensieri, F. et al. (2013) Proc. Natl Acad. Sci. USA 110:14330-14335; Hale, J. S. et al. (2013) Immunity 38:805-817), and the ability of pMHCII-NPs to turn T cells primed by active immunization into $T_R1$ suppressors suggest that these $T_R1$ precursors are effector/memory $T_H1$ cells. Applicant defines the mechanisms of action and uncover a cascade of cellular interactions downstream of the pMHC-NP-expanded $T_R1$-like cells, including $B_{reg}$ cell formation, that coordinately lead to the resolution of inflammation in an antigendependent but antigen-non-specific manner (FIG. 21).

Collectively, Applicant's data support the contention that any single pMHC involved in a given autoimmune disease could be used to blunt complex autoimmune responses via this approach. Consistent with this prediction, the 20 pMHCI/II-based nanomedicines tested to date have similar efficacy, regardless of antigen prevalence, dominance or role in the disease process. Neither pMHC monomers nor peptides or peptide-coated nanoparticles/microparticles trigger cognate $T_R1$ cell formation/expansion from the polyclonal T-cell repertoires or reverse T1D, CIA or EAE in the chronic models tested here. pMHC-based nanomedicines thus represent a new class of therapeutics in autoimmunity, capable of resolving cellularly and antigenically complex autoimmune responses in a disease- and organ-specific manner without compromising systemic immunity.

Methods

Mice. NOD/Ltj, NOD scid, BDC2.5-NOD, NOD Il10$^{-/-}$, C57BL/6, C57BL/6 Il27r$^{-/-}$, C57BL/10.M, NOD Foxp3- egfp and NOD scid Il2rg$^{-/-}$ (NSG) mice were purchased from the Jackson Lab. NOD Ifng$^{-/-}$ and LCMV Gp33-specific TCR-transgenic NOD mice were from D. Serreze (Jackson Lab). HLA-DR4-IE-transgenic C57BL/6IAb$^{null}$ mice were purchased from Taconic Farms. NOD Il10$^{GFP}$ (tiger) mice were obtained by backcrossing the Il10$^{GFP}$ allele from C57BL/6 Il10$^{GFP}$ mice (Jackson Lab) onto the NOD/Ltj background for 10 generations. 8.3-NOD and NOD G6pc2$^{-/-}$ mice have been described elsewhere (Verdaguer, J. et al. (1997) J. Exp. Med. 186:1663-1676; Wang, J. et al. (2010) Proc. Natl Acad. Sci. USA 107:9317-9322). These studies were approved by the corresponding institutional animal care committees. No statistical methods were used to predetermine sample size.

Antibodies, Tetramer Staining and Flow Cytometry.

FITC, PE, PerCP or biotin-conjugated mAbs against mouse CD4 (RM4-5), CD8a (53-6.7), B220 (RA36B2), CD62L (MEL-1), CD69 (H1.2F3), CD44 (IM7), and CD49b (DX5) and streptavidin-PerCP were purchased from BD Pharmingen. The antibody against murine LAG-3 (C9B7W) was from eBioscience. Anti-latent-associated-TGF-β antibody (TW7-16B4) was from BioLegend. PE-conjugated pMHC class II tetramers were prepared using biotinylated pMHC monomers. Peripheral blood mononuclear cells, splenocytes, lymph node and bone marrow CD4$^+$ T cells were incubated with avidin for 15 min at room temperature and stained with tetramer (5 μg ml$^{-1}$) in FACS buffer (0.05% sodium azide and 1% FBS in PBS) for 30-120 minutes at 4° C. or 37° C., depending on the tetramer, washed, and incubated with FITC-conjugated anti-CD4 (5 μg ml$^{-1}$) and PerCP-conjugated anti-B220 (2 μg ml$^{-1}$; as a 'dump' channel) for 30 min at 4° C. Cells were washed, fixed in 1% paraformaldehyde (PFA) in PBS and analysed with FACScan, FACSaria, or BD LSRII flow cytometers. For other phenotypic analyses, single-cell suspensions were stained with pMHC tetramers and antibodies diluted 1:100 in FACS buffer (all used at 4° C. except anti-LAG-3, which was used at 37° C.), washed, fixed in 1% PFA, and analysed by FACS. All phenotypic staining were performed in the presence of an anti-CD16/CD32 mAb (2.4G2; BD Pharmingen) to block Fc receptors. Analysis was done using FlowJo software.

NSG-engrafted human T cells were analysed using the following mAbs: FITC-conjugated anti-CD4 (OKT4, BioLegend), APC-conjugated anti-CD19 (HIB19, BD Pharmingen), PerCP-conjugated polyclonal goat anti-LAG-3 IgG (R&D Systems), biotin-conjugated anti-CD49b (AK7, Pierce Antibodies, Thermo Scientific), and EF450-conjugated streptavidin (eBioscience). Briefly, splenocytes and pancreatic lymph node cells were incubated with avidin (0.25 mg ml$^{-1}$ in FACS buffer) for 30 min at room temperature, washed and stained with tetramer (5 μg ml-1) for 1 hour at 37° C., washed, and incubated with FITC-conjugated anti-CD4 (2/100), APC-conjugated anti-CD19 (5/100; used as a 'dump' channel), PerCP-conjugated anti-LAG-3 (8/100) and biotin-conjugated anti-CD49b (4/100) at 4° C. for 45 minutes. After washing, the cells were incubated with EF450-conjugated streptavidin for 30 minutes at 4° C., washed, fixed in 1% PFA in PBS and cells within the hCD4$^+$/hCD19$^-$ gate analysed with a FACSCanto II (BD Bioscience).

Peptides and pMHCs.

Unless specified otherwise, recombinant pMHC class II monomers were purified from culture supernatants of induced *Drosophila* SC2 cells transfected with constructs encoding I-Aβ and I-Aα chains carrying c-Jun or c-Fos leucine zippers, respectively, and a BirA and 6×His tags (SEQ ID NO: 504). In these constructs, the peptide-coding sequence was tethered to the amino-terminal end of the I-Aβ chain via a flexible Gly-Ser linker as described (Stratmann, T. et al. (2003) J. Clin. Invest. 112:902-914). GAD65$_{555(557I)-567}$/DR4, PPI$_{76-90(88S)}$/DR4 and IGRP$_{13-25}$/DR3 monomers were produced by loading the corresponding peptides onto DR4 and DR3 complexes purified from supernatants of induced SC2 cells, as described (Yang, J. et al. (2006) J. Immunol. 176:2781-2789). Other constructs (those encoding 2.5 mi/IA$^{g7}$, pMOG$_{35-55}$/IA$^b$, hMOG$_{97-108}$/DR4-IE, hPLP$_{175-192}$/DR4-IE and mCII$_{259-273}$/DR4-IE) were purified from supernatants of Chinese Hamster Ovary (CHO) cells transduced with lentiviruses encoding a monocistronic message in which the peptide-MHCβ and MHCα chains of the complex were separated by the ribosome skipping P2A sequence (Hoist, J. et al. (2006) Nature Protocols 1:406-417). These monomers were engineered to encode a BirA site, a 6×His tag (SEQ ID NO: 504) and a free Cys at the carboxyterminal end of the construct. The self-assembled pMHC class II complexes were purified by nickel chromatography and used for coating onto nanoparticles or processed for biotinylation and tetramer formation as described above. The epitopes encoded in the different monomeric constructs used here include: 2.5 mi; AHHPI-WARMDA (SEQ ID NO: 476)) (Stratmann, T. et al. (2003) J. Clin. Invest. 112:902-914); IGRP$_{128-145}$ (TAALSYTIS-RMEESSVTL (SEQ ID NO: 477)) and IGRP$_{4-22}$ (LHRS-GVLIII-IFILQEDYRTY (SEQ ID NO: 478)) (15); HEL$_{14-22}$ (RHGLDNYRG (SEQ ID NO: 479)); GAD65$_{555(557I)-567}$ (NFIRMVISNPAAT (SEQ ID NO: 161)) (Reijonen, H. et al. (2002) Diabetes 51:1375-1382); PPI$_{76-90}$(88S) (SLQPLA-LEGSLQSRG (SEQ ID NO: 158)) (Yang, J. et al. (2008) J. Autoimmun. 31:30-41); IGRP$_{13-25}$ (QHLQKDYRAYYTF (SEQ ID NO: 159)) (Yang, J. et al. (2006) J. Immunol. 176:2781-2789); pMOG$_{38-49}$ (GWYRSPFSRVVH (SEQ ID NO: 480)); hMOG$_{97-108}$ (TCFFRDHSYQEE (SEQ ID NO: 481)); hPLP$_{175-192}$ (YIYFNTWTTCQSIAFPSK (SEQ ID NO: 203)); and mCII$_{259-273}$ (GIAGFKGDQGPKGET (SEQ ID NO: 482)). IGRP$_{4-22}$, IGRP$_{128-145}$ and GPI$_{282-292}$ (LSIALHVGFDH (SEQ ID NO: 483)) or 2.5 mi, pMOG$_{35-55}$ (MEVGWYRSPFSRVVHLYRNGK (SEQ ID NO: 186)), pMOG$_{38-49}$, hMOG$_{97-108}$ and hPLP$_{175-192}$ peptides were purchased from Sigma Genosys, Mimotopes or Genscript.

Nanoparticles, pMHC-NP, Peptide-NP and Peptide-MP Synthesis and Purification.

Applicant coated pMHCs onto crosslinked dextran-coated or pegylated iron oxide NPs (CLIO- or PFM-NPs, respectively). Briefly, CLIO-NPs were treated with ammonia to produce amino groups (NH$_2$). Avidin was oxidized with sodium periodate and added to the amino-NPs. Further incubation with sodium cyanoborohydride was used to generate a stable covalent bond. Finally, biotinylated monomers were added to the nanoparticles at a molar ratio of 4 mol biotin/mol avidin (Moore, A. et al. (2004) Diabetes 53:1459-1466). PFM-NPs were produced by thermal decomposition of Fe(acac)$_3$ in the presence of 2 kDa methoxypolyethylene glycol maleimide (Singha, S. et al., unpublished data). The NPs were purified using magnetic (MACS) columns (Miltenyi Biotec) or an IMag cell separation system (BD BioSciences). To conjugate pMHC or free peptide to PFM-NPs, we incubated pMHCs or peptide carrying a free carboxyterminal Cys with nanoparticles in 40 mM phosphate buffer, pH 6.0, containing 2 mM EDTA, 150 mM NaCl overnight at room temperature. The pMHC-conjugated nanoparticles were separated from free pMHC or peptide using magnetic columns, sterilized by filtration through 0.2 μm filters and stored in water or PBS at 4° C. Quality control was performed using transmission electron microscopy, dynamic light scattering, and native and denaturing gel electrophoresis. pMHC or peptide content was measured using different approaches, including Bradford assay (Thermo Scientific), denaturing SDS-PAGE, amino acid analysis (HPLC-based quantification of 17 different amino acids in hydrolyzed pMHC-NP preparations) or dot-ELISA (Singha, S. et al., unpublished data).

Peptide-coated microparticles were made using carboxylated 500 nm diameter polystyrene beads from Polysciences (Warrington, Pa.) as previously described (Getts, D. R. et al. (2012) Nature Biotechnol. 30:1217-1224). The peptides were conjugated to polystyrene beads via carbodiimide chemistry following the manufacturer's instructions. Briefly, Applicant incubated 250 µl PSB (containing ~9×10$^{11}$ beads) with 250 µg peptide in 0.1 M MES buffer, pH 5.0 at room temperature with gentle rolling in the presence of 1 mg EDC for 2 hours. The peptide-conjugated polystyrene beads were washed with PBS to remove unconjugated peptides and analysed with native and denaturing PAGE against serial dilutions of unconjugated peptide and microparticle controls.

pMHC-NP and Peptide or Peptide-NP Therapy in NOD Mice.

Experiments in pre-diabetic NOD mice involved treating (i.v.) cohorts of 10-week-old female mice with 7.5 µg of pMHC-NPs, or equivalent amounts of soluble pMHC monomers or uncoated nanoparticles twice weekly for 5 consecutive weeks. Experiments in diabetic mice involved following cohorts of 10-week-old female NOD/Ltj, NOD G6pc2$^{-/-}$, NOD Il10$^{-/-}$ or NOD Ifng$^{-/-}$ mice for diabetes development by measuring blood glucose levels with Accucheck Strips (Roche) twice a week. Mice displaying two consecutive measurements >11 mM were considered diabetic and treated twice weekly with 7.5 µg pMHC-NPs, nanoparticles delivering a molecular equivalent of peptide or free peptide (8 µg per dose) (Burton, B. R. et al. (2014) Nature Commun. 5:4741-4747), until stably normoglycaemic (defined as 8 consecutive measurements <11 mM) or until hyperglycaemia was considered irreversible (3 measurements >25 mM). In FIGS. 9G, 12B, and 14H, mice were randomized into treatment with 2.5 mi/IA$^{g7}$-NPs or HEL$_{14-22}$/IA$^{g7}$-NPs (FIG. 9G) or with 2.5 mi/IA$^{g7}$-NPs or IGRP$_{4-22}$/IA$^{g7}$-NPs (FIG. 12B). In FIG. 9G, IGRP$_{4-22}$/IA$^{g7}$ and IGRP$_{128-145}$/IA$^{g7}$ were tested in separate cohorts of mice. Mice treated with peptide or peptide-NPs (FIG. 9G) were randomized into either treatment within the same experiment. In vivo cytokine neutralization experiments involved administering mAbs against CD20 (5D2, a gift from A. Chan, Genentech; three doses of 250 µg i.v. on days 0-2 relative to the onset of hyperglycaemia) or 500 µg of HRPN (rIgG1), IFNγ (R4-6A2), IL-10 (DESS-2A5), TGF-β (1D11) or IL-21R (4A9) (BioXcell) i.p. twice a week for 2 weeks, followed by 200 µg per dose for 3 additional weeks. Mice were randomized into cytokine-blocking mAb-treatment (IFNγ, IL-10, TGFβ) or HRPN rat-IgG1 groups. Anti-CD20 and anti-IL21R mAbs were tested in separate cohorts of diabetic mice (FIG. 11A). Animals were assessed daily for glycosuria (corresponding to >16 Mm blood glucose) and given human insulin isophane (1 IU per day) s.c. if positive. Upon treatment withdrawal, NOD mice were monitored for recurrence of hyperglycaemia until 50 weeks of age.

Peptide, pMHC, pMHC-NP, Peptide-NP or Peptide-MP Therapy in EAE.

Figure 17H:
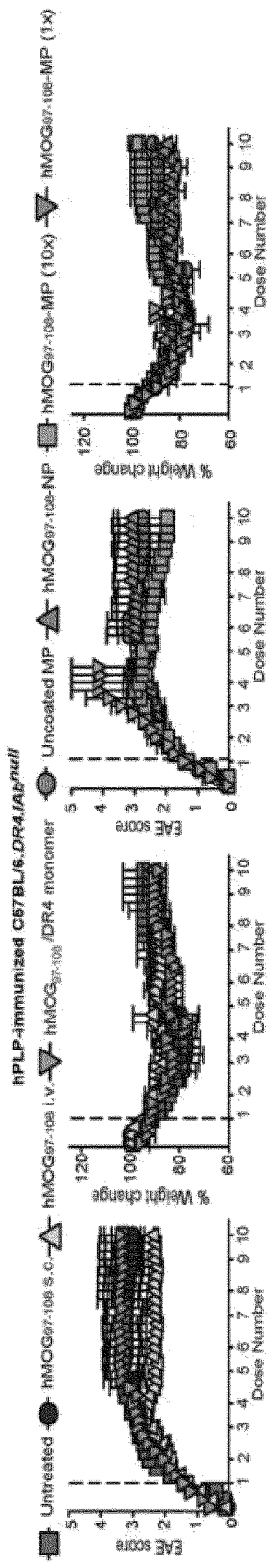
Figure 17I:
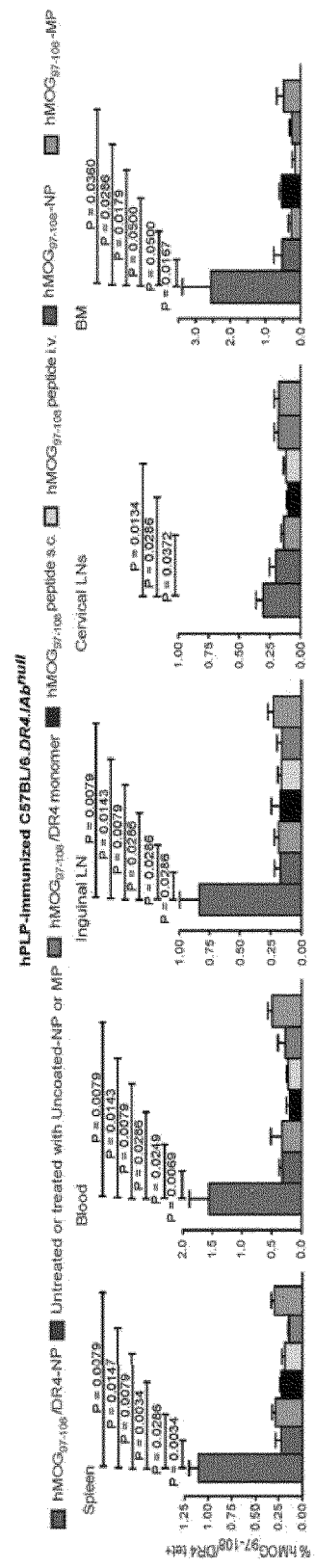

Six-to eight-week-old female C57BL/6, C57BL/6 I127r$^{-/-}$ or HLA-DR4-IE-transgenic C57BL/6 IAb$^{null}$ mice were immunized with 150 µg of pMOG$_{35-55}$ or hMOG$_{97-108}$ or hPLP$_{175-192}$, respectively in CFA s.c. at the base of the tail, under isofluorane anaesthesia. The mice received 300 ng of Pertussis toxin i.v. on days 0 and 3. Mice were weighed and scored daily starting on day 10 after immunization. The score system used was been reported elsewhere30 and plotted over a 5-point scale. When most of the mice showed signs of advanced disease (day 14) or reached maximum disease scores (day 21), mice were divided into different treatment groups, synchronized for weight and disease score averages, and treated twice a week with pMHC-coated and uncoated nanoparticles, an identical amount of pMHC monomer, peptide-coated nanoparticles (at an equivalent dose of peptide), free peptide (8 µg per dose i.v. or s.c.) (Burton, B. R. et al. (2014) Nature Commun. 5:4741-4747), peptide-conjugated microparticles (15 µg of peptide per dose) (Getts, D. R. et al. (2012) Nature Biotechnol. 30:1217-1224) or unconjugated microparticles for 5 weeks. Mice were randomized into treatment with pMHC-NPs (one or two different types, depending on the experiment, as described in FIGS. 9J-9N, 10E-10H, 16A-16F, 17A-17I), uncoated nanoparticles or no treatment. Peptide, peptide-MPs, peptide-NPs, pMHC monomers and uncoated microparticles were tested together; mice were randomized into each treatment group as mice reached the indicated disease score (FIGS. 10F, 17F-17I). An additional control cohort was treated with a single dose of peptide-conjugated microparticles (FIG. 17H). Anti-cytokine and cytokine receptor mAb blocking studies (FIG. 18G) involved randomization of mice into each treatment group.

Peptide, pMHC-NP or Peptide-MP Therapy in CIA.

Bovine collagen II (bCII) dissolved in 0.05M acetic acid at 2 mg ml$^{-1}$ was emulsified in CFA (v/v) containing 4 mg ml$^{-1}$ of killed *Mycobacterium tuberculosis* (H37Ra). Eight- to twelve-week-old HLA-DR4-IE-transgenic C57BL/10.M mice were immunized intradermally at the base of the tail with 100 µg of bCII in CFA and boosted with 100 µg of bCII in IFA on days 14 and 28. The size of all four paws was measured using a caliper before immunization (day 0) and daily upon disease onset. Disease progression was measured as percentage increase in joint swelling relative to day 0. When this value reached 130%, mice were divided into different treatment groups and treated with pMHC-NPs, Cys-coated (pMHC unconjugated) NPs (25 µg of pMHC for pMHCNPs, or an equivalent amount of iron for Cys-conjugated NPs), free peptide (8 µg per dose s.c.) (Burton, B. R. et al. (2014) Nature Commun. 5:4741-4747) or peptide-conjugated MPs (15 µg of peptide per dose) (Getts, D. R. et al. (2012) Nature Biotechnol. 30:1217-1224) i.v. twice a week for 5 weeks. Mice were randomized into treatment with either pMHC-NP or uncoated nanoparticles, or into peptide or peptide-MP, respectively (FIG. 10A and FIG. 14-21). Mice were also assessed for clinical signs of disease up to a maximum clinical score of 12 as reported elsewhere (Leavenworth, J. W. et al. (2013) J. Clin. Invest. 123:1382-1389).

Peptide, pMHC-NP, Peptide-NP and Peptide-MP Therapy in Human PBMCreconstituted NSG Hosts.

PBMCs from new or recently diagnosed HLA-DRB1*0401$^+$ or -DRB1*0301$^+$ T1D patients (recruited with informed consent, approved by the Institutional Review Board at Hospital Clinic) were depleted of CD8$^+$ T cells using anti-CD8 mAb-coated magnetic beads (Miltenyi Biotech) and injected i.v. (2×10$^7$) into 8-10-week-old NSG hosts. Mice were treated with pMHC-NPs at the indicated doses, peptide-coated-NPs (at an equivalent dose of peptide), peptide alone (8 µg per dose s.c.) (Burton, B. R. et al. (2014) Nature Commun. 5:4741-4747) or peptide-conjugated microparticles (15 µg of peptide per dose) (Getts, D.

R. et al. (2012) Nature Biotechnol. 30:1217-1224) starting on day 5 after PBMC transfusion, twice a week for 5 consecutive weeks, or left untreated. Individual patient samples were processed separately and injected into two (for pMHC-NP and peptide-NP experiments) or three separate mice (for peptide and peptide-MP experiments); one or two of the two-to-three hosts used in each of these experiments were treated and the other was left untreated (Tables 4A-4C). Therapy-induced expansion of cognate $CD4^+$ T cells was measured in PLNs and/or spleen as described above. The HLA genotype, gender, age, months from diagnosis and type of pMHC-NP tested for each patient are summarized in Tables 4A-4C.

Intraperitoneal Glucose Tolerance Tests.

Animals were fasted overnight and challenged with 2 mg kg-1 of d-glucose i.p. Blood glucose was monitored from the tail vein with a glucometer at different time points before and after glucose challenge. Serum insulin content was measured using the Mouse Ultrasensitive Insulin ELISA (ALPCO).

Evaluation of Systemic Cellular and Humoral Immunity.

For the evaluation of cellular responses, pMHC-NP-treated and untreated female mice were injected with $2\times10^6$ plaque-forming units (pfu) of recombinant Vaccinia Virus (rVV) i.v. Cohorts of mice were killed on day 4 and 14 after infection and processed for pMHC tetramer staining and rVV titre measurements. Briefly, the ovaries were weighed, homogenized using a pestle in 300 ul of RPMI-1640 containing 10% FBS, freezed-thawed 3 times followed by 3 rounds of sonication (20 seconds each). Serial dilutions of the lysates were added to confluent BSC-1 cell cultures in 6-well plates, incubated at 37° C. for 2 hours, washed twice with PBS and cultured in DMEM10. On day 2, the supernatants were discarded and the cell layers were stained with crystal violet to reveal plaques.

To evaluate humoral immunity, pMHC-NP-treated and untreated mice were immunized i.p. with 100 μg of DNP-KLH (Alpha Diagnostic International) in CFA. An identical boost was performed 3 weeks later. Mice were killed 10 days later. Anti-DNP antibody titres were measured by diluting serum samples in PBS containing 0.05% Tween 20. Anti-DNP antibodies were semi-quantified using an anti-DNP Ig ELISA Kit (Alphadiagnostic International) following the manufacturer's instructions.

Proliferation and Cytokine Secretion Assays.

$CD4^+$ T cells from pMHC-NP-treated mice were enriched from peripheral lymphoid organs using a BD Imag enrichment kit, stained with pMHC tetramers as described above and sorted by flow cytometry. For assays using memory and naive BDC2.5 $CD4^+$ T cells, cells were enriched using Stem Cell Technologies enrichment kit, stained with antibodies and sorted. FACS-sorted cells ($2-3\times10^4$) were co-cultured with bone marrow-derived DCs ($2\times10^4$) pulsed with 2 μg $ml^{-1}$ of peptide. Supernatants were collected 48 hours later for measurement of cytokines via Luminex and the cells were pulsed with 1 microcurie (μCi) of ($^3$H)-thymidine and collected after 24 hours to measure thymidine incorporation in triplicates.

To ascertain whether pMHC-NP therapy promoted the generation of IL-10-secreting B-cells in the PLNs of PBMC-engrafted NSG hosts, Applicant stained the PLN and splenic cell suspensions of individual mice with anti-hCD4-FITC, antihCD19-APC and tetramer-PE as described above, and sorted B-cells by flow cytometry (FACSAria-BD Biosciences). The B cells sorted from each organ were stimulated with LPS (1 μg $ml^{-1}$, Sigma) for 24 hours in RPMI-1640 supplemented with 10% human AB serum. The IL-10 content in the supernatants was measured in duplicates via Meso Scale technology using a V-PLEX Custom Human Cytokine kit for hIL-10 (Meso Scale Discovery). Data were normalized to the splenic B-cell values and reported as fold-change.

Isolation and In Vitro Stimulation of $CD11b^+$ Cells from the PLNs and MLNs.

$CD11b^+$ cells from LNs were obtained by digestion in collagenase D (1.25 μg $ml^{-1}$) and DNase I (0.1 μg $ml^{-1}$) for 15 min at 37° C. followed by purification with CD11b (BD Imag) mAb-coated magnetic beads. Cells were stimulated for 3 days with LPS (2 μg $ml^{-1}$) and the supernatants analysed for cytokine content with a Luminex multiplex cytokine assay.

In Vitro Suppression Assays.

FACS-sorted 2.5 mi/$IA^{g7}$ tetramer positive or negative cells ($2\times10^4$) were co-cultured with bone marrow-derived DCs ($2\times10^4$) pulsed with 2 μg $ml^{-1}$ 'suppressor' (2.5 mi or $GPI_{282-292}$) and 'responder' (gp33 or NRP-V7) peptides. Responder cells were $CD8^+$ T cells ($2\times10^4$) purified from from 8.3-NOD or LCMV-Gp33-specific TCR-transgenic NOD mice using BD-Imag beads. These cells were labelled with CFSE (5 μM) and added to the DC cultures in duplicates or triplicates. Dilution of CFSE in the responder cells was measured 48 hours later by FACS. In other experiments, the wells were supplemented within 24 hours of co-culture with HRPN rIgG, anti-IFNγ, anti-IL10 or anti-TGF-β (all 10 μg $ml^{-1}$) or the IDO inhibitor, 1-methyl tryptophan (1-MT; 400 μM).

In Vivo Suppression of Crosspresentation.

For crosspresentation assays in non-transgenic mice, Applicant transfused CFSE-labelled 8.3-$CD8^+$ reporter cells ($5-10\times10^6$) into untreated or pMHC-NP-treated mice and measured CFSE dilution in the hosts' lymphoid organs within 7 days after transfer.

Adoptive Transfer of Suppression.

Splenic $CD4^+$ or $CD8^+$ T cells ($10^7$) from untreated mice or mice treated with 10 doses of 2.5 mi/$IA^{g7}$-NPs or uncoated nanoparticles were transfused into 5-10 week-old NOD scid females. The hosts were transfused 24 hours later with $2\times10^7$ $CD4^+$ or $CD8^+$ T-cell splenocyte mixtures purified from female NOD donors. The hosts were monitored for development of diabetes for at least 90 days after transfer (FIG. 9E). In another experiment, the hosts were treated twice a week with 2.5 mi/$IA^{g7}$-NPs (FIG. 9E). In other experiments (FIG. 11E), $CD4^+$ or $CD8^+$ T-cell-reconstituted 5-6-week-old NOD scid females were transfused with $5\times10^5$ $CD19^+$ cells purified from the PLNs of mice treated with 10 doses of uncoated or 2.5 mi/$IA^{g7}$-coated NPs during the preceding 5 week (FIG. 11D). B-cells were purified using the EasySep Mouse CD19-positive selection Kit II (Stem-Cell Technologies). Other cohorts, studied separately (FIG. 11E), received PLN or MLN CD19+ cells ($5\times10^5$) plus total splenic $CD4^+$ T cells ($10^7$) or 2.5 mi/$IA^{g7}$ tetramer$^+$ ($2\times10^5$) or tetramer$^-$$CD4^+$ T cells ($10^7$) from 2.5 mi/$IA^{g7}$-NP-treated donors. The hosts were randomized into each transfusion group and monitored for development of diabetes together. FIG. 11E includes data from the corresponding cohorts studied in FIGS. 9E and 11D. Isolation of 2.5 mi/$IA^{g7}$ tetramer$^+$ and tetramer cells from total splenic $CD4^+$ T cells of 2.5 mi/$IA^{g7}$-NP-treated mice was performed using anti-PE mAb-coated microbeads and MACS LD columns (Miltenyi Biotec).

B-Cell Proliferation and $B_{reg}$ Induction In Vivo and $B_{reg}$ Suppression In Vitro.

To isolate splenic DCs, spleens were digested in collagenase D and DNase for 15 minutes at 37° C. and DCs purified using anti-CD11c mAb-coated magnetic beads (MACS).

The cells were pulsed with 10 μg ml$^{-1}$ of 2.5 mi or GPI$_{282-292}$ peptide for 2 hours at 37° C. and labelled with CFSE (0.5 μM) or PKH26 (2 μM), respectively. Labelled cells (5-10×10$^6$; mixed at 1:1 ratio) were administered i.v. into pMHC-NP-treated or untreated NOD mice. Three days later, Applicant compared the ratios of CFSE$^+$ versus PKH26$^+$ cells in the spleens of the different hosts by FACS. Similar experiments were done using peptide-pulsed splenic B cells isolated from female donor mice using anti-B220 mAb-coated magnetic beads (MACS).

For in vivo B$_{reg}$ induction assays, B cells from NOD Il10$^{GFP}$ (tiger) mice were enriched using a CD19 enrichment kit (Stem Cell Technologies) and pulsed with 2.5 mi or GPI$_{282-292}$ peptides (10 μg ml$^{-1}$) for 2 hours at 37° C. The peptide-pulsed B cells were washed twice with PBS, labelled with PKH26 and transfused (1×10$^6$) into pMHC-NP-treated or untreated mice. The hosts were killed 7 days later and their spleens labelled with anti-B220-APC and biotinylated anti-CD1d or anti-CD5 mAbs and Streptavidin-PerCP. PKH26$^+$ cells were analysed for presence of eGFP$^+$ CD1d$^{high}$ or CD5$^+$ cells by flow cytometry.

To determine the role of T$_R$1-derived cytokines in B$_{reg}$ formation (FIG. 18U), Applicant repeated the experiments described above but using 3×10$^6$ B cells and hosts treated with 250 or 500 μg (given i.p. daily from day—3 to day 6 relative to B-cell transfer) of anti-HRPN (rIgG1), anti-IL-10 (JES5-2A5), anti-TGFβ (1D11) or anti-IL-21R (4A9) mAbs (BioXcell). Hosts were randomized into each antibody-treatment group and studied together.

To measure the ability of the T$_R$1-induced B$_{reg}$ cells to suppress the antigen-induced activation of T cells in vitro, Applicant isolated CD19$^+$ B cells from the PLNs of age-matched untreated NOD mice or NOD mice treated with 10 doses of 2.5 mi/IA$^{g7}$-NPs and cultured these cells with LPS (10 μg ml$^{-1}$) overnight. Applicant then cultured these cells (2×10$^4$) with 2.5 mi-peptide-pulsed (0.1 μg ml$^{-1}$) bone marrow-derived DCs (2×10$^4$) and CFSE-labelled BDC2.5 CD4+ cells (4×10$^4$). Dilution of CFSE in CD4$^+$ cells was measured 3 days later.

CD25$^+$CD4$^+$ T$_{reg}$ Depletion.

NOD mice were treated with 500 μg of anti-CD25 (PC61.5.3, BioXcell) i.p. 3 times weekly from 8 weeks of age, followed by 10-injections of pMHC-NPs given twice weekly starting at 10 weeks of age. Average CD4$^+$CD25$^+$ and FOXP3-eGFP$^+$CD4$^+$ T-cell depletion was 90% and 70%, respectively.

Histology.

Tissues were fixed in 10% formalin and embedded in paraffin. H&Estained pancreata were scored for insulitis as reported (Verdaguer, J. et al. (1997) J. Exp. Med. 186:1663-1676). Briefly, insulitis was scored as: 0, none; 1, peri-insulitis; 2, infiltration covering <25% of the islet; 3, covering 25-50% of the islet; and 4, covering >50% of the islet.

Spinal cord and brain tissues were fixed in 10% buffered formalin for a minimum of 24 hours, embedded in paraffin and sectioned at 6 μm. Slides from paraffinembedded tissues were deparaffinized and subjected to antigen retrieval by steaming the slides in 10 mM sodium citrate buffer (pH 6.0) for 20 min and cooling at room temperature for 20 min. For immunohistochemistry, slides were fixed with 10% formalin and treated with 3% H$_2$O$_2$ in methanol at −20° C. Sections were permeabilized with 0.25% Triton-X 100 and blocked with a skim milk blocking solution. Rabbit anti-IBA1 (Wako, 1:500) or rat anti-MBP (Abcam) were incubated at 4° C. overnight followed by respective biotinylated secondary antibodies (1:500), avidin-biotin complex, and 3,3′-diaminobenzidine. Sections were counterstained with haematoxylin and eosin, dehydrated with graded ethanol and mounted with Acrytol. For histological myelin staining, slides were fixed with 10% formalin or deparaffinized, dehydrated with graded ethanol, and incubated with 0.2% luxol fast blue in 95% ethanol at 65° C. Slides were developed in 0.05% lithium carbonate, counterstained with haematoxylin and eosin, and mounted with Acrytol. Images of cerebellum were taken on an Olympus bright-field microscope. Inflammatory foci (dense nuclear clusters or perivascular cuffs with corresponding demyelination) were counted and their size measured using ImageJ software. For quantification of relative IBA1 intensity, blinded observers ranked images from highest to lowest intensity.

Knee joints from bCII-immunized mice were fixed in 4% buffered formalin overnight, and decalcified with 14% EDTA over 3 weeks. Decalcified paws were embedded in paraffin, sectioned at 8 μm and stained with haematoxylin and eosin to score infiltration and pannus formation on a scale of 5, where 5 corresponds to erosive arthritis, with severe infiltration and pannus covering 60% of the joint space. Proteoglycan depletion at the articular surface of the tibia and femur was assessed by the loss of safranin-O stain intensity. For this, sections were deparaffinized, hydrated and stained with haematoxylin before staining with 0.05% aqueous fast green for 5 min. Slides were fixed with 1% acetic acid and stained with 0.1% aqueous safranin-O for 2 min, dehydrated with graded ethanol, cleared with xylene and mounted with DPX. Scoring was done on a scale of 0 to 3 corresponding to: 0, 0% depletion, 1, low (<25%), 2, moderate (25-50%), and 3, severe (>50%). Destruction of articular cartilage included an assessment of the presence of dead chondrocytes (empty lacunae) and was scored on a scale of 3 (0, no empty lacunae; 3, complete loss of chondrocytes on articular cartilage/severe cartilage erosion).

Isolation of CNS-Infiltrating Lymphocytes.

Mice were anesthetized with Ketamine-Xylazine and perfused with PBS through the heart left ventricle. The brain and spinal cord were isolated manually, cut into small fragments and digested with a solution of collagenase D (1.25 μg ml$^{-1}$) and DNase I (1% w/v) in HBSS for 30 min at 37° C. The digested CNS was passed through a 70 μm cell strainer. Cells were resuspended in DMEM (supplemented with 2% FBS and 10 mM HEPES) and 100% Percoll (to a final Percoll concentration of 30%). The solution was layered onto 65% Percoll and centrifuged at 380 g for 30 min at room temperature. The mononuclear cell layer lying at the interphase was washed with RPMI before further analyses.

Quantitative RT-PCR.

RNA was extracted from 2.5 mi/IA$^{g7}$ tetramer$^+$ or tetramer$^-$ CD4$^+$ T cells sorted from 2.5 mi/IA$^{g7}$-NP-treated NOD mice and stimulated in vitro with anti-CD3/anti-CD28 mAb-coated dynabeads.

Each tetramer$^+$ sample corresponded to cells pooled from 2-3 mice. RNA was reverse transcribed and cDNA plated in Mouse Immunology 384 StellArray qPCR plates (Bar Harbour BioTechnology) with 2×SYBR Green Master Mix (Applied Biosystems). The plate was run in a 7900HT Applied Biosystems realtime PCR instrument, and the raw data was analysed using the Global Pattern Recognition (GPR) analysis tool (http://www.gene-quantification.com/qper-array.html). mRNA isolated from additional samples was subjected to RT-qPCR using primers specific for IL-21 (Forward: 5′-TCATCATTGACCTCGTGGCCC-3′ (SEQ ID NO: 484); Reverse: 5′-ATCGTACTTCTCCACTTG-CAATCC-3′ (SEQ ID NO: 485)), IL-10 (Forward: 5′-CTT-GCACTACCAAAGCCACA-3′ (SEQ ID NO: 486); Reverse: 5′-GTTATTGTCTTCCCGGCTGT-3′ (SEQ ID NO: 487)), c-Maf (Forward: 5'-AGCAGTTGGTGACCAT-GTCG-3' (SEQ ID NO: 488); Reverse: 5'-TGGA GATCTC-CTGCTTGAGG-3' (SEQ ID NO: 489)), IFN-γ (Forward: 5'-TGAACGCTACACACTGCA TCTTGG-3' (SEQ ID NO: 490); Reverse: 5'-CGACTCCTTTTCCGCTTCCTGAG-3' (SEQ ID NO: 491)), LAG-3 (Forward: 5'-TCCCAAATC-CTTCGGGTTAC-3' (SEQ ID NO: 492); Reverse: 5'-GAGCTAGACTCTGCGGCGTA-3' (SEQ ID NO: 493)), CD49b (Forward: 5'-CCGGGTGCTACAAAAGTCAT-3' (SEQ ID NO: 494); Reverse: 5'-GTCGGCCACATT-GAAAAAGT-3' (SEQ ID NO: 495)), Aryl Hydrocarbon Receptor (Forward: 5'-CGTCCCTGCATCCCACTACTT-3' (SEQ ID NO: 496); Reverse: 5'-GGACATGGCCCCAG-CATAG-3' (SEQ ID NO: 497)) and ICOS (Forward: 5'-TGACCCACCTCCTTTTCAAG-3' (SEQ ID NO: 498); Reverse: 5'-TTAGGGTCATGCACACTGGA-3' (SEQ ID NO: 499)).

pMHC-NP-induced upregulation of $T_R1$ transcripts in in vitro-activated CD4$^+$ T cells was performed by culturing mouse naive eGFP$^-$BDC2.5-CD4$^+$ T cells from BDC2.5 NOD Foxp3-eGFP mice (CD62L$^{hi}$FOXP3$^-$eGFP$^-$; 1.5×10$^6$ ml$^{-1}$) with anti-CD3/anti-CD28 mAb-coated microparticles (1 bead per cell) for three days in the absence of APCs, followed by a one day culture of re-purified (micro particle-free) CD4$^+$ T cells in rhIL-2 (30 IU ml$^{-1}$), and a 6-day culture with 2.5 mi peptide (10 μg ml$^{-1}$), 2.5 mi/IA$^{g7}$ monomers (25 μg pMHC per ml), 2.5 mi/IA$^{g7}$-NPs (25 μg pMHC per ml and 50 μg ml$^{-1}$ iron), or unconjugated nanoparticles (50 μg iron per ml). Relative gene expression was calculated using unstimulated cultures as controls.

pMHC-NP-induced upregulation of $T_R1$ transcripts in naive compared to memory BDC2.5 CD4$^+$ T cells in vivo was done by transfusing naive (CD44$^{med}$CD62L$^{hi}$) or memory (CD44$^{hi}$CD62L$^{low}$) eGFP-CD4$^+$ T cells from BDC2.5-TCR-transgenic NOD or NOD Foxp3-eGFP mice (Thy1$^{b+}$) (1-1.5×10$^6$ cells per host) into NOD. Thy1$^a$ hosts and by treating the hosts with four doses of 2.5 mi/IA$^{g7}$-NPs over two weeks or leaving them untreated. Two and a half weeks later, Thy1$^{b+}$CD4$^+$ T cells were sorted from the hosts and challenged with anti-CD3 and anti-CD28-coated magnetic Dynabeads for 3 days before mRNA extraction and RT-qPCR using primers specific for c-Maf, IL-21, IL-10, IFNγ, LAG-3 and CD49b.

To compare levels of IL-10 mRNA in the tetramer$^+$ compared with tetramer$^-$CD4$^+$ T cells of pMHC-NP-treated PBMC-engrafted NSG hosts, Applicant stained splenocytes with anti-hCD4-FITC, anti-hCD19-APC and tetramer-PE as described above, and sorted tetramer$^+$ and tetramer$^-$ cells from individual hosts by FACS (FACSAria-BD Biosciences). Sorted cells were cultured for 72 h in RPMI-1640 containing 10% human AB serum, in the presence of Dynabeads Human T-Activator CD3/CD28 (LifeTechnologies) using a 1:1 cell to bead ratio. Total RNA from cell pellets was reverse-transcribed using a dual reverse transcriptase/lysis solution containing 5 mM DTT, 2 U ml$^{-1}$ RNAase, 500 mM dNTPs, 10 U ml$^{-1}$ of Superscript reverse transcriptase (Invitrogen, LifeTechnologies), 100 mg ml$^{-1}$ bovine serum albumin, 1% Triton X-100, 25 ng ml$^{-1}$ Oligo dT (Invitrogen), 0.5 nM spermidine, and 1× First Strant buffer (Invitrogen) in 20 μl for 60 min at 50° C. and 15 min at 70° C. We then mixed 1 μl of the cDNA reaction volume with 12.5 μl of Power SyBRGreen PCR master mix solution (Applied Biosystem) and amplified with a real-time PCR machine (7900HT, Applied Biosystems) using the following primers: β-actin (Forward: 5'-CTGGAACGGTGAAGGTGACA-3' (SEQ ID NO: 500); Reverse: 5'-AAGGGACTTCCTG-TAACAATGCA-3' (SEQ ID NO: 501)), IL-10 (Forward: 5'-AA GACCCAGACATCAAGGCG-3' (SEQ ID NO: 502); Reverse: 5'-AATCGATGACAGCGCCGT AG-3' (SEQ ID NO: 503)).

Statistical Analyses.

The sample size values described in the figure legends correspond to the number of individual mice tested (not replicates) and data shown correspond to pooled data from different experiments. Data were compared by Student's t-test, Mann-Whitney U-test, chi-square, log-rank (Mantel-Cox), Pearson correlation or two-way ANOVA tests. Statistical significance was assumed at P<0.05.

Example 3. pMHC Valency and Density Effects In Vivo

Figure 22A:
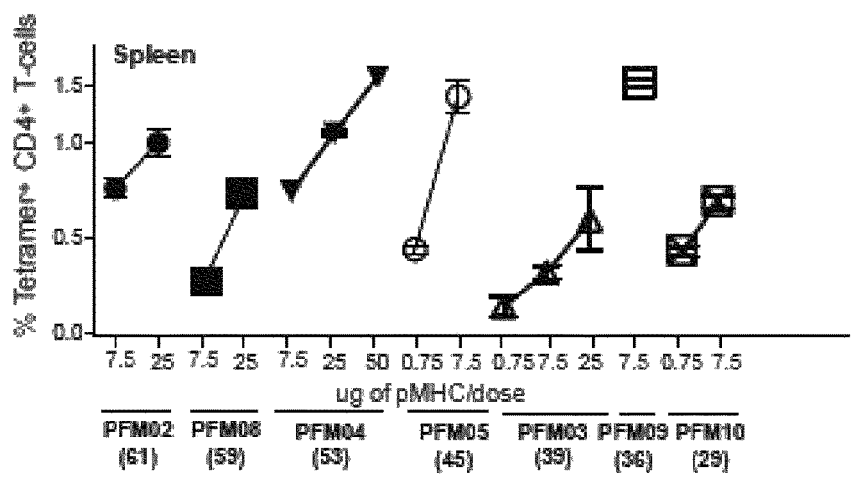
FIGS. 22A-22C show autoregulatory T-cell expansion properties of pMHC class I and class II-coated PF-M NPs in vivo as a function of pMHC density and dose.
Figure 22B:
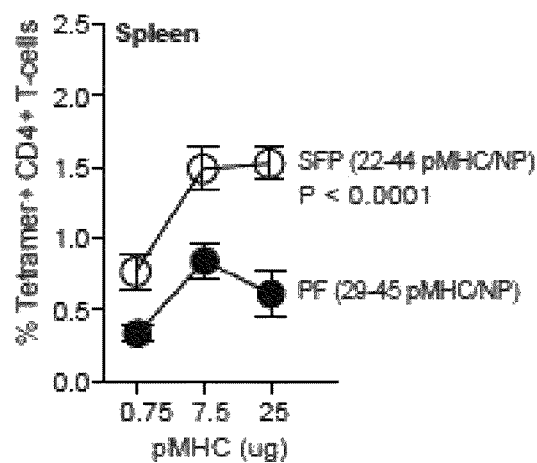

Applicant next tested the predictions of the mathematical model experimentally, by comparing the Treg cell expanding properties of various preparations of PF-M (~20 nm) and SFP-Z (~8 nm) NPs coated with 2.5 mi/IA$^{g7}$ pMHCs, which expand cognate T-regulatory-1 ($T_R1$) type CD4+ T-cells. Comparison of the Treg expanding properties of 7 different 2.5 mi-IA$^{g7}$-PF-M preparations, carrying from 29-59 pMHCs/NP demonstrated clear pMHC dose-dependent effects within individual preparations, but also no significant effects of pMHC valency across batches (FIG. 22A). Importantly, however, studies using the smaller 2.5 mi-IA$^{g7}$-SFP-Z preparations carrying 22-44 pMHCs/NP indicated significantly higher Treg expanding effects, at all doses tested (0.75-1 μg, 7.5-10 μg and 25 μg of total pMHC/dose), than 2.5 mi-IA$^{g7}$-PF-M particles carrying 29-45 pMHCs/NP (FIG. 22B). These results were further confirmed by producing 11 nm diameter PF-M NPs and testing the ability of their 2.5 mi-IA$^{g7}$-coated counterparts to expand cognate $T_R1$ T-cells in vivo. Remarkably, 11 nm PF-M NPs delivering 7.5 μg of total pMHC at 15 pMHCs/NP expanded cognate TR1 cells to 1.6±0.3% of total splenic CD4+ T-cells, a value comparable to the SFP series of NPs delivering 7.5 μg of 22-44 pMHCs/NP.

Figure 22C:
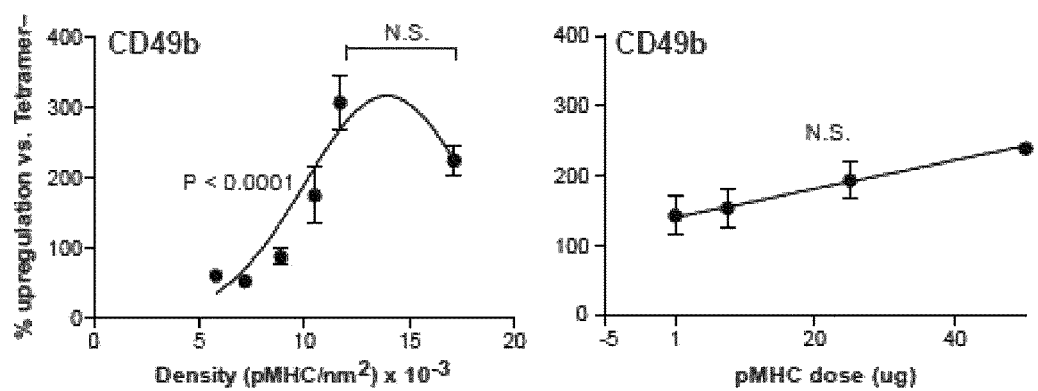

As noted above, Applicants have shown that autoreactive memory CD4+ T-cells express a T-regulatory type 1 ($T_R0$-poised transcriptional program and export LAG3 but not CD49b ($T_R1$ markers) to the cell surface. Since 2.5 mi-IA$^{g7}$-NP therapy triggers the expression of IL-10 and the upregulation of CD49b on $T_R1$-poised memory T-cells, hence promoting their conversion into stable $T_R1$ cells, Applicant questioned if the efficiency of these processes was also regulated by pMHC density on the NP surface. Remarkably, there was a statistically significant correlation between 2.5 mi/IA$^{g7}$ density (but not total pMHC dose) and CD49b (but not LAG3) upregulation on the $T_R1$-like CD4+ T-cells that expand in wild-type NOD mice in response to 2.5 mi/IA$^{g7}$-NP therapy; this effect peaked at 0.012 pMHC/nm$^2$ (FIG. 22C). Together, these results support the idea that pMHC density is a critical parameter in the design of pMHC-based nanomedicines.

These effects of pMHC density on biological activity were also seen in vivo; increases in pMHC density led to enhanced upregulation of the $T_R1$ cell marker CD49b in pMHC-NP-treated mice, suggesting that pMHC density is responsible for promoting Treg fitness. Whereas total pMHC dose was associated with the Treg-expanding properties of these nanomedicines, it only had minor effects on this phenotype, suggesting that pMHC density and pMHC dose have separate roles in promoting Treg conversion and expansion, respectively.

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Throughout this disclosure, various publications, patents and published patent specifications are referenced by an identifying citation. All publications, patent applications, patents, and other references mentioned herein are expressly incorporated by reference in their entirety, to the same extent as if each were incorporated by reference individually. In case of conflict, the present specification, including definitions, will control.

TABLE 1

Functionalized PEG linkers

| Linker Code | Types of Nanoparticle | PEG linkers | M.W. (kDa) | Functional group | Structure |
|---|---|---|---|---|---|
| A1 | Gold nanoparticle (GNP-C) | Thiol-PEG-carboxyl | 3.5 | Amine (—NH$_2$) | 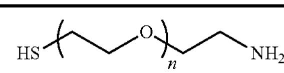 |
| A2 | Gold nanoparticle (GNP-N) | Thiol-PEG-amine | 3.5 | Carboxyl (—COOH) | 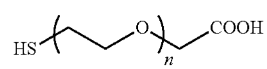 |
| S1 | Iron oxide Nanoparticle (SFP-C) | Dopamine-PEG-carboxyl | 3.5 | Carboxyl (—COOH) | 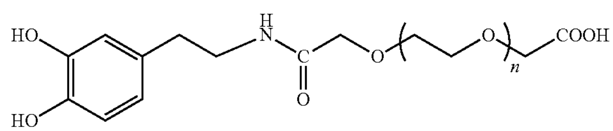 |
| S2 | Iron oxide Nanoparticle (SFP-N) | Dopamine-PEG-amine | 3.5 | Amine (—NH$_2$) | 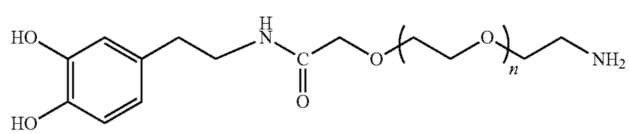 |
| S3 | Iron oxide Nanoparticle (SFP-Z) | Dopamine-PEG-azide | 3.5 | Azide (—N$_3$) | 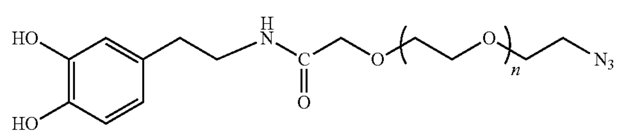 |
| S4 | Iron oxide Nanoparticle (SFP-M) | Dopamine-PEG-maleimide | 3.5 | Maleimide | 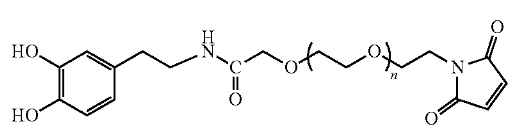 |
| S5 | Iron oxide Nanoparticle (SFP-O) | Dopamine-PEG-Orthopyridyl disulfide | 3.5 | Orthopyridyl disulfide | 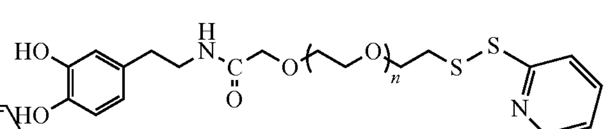 |
| P1 | Iron oxide Nanoparticle (PF-C) | carbonyl-PEG-carboxyl | 2.0 | Carboxyl (—COOH) | 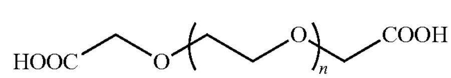 |

TABLE 1-continued

Functionalized PEG linkers

| Linker Code | Types of Nanoparticle | PEG linkers | M.W. (kDa) | Functional group | Structure |
|---|---|---|---|---|---|
| P2 | Iron oxide Nanoparticle (PF-N) | Methoxy-PEG-amine | 2.0 | Amine (—NH$_2$) | H$_3$C−O−(−O−)$_n$−NH$_2$ |
| P3 | Iron oxide Nanoparticle (PF-M) | Methoxy-PEG-maleimide | 2.0 | Maleimide | (maleimide structure) |
| P4 | Iron oxide Nanoparticle (PF-O) | Methoxy-PEG-Orthopyridyl disulfide | 2.0 | Orthopyridyl disulfide | (orthopyridyl disulfide structure) |
| P5 | Iron oxide Nanoparticle (PF) | PEG | 2.0 | Hydroxyl (—OH) | HO−(−O−)$_n$−H |

TABLE 2

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

TABLE 3A

Real-time RT-PCR for 384 immunological markers

| Gene Name | Protein | Function | GPR P-value | GPR Fold Change |
|---|---|---|---|---|
| Spp1 | Osteopontin | ECM protein component | 0.001285 | 123.4154 |
| Il10 | IL-10 | Immunosuppressive cytokine | 0.000677 | 41.61113 |
| Gzma | Granzyme A | Cytolytic enzyme | 0.008105 | 41.933044 |
| Lepr | Leptin R | Regulator of survival and activation of T-cells. | 0.049202 | 17.752507 |
| Ido1 | Indoleamine 2,3-dioxygenase (IDO1) | Key enzyme of the tryptophan catabolism. Inhibitory enzyme. | 0.036635 | 14.462784 |
| Il13 | IL-13 | Th2 and anti-inflammatory cytokine | 0.021696 | 11.702363 |
| Entpd1 | Ectonucleotide triphosphate diphosphate 1 (CD39) | ATP/ADP hydrolase Memory marker and inhibitory enzyme | 0.006004 | 8.192557 |
| Prdm1 | Blimp-1 | Transcription factor | 0.006751 | 8.826929 |

TABLE 3A-continued

Real-time RT-PCR for 384 immunological markers

| Gene Name | Protein | Function | GPR P-value | GPR Fold Change |
|---|---|---|---|---|
| Tbx21 | T-bet | ($T_R1$ cells) Th1 Transcription factor | 0.01586 | 7.829291 |
| Pdcd1 | PD-1 | Inhibitory receptor | 0.022 | 6.5673 |
| Il9 | IL-9 | Th2 cytokine | 0.039733 | 6.322661 |
| Il21 | IL-21 | Th1 and $T_R1$ cytokine | 0.019428 | 6.169626 |
| Csf1 | M-CSF | Macrophage growth factor | 0.01446 | 5.397609 |
| Il1r2 | IL-1R2 | IL-1 Decoy receptor. Inhibits IL-1 signaling | 0.038197 | 3.470605 |
| Casp1 | Caspase-1 | Pro-inflammatory zymogen that cleaves IL-1β and IL-18 | 0.037868 | 2.966331 |
| Cx3cr1 | CX3CR1 | CX3CL1 (fractalkine) receptor; T-cell chemokine | 0.004775 | −139.568489 |
| Foxp3 | Foxp3 | nTreg-specific transcription factor | 0.047705 | −57.878553 |
| Cxcl9 | CXCL9 | Th1 T-cell chemokine | 0.00246 | −54.48584 |
| Il18r1 | IL-18R | IL-18 (Th1 amplifying factor) | 0.011622 | −7.293964 |
| Sell | CD62L | Selectin present in naïve T-cells | 0.012487 | −6.23221 |
| Ccr7 | CCR7 | Thymus and LN-driving chemokine Naïve/memory marker | 0.027056 | −3.383342 |
| Tfrc | Transferrin | Iron-binding regulator of iron homeostatis | 0.035692 | −2.928147 |

TABLE 3B

Real-time RT-PCR for $T_R1$ transcripts

| Gene Name | Protein | Function | P-value | Fold Change |
|---|---|---|---|---|
| Il21 | IL-21 | Th1 and $T_R1$ cytokine | 0.0061 | 104.15 |
| Il10 | IL-10 | Immunosuppressive cytokine | 0.0061 | 79.65 |
| c-Maf | c-MAF | IL-10-regulating transcription factor | 0.0061 | 18.455 |
| Ifng | IFNγ | Th1 cytokine | 0.0061 | 11.2 |
| Lag-3 | Lag-3 | Inhibitory receptor. $T_R1$ marker | 0.0061 | 5.471 |
| Itga2 | CD49b | Integrin $T_R1$ marker | 0.1091 | 5.054 |
| Ahr | Aryl hydrocarbon receptor | $T_R1$-inducer receptor | 0.0727 | 3.138 |
| Icos | ICOS | Costimulatory molecule | 0.0424 | 3.033 |

TABLE 4A

DRB1*0401 + patients/GAD65$_{555\text{-}567\ (557I)}$/DR4- or PPI$_{76\text{-}90\ (88S)}$/DR4-NP

| Code | Gender | Age (yr) | Age at onset (yr) | Anti-GAD | Anti-IA2 | Anti-INS | pMHC-N (10 ug/dose) | hCD4 (% of MNCs) | Tetramer (% of hCD4)* | Tetramer control (% of hCD4) | Outcome |
|---|---|---|---|---|---|---|---|---|---|---|---|
| 8007 | M | 35 | 34 | + | + | + | GAD65$_{555\text{-}567\ (557I)}$/DR4 | 80 | 0.098 | 0.170 | − |
| 8014 | F | 44 | 43 | + | − | ND | GAD65$_{555\text{-}567\ (557I)}$/DR4 | 52.5 | 1.310 | 0.312 | + |
| 7005 | F | 52 | 50 | + | + | ND | GAD65$_{555\text{-}567\ (557I)}$/DR4 | 55.2 | 0.127 | 0.418 | − |
| 8015 | F | 41 | 40 | ND | ND | ND | GAD65$_{555\text{-}567\ (557I)}$/DR4 | 67.4 | 0.087 | 0.128 | − |
| 7005 | F | 52 | 50 | + | + | ND | PPI$_{76\text{-}90\ (88S)}$/DR4 | 65.5 | 3.080 | 0.062 | + |
| 8015 | F | 41 | 40 | ND | ND | ND | PPI$_{76\text{-}90\ (88S)}$/DR4 | 83.0 | 0.125 | 0.051 | − |
| Mean (SE) | | 44.2 (2.8) | 42.8 (2.56) | | | | | 67.3 (5.1) | 0.805 (0.496) | 0.190 (0.060) | |
| Median (range) | | 42.5 (35-52) | 41.5 (34-50) | | | | | | | | |

*Result was considered (+) if greater than the mean + 3 S.E. from the samples stained with control tetramer

TABLE 4B

DRB1*0301 + patients/IGRP$_{13\text{-}25}$-DR3-NP

| Code | Gender | Age (yr) | Age at onset (yr) | Anti-GAD | Anti-IA2 | Anti-INS | Spleen (% of hCD4) Treated (20 ug/dose)* | Untreated | LN (% of hCD4) Treated (20 ug/dose)* | Untreated | Outcome |
|---|---|---|---|---|---|---|---|---|---|---|---|
| 8030 | M | 27 | 27 | + | + | ND | 0.859 | 0.168 | 3.170 | 0.198 | + |
| 8025 | M | 46 | 46 | + | + | ND | 0.376 | 0.167 | 0.174 | 0.000 | + |

TABLE 4B-continued

DRB1*0301 + patients/IGRP₁₃₋₂₅-DR3-NP

| Code | Gender | Age (yr) | Age at onset (yr) | Anti-GAD | Anti-IA2 | Anti-INS | Spleen (% of hCD4) Treated (20 ug/dose)* | Untreated | LN (% of hCD4) Treated (20 ug/dose)* | Untreated | Outcome |
|---|---|---|---|---|---|---|---|---|---|---|---|
| 8033 | M | 39 | 39 | + | − | ND | 0.495 | 0.310 | 0.034 | 0.048 | + |
| 8020 | F | 20 | 19 | + | + | − | 0.641 | dead | no cells | dead | + |
| 8028 | F | 22 | 21 | + | + | − | 0.044 | 0.086 | 0.627 | 0.101 | + |
| 8016 | M | 45 | 45 | + | − | ND | 0.539 | sick | 1.270 | sick | + |
| 8038 | F | 31 | 31 | + | − | ND | 0.130 | 0.163 | 2.410 | no cells | + |
| Mean (SE) | | 32.9 (4.0) | 32.6 (4.2) | | | | 0.441 (0.108) | 0.224 (0.036) | 1.281 (0.518) | 0.087 (0.037) | |
| Median (range) | | 31 (20-46) | 31 (19-46) | | | | | | | | |
| P vs. DR4 patients | 0.135 | 0.02 | 0.032 | | | | | | | | |
| P treated vs untreated | | | | | | | 0.027 (%) 0.042 (abs #) | | 0.035 (%) 0.028 (abs #) | | |
| % in hCD4 in MNC - Mean (SE) | | | | | | | 44.7 (6.2) | 49.6 (3.2) | 54.7 (8.6) | 45.6 (10.9) | |

*Result was considered (+) if greater than the mean + 3 S.E. corresponding to the samples from PBMC-reconstituted but pMHC-NP-untreated NSG hosts.
**The PLN samples with increased IGRP 13-25/DR3 tetramer+ cells were significantly enlarged and had increased cellularity as compared to those from treated mice lacking such increases (P = 0.048) or from untreated mice (P = 0.036). There was a statistically significant correlation between % tetramer + cells and total PLN cell number (r2 = 0.455; P = 0.032)

TABLE 4C

DRB1*0301 + patients (IGRP₁₃₋₂₅ peptide, IGRP₁₃₋₂₅-peptide-NP and IGRP₁₃₋₂₅ peptide-MP)

| Code | Gender | Age (yr) | Age at onset (yr) | Anti-GAD | Anti-IA2 | Anti-INS | Spleen (% of hCD4) Peptide treated | MC treated | Peptide-NP | Untreated | PLN (% of hCD4) Peptide treated | MC treated | Peptide-NP | Untreated | Outcome |
|---|---|---|---|---|---|---|---|---|---|---|---|---|---|---|---|
| 8049 | M | 28 | 25 | − | + | ND | 0.026 | 0.023 | | dead | No cells | No cells | | dead | − |
| 8035 | M | 30 | 28 | + | − | − | 0.121 | 0.073 | | 0.050 | No cells | No cells | No cells | | − |
| 8040 | M | 24 | 23 | + | + | − | 0.145 | 0.085 | | 0.161 | No cells | No cells | No cells | | − |
| 8047 | F | 25 | 25 | + | + | − | 0.116 | 0.127 | | 0.093 | No cells | No cells | No cells | | − |
| 8042 | M | 33 | 31 | + | − | ND | 0.010 | 0.005 | | dead | No cells | 0.002 | | dead | − |
| 8050 | M | 23 | 23 | − | − | − | | | 0.041 | dead | | | 0.049 | dead | − |
| 8020 | F | 21 | 20 | + | + | − | | | 0.089 | 0.051 | | | No cells | No cells | − |
| 7010 | M | 21 | 17 | ND | ND | ND | | | 0.109 | dead | | | 0.020 | dead | − |
| 5023 | M | 12 | 12 | ND | ND | ND | | | 0.143 | dead | | | No cells | dead | − |
| Mean (SE) | | 24.1 (2.0) | 22.7 (1.9) | | | | 0.084 (0.027) | 0.063 (0.022) | 0.096 (0.021) | 0.089 (0.026) | 0.002 (0.000) | 0.335 (0.015) | | | |
| Median (range) | | 24.0 (12-33) | 23.0 (12-31) | | | | | | | | | | | | |
| p** treated vs untreated | | | | | | | 0.448 (%) 0.227 (abs #) | 0.236 (%) 0.437 (abs #) | 0.424 (%) 0.231 (abs #) | | | | | | |
| % hCD4 in MNC - Mean (SE) | | | | | | | 56.9 (2.9) | 43.8 (4.2) | 47.6 (3.8) | 39.9 (5.7) | 43.2 (0.0) | 43.3 (3.0) | | | |

*Result was considered (+) if greater than the mean + S.E. corresponding to the samples from PBMC-reconstituted but untreated NSG hosts.

REFERENCES

1 Lieberman, S. & DiLorenzo, T. A comprehensive guide to antibody and T-cell responses in type 1 diabetes. *Tissue Antigens* 62, 359-377 (2003).
2 Tsai, S., Shameli, A. & Santamaria, P. CD8+ T-cells in autoimmune diabetes. *Adv. Immunol.* 100, 79-124 (2008).
3 Santamaria, P. The long and winding road to understanding and conquering type 1 diabetes. *Immunity* 32, 437-445 (2010).
4 Babbe, H. et al. Clonal expansions of CD8(+) T cells dominate the T cell infiltrate in active multiple sclerosis lesions as shown by micromanipulation and single cell polymerase chain reaction. *J. Exp. Med.* 192, 393-404 (2000).

5 Zang, Y. C. et al. Increased CD8+ cytotoxic T cell responses to myelin basic protein in multiple sclerosis. *J. Immunol.* 172, 5120-5127 (2004).

6 Walter, U. & Santamaria, P. CD8+ T cells in autoimmunity. *Curr. Opin. Immunol.* 17, 624-631 (2005).

7 Firestein, G. S. Evolving concepts of rheumatoid arthritis. *Nature* 423, 356-361 (2003).

8 Sakaguchi, S. et al. Foxp3+ CD25+CD4+ natural regulatory T cells in dominant self-tolerance and autoimmune disease. *Immunol. Rev.* 212, 8-27 (2006).

9 Miyara, M. et al. Functional delineation and differentiation dynamics of human CD4+ T cells expressing the FoxP3 transcription factor. *Immunity* 30, 899-911 (2009).

10 Chen, Q., Kim, Y. C., Laurence, A., Punkosdy, G. A. & Shevach, E. M. IL-2 controls the stability of Foxp3 expression in TGF-beta-induced Foxp3+ T cells in vivo. *J. Immunol.* 186, 6329-6337 (2011).

11 Yang, X. P. et al. Opposing regulation of the locus encoding IL-17 through direct, reciprocal actions of STAT3 and STAT5. *Nat. Immunol.* 12, 247-25 (2011).

12 Marwaha, A. K. et al. Cutting edge: Increased IL-17-secreting T cells in children with new-onset type 1 diabetes. *J. Immunol.* 185, 3814-3818 (2010).

13 McClymont, S. A. et al. Plasticity of human regulatory T cells in healthy subjects and patients with type 1 diabetes. *J. Immunol.* 186, 3918-3926 (2011).

14 Komatsu, N. et al. Heterogeneity of natural Foxp3+ T cells: a committed regulatory T-cell lineage and an uncommitted minor population retaining plasticity. *Proc. Natl. Acad. Sci. U.S.A.* 106, 1903-1908 (2009).

15 Zhou, L., Chong, M. M. & Littman, D. R. Plasticity of CD4+ T cell lineage differentiation. *Immunity* 30, 646-655 (2009).

16 Zhou, X. et al. Instability of the transcription factor Foxp3 leads to the generation of pathogenic memory T cells in vivo. *Nat. Immunol.* 10, 1000-1007 (2009).

17 Komatsu, N. et al. Pathogenic conversion of Foxp3+ T cells into TH17 cells in autoimmune arthritis. *Nat. Med.* 20, 62-68 (2014).

18 Bailey-Bucktrout, S. L. et al. Self-antigen-driven activation induces instability of regulatory T cells during an inflammatory autoimmune response. *Immunity* 39, 949-962 (2013).

19 Bacchetta, R. et al. High levels of interleukin 10 production in vivo are associated with tolerance in SCID patients transplanted with HLA mismatched hematopoietic stem cells. *J. Exp. Med.* 179, 493-502 (1994).

20 Roncarolo, M. G. et al. Interleukin-10-secreting type 1 regulatory T cells in rodents and humans. *Immunol. Rev.* 212, 28-50 (2006).

21 Gagliani, N. et al. Coexpression of CD49b and LAG-3 identifies human and mouse T regulatory type 1 cells. *Nat. Med.* 19, 739-746 (2013).

22 McLarnon, A. IBD: Regulatory T-cell therapy is a safe and well-tolerated potential approach for treating refractory Crohn's disease. *Nature Rev Gastroenterol Hepatol* 9, 559 (2012).

23 Desreumaux, P. et al. Safety and Efficacy of Antigen-Specific Regulatory T-Cell Therapy for Patients With Refractory Crohn's Disease. *Gastroenterology* 143, 1207-1217 (2012).

24 Roncarolo, M. G., Gregori, S., Lucarelli, B., Ciceri, F. & Bacchetta, R. Clinical tolerance in allogeneic hematopoietic stem cell transplantation. *Immunol. Rev.* 241, 145-163 (2011).

25 Tsai, S. et al. Reversal of autoimmunity by boosting memory-like autoregulatory T cells. *Immunity* 32, 568-580 (2010).

26 Clemente-Casares, X., Tsai, S., Yang, Y. & Santamaria, P. Peptide-MHC-based nanovaccines for the treatment of autoimmunity: a "one size fits all" approach? *J. Mol. Med.* 89, 733-742 (2011).

27 Stratmann, T. et al. Susceptible MHC alleles, not background genes, select an autoimmune T cell reactivity. *J. Clin. Invest.* 112, 902-914 (2003).

28 Mukherjee, R., Wagar, D., Stephens, T., Le-Chan, E. & Singh, B. Identification of CD4+ T cell-specific epitopes of islet-specific glucose-6-phosphatase-catalytic subunit-related protein: a novel beta cell autoantigen in type 1 diabetes. *J. Immunol.* 174, 5306-5315 (2005).

29 Kamanaka, M. et al. Expression of interleukin-10 in intestinal lymphocytes detected by an interleukin-10 reporter knockin tiger mouse. *Immunity* 25, 941-952 (2006).

30 Yoshizaki, A. et al. Regulatory B cells control T-cell autoimmunity through IL-21-dependent cognate interactions. *Nature* 491, 264-268 (2012).

31 Onoda, T. et al. Human CD4+ central and effector memory T cells produce IL-21: effect on cytokine-driven proliferation of CD4+ T cell subsets. *Int. Immunol.* 19, 1191-1199 (2007).

32 Pot, C. et al. Cutting edge: IL-27 induces the transcription factor c-Maf, cytokine IL-21, and the costimulatory receptor ICOS that coordinately act together to promote differentiation of IL-10-producing $T_R1$ cells. *J. Immunol.* 183, 797-801 (2009).

33 Spensieri, F. et al. Human circulating influenza-CD4+ ICOS1+IL-21+ T cells expand after vaccination, exert helper function, and predict antibody responses. *Proc. Natl. Acad. Sci. U.S.A.* 110, 14330-14335 (2013).

34 Hale, J. S. et al. Distinct memory CD4+ T cells with commitment to T follicular helper- and T helper 1-cell lineages are generated after acute viral infection. *Immunity* 38, 805-817 (2013).

35 Sato, K. et al. Marked induction of c-Maf protein during Th17 cell differentiation and its implication in memory Th cell development. *J. Biol. Chem.* 286, 14963-14971 (2011).

36 Saraiva, M. et al. Interleukin-10 production by Th1 cells requires interleukin-12-induced STAT4 transcription factor and ERK MAP kinase activation by high antigen dose. *Immunity* 31, 209-219 (2009).

37 Verdaguer, J. et al. Spontaneous autoimmune diabetes in monoclonal T cell nonobese diabetic mice. *J. Exp. Med.* 186, 1663-1676 (1997).

38 Wang, J. et al. In situ recognition of autoantigen as an essential gatekeeper in autoimmune CD8+ T cell inflammation. *Proc. Natl. Acad. Sci. U.S.A.* 107, 9317-9322 (2010).

39 Amrani, A. et al. Progression of autoimmune diabetes driven by avidity maturation of a T-cell population. *Nature* 406, 739-742 (2000).

40 Stratmann, T. et al. The I-Ag7 MHC class II molecule linked to murine diabetes is a promiscuous peptide binder. *J. Immunol.* 165, 3214-3225 (2000).

41 Yang, J. et al. Islet-specific glucose-6-phosphatase catalytic subunit-related protein-reactive CD4+ T cells in human subjects. *J. Immunol.* 176, 2781-2789 (2006).

42 Holst, J. et al. Generation of T-cell receptor retrogenic mice. *Nat. Protoc.* 1, 406-417 (2006).

43 Yoshida, K. et al. Evidence for shared recognition of a peptide ligand by a diverse panel of non-obese diabetic mice-derived, islet-specific, diabetogenic T cell clones. *Int. Immunol.* 14, 1439-1447 (2002).

44 Reijonen, H. et al. Detection of GAD65-specific T-cells by major histocompatibility complex class II tetramers in type 1 diabetic patients and at-risk subjects. *Diabetes* 51, 1375-1382 (2002).

45 Yang, J. et al. CD4+ T cells from type 1 diabetic and healthy subjects exhibit different thresholds of activation to a naturally processed proinsulin epitope. *J. Autoimmun.* 31, 30-41 (2008).

46 Moore, A., Grimm, J., Han, B. & Santamaria, P. Tracking the recruitment of diabetogenic CD8+ T cells to the pancreas in real time. *Diabetes* 53, 1459-1466 (2004).

47 Giuliani, F. et al. Additive effect of the combination of glatiramer acetate and minocycline in a model of MS. *J. Neuroimmunol.* 158, 213-221 (2005).

48 Leavenworth, J. W., Tang, X., Kim, H. J., Wang, X. & Cantor, H. Amelioration of arthritis through mobilization of peptide-specific CD8+ regulatory T cells. *J. Clin. Invest.* 123, 1382-1389 (2013).

What is claimed is:

1. A complex comprising a nanoparticle core coupled to a plurality of antigen-MHC class II complexes (pMHCIIs), the nanoparticle core comprising iron or an iron oxide and having a diameter which is from about 5 nm to about 25 nm, wherein the antigen is an autoimmune disease relevant antigen and wherein the number of coupled pMHCIIs per nanoparticle surface area is from about 0.4 pMHC/100 nm$^2$ to about 5 pMHC/100 nm$^2$, wherein the pMHCIIs are coupled to a maleimide functionalized end of a polyethylene glycol (PEG) linker that is less than about 5 kilodaltons in molecular weight, wherein a non-maleimide functionalized end of the polyethylene glycol (PEG) linker is coupled to the nanoparticle core, and the non-maleimide functionalized end comprises an alkoxy, an alkyl, alkyl-amide-alkyl, alkyl-ester-alkyl, alkyl-amide, alkyl-acid, or alkyl-ester, wherein the complex differentiates an activated T cell or a memory T cell into an IL-10 producing TR1 cell.

2. The complex of claim 1, wherein the number of coupled pMHCIIs per nanoparticle surface area is from about 0.4 pMHCII/100 nm$^2$ to about 1.3 pMHCII/100 nm$^2$.

3. The complex of claim 1, wherein the number of coupled pMHCIIs per nanoparticle surface area is from about 0.5 pMHCII/100 nm$^2$ to about 0.9 pMHCII/100 nm$^2$.

4. The complex of claim 1, wherein the diameter is from about 15 nm to about 25 nm.

5. The complex of claim 1, wherein the pMHCIIs are covalently coupled to the nanoparticle core via the formation of a carbon-sulfur bond between the thiol (—SH) group of a cysteine residue added to the carboxyl terminus of the pMHCIIs and maleimide.

6. The complex of claim 1, wherein the IL-10 producing TR1 cell expresses CD49b.

7. A pharmaceutical composition comprising the complex of claim 1 and a biocompatible excipient.

8. The complex of claim 1, wherein the non-maleimide functionalized end comprises an alkoxy or an alkyl.

9. The complex of claim 8, wherein the non-maleimide functionalized end comprises an alkoxy.

10. The complex of claim 9, wherein the alkoxy comprises $C_1$ to $C_3$ alkyl.

11. The complex of claim 8, wherein the non-maleimide functionalized end comprises an alkyl.

* * * * *